US012398406B2

(12) United States Patent
Liu et al.

(10) Patent No.: US 12,398,406 B2
(45) **Date of Patent: *Aug. 26, 2025**

(54) CAS9 PROTEINS INCLUDING LIGAND-DEPENDENT INTEINS

(71) Applicant: President and Fellows of Harvard College, Cambridge, MA (US)

(72) Inventors: David R. Liu, Cambridge, MA (US); Kevin Davis, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/069,898

(22) Filed: Dec. 21, 2022

(65) Prior Publication Data

US 2023/0279443 A1 Sep. 7, 2023

Related U.S. Application Data

(63) Continuation of application No. 16/888,646, filed on May 29, 2020, now Pat. No. 11,578,343, which is a (Continued)

(51) Int. Cl.
*C12N 9/22* (2006.01)
*C07K 14/35* (2006.01)
(Continued)

(52) U.S. Cl.
CPC ............ *C12N 15/907* (2013.01); *C07K 14/35* (2013.01); *C07K 14/721* (2013.01);
(Continued)

(58) Field of Classification Search
None
See application file for complete search history.

(56) References Cited

U.S. PATENT DOCUMENTS 4,182,449 A 1/1980 Kozlow
4,186,183 A 1/1980 Steck et al.
(Continued)

FOREIGN PATENT DOCUMENTS

AU 2012244264 A1 11/2012
AU 2012354062 A1 7/2014
(Continued)

OTHER PUBLICATIONS

Truong et al. Nucleic Acids Research, vol. 43, No. 13, pp. 6450-6458, Jun. 16, 2015.*
(Continued)

*Primary Examiner* — Richard G Hutson
(74) *Attorney, Agent, or Firm* — Wolf, Greenfield & Sacks, P.C.

(57) ABSTRACT

Some aspects of this disclosure provide compositions, methods, systems, and kits for controlling the activity of RNA-programmable endonucleases, such as Cas9, or for controlling the activity of proteins comprising a Cas9 variant fused to a functional effector domain, such as a nuclease, nickase, recombinase, deaminase, transcriptional activator, transcriptional repressor, or epigenetic modifying domain. For example, the inventive proteins provided comprise a ligand-dependent intein, the presence of which inhibits one or more activities of the protein (e.g., gRNA binding, enzymatic activity, target DNA binding). The binding of a ligand to the intein results in self-excision of the intein, restoring the activity of the protein.

33 Claims, 14 Drawing Sheets

Specification includes a Sequence Listing.

Related U.S. Application Data continuation of application No. 16/132,276, filed on Sep. 14, 2018, now Pat. No. 10,704,062, which is a continuation of application No. 15/329,925, filed as application No. PCT/US2015/042770 on Jul. 30, 2015, now Pat. No. 10,077,453.

(60) Provisional application No. 62/135,629, filed on Mar. 19, 2015, provisional application No. 62/030,943, filed on Jul. 30, 2014.

(51) Int. Cl.

| | |
|---|---|
| ***C07K 14/72*** | (2006.01) |
| ***C12N 9/02*** | (2006.01) |
| ***C12N 9/78*** | (2006.01) |
| ***C12N 15/63*** | (2006.01) |
| ***C12N 15/90*** | (2006.01) |
| ***C12P 19/34*** | (2006.01) |

(52) U.S. Cl.

CPC ............. *C12N 9/0071* (2013.01); *C12N 9/22* (2013.01); *C12N 9/78* (2013.01); *C12N 15/63* (2013.01); *C12P 19/34* (2013.01); *C12Y 114/11* (2013.01); *C12Y 305/04* (2013.01); *C07K 2319/92* (2013.01)

(56) References Cited

U.S. PATENT DOCUMENTS

| | | | |
|---|---|---|---|
| 4,217,344 | A | 8/1980 | Vanlerberghe et al. |
| 4,235,871 | A | 11/1980 | Papahadjopoulos et al. |
| 4,261,975 | A | 4/1981 | Fullerton et al. |
| 4,485,054 | A | 11/1984 | Mezei et al. |
| 4,501,728 | A | 2/1985 | Geho et al. |
| 4,663,290 | A | 5/1987 | Weis et al. |
| 4,737,323 | A | 4/1988 | Martin et al. |
| 4,774,085 | A | 9/1988 | Fidler |
| 4,797,368 | A | 1/1989 | Carter et al. |
| 4,837,028 | A | 6/1989 | Allen |
| 4,873,316 | A | 10/1989 | Meade et al. |
| 4,880,635 | A | 11/1989 | Janoff et al. |
| 4,889,818 | A | 12/1989 | Gelfand et al. |
| 4,897,355 | A | 1/1990 | Eppstein et al. |
| 4,906,477 | A | 3/1990 | Kurono et al. |
| 4,911,928 | A | 3/1990 | Wallach |
| 4,917,951 | A | 4/1990 | Wallach |
| 4,920,016 | A | 4/1990 | Allen et al. |
| 4,921,757 | A | 5/1990 | Wheatley et al. |
| 4,946,787 | A | 8/1990 | Eppstein et al. |
| 4,965,185 | A | 10/1990 | Grischenko et al. |
| 5,017,492 | A | 5/1991 | Kotewicz et al. |
| 5,047,342 | A | 9/1991 | Chatterjee |
| 5,049,386 | A | 9/1991 | Eppstein et al. |
| 5,079,352 | A | 1/1992 | Gelfand et al. |
| 5,139,941 | A | 8/1992 | Muzyczka et al. |
| 5,173,414 | A | 12/1992 | Lebkowski et al. |
| 5,223,409 | A | 6/1993 | Ladner et al. |
| 5,244,797 | A | 9/1993 | Kotewicz et al. |
| 5,270,179 | A | 12/1993 | Chatterjee |
| 5,374,553 | A | 12/1994 | Gelfand et al. |
| 5,405,776 | A | 4/1995 | Kotewicz et al. |
| 5,436,149 | A | 7/1995 | Barnes |
| 5,449,639 | A | 9/1995 | Wei et al. |
| 5,496,714 | A | 3/1996 | Comb et al. |
| 5,512,462 | A | 4/1996 | Cheng |
| 5,580,737 | A | 12/1996 | Polisky et al. |
| 5,614,365 | A | 3/1997 | Tabor et al. |
| 5,652,094 | A | 7/1997 | Usman et al. |
| 5,658,727 | A | 8/1997 | Barbas et al. |
| 5,668,005 | A | 9/1997 | Kotewicz et al. |
| 5,677,152 | A | 10/1997 | Birch et al. |
| 5,767,099 | A | 6/1998 | Harris et al. |
| 5,780,053 | A | 7/1998 | Ashley et al. |
| 5,830,430 | A | 11/1998 | Unger et al. |
| 5,834,247 | A | 11/1998 | Comb et al. |
| 5,835,699 | A | 11/1998 | Kimura |
| 5,844,075 | A | 12/1998 | Kawakami et al. |
| 5,849,548 | A | 12/1998 | Haseloff et al. |
| 5,851,548 | A | 12/1998 | Dattagupta et al. |
| 5,855,910 | A | 1/1999 | Ashley et al. |
| 5,856,463 | A | 1/1999 | Blankenborg et al. |
| 5,962,313 | A | 10/1999 | Podsakoff et al. |
| 5,981,182 | A | 11/1999 | Jacobs, Jr. et al. |
| 6,015,794 | A | 1/2000 | Haseloff et al. |
| 6,057,153 | A | 5/2000 | George et al. |
| 6,063,608 | A | 5/2000 | Kotewicz et al. |
| 6,077,705 | A | 6/2000 | Duan et al. |
| 6,156,509 | A | 12/2000 | Schellenberger |
| 6,183,998 | B1 | 2/2001 | Ivanov et al. |
| 6,355,415 | B1 | 3/2002 | Wagner et al. |
| 6,429,298 | B1 | 8/2002 | Ellington et al. |
| 6,453,242 | B1 | 9/2002 | Eisenberg et al. |
| 6,479,264 | B1 | 11/2002 | Louwrier |
| 6,503,717 | B2 | 1/2003 | Case et al. |
| 6,534,261 | B1 | 3/2003 | Cox, III et al. |
| 6,558,671 | B1 | 5/2003 | Slingluff et al. |
| 6,589,768 | B1 | 7/2003 | Kotewicz et al. |
| 6,599,692 | B1 | 7/2003 | Case et al. |
| 6,607,882 | B1 | 8/2003 | Cox, III et al. |
| 6,610,522 | B1 | 8/2003 | Kotewicz et al. |
| 6,689,558 | B2 | 2/2004 | Case |
| 6,716,973 | B2 | 4/2004 | Baskerville et al. |
| 6,824,978 | B1 | 11/2004 | Cox, III et al. |
| 6,933,113 | B2 | 8/2005 | Case et al. |
| 6,979,539 | B2 | 12/2005 | Cox, III et al. |
| 7,013,219 | B2 | 3/2006 | Case et al. |
| 7,045,337 | B2 | 5/2006 | Schultz et al. |
| 7,067,650 | B1 | 6/2006 | Tanaka |
| 7,070,928 | B2 | 7/2006 | Liu et al. |
| 7,078,208 | B2 | 7/2006 | Smith et al. |
| 7,083,970 | B2 | 8/2006 | Schultz et al. |
| 7,163,824 | B2 | 1/2007 | Cox, III et al. |
| 7,192,739 | B2 | 3/2007 | Liu et al. |
| 7,223,545 | B2 | 5/2007 | Liu et al. |
| 7,354,761 | B2 | 4/2008 | Schultz et al. |
| 7,368,275 | B2 | 5/2008 | Schultz et al. |
| 7,419,669 | B2 | 9/2008 | Kosmatopoulos et al. |
| 7,442,160 | B2 | 10/2008 | Liu et al. |
| 7,476,500 | B1 | 1/2009 | Liu et al. |
| 7,476,734 | B2 | 1/2009 | Liu |
| 7,479,573 | B2 | 1/2009 | Chu et al. |
| 7,488,718 | B2 | 2/2009 | Scheinberg et al. |
| 7,491,494 | B2 | 2/2009 | Liu et al. |
| 7,541,450 | B2 | 6/2009 | Liu et al. |
| 7,557,068 | B2 | 7/2009 | Liu et al. |
| 7,595,179 | B2 | 9/2009 | Chen et al. |
| 7,638,300 | B2 | 12/2009 | Schultz et al. |
| 7,670,807 | B2 | 3/2010 | Lampson et al. |
| 7,678,554 | B2 | 3/2010 | Liu et al. |
| 7,713,721 | B2 | 5/2010 | Schultz et al. |
| 7,771,935 | B2 | 8/2010 | Liu et al. |
| 7,794,931 | B2 | 9/2010 | Breaker et al. |
| 7,807,408 | B2 | 10/2010 | Liu et al. |
| 7,851,658 | B2 | 12/2010 | Liu et al. |
| 7,915,025 | B2 | 3/2011 | Schultz et al. |
| 7,919,277 | B2 | 4/2011 | Russell et al. |
| 7,993,672 | B2 | 8/2011 | Huang et al. |
| 7,998,904 | B2 | 8/2011 | Liu et al. |
| 7,999,071 | B2 | 8/2011 | Schlom et al. |
| 8,012,739 | B2 | 9/2011 | Schultz et al. |
| 8,017,323 | B2 | 9/2011 | Liu et al. |
| 8,017,755 | B2 | 9/2011 | Liu et al. |
| 8,030,074 | B2 | 10/2011 | Schultz et al. |
| 8,067,556 | B2 | 11/2011 | Hogrefe et al. |
| 8,114,648 | B2 | 2/2012 | Schultz et al. |
| 8,173,364 | B2 | 5/2012 | Schultz et al. |
| 8,173,392 | B2 | 5/2012 | Schultz et al. |
| 8,183,012 | B2 | 5/2012 | Schultz et al. |
| 8,183,178 | B2 | 5/2012 | Liu et al. |
| 8,206,914 | B2 | 6/2012 | Liu et al. |
| 8,354,380 | B2 | 1/2013 | Liu et al. |
| 8,361,725 | B2 | 1/2013 | Russell et al. |
| 8,394,604 | B2 | 3/2013 | Liu et al. |

(56) References Cited

U.S. PATENT DOCUMENTS 8,440,431 B2 5/2013 Voytas et al.
8,440,432 B2 5/2013 Voytas et al.
8,450,471 B2 5/2013 Voytas et al.
8,492,082 B2 7/2013 De Franciscis et al.
8,546,553 B2 10/2013 Terns et al.
8,569,256 B2 10/2013 Heyes et al.
8,586,363 B2 11/2013 Voytas et al.
8,680,069 B2 3/2014 De Fougerolles et al.
8,691,729 B2 4/2014 Liu et al.
8,691,750 B2 4/2014 Constien et al.
8,697,359 B1 4/2014 Zhang
8,697,439 B2 4/2014 Mangeot et al.
8,697,853 B2 4/2014 Voytas et al.
8,709,466 B2 4/2014 Coady et al.
8,728,526 B2 5/2014 Heller
8,748,667 B2 6/2014 Budzik et al.
8,758,810 B2 6/2014 Okada et al.
8,759,103 B2 6/2014 Kim et al.
8,759,104 B2 6/2014 Unciti-Broceta et al.
8,771,728 B2 7/2014 Huang et al.
8,790,664 B2 7/2014 Pitard et al.
8,795,965 B2 8/2014 Zhang
8,822,663 B2 9/2014 Schrum et al.
8,835,148 B2 9/2014 Janulaitis et al.
8,846,578 B2 9/2014 McCray et al.
8,871,445 B2 10/2014 Cong et al.
8,889,418 B2 11/2014 Zhang et al.
8,900,814 B2 12/2014 Yasukawa et al.
8,945,839 B2 2/2015 Zhang
8,975,232 B2 3/2015 Liu et al.
8,993,233 B2 3/2015 Zhang et al.
8,999,641 B2 4/2015 Zhang et al.
9,023,594 B2 5/2015 Liu et al.
9,023,649 B2 5/2015 Mali et al.
9,034,650 B2 5/2015 Padidam
9,068,179 B1 6/2015 Liu et al.
9,150,626 B2 10/2015 Liu et al.
9,163,271 B2 10/2015 Schultz et al.
9,163,284 B2 10/2015 Liu et al.
9,181,535 B2 11/2015 Liu et al.
9,200,045 B2 12/2015 Liu et al.
9,221,886 B2 12/2015 Liu et al.
9,228,207 B2 1/2016 Liu et al.
9,234,213 B2 1/2016 Wu
9,243,038 B2 1/2016 Liu et al.
9,267,127 B2 2/2016 Liu et al.
9,322,006 B2 4/2016 Liu et al.
9,322,037 B2 4/2016 Liu et al.
9,340,799 B2 5/2016 Liu et al.
9,340,800 B2 5/2016 Liu et al.
9,359,599 B2 6/2016 Liu et al.
9,388,430 B2 7/2016 Liu et al.
9,394,537 B2 7/2016 Liu et al.
9,434,774 B2 9/2016 Liu et al.
9,458,484 B2 10/2016 Ma et al.
9,512,446 B1 12/2016 Joung et al.
9,526,724 B2 12/2016 Oshlack et al.
9,526,784 B2 12/2016 Liu et al.
9,534,210 B2 1/2017 Park et al.
9,580,698 B1 2/2017 Xu et al.
9,610,322 B2 4/2017 Liu et al.
9,637,739 B2 5/2017 Siksnys et al.
9,663,770 B2 5/2017 Rogers et al.
9,695,446 B2 7/2017 Mangeot et al.
9,737,604 B2 8/2017 Liu et al.
9,816,093 B1 11/2017 Donohoue et al.
9,840,690 B2 12/2017 Karli et al.
9,840,699 B2 12/2017 Liu et al.
9,873,907 B2 1/2018 Zeiner et al.
9,879,270 B2 1/2018 Hittinger et al.
9,938,288 B1 4/2018 Kishi et al.
9,944,933 B2 4/2018 Storici et al.
9,982,279 B1 5/2018 Gill et al.
9,999,671 B2 6/2018 Liu et al.
10,059,940 B2 8/2018 Zhong
10,077,453 B2 9/2018 Liu et al.
10,113,163 B2 10/2018 Liu et al.
10,167,457 B2 1/2019 Liu et al.
10,227,581 B2 3/2019 Liu et al.
10,323,236 B2 6/2019 Liu et al.
10,465,176 B2 11/2019 Liu et al.
10,508,298 B2 12/2019 Liu et al.
10,597,679 B2 3/2020 Liu et al.
10,612,011 B2 4/2020 Liu et al.
10,682,410 B2 6/2020 Liu et al.
10,704,062 B2 7/2020 Liu et al.
10,745,677 B2 8/2020 Maianti et al.
10,858,639 B2 12/2020 Liu et al.
10,912,833 B2 2/2021 Liu et al.
10,930,367 B2 2/2021 Zhang et al.
10,947,530 B2 3/2021 Liu et al.
10,954,548 B2 3/2021 Liu et al.
11,046,948 B2 6/2021 Liu et al.
11,053,481 B2 7/2021 Liu et al.
11,124,782 B2 9/2021 Liu et al.
11,214,780 B2 1/2022 Liu et al.
11,268,082 B2 3/2022 Liu et al.
11,299,755 B2 4/2022 Liu et al.
11,306,324 B2 4/2022 Liu et al.
11,319,532 B2 5/2022 Liu et al.
11,447,770 B1 9/2022 Liu et al.
11,542,496 B2 1/2023 Liu et al.
11,542,509 B2 1/2023 Maianti et al.
11,560,566 B2 1/2023 Liu et al.
11,578,343 B2 2/2023 Liu et al.
11,643,652 B2 5/2023 Liu et al.
11,661,590 B2 5/2023 Liu et al.
11,702,651 B2 7/2023 Liu et al.
11,732,274 B2 8/2023 Liu et al.
11,795,443 B2 10/2023 Liu et al.
11,795,452 B2 10/2023 Liu et al.
11,820,969 B2 11/2023 Maianti et al.
11,898,179 B2 2/2024 Maianti et al.
11,912,985 B2 2/2024 Liu et al.
11,920,181 B2 3/2024 Liu et al.
11,932,884 B2 3/2024 Liu et al.
11,999,947 B2 6/2024 Liu et al.
12,006,520 B2 6/2024 Liu et al.
12,031,126 B2 7/2024 Liu et al.
12,043,852 B2 7/2024 Liu et al.
12,084,663 B2 9/2024 Maianti et al.
2003/0082575 A1 5/2003 Schultz et al.
2003/0087817 A1 5/2003 Cox et al.
2003/0096337 A1 5/2003 Hillman et al.
2003/0108885 A1 6/2003 Schultz et al.
2003/0119764 A1 6/2003 Loeb et al.
2003/0167533 A1 9/2003 Yadav et al.
2003/0203480 A1 10/2003 Kovesdi et al.
2004/0003420 A1 1/2004 Kuhn et al.
2004/0115184 A1 6/2004 Smith et al.
2004/0156861 A1 8/2004 Figdor et al.
2004/0197892 A1 10/2004 Moore et al.
2004/0203109 A1 10/2004 Lal et al.
2005/0136429 A1 6/2005 Guarente et al.
2005/0222030 A1 10/2005 Allison
2005/0260626 A1 11/2005 Lorens et al.
2006/0088864 A1 4/2006 Smolke et al.
2006/0104984 A1 5/2006 Littlefield et al.
2006/0246568 A1 11/2006 Honjo et al.
2007/0015238 A1 1/2007 Snyder et al.
2007/0049533 A1 3/2007 Liu et al.
2007/0264692 A1 * 11/2007 Liu ........................ C07H 21/04
435/69.7
2007/0269817 A1 11/2007 Shapero
2008/0008697 A1 1/2008 Mintier et al.
2008/0051317 A1 2/2008 Church et al.
2008/0124725 A1 5/2008 Barrangou et al.
2008/0182254 A1 7/2008 Hall et al.
2008/0220502 A1 9/2008 Schellenberger et al.
2008/0241917 A1 10/2008 Akita et al.
2008/0268516 A1 10/2008 Perreault et al.
2009/0111119 A1 4/2009 Doyon et al.
2009/0130718 A1 5/2009 Short
2009/0215878 A1 8/2009 Tan et al.

(56) References Cited

U.S. PATENT DOCUMENTS

2009/0234109 A1 9/2009 Han et al.
2010/0076057 A1 3/2010 Sontheimer et al.
2010/0093617 A1 4/2010 Barrangou et al.
2010/0104690 A1 4/2010 Barrangou et al.
2010/0273857 A1 10/2010 Thakker et al.
2010/0305197 A1 12/2010 Che
2010/0316643 A1 12/2010 Eckert et al.
2011/0016540 A1 1/2011 Weinstein et al.
2011/0059160 A1 3/2011 Essner et al.
2011/0059502 A1 3/2011 Chalasani
2011/0104787 A1 5/2011 Church et al.
2011/0177495 A1 7/2011 Liu et al.
2011/0189775 A1 8/2011 Ainley et al.
2011/0189776 A1 8/2011 Terns et al.
2011/0217739 A1 9/2011 Terns et al.
2011/0301073 A1 12/2011 Gregory et al.
2012/0129759 A1 5/2012 Liu et al.
2012/0141523 A1 6/2012 Castado et al.
2012/0244601 A1 9/2012 Bertozzi et al.
2012/0270273 A1 10/2012 Zhang et al.
2012/0322861 A1 12/2012 Byrne et al.
2013/0022980 A1 1/2013 Nelson et al.
2013/0059931 A1 3/2013 Petersen-Mahrt et al.
2013/0108657 A1 5/2013 Yee et al.
2013/0117869 A1 5/2013 Duchateau et al.
2013/0130248 A1 5/2013 Haurwitz et al.
2013/0158245 A1 6/2013 Russell et al.
2013/0165389 A1 6/2013 Schellenberger et al.
2013/0212725 A1 8/2013 Kuhn et al.
2013/0309720 A1 11/2013 Schultz et al.
2013/0344117 A1 12/2013 Mirosevich et al.
2013/0345064 A1 12/2013 Liu et al.
2014/0004280 A1 1/2014 Loomis
2014/0005269 A1 1/2014 Ngwuluka et al.
2014/0017214 A1 1/2014 Cost
2014/0018404 A1 1/2014 Chen et al.
2014/0044793 A1 2/2014 Goll et al.
2014/0065711 A1 3/2014 Liu et al.
2014/0068797 A1 3/2014 Doudna et al.
2014/0127752 A1 5/2014 Zhou et al.
2014/0128449 A1 5/2014 Liu et al.
2014/0141094 A1 5/2014 Smyth et al.
2014/0141487 A1 5/2014 Feldman et al.
2014/0179770 A1 6/2014 Zhang et al.
2014/0186843 A1 7/2014 Zhang et al.
2014/0186919 A1 7/2014 Zhang et al.
2014/0186958 A1 7/2014 Zhang et al.
2014/0201858 A1 7/2014 Ostertag et al.
2014/0234289 A1 8/2014 Liu et al.
2014/0248702 A1 9/2014 Zhang et al.
2014/0273037 A1 9/2014 Wu
2014/0273226 A1 9/2014 Wu
2014/0273230 A1 9/2014 Chen et al.
2014/0273234 A1 9/2014 Zhang et al.
2014/0283156 A1 9/2014 Zador et al.
2014/0295556 A1 10/2014 Joung et al.
2014/0295557 A1 10/2014 Joung et al.
2014/0342456 A1 11/2014 Mali et al.
2014/0342457 A1 11/2014 Mali et al.
2014/0342458 A1 11/2014 Mali et al.
2014/0349400 A1 11/2014 Jakimo et al.
2014/0356867 A1 12/2014 Peter et al.
2014/0356956 A1 12/2014 Church et al.
2014/0356958 A1 12/2014 Mali et al.
2014/0356959 A1 12/2014 Church et al.
2014/0357523 A1 12/2014 Zeiner et al.
2014/0377868 A1 12/2014 Joung et al.
2015/0010526 A1 1/2015 Liu et al.
2015/0031089 A1 1/2015 Lindstrom
2015/0031132 A1 1/2015 Church et al.
2015/0031133 A1 1/2015 Church et al.
2015/0044191 A1 2/2015 Liu et al.
2015/0044192 A1 2/2015 Liu et al.
2015/0044772 A1 2/2015 Zhao
2015/0050699 A1 2/2015 Siksnys et al.
2015/0056177 A1 2/2015 Liu et al.
2015/0056629 A1 2/2015 Guthrie-Honea
2015/0064138 A1 3/2015 Lu et al.
2015/0064789 A1 3/2015 Paschon et al.
2015/0071898 A1 3/2015 Liu et al.
2015/0071899 A1 3/2015 Liu et al.
2015/0071900 A1 3/2015 Liu et al.
2015/0071901 A1 3/2015 Liu et al.
2015/0071902 A1 3/2015 Liu et al.
2015/0071903 A1 3/2015 Liu et al.
2015/0071906 A1 3/2015 Liu et al.
2015/0079680 A1 3/2015 Bradley et al.
2015/0079681 A1 3/2015 Zhang
2015/0098954 A1 4/2015 Hyde et al.
2015/0118216 A1 4/2015 Liu et al.
2015/0128300 A1 5/2015 Warming et al.
2015/0132269 A1 5/2015 Orkin et al.
2015/0140664 A1 5/2015 Byrne et al.
2015/0159172 A1 6/2015 Miller et al.
2015/0165054 A1 6/2015 Liu et al.
2015/0166980 A1 6/2015 Liu et al.
2015/0166981 A1 6/2015 Liu et al.
2015/0166982 A1 6/2015 Liu et al.
2015/0166983 A1 6/2015 Liu et al.
2015/0166984 A1 6/2015 Liu et al.
2015/0166985 A1 6/2015 Liu et al.
2015/0191744 A1 7/2015 Wolfe et al.
2015/0197759 A1 7/2015 Xu et al.
2015/0211058 A1 7/2015 Carstens
2015/0218573 A1 8/2015 Loque et al.
2015/0225773 A1 8/2015 Farmer et al.
2015/0241440 A1 8/2015 Fasan et al.
2015/0252358 A1 9/2015 Maeder et al.
2015/0275202 A1 10/2015 Liu et al.
2015/0291965 A1 10/2015 Zhang et al.
2015/0307889 A1 10/2015 Petolino et al.
2015/0315252 A1 11/2015 Haugwitz et al.
2015/0344549 A1 12/2015 Muir et al.
2016/0015682 A2 1/2016 Cawthorne et al.
2016/0017393 A1 1/2016 Jacobson et al.
2016/0017396 A1 1/2016 Cann et al.
2016/0032292 A1 2/2016 Storici et al.
2016/0032353 A1 2/2016 Braman et al.
2016/0040155 A1 2/2016 Maizels et al.
2016/0046952 A1 2/2016 Hittinger et al.
2016/0046961 A1 2/2016 Jinek et al.
2016/0046962 A1 2/2016 May et al.
2016/0053272 A1 2/2016 Wurtzel et al.
2016/0053304 A1 2/2016 Wurtzel et al.
2016/0074535 A1 3/2016 Ranganathan et al.
2016/0076093 A1 3/2016 Shendure et al.
2016/0090603 A1 3/2016 Carnes et al.
2016/0090622 A1 3/2016 Liu et al.
2016/0115488 A1 4/2016 Zhang et al.
2016/0138046 A1 5/2016 Wu
2016/0153003 A1 6/2016 Joung et al.
2016/0186214 A1 6/2016 Brouns et al.
2016/0200779 A1 7/2016 Liu et al.
2016/0201040 A1 7/2016 Liu et al.
2016/0201089 A1 7/2016 Gersbach et al.
2016/0206566 A1 7/2016 Lu et al.
2016/0208243 A1 7/2016 Zhang et al.
2016/0208288 A1 7/2016 Liu et al.
2016/0215275 A1 7/2016 Zhong
2016/0215276 A1 7/2016 Liu et al.
2016/0215300 A1 7/2016 May et al.
2016/0244784 A1 8/2016 Jacobson et al.
2016/0244829 A1 8/2016 Bang et al.
2016/0264934 A1 9/2016 Giallourakis et al.
2016/0272593 A1 9/2016 Ritter et al.
2016/0272965 A1 9/2016 Zhang et al.
2016/0281072 A1 9/2016 Zhang
2016/0298136 A1 10/2016 Chen et al.
2016/0304846 A1 10/2016 Liu et al.
2016/0304855 A1 10/2016 Stark et al.
2016/0312304 A1 10/2016 Sorrentino et al.
2016/0319262 A1 11/2016 Doudna et al.
2016/0333389 A1 11/2016 Liu et al.
2016/0340622 A1 11/2016 Abdou

(56) References Cited

U.S. PATENT DOCUMENTS

2016/0340661 A1 11/2016 Cong et al.
2016/0340662 A1 11/2016 Zhang et al.
2016/0345578 A1 12/2016 Barrangou et al.
2016/0346360 A1 12/2016 Quake et al.
2016/0346361 A1 12/2016 Quake et al.
2016/0346362 A1 12/2016 Quake et al.
2016/0348074 A1 12/2016 Quake et al.
2016/0348096 A1 12/2016 Liu et al.
2016/0350476 A1 12/2016 Quake et al.
2016/0355796 A1 12/2016 Davidson et al.
2016/0369262 A1 12/2016 Reik et al.
2017/0009224 A1 1/2017 Liu et al.
2017/0009242 A1 1/2017 Mckinley et al.
2017/0014449 A1 1/2017 Bangera et al.
2017/0020922 A1 1/2017 Wagner et al.
2017/0022251 A1 1/2017 Rammensee et al.
2017/0037432 A1 2/2017 Donohoue et al.
2017/0044520 A1 2/2017 Liu et al.
2017/0044592 A1 2/2017 Peter et al.
2017/0053729 A1 2/2017 Kotani et al.
2017/0058271 A1 3/2017 Joung et al.
2017/0058272 A1 3/2017 Carter et al.
2017/0058298 A1 3/2017 Kennedy et al.
2017/0073663 A1 3/2017 Wang et al.
2017/0073670 A1 3/2017 Nishida et al.
2017/0087224 A1 3/2017 Quake
2017/0087225 A1 3/2017 Quake
2017/0088587 A1 3/2017 Quake
2017/0088828 A1 3/2017 Quake
2017/0107536 A1 4/2017 Zhang et al.
2017/0107560 A1 4/2017 Peter et al.
2017/0114367 A1 4/2017 Hu et al.
2017/0121693 A1 5/2017 Liu et al.
2017/0145394 A1 5/2017 Yeo et al.
2017/0145405 A1 5/2017 Tang et al.
2017/0145438 A1 5/2017 Kantor
2017/0152528 A1 6/2017 Zhang
2017/0152787 A1 6/2017 Kubo et al.
2017/0159033 A1 6/2017 Kamtekar et al.
2017/0166928 A1 6/2017 Vyas et al.
2017/0175104 A1 6/2017 Doudna et al.
2017/0175142 A1 6/2017 Zhang et al.
2017/0191047 A1 7/2017 Terns et al.
2017/0191078 A1 7/2017 Zhang et al.
2017/0198269 A1 7/2017 Zhang et al.
2017/0198277 A1 7/2017 Kmiec et al.
2017/0198302 A1 7/2017 Feng et al.
2017/0211061 A1 7/2017 Weiss et al.
2017/0224843 A1 8/2017 Deglon et al.
2017/0226522 A1 8/2017 Hu et al.
2017/0233703 A1 8/2017 Xie et al.
2017/0233708 A1 8/2017 Liu et al.
2017/0233756 A1 8/2017 Begemann et al.
2017/0247671 A1 8/2017 Yung et al.
2017/0247703 A1 8/2017 Sloan et al.
2017/0268022 A1 9/2017 Liu et al.
2017/0283797 A1 10/2017 Robb et al.
2017/0314016 A1 11/2017 Kim et al.
2017/0362635 A1 12/2017 Chamberlain et al.
2018/0064077 A1 3/2018 Dunham et al.
2018/0066258 A1 3/2018 Powell
2018/0068062 A1 3/2018 Zhang et al.
2018/0073012 A1 3/2018 Liu et al.
2018/0100147 A1 4/2018 Yates et al.
2018/0105867 A1 4/2018 Xiao et al.
2018/0119118 A1 5/2018 Lu et al.
2018/0127780 A1 5/2018 Liu et al.
2018/0155708 A1 6/2018 Church et al.
2018/0155720 A1 6/2018 Donohoue et al.
2018/0163213 A1 6/2018 Aneja et al.
2018/0170984 A1 6/2018 Harris et al.
2018/0179503 A1 6/2018 Maianti et al.
2018/0179547 A1 6/2018 Zhang et al.
2018/0201921 A1 7/2018 Malcolm
2018/0230464 A1 8/2018 Zhong
2018/0230471 A1 8/2018 Storici et al.
2018/0236081 A1 8/2018 Liu et al.
2018/0237787 A1 8/2018 Maianti et al.
2018/0245066 A1 8/2018 Yao et al.
2018/0265864 A1 9/2018 Li et al.
2018/0273939 A1 9/2018 Yu et al.
2018/0282722 A1 10/2018 Jakimo et al.
2018/0305688 A1 10/2018 Zhong
2018/0305704 A1 10/2018 Zhang
2018/0312825 A1 11/2018 Liu et al.
2018/0312828 A1 11/2018 Liu et al.
2018/0312835 A1 11/2018 Yao et al.
2018/0327756 A1 11/2018 Zhang et al.
2019/0093099 A1 3/2019 Liu et al.
2019/0185883 A1 6/2019 Liu et al.
2019/0225955 A1 7/2019 Liu et al.
2019/0233847 A1 8/2019 Savage et al.
2019/0241633 A1 8/2019 Fotin-Mleczek et al.
2019/0264202 A1 8/2019 Church et al.
2019/0322992 A1 10/2019 Liu et al.
2019/0352632 A1 11/2019 Liu et al.
2019/0367891 A1 12/2019 Liu et al.
2020/0010818 A1 1/2020 Liu et al.
2020/0010835 A1 1/2020 Maianti et al.
2020/0063127 A1 2/2020 Lu et al.
2020/0172931 A1 6/2020 Liu et al.
2020/0181619 A1 6/2020 Tang et al.
2020/0190493 A1 6/2020 Liu et al.
2020/0255868 A1 8/2020 Liu et al.
2020/0277587 A1 9/2020 Liu et al.
2020/0323984 A1 10/2020 Liu et al.
2020/0399619 A1 12/2020 Maianti et al.
2020/0399626 A1 12/2020 Liu et al.
2021/0054416 A1 2/2021 Liu et al.
2021/0115428 A1 4/2021 Maianti et al.
2021/0196809 A1 7/2021 Maianti et al.
2021/0198330 A1 7/2021 Liu et al.
2021/0214698 A1 7/2021 Liu et al.
2021/0230577 A1 7/2021 Liu et al.
2021/0254127 A1 8/2021 Liu et al.
2021/0315994 A1 10/2021 Liu et al.
2021/0317440 A1 10/2021 Liu et al.
2022/0033785 A1 2/2022 Liu et al.
2022/0119785 A1 4/2022 Liu et al.
2022/0170013 A1 6/2022 Liu et al.
2022/0177877 A1 6/2022 Church et al.
2022/0204975 A1 6/2022 Liu et al.
2022/0213507 A1 7/2022 Liu et al.
2022/0220462 A1 7/2022 Liu et al.
2022/0238182 A1 7/2022 Shen et al.
2022/0249697 A1 8/2022 Liu et al.
2022/0282275 A1 9/2022 Liu et al.
2022/0290115 A1 9/2022 Liu et al.
2022/0307001 A1 9/2022 Liu et al.
2022/0307003 A1 9/2022 Liu et al.
2022/0315906 A1 10/2022 Liu et al.
2022/0356469 A1 11/2022 Liu et al.
2022/0380740 A1 12/2022 Liu et al.
2022/0389395 A1 12/2022 Liu et al.
2023/0002745 A1 1/2023 Liu et al.
2023/0021641 A1 1/2023 Liu et al.
2023/0056852 A1 2/2023 Liu et al.
2023/0058176 A1 2/2023 Liu et al.
2023/0078265 A1 3/2023 Liu et al.
2023/0086199 A1 3/2023 Liu et al.
2023/0090221 A1 3/2023 Liu et al.
2023/0108687 A1 4/2023 Liu et al.
2023/0123669 A1 4/2023 Liu et al.
2023/0127008 A1 4/2023 Liu et al.
2023/0159913 A1 5/2023 Liu et al.
2023/0193295 A1 6/2023 Maianti et al.
2023/0220374 A1 7/2023 Liu et al.
2023/0272425 A1 8/2023 Liu et al.
2023/0332144 A1 10/2023 Liu et al.
2023/0340465 A1 10/2023 Liu et al.
2023/0340466 A1 10/2023 Liu et al.
2023/0340467 A1 10/2023 Liu et al.
2023/0348883 A1 11/2023 Liu et al.
2023/0357766 A1 11/2023 Liu et al.

(56) References Cited

U.S. PATENT DOCUMENTS

| | | | |
|---|---|---|---|
| 2023/0383289 A1 | 11/2023 | Liu et al. | |
| 2024/0035017 A1 | 2/2024 | Liu et al. | |
| 2024/0076652 A1 | 3/2024 | Liu et al. | |
| 2024/0110166 A1 | 4/2024 | Maianti et al. | |
| 2024/0124866 A1 | 4/2024 | Liu et al. | |
| 2024/0173430 A1 | 5/2024 | Liu et al. | |
| 2024/0229077 A1 | 7/2024 | Liu et al. | |

FOREIGN PATENT DOCUMENTS

| | | | |
|---|---|---|---|
| AU | 2015252023 | A1 | 11/2015 |
| AU | 2015101792 | A4 | 1/2016 |
| AU | 2012354062 | B2 | 9/2017 |
| BR | 112015013786 | A2 | 7/2017 |
| CA | 2480696 | A1 | 10/2003 |
| CA | 2894668 | A1 | 6/2014 |
| CA | 2894681 | A1 | 6/2014 |
| CA | 2894684 | A1 | 6/2014 |
| CA | 2852593 | A1 | 11/2015 |
| CN | 1069962 | A | 3/1993 |
| CN | 101460619 | A | 6/2009 |
| CN | 101873862 | A | 10/2010 |
| CN | 102057039 | A | 5/2011 |
| CN | 102892777 | A | 1/2013 |
| CN | 103224947 | A | 7/2013 |
| CN | 103233028 | A | 8/2013 |
| CN | 103388006 | A | 11/2013 |
| CN | 103614415 | A | 3/2014 |
| CN | 103642836 | A | 3/2014 |
| CN | 103668472 | A | 3/2014 |
| CN | 103820441 | A | 5/2014 |
| CN | 103820454 | A | 5/2014 |
| CN | 103911376 | A | 7/2014 |
| CN | 103923911 | A | 7/2014 |
| CN | 103088008 | A | 8/2014 |
| CN | 103981211 | A | 8/2014 |
| CN | 103981212 | A | 8/2014 |
| CN | 104004778 | A | 8/2014 |
| CN | 104004782 | A | 8/2014 |
| CN | 104017821 | A | 9/2014 |
| CN | 104109687 | A | 10/2014 |
| CN | 104178461 | A | 12/2014 |
| CN | 104342457 | A | 2/2015 |
| CN | 104404036 | A | 3/2015 |
| CN | 104450774 | A | 3/2015 |
| CN | 104480144 | A | 4/2015 |
| CN | 104498493 | A | 4/2015 |
| CN | 104504304 | A | 4/2015 |
| CN | 104531704 | A | 4/2015 |
| CN | 104531705 | A | 4/2015 |
| CN | 104560864 | A | 4/2015 |
| CN | 104561095 | A | 4/2015 |
| CN | 104593418 | A | 5/2015 |
| CN | 104593422 | A | 5/2015 |
| CN | 104611370 | A | 5/2015 |
| CN | 104651392 | A | 5/2015 |
| CN | 104651398 | A | 5/2015 |
| CN | 104651399 | A | 5/2015 |
| CN | 104651401 | A | 5/2015 |
| CN | 104673816 | A | 6/2015 |
| CN | 104725626 | A | 6/2015 |
| CN | 104726449 | A | 6/2015 |
| CN | 104726494 | A | 6/2015 |
| CN | 104745626 | A | 7/2015 |
| CN | 104762321 | A | 7/2015 |
| CN | 104805078 | A | 7/2015 |
| CN | 104805099 | A | 7/2015 |
| CN | 104805118 | A | 7/2015 |
| CN | 104846010 | A | 8/2015 |
| CN | 104894068 | A | 9/2015 |
| CN | 104894075 | A | 9/2015 |
| CN | 104928321 | A | 9/2015 |
| CN | 105039339 | A | 11/2015 |
| CN | 105039399 | A | 11/2015 |
| CN | 105063061 | A | 11/2015 |
| CN | 105087620 | A | 11/2015 |
| CN | 105112422 | A | 12/2015 |
| CN | 105112445 | A | 12/2015 |
| CN | 105112519 | A | 12/2015 |
| CN | 105121648 | A | 12/2015 |
| CN | 105132427 | A | 12/2015 |
| CN | 105132451 | A | 12/2015 |
| CN | 105177038 | A | 12/2015 |
| CN | 105177126 | A | 12/2015 |
| CN | 105210981 | A | 1/2016 |
| CN | 105219799 | A | 1/2016 |
| CN | 105238806 | A | 1/2016 |
| CN | 105255937 | A | 1/2016 |
| CN | 105274144 | A | 1/2016 |
| CN | 105296518 | A | 2/2016 |
| CN | 105296537 | A | 2/2016 |
| CN | 105316324 | A | 2/2016 |
| CN | 105316327 | A | 2/2016 |
| CN | 105316337 | A | 2/2016 |
| CN | 105331607 | A | 2/2016 |
| CN | 105331608 | A | 2/2016 |
| CN | 105331609 | A | 2/2016 |
| CN | 105331627 | A | 2/2016 |
| CN | 105400773 | A | 3/2016 |
| CN | 105400779 | A | 3/2016 |
| CN | 105400810 | A | 3/2016 |
| CN | 105441451 | A | 3/2016 |
| CN | 105462968 | A | 4/2016 |
| CN | 105463003 | A | 4/2016 |
| CN | 105463027 | A | 4/2016 |
| CN | 105492608 | A | 4/2016 |
| CN | 105492609 | A | 4/2016 |
| CN | 105505976 | A | 4/2016 |
| CN | 105505979 | A | 4/2016 |
| CN | 105518134 | A | 4/2016 |
| CN | 105518135 | A | 4/2016 |
| CN | 105518137 | A | 4/2016 |
| CN | 105518138 | A | 4/2016 |
| CN | 105518139 | A | 4/2016 |
| CN | 105518140 | A | 4/2016 |
| CN | 105543228 | A | 5/2016 |
| CN | 105543266 | A | 5/2016 |
| CN | 105543270 | A | 5/2016 |
| CN | 105567688 | A | 5/2016 |
| CN | 105567689 | A | 5/2016 |
| CN | 105567734 | A | 5/2016 |
| CN | 105567735 | A | 5/2016 |
| CN | 105567738 | A | 5/2016 |
| CN | 105593367 | A | 5/2016 |
| CN | 105594664 | A | 5/2016 |
| CN | 105602987 | A | 5/2016 |
| CN | 105624146 | A | 6/2016 |
| CN | 105624187 | A | 6/2016 |
| CN | 105646719 | A | 6/2016 |
| CN | 105647922 | A | 6/2016 |
| CN | 105647962 | A | 6/2016 |
| CN | 105647968 | A | 6/2016 |
| CN | 105647969 | A | 6/2016 |
| CN | 105671070 | A | 6/2016 |
| CN | 105671083 | A | 6/2016 |
| CN | 105695485 | A | 6/2016 |
| CN | 105779448 | A | 7/2016 |
| CN | 105779449 | A | 7/2016 |
| CN | 105802980 | A | 7/2016 |
| CN | 105821039 | A | 8/2016 |
| CN | 105821040 | A | 8/2016 |
| CN | 105821049 | A | 8/2016 |
| CN | 105821072 | A | 8/2016 |
| CN | 105821075 | A | 8/2016 |
| CN | 105821116 | A | 8/2016 |
| CN | 105838733 | A | 8/2016 |
| CN | 105861547 | A | 8/2016 |
| CN | 105861552 | A | 8/2016 |
| CN | 105861554 | A | 8/2016 |
| CN | 105886498 | A | 8/2016 |
| CN | 105886534 | A | 8/2016 |
| CN | 105886616 | A | 8/2016 |
| CN | 105907758 | A | 8/2016 |
| CN | 105907785 | A | 8/2016 |

(56) References Cited

FOREIGN PATENT DOCUMENTS

| | | | |
|---|---|---|---|
| CN | 105925608 | A | 9/2016 |
| CN | 105934516 | A | 9/2016 |
| CN | 105950560 | A | 9/2016 |
| CN | 105950626 | A | 9/2016 |
| CN | 105950633 | A | 9/2016 |
| CN | 105950639 | A | 9/2016 |
| CN | 105985985 | A | 10/2016 |
| CN | 106011104 | A | 10/2016 |
| CN | 106011150 | A | 10/2016 |
| CN | 106011167 | A | 10/2016 |
| CN | 106011171 | A | 10/2016 |
| CN | 106032540 | A | 10/2016 |
| CN | 106047803 | A | 10/2016 |
| CN | 106047877 | A | 10/2016 |
| CN | 106047930 | A | 10/2016 |
| CN | 106086008 | A | 11/2016 |
| CN | 106086028 | A | 11/2016 |
| CN | 106086061 | A | 11/2016 |
| CN | 106086062 | A | 11/2016 |
| CN | 106103475 | A | 11/2016 |
| CN | 106109417 | A | 11/2016 |
| CN | 106119275 | A | 11/2016 |
| CN | 106119283 | A | 11/2016 |
| CN | 106148286 | A | 11/2016 |
| CN | 106148370 | A | 11/2016 |
| CN | 106148416 | A | 11/2016 |
| CN | 106167525 | A | 11/2016 |
| CN | 106167808 | A | 11/2016 |
| CN | 106167810 | A | 11/2016 |
| CN | 106167821 | A | 11/2016 |
| CN | 106172238 | A | 12/2016 |
| CN | 106190903 | A | 12/2016 |
| CN | 106191057 | A | 12/2016 |
| CN | 106191061 | A | 12/2016 |
| CN | 106191062 | A | 12/2016 |
| CN | 106191064 | A | 12/2016 |
| CN | 106191071 | A | 12/2016 |
| CN | 106191099 | A | 12/2016 |
| CN | 106191107 | A | 12/2016 |
| CN | 106191113 | A | 12/2016 |
| CN | 106191114 | A | 12/2016 |
| CN | 106191116 | A | 12/2016 |
| CN | 106191124 | A | 12/2016 |
| CN | 106222177 | A | 12/2016 |
| CN | 106222193 | A | 12/2016 |
| CN | 106222203 | A | 12/2016 |
| CN | 106232823 | A | 12/2016 |
| CN | 106244555 | A | 12/2016 |
| CN | 106244557 | A | 12/2016 |
| CN | 106244591 | A | 12/2016 |
| CN | 106244609 | A | 12/2016 |
| CN | 106282241 | A | 1/2017 |
| CN | 106318934 | A | 1/2017 |
| CN | 106318973 | A | 1/2017 |
| CN | 106350540 | A | 1/2017 |
| CN | 106367435 | A | 2/2017 |
| CN | 106399306 | A | 2/2017 |
| CN | 106399311 | A | 2/2017 |
| CN | 106399360 | A | 2/2017 |
| CN | 106399367 | A | 2/2017 |
| CN | 106399375 | A | 2/2017 |
| CN | 106399377 | A | 2/2017 |
| CN | 106434651 | A | 2/2017 |
| CN | 106434663 | A | 2/2017 |
| CN | 106434688 | A | 2/2017 |
| CN | 106434737 | A | 2/2017 |
| CN | 106434748 | A | 2/2017 |
| CN | 106434752 | A | 2/2017 |
| CN | 106434782 | A | 2/2017 |
| CN | 106446600 | A | 2/2017 |
| CN | 106479985 | A | 3/2017 |
| CN | 106480027 | A | 3/2017 |
| CN | 106480036 | A | 3/2017 |
| CN | 106480067 | A | 3/2017 |
| CN | 106480080 | A | 3/2017 |
| CN | 106480083 | A | 3/2017 |
| CN | 106480097 | A | 3/2017 |
| CN | 106544351 | A | 3/2017 |
| CN | 106544353 | A | 3/2017 |
| CN | 106544357 | A | 3/2017 |
| CN | 106554969 | A | 4/2017 |
| CN | 106566838 | A | 4/2017 |
| CN | 106701763 | A | 5/2017 |
| CN | 106701808 | A | 5/2017 |
| CN | 106701818 | A | 5/2017 |
| CN | 106701823 | A | 5/2017 |
| CN | 106701830 | A | 5/2017 |
| CN | 106754912 | A | 5/2017 |
| CN | 106755026 | A | 5/2017 |
| CN | 106755077 | A | 5/2017 |
| CN | 106755088 | A | 5/2017 |
| CN | 106755091 | A | 5/2017 |
| CN | 106755097 | A | 5/2017 |
| CN | 106755424 | A | 5/2017 |
| CN | 106801056 | A | 6/2017 |
| CN | 106834323 | A | 6/2017 |
| CN | 106834341 | A | 6/2017 |
| CN | 106834347 | A | 6/2017 |
| CN | 106845151 | A | 6/2017 |
| CN | 106868008 | A | 6/2017 |
| CN | 106868031 | A | 6/2017 |
| CN | 106906240 | A | 6/2017 |
| CN | 106906242 | A | 6/2017 |
| CN | 106916820 | A | 7/2017 |
| CN | 106916852 | A | 7/2017 |
| CN | 106939303 | A | 7/2017 |
| CN | 106947750 | A | 7/2017 |
| CN | 106947780 | A | 7/2017 |
| CN | 106957830 | A | 7/2017 |
| CN | 106957831 | A | 7/2017 |
| CN | 106957844 | A | 7/2017 |
| CN | 106957855 | A | 7/2017 |
| CN | 106957858 | A | 7/2017 |
| CN | 106967697 | A | 7/2017 |
| CN | 106967726 | A | 7/2017 |
| CN | 106978428 | A | 7/2017 |
| CN | 106987570 | A | 7/2017 |
| CN | 106987757 | A | 7/2017 |
| CN | 107012164 | A | 8/2017 |
| CN | 107012174 | A | 8/2017 |
| CN | 107012213 | A | 8/2017 |
| CN | 107012250 | A | 8/2017 |
| CN | 107022562 | A | 8/2017 |
| CN | 107034188 | A | 8/2017 |
| CN | 107034218 | A | 8/2017 |
| CN | 107034229 | A | 8/2017 |
| CN | 107043775 | A | 8/2017 |
| CN | 107043779 | A | 8/2017 |
| CN | 107043787 | A | 8/2017 |
| CN | 107058320 | A | 8/2017 |
| CN | 107058328 | A | 8/2017 |
| CN | 107058358 | A | 8/2017 |
| CN | 107058372 | A | 8/2017 |
| CN | 107083392 | A | 8/2017 |
| CN | 107099533 | A | 8/2017 |
| CN | 107099850 | A | 8/2017 |
| CN | 107119053 | A | 9/2017 |
| CN | 107119071 | A | 9/2017 |
| CN | 107129999 | A | 9/2017 |
| CN | 107130000 | A | 9/2017 |
| CN | 107142272 | A | 9/2017 |
| CN | 107142282 | A | 9/2017 |
| CN | 107177591 | A | 9/2017 |
| CN | 107177595 | A | 9/2017 |
| CN | 107177631 | A | 9/2017 |
| CN | 107190006 | A | 9/2017 |
| CN | 107190008 | A | 9/2017 |
| CN | 107217042 | A | 9/2017 |
| CN | 107217075 | A | 9/2017 |
| CN | 107227307 | A | 10/2017 |
| CN | 107227352 | A | 10/2017 |
| CN | 107236737 | A | 10/2017 |
| CN | 107236739 | A | 10/2017 |
| CN | 107236741 | A | 10/2017 |

(56) References Cited

FOREIGN PATENT DOCUMENTS

| | | | |
|---|---|---|---|
| CN | 107245502 | A | 10/2017 |
| CN | 107254485 | A | 10/2017 |
| CN | 107266541 | A | 10/2017 |
| CN | 107267515 | A | 10/2017 |
| CN | 107287245 | A | 10/2017 |
| CN | 107298701 | A | 10/2017 |
| CN | 107299114 | A | 10/2017 |
| CN | 107304435 | A | 10/2017 |
| CN | 107312785 | A | 11/2017 |
| CN | 107312793 | A | 11/2017 |
| CN | 107312795 | A | 11/2017 |
| CN | 107312798 | A | 11/2017 |
| CN | 107326042 | A | 11/2017 |
| CN | 107326046 | A | 11/2017 |
| CN | 107354156 | A | 11/2017 |
| CN | 107354173 | A | 11/2017 |
| CN | 107356793 | A | 11/2017 |
| CN | 107362372 | A | 11/2017 |
| CN | 107365786 | A | 11/2017 |
| CN | 107365804 | A | 11/2017 |
| CN | 107384894 | A | 11/2017 |
| CN | 107384922 | A | 11/2017 |
| CN | 107384926 | A | 11/2017 |
| CN | 107400677 | A | 11/2017 |
| CN | 107418974 | A | 12/2017 |
| CN | 107435051 | A | 12/2017 |
| CN | 107435069 | A | 12/2017 |
| CN | 107446922 | A | 12/2017 |
| CN | 107446923 | A | 12/2017 |
| CN | 107446924 | A | 12/2017 |
| CN | 107446932 | A | 12/2017 |
| CN | 107446951 | A | 12/2017 |
| CN | 107446954 | A | 12/2017 |
| CN | 107460196 | A | 12/2017 |
| CN | 107474129 | A | 12/2017 |
| CN | 107475300 | A | 12/2017 |
| CN | 107488649 | A | 12/2017 |
| CN | 107502608 | A | 12/2017 |
| CN | 107502618 | A | 12/2017 |
| CN | 107513531 | A | 12/2017 |
| CN | 107519492 | A | 12/2017 |
| CN | 107523567 | A | 12/2017 |
| CN | 107523583 | A | 12/2017 |
| CN | 107541525 | A | 1/2018 |
| CN | 107557373 | A | 1/2018 |
| CN | 107557378 | A | 1/2018 |
| CN | 107557381 | A | 1/2018 |
| CN | 107557390 | A | 1/2018 |
| CN | 107557393 | A | 1/2018 |
| CN | 107557394 | A | 1/2018 |
| CN | 107557455 | A | 1/2018 |
| CN | 107574179 | A | 1/2018 |
| CN | 107586777 | A | 1/2018 |
| CN | 107586779 | A | 1/2018 |
| CN | 107604003 | A | 1/2018 |
| CN | 107619829 | A | 1/2018 |
| CN | 107619837 | A | 1/2018 |
| CN | 107630006 | A | 1/2018 |
| CN | 107630041 | A | 1/2018 |
| CN | 107630042 | A | 1/2018 |
| CN | 107630043 | A | 1/2018 |
| CN | 107641631 | A | 1/2018 |
| CN | 107653256 | A | 2/2018 |
| CN | 107686848 | A | 2/2018 |
| CN | 206970581 | U | 2/2018 |
| CN | 107760652 | A | 3/2018 |
| CN | 107760663 | A | 3/2018 |
| CN | 107760684 | A | 3/2018 |
| CN | 107760715 | A | 3/2018 |
| CN | 107784200 | A | 3/2018 |
| CN | 107794272 | A | 3/2018 |
| CN | 107794276 | A | 3/2018 |
| CN | 107815463 | A | 3/2018 |
| CN | 107828738 | A | 3/2018 |
| CN | 107828794 | A | 3/2018 |
| CN | 107828826 | A | 3/2018 |
| CN | 107828874 | A | 3/2018 |
| CN | 107858346 | A | 3/2018 |
| CN | 107858373 | A | 3/2018 |
| CN | 107880132 | A | 4/2018 |
| CN | 107881184 | A | 4/2018 |
| CN | 107893074 | A | 4/2018 |
| CN | 107893075 | A | 4/2018 |
| CN | 107893076 | A | 4/2018 |
| CN | 107893080 | A | 4/2018 |
| CN | 107893086 | A | 4/2018 |
| CN | 107904261 | A | 4/2018 |
| CN | 107937427 | A | 4/2018 |
| CN | 107937432 | A | 4/2018 |
| CN | 107937501 | A | 4/2018 |
| CN | 107974466 | A | 5/2018 |
| CN | 107988229 | A | 5/2018 |
| CN | 107988246 | A | 5/2018 |
| CN | 107988256 | A | 5/2018 |
| CN | 107988268 | A | 5/2018 |
| CN | 108018316 | A | 5/2018 |
| CN | 108034656 | A | 5/2018 |
| CN | 108048466 | A | 5/2018 |
| CN | 108102940 | A | 6/2018 |
| CN | 108103092 | A | 6/2018 |
| CN | 108103098 | A | 6/2018 |
| CN | 108103586 | A | 6/2018 |
| CN | 108148835 | A | 6/2018 |
| CN | 108148837 | A | 6/2018 |
| CN | 108148873 | A | 6/2018 |
| CN | 108192956 | A | 6/2018 |
| CN | 108251423 | A | 7/2018 |
| CN | 108251451 | A | 7/2018 |
| CN | 108251452 | A | 7/2018 |
| CN | 108342480 | A | 7/2018 |
| CN | 108359691 | A | 8/2018 |
| CN | 108359712 | A | 8/2018 |
| CN | 108384784 | A | 8/2018 |
| CN | 108396027 | A | 8/2018 |
| CN | 108410877 | A | 8/2018 |
| CN | 108410906 | A | 8/2018 |
| CN | 108410907 | A | 8/2018 |
| CN | 108410911 | A | 8/2018 |
| CN | 108424931 | A | 8/2018 |
| CN | 108441519 | A | 8/2018 |
| CN | 108441520 | A | 8/2018 |
| CN | 108486108 | A | 9/2018 |
| CN | 108486111 | A | 9/2018 |
| CN | 108486145 | A | 9/2018 |
| CN | 108486146 | A | 9/2018 |
| CN | 108486154 | A | 9/2018 |
| CN | 108486159 | A | 9/2018 |
| CN | 108486234 | A | 9/2018 |
| CN | 108504657 | A | 9/2018 |
| CN | 108504685 | A | 9/2018 |
| CN | 108504693 | A | 9/2018 |
| CN | 108513575 | A | 9/2018 |
| CN | 108546712 | A | 9/2018 |
| CN | 108546717 | A | 9/2018 |
| CN | 108546718 | A | 9/2018 |
| CN | 108559730 | A | 9/2018 |
| CN | 108559732 | A | 9/2018 |
| CN | 108559745 | A | 9/2018 |
| CN | 108559760 | A | 9/2018 |
| CN | 108570479 | A | 9/2018 |
| CN | 108588071 | A | 9/2018 |
| CN | 108588123 | A | 9/2018 |
| CN | 108588128 | A | 9/2018 |
| CN | 108588182 | A | 9/2018 |
| CN | 108610399 | A | 10/2018 |
| CN | 108611364 | A | 10/2018 |
| CN | 108624622 | A | 10/2018 |
| CN | 108642053 | A | 10/2018 |
| CN | 108642055 | A | 10/2018 |
| CN | 108642077 | A | 10/2018 |
| CN | 108642078 | A | 10/2018 |
| CN | 108642090 | A | 10/2018 |
| CN | 108690844 | A | 10/2018 |
| CN | 108707604 | A | 10/2018 |

(56) References Cited

FOREIGN PATENT DOCUMENTS

| | | | |
|---|---|---|---|
| CN | 108707620 | A | 10/2018 |
| CN | 108707621 | A | 10/2018 |
| CN | 108707628 | A | 10/2018 |
| CN | 108707629 | A | 10/2018 |
| CN | 108715850 | A | 10/2018 |
| CN | 208034188 | A | 10/2018 |
| CN | 108728476 | A | 11/2018 |
| CN | 108728486 | A | 11/2018 |
| CN | 108753772 | A | 11/2018 |
| CN | 108753783 | A | 11/2018 |
| CN | 108753813 | A | 11/2018 |
| CN | 108753817 | A | 11/2018 |
| CN | 108753832 | A | 11/2018 |
| CN | 108753835 | A | 11/2018 |
| CN | 108753836 | A | 11/2018 |
| CN | 108795902 | A | 11/2018 |
| CN | 108822217 | A | 11/2018 |
| CN | 108823248 | A | 11/2018 |
| CN | 108823249 | A | 11/2018 |
| CN | 108823291 | A | 11/2018 |
| CN | 108841845 | A | 11/2018 |
| CN | 108853133 | A | 11/2018 |
| CN | 108866093 | A | 11/2018 |
| CN | 108893529 | A | 11/2018 |
| CN | 108913664 | A | 11/2018 |
| CN | 108913691 | A | 11/2018 |
| CN | 108913714 | A | 11/2018 |
| CN | 108913717 | A | 11/2018 |
| EP | 0264166 | A1 | 4/1988 |
| EP | 0321201 | B2 | 6/1989 |
| EP | 0519463 | A1 | 12/1992 |
| EP | 1085892 | A2 | 3/2001 |
| EP | 1092770 | A2 | 4/2001 |
| EP | 2604255 | A1 | 6/2013 |
| EP | 2840140 | A1 | 2/2015 |
| EP | 2877490 | A2 | 6/2015 |
| EP | 2966170 | A1 | 1/2016 |
| EP | 3009511 | A2 | 4/2016 |
| EP | 3031921 | A1 | 6/2016 |
| EP | 3045537 | A1 | 7/2016 |
| EP | 3115457 | A | 1/2017 |
| EP | 3115457 | A1 | 1/2017 |
| EP | 3144390 | A1 | 3/2017 |
| EP | 3199632 | A1 | 8/2017 |
| EP | 3216867 | A1 | 9/2017 |
| EP | 3252160 | A1 | 12/2017 |
| EP | 3450553 | B1 | 12/2019 |
| GB | 2528177 | A | 1/2016 |
| GB | 2531454 | A | 4/2016 |
| GB | 2531454 | A1 | 4/2016 |
| GB | 2542653 | A | 3/2017 |
| HK | 1208045 | A1 | 2/2016 |
| JP | 2007-501626 | A | 2/2007 |
| JP | 2008-515405 | A | 5/2008 |
| JP | 2010-033344 | A | 2/2010 |
| JP | 2010-535744 | A | 11/2010 |
| JP | 2010-539929 | A | 12/2010 |
| JP | 2011-081011 | A | 4/2011 |
| JP | 2011-523353 | A | 8/2011 |
| JP | 2012-525146 | A | 10/2012 |
| JP | 2012-210172 | A | 11/2012 |
| JP | 2012-531909 | A | 12/2012 |
| JP | 2015-523856 | A | 8/2015 |
| JP | 2015-532654 | A | 11/2015 |
| JP | 2016-525888 | A | 9/2016 |
| JP | 2016-534132 | A | 11/2016 |
| JP | 2017-500035 | A | 1/2017 |
| JP | 6629734 | B2 | 1/2020 |
| JP | 6633524 | B2 | 1/2020 |
| JP | 6830517 | B2 | 2/2021 |
| JP | 7324523 | B2 | 8/2023 |
| KR | 101584933 | B1 | 1/2016 |
| KR | 2016-0050069 | A | 5/2016 |
| KR | 20160133380 | A | 11/2016 |
| KR | 20170037025 | A | 4/2017 |
| KR | 20170037028 | A | 4/2017 |
| KR | 101748575 | B1 | 6/2017 |
| KR | 2018-0022465 | A | 3/2018 |
| RU | 2016104674 | A | 8/2017 |
| RU | 2634395 | C1 | 10/2017 |
| RU | 2652899 | C1 | 5/2018 |
| RU | 2015128057 | A | 3/2019 |
| RU | 2015128098 | A | 3/2019 |
| RU | 2687451 | C1 | 5/2019 |
| RU | 2019112514 | A | 6/2019 |
| RU | 2019127300 | A | 9/2019 |
| RU | 2701850 | C2 | 10/2019 |
| SG | 10201707569 | Y | 10/2017 |
| SG | 10201710486X | | 1/2018 |
| SG | 10201710487 | | 1/2018 |
| SG | 10201710488 | T | 1/2018 |
| TW | I608100 | B | 12/2017 |
| TW | 2018-29773 | A | 8/2018 |
| WO | WO 1990/002809 | | 3/1990 |
| WO | WO 1990/002809 | A1 | 3/1990 |
| WO | WO 1991/003162 | A1 | 3/1991 |
| WO | WO 1991/016024 | A1 | 10/1991 |
| WO | WO 1991/017271 | A1 | 11/1991 |
| WO | WO 1991/017424 | A1 | 11/1991 |
| WO | WO 1992/006188 | A2 | 4/1992 |
| WO | WO 1992/006200 | A1 | 4/1992 |
| WO | WO 1992/007065 | A1 | 4/1992 |
| WO | WO 1993/015187 | A1 | 8/1993 |
| WO | WO 1993/024641 | A2 | 12/1993 |
| WO | WO 1994/018316 | A2 | 8/1994 |
| WO | WO 1994/026877 | A1 | 11/1994 |
| WO | WO 1996/004403 | A1 | 2/1996 |
| WO | WO 1996/010640 | A1 | 4/1996 |
| WO | WO 1998/032845 | A1 | 7/1998 |
| WO | WO 2001/036452 | A2 | 5/2001 |
| WO | WO 2001/038547 | A2 | 5/2001 |
| WO | WO 2002/059296 | A2 | 8/2002 |
| WO | WO 2002/068676 | A2 | 9/2002 |
| WO | WO 2002/103028 | A2 | 12/2002 |
| WO | WO 2004/007684 | A2 | 1/2004 |
| WO | WO 2005/014791 | A2 | 2/2005 |
| WO | WO 2005/019415 | A2 | 3/2005 |
| WO | WO 2006/002547 | A1 | 1/2006 |
| WO | WO 2006/042112 | A2 | 4/2006 |
| WO | WO 2007/025097 | A2 | 3/2007 |
| WO | WO 2007/037444 | A1 | 4/2007 |
| WO | WO 2007/066923 | A1 | 6/2007 |
| WO | WO 2007/136815 | A2 | 11/2007 |
| WO | WO 2007/143574 | A1 | 12/2007 |
| WO | WO 2008/005529 | A2 | 1/2008 |
| WO | WO 2008/108989 | A2 | 9/2008 |
| WO | WO 2009/002418 | A2 | 12/2008 |
| WO | WO 2009/019317 | A1 | 2/2009 |
| WO | WO 2009/098290 | A1 | 8/2009 |
| WO | WO 2009/134808 | A2 | 11/2009 |
| WO | WO 2010/011961 | A2 | 1/2010 |
| WO | WO 2010/012902 | A1 | 2/2010 |
| WO | WO 2010/028347 | A2 | 3/2010 |
| WO | WO 2010/054108 | A2 | 5/2010 |
| WO | WO 2010/054154 | A2 | 5/2010 |
| WO | WO 2010/068289 | A2 | 6/2010 |
| WO | WO 2010/075424 | A2 | 7/2010 |
| WO | WO 2010/091122 | A1 | 8/2010 |
| WO | WO 2010/102257 | A2 | 9/2010 |
| WO | WO 2010/104749 | A2 | 9/2010 |
| WO | WO 2010/129019 | A2 | 11/2010 |
| WO | WO 2010/129023 | A2 | 11/2010 |
| WO | WO 2010/132092 | A2 | 11/2010 |
| WO | WO 2010/144150 | A2 | 1/2011 |
| WO | WO 2011/002503 | A1 | 1/2011 |
| WO | WO 2011/017293 | A2 | 2/2011 |
| WO | WO 2011/053868 | A1 | 5/2011 |
| WO | WO 2011/053982 | A2 | 5/2011 |
| WO | WO 2011/068810 | A1 | 6/2011 |
| WO | WO 2011/075627 | A1 | 6/2011 |
| WO | WO 2011/091311 | A2 | 7/2011 |
| WO | WO 2011/091396 | A1 | 7/2011 |
| WO | WO 2011/109031 | A1 | 9/2011 |
| WO | WO 2011/143124 | A2 | 11/2011 |

(56) References Cited

FOREIGN PATENT DOCUMENTS

| | | | | |
|---|---|---|---|---|
| WO | WO 2011/147590 | A2 | 12/2011 | |
| WO | WO 2011/159369 | A1 | 12/2011 | |
| WO | WO 2012/054726 | A1 | 4/2012 | |
| WO | WO 2012/061815 | A2 | 5/2012 | |
| WO | WO 2012/065043 | A2 | 5/2012 | |
| WO | WO 2012/088381 | A2 | 6/2012 | |
| WO | WO 2012/125445 | A2 | 9/2012 | |
| WO | WO 2012/138927 | A2 | 10/2012 | |
| WO | WO 2012/149470 | A1 | 11/2012 | |
| WO | WO 2012/158985 | A2 | 11/2012 | |
| WO | WO 2012/158986 | A2 | 11/2012 | |
| WO | WO 2012/164565 | A1 | 12/2012 | |
| WO | WO 2012/170930 | A1 | 12/2012 | |
| WO | WO 2013/012674 | A1 | 1/2013 | |
| WO | WO 2013/013105 | A1 | 1/2013 | |
| WO | WO 2013/013105 | A2 | 1/2013 | |
| WO | WO 2013/039857 | A1 | 3/2013 | |
| WO | WO 2013/039861 | A2 | 3/2013 | |
| WO | WO 2013/040093 | A2 | 3/2013 | |
| WO | WO 2013/045632 | A1 | 4/2013 | |
| WO | WO 2013/047844 | A1 | 4/2013 | |
| WO | WO 2013/066438 | A2 | 5/2013 | |
| WO | WO 2013/086441 | A2 | 6/2013 | |
| WO | WO 2013/086444 | A2 | 6/2013 | |
| WO | WO 2013/098244 | A1 | 7/2013 | |
| WO | WO 2013/119602 | A1 | 8/2013 | |
| WO | WO 2013/120022 | A2 | 8/2013 | |
| WO | WO 2013/122617 | A1 | 8/2013 | |
| WO | WO 2013/126794 | A1 | 8/2013 | |
| WO | WO 2013/130683 | A2 | 9/2013 | |
| WO | WO 2013/130824 | A1 | 9/2013 | |
| WO | WO 2013/141680 | A1 | 9/2013 | |
| WO | WO 2013/142578 | A1 | 9/2013 | |
| WO | WO 2013/142578 | A2 | 9/2013 | |
| WO | WO 2013/152359 | A1 | 10/2013 | |
| WO | WO 2013/160230 | A1 | 10/2013 | |
| WO | WO 2013/166315 | A1 | 11/2013 | |
| WO | WO 2013/169398 | A2 | 11/2013 | |
| WO | WO 2013/169802 | A1 | 11/2013 | |
| WO | WO 2013/176772 | A1 | 11/2013 | |
| WO | WO 2013/176772 | A2 | 11/2013 | |
| WO | WO 2013/176915 | A1 | 11/2013 | |
| WO | WO 2013/176916 | A1 | 11/2013 | |
| WO | WO 2013/181440 | A1 | 12/2013 | |
| WO | WO 2013/186754 | A2 | 12/2013 | |
| WO | WO 2013/188037 | A2 | 12/2013 | |
| WO | WO 2013/188522 | A2 | 12/2013 | |
| WO | WO 2013/188638 | A2 | 12/2013 | |
| WO | WO 2013/192278 | A1 | 12/2013 | |
| WO | WO 2013/142378 | A9 | 1/2014 | |
| WO | WO 2014/004336 | A2 | 1/2014 | |
| WO | WO 2014/005042 | A2 | 1/2014 | |
| WO | WO 2014/011237 | A1 | 1/2014 | |
| WO | WO 2014/011901 | A2 | 1/2014 | |
| WO | WO-2014018423 | A2 * | 1/2014 | ........... C12N 15/102 |
| WO | WO 2014/020608 | A1 | 2/2014 | |
| WO | WO 2014/022120 | A1 | 2/2014 | |
| WO | WO 2014/022702 | A2 | 2/2014 | |
| WO | WO 2014/036219 | A2 | 3/2014 | |
| WO | WO 2014/039513 | A2 | 3/2014 | |
| WO | WO 2014/039523 | A1 | 3/2014 | |
| WO | WO 2014/039585 | A2 | 3/2014 | |
| WO | WO 2014/039684 | A1 | 3/2014 | |
| WO | WO 2014/039692 | A2 | 3/2014 | |
| WO | WO 2014/039702 | A2 | 3/2014 | |
| WO | WO 2014/039872 | A1 | 3/2014 | |
| WO | WO 2014/039970 | A1 | 3/2014 | |
| WO | WO 2014/041327 | A1 | 3/2014 | |
| WO | WO 2014/043143 | A1 | 3/2014 | |
| WO | WO 2014/047103 | A2 | 3/2014 | |
| WO | WO 2014/055782 | A1 | 4/2014 | |
| WO | WO 2014/059173 | A2 | 4/2014 | |
| WO | WO 2014/059255 | A1 | 4/2014 | |
| WO | WO 2014/065596 | A1 | 5/2014 | |
| WO | WO 2014/066505 | A1 | 5/2014 | |
| WO | WO 2014/068346 | A2 | 5/2014 | |
| WO | WO 2014/070887 | A1 | 5/2014 | |
| WO | WO 2014/071006 | A1 | 5/2014 | |
| WO | WO 2014/071219 | A1 | 5/2014 | |
| WO | WO 2014/071235 | A1 | 5/2014 | |
| WO | WO 2014/072941 | A1 | 5/2014 | |
| WO | WO 2014/081729 | A1 | 5/2014 | |
| WO | WO 2014/081730 | A1 | 5/2014 | |
| WO | WO 2014/081855 | A1 | 5/2014 | |
| WO | WO 2014/082644 | A1 | 6/2014 | |
| WO | WO 2014/085261 | A1 | 6/2014 | |
| WO | WO 2014/085593 | A1 | 6/2014 | |
| WO | WO 2014/085830 | A2 | 6/2014 | |
| WO | WO 2014/089212 | A1 | 6/2014 | |
| WO | WO 2014/089290 | A1 | 6/2014 | |
| WO | WO 2014/089348 | A1 | 6/2014 | |
| WO | WO 2014/089513 | A1 | 6/2014 | |
| WO | WO 2014/089533 | A2 | 6/2014 | |
| WO | WO 2014/089541 | A2 | 6/2014 | |
| WO | WO 2014/093479 | A1 | 6/2014 | |
| WO | WO 2014/093595 | A1 | 6/2014 | |
| WO | WO 2014/093622 | A2 | 6/2014 | |
| WO | WO 2014/093635 | A1 | 6/2014 | |
| WO | WO 2014/093655 | A2 | 6/2014 | |
| WO | WO 2014/093661 | A2 | 6/2014 | |
| WO | WO 2014/093694 | A1 | 6/2014 | |
| WO | WO 2014/093701 | A1 | 6/2014 | |
| WO | WO 2014/093709 | A1 | 6/2014 | |
| WO | WO 2014/093712 | A1 | 6/2014 | |
| WO | WO 2014/093718 | A1 | 6/2014 | |
| WO | WO 2014/093736 | A1 | 6/2014 | |
| WO | WO 2014/093768 | A1 | 6/2014 | |
| WO | WO 2014/093852 | A1 | 6/2014 | |
| WO | WO 2014/096972 | A2 | 6/2014 | |
| WO | WO 2014/099744 | A1 | 6/2014 | |
| WO | WO 2014/099750 | A2 | 6/2014 | |
| WO | WO 2014/104878 | A1 | 7/2014 | |
| WO | WO 2014/110006 | A1 | 7/2014 | |
| WO | WO 2014/110552 | A1 | 7/2014 | |
| WO | WO 2014/113493 | A1 | 7/2014 | |
| WO | WO 2014/123967 | A2 | 8/2014 | |
| WO | WO 2014/124226 | A1 | 8/2014 | |
| WO | WO 2014/125668 | A1 | 8/2014 | |
| WO | WO 2014/127287 | A1 | 8/2014 | |
| WO | WO 2014/128324 | A1 | 8/2014 | |
| WO | WO 2014/128659 | A1 | 8/2014 | |
| WO | WO 2014/130706 | A1 | 8/2014 | |
| WO | WO 2014/130955 | A1 | 8/2014 | |
| WO | WO 2014/131833 | A1 | 9/2014 | |
| WO | WO 2014/138379 | A1 | 9/2014 | |
| WO | WO 2014/143381 | A1 | 9/2014 | |
| WO | WO 2014/144094 | A1 | 9/2014 | |
| WO | WO 2014/144155 | A1 | 9/2014 | |
| WO | WO 2014/144288 | A1 | 9/2014 | |
| WO | WO 2014/144592 | A2 | 9/2014 | |
| WO | WO 2014/144761 | A2 | 9/2014 | |
| WO | WO 2014/144951 | A1 | 9/2014 | |
| WO | WO 2014/145599 | A2 | 9/2014 | |
| WO | WO 2014/145736 | A2 | 9/2014 | |
| WO | WO 2014/150624 | A1 | 9/2014 | |
| WO | WO 2014/152432 | A2 | 9/2014 | |
| WO | WO 2014/152940 | A1 | 9/2014 | |
| WO | WO 2014/153118 | A1 | 9/2014 | |
| WO | WO 2014/153470 | A2 | 9/2014 | |
| WO | WO 2014/158593 | A1 | 10/2014 | |
| WO | WO 2014/161821 | A1 | 10/2014 | |
| WO | WO 2014/164466 | A1 | 10/2014 | |
| WO | WO 2014/165177 | A1 | 10/2014 | |
| WO | WO 2014/165349 | A1 | 10/2014 | |
| WO | WO 2014/165612 | A2 | 10/2014 | |
| WO | WO 2014/165707 | A2 | 10/2014 | |
| WO | WO 2014/165825 | A2 | 10/2014 | |
| WO | WO 2014/172458 | A1 | 10/2014 | |
| WO | WO 2014/172470 | A2 | 10/2014 | |
| WO | WO 2014/172489 | A2 | 10/2014 | |
| WO | WO 2014/173955 | A1 | 10/2014 | |
| WO | WO 2014/182700 | A1 | 11/2014 | |
| WO | WO 2014/183071 | A2 | 11/2014 | |
| WO | WO 2014/184143 | A1 | 11/2014 | |

(56) References Cited

FOREIGN PATENT DOCUMENTS

| | | | |
|---|---|---|---|
| WO | WO 2014/184741 | A1 | 11/2014 |
| WO | WO 2014/184744 | A1 | 11/2014 |
| WO | WO 2014/186585 | A2 | 11/2014 |
| WO | WO 2014/186686 | A2 | 11/2014 |
| WO | WO 2014/190181 | A1 | 11/2014 |
| WO | WO 2014/191128 | A1 | 12/2014 |
| WO | WO 2014/191518 | A1 | 12/2014 |
| WO | WO 2014/191521 | A2 | 12/2014 |
| WO | WO 2014/191525 | A1 | 12/2014 |
| WO | WO 2014/191527 | A1 | 12/2014 |
| WO | WO 2014/193583 | A2 | 12/2014 |
| WO | WO 2014/194190 | A1 | 12/2014 |
| WO | WO 2014/197568 | A2 | 12/2014 |
| WO | WO 2014/197748 | A2 | 12/2014 |
| WO | WO 2014/199358 | A1 | 12/2014 |
| WO | WO 2014/200659 | A1 | 12/2014 |
| WO | WO 2014/201015 | A2 | 12/2014 |
| WO | WO 2014/204578 | A1 | 12/2014 |
| WO | WO 2014/204723 | A1 | 12/2014 |
| WO | WO 2014/204724 | A1 | 12/2014 |
| WO | WO 2014/204725 | A1 | 12/2014 |
| WO | WO 2014/204726 | A1 | 12/2014 |
| WO | WO 2014/204727 | A1 | 12/2014 |
| WO | WO 2014/204728 | A1 | 12/2014 |
| WO | WO 2014/204729 | A1 | 12/2014 |
| WO | WO 2014/205192 | A2 | 12/2014 |
| WO | WO 2014/207043 | A1 | 12/2014 |
| WO | WO 2015/002780 | A1 | 1/2015 |
| WO | WO 2015/004241 | A2 | 1/2015 |
| WO | WO 2015/006290 | A1 | 1/2015 |
| WO | WO 2015/006294 | A2 | 1/2015 |
| WO | WO 2015/006437 | A1 | 1/2015 |
| WO | WO 2015/006498 | A2 | 1/2015 |
| WO | WO 2015/006747 | A2 | 1/2015 |
| WO | WO 2015/007194 | A1 | 1/2015 |
| WO | WO 2015/010114 | A1 | 1/2015 |
| WO | WO 2015/011483 | A1 | 1/2015 |
| WO | WO 2015/013583 | A2 | 1/2015 |
| WO | WO 2015/017866 | A1 | 2/2015 |
| WO | WO 2015/018503 | A1 | 2/2015 |
| WO | WO 2015/021353 | A1 | 2/2015 |
| WO | WO 2015/021426 | A1 | 2/2015 |
| WO | WO 2015/021990 | A1 | 2/2015 |
| WO | WO 2015/024017 | A2 | 2/2015 |
| WO | WO 2015/024986 | A1 | 2/2015 |
| WO | WO 2015/026883 | A1 | 2/2015 |
| WO | WO 2015/026885 | A1 | 2/2015 |
| WO | WO 2015/026886 | A1 | 2/2015 |
| WO | WO 2015/026887 | A1 | 2/2015 |
| WO | WO 2015/027134 | A1 | 2/2015 |
| WO | WO 2015/028969 | A2 | 3/2015 |
| WO | WO 2015/030881 | A1 | 3/2015 |
| WO | WO 2015/031619 | A1 | 3/2015 |
| WO | WO 2015/031775 | A1 | 3/2015 |
| WO | WO 2015/032494 | A2 | 3/2015 |
| WO | WO 2015/033293 | A1 | 3/2015 |
| WO | WO 2015/034872 | A2 | 3/2015 |
| WO | WO 2015/034885 | A1 | 3/2015 |
| WO | WO 2015/035136 | A2 | 3/2015 |
| WO | WO 2015/035139 | A2 | 3/2015 |
| WO | WO 2015/035162 | A2 | 3/2015 |
| WO | WO 2015/040075 | A1 | 3/2015 |
| WO | WO 2015/040402 | A1 | 3/2015 |
| WO | WO 2015/042393 | A2 | 3/2015 |
| WO | WO 2015/042585 | A1 | 3/2015 |
| WO | WO 2015/048577 | A2 | 4/2015 |
| WO | WO 2015/048690 | A1 | 4/2015 |
| WO | WO 2015/048707 | A2 | 4/2015 |
| WO | WO 2015/048801 | A2 | 4/2015 |
| WO | WO 2015/049897 | A1 | 4/2015 |
| WO | WO 2015/051191 | A1 | 4/2015 |
| WO | WO 2015/052133 | A1 | 4/2015 |
| WO | WO 2015/052231 | A2 | 4/2015 |
| WO | WO 2015/052335 | A1 | 4/2015 |
| WO | WO 2015/053995 | A1 | 4/2015 |
| WO | WO 2015/054253 | A1 | 4/2015 |
| WO | WO 2015/054315 | A1 | 4/2015 |
| WO | WO 2015/057671 | A1 | 4/2015 |
| WO | WO 2015/057834 | A1 | 4/2015 |
| WO | WO 2015/057852 | A1 | 4/2015 |
| WO | WO 2015/057976 | A1 | 4/2015 |
| WO | WO 2015/057980 | A1 | 4/2015 |
| WO | WO 2015/059265 | A1 | 4/2015 |
| WO | WO 2015/065964 | A1 | 5/2015 |
| WO | WO 2015/066119 | A1 | 5/2015 |
| WO | WO 2015/066634 | A2 | 5/2015 |
| WO | WO 2015/066636 | A2 | 5/2015 |
| WO | WO 2015/066637 | A1 | 5/2015 |
| WO | WO 2015/066638 | A2 | 5/2015 |
| WO | WO 2015/066643 | A1 | 5/2015 |
| WO | WO 2015/069682 | A2 | 5/2015 |
| WO | WO 2015/070083 | A1 | 5/2015 |
| WO | WO 2015/070193 | A1 | 5/2015 |
| WO | WO 2015/070212 | A1 | 5/2015 |
| WO | WO 2015/071474 | A2 | 5/2015 |
| WO | WO 2015/073683 | A2 | 5/2015 |
| WO | WO 2015/073867 | A1 | 5/2015 |
| WO | WO 2015/073990 | A1 | 5/2015 |
| WO | WO 2015/075056 | A1 | 5/2015 |
| WO | WO 2015/075154 | A2 | 5/2015 |
| WO | WO 2015/075175 | A1 | 5/2015 |
| WO | WO 2015/075195 | A1 | 5/2015 |
| WO | WO 2015/075557 | A2 | 5/2015 |
| WO | WO 2015/077058 | A2 | 5/2015 |
| WO | WO 2015/077290 | A2 | 5/2015 |
| WO | WO 2015/077318 | A1 | 5/2015 |
| WO | WO 2015/079056 | A1 | 6/2015 |
| WO | WO 2015/079057 | A2 | 6/2015 |
| WO | WO 2015/086795 | A1 | 6/2015 |
| WO | WO 2015/086798 | A2 | 6/2015 |
| WO | WO 2015/088643 | A1 | 6/2015 |
| WO | WO 2015/089046 | A1 | 6/2015 |
| WO | WO 2015/089077 | A2 | 6/2015 |
| WO | WO 2015/089277 | A1 | 6/2015 |
| WO | WO 2015/089351 | A1 | 6/2015 |
| WO | WO 2015/089354 | A1 | 6/2015 |
| WO | WO 2015/089364 | A1 | 6/2015 |
| WO | WO 2015/089406 | A1 | 6/2015 |
| WO | WO 2015/089419 | A2 | 6/2015 |
| WO | WO 2015/089427 | A1 | 6/2015 |
| WO | WO 2015/089462 | A1 | 6/2015 |
| WO | WO 2015/089465 | A1 | 6/2015 |
| WO | WO 2015/089473 | A1 | 6/2015 |
| WO | WO 2015/089486 | A2 | 6/2015 |
| WO | WO 2015/095804 | A1 | 6/2015 |
| WO | WO 2015/099850 | A1 | 7/2015 |
| WO | WO 2015/100929 | A1 | 7/2015 |
| WO | WO 2015/103057 | A1 | 7/2015 |
| WO | WO 2015/103153 | A1 | 7/2015 |
| WO | WO 2015/105928 | A1 | 7/2015 |
| WO | WO 2015/108993 | A1 | 7/2015 |
| WO | WO 2015/109752 | A1 | 7/2015 |
| WO | WO 2015/110474 | A1 | 7/2015 |
| WO | WO 2015/112790 | A2 | 7/2015 |
| WO | WO 2015/112896 | A2 | 7/2015 |
| WO | WO 2015/113063 | A1 | 7/2015 |
| WO | WO 2015/114365 | A1 | 8/2015 |
| WO | WO 2015/115903 | A1 | 8/2015 |
| WO | WO 2015/116686 | A1 | 8/2015 |
| WO | WO 2015/116969 | A2 | 8/2015 |
| WO | WO 2015/117021 | A1 | 8/2015 |
| WO | WO 2015/117041 | A1 | 8/2015 |
| WO | WO 2015/117081 | A2 | 8/2015 |
| WO | WO 2015/118156 | A1 | 8/2015 |
| WO | WO 2015/119941 | A2 | 8/2015 |
| WO | WO 2015/121454 | A1 | 8/2015 |
| WO | WO 2015/122967 | A1 | 8/2015 |
| WO | WO 2015/123339 | A1 | 8/2015 |
| WO | WO 2015/124715 | A1 | 8/2015 |
| WO | WO 2015/124718 | A1 | 8/2015 |
| WO | WO 2015/126927 | A2 | 8/2015 |
| WO | WO 2015/127428 | A1 | 8/2015 |
| WO | WO 2015/127439 | A1 | 8/2015 |
| WO | WO 2015/129686 | A1 | 9/2015 |

(56) References Cited

FOREIGN PATENT DOCUMENTS

| | | | |
|---|---|---|---|
| WO | WO 2015/131101 A1 | 9/2015 | |
| WO | WO 2015/133554 A1 | 9/2015 | |
| WO | WO 2015/134121 A2 | 9/2015 | |
| WO | WO 2015/134812 A1 | 9/2015 | |
| WO | WO 2015/136001 A1 | 9/2015 | |
| WO | WO 2015/138510 A1 | 9/2015 | |
| WO | WO 2015/138739 A2 | 9/2015 | |
| WO | WO 2015/138855 A1 | 9/2015 | |
| WO | WO 2015/138870 A2 | 9/2015 | |
| WO | WO 2015/139008 A1 | 9/2015 | |
| WO | WO 2015/139139 A1 | 9/2015 | |
| WO | WO 2015/143046 A2 | 9/2015 | |
| WO | WO 2015/143177 A1 | 9/2015 | |
| WO | WO 2015/145417 A1 | 10/2015 | |
| WO | WO 2015/148431 A1 | 10/2015 | |
| WO | WO 2015/148670 A1 | 10/2015 | |
| WO | WO 2015/148680 A1 | 10/2015 | |
| WO | WO 2015/148761 A1 | 10/2015 | |
| WO | WO 2015/148860 A1 | 10/2015 | |
| WO | WO 2015/148863 A2 | 10/2015 | |
| WO | WO 2015/153760 A2 | 10/2015 | |
| WO | WO 2015/153780 A1 | 10/2015 | |
| WO | WO 2015/153789 A1 | 10/2015 | |
| WO | WO 2015/153791 A1 | 10/2015 | |
| WO | WO 2015/153889 A2 | 10/2015 | |
| WO | WO 2015/153940 A1 | 10/2015 | |
| WO | WO 2015/155341 A1 | 10/2015 | |
| WO | WO 2015/155686 A2 | 10/2015 | |
| WO | WO 2015/157070 A2 | 10/2015 | |
| WO | WO 2015/157534 A1 | 10/2015 | |
| WO | WO 2015/159068 A1 | 10/2015 | |
| WO | WO 2015/159086 A1 | 10/2015 | |
| WO | WO 2015/159087 A1 | 10/2015 | |
| WO | WO 2015/160683 A1 | 10/2015 | |
| WO | WO 2015/161276 A2 | 10/2015 | |
| WO | WO 2015/163733 A1 | 10/2015 | |
| WO | WO 2015/164740 A1 | 10/2015 | |
| WO | WO 2015/164748 A1 | 10/2015 | |
| WO | WO 2015/165274 A1 | 11/2015 | |
| WO | WO 2015/165275 A1 | 11/2015 | |
| WO | WO 2015/165276 A1 | 11/2015 | |
| WO | WO 2015/166272 A2 | 11/2015 | |
| WO | WO 2015/167766 A1 | 11/2015 | |
| WO | WO 2015/167956 A1 | 11/2015 | |
| WO | WO 2015/168125 A1 | 11/2015 | |
| WO | WO 2015/168158 A1 | 11/2015 | |
| WO | WO 2015/168404 A1 | 11/2015 | |
| WO | WO 2015/168547 A2 | 11/2015 | |
| WO | WO 2015/168800 A1 | 11/2015 | |
| WO | WO 2015/171603 A1 | 11/2015 | |
| WO | WO 2015/171894 A1 | 11/2015 | |
| WO | WO 2015/171932 A1 | 11/2015 | |
| WO | WO 2015/172128 A1 | 11/2015 | |
| WO | WO 2015/173436 A1 | 11/2015 | |
| WO | WO 2015/175642 A2 | 11/2015 | |
| WO | WO 2015/179540 A1 | 11/2015 | |
| WO | WO 2015/183025 A1 | 12/2015 | |
| WO | WO 2015/183026 A1 | 12/2015 | |
| WO | WO 2015/183885 A1 | 12/2015 | |
| WO | WO 2015/184259 A1 | 12/2015 | |
| WO | WO 2015/184262 A1 | 12/2015 | |
| WO | WO 2015/184268 A1 | 12/2015 | |
| WO | WO 2015/188056 A1 | 12/2015 | |
| WO | WO 2015/188065 A1 | 12/2015 | |
| WO | WO 2015/188094 A1 | 12/2015 | |
| WO | WO 2015/188109 A1 | 12/2015 | |
| WO | WO 2015/188132 A1 | 12/2015 | |
| WO | WO 2015/188135 A1 | 12/2015 | |
| WO | WO 2015/188191 A1 | 12/2015 | |
| WO | WO 2015/189693 A1 | 12/2015 | |
| WO | WO 2015/191693 A2 | 12/2015 | |
| WO | WO 2015/191899 A1 | 12/2015 | |
| WO | WO 2015/191911 A2 | 12/2015 | |
| WO | WO 2015/193858 A1 | 12/2015 | |
| WO | WO 2015/195547 A1 | 12/2015 | |
| WO | WO 2015/195621 A1 | 12/2015 | |
| WO | WO 2015/195798 A1 | 12/2015 | |
| WO | WO 2015/198020 A1 | 12/2015 | |
| WO | WO 2015/200334 A1 | 12/2015 | |
| WO | WO 2015/200378 A1 | 12/2015 | |
| WO | WO 2015/200555 A2 | 12/2015 | |
| WO | WO 2015/200805 A2 | 12/2015 | |
| WO | WO 2016/001978 A1 | 1/2016 | |
| WO | WO 2016/004010 A1 | 1/2016 | |
| WO | WO 2016/004318 A1 | 1/2016 | |
| WO | WO 2016/007347 A1 | 1/2016 | |
| WO | WO 2016/007604 A1 | 1/2016 | |
| WO | WO 2016/007948 A1 | 1/2016 | |
| WO | WO 2016/011080 A2 | 1/2016 | |
| WO | WO 2016/011210 A2 | 1/2016 | |
| WO | WO 2016/011428 A1 | 1/2016 | |
| WO | WO 2016/012544 A2 | 1/2016 | |
| WO | WO 2016/012552 A1 | 1/2016 | |
| WO | WO 2016/014409 A1 | 1/2016 | |
| WO | WO 2016/014565 A2 | 1/2016 | |
| WO | WO 2016/014794 A1 | 1/2016 | |
| WO | WO 2016/014837 A1 | 1/2016 | |
| WO | WO 2016/016119 A1 | 2/2016 | |
| WO | WO 2016/016358 A1 | 2/2016 | |
| WO | WO 2016/019144 A2 | 2/2016 | |
| WO | WO 2016/020399 A1 | 2/2016 | |
| WO | WO 2016/021972 A1 | 2/2016 | |
| WO | WO 2016/021973 A1 | 2/2016 | |
| WO | WO 2016/022363 A2 | 2/2016 | |
| WO | WO 2016/022866 A1 | 2/2016 | |
| WO | WO 2016/022931 A1 | 2/2016 | |
| WO | WO 2016/025131 A1 | 2/2016 | |
| WO | WO 2016/025469 A1 | 2/2016 | |
| WO | WO 2016/025759 A1 | 2/2016 | |
| WO | WO 2016/026444 A1 | 2/2016 | |
| WO | WO 2016/028682 A1 | 2/2016 | |
| WO | WO 2016/028843 A2 | 2/2016 | |
| WO | WO 2016/028887 A1 | 2/2016 | |
| WO | WO 2016/033088 A1 | 3/2016 | |
| WO | WO 2016/033230 A1 | 3/2016 | |
| WO | WO 2016/033246 A1 | 3/2016 | |
| WO | WO 2016/033298 A1 | 3/2016 | |
| WO | WO 2016/035044 A1 | 3/2016 | |
| WO | WO 2016/036754 A1 | 3/2016 | |
| WO | WO 2016/037157 A2 | 3/2016 | |
| WO | WO 2016/040030 A1 | 3/2016 | |
| WO | WO 2016/040594 A1 | 3/2016 | |
| WO | WO 2016/044182 A1 | 3/2016 | |
| WO | WO 2016/044416 A1 | 3/2016 | |
| WO | WO 2016/046635 A1 | 3/2016 | |
| WO | WO 2016/049024 A2 | 3/2016 | |
| WO | WO 2016/049163 A2 | 3/2016 | |
| WO | WO 2016/049230 A1 | 3/2016 | |
| WO | WO 2016/049251 A1 | 3/2016 | |
| WO | WO 2016/049258 A2 | 3/2016 | |
| WO | WO-2016035918 A1 * | 3/2016 | ............ C09K 19/00 |
| WO | WO 2016/053397 A2 | 4/2016 | |
| WO | WO 2016/054326 A1 | 4/2016 | |
| WO | WO 2016/057061 A2 | 4/2016 | |
| WO | WO 2016/057821 A2 | 4/2016 | |
| WO | WO 2016/057835 A2 | 4/2016 | |
| WO | WO 2016/057850 A1 | 4/2016 | |
| WO | WO 2016/057951 A2 | 4/2016 | |
| WO | WO 2016/057961 A1 | 4/2016 | |
| WO | WO 2016/061073 A1 | 4/2016 | |
| WO | WO 2016/061374 A1 | 4/2016 | |
| WO | WO 2016/061481 A1 | 4/2016 | |
| WO | WO 2016/061523 A1 | 4/2016 | |
| WO | WO 2016/064894 A2 | 4/2016 | |
| WO | WO 2016/065364 A1 | 4/2016 | |
| WO | WO 2016/069282 A1 | 5/2016 | |
| WO | WO 2016/069283 A1 | 5/2016 | |
| WO | WO 2016/069591 A2 | 5/2016 | |
| WO | WO 2016/069774 A1 | 5/2016 | |
| WO | WO 2016/069910 A1 | 5/2016 | |
| WO | WO 2016/069912 A1 | 5/2016 | |
| WO | WO 2016/070037 A2 | 5/2016 | |
| WO | WO 2016/070070 A1 | 5/2016 | |
| WO | WO 2016/070129 A1 | 5/2016 | |

(56) References Cited

FOREIGN PATENT DOCUMENTS

| | | | |
|---|---|---|---|
| WO | WO 2016/072399 | A1 | 5/2016 |
| WO | WO 2016/072936 | A1 | 5/2016 |
| WO | WO 2016/073433 | A1 | 5/2016 |
| WO | WO 2016/073559 | A1 | 5/2016 |
| WO | WO 2016/073990 | A2 | 5/2016 |
| WO | WO 2016/075662 | A2 | 5/2016 |
| WO | WO 2016/076672 | A1 | 5/2016 |
| WO | WO 2016/077273 | A1 | 5/2016 |
| WO | WO 2016/077350 | A1 | 5/2016 |
| WO | WO 2016/080097 | A1 | 5/2016 |
| WO | WO 2016/080795 | A1 | 5/2016 |
| WO | WO 2016/081923 | A2 | 5/2016 |
| WO | WO 2016/081924 | A1 | 5/2016 |
| WO | WO 2016/082135 | A1 | 6/2016 |
| WO | WO 2016/083811 | A1 | 6/2016 |
| WO | WO 2016/084084 | A1 | 6/2016 |
| WO | WO 2016/084088 | A1 | 6/2016 |
| WO | WO 2016/086177 | A2 | 6/2016 |
| WO | WO 2016/089433 | A1 | 6/2016 |
| WO | WO 2016/089866 | A1 | 6/2016 |
| WO | WO 2016/089883 | A1 | 6/2016 |
| WO | WO 2016/090385 | A1 | 6/2016 |
| WO | WO 2016/094679 | A1 | 6/2016 |
| WO | WO 2016/094845 | A2 | 6/2016 |
| WO | WO 2016/094867 | A1 | 6/2016 |
| WO | WO 2016/094872 | A1 | 6/2016 |
| WO | WO 2016/094874 | A1 | 6/2016 |
| WO | WO 2016/094880 | A1 | 6/2016 |
| WO | WO 2016/094888 | A1 | 6/2016 |
| WO | WO 2016/097212 | A1 | 6/2016 |
| WO | WO 2016/097231 | A2 | 6/2016 |
| WO | WO 2016/097751 | A1 | 6/2016 |
| WO | WO 2016/099887 | A1 | 6/2016 |
| WO | WO 2016/100272 | A1 | 6/2016 |
| WO | WO 2016/100389 | A1 | 6/2016 |
| WO | WO 2016/100568 | A1 | 6/2016 |
| WO | WO 2016/100571 | A1 | 6/2016 |
| WO | WO 2016/100951 | A2 | 6/2016 |
| WO | WO 2016/100955 | A2 | 6/2016 |
| WO | WO 2016/100974 | A1 | 6/2016 |
| WO | WO 2016/103233 | A2 | 6/2016 |
| WO | WO 2016/104716 | A1 | 6/2016 |
| WO | WO 2016/106236 | A1 | 6/2016 |
| WO | WO 2016/106239 | A1 | 6/2016 |
| WO | WO 2016/106244 | A1 | 6/2016 |
| WO | WO 2016/106338 | A2 | 6/2016 |
| WO | 2016/109255 | A1 | 7/2016 |
| WO | WO 2016/108926 | A1 | 7/2016 |
| WO | WO 2016/109840 | A2 | 7/2016 |
| WO | WO 2016/110214 | A1 | 7/2016 |
| WO | WO 2016/110453 | A1 | 7/2016 |
| WO | WO 2016/110511 | A1 | 7/2016 |
| WO | WO 2016/110512 | A1 | 7/2016 |
| WO | WO 2016/111546 | A2 | 7/2016 |
| WO | WO 2016/112242 | A1 | 7/2016 |
| WO | WO 2016/112351 | A1 | 7/2016 |
| WO | WO 2016/112963 | A1 | 7/2016 |
| WO | WO 2016/113357 | A1 | 7/2016 |
| WO | WO 2016/114972 | A1 | 7/2016 |
| WO | WO 2016/115179 | A1 | 7/2016 |
| WO | WO 2016/115326 | A1 | 7/2016 |
| WO | WO 2016/115355 | A1 | 7/2016 |
| WO | WO 2016/116032 | A1 | 7/2016 |
| WO | WO 2016/120480 | A1 | 8/2016 |
| WO | WO 2016/123071 | A1 | 8/2016 |
| WO | WO 2016/123230 | A1 | 8/2016 |
| WO | WO 2016/123243 | A1 | 8/2016 |
| WO | WO 2016/123578 | A1 | 8/2016 |
| WO | WO 2016/126747 | A1 | 8/2016 |
| WO | WO 2016/130600 | A2 | 8/2016 |
| WO | WO 2016/130697 | A1 | 8/2016 |
| WO | WO 2016/131009 | A1 | 8/2016 |
| WO | WO 2016/132122 | A1 | 8/2016 |
| WO | WO 2016/133165 | A1 | 8/2016 |
| WO | WO 2016/135507 | A1 | 9/2016 |
| WO | WO 2016/135557 | A2 | 9/2016 |
| WO | WO 2016/135558 | A2 | 9/2016 |
| WO | WO 2016/135559 | A2 | 9/2016 |
| WO | WO 2016/137774 | A1 | 9/2016 |
| WO | WO 2016/137949 | A1 | 9/2016 |
| WO | WO 2016/141224 | A1 | 9/2016 |
| WO | WO 2016/141893 | A1 | 9/2016 |
| WO | WO 2016/142719 | A1 | 9/2016 |
| WO | WO 2016/145150 | A2 | 9/2016 |
| WO | WO 2016/148994 | A1 | 9/2016 |
| WO | WO 2016/149484 | A2 | 9/2016 |
| WO | WO 2016/149547 | A1 | 9/2016 |
| WO | WO 2016/150336 | A1 | 9/2016 |
| WO | WO 2016/150855 | A1 | 9/2016 |
| WO | WO 2016/154016 | A2 | 9/2016 |
| WO | WO 2016/154579 | A2 | 9/2016 |
| WO | WO 2016/154596 | A1 | 9/2016 |
| WO | WO 2016/155482 | A1 | 10/2016 |
| WO | WO 2016/161004 | A1 | 10/2016 |
| WO | WO 2016/161207 | A1 | 10/2016 |
| WO | WO 2016/161260 | A1 | 10/2016 |
| WO | WO 2016/161380 | A1 | 10/2016 |
| WO | WO 2016/161446 | A1 | 10/2016 |
| WO | WO 2016/164356 | A1 | 10/2016 |
| WO | WO 2016/164797 | A1 | 10/2016 |
| WO | WO 2016/166340 | A1 | 10/2016 |
| WO | WO 2016/167300 | A1 | 10/2016 |
| WO | WO 2016/168631 | A1 | 10/2016 |
| WO | WO 2016/170484 | A1 | 10/2016 |
| WO | WO 2016/172359 | A2 | 10/2016 |
| WO | WO 2016/172727 | A1 | 10/2016 |
| WO | WO 2016/174056 | A1 | 11/2016 |
| WO | WO 2016/174151 | A1 | 11/2016 |
| WO | WO 2016/174250 | A1 | 11/2016 |
| WO | WO 2016/176191 | A1 | 11/2016 |
| WO | WO 2016/176404 | A1 | 11/2016 |
| WO | WO 2016/176690 | A2 | 11/2016 |
| WO | WO 2016/177682 | A1 | 11/2016 |
| WO | WO 2016/178207 | A1 | 11/2016 |
| WO | WO 2016/179038 | A1 | 11/2016 |
| WO | WO 2016/179112 | A1 | 11/2016 |
| WO | WO 2016/181357 | A1 | 11/2016 |
| WO | WO 2016/182893 | A1 | 11/2016 |
| WO | WO 2016/182917 | A1 | 11/2016 |
| WO | WO 2016/182959 | A1 | 11/2016 |
| WO | WO 2016/183236 | A1 | 11/2016 |
| WO | WO 2016/183298 | A2 | 11/2016 |
| WO | WO 2016/183345 | A1 | 11/2016 |
| WO | WO 2016/183402 | A2 | 11/2016 |
| WO | WO 2016/183438 | A1 | 11/2016 |
| WO | WO 2016/183448 | A1 | 11/2016 |
| WO | WO 2016/184955 | A2 | 11/2016 |
| WO | WO 2016/184989 | A1 | 11/2016 |
| WO | WO 2016/185411 | A1 | 11/2016 |
| WO | WO 2016/186745 | A1 | 11/2016 |
| WO | WO 2016/186772 | A2 | 11/2016 |
| WO | WO 2016/186946 | A1 | 11/2016 |
| WO | WO 2016/186953 | A1 | 11/2016 |
| WO | WO 2016/187717 | A1 | 12/2016 |
| WO | WO 2016/187904 | A1 | 12/2016 |
| WO | WO 2016/191684 | A1 | 12/2016 |
| WO | WO 2016/191869 | A1 | 12/2016 |
| WO | WO 2016/196273 | A1 | 12/2016 |
| WO | WO 2016/196282 | A1 | 12/2016 |
| WO | WO 2016/196308 | A1 | 12/2016 |
| WO | WO 2016/196361 | A1 | 12/2016 |
| WO | WO 2016/196499 | A1 | 12/2016 |
| WO | WO 2016/196539 | A2 | 12/2016 |
| WO | WO 2016/196655 | A1 | 12/2016 |
| WO | WO 2016/196805 | A1 | 12/2016 |
| WO | WO 2016/196887 | A1 | 12/2016 |
| WO | WO 2016/197132 | A1 | 12/2016 |
| WO | WO 2016/197133 | A1 | 12/2016 |
| WO | WO 2016/197354 | A1 | 12/2016 |
| WO | WO 2016/197355 | A1 | 12/2016 |
| WO | WO 2016/197356 | A1 | 12/2016 |
| WO | WO 2016/197357 | A1 | 12/2016 |
| WO | WO 2016/197358 | A1 | 12/2016 |
| WO | WO 2016/197359 | A1 | 12/2016 |

(56) References Cited

FOREIGN PATENT DOCUMENTS

| | | | |
|---|---|---|---|
| WO | WO 2016/197360 | A1 | 12/2016 |
| WO | WO 2016/197361 | A1 | 12/2016 |
| WO | WO 2016/197362 | A1 | 12/2016 |
| WO | WO 2016/198361 | A1 | 12/2016 |
| WO | WO 2016/198500 | A1 | 12/2016 |
| WO | WO 2016/200263 | A1 | 12/2016 |
| WO | WO 2016/201047 | A1 | 12/2016 |
| WO | WO 2016/201138 | A1 | 12/2016 |
| WO | WO 2016/201152 | A1 | 12/2016 |
| WO | WO 2016/201153 | A1 | 12/2016 |
| WO | WO 2016/201155 | A1 | 12/2016 |
| WO | WO 2016/205276 | A1 | 12/2016 |
| WO | WO 2016/205613 | A1 | 12/2016 |
| WO | WO 2016/205623 | A1 | 12/2016 |
| WO | WO 2016/205680 | A1 | 12/2016 |
| WO | WO 2016/205688 | A2 | 12/2016 |
| WO | WO 2016/205703 | A1 | 12/2016 |
| WO | WO 2016/205711 | A1 | 12/2016 |
| WO | WO 2016/205728 | A1 | 12/2016 |
| WO | WO 2016/205745 | A2 | 12/2016 |
| WO | WO 2016/205749 | A1 | 12/2016 |
| WO | WO 2016/205759 | A1 | 12/2016 |
| WO | WO 2016/205764 | A1 | 12/2016 |
| WO | WO 2017/001572 | A1 | 1/2017 |
| WO | WO 2017/001988 | A1 | 1/2017 |
| WO | WO 2017/004261 | A1 | 1/2017 |
| WO | WO 2017/004279 | A2 | 1/2017 |
| WO | WO 2017/004616 | A1 | 1/2017 |
| WO | WO 2017/005807 | A1 | 1/2017 |
| WO | WO 2017/009399 | A1 | 1/2017 |
| WO | WO 2017/010556 | A1 | 1/2017 |
| WO | WO 2017/011519 | A1 | 1/2017 |
| WO | WO 2017/011721 | A1 | 1/2017 |
| WO | WO 2017/011804 | A1 | 1/2017 |
| WO | WO 2017/015015 | A1 | 1/2017 |
| WO | WO 2017/015101 | A1 | 1/2017 |
| WO | WO 2017/015545 | A1 | 1/2017 |
| WO | WO 2017/015567 | A1 | 1/2017 |
| WO | WO 2017/015637 | A1 | 1/2017 |
| WO | WO 2017/017016 | A1 | 2/2017 |
| WO | WO 2017/019867 | A1 | 2/2017 |
| WO | WO 2017/019895 | A1 | 2/2017 |
| WO | WO 2017/023803 | A1 | 2/2017 |
| WO | WO 2017/023974 | A1 | 2/2017 |
| WO | WO 2017/024047 | A1 | 2/2017 |
| WO | WO 2017/024319 | A1 | 2/2017 |
| WO | WO 2017/024343 | A1 | 2/2017 |
| WO | WO 2017/024602 | A1 | 2/2017 |
| WO | WO 2017/025323 | A1 | 2/2017 |
| WO | WO 2017/027423 | A1 | 2/2017 |
| WO | WO 2017/028768 | A1 | 2/2017 |
| WO | WO 2017/029664 | A1 | 2/2017 |
| WO | WO 2017/031360 | A1 | 2/2017 |
| WO | WO 2017/031483 | A1 | 2/2017 |
| WO | WO 2017/035416 | A2 | 3/2017 |
| WO | WO 2017/040348 | A1 | 3/2017 |
| WO | WO 2017/040511 | A1 | 3/2017 |
| WO | WO 2017/040709 | A1 | 3/2017 |
| WO | WO 2017/040786 | A1 | 3/2017 |
| WO | WO 2017/040793 | A1 | 3/2017 |
| WO | WO 2017/040813 | A2 | 3/2017 |
| WO | WO 2017/043573 | A1 | 3/2017 |
| WO | WO 2017/043656 | A1 | 3/2017 |
| WO | WO 2017/044419 | A1 | 3/2017 |
| WO | WO 2017/044776 | A1 | 3/2017 |
| WO | WO 2017/044857 | A2 | 3/2017 |
| WO | WO 2017/048390 | A1 | 3/2017 |
| WO | WO 2017/049129 | A2 | 3/2017 |
| WO | WO 2017/050963 | A1 | 3/2017 |
| WO | WO 2017/053312 | A1 | 3/2017 |
| WO | WO 2017/053431 | A2 | 3/2017 |
| WO | WO 2017/053713 | A1 | 3/2017 |
| WO | WO 2017/053729 | A1 | 3/2017 |
| WO | WO 2017/053753 | A1 | 3/2017 |
| WO | WO 2017/053762 | A1 | 3/2017 |
| WO | WO 2017/053879 | A1 | 3/2017 |
| WO | WO 2017/054721 | A1 | 4/2017 |
| WO | WO 2017/058658 | A2 | 4/2017 |
| WO | WO 2017/059241 | A1 | 4/2017 |
| WO | WO 2017/062605 | A1 | 4/2017 |
| WO | WO 2017/062723 | A1 | 4/2017 |
| WO | WO 2017/062754 | A1 | 4/2017 |
| WO | WO 2017/062855 | A1 | 4/2017 |
| WO | WO 2017/062886 | A1 | 4/2017 |
| WO | WO 2017/062983 | A1 | 4/2017 |
| WO | WO 2017/064439 | A1 | 4/2017 |
| WO | WO 2017/064546 | A1 | 4/2017 |
| WO | WO 2017/064566 | A2 | 4/2017 |
| WO | WO 2017/066175 | A1 | 4/2017 |
| WO | WO 2017/066497 | A2 | 4/2017 |
| WO | WO 2017/066588 | A2 | 4/2017 |
| WO | WO 2017/066707 | A1 | 4/2017 |
| WO | WO 2017/066781 | A1 | 4/2017 |
| WO | WO 2017/068077 | A1 | 4/2017 |
| WO | WO 2017/068377 | A1 | 4/2017 |
| WO | WO 2017/069829 | A2 | 4/2017 |
| WO | WO 2017/070029 | A1 | 4/2017 |
| WO | WO 2017/070032 | A1 | 4/2017 |
| WO | WO 2017/070169 | A1 | 4/2017 |
| WO | WO 2017/070284 | A1 | 4/2017 |
| WO | WO 2017/070598 | A1 | 4/2017 |
| WO | WO 2017/070605 | A1 | 4/2017 |
| WO | WO 2017/070632 | A2 | 4/2017 |
| WO | WO 2017/070633 | A2 | 4/2017 |
| WO | WO 2017/072590 | A1 | 5/2017 |
| WO | WO 2017/074526 | A1 | 5/2017 |
| WO | WO 2017/074962 | A1 | 5/2017 |
| WO | WO 2017/075261 | A1 | 5/2017 |
| WO | WO 2017/075335 | A1 | 5/2017 |
| WO | WO 2017/075475 | A1 | 5/2017 |
| WO | WO 2017/077135 | A1 | 5/2017 |
| WO | WO 2017/077329 | A2 | 5/2017 |
| WO | WO 2017/078751 | A1 | 5/2017 |
| WO | WO 2017/079400 | A1 | 5/2017 |
| WO | WO 2017/079428 | A1 | 5/2017 |
| WO | WO 2017/079673 | A1 | 5/2017 |
| WO | WO 2017/079724 | A1 | 5/2017 |
| WO | WO 2017/081097 | A1 | 5/2017 |
| WO | WO 2017/081288 | A1 | 5/2017 |
| WO | WO 2017/083368 | A1 | 5/2017 |
| WO | WO 2017/083722 | A1 | 5/2017 |
| WO | WO 2017/083766 | A1 | 5/2017 |
| WO | WO 2017/087395 | A1 | 5/2017 |
| WO | WO 2017/090724 | A1 | 6/2017 |
| WO | WO 2017/091510 | A1 | 6/2017 |
| WO | WO 2017/091630 | A1 | 6/2017 |
| WO | WO 2017/092201 | A1 | 6/2017 |
| WO | WO 2017/093370 | A1 | 6/2017 |
| WO | WO 2017/093969 | A1 | 6/2017 |
| WO | WO 2017/095111 | A1 | 6/2017 |
| WO | WO 2017/096041 | A1 | 6/2017 |
| WO | WO 2017/096237 | A1 | 6/2017 |
| WO | WO 2017/100158 | A1 | 6/2017 |
| WO | WO 2017/100431 | A2 | 6/2017 |
| WO | WO 2017/104404 | A1 | 6/2017 |
| WO | WO 2017/105251 | A1 | 6/2017 |
| WO | WO 2017/105350 | A1 | 6/2017 |
| WO | WO 2017/105991 | A1 | 6/2017 |
| WO | WO 2017/106414 | A1 | 6/2017 |
| WO | WO 2017/106528 | A2 | 6/2017 |
| WO | WO 2017/106537 | A2 | 6/2017 |
| WO | WO 2017/106569 | A1 | 6/2017 |
| WO | WO 2017/106616 | A1 | 6/2017 |
| WO | WO 2017/106657 | A1 | 6/2017 |
| WO | WO 2017/106767 | A1 | 6/2017 |
| WO | WO 2017/109134 | A1 | 6/2017 |
| WO | WO 2017/109757 | A1 | 6/2017 |
| WO | WO 2017/112620 | A1 | 6/2017 |
| WO | WO 2017/115268 | A1 | 7/2017 |
| WO | WO 2017/117395 | A1 | 7/2017 |
| WO | WO 2017/118598 | A1 | 7/2017 |
| WO | WO 2017/118720 | A1 | 7/2017 |
| WO | WO 2017/123609 | A1 | 7/2017 |
| WO | WO 2017/123910 | A1 | 7/2017 |

(56) References Cited

FOREIGN PATENT DOCUMENTS

| | | | |
|---|---|---|---|
| WO | WO 2017/124086 | A1 | 7/2017 |
| WO | WO 2017/124100 | A1 | 7/2017 |
| WO | WO 2017/124652 | A1 | 7/2017 |
| WO | WO 2017/126987 | A1 | 7/2017 |
| WO | WO 2017/127807 | A1 | 7/2017 |
| WO | WO 2017/131237 | A1 | 8/2017 |
| WO | WO 2017/132112 | A1 | 8/2017 |
| WO | WO 2017/132580 | A2 | 8/2017 |
| WO | WO 2017/136520 | A1 | 8/2017 |
| WO | WO 2017/136629 | A1 | 8/2017 |
| WO | WO 2017/136794 | A1 | 8/2017 |
| WO | WO 2017/139264 | A1 | 8/2017 |
| WO | WO 2017/139505 | A2 | 8/2017 |
| WO | WO 2017/141173 | A2 | 8/2017 |
| WO | WO 2017/142835 | A1 | 8/2017 |
| WO | WO 2017/142999 | A2 | 8/2017 |
| WO | WO 2017/143042 | A2 | 8/2017 |
| WO | WO 2017/147278 | A1 | 8/2017 |
| WO | WO 2017/147432 | A1 | 8/2017 |
| WO | WO 2017/147446 | A1 | 8/2017 |
| WO | WO 2017/147555 | A1 | 8/2017 |
| WO | WO 2017/151444 | A1 | 9/2017 |
| WO | WO 2017/152015 | A1 | 9/2017 |
| WO | WO 2017/155717 | A1 | 9/2017 |
| WO | WO 2017/157422 | A1 | 9/2017 |
| WO | WO 2017/158153 | A1 | 9/2017 |
| WO | WO 2017/160689 | A1 | 9/2017 |
| WO | WO 2017/160752 | A1 | 9/2017 |
| WO | WO 2017/160890 | A1 | 9/2017 |
| WO | WO 2017/161068 | A1 | 9/2017 |
| WO | WO 2017/165826 | A1 | 9/2017 |
| WO | WO 2017/165862 | A1 | 9/2017 |
| WO | WO 2017/172644 | A2 | 10/2017 |
| WO | WO 2017/172645 | A2 | 10/2017 |
| WO | WO 2017/172860 | A1 | 10/2017 |
| WO | WO 2017/173004 | A1 | 10/2017 |
| WO | WO 2017/173054 | A1 | 10/2017 |
| WO | WO 2017/173092 | A1 | 10/2017 |
| WO | WO 2017/174329 | A1 | 10/2017 |
| WO | WO 2017/176529 | A1 | 10/2017 |
| WO | WO 2017/176806 | A1 | 10/2017 |
| WO | WO 2017/178590 | A1 | 10/2017 |
| WO | WO 2017/180694 | A1 | 10/2017 |
| WO | WO 2017/180711 | A1 | 10/2017 |
| WO | WO 2017/180915 | A2 | 10/2017 |
| WO | WO 2017/180926 | A1 | 10/2017 |
| WO | WO 2017/181107 | A2 | 10/2017 |
| WO | WO 2017/181735 | A2 | 10/2017 |
| WO | WO 2017/182468 | A1 | 10/2017 |
| WO | WO 2017/184334 | A1 | 10/2017 |
| WO | WO 2017/184768 | A1 | 10/2017 |
| WO | WO 2017/184786 | A1 | 10/2017 |
| WO | WO 2017/186550 | A1 | 11/2017 |
| WO | WO 2017/189308 | A1 | 11/2017 |
| WO | WO 2017/189336 | A1 | 11/2017 |
| WO | WO 2017/190257 | A1 | 11/2017 |
| WO | WO 2017/190664 | A1 | 11/2017 |
| WO | WO 2017/191210 | A1 | 11/2017 |
| WO | WO 2017/192172 | A1 | 11/2017 |
| WO | WO 2017/192512 | A2 | 11/2017 |
| WO | WO 2017/192544 | A1 | 11/2017 |
| WO | WO 2017/192573 | A1 | 11/2017 |
| WO | WO 2017/193029 | A2 | 11/2017 |
| WO | WO 2017/193053 | A1 | 11/2017 |
| WO | WO 2017/196768 | A1 | 11/2017 |
| WO | WO 2017/197038 | A1 | 11/2017 |
| WO | WO 2017/197238 | A1 | 11/2017 |
| WO | WO 2017/197301 | A1 | 11/2017 |
| WO | WO 2017/201476 | A1 | 11/2017 |
| WO | WO 2017/205290 | A1 | 11/2017 |
| WO | WO 2017/205423 | A1 | 11/2017 |
| WO | WO 2017/207589 | A1 | 12/2017 |
| WO | WO 2017/208247 | A1 | 12/2017 |
| WO | WO 2017/209809 | A1 | 12/2017 |
| WO | WO 2017/213896 | A1 | 12/2017 |
| WO | WO 2017/213898 | A2 | 12/2017 |
| WO | WO 2017/214460 | A1 | 12/2017 |
| WO | WO 2017/216392 | A1 | 12/2017 |
| WO | WO 2017/216771 | A2 | 12/2017 |
| WO | WO 2017/218185 | A1 | 12/2017 |
| WO | WO 2017/219027 | A1 | 12/2017 |
| WO | WO 2017/219033 | A1 | 12/2017 |
| WO | WO 2017/220751 | A1 | 12/2017 |
| WO | WO 2017/222370 | A1 | 12/2017 |
| WO | WO 2017/222773 | A1 | 12/2017 |
| WO | WO 2017/222834 | A1 | 12/2017 |
| WO | WO 2017/223107 | A1 | 12/2017 |
| WO | WO 2017/223330 | A1 | 12/2017 |
| WO | WO 2018/000657 | A1 | 1/2018 |
| WO | WO 2018/002719 | A1 | 1/2018 |
| WO | WO 2018/005117 | A1 | 1/2018 |
| WO | WO 2018/005289 | A2 | 1/2018 |
| WO | WO 2018/005691 | A1 | 1/2018 |
| WO | WO 2018/005782 | A1 | 1/2018 |
| WO | WO 2018/005873 | A1 | 1/2018 |
| WO | WO 2018/06693 | A1 | 1/2018 |
| WO | WO 2018/009520 | A1 | 1/2018 |
| WO | WO 2018/009562 | A1 | 1/2018 |
| WO | WO 2018/009822 | A1 | 1/2018 |
| WO | WO 2018/013821 | A1 | 1/2018 |
| WO | WO 2018/013990 | A1 | 1/2018 |
| WO | WO 2018/015444 | A1 | 1/2018 |
| WO | WO 2018/015936 | A2 | 1/2018 |
| WO | WO 2018/017754 | A1 | 1/2018 |
| WO | WO 2018/014384 | A1 | 2/2018 |
| WO | WO 2018/018979 | A1 | 2/2018 |
| WO | WO 2018/020248 | A1 | 2/2018 |
| WO | WO 2018/022480 | A1 | 2/2018 |
| WO | WO 2018/022634 | A1 | 2/2018 |
| WO | WO 2018/025206 | A1 | 2/2018 |
| WO | WO 2018/026723 | A1 | 2/2018 |
| WO | WO 2018/026976 | A1 | 2/2018 |
| WO | WO 2018/027078 | A1 | 2/2018 |
| WO | WO 2018/030608 | A1 | 2/2018 |
| WO | WO 2018/031683 | A1 | 2/2018 |
| WO | WO 2018/035250 | A1 | 2/2018 |
| WO | WO 2018/035300 | A1 | 2/2018 |
| WO | WO 2018/035423 | A1 | 2/2018 |
| WO | WO 2018/035503 | A1 | 2/2018 |
| WO | WO 2018/039145 | A1 | 3/2018 |
| WO | WO 2018/039438 | A1 | 3/2018 |
| WO | WO 2018/039440 | A1 | 3/2018 |
| WO | WO 2018/039448 | A1 | 3/2018 |
| WO | WO 2018/045630 | A1 | 3/2018 |
| WO | WO 2018/048827 | A1 | 3/2018 |
| WO | WO 2018/049168 | A1 | 3/2018 |
| WO | WO 2018/051347 | A1 | 3/2018 |
| WO | WO 2018/058064 | A1 | 3/2018 |
| WO | WO 2018/062866 | A2 | 4/2018 |
| WO | WO 2018/064352 | A1 | 4/2018 |
| WO | WO 2018/064371 | A1 | 4/2018 |
| WO | WO 2018/064516 | A1 | 4/2018 |
| WO | WO 2018/067546 | A1 | 4/2018 |
| WO | WO 2018/067846 | A1 | 4/2018 |
| WO | WO 2018/068053 | A2 | 4/2018 |
| WO | WO 2018/069474 | A1 | 4/2018 |
| WO | WO 2018/071623 | A2 | 4/2018 |
| WO | WO 2018/071663 | A1 | 4/2018 |
| WO | WO 2018/071868 | A1 | 4/2018 |
| WO | WO 2018/071892 | A1 | 4/2018 |
| WO | WO 2018/074979 | A1 | 4/2018 |
| WO | WO 2018/079134 | A1 | 5/2018 |
| WO | WO 2018/080573 | A1 | 5/2018 |
| WO | WO 2018/081504 | A1 | 5/2018 |
| WO | WO 2018/081535 | A2 | 5/2018 |
| WO | WO 2018/081728 | A1 | 5/2018 |
| WO | WO 2018/083128 | A2 | 5/2018 |
| WO | WO 2018/083606 | A1 | 5/2018 |
| WO | WO 2018/085288 | A1 | 5/2018 |
| WO | WO 2018/085414 | A1 | 5/2018 |
| WO | WO 2018/086623 | A1 | 5/2018 |
| WO | WO 2018/093990 | A1 | 5/2018 |
| WO | WO 2018/098383 | A1 | 5/2018 |
| WO | WO 2018/098480 | A1 | 5/2018 |

(56) References Cited

FOREIGN PATENT DOCUMENTS

WO WO 2018/098587 A1 6/2018
WO WO 2018/099256 A1 6/2018
WO WO 2018/103686 A1 6/2018
WO WO 2018/106268 A1 6/2018
WO WO 2018/107028 A1 6/2018
WO WO 2018/107103 A1 6/2018
WO WO 2018/107129 A1 6/2018
WO WO 2018/108272 A1 6/2018
WO WO 2018/109101 A1 6/2018
WO WO 2018/111946 A1 6/2018
WO WO 2018/111947 A1 6/2018
WO WO 2018/112336 A1 6/2018
WO WO 2018/112446 A2 6/2018
WO WO 2018/119354 A1 6/2018
WO WO 2018/119359 A1 6/2018
WO WO 2018/130830 A1 7/2018
WO WO 2018/135838 A2 7/2018
WO WO 2018/136396 A2 7/2018
WO WO 2018/138385 A1 8/2018
WO WO 2018/148246 A1 8/2018
WO WO 2018/148256 A1 8/2018
WO WO 2018/148647 A2 8/2018
WO WO 2018/149418 A1 8/2018
WO WO 2018/149888 A1 8/2018
WO WO 2018/152418 A1 8/2018
WO WO 2018/154380 A1 8/2018
WO WO 2018/154387 A1 8/2018
WO WO 2018/154412 A1 8/2018
WO WO 2018/154413 A1 8/2018
WO WO 2018/154418 A1 8/2018
WO WO 2018/154439 A1 8/2018
WO WO 2018/154459 A1 8/2018
WO WO 2018/154462 A2 8/2018
WO WO 2018/156372 A1 8/2018
WO WO 2018/156824 A1 8/2018
WO WO 2018/161009 A1 9/2018
WO WO 2018/165504 A1 9/2018
WO WO 2018/165629 A1 9/2018
WO WO 2018/170015 A1 9/2018
WO WO 2018/170340 A1 9/2018
WO WO 2018/175502 A2 9/2018
WO WO 2018/176009 A1 9/2018
WO WO 2018/177351 A1 10/2018
WO WO 2018/179578 A1 10/2018
WO WO 2018/183403 A1 10/2018
WO WO 2018/195402 A1 10/2018
WO WO 2018/195545 A2 10/2018
WO WO 2018/195555 A1 10/2018
WO WO 2018/197020 A1 11/2018
WO WO 2018/197495 A1 11/2018
WO WO 2018/202800 A1 11/2018
WO WO 2018/204493 A1 11/2018
WO WO 2018/208755 A1 11/2018
WO WO 2018/208998 A1 11/2018
WO WO 2018/209158 A2 11/2018
WO WO 2018/209320 A1 11/2018
WO WO 2018/213708 A1 11/2018
WO WO 2018/213726 A1 11/2018
WO WO 2018/213771 A1 11/2018
WO WO 2018/213791 A1 11/2018
WO WO 2018/217852 A1 11/2018
WO WO 2018/217981 A1 11/2018
WO WO 2018/218166 A1 11/2018
WO WO 2018/218188 A2 11/2018
WO WO 2018/218206 A1 11/2018
WO WO 2019/005884 A1 1/2019
WO WO 2019/005886 A1 1/2019
WO WO 2019/010384 A1 1/2019
WO WO 2019/023680 A1 1/2019
WO WO 2019/079347 A1 4/2019
WO WO 2019/084062 A1 5/2019
WO WO 2019/118949 A1 6/2019
WO WO 2019/126709 A1 6/2019
WO WO 2019/139645 A2 7/2019
WO WO 2019/161251 A1 8/2019
WO WO 2019/168953 A1 9/2019
WO WO 2019/226953 A1 11/2019
WO WO 2019/241649 A1 12/2019
WO WO 2020/014261 A1 1/2020
WO WO 2020/028555 A2 2/2020
WO WO 2020/041751 A1 2/2020
WO WO 2020/051360 A1 3/2020
WO WO 2020/086908 A1 4/2020
WO WO 2020/092453 A1 5/2020
WO WO 2020/102659 A1 5/2020
WO WO 2020/154500 A1 7/2020
WO WO 2020/180975 A1 9/2020
WO WO 2020/181178 A1 9/2020
WO WO 2020/181180 A1 9/2020
WO WO 2020/181193 A1 9/2020
WO WO 2020/181195 A1 9/2020
WO WO 2020/181202 A1 9/2020
WO WO 2020/191153 A1 9/2020
WO WO 2020/191153 A2 9/2020
WO WO 2020/191171 A1 9/2020
WO WO 2020/191233 A1 9/2020
WO WO 2020/191234 A1 9/2020
WO WO 2020/191239 A1 9/2020
WO WO 2020/191241 A1 9/2020
WO WO 2020/191242 A1 9/2020
WO WO 2020/191243 A1 9/2020
WO WO 2020/191245 A1 9/2020
WO WO 2020/191246 A1 9/2020
WO WO 2020/191248 A1 9/2020
WO WO 2020/191249 A1 9/2020
WO WO 2020/210751 A1 10/2020
WO WO 2020/214842 A1 10/2020
WO WO 2020/236982 A1 11/2020
WO WO 2021/025750 A1 2/2021
WO WO 2021/030666 A1 2/2021
WO WO 2021/072328 A1 4/2021
WO WO 2021/108717 A2 6/2021
WO WO 2021/138469 A1 7/2021
WO WO 2021/155065 A1 8/2021
WO WO 2021/158921 A2 8/2021
WO WO 2021/158995 A1 8/2021
WO WO 2021/158999 A1 8/2021
WO WO 2021/222318 A1 11/2021
WO WO 2021/226558 A1 11/2021
WO WO 2022/067130 A2 3/2022
WO WO 2022/150790 A2 7/2022
WO WO 2023/015309 A2 2/2023

OTHER PUBLICATIONS

Bertsimas et al., Simulated annealing. Statistical Science. Feb. 1993;8(1):10-15. doi: 10.1214/ss/1177011077.
Chen et al., Dynamic imaging of genomic loci in living human cells by an optimized CRISPR/Cas system. Cell. Dec. 19, 2013;155(7):1479-91. doi: 10.1016/j.cell.2013.12.001. Erratum in: Cell. Jan. 16, 2014;156(1-2):373.
Fang et al., The Menu of Features that Define Primary MicroRNAs and Enable De Novo Design of MicroRNA Genes. Mol Cell. Oct. 1, 2015;60(1):131-45. doi: 10.1016/j.molcel.2015.08.015. Epub Sep. 24, 2015.
Geisberg et al., Global analysis of mRNA isoform half-lives reveals stabilizing and destabilizing elements in yeast. Cell. Feb. 13, 2014;156(4):812-24. doi: 10.1016/j.cell.2013.12.026.
Green et al., Characterization of the mechanical unfolding of RNA pseudoknots. J Mol Biol. Jan. 11, 2008;375(2):511-28. doi: 10.1016/j.jmb.2007.05.058. Epub May 26, 2007.
Hänsel-Hertsch et al., DNA G-quadruplexes in the human genome: detection, functions and therapeutic potential. Nat Rev Mol Cell Biol. May 2017;18(5):279-284. doi: 10.1038/nrm.2017.3. Epub Feb. 22, 2017.
Houck-Loomis et al., An equilibrium-dependent retroviral mRNA switch regulates translational recoding. Nature. Nov. 27, 2011;480(7378):561-4. doi: 10.1038/nature10657.
Houseley et al., The many pathways of RNA degradation. Cell. Feb. 20, 2009;136(4):763-76. doi: 10.1016/j.cell.2009.01.019.

(56) References Cited

OTHER PUBLICATIONS

Ibrahim et al., RNA recognition by 3'-to-5' exonucleases: the substrate perspective. Biochim Biophys Acta. Apr. 2008;1779(4):256-65. doi: 10.1016/j.bbagrm.2007.11.004. Epub Dec. 3, 2007.
Ku et al., Nucleic Acid Aptamers: An Emerging Tool for Biotechnology and Biomedical Sensing. Sensors (Basel). Jul. 6, 2015;15(7):16281-313. doi: 10.3390/s150716281.
Millevoi et al., G-quadruplexes in RNA biology. Wiley Interdiscip Rev RNA. Jul.-Aug. 2012;3(4):495-507. doi: 10.1002/wrna. 1113. Epub Apr. 4, 2012.
Micozzi et al., Human cytidine deaminase: a biochemical characterization of its naturally occurring variants. Int J Biol Macromol. Feb. 2014;63:64-74. doi: 10.1016/j.ijbiomac.2013.10.029. Epub Oct. 29, 2013. Erratum in: Int J Biol Macromol. Feb. 2014;63:262.
Pandey et al., Effect of loops and G-quartets on the stability of RNA G-quadruplexes. J Phys Chem B. Jun. 13, 2013;117(23):6896-905. doi: 10.1021/jp401739m. Epub May 29, 2013. Supplementary Information, 21 pages.
Piotukh et al., Directed evolution of sortase A mutants with altered substrate selectivity profiles. J Am Chem Soc. Nov. 9, 2011;133(44):17536-9. doi: 10.1021/ja205630g. Epub Oct. 13, 2011.
Robert et al., Virus-Like Particles Derived from HIV-1 for Delivery of Nuclear Proteins: Improvement of Production and Activity by Protein Engineering. Mol Biotechnol. Jan. 2017;59(1):9-23. doi: 10.1007/s12033-016-9987-1.
Wu et al., MLV based viral-like-particles for delivery of toxic proteins and nuclear transcription factors. Biomaterials. Sep. 2014;35(29):8416-26. doi: 10.1016/j.biomaterials.2014.06.006. Epub Jul. 3, 2014.
Wu et al., Widespread Influence of 3'-End Structures on Mammalian mRNA Processing and Stability. Cell. May 18, 2017;169(5):905-917.e11. doi: 10.1016/j.cell.2017.04.036.
Yi et al., Engineering of TEV protease variants by yeast ER sequestration screening (YESS) of combinatorial libraries. Proc Natl Acad Sci U S A. Apr. 30, 2013;110(18):7229-34. doi: 10.1073/pnas.1215994110. Epub Apr. 15, 2013.
U.S. Appl. No. 61/716,256, filed Oct. 19, 2012, Jinek et al..
U.S. Appl. No. 61/717,324, filed Oct. 23, 2012, Cho et al..
U.S. Appl. No. 61/734,256, filed Dec. 6, 2012, Chen et al..
U.S. Appl. No. 61/758,624, filed Jan. 30, 2013, Chen et al..
U.S. Appl. No. 61/761,046, filed Feb. 5, 2013, Knight et al..
U.S. Appl. No. 61/794,422, filed Mar. 15, 2013, Knight et al..
U.S. Appl. No. 61/803,599, filed Mar. 20, 2013, Kim et al..
U.S. Appl. No. 61/837,481, filed Jun. 20, 2013, Cho et al..
U.S. Appl. No. 61/838,178, filed Jun. 21, 2013, Joung et al..
U.S. Appl. No. 61/874,682, filed Sep. 6, 2013, Liu et al..
U.S. Appl. No. 61/874,746, filed Sep. 6, 2013, Liu et al..
U.S. Appl. No. 62/288,661, filed Jan. 29, 2016, Muir et al..
U.S. Appl. No. 62/357,332, filed Jun. 30, 2016, Liu et al..
Extended European Search Report for EP 15830407.1, mailed Mar. 2, 2018.
Extended European Search Report for EP 19181479.7, mailed Oct. 31, 2019.
Extended European Search Report for EP 22156453.7, mailed Sep. 26, 2022.
International Preliminary Report on Patentability for PCT/US2014/048390, mailed on Mar. 7, 2019.
International Preliminary Report on Patentability for PCT/US2016/058344, mailed May 3, 2018.
International Preliminary Report on Patentability for PCT/US2017/045381, mailed Feb. 14, 2019.
International Preliminary Report on Patentability for PCT/US2017/046144, mailed Feb. 21, 2019.
International Preliminary Report on Patentability for PCT/US2017/056671, mailed on Apr. 25, 2019.
International Preliminary Report on Patentability for PCT/US2017/068105, mailed on Jul. 4, 2019.
International Preliminary Report on Patentability for PCT/US2017/068114, mailed on Jul. 4, 2019.
International Preliminary Report on Patentability for PCT/US2012/047778, mailed Feb. 6, 2014.
International Preliminary Report on Patentability for PCT/US2014/050283, mailed Feb. 18, 2016.
International Preliminary Report on Patentability for PCT/US2014/052231, mailed Mar. 3, 2016.
International Preliminary Report on Patentability for PCT/US2014/054247, mailed Mar. 17, 2016.
International Preliminary Report on Patentability for PCT/US2014/054291, mailed Mar. 17, 2016.
International Preliminary Report on Patentability for PCT/US2014/070038, mailed Jun. 23, 2016.
International Preliminary Report on Patentability for PCT/US2015/042770, mailed Dec. 19, 2016.
International Preliminary Report on Patentability for PCT/US2015/058479, mailed May 11, 2017.
International Preliminary Report on Patentability for PCT/US2018/021664, mailed on Sep. 19, 2019.
International Preliminary Report on Patentability for PCT/US2018/021878, mailed on Sep. 19, 2019.
International Preliminary Report on Patentability for PCT/US2018/021880, mailed on Sep. 19, 2019.
International Preliminary Report on Patentability for PCT/US2018/024208, mailed on Oct. 3, 2019.
International Preliminary Report on Patentability for PCT/US2018/032460, mailed Nov. 21, 2019.
International Preliminary Report on Patentability or PCT/US2014/054252, mailed Mar. 17, 2016.
International Search Report and Written Opinion for PCT/US2012/047778, mailed May 30, 2013.
International Search Report and Written Opinion for PCT/US2014/050283, mailed Nov. 6, 2014.
International Search Report and Written Opinion for PCT/US2014/052231, mailed Dec. 4, 2014.
International Search Report and Written Opinion for PCT/US2014/052231, mailed Jan. 30, 2015.(Corrected Version).
International Search Report and Written Opinion for PCT/US2014/054247, mailed Mar. 27, 2015.
International Search Report and Written Opinion for PCT/US2014/054252, mailed Mar. 5, 2015.
International Search Report and Written Opinion for PCT/US2014/054291, mailed Mar. 27, 2015.
International Search Report and Written Opinion for PCT/US2014/070038, mailed Apr. 14, 2015.
International Search Report and Written Opinion for PCT/US2015/042770, mailed Feb. 23, 2016.
International Search Report and Written Opinion for PCT/US2015/058479, mailed Feb. 11, 2016.
International Search Report and Written Opinion for PCT/US2016/044546, mailed Dec. 28, 2016.
International Search Report and Written Opinion for PCT/US2016/058344, mailed Apr. 20, 2017.
International Search Report and Written Opinion for PCT/US2017/045381, mailed Oct. 26, 2017.
International Search Report and Written Opinion for PCT/US2017/046144, mailed Oct. 10, 2017.
International Search Report and Written Opinion for PCT/US2017/056671, mailed Feb. 20, 2018.
International Search Report and Written Opinion for PCT/US2017/068105, mailed Apr. 4, 2018.
International Search Report and Written Opinion for PCT/US2017/068114, mailed Mar. 20, 2018.
International Search Report and Written Opinion for PCT/US2017/48390, mailed Jan. 9, 2018.
International Search Report for PCT/US2013/032589, mailed Jul. 26, 2013.
International Search Report for PCT/US2018/021664, mailed Jun. 21, 2018.
International Search Report for PCT/US2018/021878, mailed Aug. 20, 2018.
International Search Report for PCT/US2018/021880, mailed Jun. 20, 2018.

(56) References Cited

OTHER PUBLICATIONS

International Search Report for PCT/US2018/024208, mailed Aug. 23, 2018.
International Search Report for PCT/US2018/025887, mailed Jun. 21, 2018.
International Search Report for PCT/US2018/032460, mailed Jul. 11, 2018.
International Search Report for PCT/US2018/048969, mailed Jul. 31, 2019.
Invitation to Pay Additional Fees for PCT/US2014/054291, mailed Dec. 18, 2014.
Invitation to Pay Additional Fees for PCT/US2016/058344, mailed Mar. 1, 2017.
Invitation to Pay Additional Fees for PCT/US2017/056671, mailed Dec. 21, 2017.
Invitation to Pay Additional Fees for PCT/US2017/48390, mailed Nov. 7, 2017.
Invitation to Pay Additional Fees for PCT/US2018/021878, mailed Jun. 8, 2018.
Partial European Search Report for Application No. EP 19187331.4, mailed Dec. 19, 2019.
Partial Supplementary European Search Report for Application No. EP 12845790.0, mailed Mar. 18, 2015.
Supplementary European Search Report for Application No. EP 12845790.0, mailed Oct. 12, 2015.
[No Author Listed] HyPhy—Hypothesis testing using Phylogenies. Last modified Apr. 21, 2017. Accessed online via http://hyphy.org/w/index.php/Main_Page on Apr. 28, 2021.
[No Author Listed] NCBI Accession No. XP_015843220.1. C ->U editing enzyme APOBEC-1 [Peromyscus maniculatus bairdii], XP002793540. Mar. 21, 2016.
[No Author Listed] Ncbi Accession No. XP_021505673.1. C ->U editing enzyme APOBEC-1 [Meriones unguiculatus], XP002793541. Jun. 27, 2017.
[No Author Listed] Score result for SEQ 355 to W02017032580. Muir et al. 2016.
[No Author Listed], "Lambda DNA" from Catalog & Technical Reference. New England Biolabs Inc. 2002/2003. pp. 133 and 270-273.
[No Author Listed], EMBL Accession No. Q99ZW2. Nov. 2012. 2 pages.
[No. Author Listed], Invitrogen Lipofectamine™ 2000 product sheets, 2002. 2 pages.
[No Author Listed], Invitrogen Lipofectamine™ 2000 product sheets, 2005. 3 pages.
[No Author Listed], Invitrogen Lipofectamine™ LTX product sheets, 2011. 4 pages.
[No Author Listed], Mus musculus (Mouse). UniProtKB Accession No. P51908 (ABEC1_MOUSE). Oct. 1, 1996. 10 pages.
[No Author Listed], Thermo Fisher Scientific—How Cationic Lipid Mediated Transfection Works, retrieved from the internet Aug. 27, 2015. 2 pages.
Abremski et al., Bacteriophage P1 site-specific recombination. Purification and properties of the Cre recombinase protein. J Biol Chem. Feb. 10, 1984;259(3):1509-14.
Abudayyeh et al., C2c2 is a single-component programmable RNA-guided RNA-targeting CRISPR effector. Science. Aug. 5, 2016;353(6299):aaf5573. doi: 10.1126/science.aaf5573. Epub Jun. 2, 2016.
Ada et al., Carbohydrate-protein conjugate vaccines. Clin Microbiol Infect. Feb. 2003;9(2):79-85. doi: 10.1046/j.1469-0691.2003.00530.x.
Adamala et al., Programmable RNA-binding protein composed of repeats of a single modular unit. Proc Natl Acad Sci U S A. May 10, 2016;113(19):E2579-88. doi: 10.1073/pnas.1519368113. Epub Apr. 26, 2016.
Adams et al., New biarsenical ligands and tetracysteine motifs for protein labeling in vitro and in vivo: synthesis and biological applications. J Am Chem Soc. May 29, 2002;124(21):6063-76. doi: 10.1021/ja017687n.
Addgene Plasmid # 44246. pdCas9-humanized, 2017, Stanley Qi.
Addgene Plasmid # 73021. PCMV-BE3, 2017, David Liu.
Addgene Plasmid # 79620. pcDNA3.1_pCMV-nCas-PmCDA1-ugi pH1-gRNA(HPRT), 2017, Akihiko Kondo.
Adrian et al., Targeted SAINT-O-Somes for improved intracellular delivery of siRNA and cytotoxic drugs into endothelial cells. J Control Release. Jun. 15, 2010;144(3):341-9. doi: 10.1016/j.jconrel.2010.03.003. Epub Mar. 11, 2010.
Aguilera et al., Systemic in vivo distribution of activatable cell penetrating peptides is superior to that of cell penetrating peptides. Integr Biol (Camb). Jun. 2009;1(5-6):371-81. doi: 10.1039/b904878b. Epub May 11, 2009.
Aguilo et al., Coordination of m(6)A mRNA Methylation and Gene Transcription by ZFP217 Regulates Pluripotency and Reprogramming. Cell Stem Cell. Dec. 3, 2015;17(6):689-704. doi: 10.1016/j.stem.2015.09.005. Epub Oct. 29, 2015.
Ahmad et al., Antibody-mediated specific binding and cytotoxicity of liposome-entrapped doxorubicin to lung cancer cells in vitro. Cancer Res. Sep. 1, 1992;52(17):4817-20.
Ai et al., C-terminal Loop Mutations Determine Folding and Secretion Properties of PCSK9. iMedPub J: Biochem Mol Biol J. Nov. 5, 2016;2(3):17. doi: 10.21767/2471-8084.100026. 12 pages.
Aihara et al., A conformational switch controls the DNA cleavage activity of lambda integrase. Mol Cell. Jul. 2003;12(1):187-98.
Aik et al., Structure of human RNA N6-methyladenine demethylase ALKBH5 provides insights into its mechanisms of nucleic acid recognition and demethylation. Nucleic Acids Res. Apr. 2014;42(7):4741-54. doi: 10.1093/nar/gku085. Epub Jan. 30, 2014.
Akinc et al., A combinatorial library of lipid-like materials for delivery of RNAi; therapeutics. Nat Biotechnol. May 2008;26(5):561-9. doi: 10.1038/nbt1402. Epub; Apr. 27, 20087
Akins et al., Mitochondrial plasmids of Neurospora: integration into mitochondrial DNA and evidence for reverse transcription in mitochondria. Cell. Nov. 12, 1986;47(4):505-16. doi: 10.1016/0092-8674(86)90615-x.
Akinsheye et al., Fetal hemoglobin in sickle cell anemia. Blood. Jul. 7, 2011;118(1):19-27. doi: 10.1182/blood-2011-03-325258. Epub Apr. 12, 2011.
Akopian et al., Chimeric recombinases with designed DNA sequence recognition. Proc Natl Acad Sci U S A. Jul. 22, 2003;100(15):8688-91. Epub Jul. 1, 2003.
Al-Taei et al., Intracellular traffic and fate of protein transduction domains HIV-1 Tat peptide and octaarginine. Implications for their utilization as drug delivery vectors. Bioconjug Chem. Jan.-Feb. 2006;17(1):90-100.
Alarcón et al., HNRNPA2B1 Is a Mediator of m(6)A-Dependent Nuclear RNA Processing Events. Cell. Sep. 10, 2015;162(6):1299-308. doi: 10.1016/j.cell.2015.08.011. Epub Aug. 27, 2015.
Alarcón et al., N6-methyladenosine marks primary microRNAs for processing. Nature. Mar. 26, 2015;519(7544):482-5. doi: 10.1038/nature14281. Epub Mar. 18, 2015.
Alexander, HFE-associated hereditary hemochromatosis. Genet Med. May 2009;11(5):307-13. doi: 10.1097/GIM.0b013e31819d30f2.
Alexandrov et al., Signatures of mutational processes in human cancer. Nature. Aug. 22, 2013;500(7463):415-21. doi: 10.1038/nature12477. Epub Aug. 14, 2013.
Ali et al., Novel genetic abnormalities in Bernard-Soulier syndrome in India. Ann Hematol. Mar. 2014;93(3):381-4. doi: 10.1007/s00277-013-1895-x. Epub Sep. 1, 2013.
Allen et al., Liposomal drug delivery systems: from concept to clinical applications. Adv Drug Deliv Rev. Jan. 2013;65(1):36-48. doi: 10.1016/j.addr.2012.09.037. Epub Oct. 1, 2012.
Altschul et al., Basic local alignment search tool. J Mol Biol. Oct. 5, 1990;215(3):403-10. doi: 10.1016/S0022-2836(05)80360-2.
Amato et al., Interpreting elevated fetal hemoglobin in pathology and health at the basic laboratory level: new and known Y- gene mutations associated with hereditary persistence of fetal hemoglobin. Int J Lab Hematol. Feb. 2014;36(1):13-9. doi: 10.1111/ijlh.12094. Epub Apr. 29, 2013.
Ames et al., A eubacterial riboswitch class that senses the coenzyme tetrahydrofolate. Chem Biol. Jul. 30, 2010;17(7):681-5. doi: 10.1016/j.chembiol.2010.05.020.

(56) References Cited

OTHER PUBLICATIONS

Amrann et al., Tightly regulated tac promoter vectors useful for the expression of unfused and fused proteins in *Escherichia coli*. Gene. Sep. 30, 1988;69(2):301-15.
Anders et al., Chapter One: In Vitro Enzymology of Cas9. in Methods in Enzymology, eds Doudna et al. 2014: 546:1-20.
Anders et al., Structural basis of PAM-dependent target DNA recognition by the Cas9 endonuclease. Nature. Sep. 25, 2014;513(7519):569-73. doi: 10.1038/nature13579. Epub Jul. 27, 2014.
Anderson, Human gene therapy. Science. May 8, 1992;256(5058):808-13. doi: 10.1126/science.1589762.
Andrŕ et al., Axotomy-induced expression of calcium-activated chloride current in subpopulations of mouse dorsal root ganglion neurons. J Neurophysiol. Dec. 2003;90(6):3764-73. doi: 10.1152/jn.00449.2003. Epub Aug. 27, 2003.
Anzalone et al., Reprogramming eukaryotic translation with ligand-responsive synthetic RNA switches. Nat Methods. May 2016;13(5):453-8. doi: 10.1038/nmeth.3807. Epub Mar. 21, 2016.
Aplan, Causes of oncogenic chromosomal translocation. Trends Genet. Jan. 2006;22(1):46-55. doi: 10.1016/j.tig.2005.10.002. Epub Oct. 28, 2005.
Arakawa et al., A method to convert mRNA into a gRNA library for CRISPR/Cas9 editing of any organism. Sci Adv. Aug. 24, 2016;2(8):e1600699. doi: 10.1126/sciadv.1600699.
Araki et al., Comparative analysis of right element mutant lox sites on recombination efficiency in embryonic stem cells. BMC Biotechnol. Mar. 31, 2010;10:29. doi: 10.1186/1472-6750-10-29.
Araki et al., Site-specific recombinase, R, encoded by yeast plasmid pSR1. J Mol Biol. May 5, 1992;225(1):25-37. doi: 10.1016/0022-2836(92)91023-i.
Araki et al., Targeted integration of DNA using mutant lox sites in embryonic stem cells. Nucleic Acids Res. Feb. 15, 1997;25(4):868-72. doi: 10.1093/nar/25.4.868.
Arambula et al., Surface display of a massively variable lipoprotein by a Legionella diversity-generating retroelement. Proc Natl Acad Sci U S A. May 14, 2013;110(20):8212-7. doi: 10.1073/pnas.1301366110. Epub Apr. 30, 2013.
Arbab et al., Cloning-free CRISPR. Stem Cell Reports. Nov. 10, 2015;5(5):908-917. doi: 10.1016/j.stemcr.2015.09.022. Epub Oct. 29, 2015.
Arezi et al., Novel mutations in Moloney Murine Leukemia Virus reverse transcriptase increase thermostability through tighter binding to template-primer. Nucleic Acids Res. Feb. 2009;37(2):473-81. doi: 10.1093/nar/gkn952. Epub Dec. 4, 2008.
Arnold et al., Mutants of Tn3 resolvase which do not require accessory binding sites for recombination activity. EMBO J. Mar. 1, 1999;18(5):1407-14.
Asante et al., A naturally occurring variant of the human prion protein completely prevents prion disease. Nature. Jun. 25, 2015;522(7557):478-81. doi: 10.1038/nature14510. Epub Jun. 10, 2015.
Asokan et al., The AAV vector toolkit: poised at the clinical crossroads. Mol Ther. Apr. 2012;20(4):699-708. doi: 10.1038/mt.2011.287. Epub Jan. 24, 2012.
Atkins et al., Ribosomal frameshifting and transcriptional slippage: From genetic steganography and cryptography to adventitious use. Nucleic Acids Res. Sep. 6, 2016;44(15):7007-78. doi: 10.1093/nar/gkw530. Epub Jul. 19, 2016.
Auer et al., Highly efficient CRISPR/Cas9-mediated knock-in in zebrafish by homology-independent DNA repair. Genome Res. Jan. 2014;24(1):142-53. doi: 10.1101/gr.161638.113. Epub Oct. 31, 2013.
Auricchio et al., Exchange of surface proteins impacts on viral vector cellular specificity and transduction characteristics: the retina as a model. Hum Mol Genet. Dec. 15, 2001;10(26):3075-81. doi: 10.1093/hmg/10.26.3075.
Autieri et al., IRT-1, a novel interferon-gamma-responsive transcript encoding a growth-suppressing basic leucine zipper protein. J Biol Chem. Jun. 12, 1998;273(24):14731-7. doi: 10.1074/jbc.273.24.14731.
Avidan et al., The processivity and fidelity of DNA synthesis exhibited by the reverse transcriptase of bovine leukemia virus. Eur J Biochem. Feb. 2002;269(3):859-67. doi: 10.1046/j.0014-2956.2001.02719.x.
Baba et al., Construction of *Escherichia coli* K-12 in-frame, single-gene knockout mutants: the Keio collection. Mol Syst Biol. 2006;2:2006.0008. doi: 10.1038/msb4100050. Epub Feb. 21, 2006.
Bacman et al., Specific elimination of mutant mitochondrial genomes in patient-derived cells by mitoTALENs. Nat Med. Sep. 2013;19(9):1111-3. doi: 10.1038/nm.3261. Epub Aug. 4, 2013.
Badran et al., Continuous evolution of Bacillus thuringiensis toxins overcomes insect resistance. Nature. May 5, 2016;533(7601):58-63. doi: 10.1038/nature17938. Epub Apr. 27, 2016.
Badran et al., Development of potent in vivo mutagenesis plasmids with broad mutational spectra. Nat Commun. Oct. 7, 2015;6:8425. doi: 10.1038/ncomms9425.
Badran et al., In vivo continuous directed evolution. Curr Opin Chem Biol. Feb. 2015;24:1-10. doi: 10.1016/j.cbpa.2014.09.040. Epub Nov. 7, 2014.
Bae et al., Cas-OFFinder: a fast and versatile algorithm that searches for potential off-target sites of Cas9 RNA-guided endonucleases. Bioinformatics. May 15, 2014;30(10):1473-5. doi: 10.1093/bioinformatics/btu048. Epub Jan. 24, 2014.
Bae et al., Microhomology-based choice of Cas9 nuclease target sites. Nat Methods. Jul. 2014;11(7):705-6. doi: 10.1038/nmeth.3015.
Bae et al., Protective anti-tumour immune responses by murine dendritic cells pulsed with recombinant Tat-carcinoembryonic antigen derived from *Escherichia coli*. Clin Exp Immunol. Jul. 2009; 157(1):128-38. doi: 10.1111/j.1365-2249.2009.03943.x.
Bagal et al., Recent progress in sodium channel modulators for pain. Bioorg Med Chem Lett. Aug. 15, 2014;24(16):3690-9. doi: 10.1016/j.bmcl.2014.06.038. Epub Jun. 21, 2014.
Balakrishnan et al., Flap endonuclease 1. Annu Rev Biochem. 2013;82:119-38. doi: 10.1146/annurev-biochem-072511-122603. Epub Feb. 28, 2013.
Baldari et al., A novel leader peptide which allows efficient secretion of a fragment of human interleukin 1 beta in Saccharomyces cerevisiae. EMBO J. Jan. 1987;6(1):229-34.
Banerjee et al., Cadmium inhibits mismatch repair by blocking the ATPase activity of the MSH2-MSH6 complex [published correction appears in Nucleic Acids Res. 2005;33(5): 1738]. Nucleic Acids Res. 2005;33(4):1410-1419. Published Mar. 3, 2005. doi: 10.1093/nar/gki291.
Banerji et al., A lymphocyte-specific cellular enhancer is located downstream of the joining region in immunoglobulin heavy chain genes. Cell. Jul. 1983;33(3):729-40. doi: 10.1016/0092-8674(83)90015-6.
Bannert et al., Retroelements and the human genome: new perspectives on an old relation. Proc Natl Acad Sci U S A. Oct. 5, 2004;101 Suppl 2(Suppl 2):14572-9. doi: 10.1073/pnas.0404838101. Epub Aug. 13, 2004.
Baranauskas et al., Generation and characterization of new highly thermostable and processive M-MuLV reverse transcriptase variants. Protein Eng Des Sel. Oct. 2012;25(10):657-68. doi: 10.1093/protein/gzs034. Epub Jun. 12, 2012.
Barmania et al., C—C chemokine receptor type five (CCR5): An emerging target for the control of HIV infection. Appl Transl Genom. May 26, 2013;2:3-16. doi: 10.1016/j.atg.2013.05.004.
Barnes et al., Repair and genetic consequences of endogenous DNA base damage in mammalian cells. Annu Rev Genet. 2004;38:445-76.
Barnes et al., The fidelity of Taq polymerase catalyzing PCR is improved by an N-terminal deletion. Gene. Mar. 1, 1992;112(1):29-35. doi: 10.1016/0378-1119(92)90299-5.
Barrangou et al., CRISPR provides acquired resistance against viruses in prokaryotes. Science. Mar. 23, 2007;315(5819):1709-12.
Barrangou, RNA-mediated programmable DNA cleavage. Nat Biotechnol. Sep. 2012;30(9):836-8. doi: 10.1038/nbt.2357.
Bartlett et al., Efficient expression of protein coding genes from the murine Ul small nuclear RNA promoters. Proc Natl Acad Sci U S A. Aug. 20, 1996;93(17):8852-7. doi: 10.1073/pnas.93.17.8852.

(56) References Cited

OTHER PUBLICATIONS

Basha et al., Influence of cationic lipid composition on gene silencing properties of lipid nanoparticle formulations of siRNA in antigen-presenting cells. Mol Ther. Dec. 2011; 19(12):2186-200. doi: 10.1038/mt.2011.190. Epub Oct. 4, 2011.
Bass, B.L., RNA editing by adenosine deaminases that act on RNA. Annu Rev Biochem. 2002;71:817-46. doi: 10.1146/annurev.biochem.71.110601.135501. Epub Nov. 9, 2001.
Basturea et al., Substrate specificity and properties of the *Escherichia coli* 16S rRNA methyltransferase, RsmE. RNA. Nov. 2007;13(11):1969-76. doi: 10.1261/rna.700507. Epub Sep. 13, 2007.
Batey et al., Structure of a natural guanine-responsive riboswitch complexed with the metabolite hypoxanthine. Nature. Nov. 18, 2004;432(7015):411-5.
Beale et al., Comparison of the differential context-dependence of DNA deamination by APOBEC enzymes: correlation with mutation spectra in vivo. J Mol Biol. Mar. 26, 2004;337(3):585-96.
Beaudry et al., Directed evolution of an RNA enzyme. Science. Jul. 31, 1992;257(5070):635-41. doi: 10.1126/science.1496376.
Bebenek et al., Error-prone polymerization by HIV-1 reverse transcriptase. Contribution of template-primer misalignment, miscoding, and termination probability to mutational hot spots. J Biol Chem. May 15, 1993;268(14):10324-34.
Bedell et al., In vivo genome editing using a high-efficiency TALEN system. Nature. Nov. 1, 2012;491(7422):114-8. Doi: 10.1038/nature11537. Epub Sep. 23, 2012.
Begley, Scientists unveil the 'most clever CRISPR gadget' so far. STAT, Apr. 20, 2016. https://www.statnews.com/2016/04/20/clever-crispr-advance-unveiled/.
Behr, Gene transfer with synthetic cationic amphiphiles: prospects for gene therapy. Bioconjug Chem. Sep. 1994-Oct;5(5):382-9. doi: 10.1021/bc00029a002.
Bell et al., Ribozyme-catalyzed excision of targeted sequences from within RNAs. Biochemistry. Dec. 24, 2002;41(51):15327-33. doi: 10.1021/bi0267386.
Belshaw et al., Controlling programmed cell death with a cyclophilin-cyclosporin-based chemical inducer of dimerization. Chem Biol. Sep. 1996;3(9):731-8. doi: 10.1016/s1074-5521(96)90249-5.
Belshaw et al., Controlling protein association and subcellular localization with a synthetic ligand that induces heterodimerization of proteins. Proc Natl Acad Sci U S A. May 14, 1996;93(10):4604-7. doi: 10.1073/pnas.93.10.4604.
Benarroch, HCN channels: function and clinical implications. Neurology. Jan. 15, 2013;80(3):304-10. doi: 10.1212/WNL.0b013e31827dec42.
Bennett et al., Painful and painless channelopathies. Lancet Neurol. Jun. 2014;13(6):587-99. doi: 10.1016/S1474-4422(14)70024-9. Epub May 6, 2014.
Bentin, T., A ribozyme transcribed by a ribozyme. Artif DNA PNA XNA. Apr. 2011;2(2):40-42. doi: 10.4161/adna.2.2.16852.
Berger et al., Reverse transcriptase and its associated ribonuclease H: interplay of two enzyme activities controls the yield of single-stranded complementary deoxyribonucleic acid. Biochemistry. May 10, 1983;22(10):2365-72. doi: 10.1021/bi00279a010.
Berges et al., Transduction of brain by herpes simplex virus vectors. Mol Ther. Jan. 2007;15(1):20-9. doi: 10.1038/sj.mt.6300018.
Berkhout et al., Identification of an active reverse transcriptase enzyme encoded by a human endogenous HERV-K retrovirus. J Virol. Mar. 1999;73(3):2365-75. doi: 10.1128/JVI.73.3.2365-2375.1999.
Bernhart et al., Local RNA base pairing probabilities in large sequences. Bioinformatics. Mar. 1, 2006;22(5):614-5. doi: 10.1093/bioinformatics/btk014. Epub Dec. 20, 2005.
Bernstein et al., Role for a bidentate ribonuclease in the initiation step of RNA interference. Nature. Jan. 18, 2001;409(6818):363-6. doi: 10.1038/35053110.
Bershtein et al., Advances in laboratory evolution of enzymes. Curr Opin; Chem Biol. Apr. 2008; 12(2):151-8. doi: 10.1016/j.cbpa.2008.01.027. Epub Mar. 7, 2008. Review.
Bertolotti et al., Toward genosafe endonuclease-boosted gene targeting using breakthrough CRISP/Cas9 for next generation stem cell gene therapy culminating in efficient ex VIVO in VIVO gene repair/genomic editing. Molecular Therapy. May 2015;23(Suppl1):S139. Abstract 350. 18th Ann Meeting of the American Society of Gene and Cell Therapy. ASGCT 2015. New Orleans, LA. May 13, 2015-May 16, 2015.
Bertrand et al., Localization of ASH1 mRNA particles in living yeast. Mol Cell. Oct. 1998;2(4):437-45. doi: 10.1016/s1097-2765(00)80143-4.
Beumer et al., Efficient gene targeting in Drosophila with zinc-finger nucleases. Genetics. Apr. 2006;172(4):2391-403. Epub Feb. 1, 2006.
Bhagwat, DNA-cytosine deaminases: from antibody maturation to antiviral defense. DNA Repair (Amst). Jan. 5, 2004;3(1):85-9.
Bi et al., Pseudo attP sites in favor of transgene integration and expression in cultured porcine cells identified by Streptomyces phage phiC31 integrase. BMC Mol Biol. Sep. 8, 2013;14:20. doi: 10.1186/1471-2199-14-20.
Bibb et al., Integration and excision by the large serine recombinase phiRv1 integrase. Mol Microbiol. Mar. 2005;55(6): 1896-910. doi: 10.1111/j.1365-2958.2005.04517.x.
Bibikova et al., Stimulation of homologous recombination through targeted cleavage by chimeric nucleases. Mol Cell Biol. Jan. 2001;21(1):289-97.
Bibikova et al., Targeted chromosomal cleavage and mutagenesis in Drosophila using zinc-finger nucleases. Genetics. Jul. 2002;161(3):1169-75. doi: 10.1093/genetics/161.3.1169.
Biehs et al., DNA Double-Strand Break Resection Occurs during Non-homologous End Joining in G1 but Is Distinct from Resection during Homologous Recombination. Mol Cell. Feb. 16, 2017;65(4):671-684.e5. doi: 10.1016/j.molcel.2016.12.016. Epub Jan. 26, 2017.
Billon et al., CRISPR-Mediated Base Editing Enables Efficient Disruption of Eukaryotic Genes through Induction of STOP Codons. Mol Cell. Sep. 21, 2017;67(6):1068-1079.e4. doi: 10.1016/j.molcel.2017.08.008. Epub Sep. 7, 2017.
Birling et al., Site-specific recombinases for manipulation of the mouse genome. Methods Mol Biol. 2009;561:245-63. doi: 10.1007/978-1-60327-019-9_16.
Biswas et al., A structural basis for allosteric control of DNA recombination by lambda integrase. Nature. Jun. 23, 2005;435(7045):1059-66. doi: 10.1038/nature03657.
Bitinaite et al., FokI dimerization is required for DNA cleavage. Proc Natl Acad Sci U S A. Sep. 1, 1998;95(18):10570-5.
Blaese et al., Vectors in cancer therapy: how will they deliver? Cancer Gene Ther. Dec. 1995;2(4):291-7.
Blain et al., Nuclease activities of Moloney murine leukemia virus reverse transcriptase. Mutants with altered substrate specificities. J Biol Chem. Nov. 5, 1993;268(31):23585-92.
Blaisonneau et al., A circular plasmid from the yeast Torulaspora delbrueckii. Plasmid. 1997;38(3):202-9. doi: 10.1006/plas.1997.1315.
Blau et al., A proliferation switch for genetically modified cells. PNAS Apr. 1, 1997 94 (7) 3076-3081; https://doi.org/10.1073/pnas.94.7.3076.
Blauw et al., SMN1 gene duplications are associated with sporadic ALS. Neurology. Mar. 13, 2012;78(11):776-80. doi: 10.1212/WNL.0b013e318249f697. Epub Feb. 8, 2012.
Bloom et al., Evolving strategies for enzyme engineering. Curr Opin Struct Biol. Aug. 2005; 15(4):447-52.
Boch et al., Breaking the code of DNA binding specificity of TAL-type III effectors. Science. Dec. 11, 2009;326(5959):1509-12. Doi: 10.1126/science.1178811.
Boch, TALEs of genome targeting. Nat Biotechnol. Feb. 2011;29(2):135-6. Doi: 10.1038/nbt.1767.
Bodi et al., Yeast m6A Methylated mRNAs Are Enriched on Translating Ribosomes during Meiosis, and under Rapamycin Treatment. PLoS One. Jul. 17, 2015;10(7):e0132090. doi: 10.1371/journal.pone.0132090.
Boeckle et al., Melittin analogs with high lytic activity at endosomal pH enhance transfection with purified targeted PEI polyplexes. J Control Release. May 15, 2006;112(2):240-8. Epub Mar. 20, 2006.

(56) References Cited

OTHER PUBLICATIONS

Boersma et al., Selection strategies for improved biocatalysts. Febs J. May 2007;274(9):2181-95.
Bogdanove et al., TAL effectors: customizable proteins for DNA targeting. Science. Sep. 30, 2011;333(6051):1843-6. doi: 10.1126/science.1204094.
Bohlke et al., Sense codon emancipation for proteome-wide incorporation of noncanonical amino acids: rare isoleucine codon AUA as a target for genetic code expansion. FEMS Microbiol Lett. Feb. 2014;351(2):133-44. doi: 10.1111/1574-6968.12371. Epub Jan. 27, 2014.
Bolotin et al., Clustered regularly interspaced short palindrome repeats (CRISPRs) have spacers of extrachromosomal origin. Microbiology. Aug. 2005;151(Pt 8):2551-61.
Bolusani et al., Evolution of variants of yeast site-specific recombinase Flp that utilize native genomic sequences as recombination target sites. Nucleic Acids Res. 2006;34(18):5259-69. Epub Sep. 26, 2006.
Bondeson et al., Inversion of the IDS gene resulting from recombination with IDS-related sequences is a common cause of the Hunter syndrome. Hum Mol Genet. Apr. 1995;4(4):615-21. doi: 10.1093/hmg/4.4.615.
Borchardt et al., Controlling mRNA stability and translation with the CRISPR endoribonuclease Csy4. RNA. Nov. 2015;21(11):1921-30. doi: 10.1261/rna.051227.115. Epub Sep. 9, 2015.
Borman, Improved route to single-base genome editing. Chemical & Engineering News, Apr. 25, 2016;94(17)p5. http://cen.acs.org/articles/94/i17/Improved-route-single-base-genome.html.
Bothmer et al., Characterization of the interplay between DNA repair and CRISPR/Cas9-induced DNA lesions at an endogenous locus. Nat Commun. Jan. 9, 2017;8:13905. doi: 10.1038/ncomms13905.
Bourinet et al., Silencing of the Cav3.2 T-type calcium channel gene in sensory neurons demonstrates its major role in nociception. EMBO J. Jan. 26, 2005;24(2):315-24. doi: 10.1038/sj.emboj.7600515. Epub Dec. 16, 2004.
Boutabout et al., DNA synthesis fidelity by the reverse transcriptase of the yeast retrotransposon Ty1. Nucleic Acids Res. Jun. 1, 2001;29(11):2217-22. doi: 10.1093/nar/29.11.2217.
Box et al., A multi-domain protein system based on the HC fragment of tetanus toxin for targeting DNA to neuronal cells. J Drug Target. Jul. 2003;11(6):333-43. doi: 10.1080/1061186310001634667.
Branden and Tooze, Introduction to Protein Structure. 1999; 2nd edition. Garland Science Publisher: 3-12.
Braun et al., Immunogenic duplex nucleic acids are nuclease resistant. J Immunol. Sep. 15, 1988;141(6):2084-9.
Brierley et al., Viral RNA pseudoknots: versatile motifs in gene expression and replication. Nat Rev Microbiol. Aug. 2007;5(8):598-610. doi: 10.1038/nrmicro1704.
Briner et al., Guide RNA functional modules direct Cas9 activity and orthogonality. Mol Cell. Oct. 2, 20143;56(2):333-339. doi: 10.1016/j.molcel.2014.09.019 ..
Britt et al., Re-engineering plant gene targeting. Trends Plant Sci. Feb. 2003;8(2):90-5.
Brouns et al., Small CRISPR RNAs guide antiviral defense in prokaryotes. Science. Aug. 15, 2008;321(5891):960-4. doi: 10.1126/science.1159689.
Brown et al., A mammalian protein targeted by G1-arresting rapamycin-receptor complex. Nature. Jun. 30, 1994;369(6483):756-8. doi: 10.1038/369756a0.
Brown et al., Characterization of the genetic elements required for site-specific integration of plasmid pSE211 in Saccharopolyspora erythraea. J Bacteriol. Apr. 1990; 172(4):1877-88. doi: 10.1128/jb.172.4.1877-1888.1990.
Brown et al., Serine recombinases as tools for genome engineering. Methods. Apr. 2011;53(4):372-9. doi: 10.1016/j.ymeth.2010.12.031. Epub Dec. 30, 2010.
Brown et al., Structural insights into the stabilization of MALATI noncoding RNA by a bipartite triple helix. Nat Struct Mol Biol. Jul. 2014;21(7):633-40. doi: 10.1038/nsmb.2844. Epub Jun. 22, 2014.
Brusse et al., Spinocerebellar ataxia associated with a mutation in the fibroblast growth factor 14 gene (SCA27): A new phenotype. Mov Disord. Mar. 2006;21(3):396-401.
Brutlag et al., Improved sensitivity of biological sequence database searches. Comput Appl Biosci. Jul. 1990;6(3):237-45. doi: 10.1093/bioinformatics/6.3.237.
Brzezicha et al., Identification of human tRNA:m5C methyltransferase catalysing intron- dependent m5C formation in the first position of the anticodon of the pre-tRNA Leu (CAA). Nucleic Acids Res. 2006;34(20):6034-43. doi: 10.1093/nar/gkl765. Epub Oct. 27, 2006.
Buchholz et al., Alteration of Cre recombinase site specificity by substrate-linked protein evolution. Nat Biotechnol. Nov. 2001;19(11):1047-52.
Buchschacher et al., Human immunodeficiency virus vectors for inducible expression of foreign genes. J Virol. May 1992;66(5):2731-9. doi: 10.1128/JVI.66.5.2731-2739.1992.
Buchwald et al., Long-term, continuous intravenous heparin administration by an implantable infusion pump in ambulatory patients with recurrent venous thrombosis. Surgery. Oct. 1980;88(4):507-16.
Buckley et al., Targeting the von Hippel-Lindau E3 ubiquitin ligase using small molecules to disrupt the VHL/HIF-1 a interaction. J Am Chem Soc. Mar. 14, 2012;134(10):4465-8. doi: 10.1021/ja209924v. Epub Feb. 27, 2012.
Budisa et al., Residue-specific bioincorporation of non-natural, biologically active amino acids into proteins as possible drug carriers: structure and stability of the per-thiaproline mutant of annexin V. Proc Natl Acad Sci U S A. Jan. 20, 1998;95(2):455-9.
Budker et al., Protein/amphipathic polyamine complexes enable highly efficient transfection with minimal toxicity. Biotechniques. Jul. 1997;23(1):139, 142-7. doi: 10.2144/97231rr02.
Budworth et al., A brief history of triplet repeat diseases. Methods Mol Biol. 2013;1010:3-17.doi: 10.1007/978-1-62703-411-1_1.
Bulow et al., Multienzyme systems obtained by gene fusion. Trends Biotechnol. Jul. 1991;9(7):226-31.
Bulyk et al., Exploring the DNA-binding specificities of zinc fingers with DNA microarrays. Proc Natl Acad Sci U S A. Jun. 19, 2001;98(13):7158-63. Epub Jun. 12, 2001.
Burke et al., Activating mutations of Tn3 resolvase marking interfaces important in recombination catalysis and its regulation. Mol Microbiol. Feb. 2004;51(4):937-48.
Burke et al., RNA Aptamers to the Adenosine Moiety of S-adenosyl Methionine: Structural Inferences From Variations on a Theme and the Reproducibility of SELEX. Nucleic Acids Res. May 15, 1997;25(10):2020-4. doi: 10.1093/nar/25.10.2020.
Burstein et al., New CRISPR-Cas systems from uncultivated microbes. Nature Feb. 2017;542(7640):237-240.
Burton et al., Gene delivery using herpes simplex virus vectors. DNA Cell Biol. Dec. 2002;21(12):915-36. doi: 10.1089/104454902762053864.
Buskirk et al., Directed evolution of ligand dependence: small-molecule-activated protein splicing. Proc Natl Acad Sci U S A. Jul. 20, 2004;101(29):10505-10. Epub Jul. 9, 2004.
Buskirk et al., In vivo evolution of an RNA-based transcriptional activator. Chem Biol. Jun. 2003; 10(6):533-40. doi: 10.1016/s1074-5521(03)00109-1.
Byrne et al., Multiplex gene regulation: a two-tiered approach to transgene regulation in transgenic mice. Proc Natl Acad Sci U S A. Jul. 1989;86(14):5473-7. doi: 10.1073/pnas.86.14.5473.
Böck et al., Selenocysteine: the 21st amino acid. Mol Microbiol. Mar. 1991;5(3):515-20.
Cade et al., Highly efficient generation of heritable zebrafish gene mutations using homo- and heterodimeric TALENs. Nucleic Acids Res. Sep. 2012;40(16):8001-10. Doi: 10.1093/nar/gks518. Epub Jun. 7, 2012.
Cadwell et al., Randomization of genes by PCR mutagenesis. PCR Methods Appl. Aug. 1992;2(1):28-33. doi: 10.1101/gr.2.1.28.
Cai et al., Reconstruction of ancestral protein sequences and its applications. BMC Evol Biol. Sep. 17, 2004;4:33. doi: 10.1186/1471-2148-4-33.
Calame et al., Transcriptional controlling elements in the immunoglobulin and T cell receptor loci. Adv Immunol. 1988;43:235-75. doi: 10.1016/s0065-2776(08)60367-3.

(56) References Cited

OTHER PUBLICATIONS

Caldecott et al., Single-strand break repair and genetic disease. Nat Rev Genet. Aug. 2008;9(8):619-31. doi: 10.1038/nrg2380.
Camarero et al., Biosynthesis of a Head-to-Tail Cyclized Protein with Improved Biological Activity. J. Am. Chem. Soc. May 29, 1999; 121(23):5597-5598. https://doi.org/10.1021/ja990929n.
Cameron, Recent advances in transgenic technology. Mol Biotechnol. Jun. 1997;7(3):253-65.
Camper et al., Postnatal repression of the alpha-fetoprotein gene is enhancer independent. Genes Dev. Apr. 1989;3(4):537-46. doi: 10.1101/gad.3.4.537.
Camps et al., Targeted gene evolution in Escherichia coli using a highly error-prone DNA polymerase I. Proc Natl Acad Sci U S A. Aug. 19, 2003;100(17):9727-32. Epub Aug. 8, 2003.
Canchaya et al., Genome analysis of an inducible prophage and prophage remnants integrated in the Streptococcus pyogenes strain SF370. Virology. Oct. 25, 2002;302(2):245-58. doi: 10.1006/viro.2002.1570.
Canver et al., Customizing the genome as therapy for the β-hemoglobinopathies. Blood. May 26, 2016;127(21):2536-45. doi: 10.1182/blood-2016-01-678128. Epub Apr. 6, 2016.
Cao et al., Rapamycin reverses cellular phenotypes and enhances mutant protein clearance in Hutchinson-Gilford progeria syndrome cells. Sci Transl Med. Jun. 29, 2011;3(89):89ra58. doi: 10.1126/scitranslmed.3002346.
Cargill et al., Characterization of single-nucleotide polymorphisms in coding regions of human genes. Nat Genet. Jul. 1999;22(3):231-8.
Carlier et al., Burkholderia cenocepacia H111 Rhy-family protein. Apr. 16, 2015. Retrieved from the Internet via https://www.ebi.ac.uk/ena/browser/api/embl/CDN65395.1?lineLimit=1000. Last retrieved Apr. 26, 2021.
Carlier et al., Genome Sequence of Burkholderia cenocepacia H111, a Cystic Fibrosis Airway Isolate. Genome Announc. Apr. 10, 2014;2(2):e00298-14. doi: 10.1128/genomeA.00298-14.
Carlson et al., Negative selection and stringency modulation in phage-assisted continuous evolution. Nat Chem Biol. Mar. 2014;10(3):216-22. doi: 10.1038/nchembio.1453. Epub Feb. 2, 2014. With Supplementary Results.
Caron et al., Intracellular delivery of a Tat-eGFP fusion protein into muscle cells. Mol Ther. Mar. 2001;3(3):310-8.
Carr et al., Genome engineering. Nat Biotechnol. Dec. 2009;27(12):1151-62. doi: 10.1038/nbt.1590.
Carroll et al., Gene targeting in Drosophila and Caenorhabditis elegans with zinc-finger nucleases. Methods Mol Biol. 2008;435:63-77. doi: 10.1007/978-1-59745-232-8_5.
Carroll et al., Progress and prospects: zinc-finger nucleases as gene therapy agents. Gene Ther. Nov. 2008;15(22):1463-8. doi: 10.1038/gt.2008.145. Epub Sep. 11, 2008.
Carroll, A CRISPR approach to gene targeting. Mol Ther. Sep. 2012;20(9):1658-60. doi: 10.1038/mt.2012.171.
Carroll, Genome engineering with zinc-finger nucleases. Genetics. Aug. 2011;188(4):773-82. doi: 10.1534/genetics.111.131433. Review.
Cartegni et al., Determinants of exon 7 splicing in the spinal muscular atrophy genes, SMN1 and SMN2. Am J Hum Genet. Jan. 2006;78(1):63-77. doi: 10.1086/498853. Epub Nov. 16, 2005.
Carvalho et al., Evolution in health and medicine Sackler colloquium: Genomic disorders: a window into human gene and genome evolution. Proc Natl Acad Sci U S A. Jan. 26, 2010;107 Suppl 1(Suppl 1):1765-71. doi: 10.1073/pnas.0906222107. Epub Jan. 13, 2010.
Caspi et al., Distribution of split DnaE inteins in cyanobacteria. Mol Microbiol. Dec. 2003;50(5):1569-77. doi: 10.1046/j.1365-2958.2003.03825.x.
Cattaneo et al., SELIL affects human pancreatic cancer cell cycle and invasiveness through modulation of PTEN and genes related to cell-matrix interactions. Neoplasia. 2005;7(11):1030- 1038.
Ceccaldi et al., Repair Pathway Choices and Consequences at the Double-Strand Break. Trends Cell Biol. Jan. 2016;26(1):52-64. doi: 10.1016/j.tcb.2015.07.009. Epub Oct. 1, 2015.
Cermak et al., Efficient design and assembly of custom TALEN and other TAL effector- based constructs for DNA targeting. Nucleic Acids Res. Jul. 2011;39(12):e82. Doi: 10.1093/nar/gkr218. Epub Apr. 14, 2011.
Chadalavada et al., Wild-type is the optimal sequence of the HDV ribozyme under cotranscriptional conditions. RNA. Dec. 2007; 13(12):2189-201. doi: 10.1261/rna.778107. Epub Oct. 23, 2007.
Chadwick et al., In Vivo Base Editing of PCSK9 (Proprotein Convertase Subtilisin/Kexin Type 9) as a Therapeutic Alternative to Genome Editing. Arterioscler Thromb Vasc Biol. Sep. 2017;37(9):1741-1747. doi: 10.1161/ATVBAHA.117.309881. Epub Jul. 27, 2017.
Chaikind et al., A programmable Cas9-serine recombinase fusion protein that operates on DNA sequences in mammalian cells. Nucleic Acids Res. Nov. 16, 2016;44(20):9758-9770. Epub Aug. 11, 2016.
Chalberg et al., Integration specificity of phage phiC31 integrase in the human genome. J Mol Biol. Mar. 17, 2006;357(1):28-48. doi: 10.1016/j.jmb.2005.11.098. Epub Dec. 22, 2005.
Chalberg et al., phiC31 integrase confers genomic integration and long-term transgene expression in rat retina. Invest Ophthalmol Vis Sci. Jun. 2005;46(6):2140-6. doi: 10.1167/iovs.04-1252.
Chan et al., Novel selection methods for DNA-encoded chemical libraries. Curr Opin Chem Biol. 2015;26:55-61. doi:10.1016/j.cbpa.2015.02.010.
Chan et al., The choice of nucleotide inserted opposite abasic sites formed within chromosomal DNA reveals the polymerase activities participating in translesion DNA synthesis. DNA Repair (Amst). Nov. 2013;12(11):878-89. doi: 10.1016/j.dnarep.2013.07.008. Epub Aug. 26, 2013.
Chang et al., Degradation of survival motor neuron (SMN) protein is mediated via the ubiquitin/proteasome pathway. Neurochem Int. Dec. 2004;45(7):1107-12. doi: 10.1016/j.neuint.2004.04.005.
Chang et al., Modification of DNA ends can decrease end joining relative to homologous recombination in mammalian cells. Proc Natl Acad Sci U S A. Jul. 1987;84(14):4959-63.
Chapman et al., Playing the end game: DNA double-strand break repair pathway choice. Mol Cell. Aug. 24, 2012;47(4):497-510. doi: 10.1016/j.molcel.2012.07.029.
Chari et al., Unraveling CRISPR-Cas9 genome engineering parameters via a library-on-library approach. Nat Methods. Sep. 2015;12(9):823-6. doi: 10.1038/nmeth.3473. Epub Jul. 13, 2015.
Charpentier et al., Biotechnology: Rewriting a genome. Nature. Mar. 7, 2013;495(7439):50-1. doi: 10.1038/495050a.
Chaturvedi et al., Stabilization of triple-stranded oligonucleotide complexes: use of probes containing alternating phosphodiester and stereo-uniform cationic phosphoramidate linkages. Nucleic Acids Res. Jun. 15, 1996;24(12):2318-23.
Chavez et al., Highly efficient Cas9-mediated transcriptional programming. Nat Methods. Apr. 2015; 12(4):326-8. doi: 10.1038/nmeth.3312. Epub Mar. 2, 2015.
Chavez et al., Precise Cas9 targeting enables genomic mutation prevention. bioRxiv. Jun. 14, 2016; http://dx/doi.oreg/10.1101/058974. 6 pages. bioRxiv preprint first posted online Jun. 14, 2016.
Chavez et al., Precise Cas9 targeting enables genomic mutation prevention. Proc Natl Acad Sci U S A. Apr. 3, 2018;115(14):3669-3673. doi: 10.1073/pnas.1718148115. Epub Mar. 19, 2018.
Chavez et al., Therapeutic applications of the PhiC31 integrase system. Curr Gene Ther. Oct. 2011;11(5):375-81. Review.
Chawla et al., An atlas of RNA base pairs involving modified nucleobases with optimal geometries and accurate energies. Nucleic Acids Res. Aug. 18, 2015;43(14):6714-29. doi: 10.1093/nar/gkv606. Epub Jun. 27, 2015.
Chelico et al., Biochemical basis of immunological and retroviral responses to DNA-targeted cytosine deamination by activation-induced cytidine deaminase and APOBEC3G. J Biol Chem. Oct. 9, 2009;284(41):27761-5. doi: 10.1074/jbc.R109.052449. Epub Aug. 12, 2009.
Chelico et al., Stochastic properties of processive cytidine DNA deaminases AID and APOBEC3G. Philos Trans R Soc Lond B Biol Sci. Mar. 12, 2009;364(1517):583-93. doi: 10.1098/rstb.2008.0195.

(56) References Cited

OTHER PUBLICATIONS

Chen et al., A general strategy for the evolution of bond-forming enzymes using yeast display. Proc Natl Acad Sci U S A. Jul. 12, 2011;108(28):11399-404. doi: 10.1073/pnas.1101046108. Epub Jun. 22, 2011.
Chen et al., Alterations in PMS2, MSH2 and MLH1 expression in human prostate cancer. Int J Oncol. May 2003;22(5):1033-43.
Chen et al., Fusion protein linkers: property, design and functionality. Adv Drug Deliv Rev. Oct. 2013;65(10):1357-69. doi: 10.1016/j.addr.2012.09.039. Epub Sep. 29, 2012.
Chen et al., Genome-wide CRISPR screen in a mouse model of tumor growth and metastasis. Cell. Mar. 12, 2015;160(6):1246-60. doi: 10.1016/j.cell.2015.02.038. Epub Mar. 5, 2015.
Chen et al., Highly Efficient Mouse Genome Editing by CRISPR Ribonucleoprotein Electroporation of Zygotes. J Biol Chem. Jul. 8, 2016;291(28):14457-67. doi: 10.1074/jbc.M116.733154. Epub May 5, 2016.
Chen et al., m(6)A RNA methylation is regulated by microRNAs and promotes reprogramming to pluripotency. Cell Stem Cell. Mar. 5, 2015;16(3):289-301. doi: 10.1016/j.stem.2015.01.016. Epub Feb. 12, 2015.
Chen et al., Structure of the DNA deaminase domain of the HIV-1 restriction factor APOBEC3G. Nature. Mar. 6, 2008;452(7183):116-9. doi: 10.1038/nature06638. Epub Feb. 20, 2008.
Chen et al., Targeting genomic rearrangements in tumor cells through Cas9-mediated insertion of a suicide gene. Nat Biotechnol. Jun. 2017;35(6):543-550. doi: 10.1038/nbt.3843. Epub May 1, 2017.
Cheng et al., [Cloning,expression and activity identification of human innate immune protein apolipoprotein B mRNA editing enzyme catalytic subunit 3A(APOBEC3A)]. Xi Bao Yu Fen Zi Mian Yi Xue Za Zhi. Chinese Journal of Cellular and Molecular Immunology, Feb. 2017;33(2):179-84. Chinese.
Cheng et al., Multiplexed activation of endogenous genes by CRISPR-on, an RNA-guided transcriptional activator system. Cell Res. Oct. 2013;23(10):1163-71. doi: 10.1038/cr.2013.122. Epub Aug. 27, 2013.
Chesnoy et al., Structure and function of lipid-DNA complexes for gene delivery. Annu Rev Biophys Biomol Struct. 2000;29:27-47.
Chester et al., The apolipoprotein B mRNA editing complex performs a multifunctional cycle and suppresses nonsense-mediated decay. EMBO J. Aug. 1, 2003;22(15):3971-82. doi: 10.1093/emboj/cdg369.
Chew et al., A multifunctional AAV-CRISPR-Cas9 and its host response. Nat Methods. Oct. 2016; 13(10):868-74. doi: 10.1038/nmeth.3993. Epub Sep. 5, 2016.
Chew et al., A multifunctional AAV-CRISPR-Cas9 and its host response. Nat Methods. Oct. 2016;13(10):868-74. doi: 10.1038/nmeth.3993. Epub Sep. 5, 2016. Supplementary Information.
Chichili et al., Linkers in the structural biology of protein-protein interactions. Protein Science. 2013;22:153-67.
Chin, Expanding and reprogramming the genetic code of cells and animals. Annu Rev Biochem. 2014;83:379-408. doi: 10.1146/annurev-biochem-060713-035737. Epub Feb. 10, 2014.
Chipev et al., A leucine . . . proline mutation in the H1 subdomain of keratin 1 causes epidermolytic hyperkeratosis. Cell. Sep. 4, 1992;70(5):821-8.
Cho et al., A degron created by SMN2 exon 7 skipping is a principal contributor to spinal muscular atrophy severity. Genes Dev. Mar. 1, 2010;24(5):438-42. doi: 10.1101/gad.1884910.
Cho et al., Analysis of off-target effects of CRISPR/Cas-derived RNA-guided endonucleases and nickases. Genome Res. Jan. 2014;24(1):132-41. doi: 10.1101/gr.162339.113. Epub Nov. 19, 2013.
Cho et al., Site-specific recombination of bacteriophage P22 does not require integration host factor. J Bacteriol. Jul. 1999; 181(14):4245-9. doi: 10.1128/JB.181.14.4245-4249.1999.
Cho et al., Targeted genome engineering in human cells with the Cas9 RNA-guided endonuclease. Nat Biotechnol. Mar. 2013;31(3):230-2. doi: 10.1038/nbt.2507. Epub Jan. 29, 2013.
Cho et al., The calcium-activated chloride channel anoctamin 1 acts as a heat sensor in nociceptive neurons. Nat Neurosci. May 27, 2012;15(7):1015-21. doi: 10.1038/nn.3111.
Choe et al., Forging Ahead through Darkness: PCNA, Still the Principal Conductor at the Replication Fork. Mol Cell. Feb. 2, 2017;65(3):380-392. doi: 10.1016/j.molcel.2016.12.020.
Choi et al., N(6)-methyladenosine in mRNA disrupts tRNA selection and translation-elongation dynamics. Nat Struct Mol Biol. Feb. 2016;23(2):110-5. doi: 10.1038/nsmb.3148. Epub Jan. 11, 2016.
Choi et al., Protein trans-splicing and characterization of a split family B-type DNA polymerase from the hyperthermophilic archaeal parasite Nanoarchaeum equitans. J Mol Biol. Mar. 10, 2006;356(5):1093-106. doi: 10.1016/j.jmb.2005.12.036. Epub Dec. 27, 2005.
Choi et al., Translesion synthesis across abasic lesions by human B-family and Y-family DNA polymerases α, δ, η, ι, κ, and REV1. J Mol Biol. Nov. 19, 2010;404(1):34-44. doi: 10.1016/j.jmb.2010.09.015. Epub Oct. 1, 2010.
Chong et al., Utilizing the C-terminal cleavage activity of a protein splicing element to purify recombinant proteins in a single chromatographic step. Nucleic Acids Res. Nov. 15, 1998;26(22):5109-15. doi: 10.1093/nar/26.22.5109.
Chong et al., Modulation of protein splicing of the Saccharomyces cerevisiae vacuolar membrane ATPase intein. J Biol Chem. Apr. 24, 1998;273(17):10567-77. doi: 10.1074/jbc.273.17.10567.
Chong et al., Protein splicing involving the *Saccharomyces cerevisiae* VMA intein. The steps in the splicing pathway, side reactions leading to protein cleavage, and establishment of an in vitro splicing system. J Biol Chem. Sep. 6, 1996;271(36):22159-68. doi: 10.1074/jbc.271.36.22159.
Chong et al., Protein splicing of the *Saccharomyces cerevisiae* VMA intein without the endonuclease motifs. J Biol Chem. Jun. 20, 1997;272(25):15587-90. doi: 10.1074/jbc.272.25.15587.
Chong et al., Single-column purification of free recombinant proteins using a self-cleavable affinity tag derived from a protein splicing element. Gene. Jun. 19, 1997;192(2):271-81. doi: 10.1016/s0378-1119(97)00105-4.
Choudhury et al., CRISPR-dCas9 mediated TET1 targeting for selective DNA demethylation at BRCA1 promoter. Oncotarget. Jul. 19, 2016;7(29):46545-46556. doi: 10.18632/oncotarget.10234.
Choudhury et al., Engineering RNA endonucleases with customized sequence specificities. Nat Commun. 2012;3:1147. doi: 10.1038/ncomms2154.
Choulika et al., Induction of homologous recombination in mammalian chromosomes by using the I-SceI system of Saccharomyces cerevisiae. Mol Cell Biol. Apr. 1995; 15(4): 1968-73. doi: 10.1128/MCB.15.4.1968.
Christian et al., Targeting G with TAL effectors: a comparison of activities of TALENs constructed with NN and NK repeat variable di-residues. PLoS One. 2012;7(9):e45383. doi: 10.1371/journal.pone.0045383. Epub Sep. 24, 2012.
Christian et al., Targeting DNA double-strand breaks with TAL effector nucleases. Genetics. Oct. 2010;186(2):757-61. Doi: 10.1534/genetics.110.120717. Epub Jul. 26, 2010.
Christiansen et al., Characterization of the lactococcal temperate phage TP901-1 and its site-specific integration. J Bacteriol. Feb. 1994;176(4):1069-76. doi: 10.1128/jb.176.4.1069-1076.1994.
Chu et al., Increasing the efficiency of homology-directed repair for CRISPR-Cas9-induced precise gene editing in mammalian cells. Nat Biotech. Feb. 13, 2015;33:543-8. doi: 10.1038/nbt.3198. Epub Mar. 24, 2015.
Chuai et al., In Silico Meets In Vivo: Towards Computational CRISPR-Based sgRNA Design. Trends Biotechnol. Jan. 2017;35(1):12-21. doi: 10.1016/j.tibtech.2016.06.008. Epub Jul. 11, 2016.
Chuang et al., Novel Heterotypic Rox Sites for Combinatorial Dre Recombination Strategies. G3 (Bethesda). Dec. 29, 2015;6(3):559-71. doi: 10.1534/g3.115.025841.
Chujo et al., Trmt61B is a methyltransferase responsible for 1-methyladenosine at position 58 of human mitochondrial tRNAs. RNA. Dec. 2012;18(12):2269-76. doi: 10.1261/rna.035600.112. Epub Oct. 24, 2012.

(56) References Cited

OTHER PUBLICATIONS

Chung-IL et al., Artificial control of gene expression in mammalian cells by modulating RNA interference through aptamer-small molecule interaction. RNA. May 2006;12(5):710-6. Epub Apr. 10, 2006.
Chylinski et al., The tracrRNA and Cas9 families of type II CRISPR-Cas immunity systems. RNA Biol. May 2013;10(5):726-37. doi: 10.4161/rna.24321. Epub Apr. 5, 2013.
Clackson et al., Redesigning an FKBP-ligand interface to generate chemical dimerizers with novel specificity. Proc Natl Acad Sci U S A. Sep. 1, 1998;95(18):10437-42. doi: 10.1073/pnas.95.18.10437.
Cobb et al., Directed evolution as a powerful synthetic biology tool. Methods. Mar. 15, 2013;60(1):81-90. doi: 10.1016/j.ymeth.2012.03.009. Epub Mar. 23, 2012.
Cobb et al., Directed evolution: an evolving and enabling synthetic biology tool. Curr Opin Chem Biol. Aug. 2012;16(3-4):285-91. doi:10.1016/j.cbpa.2012.05.186. Epub Jun. 4, 2012. Review.
Coelho et al., Safety and efficacy of RNAi therapy for transthyretin amyloidosis. N Engl J Med. Aug. 29, 2013;369(9):819-29. doi: 10.1056/NEJMoa1208760.
Cokol et al., Finding nuclear localization signals. EMBO Rep. Nov. 2000;1(5):411-5. doi: 10.1093/embo-reports/kvd092.
Cole et al., Reconstructing evolutionary adaptive paths for protein engineering. Methods Mol Biol. 2013;978:115-25. doi: 10.1007/978-1-62703-293-3_8.
Cole-Strauss et al., Correction of the mutation responsible for sickle cell anemia by an RNA-DNA oligonucleotide. Science. Sep. 6, 1996;273(5280):1386-9.
Colletier et al., Protein encapsulation in liposomes: efficiency depends on interactions between protein and phospholipid bilayer. BMC Biotechnol. May 10, 2002;2:9.
Collinge, Prion diseases of humans and animals: their causes and molecular basis. Annu Rev Neurosci. 2001;24:519-50. doi: 10.1146/annurev.neuro.24.1.519.
Cong et al., Comprehensive interrogation of natural TALE DNA-binding modules and transcriptional repressor domains. Nat Commun. Jul. 24, 2012;3:968. doi: 10.1038/ncomms1962.
Cong et al., Multiplex genome engineering using CRISPR/Cas systems. Science. Feb. 15, 2013;339(6121):819-23. doi: 10.1126/science.1231143. Epub Jan. 3, 2013.
Conrad et al., A Kaposi's sarcoma virus RNA element that increases the nuclear abundance of intronless transcripts. Embo J. May 18, 2005;24(10):1831-41. doi: 10.1038/sj.emboj.7600662. Epub Apr. 28, 2005.
Conticello, The AID/APOBEC family of nucleic acid mutators. Genome Biol. 2008;9(6):229. doi: 10.1186/GB-2008-9-6-229. Epub Jun. 17, 2008.
Corcia et al., The importance of the SMN genes in the genetics of sporadic ALS. Amyotroph Lateral Scler. Oct.-Dec. 2009;10(5-6):436-40. doi: 10.3109/17482960902759162.
Cornu et al., DNA-binding specificity is a major determinant of the activity and toxicity of zinc-finger nucleases. Mol Ther. Feb. 2008; 16(2):352-8. Epub Nov. 20, 2007.
Cornu et al., Refining strategies to translate genome editing to the clinic. Nat Med. Apr. 3, 2017;23(4):415-423. doi: 10.1038/nm.4313.
Corti et al., Genetic correction of human induced pluripotent stem cells from patients with spinal muscular atrophy. Sci Transl Med. Dec. 19, 2012;4(165):165ra162. doi: 10.1126/scitranslmed.3004108.
Costa et al., Frequent use of the same tertiary motif by self-folding RNAs. Embo J. Mar. 15, 1995;14(6):1276-85.
Cotton et al., Insertion of a Synthetic Peptide into a Recombinant Protein Framework: A Protein Biosensor. J. Am. Chem. Soc. Jan. 22, 1999; 121(5):1100-1. https://doi.org/10.1021/ja983804b.
Covino et al., The CCL2/CCR2 Axis in the Pathogenesis of HIV-1 Infection: A New Cellular Target for Therapy? Current Drug Targets Dec. 2016;17(1):76-110. DOI: 10.2174/138945011701151217110917.
Cox et al., An SCN9A channelopathy causes congenital inability to experience pain. Nature. Dec. 14, 2006;444(7121):894-8. doi: 10.1038/nature05413.
Cox et al., Conditional gene expression in the mouse inner ear using Cre-loxP. J Assoc Res Otolaryngol. Jun. 2012;13(3):295-322. doi: 10.1007/s10162-012-0324-5. Epub Apr. 24, 2012.
Cox et al., Congenital insensitivity to pain: novel SCN9A missense and in-frame deletion mutations. Hum Mutat. Sep. 2010;31(9):E1670-86. doi: 10.1002/humu.21325.
Cox et al., Therapeutic genome editing: prospects and challenges. Nat Med. Feb. 2015;21(2):121-31. doi: 10.1038/nm.3793.
Cox, Proteins pinpoint double strand breaks. Elife. Oct. 29, 2013;2:e01561. doi: 10.7554/eLife.01561.
Crabtree et al., Three-part inventions: intracellular signaling and induced proximity. Trends Biochem Sci. Nov. 1996;21(11):418-22. doi: 10.1016/s0968-0004(96)20027-1.
Cradick et al., CRISPR/Cas9 systems targeting ?—globin and CCR5 genes have substantial off-target activity. Nucleic Acids Res. Nov. 1, 2013;41(20):9584-92. doi: 10.1093/nar/gkt714. Epub Aug. 11, 2013.
Cradick et al., ZFN-site searches genomes for zinc finger nuclease target sites and off-target sites. BMC Bioinformatics. May 13, 2011;12:152. doi: 10.1186/1471-2105-12-152.
Cradick et al., Zinc-finger nucleases as a novel therapeutic strategy for targeting hepatitis B virus DNAs. Mol Ther. May 2010;18(5):947-54. Doi: 10.1038/mt.2010.20. Epub Feb. 16, 2010.
Crick, On protein synthesis. Symp Soc Exp Biol. 1958; 12:138-63.
Cronican et al., A class of human proteins that deliver functional proteins into mammalian cells in vitro and in vivo. Chem Biol. Jul. 29, 2011;18(7):833-8. doi: 10.1016/j.chembiol.2011.07.003.
Cronican et al., Potent delivery of functional proteins into mammalian cells in vitro and in vivo using a supercharged protein. ACS Chem Biol. Aug. 20, 2010;5(8):747-52. doi: 10.1021/cb1001153.
Crystal, Transfer of genes to humans: early lessons and obstacles to success. Science. Oct. 20, 1995;270(5235):404-10. doi: 10.1126/science.270.5235.404.
Cucchiarini et al., Enhanced expression of the central survival of motor neuron (SMN) protein during the pathogenesis of osteoarthritis. J Cell Mol Med. Jan. 2014;18(1):115-24. doi: 10.1111/jcmm.12170. Epub Nov. 17, 2013.
Cui et al., Consequences of Cas9 cleavage in the chromosome of Escherichia coli. Nucleic Acids Res. May 19, 2016;44(9):4243-51. doi: 10.1093/nar/gkw223. Epub Apr. 8, 2016.
Cui et al., m6A RNA Methylation Regulates the Self-Renewal and Tumorigenesis of Glioblastoma Stem Cells. Cell Rep. Mar. 14, 2017;18(11):2622-2634. doi: 10.1016/j.celrep.2017.02.059.
Cui et al., Targeted integration in rat and mouse embryos with zinc-finger nucleases. Nat Biotechnol. Jan. 2011;29(1):64-7. Doi: 10.1038/nbt.1731. Epub Dec. 12, 2010.
Cunningham et al., Ensembl 2015. Nucleic Acids Res. Jan. 2015;43(Database issue):D662-9. doi: 10.1093/nar/gku1010. Epub Oct. 28, 2014.
Cupples et al., A set of lacZ mutations in *Escherichia coli* that allow rapid detection of each of the six base substitutions. Proc Natl Acad Sci U S A. Jul. 1989;86(14):5345-9.
Czerwinski et al., Cytotoxic agents directed to peptide hormone receptors: defining the requirements for a successful drug. Proc Natl Acad Sci U S A. Sep. 29, 1998;95(20):11520-5.
D'adda di Fagagna et al., The Gam protein of bacteriophage Mu is an orthologue of eukaryotic Ku. EMBO Rep. Jan. 2003;4(1):47-52.
D'ydewalle et al., The Antisense Transcript SMN-AS1 Regulates SMN Expression and Is a Novel Therapeutic Target for Spinal Muscular Atrophy. Neuron. Jan. 4, 2017;93(1):66-79 and Supplemental Information. doi: 10.1016/j.neuron.2016.11.033. Epub Dec. 22, 2016.
Dahlem et al., Simple methods for generating and detecting locus-specific mutations induced with TALENs in the zebrafish genome. PLoS Genet. 2012;8(8):e1002861. doi: 10.1371/journal.pgen.1002861. Epub Aug. 16, 2012.
Dahlgren et al., A novel mutation in ribosomal protein S4 that affects the function of a mutated RF1. Biochimie. Aug. 2000;82(8):683-91.

(56) References Cited

OTHER PUBLICATIONS

Dahlman et al., Orthogonal gene knockout and activation with a catalytically active Cas9 nuclease. Nat Biotechnol. Nov. 2015;33(11): 1159-61. doi: 10.1038/nbt.3390.
Dang et al., Optimizing sgRNA structure to improve CRISPR-Cas9 knockout efficiency. Genome Biol. Dec. 15, 2015;16:280. doi: 10.1186/s13059-015-0846-3.
Daniels et al., Intrinsically cell-permeable miniature proteins based on a minimal cationic PPII motif. J Am Chem Soc. Nov. 28, 2007;129(47):14578-9. Epub Nov. 6, 2007.
Das et al., The crystal structure of the monomeric reverse transcriptase from Moloney murine leukemia virus. Structure. May 2004;12(5):819-29. doi: 10.1016/j.str.2004.02.032.
Dassa et al., Fractured genes: a novel genomic arrangement involving new split inteins and a new homing endonuclease family. Nucleic Acids Res. May 2009;37(8):2560-73. doi: 10.1093/nar/gkp095. Epub Mar. 5, 2009.
Dassa et al., Trans protein splicing of cyanobacterial split inteins in endogenous and exogenous combinations. Biochemistry. Jan. 9, 2007;46(1):322-30. doi: 10.1021/bi0611762.
Database EBI Accession No. ADE34233 Jan. 29, 2004.
Database UniProt Accession No. G8I3E0. Jan. 14, 2012.
Datsenko et al., One-step inactivation of chromosomal genes in *Escherichia coli* K-12 using PCR products. Proc Natl Acad Sci U S A. Jun. 6, 2000;97(12):6640-5.
Davidson et al., Viral vectors for gene delivery to the nervous system. Nat Rev Neurosci. May 2003;4(5):353-64. doi: 10.1038/nrn1104.
Davis et al., DNA double strand break repair via non-homologous end-joining. Transl Cancer Res. Jun. 2013;2(3):130-143.
Davis et al., Homology-directed repair of DNA nicks via pathways distinct from canonical double-strand break repair. Proc Natl Acad Sci U S A. Mar. 11, 2014;111(10):E924-32. doi: 10.1073/pnas.1400236111. Epub Feb. 20, 2014.
Davis et al., Small molecule-triggered Cas9 protein with improved genome-editing specificity. Nat Chem Biol. May 2015;11(5):316-8. doi: 10.1038/nchembio.1793. Epub Apr. 6, 2015.
Davis et al., Two Distinct Pathways Support Gene Correction by Single-Stranded Donors at DNA Nicks. Cell Rep. Nov. 8, 2016;17(7):1872-1881. doi: 10.1016/j.celrep.2016.10.049.
De Felipe et al., Co-translational, intraribosomal cleavage of polypeptides by the foot-and- mouth disease virus 2A peptide. J Biol Chem. Mar. 28, 2003;278(13):11441-8. doi: 10.1074/jbc.M211644200. Epub Jan. 8, 2003.
De La Peña et al., The Hammerhead Ribozyme: A Long History for a Short RNA. Molecules. Jan. 4, 2017;22(1):78. doi: 10.3390/molecules22010078.
De Sandre-Giovannoli et al., Lamin a truncation in Hutchinson-Gilford progeria. Science. Jun. 27, 2003;300(5628):2055. doi: 10.1126/science.1084125. Epub Apr. 17, 2003.
De Souza, Primer: genome editing with engineered nucleases. Nat Methods. Jan. 2012;9(1):27.
Dean et al., Genetic restriction of HIV-1 infection and progression to AIDS by a deletion allele of the CKR5 structural gene. Hemophilia Growth and Development Study, Multicenter AIDS Cohort Study, Multicenter Hemophilia Cohort Study, San Francisco City Cohort, ALIVE Study. Science. Sep. 27, 1996;273(5283):1856-62. doi: 10.1126/science.273.5283.1856.
Dekosky et al., Large-scale sequence and structural comparisons of human naive and antigen- experienced antibody repertoires. Proc Natl Acad Sci U S A. May 10, 2016;113(19):E2636-45. doi: 10.1073/pnas.1525510113. Epub Apr. 25, 2016.
Delebecque et al., Organization of intracellular reactions with rationally designed RNA assemblies. Science. Jul. 22, 2011;333(6041):470-4. doi: 10.1126/science.1206938. Epub Jun. 23, 2011.
Deltcheva et al., CRISPR RNA maturation by trans-encoded small RNA and host factor RNase III. Nature. Mar. 31, 2011;471(7340):602-7. doi: 10.1038/nature09886.
Deng et al., Widespread occurrence of N6-methyladenosine in bacterial mRNA. Nucleic Acids Res. Jul. 27, 2015;43(13):6557-67. doi: 10.1093/nar/gkv596. Epub Jun. 11, 2015.
Deriano et al., Modernizing the nonhomologous end-joining repertoire: alternative and classical NHEJ share the stage. Annu Rev Genet. 2013;47:433-55. doi: 10.1146/annurev-genet-110711-155540. Epub Sep. 11, 2013.
Deussing, Targeted mutagenesis tools for modelling psychiatric disorders. Cell Tissue Res. Oct. 2013;354(1):9-25. doi: 10.1007/s00441-013-1708-5. Epub Sep. 10, 2013.
Dever et al., CRISPR/Cas9 ß-globin gene targeting in human haematopoietic stem cells. Nature. Nov. 17, 2016;539(7629):384-389. doi: 10.1038/nature20134. Epub Nov. 7, 2016.
Deverman et al., Cre-dependent selection yields AAV variants for widespread gene transfer to the adult brain. Nat Biotechnol. Feb. 2016;34(2):204-9. doi: 10.1038/nbt.3440. Epub Feb. 1, 2016.
Devigili et al., Paroxysmal itch caused by gain-of-function Nav1.7 mutation. Pain. Sep. 2014;155(9):1702-1707. doi: 10.1016/j.pain.2014.05.006. Epub May 10, 2014.
Dianov et al., Mammalian base excision repair: the forgotten archangel. Nucleic Acids Res. Apr. 1, 2013;41(6):3483-90. doi: 10.1093/nar/gkt076. Epub Feb. 13, 2013.
Dicarlo et al., Genome engineering in Saccharomyces cerevisiae using CRISPR-Cas systems. Nucleic Acids Research Apr. 2013;41(7):4336-43.
Dicarlo et al., Genome engineering in *Saccharomyces cerevisiae* using CRISPR-Cas systems. Nucleic Acids Res. Apr. 2013;41(7):4336-43. doi: 10.1093/nar/gkt135. Epub Mar. 4, 2013.
Dicarlo et al., Safeguarding CRISPR-Cas9 gene drives in yeast. Nat Biotechnol. Dec. 2015;33(12):1250-1255. doi: 10.1038/nbt.3412. Epub Nov. 16, 2015.
Dickey et al., Single-stranded DNA-binding proteins: multiple domains for multiple functions. Structure. Jul. 2, 2013;21(7):1074-84. doi: 10.1016/j.str.2013.05.013.
Dickinson et al., A system for the continuous directed evolution of proteases rapidly reveals drug-resistance mutations. Nat Commun. Oct. 30, 2014;5:5352. doi: 10.1038/ncomms6352.
Dickinson et al., Experimental interrogation of the path dependence and stochasticity of protein evolution using phage-assisted continuous evolution. Proc Natl Acad Sci USA. May 2013;110(22):9007-12.
Dillon, Regulating gene expression in gene therapy. Trends Biotechnol. May 1993;11(5):167- 73. doi: 10.1016/0167-7799(93)90109-M.
Ding et al., A Talen genome-editing system for generating human stem cell-based disease models. Cell Stem Cell. Feb. 7, 2013;12(2):238-51. Doi: 10.1016/j.stem.2012.11.011. Epub Dec. 13, 2012.
Ding et al., Permanent alteration of PCSK9 with in vivo CRISPR-Cas9 genome editing. Circ Res. Aug. 15, 2014;115(5):488-92. doi: 10.1161/CIRCRESAHA.115.304351. Epub Jun. 10, 2014.
Dingwall et al., Nuclear targeting sequences . . . a consensus? Trends Biochem Sci. Dec. 1991; 16(12):478-81. doi: 10.1016/0968-0004(91)90184-w.
Diver et al., Single-Step Synthesis of Cell-Permeable Protein Dimerizers That Activate Signal Transduction and Gene Expression. J. Am. Chem. Soc. Jun. 4, 1997;119(22):5106-5109. https://doi.org/10.1021/ja963891c.
Dixon et al., Reengineering orthogonally selective riboswitches. Proc Natl Acad Sci U S A. Feb. 16, 2010;107(7):2830-5. doi: 10.1073/pnas.0911209107. Epub Jan. 26, 2010.
Doench et al., Optimized sgRNA design to maximize activity and minimize off-target effects of CRISPR-Cas9. Nat Biotechnol. Feb. 2016;34(2):184-191. doi: 10.1038/nbt.3437.
Doench et al., Rational design of highly active sgRNAs for CRISPR-Cas9-mediated gene inactivation. Nat Biotechnol. Dec. 2014;32(12):1262-7. doi: 10.1038/nbt.3026. Epub Sep. 3, 2014.
Dolan et al., Trans-splicing with the group I intron ribozyme from Azoarcus. RNA. Feb. 2014;20(2):202-13. doi: 10.1261/rna.041012.113. Epub Dec. 16, 2013.
Dominissini et al., Topology of the human and mouse m6A RNA methylomes revealed by m6A-seq. Nature. Apr. 29, 2012;485(7397):201-6. doi: 10.1038/nature11112.

(56) References Cited

OTHER PUBLICATIONS

Dorgan et al., An enzyme-coupled continuous spectrophotometric assay for S- adenosylmethionine-dependent methyltransferases. Anal Biochem. Mar. 15, 2006;350(2):249-55. doi: 10.1016/j.ab.2006.01.004. Epub Feb. 7, 2006.
Dormiani et al., Long-term and efficient expression of human β-globin gene in a hematopoietic cell line using a new site-specific integrating non-viral system. Gene Ther. Aug. 2015;22(8):663-74. doi: 10.1038/gt.2015.30. Epub Apr. 1, 2015.
Dorr et al., Reprogramming the specificity of sortase enzymes. Proc Natl Acad Sci U S A. Sep. 16, 2014;111(37):13343-8. doi: 10.1073/pnas.1411179111. Epub Sep. 3, 2014.
Doudna et al., Genome editing. The new frontier of genome engineering with CRISPR-Cas9. Science. Nov. 28, 2014;346(6213):1258096. doi: 10.1126/science.1258096.
Dove et al., Conversion of the omega subunit of *Escherichia coli* RNA polymerase into a transcriptional activator or an activation target. Genes Dev. Mar. 1, 1998;12(5):745-54.
Doyon et al., Directed evolution and substrate specificity profile of homing endonuclease I-SceI. J Am Chem Soc. Feb. 22, 2006;128(7):2477-84.
Doyon et al., Enhancing zinc-finger-nuclease activity with improved obligate heterodimeric architectures. Nat Methods. Jan. 2011;8(1):74-9. Doi: 10.1038/nmeth.1539. Epub Dec. 5, 2010.
Doyon et al., Heritable targeted gene disruption in zebrafish using designed zinc-finger nucleases. Nat Biotechnol. Jun. 2008;26(6):702-8. Doi: 10.1038/nbt1409. Epub May 25, 2008.
Drake, A constant rate of spontaneous mutation in DNA-based microbes. Proc Natl Acad Sci USA. Aug. 15, 1991;88(16):7160-4.
Drenth et al., Mutations in sodium-channel gene SCN9A cause a spectrum of human genetic pain disorders. J Clin Invest. Dec. 2007;117(12):3603-9. doi: 10.1172/JCI33297.
Drost et al., Inactivation of DNA mismatch repair by variants of uncertain significance in the PMS2 gene. Hum Mutat. Nov. 2013;34(11):1477-80. doi: 10.1002/humu.22426. Epub Sep. 11, 2013.
Duan et al., Enhancement of muscle gene delivery with pseudotyped adeno-associated virus type 5 correlates with myoblast differentiation. J Virol. Aug. 2001;75(16):7662-71. doi: 10.1128/JVI.75.16.7662-7671.2001.
Dubowchik et al., Cathepsin B-labile dipeptide linkers for lysosomal release of doxorubicin from internalizing immunoconjugates: model studies of enzymatic drug release and antigen- specific in vitro anticancer activity.
Dugar et al., CRISPR RNA-Dependent Binding and Cleavage of Endogenous RNAs by the Campylobacter jejuni Cas9. Mol Cell. Mar. 1, 2018;69(5):893-905.e7. doi: 10.1016/j.molcel.2018.01.032.
Dumas et al., Designing logical codon reassignment—Expanding the chemistry in biology. Chem Sci. Jan. 1, 2015;6(1):50-69. doi: 10.1039/c4sc01534g. Epub Jul. 14, 2014. Review.
Dunaime, Breakthrough method means CRISPR just got a lot more relevant to human health. The Verge. Apr. 20, 2016. http://www.theverge.com/2016/4/20/11450262/crispr-base-editing-single-nucleotides-dna-gene-liu-harvard.
Duncan et al., Degradation of side-chains of N-(2-hydroxypropyl)methacrylamide copolymers by lysosomal thiol-proteinases.
Dupuy et al., Le syndrome de De La Chapelle [De La Chapelle syndrome]. Presse Med. Mar. 3, 2001;30(8):369-72. French.
Durai et al., A bacterial one-hybrid selection system for interrogating zinc finger-DNA interactions. Comb Chem High Throughput Screen. May 2006;9(4):301-11.
Durai et al., Zinc finger nucleases: custom-designed molecular scissors for genome engineering of plant and mammalian cells. Nucleic Acids Res. Oct. 26, 2005;33(18):5978-90. doi: 10.1093/nar/gki912.
During et al., Controlled release of dopamine from a polymeric brain implant: in vivo characterization. Ann Neurol. Apr. 1989;25(4):351-6.
East-Seletsky et al., Two distinct RNase activities of CRISPR-C2c2 enable guide-RNA processing and RNA detection. Nature Oct. 2016;538(7624):270-3.
Edlund et al., Cell-specific expression of the rat insulin gene: evidence for role of two distinct 5' flanking elements. Science. Nov. 22, 1985;230(4728):912-6. doi: 10.1126/science.3904002.
Edwards et al., An *Escherichia coli* tyrosine transfer RNA is a leucine-specific transfer RNA in the yeast *Saccharomyces cerevisiae*. Proc Natl Acad Sci U S A. Feb. 15, 1991;88(4):1153-6.
Edwards et al., Crystal structures of the thi-box riboswitch bound to thiamine pyrophosphate analogs reveal adaptive RNA-small molecule recognition. Structure. Sep. 2006;14(9):1459-68.
Edwards et al., Structural basis for recognition of S-adenosylhomocysteine by riboswitches. RNA. Nov. 2010;16(11):2144-55. doi:10.1261/rna.2341610. Epub Sep. 23, 2010.
Eick et al., Robustness of Reconstructed Ancestral Protein Functions to Statistical Uncertainty. Mol Biol Evol. Feb. 1, 2017;34(2):247-261. doi: 10.1093/molbev/msw223.
Eiler et al., Structural Basis for the Fast Self-Cleavage Reaction Catalyzed by the Twister Ribozyme. Proc Natl Acad Sci U S A. Sep. 9, 2014;111(36):13028-33. doi: 10.1073/pnas.1414571111. Epub Aug. 25, 2014.
Ekstrand et al., Frequent alterations of the PI3K/AKT/mTOR pathways in hereditary nonpolyposis colorectal cancer. Fam Cancer. Jun. 2010;9(2):125-9. doi: 10.1007/s10689-009-9293-1.
Ellington et al., In vitro selection of RNA molecules that bind specific ligands. Nature. Aug. 30, 1990;346(6287):818-22.
Eltoukhy et al., Nucleic acid-mediated intracellular protein delivery by lipid-like nanoparticles. Biomaterials. Aug. 2014;35(24):6454-61. doi: 10.1016/j.biomaterials.2014.04.014. Epub May 13, 2014.
Emery et al., HCN2 ion channels play a central role in inflammatory and neuropathic pain. Science. Sep. 9, 2011;333(6048):1462-6. doi: 10.1126/science.1206243.
Endo et al., Toward establishing an efficient and versatile gene targeting system in higher plants. Biocatalysis and Agricultural Biotechnology 2014;3,(1):2-6.
Engelward et al., Base excision repair deficient mice lacking the Aag alkyladenine DNA glycosylase. Proc Natl Acad Sci U S A. Nov. 25, 1997;94(24):13087-92.
England, Unnatural amino acid mutagenesis: a precise tool for probing protein structure and function. Biochemistry. Sep. 21, 2004;43(37):11623-9.
Entin-Meer et al., The role of phenylalanine-119 of the reverse transcriptase of mouse mammary tumour virus in DNA synthesis, ribose selection and drug resistance. Biochem J. Oct. 15, 2002;367(Pt 2):381-91. doi: 10.1042/BJ20020712.
Enyeart et al., Biotechnological applications of mobile group II introns and their reverse transcriptases: gene targeting, RNA-seq, and non-coding RNA analysis. Mobile DNA 5, 2 (2014). https://doi.org/10.1186/1759-8753-5-2. https://doi.org/10.1186/1759-8753-5-2.
Epstein, HSV-1-based amplicon vectors: design and applications. Gene Ther. Oct. 2005;12 Suppl 1:S154-8. doi: 10.1038/sj.gt.3302617.
Eriksson et al., Recurrent de novo point mutations in lamin A cause Hutchinson-Gilford progeria syndrome. Nature. May 15, 2003;423(6937):293-8. doi: 10.1038/nature01629. Epub Apr. 25, 2003. PMID: 12714972.
Estacion et al., A sodium channel gene SCN9A polymorphism that increases nociceptor excitability. Ann Neurol. Dec. 2009;66(6):862-6. doi: 10.1002/ana.21895.
Esvelt et al., A system for the continuous directed evolution of biomolecules. Nature. Apr. 28, 2011;472(7344):499-503. doi: 10.1038/nature09929. Epub Apr. 10, 2011.
Esvelt et al., Genome-scale engineering for systems and synthetic biology. Mol Syst Biol. 2013;9:641. doi: 10.1038/msb.2012.66.
Esvelt et al., Orthogonal Cas9 proteins for RNA-guided gene regulation and editing. Nat Methods. Nov. 2013;10(11):1116-21. doi: 10.1038/nmeth.2681. Epub Sep. 29, 2013.
Evans et al., Protein trans-splicing and cyclization by a naturally split intein from the dnaE gene of Synechocystis species PCC6803. J Biol Chem. Mar. 31, 2000;275(13):9091-4. doi: 10.1074/jbc.275.13.9091.

(56) References Cited

OTHER PUBLICATIONS

Evans et al., Semisynthesis of cytotoxic proteins using a modified protein splicing element. Protein Sci. Nov. 1998;7(11):2256-64. doi: 10.1002/pro.5560071103.
Evans et al., The cyclization and polymerization of bacterially expressed proteins using modified self-splicing inteins. J Biol Chem. Jun. 25, 1999;274(26):18359-63. doi: 10.1074/jbc.274.26.18359.
Evans et al., The in vitro ligation of bacterially expressed proteins using an intein from Methanobacterium thermoautotrophicum. J Biol Chem. Feb. 12, 1999;274(7):3923-6. doi: 10.1074/jbc.274.7.3923.
Evans et al., The Rise of Azide-Alkyne 1,3-Dipolar 'Click' Cycloaddition and its Application to Polymer Science and Surface Modification. Aust J Chem. 2007;60:384-95.
Evers et al., CRISPR knockout screening outperforms shRNA and CRISPRi in identifying essential genes. Nat Biotechnol. Jun. 2016;34(6):631-3. doi: 10.1038/nbt.3536. Epub Apr. 25, 2016.
Fagerlund et al., The Cpf1 CRISPR-Cas protein expands genome-editing tools. Genome Biology Nov. 17, 2015;16:251. https://doi.org/10.1186/s13059-015-0824-9.
Falnes et al., DNA repair by bacterial AlkB proteins. Res Microbiol. Oct. 2003;154(8):531-8. doi: 10.1016/S0923-2508(03)00150-5.
Falnes et al., Repair of methyl lesions in DNA and RNA by oxidative demethylation. Neuroscience. Apr. 14, 2007;145(4):1222-32. doi: 10.1016/j.neuroscience.2006.11.018. Epub Dec. 18, 2006.
Fang et al., Synthetic Studies Towards Halichondrins: Synthesis of the Left Halves of Norhalichondrins and Homohalichondrins. Tetrahedron Letters 1992;33(12):1557-1560.
Farboud et al., Dramatic enhancement of genome editing by CRISPR/Cas9 through improved guide RNA design. Genetics. Apr. 2015;199(4):959-71. doi: 10.1534/genetics.115.175166. Epub Feb. 18, 2015.
Farhood et al., Codelivery to mammalian cells of a transcriptional factor with cis-acting element using cationic liposomes. Anal Biochem. Feb. 10, 1995;225(1):89-93.
Fawcett et al., Transposable elements controlling I-R hybrid dysgenesis in D. melanogaster are similar to mammalian LINEs. Cell. Dec. 26, 1986;47(6):1007-15. doi: 10.1016/0092-8674(86)90815-9.
Feldstein et al., Two sequences participating in the autolytic processing of satellite tobacco ringspot virus complementary RNA. Gene. Oct. 15, 1989;82(1):53-61. doi: 10.1016/0378-1119(89)90029-2.
Felletti et al., Twister Ribozymes as Highly Versatile Expression Platforms for Artificial Riboswitches. Nat Commun. Sep. 27, 2016;7:12834. doi: 10.1038/ncomms12834.
Feng et al., Crystal structures of the human RNA demethylase Alkbh5 reveal basis for substrate recognition. J Biol Chem. Apr. 25, 2014;289(17):11571-11583. doi: 10.1074/jbc.M113.546168. Epub Mar. 10, 2014.
Feng et al., Human L1 retrotransposon encodes a conserved endonuclease required for retrotransposition. Cell. Nov. 29, 1996;87(5):905-16. doi: 10.1016/s0092-8674(00)81997-2.
Ferretti et al., Complete genome sequence of an M1 strain of *Streptococcus pyogenes*. Proc Natl Acad Sci U S A. Apr. 10, 2001;98(8):4658-63.
Ferry et al., Rational design of inducible CRISPR guide RNAs for de novo assembly of transcriptional programs. Nat Commun. Mar. 3, 2017;8:14633. doi: 10.1038/ncomms14633.
Feuk, Inversion variants in the human genome: role in disease and genome architecture. Genome Med. Feb. 12, 2010;2(2):11. doi: 10.1186/gm132.
Filippov et al., A novel type of RNase III family proteins in eukaryotes. Gene. Mar. 7, 2000;245(1):213-21. doi: 10.1016/s0378-1119(99)00571-5.
Fine et al., Trans-spliced Cas9 allows cleavage of HBB and CCR5 genes in human cells using compact expression cassettes. Scientific Reports 2015;5(1):Article No. 10777. doi:10.1038/srep10777. With Supplementary Information.
Fire et al., Potent and specific genetic interference by double-stranded RNA in Caenorhabditis elegans. Nature. Feb. 19, 1998;391(6669):806-11. doi: 10.1038/35888.
Fischbach et al., Directed evolution can rapidly improve the activity of chimeric assembly-line enzymes. Proc Natl Acad Sci U S A. Jul. 17, 2007;104(29):11951-6. doi: 10.1073/pnas.0705348104. Epub Jul. 9, 2007.
Fischer et al., Cryptic epitopes induce high-titer humoral immune response in patients with cancer. J Immunol. Sep. 1, 2010;185(5):3095-102. doi: 10.4049/jimmunol.0902166. Epub Jul. 26, 2010.
Fitzjohn, Diversitree: comparative phylogenetic analyses of diversification in R. Methods in Evology and Evolution. Dec. 2012;3(6):1084-92 .doi: 10.1111/j.2041-210X.2012.00234.x.
Flajolet et al., Woodchuck hepatitis virus enhancer I and enhancer II are both involved in N-myc2 activation in woodchuck liver tumors. J Virol. Jul. 1998;72(7):6175-80. doi: 10.1128/JVI.72.7.6175-61801998.
Flaman et al., A rapid PCR fidelity assay. Nucleic Acids Res. Aug. 11, 1994;22(15):3259-60. doi: 10.1093/nar/22.15.3259.
Flynn et al., CRISPR-mediated genotypic and phenotypic correction of a chronic granulomatous disease mutation in human iPS cells. Exp Hematol. Oct. 2015;43(10):838-848.e3. doi: 10.1016/j.exphem.2015.06.002. Epub Jun. 19, 2015. Including supplementary figures and data.
Fogg et al., Genome Integration and Excision by a New Streptomyces Bacteriophage, ϕJoe. Appl Environ Microbiol. Feb. 15, 2017;83(5):e02767-16. doi: 10.1128/AEM.02767-16.
Fogg et al., New applications for phage integrases. J Mol Biol. Jul. 29, 2014;426(15):2703-16. doi: 10.1016/j.jmb.2014.05.014. Epub May 22, 2014.
Fonfara et al., Phylogeny of Cas9 determines functional exchangeability of dual-RNA and Cas9 among orthologous type II CRISPR-Cas systems. Nucleic Acids Res. Feb. 2014;42(4):2577-90. doi: 10.1093/nar/gkt1074. Epub Nov. 22, 2013.
Fonfara et al., Phylogeny of Cas9 determines functional exchangeability of dual-RNA and Cas9 among orthologous type II CRISPR-Cas systems. Nucleic Acids Res. Feb. 2014;42(4):2577-90. doi: 10.1093/nar/gkt1074. Epub Nov. 22, 2013. Including Supplementary Information.
Forster et al., Self-cleavage of virusoid RNA is performed by the proposed 55-nucleotide active site. Cell. Jul. 3, 1987;50(1):9-16. doi: 10.1016/0092-8674(87)90657-x.
Fortini et al., Different DNA polymerases are involved in the short- and long-patch base excision repair in mammalian cells. Biochemistry. Mar. 17, 1998;37(11):3575-80. doi: 10.1021/bi972999h.
Fouts et al., Sequencing Bacillus anthracis typing phages gamma and cherry reveals a common ancestry. J Bacteriol. May 2006;188(9):3402-8. doi: 10.1128/JB.188.9.3402-3408.2006.
Freitas et al., Mechanisms and signals for the nuclear import of proteins. Curr Genomics. Dec. 2009;10(8):550-7. doi: 10.2174/138920209789503941.
Freshney, Culture of Animal Cells. A Manual of Basic Technique. Alan R. Liss, Inc. New York. 1983;4.
Friedman, J. H., Greedy function approximation: A gradient boosting machine. Ann. Statist. Oct. 2001;29(5):1189-232. doi: 10.1214/aos/1013203451.
Fu et al., High-frequency off-target mutagenesis induced by CRISPR-Cas nucleases in human cells. Nat Biotechnol. Sep. 2013;31(9):822-6. doi: 10.1038/nbt.2623. Epub Jun. 23, 2013.
Fu et al., Improving CRISPR-Cas nuclease specificity using truncated guide RNAs. Nat Biotechnol. Mar. 2014;32(3):279-84. doi: 10.1038/nbt.2808. Epub Jan. 26, 2014.
Fu et al., Promises and Pitfalls of Intracellular Delivery of Proteins. Bioconjugate Chemistry. Aug. 2014;25:1602-8.
Fuchs et al., Polyarginine as a multifunctional fusion tag. Protein Sci. Jun. 2005; 14(6):1538-44.
Fujisawa et al., Disease-associated mutations in CIAS1 induce cathepsin B-dependent rapid cell death of human THP-1 monocytic cells. Blood. Apr. 1, 2007;109(7):2903-11.
Fukui et al., DNA Mismatch Repair in Eukaryotes and Bacteria. J Nucleic Acids. Jul. 27, 2010;2010. pii: 260512. doi: 10.4061/2010/260512.

(56) References Cited

OTHER PUBLICATIONS

Fung et al., Repair at single targeted DNA double-strand breaks in pluripotent and differentiated human cells. PLoS One. 2011;6(5):e20514. doi: 10.1371/journal.pone.0020514. Epub May 25, 2011.
Furukawa et al., In vitro selection of allosteric ribozymes that sense the bacterial second messenger c-di-GMP. Methods Mol Biol. 2014;1111:209-20. doi: 10.1007/978-1-62703-755-6_15.
Fusi et al., In Silico Predictive Modeling of CRISPR/Cas9 guide efficiency. Jun. 26, 2015; bioRxiv. http://dx.doi.org/10.1101/021568.
Gabel et al., Mannose 6-phosphate receptor-mediated endocytosis of acid hydrolases: internalization of beta-glucuronidase is accompanied by a limited dephosphorylation. J Cell Biol. Nov. 1986; 103(5):1817-27.
Gabriel et al., An unbiased genome-wide analysis of zinc-finger nuclease specificity. Nat Biotechnol. Aug. 7, 2011;29(9):816-23. doi: 10.1038/nbt.1948.
Gaj et al., 3rd. Genome engineering with custom recombinases. Methods Enzymol. 2014;546:79-91. doi: 10.1016/B978-0-12-801185-0.00004-0.
Gaj et al., A comprehensive approach to zinc-finger recombinase customization enables genomic targeting in human cells. Nucleic Acids Res. Feb. 6, 2013;41(6):3937-46.
Gaj et al., Enhancing the specificity of recombinase-mediated genome engineering through dimer interface redesign. J Am Chem Soc. Apr. 2, 2014;136(13):5047-56. doi: 10.1021/ja4130059. Epub Mar. 20, 2014.
Gaj et al., Expanding the scope of site-specific recombinases for genetic and metabolic engineering. Biotechnol Bioeng. Jan. 2014;111(1):1-15. doi: 10.1002/bit.25096. Epub Sep. 13, 2013.
Gaj et al., Structure-guided reprogramming of serine recombinase DNA sequence specificity. Proc Natl Acad Sci U S A. Jan. 11, 2011;108(2):498-503. doi: 10.1073/pnas.1014214108. Epub Dec. 27, 2010.
Gaj et al., ZFN, TALEN, and CRISPR/Cas-based methods for genome engineering. Trends Biotechnol. Jul. 2013;31(7):397-405. doi: 10.1016/j.tibtech.2013.04.004. Epub May 9, 2013.
Gallo et al., A novel pathogenic PSEN1 mutation in a family with Alzheimer's disease: phenotypical and neuropathological features. J Alzheimers Dis. 2011;25(3):425-31. doi: 10.3233/JAD-2011-110185.
Gao et al., Cationic liposome-mediated gene transfer. Gene Ther. Dec. 1995;2(10):710-22.
Gao et al., Crystal structure of a TALE protein reveals an extended N-terminal DNA binding region. Cell Res. Dec. 2012;22(12):1716-20. doi: 10.1038/cr.2012.156. Epub Nov. 13, 2012.
Gao et al., DNA-guided genome editing using the Natronobacterium gregoryi Argonaute. Nat Biotechnol. Jul. 2016;34(7):768-73. doi: 10.1038/nbt.3547. Epub May 2, 2016.
Gao et al., Self-processing of ribozyme-flanked RNAs into guide RNAs in vitro and in vivo for CRISPR-mediated genome editing. J Integr Plant Biol. Apr. 2014;56(4):343-9. doi: 10.1111/jipb.12152. Epub Mar. 6, 2014.
Garcia et al., Transglycosylation: a mechanism for RNA modification (and editing?). Bioorg Chem. Jun. 2005;33(3):229-51. doi: 10.1016/j.bioorg.2005.01.001. Epub Feb. 23, 2005.
Gardlik et al., Vectors and delivery systems in gene therapy. Med Sci Monit. Apr. 2005; 11(4):RA110-21. Epub Mar. 24, 2005.
Garibyan et al., Use of the rpoB gene to determine the specificity of base substitution mutations on the *Escherichia coli* chromosome. DNA Repair (Amst). May 12, 2003;2(5):593-608.
Garneau et al., The CRISPR/Cas bacterial immune system cleaves bacteriophage and plasmid DNA. Nature. Nov. 4, 2010;468(7320):67-71. doi: 10.1038/nature09523.
Gasiunas et al., Cas9-crRNA ribonucleoprotein complex mediates specific DNA cleavage for adaptive immunity in bacteria. Proc Natl Acad Sci U S A. Sep. 25, 2012;109(39):E2579-86. Epub Sep. 4, 2012. Supplementary materials included.
Gasiunas et al., RNA-dependent DNA endonuclease Cas9 of the CRISPR system: Holy Grail of genome editing? Trends Microbiol. Nov. 2013;21(11):562-7. doi: 10.1016/j.tim.2013.09.001. Epub Oct. 1, 2013.
Geissler et al., Transcriptional activators of human genes with programmable DNA-specificity. PLoS One. 2011;6(5):e19509. doi: 10.1371/journal.pone.0019509. Epub May 19, 2011.
GenBank Accession No. J01600.1. Brooks et al., *E.coli* dam gene coding for DNA adenine methylase. Apr. 26, 1993.
GenBank Accession No. U07651.1. Lu, *Escherichia coli* K12 negative regulator of replication initiation (seqA) gene, complete cds. Jul. 19, 1994.
GENBANK Submission; NIH/NCBI Accession No. 4UN5_B. Anders et al., Jul. 23, 2014. 5 pages.
GENBANK Submission; NIH/NCBI, Accession No. AAA66622.1. Martinelli et al., May 18, 1995. 2 pages.
GENBANK Submission; NIH/NCBI, Accession No. AAB03530.1. Shannon et al., Jul. 9, 1996. 1 page.
GENBANK Submission; NIH/NCBI, Accession No. AAD20972.1. Zhang et al., Nov. 21, 2002. 1 page.
GENBANK Submission; NIH/NCBI, Accession No. AGT42196. Farzadfar et al., Nov. 2, 2013. 2 pages.
GENBANK Submission; NIH/NCBI, Accession No. AIT42264.1. Hyun et al., Oct. 15, 2014. 2 pages.
GENBANK Submission; NIH/NCBI, Accession No. AKA60242.1. Tong et al., Apr. 5, 2015. 1 page.
GENBANK Submission; NIH/NCBI, Accession No. AKQ21048.1. Gilles et al., Jul. 19, 2015. 1 page.
GENBANK Submission; NIH/NCBI, Accession No. AKS40380.1. Nodvig et al., Aug. 2, 2015. 1 page.
GENBANK Submission; NIH/NCBI, Accession No. APG80656.1. Burstein et al., Dec. 10, 2016. 1 pages.
GENBANK Submission; NIH/NCBI, Accession No. BDB43378. Zhang et al., Aug. 11, 2016. 2 pages.
GENBANK Submission; NIH/NCBI, Accession No. CAB52478.1. Hearn, Nov. 14, 2006. 1 page.
GENBANK Submission; NIH/NCBI, Accession No. CAM27971.1. Tracey, May 3, 2008. 2 pages.
GENBANK Submission; NIH/NCBI, Accession No. J04623. Kita et al., Apr. 26, 1993. 2 pages.
GENBANK Submission; NIH/NCBI, Accession No. KR710351.1. Sahni et al., Jun. 1, 2015. 2 pages.
GENBANK Submission; NIH/NCBI, Accession No. NC_000001.11. Gregory et al., Jun. 6, 2016. 3 pages.
GENBANK Submission; NIH/NCBI, Accession No. NC_002737.1. Ferretti et al., Jun. 27, 2013. 1 page.
GENBANK Submission; NIH/NCBI, Accession No. NC_015683.1. Trost et al., Jul. 6, 2013. 1 page.
GENBANK Submission; NIH/NCBI, Accession No. NC_016782.1. Trost et al., Jun. 11, 2013. 1 page.
GENBANK Submission; NIH/NCBI, Accession No. NC_016786.1. Trost et al., Aug. 28, 2013. 1 page.
GENBANK Submission; NIH/NCBI, Accession No. NC_017053.1. Fittipaldi et al., Jul. 6, 2013. 1 page.
GENBANK Submission; NIH/NCBI, Accession No. NC_017317.1. Trost et al., Jun. 11, 2013. 1 page.
GENBANK Submission; NIH/NCBI, Accession No. NC_017861.1. Heidelberg et al., Jun. 11, 2013. 1 page.
GENBANK Submission; NIH/NCBI, Accession No. NC_018010.1. Lucas et al., Jun. 11, 2013. 2 pages.
GENBANK Submission; NIH/NCBI, Accession No. NC_018721.1. Feng et al., Jun. 11, 2013. 1 pages.
GENBANK Submission; NIH/NCBI, Accession No. NC_021284.1. Ku et al., Jul. 12, 2013. 1 page.
GENBANK Submission; NIH/NCBI, Accession No. NC_021314.1. Zhang et al., Jul. 15, 2013. 1 page.
GENBANK Submission; NIH/NCBI, Accession No. NC_021846.1. Lo et al., Jul. 22, 2013. 1 page.
GENBANK Submission; NIH/NCBI, Accession No. NM_174936. Guo et al., Oct. 28, 2015. 6 pages.
GENBANK Submission; NIH/NCBI, Accession No. NP_358988.1. Hoskins et al., Jan. 11, 2017. 2 pages.

(56) References Cited

OTHER PUBLICATIONS

GENBANK Submission; NIH/NCBI, Accession No. NP_472073.1. Glaser et al., Jun. 27, 2013. 2 pages.
GENBANK Submission; NIH/NCBI, Accession No. NP_628093.1. Hsiao et al., Aug. 3, 2016. 2 pages.
GENBANK Submission; NIH/NCBI, Accession No. P42212. Prasher et al., Mar. 19, 2014. 7 pages.
GENBANK Submission; NIH/NCBI, Accession No. WP_002989955.1. No Author Listed, May 6, 2013. 1 page.
GENBANK Submission; NIH/NCBI, Accession No. WP_010922251.1. No Author Listed, May 15, 2013. 1 page.
GENBANK Submission; NIH/NCBI, Accession No. WP_011054416.1. No Author Listed, May 15, 2013. 1 page.
GENBANK Submission; NIH/NCBI, Accession No. WP_011284745.1. No Author Listed, May 16, 2013. 1 page.
GENBANK Submission; NIH/NCBI, Accession No. WP_011285506.1. No Author Listed, May 16, 2013. 1 page.
GENBANK Submission; NIH/NCBI, Accession No. WP_011527619.1. No Author Listed, May 16, 2013. 1 page.
GENBANK Submission; NIH/NCBI, Accession No. WP_012560673.1. No Author Listed, May 17, 2013. 1 page.
GENBANK Submission; NIH/NCBI, Accession No. WP_014407541.1. No Author Listed, May 18, 2013. 1 page.
GENBANK Submission; NIH/NCBI, Accession No. WP_020905136.1. No Author Listed, Jul. 25, 2013. 1 page.
GENBANK Submission; NIH/NCBI, Accession No. WP_023080005.1. No Author Listed, Oct. 27, 2013. 1 page.
Genbank Submission; NIH/NCBI, Accession No. WP_023610282.1. No Author Listed, Nov. 27, 2013. 1 page.
Genbank Submission; NIH/NCBI, Accession No. WP_030125963.1. No Author Listed, Jul. 9, 2014. 1 page.
Genbank Submission; NIH/NCBI, Accession No. WP_030126706.1. No Author Listed, Jul. 9, 2014. 1 page.
Genbank Submission; NIH/NCBI, Accession No. WP_031488318.1. No Author Listed., Aug. 5, 2014. 1 page.
Genbank Submission; NIH/NCBI, Accession No. WP_032460140.1. No Author Listed, Oct. 4, 2014. 1 page.
Genbank Submission; NIH/NCBI, Accession No. WP_032461047.1. No Author Listed, Oct. 4, 2014. 1 page.
Genbank Submission; NIH/NCBI, Accession No. WP_032462016.1. Haft et al., Oct. 4, 2014. 1 page.
Genbank Submission; NIH/NCBI, Accession No. WP_032462936.1. No Author Listed, Oct. 4, 2014. 1 page.
Genbank Submission; NIH/NCBI, Accession No. WP_032464890.1. No Author Listed, Oct. 4, 2014. 1 page.
Genbank Submission; NIH/NCBI, Accession No. WP_038431314.1. No Author Listed, Dec. 26, 2014. 1 page.
Genbank Submission; NIH/NCBI, Accession No. WP_038432938.1. No Author Listed, Dec. 26, 2014. 1 page.
Genbank Submission; NIH/NCBI, Accession No. WP_038434062.1. No Author Listed, Dec. 26, 2014. 1 page.
Genbank Submission; NIH/NCBI, Accession No. WP_048327215.1. No Author Listed, Jun. 26, 2015. 1 page.
Genbank Submission; NIH/NCBI, Accession No. WP_049519324.1. No Author Listed, Jul. 20, 2015. 1 page.
Genbank Submission; NIH/NCBI, Accession No. YP_002342100.1. Bernardini et al., Jun. 10, 2013. 2 pages.
Genbank Submission; NIH/NCBI, Accession No. YP_002344900.1. Gundogdu et al., Mar. 19, 2014. 2 pages.
Genbank Submission; NIH/NCBI, Accession No. YP_009283008.1. Bernardini et al., Sep. 23, 2016. 2 pages.
Genbank Submission; NIH/NCBI, Accession No. YP_820832.1. Makarova et al., Aug. 27, 2013. 2 pages.
George et al., Adenosine deaminases acting on RNA, RNA editing, and interferon action. J Interferon Cytokine Res. Jan. 2011;31(1):99-117. doi: 10.1089/jir.2010.0097. Epub Dec. 23, 2010. PMID: 21182352; PMCID: PMC3034097.
Gerard et al., Influence on stability in *Escherichia coli* of the carboxy-terminal structure of cloned Moloney murine leukemia virus reverse transcriptase. DNA. Aug. 1986;5(4):271-9. doi: 10.1089/dna.1986.5.271.
Gerard et al., Purification and characterization of the DNA polymerase and RNase H activities in Moloney murine sarcoma-leukemia virus. J Virol. Apr. 1975;15(4):785-97. doi: 10.1128/JVI.15.4.785-797.1975.
Gerard et al., The role of template-primer in protection of reverse transcriptase from thermal inactivation. Nucleic Acids Res. Jul. 15, 2002;30(14):3118-29. doi: 10.1093/nar/gkf417.
Gerber et al., An adenosine deaminase that generates inosine at the wobble position of tRNAs. Science. Nov. 5, 1999;286(5442):1146-9. doi: 10.1126/science.286.5442.1146.
Gerber et al., RNA editing by base deamination: more enzymes, more targets, new mysteries. Trends Biochem Sci. Jun. 2001;26(6):376-84.
Gersbach et al., Directed evolution of recombinase specificity by split gene reassembly. Nucleic Acids Res. Jul. 2010;38(12):4198-206. doi: 10.1093/nar/gkq125. Epub Mar. 1, 2010.
Gersbach et al., Targeted plasmid integration into the human genome by an engineered zinc- finger recombinase. Nucleic Acids Res. Sep. 1, 2011;39(17):7868-78. doi: 10.1093/nar/gkr421. Epub Jun. 7, 2011.
Gibson et al., Enzymatic assembly of DNA molecules up to several hundred kilobases. Nat Methods. May 2009;6(5):343-5. doi: 10.1038/nmeth.1318. Epub Apr. 12, 2009.
Gil, Position-dependent sequence elements downstream of AAUAAA are required for efficient rabbit beta-globin mRNA 3' end formation. Cell. May 8, 1987;49(3):399-406. doi: 10.1016/0092-8674(87)90292-3.
Gilbert et al., CRISPR-mediated modular RNA-guided regulation of transcription in eukaryotes. Cell. 2013 154(2):442-51.
Gilleron et al., Image-based analysis of lipid nanoparticle-mediated siRNA delivery, intracellular trafficking and endosomal escape. Nat Biotechnol. Jul. 2013;31(7):638-46. doi: 10.1038/nbt.2612. Epub Jun. 23, 2013.
Glasgow et al.,DNA-binding properties of the Hin recombinase. J Biol Chem. Jun. 15, 1989;264(17):10072-82.
Glassner et al., Generation of a strong mutator phenotype in yeast by imbalanced base excision repair. Proc Natl Acad Sci U S A. Aug. 18, 1998;95(17):9997-10002.
Goldberg et al., Epigenetics: a landscape takes shape. Cell. Feb. 2, 20073;128(4):635-8. doi: 10.1016/j.cell.2007.02.006.
Goldberg et al., Loss-of-function mutations in the Nav1.7 gene underlie congenital indifference to pain in multiple human populations. Clin Genet. Apr. 2007;71(4):311-9. doi: 10.1111/j.1399-0004.2007.00790.x.
Gong et al., Active DNA demethylation by oxidation and repair. Cell Res. Dec. 2011;21(12):1649-51. doi: 10.1038/cr.2011.140. Epub Aug. 23, 2011.
Gonzalez et al., An iCRISPR platform for rapid, multiplexable, and inducible genome editing in human pluripotent stem cells. Cell Stem Cell. Aug. 7, 2014;15(2):215-26. doi: 10.1016/j.stem.2014.05.018. Epub Jun. 12, 2014.
Goodnough et al., Development of a delivery vehicle for intracellular transport of botulinum neurotoxin antagonists. FEBS Lett. Feb. 27, 2002;513(2-3):163-8.
Gordley et al., Evolution of programmable zinc finger-recombinases with activity in human cells. J Mol Biol. Mar. 30, 2007;367(3):802-13. Epub Jan. 12, 2007.
Gordley et al., Synthesis of programmable integrases. Proc Natl Acad Sci U S A. Mar. 31, 2009;106(13):5053-8. doi: 10.1073/pnas.0812502106. Epub Mar. 12, 2009.
Grainge et al., The integrase family of recombinase: organization and function of the active site. Mol Microbiol. Aug. 1999;33(3):449-56.
Grati et al., Localization of PDZD7 to the stereocilia ankle-link associates this scaffolding protein with the Usher syndrome protein network. J Neurosci. Oct. 10, 2012;32(41):14288-93. doi: 10.1523/JNEUROSCI.3071-12.2012.

(56) References Cited

OTHER PUBLICATIONS

Green and Sambrook, Molecular Cloning: A Laboratory Manual. 4th ed., Cold Spring Harbor Laboratory Press, Cold Spring Harbor, N.Y. (2012).
Gregory et al., Integration site for Streptomyces phage phiBT1 and development of site- specific integrating vectors. J Bacteriol. Sep. 2003;185(17):5320-3. doi: 10.1128/jb.185.17.5320- 5323.2003.
Griffiths, Endogenous retroviruses in the human genome sequence. Genome Biol. 2001;2(6):REVIEWS1017. doi: 10.1186/GB-2001-2-6-reviews1017. Epub Jun. 5, 2001.
Grindley et al., Mechanisms of site-specific recombination. Annu Rev Biochem. 2006;75:567-605. doi: 10.1146/annurev.biochem.73.011303.073908.
Grishok et al., Genes and Mechanisms Related to RNA Interference Regulate Expression of the Small Temporal RNAs that Control C. elegans Developmental Timing. Jul. 13, 2001:106(1):P23-4.
Groher et al., Synthetic riboswitches—A tool comes of age. Biochim Biophys Acta. Oct. 2014; 1839(10):964-973. doi: 10.1016/j.bbagrm.2014.05.005. Epub May 17, 2014.
Groth et al., Construction of transgenic *Drosophila* by using the site-specific integrase from phage phiC31. Genetics. Apr. 2004; 166(4):1775-82. doi: 10.1534/genetics.166.4.1775.
Groth et al., Phage integrases: biology and applications. J Mol Biol. Jan. 16, 2004;335(3):667-78.
Gruber et al., Strategies for measuring evolutionary conservation of RNA secondary structures. BMC Bioinformatics. Feb. 26, 2008;9:122. doi: 10.1186/1471-2105-9-122.
Gruber et al., The Vienna RNA websuite. Nucleic Acids Res. Jul. 1, 2008;36(Web Server issue): W70-4. doi: 10.1093/nar/gkn188. Epub Apr. 19, 2008.
Grundy et al., The L box regulon: lysine sensing by leader RNAs of bacterial lysine biosynthesis genes. Proc Natl Acad Sci U S A. Oct. 14, 2003;100(21):12057-62. Epub Oct. 1, 2003.
Grunebaum et al., Recent advances in understanding and managing adenosine deaminase and purine nucleoside phosphorylase deficiencies. Curr Opin Allergy Clin Immunol. Dec. 2013;13(6):630-8. doi: 10.1097/ACI.0000000000000006.
Guedon et al., Current gene therapy using viral vectors for chronic pain. Mol Pain. May 13, 2015;11:27. doi: 10.1186/s12990-015-0018-1.
Guilinger et al., Broad specificity profiling of TALENs results in engineered nucleases with improved DNA-cleavage specificity. Nat Methods. Apr. 2014;11(4):429-35. doi: 10.1038/nmeth.2845. Epub Feb. 16, 2014.
Guilinger et al., Fusion of catalytically inactive Cas9 to FokI nuclease improves the specificity of genome modification. Nat Biotechnol. Jun. 2014;32(6):577-82. doi: 10.1038/nbt.2909. Epub Apr. 25, 2014.
Gumulya et al., Exploring the past and the future of protein evolution with ancestral sequence reconstruction: the 'retro' approach to protein engineering. Biochem J. Jan. 1, 2017;474(1):1-19. doi: 10.1042/BCJ20160507.
Guo et al., Directed evolution of an enhanced and highly efficient FokI cleavage domain for zinc finger nucleases. J Mol Biol. Jul. 2, 2010;400(1):96-107. doi: 10.1016/j.jmb.2010.04.060. Epub May 4, 2010.
Guo et al., Evolution of Tetrahymena ribozyme mutants with increased structural stability. Nat Struct Biol. Nov. 2002;9(11):855-61. doi: 10.1038/nsb850.
Guo et al., Facile functionalization of FK506 for biological studies by the thiol-ene 'click' reaction. RSC Advances. 2014;22:11400-3.
Guo et al., Protein tolerance to random amino acid change. Proc Natl Acad Sci U S A. Jun. 22, 2004;101(25):9205-10. Epub Jun. 14, 2004.
Guo et al., Structure of Cre recombinase complexed with DNA in a site-specific recombination synapse. Nature. Sep. 4, 1997;389(6646):40-6.
Gupta et al., Cross-talk between cognate and noncognate RpoE sigma factors and Zn(2+)- binding anti-sigma factors regulates photooxidative stress response in Azospirillum brasilense. Antioxid Redox Signal. Jan. 1, 2014;20(1):42-59. doi: 10.1089/ars.2013.5314. Epub Jul. 19, 2013.
Gupta et al., Sequences in attB that affect the ability of phiC31 integrase to synapse and to activate DNA cleavage. Nucleic Acids Res. 2007;35(10):3407-19. doi: 10.1093/nar/gkm206. Epub May 3, 2007.
Gupta et al., Zinc finger protein-dependent and -independent contributions to the in vivo off-target activity of zinc finger nucleases. Nucleic Acids Res. Jan. 2011;39(1):381-92. doi: 10.1093/nar/gkq787. Epub Sep. 14, 2010.
Guschin et al., A rapid and general assay for monitoring endogenous gene modification. Methods Mol Biol. 2010;649:247-56. doi: 10.1007/978-1-60761-753-2_15.
Gutschner et al., Post-translational Regulation of Cas9 during G1 Enhances Homology- Directed Repair. Cell Rep. Feb. 16, 2016;14(6):1555-1566. doi: 10.1016/j.celrep.2016.01.019. Epub Feb. 4, 2016.
Guzman et al., Tight regulation, modulation, and high-level expression by vectors containing the arabinose PBAD promoter. J Bacteriol. 1995;177(14):4121-4130.
Haddada et al., Gene therapy using adenovirus vectors. Curr Top Microbiol Immunol. 1995;199 ( Pt 3):297-306. doi: 10.1007/978-3-642-79586-2_14.
Haeussler et al., Evaluation of off-target and on-target scoring algorithms and integration into the guide RNA selection tool CRISPOR. Genome Biol. Jul. 5, 2016;17(1):148. doi: 10.1186/s13059-016-1012-2.
Halbert et al., Repeat transduction in the mouse lung by using adeno-associated virus vectors with different serotypes. J Virol. Feb. 2000;74(3):1524-32. doi: 10.1128/jvi.74.3.1524-1532.2000.
Hale et al., RNA-guided RNA cleavage by a CRISPR RNA-Cas protein complex. Cell. Nov. 25, 2009;139(5):945-56. doi: 10.1016/j.cell.2009.07.040.
Halvas et al., Role of murine leukemia virus reverse transcriptase deoxyribonucleoside triphosphate-binding site in retroviral replication and in vivo fidelity. J Virol. Nov. 2000;74(22):10349-58. doi: 10.1128/jvi.74.22.10349-10358.2000.
Hamano-Takaku et al., A mutant *Escherichia coli* tyrosyl-tRNA synthetase utilizes the unnatural amino acid azatyrosine more efficiently than tyrosine. J Biol Chem. Dec. 22, 2000;275(51):40324-8.
Hampel et al., Evidence for preorganization of the glmS ribozyme ligand binding pocket. Biochemistry. 2006; 45(25):7861-71.
Han, New CRISPR/Cas9-based Tech Edits Single Nucleotides Without Breaking DNA. Genome Web, Apr. 20, 2016. https://www.genomeweb.com/gene-silencinggene-editing/new-crisprcas9-based-tech-edits-single-nucleotides-without-breaking-dna.
Hardt et al.,Missense variants in hMLH1 identified in patients from the German HNPCC consortium and functional studies. Fam Cancer. Jun. 2011;10(2):273-84. doi: 10.1007/s10689-011-9431-4.
Harms et al., Evolutionary biochemistry: revealing the historical and physical causes of protein properties. Nat Rev Genet. Aug. 2013;14(8):559-71. doi: 10.1038/nrg3540.
Harrington et al., A thermostable Cas9 with increased lifetime in human plasma. Nat Commun. Nov. 10, 2017;8(1):1424. doi: 10.1038/s41467-017-01408-4. Posted May 16, 2017 as bioRxiv preprint. Doi.org/10.1101/138867.
Harrington et al., Programmed DNA destruction by miniature CRISPR-Cas14 enzymes. Science. Nov. 16, 2018;362(6416):839-842. doi: 10.1126/science.aav4294. Epub Oct. 18, 2018.
Harris et al., RNA Editing Enzyme APOBEC1 and Some of Its Homologs Can Act as DNA Mutators. Mol Cell. Nov. 2002; 10(5):1247-53.
Hart et al., High-Resolution CRISPR Screens Reveal Fitness Genes and Genotype-Specific Cancer Liabilities. Cell. Dec. 3, 2015;163(6):1515-26. doi: 10.1016/j.cell.2015.11.015. Epub Nov. 25, 2015.
Hartung et al., Correction of metabolic, craniofacial, and neurologic abnormalities in MPS I mice treated at birth with adeno-associated virus vector transducing the human alpha-L-iduronidase gene. Mol Ther. Jun. 2004;9(6):866-75.

(56) References Cited

OTHER PUBLICATIONS

Hartung et al., Cre mutants with altered DNA binding properties. J Biol Chem. Sep. 4, 1998;273(36):22884-91.
Hasadsri et al., Functional protein delivery into neurons using polymeric nanoparticles. J Biol Chem. Mar. 13, 2009;284(11):6972-81. doi: 10.1074/jbc.M805956200. Epub Jan. 7, 2009.
Hasegawa et al., Spontaneous mutagenesis associated with nucleotide excision repair in *Escherichia coli*. Genes Cells. May 2008;13(5):459-69. doi: 10.1111/j.1365-2443.2008.01185.x.
Hawley-Nelson et al., Transfection of Cultured Eukaryotic Cells Using Cationic Lipid Reagents. Curr Prot Mol Biol. Jan. 2008;9.4. 1-9.4.17. doi: 10.102/0471142727.mb0904s81. 17 pages.
Hayes et al., Stop codons preceded by rare arginine codons are efficient determinants of SsrA tagging in *Escherichia coli*. Proc Natl Acad Sci U S A. Mar. 19, 2002;99(6):3440-5. Epub Mar. 12, 2002.
Heidenreich et al., Non-homologous end joining as an important mutagenic process in cell cycle-arrested cells. Embo J. May 1, 2003;22(9):2274-83. doi: 10.1093/emboj/cdg203.
Heitz et al., Twenty years of cell-penetrating peptides: from molecular mechanisms to therapeutics. Br J Pharmacol. May 2009;157(2):195-206. doi: 10.1111/j.1476-5381.2009.00057.x. Epub Mar. 20, 2009.
Held et al., In vivo correction of murine hereditary tyrosinemia type I by phiC31 integrase- mediated gene delivery. Mol Ther. Mar. 2005;11(3):399-408. doi: 10.1016/j.ymthe.2004.11.001.
Heller et al., Replisome assembly and the direct restart of stalled replication forks. Nat Rev Mol Cell Biol. Dec. 2006;7(12):932-43. Epub Nov. 8, 2006.
Hendel et al., Chemically modified guide RNAs enhance CRISPR-Cas genome editing in human primary cells. Nat Biotechnol. Sep. 2015;33(9):985-989. doi: 10.1038/nbt.3290. Epub Jun. 29, 2015. Author Manuscript. 14 pages.
Hendricks et al., The S. cerevisiae Mag1 3-methyladenine DNA glycosylase modulates susceptibility to homologous recombination. DNA Repair (Amst). 2002;1(8):645-659.
Hermonat et al., Use of adeno-associated virus as a mammalian DNA cloning vector: transduction of neomycin resistance into mammalian tissue culture cells. Proc Natl Acad Sci U S A. Oct. 1984;81(20):6466-70. doi: 10.1073/pnas.81.20.6466.
Herschhorn et al., Retroviral reverse transcriptases. Cell Mol Life Sci. Aug. 2010;67(16):2717-47. doi: 10.1007/s00018-010-0346-2. Epub Apr. 1, 2010.
Herzig et al., A Novel Leu92 Mutant of HIV-1 Reverse Transcriptase with a Selective Deficiency in Strand Transfer Causes a Loss of Viral Replication. J Virol. Aug. 2015;89(16):8119-29. doi: 10.1128/JVI.00809-15. Epub May 20, 2015.
Hess et al., Directed evolution using dCas9-targeted somatic hypermutation in mammalian cells. Nat Methods. Dec. 2016;13(12):1036-1042. doi: 10.1038/nmeth.4038. Epub Oct. 31, 2016.
Heyer et al., Regulation of homologous recombination in eukaryotes. Annu Rev Genet. 2010;44:113-39. doi: 10.1146/annurev-genet-051710-150955. Author Manuscript. 33 pages.
Hickford et al., Antitumour polyether macrolides: four new halichondrins from the New Zealand deep-water marine sponge *Lissodendoryx* sp. Bioorg Med Chem. Mar. 15, 2009;17(6):2199-203. doi: 10.1016/j.bmc.2008.10.093. Epub Nov. 19, 2008.
Hida et al., Directed evolution for drug and nucleic acid; delivery. Adv Drug Deliv Rev. Dec. 22, 2007;59(15):1562-78. Epub Aug. 28, 2007.; Review.
Higgs et al., Genetic complexity in sickle cell disease. Proc Natl Acad Sci U S A. Aug. 19, 2008;105(33):11595-6. doi: 10.1073/pnas.0806633105. Epub Aug. 11, 2008.
Hilbers et al., New developments in structure determination of pseudoknots. Biopolymers. 1998;48(2-3):137-53. doi: 10.1002/(SICI)1097-0282(1998)48:2<137::AID-BIP4>3.0.CO;2-H.
Hill et al., Functional analysis of conserved histidines in ADP-glucose pyrophosphorylase from *Escherichia coli*.Biochem Biophys Res Commun. Mar. 17, 1998;244(2):573-7.
Hilton et al., Enabling functional genomics with genome engineering. Genome Res. Oct. 2015;25(10):1442-55. doi: 10.1101/gr.190124.115.
Hirano et al., Site-specific recombinases as tools for heterologous gene integration. Appl Microbiol Biotechnol. Oct. 2011;92(2):227-39. doi: 10.1007/s00253-011-3519-5. Epub Aug. 7, 2011. Review.
Hirano et al., Structural Basis for the Altered PAM Specificities of Engineered CRISPR-Cas9. Mol Cell. Mar. 17, 2016;61(6):886-94. doi: 10.1016/j.molcel.2016.02.018.
Hockemeyer et al., Efficient targeting of expressed and silent genes in human ESCs and iPSCs using zinc-finger nucleases. Nat Biotechnol. Sep. 2009;27(9):851-7. doi: 10.1038/nbt.1562. Epub Aug. 13, 2009.
Hockemeyer et al., Genetic engineering of human pluripotent cells using TALE nucleases. Nat Biotechnol. Jul. 7, 2011;29(8):731-4. doi: 10.1038/nbt.1927.
Hoernes et al., Translating the epitranscriptome. Wiley Interdiscip Rev RNA. Jan. 2017;8(1):e1375. doi: 10.1002/wrna.1375. Epub Jun. 27, 2016.
Hoess et al., DNA specificity of the Cre recombinase resides in the 25 kDa carboxyl domain of the protein. J Mol Biol. Dec. 20, 1990;216(4):873-82. doi: 10.1016/S0022-2836(99)80007-2.
Holden et al., Crystal structure of the anti-viral APOBEC3G catalytic domain and functional implications. Nature. Nov. 6, 2008;456(7218):121-4. doi: 10.1038/nature07357. Epub Oct. 12, 2008.
Hollis et al., Phage integrases for the construction and manipulation of transgenic mammals. Reprod Biol Endocrinol. Nov. 7, 2003;1:79. doi: 10.1186/1477-7827-1-79.
Holsinger et al., Signal transduction in T lymphocytes using a conditional allele of Sos. Proc Natl Acad Sci U S A. Oct. 10, 1995;92(21):9810-4. doi: 10.1073/pnas.92.21.9810.
Holt et al., Human hematopoietic stem/progenitor cells modified by zinc-finger nucleases targeted to CCR5 control HIV-1 in vivo. Nat Biotechnol. Aug. 2010;28(8):839-47. doi: 10.1038/nbt.1663. Epub Jul. 2, 2010.
Hondares et al., Peroxisome Proliferator-activated Receptor a (PPARα) Induces PPARY Coactivator 1a (PGC-1a) Gene Expression and Contributes to Thermogenic Activation of Brown Fat. J Biol. Chem Oct. 2011; 286(50):43112-22. doi: 10.1074/jbc.M111.252775.
Hoogenboom et al., Natural and designer binding sites made by phage display technology. Immunol Today. Aug. 2000;21(8):371-8.
Hope et al., Cationic lipids, phosphatidylethanolamine and the intracellular delivery of polymeric, nucleic acid-based drugs (review). Mol Membr Biol. 1998; Jan-Mar. 15(1): 1-14.
Horvath et al., CRISPR/Cas, the immune system of bacteria and archaea. Science. Jan. 8, 2010;327(5962):167-70. doi: 10.1126/science.1179555.
Horvath et al., Diversity, Activity, and Evolution of CRISPR Loci in Streptococcus Thermophilus. J Bacteriol. Feb. 2008;190(4):1401-12. doi: 10.1128/JB.01415-07. Epub Dec. 7, 2007.
Hotta et al., [Neurotropic viruses—classification, structure and characteristics]. Nihon Rinsho. Apr. 1997;55(4):777-82. Japanese.
Hou et al., Efficient genome engineering in human pluripotent stem cells using Cas9 from Neisseria meningitidis. Proc Natl Acad Sci U S A. Sep. 24, 2013;110(39):15644-9. doi: 10.1073/pnas.1313587110. Epub Aug. 12, 2013.
Houdebine, The methods to generate transgenic animals and to control transgene expression. J Biotechnol. Sep. 25, 2002;98(2-3):145-60.
Housden et al., Identification of potential drug targets for tuberous sclerosis complex by synthetic screens combining CRISPR-based knockouts with RNAi. Sci Signal. Sep. 8, 2015;8(393):rs9. doi: 10.1126/scisignal.aab3729.
Howard et al., Intracerebral drug delivery in rats with lesion-induced memory deficits. J Neurosurg. Jul. 1989;71(1):105-12.
Hower et al., Shape-based peak identification for ChIP-Seq. BMC Bioinformatics. Jan. 12, 2011;12:15. doi: 10.1186/1471-2105-12-15.
Hsu et al., DNA targeting specificity of RNA-guided Cas9 nucleases. Nat Biotechnol. Sep. 2013;31(9):827-32. doi: 10.1038/nbt.2647. Epub Jul. 21, 2013.
Hsu et al., DNA targeting specificity of RNA-guided Cas9 nucleases. Nat Biotechnol. Sep. 2013;31(9):827-32. doi: 10.1038/nbt.2647. Epub Jul. 21, 2013. Supplementary Information. 27 pages.

(56) References Cited

OTHER PUBLICATIONS

Hu et al., Chemical Biology Approaches to Genome Editing: Understanding, Controlling, and Delivering Programmable Nucleases. Cell Chem Biol. Jan. 21, 2016;23(1):57-73. doi: 10.1016/j.chembiol.2015.12.009.
Hu et al., Evolved Cas9 variants with broad PAM compatibility and high DNA specificity. Nature. Apr. 5, 2018;556(7699):57-63. doi: 10.1038/nature26155. Epub Feb. 28, 2018.
Huang et al., Gain-of-function mutations in sodium channel Na(v)1.9 in painful neuropathy. Brain. Jun. 2014;137(Pt 6):1627-42. doi: 10.1093/brain/awu079. Epub Apr. 27, 2014.
Huang et al., Heritable gene targeting in zebrafish using customized TALENs. Nat Biotechnol. Aug. 5, 2011;29(8):699-700. doi: 10.1038/nbt.1939.
Huang et al., Long-range pseudoknot interactions dictate the regulatory response in the tetrahydrofolate riboswitch. Proc Natl Acad Sci U S A. Sep. 6, 2011;108(36):14801-6. doi: 10.1073/pnas.1111701108. Epub Aug. 22, 2011.
Hubbard et al., Continuous directed evolution of DNA-binding proteins to improve TALEN specificity. Nat Methods. Oct. 2015; 12(10):939-42. doi: 10.1038/nmeth.3515. Epub Aug. 10, 2015.
Huggins et al., Flap endonuclease 1 efficiently cleaves base excision repair and DNA replication intermediates assembled into nucleosomes. Mol Cell. Nov. 2002;10(5):1201-11. doi: 10.1016/s1097-2765(02)00736-0.
Humbert et al., Targeted gene therapies: tools, applications, optimization. Crit Rev Biochem Mol Biol. May-Jun. 2012;47(3):264-81. doi: 10.3109/10409238.2012.658112.
Hung et al., Protein localization in disease and therapy. J Cell Sci. Oct. 15, 2011;124(Pt 20):3381-92. doi: 10.1242/jcs.089110.
Hurt et al., Highly specific zinc finger proteins obtained by directed domain shuffling and cell- based selection. Proc Natl Acad Sci U S A. Oct. 14, 2003;100(21):12271-6. Epub Oct. 3, 2003.
Husimi, Selection and evolution of bacteriophages in cellstat. Adv Biophys.; 1989;25:1-43. Review.
Hwang et al., Efficient genome editing in zebrafish using a CRISPR-Cas system. Nat Biotechnol. Mar. 2013;31(3):227-9. doi: 10.1038/nbt.2501. Epub Jan. 29, 2013.
Hwang et al., Efficient In Vivo Genome Editing Using RNA-Guided Nucleases. Nat Biotechnol. Mar. 2013; 31(3):227-229. doi: 10.1038/nbt.2501. Epub Jan. 29, 2013.
Händel et al., Expanding or restricting the target site repertoire of zinc-finger nucleases: the inter-domain linker as a major determinant of target site selectivity. Mol Ther. Jan. 2009;17(1):104-11. doi: 10.1038/mt.2008.233. Epub Nov. 11, 2008.
Ibba et al., Relaxing the substrate specificity of an aminoacyl-tRNA synthetase allows in vitro and in vivo synthesis of proteins containing unnatural amino acids. FEBS Lett. May 15, 1995;364(3):272-5.
Ibba et al., Substrate specificity is determined by amino acid binding pocket size in Escherichia coli phenylalanyl-tRNA synthetase. Biochemistry. Jun. 14, 1994;33(23):7107-12.
Iida et al., A site-specific, conservative recombination system carried by bacteriophage P1. Mapping the recombinase gene cin and the cross-over sites cix for the inversion of the C segment. EMBO J. 1982;1(11):1445-53.
Iida et al., The Min DNA inversion enzyme of plasmid p15B of *Escherichia coli* 15T-: a new member of the Din family of site-specific recombinases. Mol Microbiol. Jun. 1990;4(6):991-7. doi: 10.1111/j.1365-2958.1990.tb00671.x.
Ikediobi et al., Mutation analysis of 24 known cancer genes in the NCI-60 cell line set. Mol Cancer Ther. Nov. 2006;5(11):2606-12. Epub Nov. 6, 2006.
Imburgio et al., Studies of promoter recognition and start site selection by T7 RNA polymerase using a comprehensive collection of promoter variants. Biochemistry. Aug. 29, 2000;39(34):10419-30.
Ingram, A specific chemical difference between the globins of normal human and sickle-cell anaemia haemoglobin. Nature. Oct. 13, 1956;178(4537):792-4. doi: 10.1038/178792a0.
Irion et al., Identification and targeting of the ROSA26 locus in human embryonic stem cells. Nat Biotechnol. Dec. 2007;25(12):1477-82. doi: 10.1038/nbt1362. Epub Nov. 25, 2007.
Irrthum et al., Congenital hereditary lymphedema caused by a mutation that inactivates VEGFR3 tyrosine kinase. Am J Hum Genet. Aug. 2000;67(2):295-301. Epub Jun. 9, 2000.
Isaacs et al., Engineered riboregulators enable post-transcriptional control of gene expression. Nat Biotechnol. Jul. 2004;22(7):841-7. doi: 10.1038/nbt986. Epub Jun. 20, 2004.
Ishino et al., Nucleotide sequence of the iap gene, responsible for alkaline phosphatase isozyme conversion in *Escherichia coli*, and identification of the gene product. J Bacteriol. Dec. 1987;169(12):5429-33.
Iwai et al., Circular beta-lactamase: stability enhancement by cyclizing the backbone. FEBS Lett. Oct. 8, 1999;459(2):166-72. doi: 10.1016/s0014-5793(99)01220-x.
Iwai et al., Highly efficient protein trans-splicing by a naturally split DnaE intein from Nostoc punctiforme. FEBS Lett. Mar. 20, 2006;580(7):1853-8. doi: 10.1016/j.febslet.2006.02.045. Epub Feb. 24, 2006.
Iyama et al., DNA repair mechanisms in dividing and non-dividing cells. DNA Repair (Amst). Aug. 2013;12(8):620-36. doi: 10.1016/j.dnarep.2013.04.015. Epub May 16, 2013.
Jaffrey et al., Emerging links between m6A and misregulated mRNA methylation in cancer. Genome Med. Jan. 12, 2017;9(1):2. doi: 10.1186/s13073-016-0395-8.
Jamieson et al., Drug discovery with engineered zinc-finger proteins. Nat Rev Drug Discov. May 2003;2(5):361-8.
Jansen et al., Backbone and nucleobase contacts to glucosamine-6-phosphate in the glmS ribozyme. Nat Struct Mol Biol. Jun. 2006;13(6):517-23. Epub May 14, 2006.
Jansen et al., Identification of genes that are associated with DNA repeats in prokaryotes. Mol Microbiol. Mar. 2002;43(6):1565-75.
Jardine et al., HIV-1 Vaccines. Priming a broadly neutralizing antibody response to HIV-1 using a germline-targeting immunogen. Science. Jul. 10, 2015;349(6244):156-61. doi: 10.1126/science.aac5894. Epub Jun. 18, 2015.
Jasin et al., Repair of strand breaks by homologous recombination. Cold Spring Harb Perspect Biol. Nov. 1, 2013;5(11):a012740. doi: 10.1101/cshperspect.a012740.
Jeggo, DNA breakage and repair. Adv Genet. 1998;38:185-218. doi: 10.1016/s0065-2660(08)60144-3.
Jemielity et al., Novel "anti-reverse" cap analogs with superior translational properties. RNA. Sep. 2003;9(9):1108-22. doi: 10.1261/rna.5430403.
Jenkins et al., Comparison of a preQ1 riboswitch aptamer in metabolite-bound and free states with implications for gene regulation. J Biol Chem. Jul. 15, 2011;286(28):24626-37. doi: 10.1074/jbc.M111.230375. Epub May 18, 2011.
Jeong et al., Measurement of deoxyinosine adduct: Can it be a reliable tool to assess oxidative or nitrosative DNA damage? Toxicol Lett. Oct. 17, 2012;214(2):226-33. doi: 10.1016/j.toxlet.2012.08.013. Epub Aug. 23, 2012.
Jiang et al., CRISPR-Cas9 Structures and Mechanisms. Annu Rev Biophys. May 22, 2017;46:505-529. doi: 10.1146/annurev-biophys-062215-010822. Epub Mar. 30, 2017.
Jiang et al., RNA-guided editing of bacterial genomes using CRISPR-Cas systems. Nat Biotechnol. Mar. 2013;31(3):233-9. doi: 10.1038/nbt.2508. Epub Jan. 29, 2013.
Jiang et al., Structural Biology. A Cas9-guide RNA Complex Preorganized for Target DNA Recognition. Science. Jun. 26, 2015;348(6242):1477-81. doi: 10.1126/science.aab1452.
Jiang et al., Structures of a CRISPR-Cas9 R-loop complex primed for DNA cleavage. Science. Feb. 19, 2016;351(6275):867-71. doi: 10.1126/science.aad8282. Epub Jan. 14, 2016.
Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.
Jinek et al., RNA-programmed genome editing in human cells. Elife. Jan. 29, 2013;2:e00471. doi: 10.7554/eLife.00471.
Jinek et al., Structures of Cas9 endonucleases reveal RNA-mediated conformational activation. Science. Mar. 14, 2014;343(6176):1247997. doi: 10.1126/science.1247997. Epub Feb. 6, 2014.

(56) References Cited

OTHER PUBLICATIONS

Jiricny, The multifaceted mismatch-repair system. Nat Rev Mol Cell Biol. May 2006;7(5):335-46. doi: 10.1038/nrm1907.
Johann et al., GLVR1, a receptor for gibbon ape leukemia virus, is homologous to a phosphate permease of Neurospora crassa and is expressed at high levels in the brain and thymus. J Virol. Mar. 1992;66(3):1635-40. doi: 10.1128/JVI.66.3.1635-1640.1992.
Johansson et al., RNA Recognition by the MS2 Phage Coat Protein. Seminars in Virology. 1997;8(3):176-85. https://doi.org/10.1006/smvy.1997.0120.
Johansson et al., Selenocysteine in proteins-properties and biotechnological use. Biochim Biophys Acta. Oct. 30, 2005;1726(1):1-13. Epub Jun. 1, 2005.
Johns et al., The promise and peril of continuous in vitro evolution. J Mol Evol. Aug. 2005;61(2):253-63. Epub Jun. 27, 2005.
Johnson et al., Trans insertion-splicing: ribozyme-catalyzed insertion of targeted sequences into RNAs. Biochemistry. Aug. 9, 2005;44(31):10702-10. doi: 10.1021/bi0504815.
Joho et al., Identification of a region of the bacteriophage T3 and T7 RNA polymerases that determines promoter specificity. J Mol Biol. Sep. 5, 1990;215(1):31-9.
Jopling et al., Dedifferentiation, transdifferentiation and reprogramming: three routes to regeneration. Nat Rev Mol Cell Biol. Feb. 2011;12(2):79-89. doi: 10.1038/nrm3043.
Jore et al., Structural basis for CRISPR RNA-guided DNA recognition by Cascade. Nat Struct Mol Biol. May 2011;18(5):529-36. doi: 10.1038/nsmb.2019. Epub Apr. 3, 2011.
Joung et al., TALENs: a widely applicable technology for targeted genome editing. Nat Rev Mol Cell Biol. Jan. 2013; 14(1):49-55. doi: 10.1038/nrm3486. Epub Nov. 21, 2012.
Joyce et al., Amplification, mutation and selection of catalytic RNA. Gene. Oct. 15, 1989;82(1):83-7. doi: 10.1016/0378-1119(89)90033-4.
Judge et al., Design of noninflammatory synthetic siRNA mediating potent gene silencing in vivo. Mol Ther. Mar. 2006; 13(3):494-505. Epub Dec. 15, 2005.
Jyothy et al., Translocation Down syndrome. Indian J Med Sci. Mar. 2002;56(3):122-6.
Kacian et al., Purification of the DNA polymerase of avian myeloblastosis virus. Biochim Biophys Acta. Sep. 24, 1971;246(3):365-83. doi: 10.1016/0005-2787(71)90773-8.
Kaczmarczyk et al., Manipulating the Prion Protein Gene Sequence and Expression Levels with CRISPR/Cas9. PLoS One. Apr. 29, 2016;11(4):e0154604. doi: 10.1371/journal.pone.0154604.
Kadoch et al., Reversible disruption of mSWI/SNF (BAF) complexes by the SS18-SSX oncogenic fusion in synovial sarcoma. Cell. Mar. 28, 2013;153(1):71-85. doi: 10.1016/j.cell.2013.02.036.
Kahmann et al., G inversion in bacteriophage Mu DNA is stimulated by a site within the invertase gene and a host factor. Cell. Jul. 1985;41(3):771-80. doi: 10.1016/s0092-8674(85)80058-1.
Kaiser et al., Gene therapy. Putting the fingers on gene repair. Science. Dec. 23, 2005;310(5756):1894-6.
Kakiyama et al., A peptide release system using a photo-cleavable linker in a cell array format for cell-toxicity analysis. Polymer J. Feb. 27, 2013;45:535-9.
Kalyaanamoorthy et al., ModelFinder: fast model selection for accurate phylogenetic estimates. Nat Methods. Jun. 2017; 14(6):587-589. doi: 10.1038/nmeth.4285. Epub May 8, 2017.
Kan et al., Mechanisms of precise genome editing using oligonucleotide donors. Genome Res. Jul. 2017;27(7):1099-1111. doi: 10.1101/gr.214775.116. Epub Mar. 29, 2017.
Kandavelou et al., Targeted manipulation of mammalian genomes using designed zinc finger nucleases. Biochem Biophys Res Commun. Oct. 9, 2009;388(1):56-61. doi: 10.1016/j.bbrc.2009.07.112. Epub Jul. 25, 2009.
Kang et al., Structural Insights into riboswitch control of the biosynthesis of queuosine, a modified nucleotide found in the anticodon of tRNA. Mol Cell. Mar. 27, 2009;33(6):784-90. doi: 10.1016/j.molcel.2009.02.019. Epub Mar. 12, 2009.
Kao et al., Cleavage specificity of Saccharomyces cerevisiae flap endonuclease 1 suggests a double-flap structure as the cellular substrate. J Biol Chem. Apr. 26, 2002;277(17):14379-89. doi: 10.1074/jbc.M110662200. Epub Feb. 1, 2002.
Kappel et al., Regulating gene expression in transgenic animals. Curr Opin Biotechnol. Oct. 1992;3(5):548-53.
Karimova et al., Discovery of Nigri/nox and Panto/pox site-specific recombinase systems facilitates advanced genome engineering. Sci Rep. Jul. 22, 2016;6:30130. doi: 10.1038/srep30130.
Karimova et al., Vika/vox, a novel efficient and specific Cre/loxP-like site-specific recombination system. Nucleic Acids Res. Jan. 2013;41(2):e37. doi: 10.1093/nar/gks1037. Epub Nov. 9, 2012.
Karpenshif et al., From yeast to mammals: recent advances in genetic control of homologous recombination. DNA Repair (Amst). Oct. 1, 2012;11(10):781-8. doi: 10.1016/j.dnarep.2012.07.001. Epub Aug. 11, 2012. Review.
Karpinsky et al., Directed evolution of a recombinase that excises the provirus of most HIV-1 primary isolates with high specificity. Nat Biotechnol. Apr. 2016;34(4):401-9. doi: 10.1038/nbt.3467. Epub Feb. 22, 2016.
Katafuchi et al., DNA polymerases involved in the incorporation of oxidized nucleotides into DNA: their efficiency and template base preference. Mutat Res. Nov. 28, 2010;703(1):24-31. doi: 10.1016/j.mrgentox.2010.06.004. Epub Jun. 11, 2010.
Kato et al., Improved purification and enzymatic properties of three forms of reverse transcriptase from avian myeloblastosis virus. J Virol Methods. Dec. 1984;9(4):325-39. doi: 10.1016/0166-0934(84)90058-2.
Katoh et al., MAFFT multiple sequence alignment software version 7: improvements in performance and usability. Mol Biol Evol. Apr. 2013;30(4):772-80. doi: 10.1093/molbev/mst010. Epub Jan. 16, 2013.
Kaufman et al., Translational efficiency of polycistronic mRNAs and their utilization to express heterologous genes in mammalian cells. EMBO J. Jan. 1987;6(1):187-93.
Kavli et al., Excision of cytosine and thymine from DNA by mutants of human uracil-DNA glycosylase. EMBO J. Jul. 1, 1996;15(13):3442-7.
Kawarasaki et al., Enhanced crossover SCRATCHY: construction and high-throughput screening of a combinatorial library containing multiple non-homologous crossovers. Nucleic Acids Res. Nov. 1, 2003;31(21):e126.
Kay et al., Viral vectors for gene therapy: the art of turning infectious agents into vehicles of therapeutics. Nat Med. Jan. 2001;7(1):33-40.
Kaya et al., A bacterial Argonaute with noncanonical guide RNA specificity. Proc. Natl. Acad. Sci. USA Apr. 2016;113(15):4057-62.
Keijzers et al., Human exonuclease 1 (EXO1) activity characterization and its function on flap structures. Biosci Rep. Apr. 25, 2015;35(3):e00206. doi: 10.1042/BSR20150058.
Kellendonk et al., Regulation of Cre recombinase activity by the synthetic steroid RU 486. Nucleic Acids Res. Apr. 15, 1996;24(8):1404-11.
Kelman, PCNA: structure, functions and interactions. Oncogene. Feb. 12, 1997;14(6):629-40. doi: 10.1038/sj.onc.1200886.
Keravala et al., A diversity of serine phage integrases mediate site-specific recombination in mammalian cells. Mol Genet Genomics. Aug. 2006;276(2):135-46. doi: 10.1007/s00438-006-0129-5. Epub May 13, 2006.
Kessel et al., Murine developmental control genes. Science. Jul. 27, 1990;249(4967):374-9. doi: 10.1126/science. 1974085.
Kessler et al., Gene delivery to skeletal muscle results in sustained expression and systemic delivery of a therapeutic protein. Proc Natl Acad Sci U S A. Nov. 26, 1996;93(24):14082-7. doi: 10.1073/pnas.93.24.14082.
Ketha et al., Application of bioinformatics-coupled experimental analysis reveals a new transport-competent nuclear localization signal in the nucleoprotein of Influenza A virus strain. BMC Cell Biol. Apr. 28, 2008; 9:22. https://doi.org/10.1186/1471-2121-9-22.
Kiga et al., An engineered Escherichia coli tyrosyl-tRNA synthetase for site-specific incorporation of an unnatural amino acid into

(56) References Cited

OTHER PUBLICATIONS proteins in eukaryotic translation and its application in a wheat germ cell-free system. Proc Natl Acad Sci U S A. Jul. 23, 2002;99(15):9715-20. Epub Jul. 3, 2002.

Kilbride et al., Determinants of product topology in a hybrid Cre-Tn3 resolvase site-specific recombination system. J Mol Biol. Jan. 13, 2006;355(2):185-95. Epub Nov. 9, 2005.

Kilcher et al., Brochothrix thermosphacta bacteriophages feature heterogeneous and highly mosaic genomes and utilize unique prophage insertion sites. J Bacteriol. Oct. 2010; 192(20):5441-53. doi: 10.1128/JB.00709-10. Epub Aug. 13, 2010.

Kim et al., DJ-1, a novel regulator of the tumor suppressor PTEN. Cancer Cell. 2005;7(3):263-273.

Kim et al., A library of TAL effector nucleases spanning the human genome. Nat Biotechnol. Mar. 2013;31(3):251-8. Doi: 10.1038/nbt.2517. Epub Feb. 17, 2013.

Kim et al., Genome-wide target specificities of CRISPR RNA-guided programmable deaminases. Nat Biotechnol. May 2017;35(5):475-480. doi: 10.1038/nbt.3852. Epub Apr. 10, 2017.

Kim et al., High cleavage efficiency of a 2A peptide derived from porcine teschovirus-1 in human cell lines, zebrafish and mice. PLoS One. 2011;6(4):e18556. doi: 10.1371/journal.pone.0018556. Epub Apr. 29, 2011.

Kim et al., Highly efficient RNA-guided base editing in mouse embryos. Nat Biotechnol. May 2017;35(5):435-437. doi: 10.1038/nbt.3816. Epub Feb. 27, 2017.

Kim et al., Highly efficient RNA-guided genome editing in human cells via delivery of purified Cas9 ribonucleoproteins. Genome Res. Jun. 2014;24(6):1012-9. doi: 10.1101/gr.171322.113. Epub Apr. 2, 2014.

Kim et al., Hybrid restriction enzymes: zinc finger fusions to Fok I cleavage domain. Proc Natl Acad Sci U S A. Feb. 6, 1996;93(3):1156-60.

Kim et al., In vivo genome editing with a small Cas9 orthologue derived from Campylobacter jejuni. Nat Commun. Feb. 21, 2017;8:14500. doi: 10.1038/ncomms14500. PMID: 28220790; Pmcid: PMC5473640.

Kim et al., In vivo high-throughput profiling of CRISPR-Cpf1 activity. Nat Methods. Feb. 2017;14(2): 153-159. doi: 10.1038/nmeth.4104. Epub Dec. 19, 2016.

Kim et al., Increasing the genome-targeting scope and precision of base editing with engineered Cas9-cytidine deaminase fusions. Nat Biotechnol. Apr. 2017;35(4):371-376. doi: 10.1038/nbt.3803. Epub Feb. 13, 2017.

Kim et al., Mycobacteriophage Bxb1 integrates into the Mycobacterium smegmatis groEL1 gene. Mol Microbiol. Oct. 2003;50(2):463-73. doi: 10.1046/j.1365-2958.2003.03723.x.

Kim et al., RAD51 mutants cause replication defects and chromosomal instability. Mol Cell Biol. Sep. 2012;32(18):3663-80. doi: 10.1128/MCB.00406-12. Epub Jul. 9, 2012.

Kim et al., Structural and kinetic characterization of *Escherichia coli* TadA, the wobble-specific tRNA deaminase. Biochemistry. May 23, 2006;45(20):6407-16. doi: 10.1021/bi0522394. PMID: 16700551.

Kim et al., TALENs and ZFNs are associated with different mutationsignatures. Nat Methods. Mar. 2013;10(3):185. doi: 10.1038/nmeth.2364. Epub Feb. 10, 2013.

Kim et al., Targeted genome editing in human cells with zinc finger nucleases constructed via modular assembly. Genome Res. Jul. 2009;19(7):1279-88. doi: 10.1101/gr.089417.108. Epub May 21, 2009.

Kim et al., The role of apolipoprotein E in Alzheimer's disease. Neuron. Aug. 13, 2009;63(3):287-303. doi: 10.1016/j.neuron.2009.06.026.

Kim et al., Transcriptional repression by zinc finger peptides. Exploring the potential for applications in gene therapy. J Biol Chem. Nov. 21, 1997;272(47):29795-800.

King et al., No gain, no pain: NaV1.7 as an analgesic target. ACS Chem Neurosci. Sep. 17, 2014;5(9):749-51. doi: 10.1021/cn500171p. Epub Aug. 11, 2014.

Kitamura et al., Uracil DNA glycosylase counteracts APOBEC3G-induced hypermutation of hepatitis B viral genomes: excision repair of covalently closed circular DNA. PLoS Pathog. 2013;9(5):e1003361. doi: 10.1371/journal.ppat. 1003361. Epub May 16, 2013.

Klapacz et al., Frameshift mutagenesis and microsatellite instability induced by human alkyladenine DNA glycosylase. Mol Cell. Mar. 26, 2010;37(6):843-53. doi: 10.1016/j.molcel.2010.01.038.

Klauser et al., An engineered small RNA-mediated genetic switch based on a ribozyme expression platform. Nucleic Acids Res. May 1, 2013;41(10):5542-52. doi: 10.1093/nar/gkt253. Epub Apr. 12, 2013.

Klein et al., Cocrystal structure of a class I preQ1 riboswitch reveals a pseudoknot recognizing an essential hypermodified nucleobase. Nat Struct Mol Biol. Mar. 2009; 16(3):343-4. doi: 10.1038/nsmb.1563.Epub Feb. 22, 2009.

Kleiner et al., In vitro selection of a DNA-templated small-molecule library reveals a class of macrocyclic kinase inhibitors. J Am Chem Soc. Aug. 25, 2010;132(33):11779-91. doi: 10.1021/ja104903x.

Kleinstiver et al., Broadening the targeting range of Staphylococcus aureus CRISPR-Cas9 by modifying PAM recognition. Nat Biotechnol. Dec. 2015;33(12):1293-1298. doi: 10.1038/nbt.3404. Epub Nov. 2, 2015.

Kleinstiver et al., Engineered CRISPR-Cas9 nucleases with altered PAM specificities. Nature. Jul. 23, 2015;523(7561):481-5 and Supplementary Materials. doi: 10.1038/nature14592. Epub Jun. 22, 2015. 27 pages.

Kleinstiver et al., Engineered CRISPR-Cas9 nucleases with altered PAM specificities. Nature. Jul. 23, 2015;523(7561):481-5. doi: 10.1038/nature14592. Epub Jun. 22, 2015.

Kleinstiver et al., High-fidelity CRISPR-Cas9 nucleases with No. detectable genome-wide off-target effects. Nature. Jan. 28, 2016;529(7587):490-5. doi: 10.1038/nature16526. Epub Jan. 6, 2016.

Kleinstiver et al., Monomeric site-specific nucleases for genome editing. Proc Natl Acad Sci U S A. May 22, 2012;109(21):8061-6. doi: 10.1073/pnas.1117984109. Epub May 7, 2012.

Klement et al., Discrimination between bacteriophage T3 and T7 promoters by the T3 and T7 RNA polymerases depends primarily upon a three base-pair region located 10 to 12 base-pairs upstream from the start site. J Mol Biol. Sep. 5, 1990;215(1):21-9.

Klippel et al., Isolation and characterization of unusual gin mutants. EMBO J. Dec. 1, 1988;7(12):3983-9.

Klippel et al., The DNA invertase Gin of phage Mu: formation of a covalent complex with DNA via a phosphoserine at amino acid position 9. Embo J. Apr. 1988;7(4):1229-37.

Klug et al., Zinc fingers: a novel protein fold for nucleic acid recognition. Cold Spring Harb Symp Quant Biol. 1987;52:473-82.

Kobori et al., Deep Sequencing Analysis of Aptazyme Variants Based on a Pistol Ribozyme. ACS Synth Biol. Jul. 21, 2017;6(7):1283-1288. doi: 10.1021/acssynbio.7b00057. Epub Apr. 14, 2017.

Kohli et al., A portable hot spot recognition loop transfers sequence preferences from APOBEC family members to activation-induced cytidine deaminase. J Biol Chem. Aug. 21, 2009;284(34):22898-904. doi: 10.1074/jbc.M109.025536. Epub Jun. 26, 2009.

Kohli et al., Local sequence targeting in the AID/APOBEC family differentially impacts retroviral restriction and antibody diversification. J Biol Chem. Dec. 24, 2010;285(52):40956-64. doi: 10.1074/jbc.M110.177402. Epub Oct. 6, 2010.

Koike-Yusa et al., Genome-wide recessive genetic screening in mammalian cells with a lentiviral CRISPR-guide RNA library. Nat Biotechnol. Mar. 2014;32(3):267-73. doi: 10.1038/nbt.2800. Epub Dec. 23, 2013.

Kolb et al., Click Chemistry: Diverse Chemical Function from a Few Good Reactions. Angew Chem Int Ed Engl. Jun. 1, 2001;40(11):2004-2021.

Kolot et al., Site promiscuity of coliphage HK022 integrase as a tool for gene therapy. Gene Ther. Jul. 2015;22(7):521-7. doi: 10.1038/gt.2015.9. Epub Mar. 12, 2015.

Kolot et al., Site-specific recombination in mammalian cells expressing the Int recombinase of bacteriophage HK022. Mol Biol Rep. Aug. 1999;26(3):207-13. doi: 10.1023/a:1007096701720.

(56) References Cited

OTHER PUBLICATIONS

Komor et al., CRISPR-Based Technologies for the Manipulation of Eukaryotic Genomes. Cell. Jan. 12, 2017;168(1-2):20-36. doi: 10.1016/j.cell.2016.10.044.
Komor et al., Improved base excision repair inhibition and bacteriophage Mu Gam protein yields C:G-to-T:A base editors with higher efficiency and product purity. Sci Adv. Aug. 30, 2017;3(8):eaao4774. doi: 10.1126/sciadv.aao4774. eCollection Aug. 2017.
Komor et al., Programmable editing of a target base in genomic DNA without double-stranded DNA cleavage. Nature. Apr. 20, 2016;533(7603):420-4. doi: 10.1038/nature17946.
Konermann et al., Genome-scale transcriptional activation by an engineered CRISPR-Cas9 complex. Nature. Jan. 29, 2015;517(7536):583-8. doi: 10.1038/nature14136. Epub Dec. 10, 2014.
Konermann et al., Optical control of mammalian endogenous transcription and epigenetic states. Nature. Aug. 22, 2013;500(7463):472-6. doi: 10.1038/nature12466. Epub Aug. 23, 2013.
Konishi et al., Amino acid substitutions away from the RNase H catalytic site increase the thermal stability of Moloney murine leukemia virus reverse transcriptase through RNase H inactivation. Biochem Biophys Res Commun. Nov. 14, 2014;454(2):269-74. doi: 10.1016/j.bbrc.2014.10.044. Epub Oct. 17, 2014.
Koonin et al., Diversity, classification and evolution of CRISPR-Cas systems. Curr Opin Microbiol. 2017;37:67?78. doi:10.1016/j.mib.2017.05.008.
Kotewicz et al., Cloning and overexpression of Moloney murine leukemia virus reverse transcriptase in *Escherichia coli*. Gene. 1985;35(3):249-58. doi: 10.1016/0378-1119(85)90003-4.
Kotewicz et al., Isolation of cloned Moloney murine leukemia virus reverse transcriptase lacking ribonuclease H activity. Nucleic Acids Res. Jan. 11, 1988;16(1):265-77. doi: 10.1093/nar/16.1.265.
Kotin, Prospects for the use of adeno-associated virus as a vector for human gene therapy. Hum Gene Ther. Jul. 1994;5(7):793-801. doi: 10.1089/hum.1994.5.7-793.
Kouzminova et al., Patterns of chromosomal fragmentation due to uracil-DNA incorporation reveal a novel mechanism of replication-dependent double-stranded breaks. Mol Microbiol. Apr. 2008;68(1):202-15. doi: 10.1111/j.1365-2958.2008.06149.x.
Kowal et al., Exploiting unassigned codons in Micrococcus luteus for tRNA-based amino acid mutagenesis. Nucleic Acids Res. Nov. 15, 1997;25(22):4685-9.
Kozak, An analysis of 5'-noncoding sequences from 699 vertebrate messenger RNAs. Nucleic Acids Res. Oct. 26, 1987;15(20):8125-48. doi: 10.1093/nar/15.20.8125.
Kraft et al., Deletions, Inversions, Duplications: Engineering of Structural Variants using CRISPR/Cas in Mice. Cell Rep. Feb. 10, 2015;10(5):833-839. doi: 10.1016/j.celrep.2015.01.016. Epub Feb. 7, 2015.
Kremer et al., Adenovirus and adeno-associated virus mediated gene transfer. Br Med Bull. Jan. 1995;51(1):31-44. doi: 10.1093/oxfordjournals.bmb.a072951.
Krishna et al., Structural classification of zinc fingers: survey and summary. Nucleic Acids Res. Jan. 15, 2003;31(2):532-50.
Krokan et al., Uracil in DNA—occurrence, consequences and repair. Oncogene. Dec. 15, 2002;21(58):8935-48. doi: 10.1038/sj.onc.1205996.
Krokan et al., Base excision repair. Cold Spring Harb Perspect Biol. Apr. 1, 2013;5(4):a012583. doi: 10.1101/cshperspect.a012583.
Kuan et al., A systematic evaluation of nucleotide properties for CRISPR sgRNA design. BMC Bioinformatics. Jun. 6, 2017;18(1):297. doi: 10.1186/s12859-017-1697-6.
Kumar et al., Gene therapy for chronic neuropathic pain: how does it work and where do we stand today? Pain Med. May 2011;12(5):808-22. doi: 10.1111/j.1526-4637.2011.01120.x.
Kumar et al., Structural and functional consequences of the mutation of a conserved arginine residue in alphaA and alphaB crystallins. J Biol Chem. Aug. 20, 1999;274(34):24137-41.
Kundu et al., Leucine to proline substitution by SNP at position 197 in Caspase-9 gene expression leads to neuroblastoma: a bioinformatics analysis. 3 Biotech. 2013; 3:225-34.
Kunkel et al., Eukaryotic Mismatch Repair in Relation to DNA Replication. Annu Rev Genet. 2015;49:291-313. doi: 10.1146/annurev-genet-112414-054722.
Kunz et al., DNA Repair in mammalian cells: Mismatched repair: variations on a theme. Cell Mol Life Sci. Mar. 2009;66(6):1021-38. doi: 10.1007/s00018-009-8739-9.
Kurjan et al., Structure of a yeast pheromone gene (MF alpha): a putative alpha-factor precursor contains four tandem copies of mature alpha-factor. Cell. Oct. 1982;30(3):933-43. doi: 10.1016/0092-8674(82)90298-7.
Kury et al., De Novo Disruption of the Proteasome Regulatory Subunit PSMD12 Causes a Syndromic Neurodevelopmental Disorder. Am J Hum Genet. Feb. 2, 2017;100(2):352-363. doi: 10.1016/j.ajhg.2017.01.003. Epub Jan. 26, 2017.
Kuscu et al., CRISPR-Cas9-AID base editor is a powerful gain-of-function screening tool. Nat Methods. Nov. 29, 2016;13(12):983-984. doi: 10.1038/nmeth.4076.
Kuscu et al., CRISPR-STOP: gene silencing through base-editing-induced nonsense mutations. Nat Methods. Jul. 2017; 14(7):710-712. doi: 10.1038/nmeth.4327. Epub Jun. 5, 2017.
Kuscu et al., Genome-wide analysis reveals characteristics of off-target sites bound by the Cas9 endonuclease. Nat Biotechnol. Jul. 2014;32(7):677-83. doi: 10.1038/nbt.2916. Epub May 18, 2014.
Kwart et al., Precise and efficient scarless genome editing in stem cells using CORRECT. Nat Protoc. Feb. 2017; 12(2):329-354. doi: 10.1038/nprot.2016.171. Epub Jan. 19, 2017.
Kwon et al., Chemical basis of glycine riboswitch cooperativity. RNA. Jan. 2008; 14(1):25-34. Epub Nov. 27, 2007.
Köhrer et al., A possible approach to site-specific insertion of two different unnatural amino acids into proteins in mammalian cells via nonsense suppression. Chem Biol. Nov. 2003;10(11):1095-102.
Köhrer et al., Complete set of orthogonal 21st aminoacyl-tRNA synthetase-amber, ochre and opal suppressor tRNA pairs: concomitant suppression of three different termination codons in an mRNA in mammalian cells. Nucleic Acids Res. Dec. 1, 2004;32(21):6200-11. Print 2004.
Kügler et al., Human synapsin 1 gene promoter confers highly neuron-specific long-term transgene expression from an adenoviral vector in the adult rat brain depending on the transduced area. Gene Ther. Feb. 2003; 10(4):337-47. doi: 10.1038/sj.gt.3301905.
Lada et al., Mutator effects and mutation signatures of editing deaminases produced in bacteria and yeast. Biochemistry (Mosc). Jan. 2011;76(1):131-46.
Lai et al., Vault nanoparticles containing an adenovirus-derived membrane lytic protein facilitate toxin and gene transfer. ACS Nano. Mar. 24, 2009;3(3):691-9. doi: 10.1021/nn8008504.
Lakich et al., Inversions disrupting the factor VIII gene are a common cause of severe haemophilia A. Nat Genet. Nov. 1993;5(3):236-41. doi: 10.1038/ng1193-236.
Lancaster et al., Limited trafficking of a neurotropic virus through inefficient retrograde axonal transport and the type I interferon response. PLoS Pathog. Mar. 5, 2010;6(3):e1000791. doi: 10.1371/journal.ppat.1000791.
Landrum et al., ClinVar: public archive of interpretations of clinically relevant variants. Nucleic Acids Res. Jan. 4, 2016;44(D1):D862-8. doi: 10.1093/nar/gkv1222. Epub Nov. 17, 2015.
Landrum et al., ClinVar: public archive of relationships among sequence variation and human phenotype. Nucleic Acids Res. Jan. 2014;42(Database issue): D980-5. doi: 10.1093/nar/gkt1113. Epub Nov. 14, 2013.
Langer and Wise, Medical Applications of Controlled Release, CRC Press, 1974. Boca Raton, Fla.
Langer et al., Chemical and Physical Structure of Polymers as Carriers for Controlled Release of Bioactive Agents: A Review. J Macromol Sci, Part C, 1983;23(1):61-126. doi: 10.1080/07366578308079439.
Langer et al., Chemical and Physical Structure of Polymers as Carriers for Controlled Release of Bioactive Agents: A Review. Journal of Macromolecular Science, 2006;23(1):61-126. DOI: 10.1080/07366578308079439.

(56) References Cited

OTHER PUBLICATIONS

Langer et al., New methods of drug delivery. Science. Sep. 28, 1990;249(4976): 1527-33.
Larson et al., CRISPR interference (CRISPRi) for sequence-specific control of gene expression. Nat Protoc. Nov. 2013;8(11):2180-96. doi: 10.1038/nprot.2013.132. Epub Oct. 17, 2013.
Lau et al., Molecular basis for discriminating between normal and damaged bases by the human alkyladenine glycosylase, AAG. Proc Natl Acad Sci U S A. Dec. 5, 2000;97(25):13573-8.
Lauer et al., Construction, characterization, and use of two Listeria monocytogenes site-specific phage integration vectors. J Bacteriol. Aug. 2002; 184(15):4177-86. doi: 10.1128/jb.184.15.4177-4186. 2002.
Lavergne et al., Defects in type IIA von Willebrand disease: a cysteine 509 to arginine substitution in the mature von Willebrand factor disrupts a disulphide loop involved in the interaction with platelet glycoprotein Ib-IX. Br J Haematol. Sep. 1992;82(1):66-72.
Lawrence et al., Supercharging proteins can impart unusual resilience. J Am Chem Soc. Aug. 22, 2007;129(33):10110-2. Epub Aug. 1, 2007.
Lawyer et al., High-level expression, purification, and enzymatic characterization of full-length Thermus aquaticus DNA polymerase and a truncated form deficient in 5' to 3' exonuclease activity. PCR Methods Appl. May 1993;2(4):275-87. doi: 10.1101/gr.2.4.275.
Lazar et al., Transforming growth factor alpha: mutation of aspartic acid 47 and leucine 48 results in different biological activities. Mol Cell Biol. Mar. 1988;8(3):1247-52.
Lazarevic et al., Nucleotide sequence of the *Bacillus subtilis* temperate bacteriophage SPbetac2. Microbiology (Reading). May 1999;145 ( Pt 5):1055-1067. doi: 10.1099/13500872-145-5-1055.
Le et al., SMNDelta7, the major product of the centromeric survival motor neuron (SMN2) gene, extends survival in mice with spinal muscular atrophy and associates with full-length SMN. Hum Mol Genet. Mar. 15, 2005;14(6):845-57. doi: 10.1093/hmg/ddi078. Epub Feb. 9, 2005.
Le Grice et al., Purification and characterization of recombinant equine infectious anemia virus reverse transcriptase. J Virol. Dec. 1991;65(12):7004-7. doi: 10.1128/JVI.65.12.7004-7007.1991.
Leader et al., Protein therapeutics: a summary and pharmacological classification. Nat Rev Drug Discov. Jan. 2008;7(1):21-39.
Leaver-Fay et al., ROSETTA3: an object-oriented software suite for the simulation and design of macromolecules. Methods Enzymol. 2011;487:545-74. doi: 10.1016/B978-0-12-381270-4.00019-6.
Leconte et al., A population-based experimental model for protein evolution: effects of mutation rate and selection stringency on evolutionary outcomes. Biochemistry. Feb. 26, 2013;52(8): 1490-9. doi: 10.1021/bi3016185. Epub Feb. 14, 2013.
Ledford, Gene-editing hack yields pinpoint precision. Nature, Apr. 20, 2016. http://www.nature.com/news/gene-editing-hack-yields-pinpoint-precision-1.19773.
Lee et al., A chimeric thyroid hormone receptor constitutively bound to DNA requires retinoid X receptor for hormone-dependent transcriptional activation in yeast. Mol Endocrinol. Sep. 1994;8(9):1245-52.
Lee et al., A monoclonal antibody that targets a NaV1.7 channel voltage sensor for pain and itch relief. Cell. Jun. 5, 2014;157(6):1393-1404. doi: 10.1016/j.cell.2014.03.064. Epub May 22, 2014. Retraction in: Cell. Jun. 25, 2020;181(7):1695.
Lee et al., An allosteric self-splicing ribozyme triggered by a bacterial second messenger. Science. Aug. 13, 2010;329(5993):845-8. doi: 10.1126/science.1190713.
Lee et al., Failure to detect DNA-guided genome editing using Natronobacterium gregoryi Argonaute. Nat Biotechnol. Nov. 28, 2016;35(1):17-18. doi: 10.1038/nbt.3753.
Lee et al., PIK3CA gene is frequently mutated in breast carcinomas and hepatocellular carcinomas. Oncogene. Feb. 17, 2005;24(8):1477-80.
Lee et al., Recognition of liposomes by cells: in vitro binding and endocytosis mediated by specific lipid headgroups and surface charge density. Biochim Biophys Acta. Jan. 31, 1992;1103(2):185-97.
Lee et al., Ribozyme Mediated gRNA Generation for In Vitro and In Vivo CRISPR/Cas9 Mutagenesis. PLoS One. Nov. 10, 2016;11(11):e0166020. doi: 10.1371/journal.pone.0166020. eCollection 2016.
Lee et al., Site-specific integration of mycobacteriophage L5: integration-proficient vectors for *Mycobacterium smegmatis, Mycobacterium tuberculosis*, and bacille Calmette-Guérin. Proc Natl Acad Sci U S A. Apr. 15, 1991;88(8):3111-5. doi: 10.1073/pnas.88.8.3111.
Lee et al., Synthetically modified guide RNA and donor DNA are a versatile platform for CRISPR-Cas9 engineering. Elife. May 2, 2017;6:e25312. doi: 10.7554/eLife.25312.
Lee et al., Targeted chromosomal deletions in human cells using zinc finger nucleases. Genome Res. Jan. 2010 20: 81-89; Published in Advance Dec. 1, 2009, doi:10.1101/gr.099747.109.
Lee et al., Transcriptional regulation and its misregulation in disease. Cell. Mar. 14, 2013;152(6): 1237-51. doi: 10.1016/j.cell. 2013.02.014.
Lefebvre et al., Identification and characterization of a spinal muscular atrophy-determining gene. Cell. Jan. 13, 1995;80(1):155-65. doi: 10.1016/0092-8674(95)90460-3.
Lei et al., Efficient targeted gene disruption in Xenopus embryos using engineered transcription activator-like effector nucleases (TALENs). Proc Natl Acad Sci U S A. Oct. 23, 2012;109(43):17484-9. Doi: 10.1073/pnas.1215421109. Epub Oct. 8, 2012.
Leipold et al., A de novo gain-of-function mutation in SCN11A causes loss of pain perception. Nat Genet. Nov. 2013;45(11):1399-404. doi: 10.1038/ng.2767. Epub Sep. 15, 2013.
Lenk et al., Pathogenic mechanism of the FIG4 mutation responsible for Charcot-Marie-Tooth disease CMT4J. PLoS Genet. Jun. 2011;7(6):e1002104. doi: 10.1371/journal.pgen.1002104. Epub Jun. 2, 2011.
Lesinski et al., The potential for targeting the STAT3 pathway as a novel therapy for melanoma. Future Oncol. Jul. 2013;9(7):925-7. doi: 10.2217/fon.13.83. Author Manuscript. 4 pages.
Levy et al., Inhibition of calcification of bioprosthetic heart valves by local controlled-release diphosphonate. Science. Apr. 12, 1985;228(4696):190-2.
Levy et al., Membrane-associated guanylate kinase dynamics reveal regional and developmental specificity of synapse stability. J Physiol. Mar. 1, 2017;595(5):1699-1709. doi: 10.1113/JP273147. Epub Jan. 18, 2017.
Lew et al., Protein splicing in vitro with a semisynthetic two-component minimal intein. J Biol Chem. Jun. 26, 1998;273(26):15887-90. doi: 10.1074/jbc.273.26.15887.
Lewis et al., A serum-resistant cytofectin for cellular delivery of antisense oligodeoxynucleotides and plasmid DNA. Proc Natl Acad Sci U S A. Apr. 16, 1996;93(8):3176-81.
Lewis et al., Building the Class 2 CRISPR-Cas Arsenal. Mol Cell 2017;65(3);377-379.
Lewis et al., Codon 129 polymorphism of the human prion protein influences the kinetics of amyloid formation. J Gen Virol. Aug. 2006;87(Pt 8):2443-9.
Lewis et al., Cytosine deamination and the precipitous decline of spontaneous mutation during Earth's history. Proc Natl Acad Sci U S A. Jul. 19, 2016;113(29):8194-9. doi: 10.1073/pnas.1607580113. Epub Jul. 5, 2016.
Lewis et al., RNA modifications and structures cooperate to guide RNA-protein interactions. Nat Rev Mol Cell Biol. Mar. 2017;18(3):202-210. doi: 10.1038/nrm.2016.163. Epub Feb. 1, 2017.
Li et al., A Radioactivity-Based Assay for Screening Human m6A-RNA Methyltransferase, METTL3-METTL14 Complex, and Demethylase ALKBH5. J Biomol Screen. Mar. 2016;21(3):290-7. doi: 10.1177/1087057115623264. Epub Dec. 23, 2015.
Li et al., Base editing with a Cpf1-cytidine deaminase fusion. Nat Biotechnol. Apr. 2018;36(4):324-327. doi: 10.1038/nbt.4102. Epub Mar. 19, 2018.
Li et al., Current approaches for engineering proteins with diverse biological properties. Adv Exp Med Biol. 2007;620:18-33.

(56) References Cited

OTHER PUBLICATIONS

Li et al., Differentiation of neurons from neural precursors generated in floating spheres from embryonic stem cells. BMC Neurosci. Sep. 24, 2009;10:122. doi: 10.1186/1471-2202-10-122.
Li et al., Fast and accurate short read alignment with Burrows-Wheeler transform. Bioinformatics. Jul. 15, 2009;25(14):1754-60. doi: 10.1093/bioinformatics/btp324. Epub May 18, 2009.
Li et al., Generation of Targeted Point Mutations in Rice by a Modified CRISPR/Cas9 System. Mol Plant. Mar. 6, 2017;10(3):526-529. doi: 10.1016/j.molp.2016.12.001. Epub Dec. 8, 2016.
Li et al., Highly efficient and precise base editing in discarded human tripronuclear embryos. Protein Cell. Aug. 19, 2017. doi: 10.1007/s13238-017-0458-7. [Epub ahead of print].
Li et al., Lagging strand DNA synthesis at the eukaryotic replication fork involves binding and stimulation of FEN-1 by proliferating cell nuclear antigen. J Biol Chem. Sep. 22, 1995;270(38):22109-12. doi: 10.1074/jbc.270.38.22109.
Li et al., Loss of post-translational modification sites in disease. Pac Symp Biocomput. 2010:337-47. doi: 10.1142/9789814295291_0036.
Li et al., Modularly assembled designer TAL effector nucleases for targeted gene knockout and gene replacement in eukaryotes. Nucleic Acids Res. Aug. 2011;39(14):6315-25. doi: 10.1093/nar/gkr188. Epub Mar. 31, 2011.
Li et al., Multiplex and homologous recombination-mediated genome editing in Arabidopsis and Nicotiana benthamiana using guide RNA and Cas9. Nat Biotechnol. Aug. 2013;31(8):688-91. doi: 10.1038/nbt.2654.
Li et al., Protein trans-splicing as a means for viral vector-mediated in vivo gene therapy. Hum Gene Ther. Sep. 2008;19(9):958-64. doi: 10.1089/hum.2008.009.
Li et al., RSEM: accurate transcript quantification from RNA-Seq data with or without a reference genome. BMC Bioinformatics. Aug. 4, 2011;12:323. doi: 10.1186/1471-2105-12-323.
Li et al., TAL nucleases (TALNs): hybrid proteins composed of TAL effectors and FokI DNA-cleavage domain. Nucleic Acids Res. Jan. 2011;39(1):359-72. doi: 10.1093/nar/gkq704. Epub Aug. 10, 2010.
Li, Mechanisms and functions of DNA mismatch repair. Cell Res. Jan. 2008;18(1):85-98. doi: 10.1038/cr.2007.115.
Liang et al., Homology-directed repair is a major double-strand break repair pathway in mammalian cells. Proc Natl Acad Sci U S A. Apr. 28, 1998;95(9):5172-7. doi: 10.1073/pnas.95.9.5172.
Liang et al., Rapid and highly efficient mammalian cell engineering via Cas9 protein transfection. Send to; J Biotechnol. Aug. 20, 2015;208:44-53. doi: 10.1016/j.jbiotec.2015.04.024.
Lieber et al., Mechanism and regulation of human non-homologous DNA end-joining. Nat Rev Mol Cell Biol. Sep. 2003;4(9):712-20.
Liefke et al., The oxidative demethylase ALKBH3 marks hyperactive gene promoters in human cancer cells. Genome Med. Jun. 30, 2015;7(1):66. doi: 10.1186/s13073-015-0180-0.
Lienert et al., Two- and three-input TALE-based AND logic computation in embryonic stem cells. Nucleic Acids Res. Nov. 2013;41(21):9967-75. doi: 10.1093/nar/gkt758. Epub Aug. 27, 2013.
Lilley, D.M. The Varkud Satellite Ribozyme. RNA. Feb. 2004;10(2):151-8.doi: 10.1261/rna.5217104.
Lim et al., Crystal structure of the moloney murine leukemia virus RNase H domain. J Virol. Sep. 2006;80(17):8379-89. doi: 10.1128/JVI.00750-06.
Lim et al., Viral vectors for neurotrophic factor delivery: a gene therapy approach for neurodegenerative diseases of the CNS. Pharmacol Res. Jan. 2010;61(1):14-26. doi: 10.1016/j.phrs.2009.10.002. Epub Oct. 17, 2009.
Lin et al., [Construction and evaluation of DnaB split intein high expression vector and a six amino acids cyclic peptide library]. Sheng Wu Gong Cheng Xue Bao. Nov. 2008;24(11):1924-30. Chinese.
Lin et al., Enhanced homology-directed human genome engineering by controlled timing of CRISPR/Cas9 delivery. Elife. Dec. 15, 2014;3:e04766. doi: 10.7554/eLife.04766.
Lin et al., The human REV1 gene codes for a DNA template-dependent dCMP transferase. Nucleic Acids Res. Nov. 15, 1999;27(22):4468-75. doi: 10.1093/nar/27.22.4468.
Lindahl, T., Instability and decay of the primary structure of DNA. Nature. Apr. 22, 1993;362(6422):709-15. doi: 10.1038/362709a0.
Link et al., Engineering ligand-responsive gene-control elements: lessons learned from natural riboswitches. Gene Ther. Oct. 2009;16(10):1189-201. doi: 10.1038/gt.2009.81. Epub Jul. 9, 2009. Review.
Liu et al., C2c1-sgRNA Complex Structure Reveals RNA-Guided DNA Cleavage Mechanism. Molecular Cell Jan. 2017;65(2):310-22.
Liu et al., Split dnaE genes encoding multiple novel inteins in Trichodesmium erythraeum. J Biol Chem. Jul. 18, 2003;278(29):26315-8. doi: 10.1074/jbc.C300202200. Epub May 24, 2003.
Liu et al., A METTL3-METTL14 complex mediates mammalian nuclear RNA N6-adenosine methylation. Nat Chem Biol. Feb. 2014;10(2):93-5. doi: 10.1038/nchembio.1432. Epub Dec. 6, 2013.
Liu et al., Adding new chemistries to the genetic code. Annu Rev Biochem. 2010;79:413-44. doi: 10.1146/annurev.biochem.052308.105824.
Liu et al., Apolipoprotein E and Alzheimer disease: risk, mechanisms and therapy. Nat Rev Neurol. Feb. 2013;9(2):106-18. doi: 10.1038/nrneurol.2012.263. Epub Jan. 8, 2013.
Liu et al., Balancing AID and DNA repair during somatic hypermutation. Trends Immunol. Apr. 2009;30(4):173-81. doi: 10.1016/j.it.2009.01.007.
Liu et al., Calcineurin is a common target of cyclophilin-cyclosporin A and FKBP-FK506 complexes. Cell. Aug. 23, 1991;66(4):807-15. doi: 10.1016/0092-8674(91)90124-h.
Liu et al., Cell-penetrating peptide-mediated delivery of TALEN proteins via bioconjugation for genome engineering. PLoS One. Jan. 20, 2014;9(1):e85755. doi: 10.1371/journal.pone.0085755. eCollection 2014.
Liu et al., Design of polydactyl zinc-finger proteins for unique addressing within complex genomes. Proc Natl Acad Sci U S A. May 27, 1997;94(11):5525-30.
Liu et al., Distance determination by GIY-YIG intron endonucleases: discrimination between repression and cleavage functions. Nucleic Acids Res. Mar. 31, 2006;34(6):1755-64. Print 2006.
Liu et al., Editing DNA Methylation in the Mammalian Genome. Cell. Sep. 22, 2016;167(1):233- 247.e17. doi: 10.1016/j.cell.2016.08.056.
Liu et al., Engineering a tRNA and aminoacyl-tRNA synthetase for the site-specific incorporation of unnatural amino acids into proteins in vivo. Proc Natl Acad Sci U S A. Sep. 16, 1997;94(19):10092-7.
Liu et al., Fast Colorimetric Sensing of Adenosine and Cocaine Based on a General Sensor Design Involving Aptamers and Nanoparticles. Angew Chem. Dec. 16, 2006;45(1):90-4. DOI: 10.1002/anie.200502589.
Liu et al., Fast Colorimetric Sensing of Adenosine and Cocaine Based on a General Sensor Design Involving Aptamers and Nanoparticles. Angew Chem. 2006;118(1):96-100.
Liu et al., Flap endonuclease 1: a central component of DNA metabolism. Annu Rev Biochem. 2004;73:589-615. doi:10.1146/annurev.biochem.73.012803.092453.
Liu et al., Functional Nucleic Acid Sensors. Chem Rev. May 2009; 109(5):1948-98. doi: 10.1021/cr030183i.
Liu et al., Genetic incorporation of unnatural amino acids into proteins in mammalian cells. Nat Methods. Mar. 2007;4(3):239-44. Epub Feb. 25, 2007.
Liu et al., Human BRCA2 protein promotes RAD51 filament formation on RPA-covered single- stranded DNA. Nat Struct Mol Biol. Oct. 2010; 17(10):1260-2. doi: 10.1038/nsmb.1904. Epub Aug. 22, 2010.
Liu et al., N(6)-methyladenosine-dependent RNA structural switches regulate RNA-protein interactions. Nature. Feb. 26, 2015;518(7540):560-4. doi: 10.1038/nature14234.
Liu et al., Probing N6-methyladenosine RNA modification status at single nucleotide resolution in mRNA and long noncoding RNA. RNA. Dec. 2013;19(12):1848-56. doi: 10.1261/rna.041178.113. Epub Oct. 18, 2013.

(56) References Cited

OTHER PUBLICATIONS

Liu et al., Reverse transcriptase of foamy virus. Purification of the enzymes and immunological identification. Arch Virol. 1977;55(3):187-200. doi: 10.1007/BF01319905.
Liu et al., Reverse transcriptase-mediated tropism switching in Bordetella bacteriophage. Science. Mar. 15, 2002;295(5562):2091-4. doi: 10.1126/science.1067467.
Liu et al., *Saccharomyces cerevisiae* flap endonuclease 1 uses flap equilibration to maintain triplet repeat stability. Mol Cell Biol. May 2004;24(9):4049-64. doi: 10.1128/MCB.24.9.4049-4064.2004.
Liu et al., The Molecular Architecture for RNA-Guided RNA Cleavage by Cas13a. Cell. Aug. 10, 2017;170(4):714-726.e10. doi: 10.1016/j.cell.2017.06.050. Epub Jul. 2, 20177.
Liu et al., Usherin is required for maintenance of retinal photoreceptors and normal development of cochlear hair cells. Proc Natl Acad Sci U S A. Mar. 13, 2007;104(11):4413-8. doi: 10.1073/pnas.0610950104. Epub Mar. 5, 2007.
Loessner et al., Complete nucleotide sequence, molecular analysis and genome structure of bacteriophage A118 of Listeria monocytogenes: implications for phage evolution. Mol Microbiol. Jan. 2000;35(2):324-40. doi: 10.1046/j.1365-2958.2000.01720.x.
Lombardo et al., Gene editing in human stem cells using zinc finger nucleases and integrase- defective lentiviral vector delivery. Nat Biotechnol. Nov. 2007;25(11):1298-306. Epub Oct. 28, 2007.
Long et al., Postnatal genome editing partially restores dystrophin expression in a mouse model of muscular dystrophy. Science. Jan. 22, 2016;351(6271):400-3. doi: 10.1126/science.aad5725. Epub Dec. 31, 2015.
Lopez-Girona et al., Cereblon is a direct protein target for immunomodulatory and antiproliferative activities of lenalidomide and pomalidomide. Leukemia. Nov. 2012;26(11):2326-35. doi: 10.1038/leu.2012.119. Epub May 3, 2012.
Lorenz et al., ViennaRNA Package 2.0. Algorithms Mol Biol. Nov. 24, 2011;6:26. doi: 10.1186/1748-7188-6-26.
Lorson et al., A single nucleotide in the SMN gene regulates splicing and is responsible for spinal muscular atrophy. Proc Natl Acad Sci U S A. May 25, 1999;96(11):6307-11. doi: 10.1073/pnas.96.11.6307.
Losey et al., Crystal structure of Staphylococcus sureus tRNA adenosine deaminase tadA in complex with RNA. Nature Struct. Mol. Biol. Feb. 2006;13(2):153-9.
Lu et al., Precise Editing of a Target Base in the Rice Genome Using a Modified CRISPR/Cas9 System. Mol Plant. Mar. 6, 2017;10(3):523-525. doi: 10.1016/j.molp.2016.11.013. Epub Dec. 6, 2016.
Luan et al., Reverse transcription of R2Bm RNA is primed by a nick at the chromosomal target site: a mechanism for non-LTR retrotransposition. Cell. Feb. 2, 19936;72(4):595-605. doi: 10.1016/0092-8674(93)90078-5.
Luckow et al., High level expression of nonfused foreign genes with Autographa californica nuclear polyhedrosis virus expression vectors. Virology. May 1989;170(1):31-9. doi: 10.1016/0042-6822(89)90348-6.
Lukacsovich et al., Repair of a specific double-strand break generated within a mammalian chromosome by yeast endonuclease I-SceI. Nucleic Acids Res. Dec. 25, 1994;22(25):5649-57. doi: 10.1093/nar/22.25.5649.
Lumpkin et al., Math1-driven GFP expression in the developing nervous system of transgenic mice. Gene Expr Patterns. Aug. 2003;3(4):389-95.
Lundberg et al., Delivery of short interfering RNA using endosomolytic cell-penetrating peptides. Faseb J. Sep. 2007;21(11):2664-71. Epub Apr. 26, 2007.
Lundquist et al., Site-directed mutagenesis and characterization of uracil-DNA glycosylase inhibitor protein. Role of specific carboxylic amino acids in complex formation with *Escherichia coli* uracil-DNA glycosylase. J Biol Chem. Aug. 22, 1997;272(34):21408-19.
Lutz et al., Postsymptomatic restoration of SMN rescues the disease phenotype in a mouse model of severe spinal muscular atrophy. J Clin Invest. Aug. 2011;121(8):3029-41. doi: 10.1172/JCI57291. Epub Jul. 25, 2011.
Lynch, Evolution of the mutation rate. Trends Genet. Aug. 2010;26(8):345-52. doi: 10.1016/j.tig.2010.05.003. Epub Jun. 30, 2010.
Lyons et al., Efficient Recognition of an Unpaired Lesion by a DNA Repair Glycosylase. J. Am. Chem. Soc., 2009;131(49):17742-3. DOI: 10.1021/ja908378y.
Lüke et al., Partial purification and characterization of the reverse transcriptase of the simian immunodeficiency virus TYO-7 isolated from an African green monkey. Biochemistry. Feb. 2, 19900;29(7):1764-9. doi: 10.1021/bi00459a015.
Ma et al., Human RAD52 interactions with replication protein A and the RAD51 presynaptic complex. J Biol Chem. Jul. 14, 2017;292(28):11702-11713. doi: 10.1074/jbc.M117.794545. Epub May 27, 2017.
Ma et al., Identification of pseudo attP sites for phage phiC31 integrase in bovine genome. Biochem Biophys Res Commun. Jul. 7, 2006;345(3):984-8. doi: 10.1016/j.bbrc.2006.04.145. Epub May 3, 2006.
Ma et al., In vitro protein engineering using synthetic tRNA(Ala) with different anticodons. Biochemistry. Aug. 10, 1993;32(31):7939-45.
Ma et al., PhiC31 integrase induces efficient site-specific recombination in the Capra hircus genome. DNA Cell Biol. Aug. 2014;33(8):484-91. doi: 10.1089/dna.2013.2124. Epub Apr. 22, 2014.
Ma et al., Single-Stranded DNA Cleavage by Divergent CRISPR-Cas9 Enzymes. Mol Cell. Nov. 5, 2015;60(3):398-407. doi: 10.1016/j.molcel.2015.10.030.
Ma et al., Targeted AID-mediated mutagenesis (TAM) enables efficient genomic diversification in mammalian cells. Nature Methods. Oct. 2016; 13:1029-35. doi:10.1038/nmeth.4027 .
Maas et al., Identification and characterization of a human tRNA-specific adenosine deaminase related to the ADAR family of pre-mRNA editing enzymes. Proc Natl Acad Sci U S A. Aug. 3, 1999;96(16):8895-900. doi: 10.1073/pnas.96.16.8895.
Macbeth et al., Inositol hexakisphosphate is bound in the ADAR2 core and required for RNA editing. Science. Sep. 2, 2005;309(5740):1534-9. doi: 10.1126/science.1113150.
Macrae et al., Ribonuclease revisited: structural insights into ribonuclease III family enzymes. Curr Opin Struct Biol. Feb. 2007;17(1):138-45. doi: 10.1016/j.sbi.2006.12.002. Epub Dec. 27, 2006.
Madura et al., Structural basis for ineffective T-cell responses to MHC anchor residue- improved "heteroclitic" peptides. Eur J Immunol. Feb. 2015;45(2):584-91. doi: 10.1002/eji.201445114. Epub Dec. 28, 2014.
Maeder et al., CRISPR RNA-guided activation of endogenous human genes. Nat Methods. Oct. 2013;10(10):977-9. doi: 10.1038/nmeth.2598. Epub Jul. 25, 2013.
Maeder et al., Rapid "open-source" engineering of customized zinc-finger nucleases for highly efficient gene modification. Mol Cell. Jul. 25, 2008;31(2):294-301. doi:10.1016/j.molcel.2008.06.016.
Maeder et al., Robust, synergistic regulation of human gene expression using TALE activators. Nat Methods. Mar. 2013;10(3):243-5. doi: 10.1038/nmeth.2366. Epub Feb. 10, 2013.
Maeder et al., Targeted DNA demethylation and activation of endogenous genes using programmable TALE-TET1 fusion proteins. Nat Biotechnol. Dec. 2013;31(12):1137-42. doi: 10.1038/nbt.2726. Epub Oct. 9, 2013.
Maerker et al., A novel Usher protein network at the periciliary reloading point between molecular transport machineries in vertebrate photoreceptor cells. Hum Mol Genet. Jan. 1, 2008;17(1):71-86. doi: 10.1093/hmg/ddm285. Epub Sep. 28, 2007.
Magin et al., Corf, the Rev/Rex homologue of HTDV/HERV-K, encodes an arginine-rich nuclear localization signal that exerts a trans-dominant phenotype when mutated. Virology. Aug. 15, 2000;274(1):11-6. doi: 10.1006/viro.2000.0438.
Mahfouz et al., De novo-engineered transcription activator-like effector (TALE) hybrid nuclease with novel DNA binding specific-

(56) References Cited

OTHER PUBLICATIONS ity creates double-strand breaks. Proc Natl Acad Sci U SA. Feb. 8, 2011;108(6):2623-8. doi: 10.1073/pnas.1019533108. Epub Jan. 24, 2011.
Mak et al., The crystal structure of TAL effector PthXol bound to its DNA target. Science. Feb. 10, 2012;335(6069):716-9. doi: 10.1126/science.1216211. Epub Jan. 5, 2012.
Makarova et al., Prokaryotic homologs of Argonaute proteins are predicted to function as key components of a novel system of defense against mobile genetic elements. Biology Direct 2009;4:29.
Makarova et al., An updated evolutionary classification of CRISPR-Cas systems. Nat Rev Microbiol. Nov. 2015;13(11):722-36. doi: 10.1038/nrmicro3569. Epub Sep. 28, 2015.
Makarova et al., Evolution and classification of the CRISPR-Cas systems. Nat Rev Microbiol. Jun. 2011;9(6):467-77. doi: 10.1038/nrmicro2577. Epub May 9, 2011.
Makarova et al., Prokaryotic homologs of Argonaute proteins are predicted to function as key components of a novel system of defense against mobile genetic elements. Biology Direct 2009;4:29. doi: 10.1186/1745-6150-4-29.
Makeyev et al., Evolutionary potential of an RNA virus. J Virol. Feb. 2004;78(4):2114-20.
Malashkevich et al., Crystal structure of tRNA adenosine deaminase TadA from Escherichia coli. Deposited: Mar. 10, 2005 Released: Feb. 21, 2006 doi:10.2210/pdb1z3a/pdb (2006).
Mali et al., Cas9 as a versatile tool for engineeringbiology. Nat Methods. Oct. 2013;10(10):957-63. doi: 10.1038/nmeth.2649.
Mali et al., CAS9 transcriptional activators for target specificity screening and paired nickases for cooperative genome engineering. Nat Biotechnol. Sep. 2013;31(9):833-8, Supplemental Info. doi: 10.1038/nbt.2675. Epub Aug. 1, 2013.
Mali et al., CAS9 transcriptional activators for target specificity screening and paired nickases for cooperative genome engineering. Nat Biotechnol. Sep. 2013;31(9):833-8. doi: 10.1038/nbt.2675. Epub Aug. 1, 2013.
Mali et al., RNA-guided human genome engineering via Cas9. Science. Feb. 15, 2013;339(6121):823-6. doi: 10.1126/science.1232033. Epub Jan. 3, 2013.
Malito et al., Structural basis for lack of toxicity of the diphtheria toxin mutant CRM197. Proc Natl Acad Sci U S A. Apr. 3, 2012;109(14):5229-34. doi: 10.1073/pnas. 1201964109. Epub Mar. 19, 2012.
Mandal et al., A glycine-dependent riboswitch that uses cooperative binding to control gene expression. Science. Oct. 8, 2004;306(5694):275-9.
Mandal et al., Adenine riboswitches and gene activation by disruption of a transcription terminator. Nat Struct Mol Biol. Jan. 2004; 11(1):29-35. Epub Dec. 29, 2003.
Mandal et al., Efficient ablation of genes in human hematopoietic stem and effector cells using CRISPR/Cas9. Cell Stem Cell. Nov. 6, 2014;15(5):643-52. doi: 10.1016/j.stem.2014.10.004. Epub Nov. 6, 2014.
Mandal et al., Riboswitches Control Fundamental Biochemical Pathways in Bacillus Subtilis and Other Bacteria. Cell. May 30, 2003;113(5):577-86. doi: 10.1016/s0092-8674(03)00391-x.
Mani et al., Design, engineering, and characterization of zinc finger nucleases. Biochem Biophys Res Commun. Sep. 23, 2005;335(2):447-57.
Marceau, Functions of single-strand DNA-binding proteins in DNA replication, recombination, and repair. Methods Mol Biol. 2012;922:1-21. doi: 10.1007/978-1-62703-032-8_1.
Marcovitz et al., Frustration in protein-DNA binding influences conformational switching and target search kinetics. Proc Natl Acad Sci U S A. Nov. 1, 2011;108(44):17957-62. doi: 10.1073/pnas.1109594108. Epub Oct. 14, 2011.
Maresca et al., Obligate ligation-gated recombination (ObLiGaRe): custom-designed nuclease-mediated targeted integration through nonhomologous end joining. Genome Res. Mar. 2013;23(3):539-46. Doi: 10.1101/gr.145441.112. Epub Nov. 14, 2012.
Marioni et al., DNA methylation age of blood predicts all-cause mortality in later life. Genome Biol. Jan. 30, 2015;16:25. doi: 10.1186/s13059-015-0584-6.
Marraffini et al., CRISPR interference limits horizontal gene transfer in *staphylococci* by targeting DNA. Science. Dec. 19, 2008;322(5909):1843-5. doi: 10.1126/science.1165771.
Marsden et al., The Tumor-Associated Variant RAD51 G151D Induces a Hyper- Recombination Phenotype. PLoS Genet. Aug. 11, 2016;12(8):e1006208. doi: 10.1371/journal.pgen.1006208.
Martinez et al., Hypermutagenesis of RNA using human immunodeficiency virus type 1 reverse transcriptase and biased dNTP concentrations. Proc Natl Acad Sci U S A. Dec. 6, 1994;91(25):11787-91. doi: 10.1073/pnas.91.25.11787.
Martsolf et al., Complete trisomy 17p a relatively new syndrome. Ann Genet. 1988;31(3):172-4.
Martz, L., Nav-i-gating antibodies for pain. Science-Business exchange. Jun. 12, 2014;7(662):1-2. doi: 10.1038/scibx.2014.662.
Maruyama et al., Increasing the efficiency of precise genome editing with CRISPR-Cas9 by inhibition of nonhomologous end joining. Nat Biotechnol. May 2015;33(5):538-42. doi: 10.1038/nbt.3190. Epub Mar. 23, 2015.
Mascola et al., HIV-1 neutralizing antibodies: understanding nature's pathways. Immunol Rev. Jul. 2013;254(1):225-44. doi: 10.1111/imr.12075.
Mathys et al., Characterization of a self-splicing mini-intein and its conversion into autocatalytic N- and C-terminal cleavage elements: facile production of protein building blocks for protein ligation. Gene. Apr. 29, 1999;231(1-2):1-13. doi: 10.1016/s0378-1119(99)00103-1.
Matsuura et al., A gene essential for the site-specific excision of actinophage r4 prophage genome from the chromosome of a lysogen. J Gen Appl Microbiol. 1995;41(1):53-61.
Matthews, Structures of human ADAR2 bound to dsRNA reveal base-flipping mechanism and basis for site selectivity. Nat Struct Mol Biol. May 2016;23(5):426-33. doi: 10.1038/nsmb.3203. Epub Apr. 11, 2016.
McCarroll et al., Copy-number variation and association studies of human disease. Nat Genet. Jul. 2007;39(7 Suppl):S37-42. doi: 10.1038/ng2080.
McDonald et al., Characterization of mutations at the mouse phenylalanine hydroxylase locus. Genomics. Feb. 1, 1997;39(3):402-5. doi: 10.1006/geno.1996.4508.
McInerney et al., Error Rate Comparison during Polymerase Chain Reaction by DNA Polymerase. Mol Biol Int. 2014;2014:287430. doi: 10.1155/2014/287430. Epub Aug. 17, 2014.
McKenna et al., Whole-organism lineage tracing by combinatorial and cumulative genome editing. Science. Jul. 29, 2016;353(6298):aaf7907. doi: 10.1126/science.aaf7907. Epub May 26, 2016.
McNaughton et al., Mammalian cell penetration, siRNA transfection, and DNA transfection by supercharged proteins. Proc Natl Acad Sci U S A. Apr. 14, 2009;106(15):6111-6. doi: 10.1073/pnas.0807883106. Epub Mar. 23, 2009.
McVey et al., MMEJ repair of double-strand breaks (director's cut): deleted sequences and alternative endings. Trends Genet. Nov. 2008;24(11):529-38. doi: 10.1016/j.tig.2008.08.007. Epub Sep. 21, 2008.
Mead et al., A novel protective prion protein variant that colocalizes with kuru exposure. N Engl J Med. Nov. 19, 2009;361(21):2056-65. doi: 10.1056/NEJMoa0809716.
Meckler et al., Quantitative analysis of TALE-DNA interactions suggests polarity effects. Nucleic Acids Res. Apr. 2013;41(7):4118-28. doi: 10.1093/nar/gkt085. Epub Feb. 13, 2013.
Mei et al., Recent Progress in CRISPR/Cas9 Technology. J Genet Genomics. Feb. 20, 2016;43(2):63-75. doi: 10.1016/j.jgg.2016.01.001. Epub Jan. 18, 2016.
Meinke et al., Cre Recombinase and Other Tyrosine Recombinases. Chem Rev. Oct. 26, 2016;116(20):12785-12820. doi: 10.1021/acs.chemrev.6b00077. Epub May 10, 2016.
Mendenhall et al., Locus-specific editing of histone modifications at endogenous enhancers. Nat Biotechnol. Dec. 2013;31(12):1133-6. doi: 10.1038/nbt.2701. Epub Sep. 8, 2013.

(56) References Cited

OTHER PUBLICATIONS

Meng et al., Profiling the DNA-binding specificities of engineered Cys2His2 zinc finger domains using a rapid cell-based method. Nucleic Acids Res. 2007;35(11):e81. Epub May 30, 2007.
Meng et al., Targeted gene inactivation in zebrafish using engineered zinc-finger nucleases. Nat Biotechnol. Jun. 2008;26(6):695-701. doi: 10.1038/nbt1398. Epub May 25, 2008.
Menéndez-Arias, Mutation rates and intrinsic fidelity of retroviral reverse transcriptases. Viruses. Dec. 2009;1(3):1137-65. doi: 10.3390/v1031137. Epub Dec. 4, 2009.
Mercer et al., Chimeric TALE recombinases with programmable DNA sequence specificity. Nucleic Acids Res. Nov. 2012;40(21):11163-72. doi: 10.1093/nar/gks875. Epub Sep. 26, 2012.
Merten et al., Viral Vectors for Gene Therapy. Humana Press 2011. ISBN 978-1-61779-095-9.
Mertens et al., Site-specific recombination in bacteriophage Mu: characterization of binding sites for the DNA invertase Gin. Embo J. Apr. 1988;7(4):1219-27.
Meyer et al., Breathing life into polycations: functionalization with pH-responsive endosomolytic peptides and polyethylene glycol enables siRNA delivery. J Am Chem Soc. Mar. 19, 2008;130(11):3272-3. doi: 10.1021/ja710344v. Epub Feb. 21, 2008.
Meyer et al., Comprehensive analysis of mRNA methylation reveals enrichment in 3' UTRs and near stop codons. Cell. Jun. 22, 2012;149(7):1635-46. doi: 10.1016/j.cell.2012.05.003. Epub May 17, 2012.
Meyer et al., Confirmation of a second natural preQ1 aptamer class in *Streptococcaceae bacteria*. RNA. Apr. 2008;14(4):685-95. doi: 10.1261/rna.937308. Epub Feb. 27, 2008.
Meyer et al., Library generation by gene shuffling. Curr Protoc Mol Biol. Jan. 6, 2014;105: Unit 15.12 . . doi: 10.1002/0471142727.mb1512s105.
Meyer et al., Ribosome biogenesis factor Tsr3 is the aminocarboxypropyl transferase responsible for 18S rRNA hypermodification in yeast and humans. Nucleic Acids Res. May 1, 20169;44(9):4304-16. doi: 10.1093/nar/gkw244. Epub Apr. 15, 2016.
Meyer et al., The dynamic epitranscriptome: N6-methyladenosine and gene expression control. Nat Rev Mol Cell Biol. May 2014; 15(5):313-26. doi: 10.1038/nrm3785. Epub Apr. 9, 2014.
Michel et al., Mitochondrial class II introns encode proteins related to the reverse transcriptases of retroviruses. Nature. Aug. 15-21, 1985;316(6029):641-3. doi: 10.1038/316641a0.
Midoux et al., Chemical vectors for gene delivery: a current review on polymers, peptides and lipids containing histidine or imidazole as nucleic acids carriers. Br J Pharmacol. May 2009;157(2):166-78. doi: 10.1111/j.1476-5381.2009.00288.x.
Mihai et al., PTEN inhibition improves wound healing in lung epithelia through changes in cellular mechanics that enhance migration. Am J Physiol Lung Cell Mol Physiol. 2012;302(3):L287-L299.
Mijakovic et al., Bacterial single-stranded DNA-binding proteins are phosphorylated on tyrosine. Nucleic Acids Res. Mar. 20, 2006;34(5):1588-96. doi: 10.1093/nar/gkj514.
Miller et al., A Tale nuclease architecture for efficient genome editing. Nat Biotechnol. Feb. 2011;29(2):143-8. doi:10.1038/nbt.1755. Epub Dec. 22, 2010.
Miller et al., An improved zinc-finger nuclease architecture for highly specific genome editing. Nat Biotechnol. Jul. 2007;25(7):778-85. Epub Jul. 1, 2007.
Miller et al., Construction and properties of retrovirus packaging cells based on gibbon ape leukemia virus. J Virol. May 1991;65(5):2220-4. doi: 10.1128/JVI.65.5.2220-2224.1991.
Miller, Human gene therapy comes of age. Nature. Jun. 11, 1992;357(6378):455-60. doi: 10.1038/357455a0.
Mills et al., Protein splicing in trans by purified N- and C-terminal fragments of the Mycobacterium tuberculosis RecA intein. Proc Natl Acad Sci U S A. Mar. 31, 1998;95(7):3543-8. doi: 10.1073/pnas.95.7.3543.
Minoche et al., Evaluation of genomic high-throughput sequencing data generated on Illumina HiSeq and genome analyzer systems. Genome Biol. Nov. 8, 2011;12(11):R112. doi: 10.1186/GB-2011-12-11-r112.
Minoretti et al., A W148R mutation in the human FOXD4 gene segregating with dilated cardiomyopathy, obsessive-compulsive disorder, and suicidality. Int J Mol Med. Mar. 2007;19(3):369-72.
Mir et al., Two Active Site Divalent Ions in the Crystal Structure of the Hammerhead Ribozyme Bound to a Transition State Analogue. Biochemistry . . . Feb. 2, 2016;55(4):633-6. doi: 10.1021/acs.biochem.5b01139. Epub Jan. 19, 2016.
Mishina et al., Conditional gene targeting on the pure C57BL/6 genetic background. Neurosci Res. Jun. 2007;58(2):105-12. doi: 10.1016/j.neures.2007.01.004. Epub Jan. 18, 2007.
Mitani et al., Delivering therapeutic genes—matching approach and application. Trends Biotechnol. May 1993;11(5):162-6. doi: 10.1016/0167-7799(93)90108-L.
Mitton-Fry et al., Poly(A) tail recognition by a viral RNA element through assembly of a triple helix. Science. Nov. 26, 2010;330(6008):1244-7. doi: 10.1126/science.1195858.
Miyaoka et al., Systematic quantification of HDR and NHEJ reveals effects of locus, nuclease, and cell type on genome-editing. Sci Rep. Mar. 31, 2016;6:23549. doi: 10.1038/srep23549.
Moede et al., Identification of a nuclear localization signal, RRMKWKK, in the homeodomain transcription factor PDX-1. Febs Lett. Nov. 19, 1999;461(3):229-34. doi: 10.1016/s0014-5793(99)01446-5.
Mohr et al., Thermostable group II intron reverse transcriptase fusion proteins and their use in cDNA synthesis and next-generation RNA sequencing. RNA. Jul. 2013;19(7):958-70. doi: 10.1261/rna.039743.113. Epub May 22, 2013.
Mojica et al., Intervening sequences of regularly spaced prokaryotic repeats derive from foreign genetic elements. J Mol Evol. Feb. 2005;60(2):174-82.
Mol et al., Crystal structure and mutational analysis of human uracil-DNA glycosylase: structural basis for specificity and catalysis. Cell. Mar. 24, 1995;80(6):869-78. doi: 10.1016/0092-8674(95)90290-2.
Mol et al., Crystal structure of human uracil-DNA glycosylase in complex with a protein inhibitor: protein mimicry of DNA. Cell. Sep. 8, 1995;82(5):701-8.
Monahan et al., Site-specific incorporation of unnatural amino acids into receptors expressed in Mammalian cells. Chem Biol. Jun. 2003;10(6):573-80.
Monani et al., A single nucleotide difference that alters splicing patterns distinguishes the SMA gene SMN1 from the copy gene SMN2. Hum Mol Genet. Jul. 1999;8(7):1177-83. doi: 10.1093/hmg/8.7.1177.
Monot et al., The specificity and flexibility of 11 reverse transcription priming at imperfect T-tracts. PLoS Genet. May 2013;9(5):e1003499. doi: 10.1371/journal.pgen.1003499. Epub May 9, 2013.
Montange et al., Structure of the S-adenosylmethionine riboswitch regulatory mRNA element. Nature. Jun. 29, 2006;441(7097):1172-5.
Moore et al., Improved somatic mutagenesis in zebrafish using transcription activator-like effector nucleases (TALENs). PloS One. 2012;7(5):e37877. Doi: 10.1371/journal.pone.0037877. Epub May 24, 2012.
Mootz et al., Conditional protein splicing: a new tool to control protein structure and function in vitro and in vivo. J Am Chem Soc. Sep. 3, 2003;125(35):10561-9.
Mootz et al., Protein splicing triggered by a small molecule. J Am Chem Soc. Aug. 7, 2002;124(31):9044-5 and Supporting Information. doi: 10.1021/ja0267690. 4 pages.
Mootz et al., Protein splicing triggered by a small molecule. J Am Chem Soc. Aug. 7, 2002;124(31):9044-5.
Morbitzer et al., Assembly of custom TALE-type DNA binding domains by modular cloning. Nucleic Acids Res. Jul. 2011;39(13):5790-9. doi: 10.1093/nar/gkr151. Epub Mar. 18, 2011.
Moreno-Mateos et al., CRISPRscan: designing highly efficient sgRNAs for CRISPR-Cas9 targeting in vivo. Nat Methods. Oct. 2015; 12(10):982-8. doi: 10.1038/nmeth.3543. Epub Aug. 31, 2015.

(56) References Cited

OTHER PUBLICATIONS

Morita et al., The site-specific recombination system of actinophage TG1. Fems Microbiol Lett. Aug. 2009;297(2):234-40. doi: 10.1111/j.1574-6968.2009.01683.x.
Morris et al., A peptide carrier for the delivery of biologically active proteins into mammalian cells. Nat Biotechnol. Dec. 2001;19(12):1173-6.
Moscou et al., A simple cipher governs DNA recognition by TAL effectors. Science. Dec. 11, 2009;326(5959):1501. doi: 10.1126/science.1178817.
Muir et al., Expressed protein ligation: a general method for protein engineering. Proc Natl Acad Sci U S A. Jun. 9, 1998;95(12):6705-10. doi: 10.1073/pnas.95.12.6705.
Mullen et al., Latent cytokines for targeted therapy of inflammatory disorders. Expert Opin Drug Deliv. Jan. 2014;11(1):101-10. doi: 10.1517/17425247.2014.863872. Epub Dec. 3, 2013.
Muller et al., Nucleotide exchange and excision technology (Next) DNA shuffling: a robust method for DNA fragmentation and directed evolution. Nucleic Acids Res. Aug. 1, 2005;33(13):e117. doi: 10.1093/nar/gni116. PMID: 16061932; PMCID: PMC1182171.
Muller, U.F., Design and Experimental Evolution of trans-Splicing Group I Intron Ribozymes. Molecules. Jan. 2, 2017;22(1):75. doi: 10.3390/molecules22010075.
Mullins et al., Transgenesis in nonmurine species. Hypertension. Oct. 1993;22(4):630-3.
Mumtsidu et al., Structural features of the single-stranded DNA-binding protein of Epstein-Barr virus. J Struct Biol. Feb. 2008; 161(2):172-87. doi: 10.1016/j.jsb.2007.10.014. Epub Nov. 1, 2007.
Murphy, Phage recombinases and their applications. Adv Virus Res. 2012;83:367-414. doi: 10.1016/B978-0-12-394438-2.00008-6. Review.
Murray et al., Selective vulnerability of motor neurons and dissociation of pre- and post-synaptic pathology at the neuromuscular junction in mouse models of spinal muscular atrophy. Hum Mol Genet. Apr. 1, 2008;17(7):949-62. doi: 10.1093/hmg/ddm367. Epub Dec. 8, 2007.
Murugan et al., The Revolution Continues: Newly Discovered Systems Expand the CRISPR-Cas Toolkit. Mol Cell. Oct. 5, 2017;68(1):15-25. doi: 10.1016/j.molcel.2017.09.007.
Mussolino et al., A novel TALE nuclease scaffold enables high genome editing activity in combination with low toxicity. Nucleic Acids Res. Nov. 2011;39(21):9283-93. Doi: 10.1093/nar/gkr597. Epub Aug. 3, 2011.
Mussolino et al., TALE nucleases: tailored genome engineering made easy. Curr Opin Biotechnol. Oct. 2012;23(5):644-50. doi: 10.1016/j.copbio.2012.01.013. Epub Feb. 17, 2012.
Muzyczka et al., Adeno-associated virus (AAV) vectors: will they work? J Clin Invest. Oct. 1994;94(4):1351. doi: 10.1172/JCI117468.
Myerowitz et al., The major defect in Ashkenazi Jews with Tay-Sachs disease is an insertion in the gene for the alpha-chain of beta-hexosaminidase. J Biol Chem. Dec. 15, 1988;263(35):18587-9.
Myers et al., Insulin signal transduction and the IRS proteins. Annu Rev Pharmacol Toxicol. 1996;36:615-58. doi: 10.1146/annurev.pa.36.040196.003151.
Myou et al., Blockade of focal clustering and active conformation in beta 2-integrin-mediated adhesion of eosinophils to intercellular adhesion molecule-1 caused by transduction of HIV TAT-dominant negative Ras. J Immunol. Sep. 1, 2002;169(5):2670-6.
Nabel et al., Direct gene transfer for immunotherapy and immunization. Trends Biotechnol. May 1993;11(5):211-5. doi: 10.1016/0167-7799(93)90117-R.
Nahvi et al., Coenzyme B12 riboswitches are widespread genetic control elements in prokaryotes. Nucleic Acids Res. Jan. 2, 2004;32(1):143-50.
Nakade et al., Microhomology-mediated end-joining-dependent integration of donor DNA in cells and animals using TALENs and CRISPR/Cas9. Nat Commun. Nov. 2, 20140;5:5560. doi: 10.1038/ncomms6560.
Nakamura et al., Codon usage tabulated from international DNA sequence databases: status for the year 2000. Nucleic Acids Res. Jan. 1, 2000;28(1):292. doi: 10.1093/nar/28.1.292.
Narayanan et al., Clamping down on weak terminal base pairs: oligonucleotides with molecular caps as fidelity-enhancing elements at the 5'- and 3'-terminal residues. Nucleic Acids Res. May 20, 2004;32(9):2901-11. Print 2004.
Navaratnam et al., An overview of cytidine deaminases. Int J Hematol. Apr. 2006;83(3):195-200.
NCBI Reference Sequence: NM_002427.3. Wu et al., May 3, 2014. 5 pages.
Neel et al., Riboswitches: Classification, function and in silico approach, International Journal of Pharma Sciences and Research. 2010;1(9):409-420.
Nelson et al., Filamentous phage DNA cloning vectors: a noninfective mutant with a nonpolar deletion in gene III. Virology. 1981; 108(2):338-50.
Nelson et al., In vivo genome editing improves muscle function in a mouse model of Duchenne muscular dystrophy. Science. Jan. 22, 2016;351(6271):403-7. doi: 10.1126/science.aad5143. Epub Dec. 31, 2015.
Nelson et al., The unstable repeats—three evolving faces of neurological disease. Neuron. Mar. 6, 2013;77(5):825-43. doi: 10.1016/j.neuron.2013.02.022.
Nern et al., Multiple new site-specific recombinases for use in manipulating animal genomes. Proc Natl Acad Sci U S A. Aug. 23, 2011;108(34):14198-203. doi: 10.1073/pnas.1111704108. Epub Aug. 9, 2011.
Nguyen et al., Evolutionary drivers of thermoadaptation in enzyme catalysis. Science. Jan. 20, 2017;355(6322):289-294. doi: 10.1126/science.aah3717. Epub Dec. 22, 2016.
Nguyen et al., IQ-TREE: a fast and effective stochastic algorithm for estimating maximum- likelihood phylogenies. Mol Biol Evol. Jan. 2015;32(1):268-74. doi: 10.1093/molbev/msu300. Epub Nov. 3, 2014.
Ni et al., A PCSK9-binding antibody that structurally mimics the EGF(A) domain of LDL-receptor reduces LDL cholesterol in vivo. J Lipid Res. 2011;52:76-86.
Ni et al., Nucleic acid aptamers: clinical applications and promising new horizons. Curr Med Chem. 2011;18(27):4206-14. Review.
Nishida et al., Targeted nucleotide editing using hybrid prokaryotic and vertebrate adaptive immune systems. Science. Sep. 16, 2016;353(6305):1248. pii: aaf8729. doi: 10.1126/science.aaf8729. Epub Aug. 4, 2016.
Nishikura, Functions and regulation of RNA editing by ADAR deaminases. Annu Rev Biochem. 2010;79:321-349. doi:10.1146/annurev-biochem-060208-105251.
Nishimasu et al., Crystal structure of Cas9 in complex with guide RNA and target DNA. Cell. Feb. 27, 2014;156(5):935-49. doi: 10.1016/j.cell.2014.02.001. Epub Feb. 13, 2014.
Nishimasu et al., Crystal Structure of Staphylococcus Aureus Cas9. Cell. Aug. 27, 2015;162(5):1113-26. doi: 10.1016/j.cell.2015.08.007.
Nomura et al., Controlling Mammalian Gene Expression by Allosteric Hepatitis Delta Virus Ribozymes. ACS Synth Biol. Dec. 20, 2013;2(12):684-9. doi: 10.1021/sb400037a. Epub May 22, 2013.
Nomura et al., Synthetic mammalian riboswitches based on guanine aptazyme. Chem Commun (Camb). Jul. 21, 2012;48(57):7215-7. doi: 10.1039/c2cc33140c. Epub Jun. 13, 2012.
Noris et al., A phenylalanine-55 to serine amino-acid substitution in the human glycoprotein IX leucine-rich repeat is associated with Bernard-Soulier syndrome. Br J Haematol. May 1997;97(2):312-20.
Nottingham et al., RNA-seq of human reference RNA samples using a thermostable group II intron reverse transcriptase. RNA. Apr. 2016;22(4):597-613. doi: 10.1261/rna.055558.115. Epub Jan. 29, 2016.
Nowak et al., Characterization of single-stranded DNA-binding proteins from the psychrophilic bacteria Desulfotalea psychrophila, Flavobacterium psychrophilum, Psychrobacter arcticus, Psychrobacter cryohalolentis, Psychromonas ingrahamii, Psychroflexus torquis, and Photobacterium profundum. BMC Microbiol. Apr. 14, 2014;14:91. doi: 10.1186/1471-2180-14-91.

(56) References Cited

OTHER PUBLICATIONS

Nowak et al., Guide RNA Engineering for Versatile Cas9 Functionality. Nucleic Acids Res. Nov. 16, 2016;44(20):9555-9564. doi: 10.1093/nar/gkw908. Epub Oct. 12, 2016.
Nowak et al., Structural analysis of monomeric retroviral reverse transcriptase in complex with an RNA/DNA hybrid. Nucleic Acids Res. Apr. 1, 2013;41(6):3874-87. doi: 10.1093/nar/gkt053. Epub Feb. 4, 2013.
Numrych et al., A comparison of the effects of single-base and triple-base changes in the integrase arm-type binding sites on the site-specific recombination of bacteriophage lambda. Nucleic Acids Res. Jul. 11, 1990;18(13):3953-9. doi: 10.1093/nar/18.13.3953.
Nyerges et al., A highly precise and portable genome engineering method allows comparison of mutational effects across bacterial species. Proc Natl Acad Sci U S A. Mar. 1, 2016;113(9):2502-7. doi: 10.1073/pnas.1520040113. Epub Feb. 16, 2016.
O'Connell et al., Programmable RNA recognition and cleavage by CRISPR/Cas9. Nature. Dec. 11, 2014;516(7530):263-6. doi: 10.1038/nature13769. Epub Sep. 28, 2014.
O'Maille et al., Structure-based combinatorial protein engineering (Scope). J Mol Biol. Aug. 23, 2002;321(4):677-91.
Oakes et al., Profiling of engineering hotspots identifies an allosteric CRISPR-Cas9 switch. Nat Biotechnol. Jun. 2016;34(6):646-51. doi: 10.1038/nbt.3528. Epub May 2, 2016.
Oakes et al., Protein engineering of Cas9 for enhanced function. Methods Enzymol. 2014;546:491-511.
Odsbu et al., Specific N-terminal interactions of the *Escherichia coli* SeqA protein are required to form multimers that restrain negative supercoils and form foci. Genes Cells. Nov. 2005; 10(11):1039-49.
Oeemig et al., Solution structure of DnaE intein from Nostoc punctiforme: structural basis for the design of a new split intein suitable for site-specific chemical modification. FEBS Lett. May 6, 2009;583(9):1451-6.
Offord, Advances in Genome Editing. The Scientist, Apr. 20, 2016. http://www.the-scientist.com/?articles.view/articleNo/45903/title/Advances-in-Genome-Editing/.
Oh et al., Positional cloning of a gene for Hermansky-Pudlak syndrome, a disorder of cytoplasmic organelles. Nat Genet. Nov. 1996;14(3):300-6. doi: 10.1038/ng1196-300.
Ohe et al., Purification and properties of xanthine dehydrogenase from *Streptomyces cyanogenus*. J Biochem. Jul. 1979;86(1):45-53.
Olivares et al., Site-specific genomic integration produces therapeutic Factor IX levels in mice. Nat Biotechnol. Nov. 2002;20(11):1124-8. doi: 10.1038/nbt753. Epub Oct. 15, 2002.
Olorunniji et al., Purification and In Vitro Characterization of Zinc Finger Recombinases. Methods Mol Biol. 2017;1642:229-245. doi: 10.1007/978-1-4939-7169-5_15.
Olorunniji et al., Site-specific recombinases: molecular machines for the Genetic Revolution. Biochem J. Mar. 15, 2016;473(6):673-84. doi: 10.1042/BJ20151112.
Olorunniji et al., Synapsis and catalysis by activated Tn3 resolvase mutants. Nucleic Acids Res. Dec. 2008;36(22):7181-91. doi: 10.1093/nar/gkn885. Epub Nov. 10, 2008.
Orlando et al., Zinc-finger nuclease-driven targeted integration into mammalian genomes using donors with limited chromosomal homology. Nucleic Acids Res. Aug. 2010;38(15):e152. doi: 10.1093/nar/gkq512. Epub Jun. 8, 2010.
Orthwein et al., A mechanism for the suppression of homologous recombination in G1 cells. Nature. Dec. 17, 2015;528(7582):422-6. doi: 10.1038/nature16142. Epub Dec. 9, 2015.
Ortiz-Urda et al., Stable nonviral genetic correction of inherited human skin disease. Nat Med. Oct. 2002;8(10):1166-70. doi: 10.1038/nm766. Epub Sep. 16, 2002. Erratum in: Nat Med. Feb. 2003;9(2):237.
Osborn et al., TALEN-based gene correction for epidermolysis bullosa. Mol Ther. Jun. 2013;21(6):1151-9. doi: 10.1038/mt.2013.56. Epub Apr. 2, 2013.
Ostermeier et al., A combinatorial approach to hybrid enzymes independent of DNA homology. Nat Biotechnol. Dec. 1999;17(12):1205-9.
Ostertag et al., Biology of mammalian L1 retrotransposons. Annu Rev Genet. 2001;35:501-38. doi: 10.1146/annurev.genet.35.102401.091032.
Otomo et al., Improved segmental isotope labeling of proteins and application to a larger protein. J Biomol NMR. Jun. 1999;14(2):105-14. doi: 10.1023/a:1008308128050.
Otomo et al., NMR observation of selected segments in a larger protein: central-segment isotope labeling through intein-mediated ligation. Biochemistry. Dec. 7, 1999;38(49):16040-4. doi: 10.1021/bi991902j.
Ottesen, ISS-N1 makes the First FDA-approved Drug for Spinal Muscular Atrophy. Transl Neurosci. Jan. 26, 2017;8:1-6. doi: 10.1515/tnsci-2017-0001.
Otto et al., The probability of fixation in populations of changing size. Genetics. Jun. 1997; 146(2):723-33.
Ousterout et al., Multiplex CRISPR/Cas9-based genome editing for correction of dystrophin mutations that cause Duchenne muscular dystrophy. Nat Commun. Feb. 18, 2015;6:6244. doi: 10.1038/ncomms7244.
Pabo et al., Design and selection of novel Cys2His2 zinc finger proteins. Annu Rev Biochem. 2001;70:313-40.
Packer et al., Methods for the directed evolution of proteins. Nat Rev Genet. Jul. 2015;16(7):379-94. doi: 10.1038/nrg3927. Epub Jun. 9, 2015.
Paige et al., RNA mimics of green fluorescent protein. Science. Jul. 29, 2011;333(6042):642-6. doi:10.1126/science.1207339.
Pan et al., Biological and biomedical applications of engineered nucleases. Mol Biotechnol. Sep. 2013;55(1):54-62. doi: 10.1007/s12033-012-9613-9.
Paquet et al., Efficient introduction of specific homozygous and heterozygous mutations using CRISPR/Cas9. Nature. May 5, 2016;533(7601): 125-9. doi: 10.1038/nature17664. Epub Apr. 27, 2016.
Park et al., Digenome-seq web tool for profiling CRISPR specificity. Nat Methods. May 30, 2017;14(6):548-549. doi: 10.1038/nmeth.4262.
Park et al., Sendai virus, an RNA virus with No. risk of genomic integration, delivers CRISPR/Cas9 for efficient gene editing. Mol Ther Methods Clin Dev. Aug. 2, 20164;3:16057. doi: 10.1038/mtm.2016.57.
Parker et al., Admixture mapping identifies a quantitative trait locus associated with FEV1/FVC in the COPDGene Study. Genet Epidemiol. Nov. 2014;38(7):652-9. doi: 10.1002/gepi.21847. Epub Aug. 11, 2014.
Passini et al., Antisense oligonucleotides delivered to the mouse CNS ameliorate symptoms of severe spinal muscular atrophy. Sci Transl Med. Mar. 2, 2011;3(72):72ra18. doi: 10.1126/scitranslmed.3001777.
Patel et al., Flap endonucleases pass 5'-flaps through a flexible arch using a disorder-thread-order mechanism to confer specificity for free 5'-ends. Nucleic Acids Res. May 2012;40(10):4507-19. doi: 10.1093/nar/gks051. Epub Feb. 8, 2012.
Pattanayak et al., Determining the specificities of TALENs, Cas9, and other genome- editing enzymes. Methods Enzymol. 2014;546:47-78. doi: 10.1016/B978-0-12-801185-0.00003- 9.
Pattanayak et al., High-throughput profiling of off-target DNA cleavage reveals RNA- programmed Cas9 nuclease specificity. Nat Biotechnol. Sep. 2013;31(9):839-43. doi: 10.1038/nbt.2673. Epub Aug. 11, 2013.
Pattanayak et al., Revealing off-target cleavage specificities of zinc-finger nucleases by in vitro selection. Nat Methods. Aug. 7, 2011;8(9):765-70. doi: 10.1038/nmeth.1670.
Pavletich et al., Zinc finger-DNA recognition: crystal structure of a Zif268-DNA complex at 2.1 A. Science. May 10, 1991;252(5007):809-17.
Pawson et al., Protein phosphorylation in signaling—50 years and counting. Trends Biochem Sci. Jun. 2005;30(6):286-90. doi: 10.1016/j.tibs.2005.04.013.
Pearl, Structure and function in the uracil-DNA glycosylase superfamily. Mutat Res. Aug. 30, 2000;460(3-4):165-81.
Peck et al., Directed evolution of a small-molecule-triggered intein with improved splicing properties in mammalian cells. Chem Biol. May 27, 2011;18(5):619-30. doi: 10.1016/j.chembiol.2011.02.014.

(56) References Cited

OTHER PUBLICATIONS

Pellegrini et al., Insights into DNA recombination from the structure of a RAD51-BRCA2 complex. Nature. Nov. 21, 2002;420(6913):287-93. doi: 10.1038/nature01230. Epub Nov. 10, 2002.
Pelletier, CRISPR-Cas systems for the study of the immune function. Nov. 15, 2016. https://doi.org/10.1002/9780470015902.a0026896.
Pennisi et al., The CRISPR craze. Science. Aug. 23, 2013;341(6148):833-6. doi: 10.1126/science.341.6148.833.
Pennisi et al., The tale of the TALEs. Science. Dec. 14, 2012;338(6113):1408-11. doi: 10.1126/science.338.6113.1408.
Perach et al., Catalytic features of the recombinant reverse transcriptase of bovine leukemia virus expressed in bacteria. Virology. Jun. 20, 1999;259(1): 176-89. doi: 10.1006/viro.1999.9761.
Perez et al., Establishment of HIV-1 resistance in CD4+ T cells by genome editing using zinc-finger nucleases. Nat Biotechnol. Jul. 2008;26(7):808-16. Doi: 10.1038/nbt1410. Epub Jun. 29, 2008.
Perez-Pinera et al., Advances in targeted genome editing. Curr Opin Chem Biol. Aug. 2012; 16(3-4):268-77. doi: 10.1016/j.cbpa.2012.06.007. Epub Jul. 20, 2012.
Perez-Pinera et al., RNA-guided gene activation by CRISPR-Cas9-based transcription factors. Nat Methods. Oct. 2013; 10(10):973-6. doi: 10.1038/nmeth.2600. Epub Jul. 25, 2013.
Perler et al., Protein splicing and autoproteolysis mechanisms. Curr Opin Chem Biol. Oct. 1997;1(3):292-9. doi: 10.1016/s1367-5931(97)80065-8.
Perler et al., Protein splicing elements: inteins and exteins—a definition of terms and recommended nomenclature. Nucleic Acids Res. Apr. 11, 1994;22(7):1125-7. doi: 10.1093/nar/22.7.1125.
Perler, InBase, the New England Biolabs Intein Database. Nucleic Acids Res. Jan. 1, 1999;27(1):346-7. doi: 10.1093/nar/27.1.346.
Perler, Protein splicing of inteins and hedgehog autoproteolysis: structure, function, and evolution. Cell. Jan. 9, 1998;92(1):1-4. doi: 10.1016/s0092-8674(00)80892-2.
Perreault et al., Mixed deoxyribo- and ribo-oligonucleotides with catalytic activity. Nature. Apr. 5, 1990;344(6266):565-7. doi: 10.1038/344565a0.
Petek et al., Frequent endonuclease cleavage at off-target locations in vivo. Mol Ther. May 2010;18(5):983-6. Doi: 10.1038/mt.2010.35. Epub Mar. 9, 2010.
Petersen-Mahrt et al., AID mutates *E. coli* suggesting a DNA deamination mechanism for antibody diversification. Nature. Jul. 4, 2002;418(6893):99-103.
Petolino et al., Editing Plant Genomes: a new era of crop improvement. Plant Biotechnol J. Feb. 2016;14(2):435-6. doi: 10.1111/pbi.12542.
Peyrottes et al., Oligodeoxynucleoside phosphoramidates (P-NH2): synthesis and thermal stability of duplexes with DNA and RNA targets. Nucleic Acids Res. May 15, 1996;24(10):1841-8.
Pfeiffer et al., Mechanisms of DNA double-strand break repair and their potential to induce chromosomal aberrations. Mutagenesis. Jul. 2000;15(4):289-302. doi: 10.1093/mutage/15.4.289.
Pham et al., Reward versus risk: DNA cytidine deaminases triggering immunity and disease. Biochemistry. Mar. 1, 2005;44(8):2703-15.
Phillips, The challenge of gene therapy and DNA delivery. J Pharm Pharmacol. Sep. 2001;53(9):1169-74.
Pickart et al., Ubiquitin: structures, functions, mechanisms. Biochim Biophys Acta. Nov. 29, 2004;1695(1-3):55-72. doi: 10.1016/j.bbamcr.2004.09.019.
Pieken et al., Kinetic characterization of ribonuclease-resistant 2'-modified hammerhead ribozymes. Science. Jul. 19, 1991;253(5017):314-7. doi: 10.1126/science.1857967.
Pinkert et al., An albumin enhancer located 10 kb upstream functions along with its promoter to direct efficient, liver-specific expression in transgenic mice. Genes Dev. May 1987;1(3):268- 76. doi: 10.1101/gad.1.3.268.
Pirakitikulr et al., PCRless library mutagenesis via oligonucleotide recombination in yeast. Protein Sci. Dec. 2010; 19(12):2336-46. doi: 10.1002/pro.513.
Plasterk et al., DNA inversions in the chromosome of Escherichia coli and in bacteriophage Mu: relationship to other site-specific recombination systems. Proc Natl Acad Sci U S A. Sep. 1983;80(17):5355-8.
Plosky et al., CRISPR-Mediated Base Editing without DNA Double-Strand Breaks. Mol Cell. May 19, 2016;62(4):477-8. doi: 10.1016/j.molcel.2016.05.006.
Pluciennik et al., PCNA function in the activation and strand direction of MutLa endonuclease in mismatch repair. Proc Natl Acad Sci U S A. Sep. 14, 2010;107(37):16066-71. doi: 10.1073/pnas.1010662107. Epub Aug. 16, 2010.
Poller et al., A leucine-to-proline substitution causes a defective alpha 1-antichymotrypsin allele associated with familial obstructive lung disease. Genomics. Sep. 1993;17(3):740-3.
Popp et al., Sortagging: a versatile method for protein labeling. Nat Chem Biol. Nov. 2007;3(11):707-8. doi: 10.1038/nchembio.2007.31. Epub Sep. 23, 2007.
Porensky et al., A single administration of morpholino antisense oligomer rescues spinal muscular atrophy in mouse. Hum Mol Genet. Apr. 1, 2012;21(7):1625-38. doi: 10.1093/hmg/ddr600. Epub Dec. 20, 2011.
Porteus, Design and testing of zinc finger nucleases for use in mammalian cells. Methods Mol Biol. 2008;435:47-61. doi: 10.1007/978-1-59745-232-8_4.
Posnick et al., Imbalanced base excision repair increases spontaneous mutation and alkylation sensitivity in Escherichia coli. J Bacteriol. Nov. 1999;181(21):6763-71.
Pospísilová et al., Hydrolytic cleavage of N6-substituted adenine derivatives by eukaryotic adenine and adenosine deaminases. Biosci Rep. 2008;28(6):335-347. doi:10.1042/BSR20080081.
Pourcel et al., CRISPR elements in Yersinia pestis acquire new repeats by preferential uptake of bacteriophage DNA, and provide additional tools for evolutionary studies. Microbiology. Mar. 2005;151(Pt 3):653-63.
Prasad et al., Rev1 is a base excision repair enzyme with 5'-deoxyribose phosphate lyase activity. Nucleic Acids Res. Dec. 15, 2016;44(22):10824-10833. doi: 10.1093/nar/gkw869. Epub Sep. 28, 2016.
Prasad et al., Visualizing the assembly of human Rad51 filaments on double-stranded Dna. J Mol Biol. Oct. 27, 2006;363(3):713-28. doi: 10.1016/j.jmb.2006.08.046. Epub Aug. 22, 2006.
Prashant et al., CAS9 transcriptional activators for target specificity screening and paired nickases for cooperative genome engineering. Nature Biotechnology 2013;31(9):833-8.
Prorocic et al., Zinc-finger recombinase activities in vitro. Nucleic Acids Res. Nov. 2011;39(21):9316-28. doi: 10.1093/nar/gkr652. Epub Aug. 17, 2011.
Proudfoot et al., Zinc finger recombinases with adaptable DNA sequence specificity. PLoS One. Apr. 29, 2011;6(4):e19537. doi: 10.1371/journal.pone.0019537.
Pruschy et al., Mechanistic studies of a signaling pathway activated by the organic dimerizer FK1012. Chem Biol. Nov. 1994;1(3):163-72. doi: 10.1016/1074-5521(94)90006-x.
Prykhozhij et al., CRISPR multitargeter: a web tool to find common and unique CRISPR single guide RNA targets in a set of similar sequences. PLoS One. Mar. 5, 2015;10(3):e0119372. doi: 10.1371/journal.pone.0119372. eCollection 2015.
Pu et al., Evolution of a split RNA polymerase as a versatile biosensor platform. Nat Chem Biol. Apr. 2017;13(4):432-438. doi: 10.1038/nchembio.2299. Epub Feb. 13, 2017.
Putnam et al., Protein mimicry of DNA from crystal structures of the uracil-DNA glycosylase inhibitor protein and its complex with *Escherichia coli* uracil-DNA glycosylase. J Mol Biol. Mar. 26, 1999;287(2):331-46.
Putney et al., Improving protein therapeutics with sustained-release formulations. Nat Biotechnol. Feb. 1998;16(2):153-7.
Qi et al., Engineering naturally occurring trans-acting non-coding RNAs to sense molecular signals. Nucleic Acids Res. Jul. 2012;40(12):5775-86. doi: 10.1093/nar/gksl168. Epub Mar. 1, 2012.
Qi et al., Repurposing CRISPR as an RNA-guided platform for sequence-specific control of gene expression. Cell. Feb. 28, 2013;152(5):1173-83. doi: 10.1016/j.cell.2013.02.022.

(56) References Cited

OTHER PUBLICATIONS

Queen et al., Immunoglobulin gene transcription is activated by downstream sequence elements. Cell. Jul. 1983;33(3):741-8. doi: 10.1016/0092-8674(83)90016-8.
Radany et al., Increased spontaneous mutation frequency in human cells expressing the phage PBS2-encoded inhibitor of uracil-DNA glycosylase. Mutat Res. Sep. 15, 2000;461(1):41-58. doi: 10.1016/s0921-8777(00)00040-9.
Raghavan et al., Abstract 27: Therapeutic Targeting of Human Lipid Genes with in vivo CRISPR-Cas9 Genome Editing. Oral Abstract Presentations: Lipoprotein Metabolism and Therapeutic Targets. Arterioscler THromb Vasc Biol. 2015;35(Suppl. 1):Abstract 27. 5 pages.
Raillard et al., Targeting sites within HIV-1 cDNA with a DNA-cleaving ribozyme. Biochemistry. Sep. 10, 1996;35(36):11693-701. doi: 10.1021/bi960845g.
Raina et al., PROTAC-induced BET protein degradation as a therapy for castration-resistant prostate cancer. Proc Natl Acad Sci U S A. Jun. 28, 2016;113(26):7124-9. doi: 10.1073/pnas.1521738113. Epub Jun. 6, 2016.
Rajagopal et al., High-throughput mapping of regulatory DNA. Nat Biotechnol. Feb. 2016;34(2):167-74. doi: 10.1038/nbt.3468. Epub Jan. 25, 2016.
Rakonjac et al., Roles of PIII in filamentous phage assembly. J Mol Biol. 1998; 282(1)25-41.
Ramakrishna et al., Gene disruption by cell-penetrating peptide-mediated delivery of Cas9 protein and guide RNA. Genome Res. Jun. 2014;24(6):1020-7. doi: 10.1101/gr.171264.113. Epub Apr. 2, 2014.
Ramirez et al., Engineered zinc finger nickases induce homology-directed repair with reduced mutagenic effects. Nucleic Acids Res. Jul. 2012;40(12):5560-8. doi: 10.1093/nar/gks179. Epub Feb. 28, 2012.
Ramirez et al., Unexpected failure rates for modular assembly of engineered zinc fingers. Nat Methods. May 2008;5(5):374-5. Doi: 10.1038/nmeth0508-374.
Ran et al., Double Nicking by RNA-guided CRISPR Cas9 for Enhanced Genome Editing Specificity. Cell. Sep. 12, 2013;154(6):1380-9. doi: 10.1016/j.cell.2013.08.021. Epub Aug. 29, 2013.
Ran et al., Genome engineering using the CRISPR-Cas9 system. Nat Protoc. Nov. 2013;8(11):2281-308.doi: 10.1038/nprot.2013.143. Epub Oct. 24, 2013.
Ran et al., In vivo genome editing using Staphylococcus aureus Cas9. Nature. Apr. 9, 2015;520(7546):186-91. doi: 10.1038/nature14299. Epub Apr. 1, 2015.
Rashel et al., A novel site-specific recombination system derived from bacteriophage phiMR11. Biochem Biophys Res Commun. Apr. 4, 2008;368(2):192-8. doi: 10.1016/j.bbrc.2008.01.045. Epub Jan. 22, 2008.
Rasila et al., Critical evaluation of random mutagenesis by error-prone polymerase chain reaction protocols, *Escherichia coli* mutator strain, and hydroxylamine treatment. Anal Biochem. May 1, 2009;388(1):71-80. doi: 10.1016/j.ab.2009.02.008. Epub Feb. 10, 2009.
Raskin et al., Substitution of a single bacteriophage T3 residue in bacteriophage T7 RNA polymerase at position 748 results in a switch in promoter specificity. J Mol Biol. Nov. 20, 1992;228(2):506-15.
Raskin et al., T7 RNA polymerase mutants with altered promoter specificities. Proc Natl Acad Sci U S A. Apr. 15, 1993;90(8):3147-51.
Rath et al., Fidelity of end joining in mammalian episomes and the impact of Metnase on joint processing. BMC Mol Biol. Mar. 22, 2014;15:6. doi: 10.1186/1471-2199-15-6.
Ravishankar et al., X-ray analysis of a complex of *Escherichia coli* uracil DNA glycosylase (EcUDG) with a proteinaceous inhibitor. The structure elucidation of a prokaryotic UDG. Nuclei Acids Res. 26 (21):4880-4887 (1998).
Ray et al., A compendium of RNA-binding motifs for decoding gene regulation. Nature. Jul. 11, 2013;499(7457):172-7. doi: 10.1038/nature12311.
Ray et al., Homologous recombination: ends as the means. Trends Plant Sci. Oct. 2002;7(10):435-40.
Rebar et al., Phage display methods for selecting zinc finger proteins with novel DNA-binding specificities. Methods Enzymol. 1996;267:129-49.
Rebuzzini et al., New mammalian cellular systems to study mutations introduced at the break site by non-homologous end-joining. DNA Repair (Amst). May 2, 2005;4(5):546-55.
Rees et al., Improving the DNA specificity and applicability of base editing through protein engineering and protein delivery. Nat Commun. Jun. 6, 2017;8:15790. doi: 10.1038/ncomms15790.
Reiners et al., Scaffold protein harmonin (USH1C) provides molecular links between Usher syndrome type 1 and type 2. Hum Mol Genet. Dec. 15, 2005;14(24):3933-43. doi: 10.1093/hmg/ddi417. Epub Nov. 21, 2005.
Relph et al., Recent developments and current status of gene therapy using viral vectors in the United Kingdom. BMJ. 2004;329(7470):839-842. doi:10.1136/bmj.329.7470.839.
Remy et al., Gene transfer with a series of lipophilic DNA-binding molecules. Bioconjug Chem. Nov.-Dec. 1994;5(6):647-54. doi: 10.1021/bc00030a021.
Ren et al., In-line Alignment and $Mg^{2+}$ Coordination at the Cleavage Site of the env22 Twister Ribozyme. Nat Commun. Nov. 20, 2014;5:5534. doi: 10.1038/ncomms6534.
Ren et al., Pistol Ribozyme Adopts a Pseudoknot Fold Facilitating Site-Specific In-Line Cleavage. Nat Chem Biol. Sep. 2016;12(9):702-8. doi: 10.1038/nchembio.2125. Epub Jul. 11, 2016.
Reynaud et al., What role for AID: mutator, or assembler of the immunoglobulin mutasome? Nat Immunol. Jul. 2003;4(7):631-8.
Reyon et al., FLASH assembly of TALENs for high-throughput genome editing. Nat Biotechnol. May 2012;30(5):460-5. doi: 10.1038/nbt.2170.
Richardson et al., Enhancing homology-directed genome editing by catalytically active and inactive CRISPR-Cas9 using asymmetric donor DNA. Nat Biotechnol. Mar. 2016;34(3):339-44. doi: 10.1038/nbt.3481. Epub Jan. 20, 2016.
Richardson et al., Frequent chromosomal translocations induced by DNA double-strand breaks. Nature. Jun. 8, 2000;405(6787):697-700. doi: 10.1038/35015097.
Richter et al., Function and regulation of clustered regularly interspaced short palindromic repeats (CRISPR) / CRISPR associated (Cas) systems. Viruses. Oct. 19, 2012;4(10):2291-311. doi: 10.3390/v4102291.
Riechmann et al., The C-terminal domain of TolA is the coreceptor for filamentous phage infection of *E. coli*. Cell. 1997; 90(2):351-60. PMID:9244308.
Ringrose et al., The Kw recombinase, an integrase from Kluyveromyces waltii. Eur J Biochem. Sep. 15, 1997;248(3):903-12. doi: 10.1111/j.1432-1033.1997.00903.x.
Risso et al., Hyperstability and substrate promiscuity in laboratory resurrections of Precambrian B-lactamases. J Am Chem Soc. Feb. 27, 2013;135(8):2899-902. doi: 10.1021/ja311630a. Epub Feb. 14, 2013 .
Ritchie et al., limma powers differential expression analyses for RNA-sequencing and microarray studies. Nucleic Acids Res. Apr. 20, 2015;43(7):e47. doi: 10.1093/nar/gkv007. Epub Jan. 20, 2015.
Rizk et al., An engineered substance P variant for receptor-mediated delivery of synthetic antibodies into tumor cells. Proc Natl Acad Sci U S A. Jul. 7, 2009;106(27):11011-5. doi: 10.1073/pnas.0904907106. Epub Jun. 22, 2009.
Robertson et al., DNA repair in mammalian cells: Base excision repair: the long and short of it. Cell Mol Life Sci. Mar. 2009;66(6):981-93. doi: 10.1007/s00018-009-8736-z.
Robertson et al., Selection in vitro of an RNA enzyme that specifically cleaves single- stranded DNA. Nature. Mar. 29, 1990;344(6265):467-8. doi: 10.1038/344467a0.
Robinson et al., The protein tyrosine kinase family of the human genome. Oncogene. Nov. 20, 2000;19(49):5548-57. doi: 10.1038/sj.onc.1203957.

(56) References Cited

OTHER PUBLICATIONS

Rodriguez-Muela et al., Single-Cell Analysis of SMN Reveals Its Broader Role in Neuromuscular Disease. Cell Rep. Feb. 7, 2017;18(6):1484-1498 and Supplemental Information. doi: 10.1016/j.celrep.2017.01.035.
Rogozin et al., Evolution and diversification of lamprey antigen receptors: evidence for involvement of an AID-APOBEC family cytosine deaminase. Nat Immunol. Jun. 2007;8(6):647- 56. doi: 10.1038/ni1463. Epub Apr. 29, 2007.
Rong et al., Homologous recombination in human embryonic stem cells using CRISPR/Cas9 nickase and a long DNA donor template. Protein Cell. Apr. 2014;5(4):258-60. doi: 10.1007/s13238-014-0032-5.
Rongrong et al., Effect of deletion mutation on the recombination activity of Cre recombinase. Acta Biochim Pol. 2005;52(2):541-4. Epub May 15, 2005.
Roth et al., A riboswitch selective for the queuosine precursor preQ1 contains an unusually small aptamer domain. Nat Struct Mol Biol. Apr. 2007;14(4):308-17. Epub Mar. 25, 2007.
Roth et al., A widespread self-cleaving ribozyme class is revealed by bioinformatics. Nat Chem Biol. Jan. 2014;10(1):56-60. doi: 10.1038/nchembio.1386. Epub Nov. 17, 2013.
Roth et al., Purification and characterization of murine retroviral reverse transcriptase expressed in *Escherichia coli*. J Biol Chem. Aug. 5, 1985;260(16):9326-35.
Rouet et al., Expression of a site-specific endonuclease stimulates homologous recombination in mammalian cells. Proc Natl Acad Sci U S A. Jun. 21, 1994;91(13):6064-8. doi: 10.1073/pnas.91.13.6064.
Rouet et al., Introduction of double-strand breaks into the genome of mouse cells by expression of a rare-cutting endonuclease. Mol Cell Biol. Dec. 1994;14(12):8096-106. doi: 10.1128/mcb.14.12.8096.
Rowland et al., Regulatory mutations in Sin recombinase support a structure-based model of the synaptosome. Mol Microbiol. Oct. 2009;74(2):282-98. doi: 10.1111/j.1365- 2958.2009.06756.x. Epub Jun. 8, 2009.
Rowland et al., Sin recombinase from Staphylococcus aureus: synaptic complex architecture and transposon targeting. Mol Microbiol. May 2002;44(3):607-19. doi: 10.1046/j.1365-2958.2002.02897.x.
Rowley, Chromosome translocations: dangerous liaisons revisited. Nat Rev Cancer. Dec. 2001;1(3):245-50. doi: 10.1038/35106108.
Rubio et al., An adenosine-to-inosine tRNA-editing enzyme that can perform C-to-U deamination of DNA. Proc Natl Acad Sci U S A. May 8, 2007;104(19):7821-6. doi: 10.1073/pnas.0702394104. Epub May 1, 2007. PMID: 17483465; PMCID: PMC1876531.
Rubio et al., Transfer RNA travels from the cytoplasm to organelles. Wiley Interdiscip Rev RNA. Nov.-Dec. 2011;2(6):802-17. doi: 10.1002/wrna.93. Epub Jul. 11, 2011.
Rudolph et al., Synthetic riboswitches for the conditional control of gene expression in Streptomyces coelicolor. Microbiology. Jul. 2013;159(Pt 7):1416-22. doi: 10.1099/mic.0.067322-0. Epub May 15, 2013.
Rutherford et al., Attachment site recognition and regulation of directionality by the serine integrases. Nucleic Acids Res. Sep. 2013;41(17):8341-56. doi: 10.1093/nar/gkt580. Epub Jul. 2, 2013.
Rüfer et al., Non-contact positions impose site selectivity on Cre recombinase. Nucleic Acids Res. Jul. 1, 2002;30(13):2764-71. doi: 10.1093/nar/gkf399.
Saayman et al., The therapeutic application of CRISPR/Cas9 technologies for HIV. Expert Opin Biol Ther. Jun. 2015;15(6):819-30. doi: 10.1517/14712598.2015.1036736. Epub Apr. 12, 2015.
Sadelain et al., Safe harbours for the integration of new DNA in the human genome. Nat Rev Cancer. Dec. 1, 2011;12(1):51-8. doi: 10.1038/nrc3179.
Sadowski, The Flp recombinase of the 2-microns plasmid of Saccharomyces cerevisiae. Prog Nucleic Acid Res Mol Biol. 1995;51:53-91.
Sage et al., Proliferation of functional hair cells in vivo in the absence of the retinoblastoma protein. Science. Feb. 18, 2005;307(5712):1114-8. Epub Jan. 13, 2005.
Sakuma et al., MMEJ-assisted gene knock-in using TALENs and CRISPR-Cas9 with the PITCh systems. Nat Protoc. Jan. 2016;11(1):118-33. doi: 10.1038/nprot.2015.140. Epub Dec. 17, 2015.
Sale et al., Y-family DNA polymerases and their role in tolerance of cellular DNA damage. Nat Rev Mol Cell Biol. Feb. 23, 2012;13(3):141-52. doi: 10.1038/nrm3289.
Saleh-Gohari et al., Conservative homologous recombination preferentially repairs DNA double-strand breaks in the S phase of the cell cycle in human cells. Nucleic Acids Res. Jul. 13, 2004;32(12):3683-8. Print 2004.
Samal et al., Cationic polymers and their therapeutic potential. Chem Soc Rev. Nov. 7, 2012;41(21):7147-94. doi: 10.1039/c2cs35094g. Epub Aug. 10, 2012.
Samulski et al., Helper-free stocks of recombinant adeno-associated viruses: normal integration does not require viral gene expression. J Virol. Sep. 1989;63(9):3822-8. doi: 10.1128/JVI.63.9.3822-3828.1989.
San Filippo et al., Mechanism of eukaryotic homologous recombination. Annu Rev Biochem. 2008;77:229-57. doi: 10.1146/annurev.biochem.77.061306.125255.
Sander et al., CRISPR-Cas systems for editing, regulating and targeting genomes. Nat Biotechnol. Apr. 2014;32(4):347-55. doi: 10.1038/nbt.2842. Epub Mar. 2, 2014.
Sander et al., In silico abstraction of zinc finger nuclease cleavage profiles reveals an expanded landscape of off-target sites. Nucleic Acids Res. Oct. 2013;41(19):e181. doi: 10.1093/nar/gkt716. Epub Aug. 14, 2013.
Sander et al., Targeted gene disruption in somatic zebrafish cells using engineered TALENs. Nat Biotechnol. Aug. 5, 2011;29(8):697-8. doi: 10.1038/nbt.1934.
Sang et al., A unique uracil-DNA binding protein of the uracil DNA glycosylase superfamily. Nucleic Acids Res. Sep. 30, 2015;43(17):8452-63. doi: 10.1093/nar/gkv854. Epub Aug. 24, 2015.
Sang, Prospects for transgenesis in the chick. Mech Dev. Sep. 2004;121(9):1179-86.
Sanjana et al., A transcription activator-like effector toolbox for genome engineering. Nat Protoc. Jan. 5, 2012;7(1):171-92. doi: 10.1038/nprot.2011.431.
Santiago et al., Targeted gene knockout in mammalian cells by using engineered zinc-finger nucleases. Proc Natl Acad Sci U S A. Apr. 15, 2008;105(15):5809-14. doi: 10.1073/pnas.0800940105. Epub Mar. 21, 2008.
Santoro et al., Directed evolution of the site specificity of Cre recombinase. Proc Natl Acad Sci U S A. Apr. 2, 2002;99(7):4185-90. Epub Mar. 19, 2002.
Saparbaev et al., Excision of hypoxanthine from DNA containing dIMP residues by the *Escherichia coli*, yeast, rat, and human alkylpurine DNA glycosylases. Proc Natl Acad Sci U S A. Jun. 21, 1994;91(13):5873-7. doi: 10.1073/pnas.91.13.5873.
Sapranauskas et al., The *Streptococcus thermophilus* CRISPR/Cas system provides immunity in *Escherichia coli*. Nucleic Acids Res. Nov. 2011;39(21):9275-82. doi: 10.1093/nar/gkr606. Epub Aug. 3, 2011.
Sapunar et al., Dorsal root ganglion—a potential new therapeutic target for neuropathic pain. J Pain Res. 2012;5:31-8. doi: 10.2147/JPR.S26603. Epub Feb. 16, 2012.
Saraconi et al., The RNA editing enzyme APOBEC1 induces somatic mutations and a compatible mutational signature is present in esophageal adenocarcinomas. Genome Biol. Jul. 31, 2014;15(7):417. doi: 10.1186/s13059-014-0417-z.
Sarkar et al., HIV-1 proviral DNA excision using an evolved recombinase. Science. Jun. 29, 2007;316(5833):1912-5. doi: 10.1126/science.1141453.
Sashital et al., Mechanism of foreign DNA selection in a bacterial adaptive immune system. Mol Cell. Jun. 8, 2012;46(5):606-15. doi: 10.1016/j.molcel.2012.03.020. Epub Apr. 19, 2012.
Sasidharan et al., The selection of acceptable protein mutations. PNAS; Jun. 12, 2007;104(24): 10080-5. www.pnas.org/cgi/doi/10.1073.pnas.0703737104.
Satomura et al., Precise genome-wide base editing by the CRISPR Nickase system in yeast. Sci Rep. May 18, 2017;7(1):2095. doi: 10.1038/s41598-017-02013-7.

(56) References Cited

OTHER PUBLICATIONS

Saudek et al., A preliminary trial of the programmable implantable medication system for insulin delivery. N Engl J Med. Aug. 31, 1989;321(9):574-9.
Sauer et al., DNA recombination with a heterospecific Cre homolog identified from comparison of the pac-c1 regions of P1-related phages. Nucleic Acids Res. Nov. 18, 2004;32(20):6086-95. doi: 10.1093/nar/gkh941.
Saville et al., A site-specific self-cleavage reaction performed by a novel RNA in Neurospora mitochondria. Cell. May 18, 1990;61(4):685-96. doi: 10.1016/0092-8674(90)90480-3.
Savva et al., The structural basis of specific base-excision repair by uracil-DNA glycosylase. Nature. Feb. 9, 1995;373(6514):487-93. doi: 10.1038/373487a0.
Schaaper et al., Base selection, proofreading, and mismatch repair during DNA replication in *Escherichia coli*. J Biol Chem. Nov. 15, 1993;268(32):23762-5.
Schaaper et al., Spectra of spontaneous mutations in *Escherichia coli* strains defective in mismatch correction: the nature of in vivo DNA replication errors. Proc Natl Acad Sci U S A. Sep. 1987;84(17):6220-4.
Schaefer et al., Understanding RNA modifications: the promises and technological bottlenecks of the 'epitranscriptome'. Open Biol. May 2017;7(5):170077. doi: 10.1098/rsob.170077.
Schechner et al., Multiplexable, locus-specific targeting of long RNAs with CRISPR- Display. Nat Methods. Jul. 2015;12(7):664-70. doi: 10.1038/nmeth.3433. Epub Jun. 1, 2015. Author manuscript entitled CRISPR Display: A modular method for locus-specific targeting of long noncoding RNAs and synthetic RNA devices in vivo.
Schek et al., Definition of the upstream efficiency element of the simian virus 40 late polyadenylation signal by using in vitro analyses. Mol Cell Biol. Dec. 1992;12(12):5386-93. doi: 10.1128/mcb.12.12.5386.
Schellenberger et al., A recombinant polypeptide extends the in vivo half-life of peptides and proteins in a tunable manner. Nat Biotechnol. Dec. 2009;27(12):1186-90. doi: 10.1038/nbt.1588.
Schenk et al., MPDU1 mutations underlie a novel human congenital disorder of glycosylation, designated type If. J Clin Invest. Dec. 2001; 108(11):1687-95. doi: 10.1172/JCI13419.
Schlacher et al., Double-strand break repair-independent role for BRCA2 in blocking stalled replication fork degradation by MRE11. Cell. May 13, 2011;145(4):529-42. doi: 10.1016/j.cell.2011.03.041. Erratum in: Cell. Jun. 10, 2011;145(6):993.
Schmid et al., Albumin-binding prodrugs of camptothecin and doxorubicin with an Ala-Leu-Ala-Leu-linker that are cleaved by cathepsin B: synthesis and antitumor efficacy.
Schmitz et al., Behavioral abnormalities in prion protein knockout mice and the potential relevance of PrP(C) for the cytoskeleton. Prion. 2014;8(6):381-6. doi: 10.4161/19336896.2014.983746.
Schneider et al., NIH Image to ImageJ: 25 years of image analysis. Nat Methods. Jul. 2012;9(7):671-5.
Schrank et al., Inactivation of the survival motor neuron gene, a candidate gene for human spinal muscular atrophy, leads to massive cell death in early mouse embryos. Proc Natl Acad Sci USA. Sep. 2, 1997;94(18):9920-5. doi: 10.1073/pnas.94.18.9920.
Schriefer et al., Low pressure DNA shearing: a method for random DNA sequence analysis. Nucleic Acids Res. Dec. 25, 1990;18(24):7455-6.
Schultz et al., Expression and secretion in yeast of a 400-kDa envelope glycoprotein derived from Epstein-Barr virus. Gene. 1987;54(1):113-23. doi: 10.1016/0378-1119(87)90353-2.
Schultz et al., Oligo-2'-fluoro-2'-deoxynucleotide N3'-->P5' phosphoramidates: synthesis and properties. Nucleic Acids Res. Aug. 1, 1996;24(15):2966-73.
Schwank et al., Functional repair of CFTR by CRISPR/Cas9 in intestinal stem cell organoids of cystic fibrosis patients. Cell Stem Cell. Dec. 5, 2013;13(6):653-8. doi:10.1016/j.stem.2013.11.002.
Schwartz et al., Post-translational enzyme activation in an animal via optimized conditional protein splicing. Nat Chem Biol. Jan. 2007;3(1):50-4. Epub Nov. 26, 2006.
Schwarze et al., In vivo protein transduction: delivery of a biologically active protein into the mouse. Science. Sep. 3, 1999;285(5433):1569-72.
Sclimenti et al., Directed evolution of a recombinase for improved genomic integration at a native human sequence. Nucleic Acids Res. Dec. 15, 2001;29(24):5044-51.
Score Results for Luetticken et al., Complete genome sequence of a *Streptococcus dysgalactiae* subsp. RT equisimilis strain possessing Lancefield's group A antigen. RL Submitted to the EMBL/GenBank/DDBJ databases. May 2012. 3 pages.
Score Results for Okumura et al., Evolutionary paths of streptococcal and staphylococcal superantigens. RL BMC Genomics. 2012;13:404-404. 3 pages.
Score Results for Shimomura et al., Complete Genome Sequencing and Analysis of a Lancefield Group G RT *Streptococcus dysagalactiae* Subsp. Equisimilis Strain Causing Streptococcal RT Toxic Shock Syndrome (STSS). RL BMC Genomics. 2011;12:17-17. 3 pages.
Scott et al., Production of cyclic peptides and proteins in vivo. Proc Natl Acad Sci U S A. Nov. 23, 1999;96(24):13638-43. doi: 10.1073/pnas.96.24.13638.
Seale et al., PRDM16 controls a brown fat/skeletal muscle switch. Nature. Aug. 21, 2008;454(7207):961-7. doi: 10.1038/nature07182.
Seed, An LFA-3 cDNA encodes a phospholipid-linked membrane protein homologous to its receptor CD2. Nature. Oct. 29-Nov. 4, 1987;329(6142):840-2. doi: 10.1038/329840a0.
Sefton et al., Implantable pumps. Crit Rev Biomed Eng. 1987;14(3):201-40.
Segal et al., Evaluation of a modular strategy for the construction of novel polydactyl zinc finger DNA-binding proteins. Biochemistry. Feb. 25, 2003;42(7):2137-48.
Segal et al., Toward controlling gene expression at will: selection and design of zinc finger domains recognizing each of the 5'-GNN-3' DNA target sequences. Proc Natl Acad Sci U S A. Mar. 16, 1999;96(6):2758-63.
Sells et al., Delivery of protein into cells using polycationic liposomes. Biotechniques. Jul. 1995;19(1):72-6, 78.
Semenova et al., Interference by clustered regularly interspaced short palindromic repeat (CRISPR) RNA is governed by a seed sequence. Proc Natl Acad Sci U S A. Jun. 21, 2011;108(25):10098-103. doi: 10.1073/pnas.1104144108. Epub Jun. 6, 2011.
Semple et al., Rational design of cationic lipids for siRNA delivery. Nat Biotechnol. Feb. 2010;28(2):172-6. doi: 10.1038/nbt.1602. Epub Jan. 17, 2010.
Serganov et al., Coenzyme recognition and gene regulation by a flavin mononucleotide riboswitch. Nature. Mar. 12, 2009;458(7235):233-7. doi: 10.1038/nature07642. Epub Jan. 25, 2009.
Serganov et al., Structural basis for discriminative regulation of gene expression by adenine-and guanine-sensing mRNAs. Chem Biol. Dec. 2004;11(12):1729-41.
Serganov et al., Structural basis for gene regulation by a thiamine pyrophosphate-sensing riboswitch. Nature. Jun. 29, 2006;441(7097):1167-71. Epub May 21, 2006.
Seripa et al., The missing ApoE allele. Ann Hum Genet. Jul. 2007;71(Pt 4):496-500. Epub Jan. 22, 2007.
Serrano-Heras et al., Protein p56 from the Bacillus subtilis phage phi29 inhibits DNA-binding ability of uracil-DNA glycosylase. Nucleic Acids Res. 2007;35(16):5393-401. Epub Aug. 13, 2007.
Severinov et al., Expressed protein ligation, a novel method for studying protein-protein interactions in transcription. J Biol Chem. Jun. 26, 1998;273(26):16205-9. doi: 10.1074/jbc.273.26.16205.
Sha et al., Monobodies and other synthetic binding proteins for expanding protein science. Protein Sci. May 2017;26(5):910-924. doi: 10.1002/pro.3148. Epub Mar. 24, 2017.
Shah et al., Inteins: nature's gift to protein chemists. Chem Sci. 2014;5(1):446-461.
Shah et al., Kinetic control of one-pot trans-splicing reactions by using a wild-type and designed split intein. Angew Chem Int Ed Engl. Jul. 11, 2011;50(29):6511-5. doi: 10.1002/anie.201102909. Epub Jun. 8, 2011.

(56) References Cited

OTHER PUBLICATIONS

Shah et al., Protospacer recognition motifs: mixed identities and functional diversity. RNA Biol. May 2013;10(5):891-9. doi: 10.4161/rna.23764. Epub Feb. 12, 2013.
Shah et al., Target-specific variants of Flp recombinase mediate genome engineering reactions in mammalian cells. FEBS J. Sep. 2015;282(17):3323-33. doi: 10.1111/febs.13345. Epub Jul. 1, 2015.
Shaikh et al., Chimeras of the Flp and Cre recombinases: tests of the mode of cleavage by Flp and Cre. J Mol Biol. Sep. 8, 2000;302(1):27-48.
Shalem et al., Genome-scale CRISPR-Cas9 knockout screening in human cells. Science. Jan. 3, 2014;343(6166):84-7. doi: 10.1126/science.1247005. Epub Dec. 12, 2013.
Shalem et al., High-throughput functional genomics using CRISPR-Cas9. Nat Rev Genet. May 2015;16(5):299-311. doi: 10.1038/nrg3899. Epub Apr. 9, 2015.
Sharbeen et al., Ectopic restriction of DNA repair reveals that UNG2 excises AID-induced uracils predominantly or exclusively during G1 phase. J Exp Med. May 7, 2012;209(5):965-74. doi: 10.1084/jem.20112379. Epub Apr. 23, 2012.
Sharer et al., The ARF-like 2 (ARL2)-binding protein, BART. Purification, cloning, and initial characterization. J Biol Chem. Sep. 24, 1999;274(39):27553-61. doi: 10.1074/jbc.274.39.27553.
Sharma et al., Efficient introduction of aryl bromide functionality into proteins in vivo. FEBS Lett. Feb. 4, 2000;467(1):37-40.
Sharma et al., Identification of novel methyltransferases, Bmt5 and Bmt6, responsible for the m3U methylations of 25S rRNA in *Saccharomyces cerevisiae*. Nucleic Acids Res. Mar. 2014;42(5):3246-60. doi: 10.1093/nar/gkt1281. Epub Dec. 11, 2013.
Shaw et al., Implications of human genome architecture for rearrangement-based disorders: the genomic basis of disease. Hum Mol Genet. Apr. 1, 2004;13 Spec No. 1:R57-64. doi: 10.1093/hmg/ddh073. Epub Feb. 5, 2004.
Shcherbakova et al., Near-infrared fluorescent proteins for multicolor in vivo imaging. Nat Methods. Aug. 2013;10(8):751-4. doi: 10.1038/nmeth.2521. Epub Jun. 16, 2013.
Shechner et al., Multiplexable, locus-specific targeting of long RNAs with CRISPR-Display. Nat Methods. Jul. 2015; 12(7):664-70. doi: 10.1038/nmeth.3433. Epub Jun. 1, 2015.
Shee et al., Engineered proteins detect spontaneous DNA breakage in human and bacterial cells. Elife. Oct. 29, 2013;2:e01222. doi: 10.7554/eLife.01222.
Shen et al., Efficient genome modification by CRISPR-Cas9 nickase with minimal off-target effects. Nat Methods. Apr. 2014;11(4):399-402. doi: 10.1038/nmeth.2857. Epub Mar. 2, 2014.
Shen et al., Herpes simplex virus 1 (HSV-1) for cancer treatment. Cancer Gene Ther. Nov. 2006;13(11):975-92. doi: 10.1038/sj.cgt.7700946. Epub Apr. 7, 2006.
Sheridan, First CRISPR-Cas patent opens race to stake out intellectual property. Nat Biotechnol. 2014;32(7):599-601.
Sheridan, Gene therapy finds its niche. Nat Biotechnol. Feb. 2011;29(2):121-8. doi: 10.1038/nbt.1769.
Sherwood et al., Discovery of directional and nondirectional pioneer transcription factors by modeling DNase profile magnitude and shape. Nat Biotechnol. Feb. 2014;32(2):171-178. doi: 10.1038/nbt.2798. Epub Jan. 19, 2014.
Shete et al., Endosomal escape: a bottleneck in intracellular delivery. J Nanosci Nanotechnol. Jan. 2014;14(1):460-74.
Shi et al., Structural basis for targeted DNA cytosine deamination and mutagenesis by APOBEC3A and APOBEC3B. Nat Struct Mol Biol. Feb. 2017;24(2):131-139. doi: 10.1038/nsmb.3344. Epub Dec. 19, 2016.
Shi et al., YTHDF3 facilitates translation and decay of N6-methyladenosine-modified RNA. Cell Res. Mar. 2017;27(3):315-328. doi: 10.1038/cr.2017.15. Epub Jan. 20, 2017.
Shimantani et al., Targeted base editing in rice and tomato using a CRISPR-Cas9 cytidine deaminase fusion. Nat Biotechnol. May 2017;35(5):441-443. doi: 10.1038/nbt.3833. Epub Mar. 27, 2017.
Shimizu et al., Adding fingers to an engineered zinc finger nuclease can reduce activity. Biochemistry. Jun. 7, 2011;50(22):5033-41. doi: 10.1021/bi200393g. Epub May 11, 2011.
Shimojima et al., Spinocerebellar ataxias type 27 derived from a disruption of the fibroblast growth factor 14 gene with mimicking phenotype of paroxysmal non-kinesigenic dyskinesia. Brain Dev. Mar. 2012;34(3):230-3. doi: 10.1016/j.braindev.2011.04.014. Epub May 1, 20119.
Shin et al., CRISPR/Cas9 targeting events cause complex deletions and insertions at 17 sites in the mouse genome. Nat Commun. May 31, 2017;8:15464. doi: 10.1038/ncomms15464.
Shindo et al., A Comparison of Two Single-Stranded DNA Binding Models by Mutational Analysis of APOBEC3G. Biology (Basel). Aug. 2, 2012;1(2):260-76. doi: 10.3390/biology1020260.
Shingledecker et al., Molecular dissection of the *Mycobacterium tuberculosis* RecA intein: design of a minimal intein and of a trans-splicing system involving two intein fragments. Gene. Jan. 30, 1998;207(2):187-95. doi: 10.1016/s0378-1119(97)00624-0.
Shmakov et al., Discovery and Functional Characterization of Diverse Class 2 CRISPR Cas Systems. Molecular Cell Nov. 2015;60(3):385-97.
Shmakov et al., Diversity and evolution of class 2 CRISPR-Cas systems. Nat Rev Microbiol. Mar. 2017;15(3):169-182. doi: 10.1038/nrmicro.2016.184. Epub Jan. 23, 2017.
Shultz et al., A genome-wide analysis of FRT-like sequences in the human genome. PLoS One. Mar. 23, 2011;6(3):e18077. doi: 10.1371/journal.pone.0018077.
Siebert et al., An improved PCR method for walking in uncloned genomic DNA. Nucleic Acids Res. Mar. 25, 1995;23(6): 1087-8.
Silas et al., Direct CRISPR spacer acquisition from RNA by a natural reverse transcriptase-Cas1 fusion protein. Science. Feb. 26, 2016;351(6276):aad4234. doi: 10.1126/science.aad4234.
Silva et al., Selective disruption of the DNA polymerase III α-β complex by the umuD gene products. Nucleic Acids Res. Jul. 2012;40(12):5511-22. doi: 10.1093/nar/gks229. Epub Mar. 9, 2012.
Simonelli et al., Base excision repair intermediates are mutagenic in mammalian cells. Nucleic Acids Res. Aug. 2, 2005;33(14):4404-11. Print 2005.
Singh et al., Cross-talk between diverse serine integrases. J Mol Biol. Jan. 23, 2014;426(2):318-31. doi: 10.1016/j.jmb.2013.10.013. Epub Oct. 22, 2013.
Singh et al., Real-time observation of DNA recognition and rejection by the RNA-guided endonuclease Cas9. Nat Commun. Sep. 14, 2016;7:12778. doi: 10.1038/ncomms12778.
Singh et al., Splicing of a critical exon of human Survival Motor Neuron is regulated by a unique silencer element located in the last intron. Mol Cell Biol. Feb. 2006;26(4):1333-46. doi: 10.1128/MCB.26.4.1333-1346.2006.
Sirk et al., Expanding the zinc-finger recombinase repertoire: directed evolution and mutational analysis of serine recombinase specificity determinants. Nucleic Acids Res. Apr. 2014;42(7):4755-66. doi: 10.1093/nar/gkt1389. Epub Jan. 21, 2014.
Sivalingam et al., Biosafety assessment of site-directed transgene integration in human umbilical cord-lining cells. Mol Ther. Jul. 2010;18(7):1346-56. doi: 10.1038/mt.2010.61. Epub Apr. 27, 2010.
Sjoblom et al., The consensus coding sequences of human breast and colorectal cancers. Science. Oct. 13, 2006;314(5797):268-74. Epub Sep. 7, 2006.
Skretas et al., Regulation of protein activity with small-molecule-controlled inteins. Protein Sci. Feb. 2005;14(2):523-32. Epub Jan. 4, 2005.
Slaymaker et al., Rationally engineered Cas9 nucleases with improved specificity. Science. Jan. 1, 2016;351(6268):84-8. doi: 10.1126/science.aad5227. Epub Dec. 1, 2015.
Sledz et al., Structural insights into the molecular mechanism of the m(6)A writer complex. Elife. Sep. 14, 2016;5:e18434. doi: 10.7554/eLife. 18434.
Slupphaug et al., A nucleotide-flipping mechanism from the structure of human uracil-DNA glycosylase bound to DNA. Nature. Nov. 7, 1996;384(6604):87-92. doi: 10.1038/384087a0.
Smargon et al., Cas13b Is a Type VI-B CRISPR-Associated RNA-Guided RNase Differentially Regulated by Accessory Proteins

(56) References Cited

OTHER PUBLICATIONS

Csx27 and Csx28. Mol Cell. Feb. 16, 2017;65(4):618-630.e7. doi: 10.1016/j.molcel.2016.12.023. Epub Jan. 5, 2017.
Smith et al., Diversity in the serine recombinases. Mol Microbiol. Apr. 2002;44(2):299-307. Review.
Smith et al., Expression of a dominant negative retinoic acid receptor ? in Xenopus embryos leads to partial resistance to retinoic acid. Roux Arch Dev Biol. Mar. 1994;203(5):254-265. doi: 10.1007/BF00360521.
Smith et al., Herpesvirus transport to the nervous system and back again. Annu Rev Microbiol. 2012;66:153-76. doi: 10.1146/annurev-micro-092611-150051. Epub Jun. 15, 2012.
Smith et al., Production of human beta interferon in insect cells infected with a baculovirus expression vector. Mol Cell Biol. Dec. 1983;3(12):2156-65. doi: 10.1128/mcb.3.12.2156.
Smith et al., Single-step purification of polypeptides expressed in *Escherichia coli* as fusions with glutathione S-transferase. Gene. Jul. 15, 1988;67(1):31-40. doi: 10.1016/0378-1119(88)90005-4.
Smith et al., Site-specific recombination by phiC31 integrase and other large serine recombinases. Biochem Soc Trans. Apr. 2010;38(2):388-94. doi: 10.1042/BST0380388.
Smith, Filamentous fusion phage: novel expression vectors that display cloned antigens on the virion surface. Science. Jun. 14, 1985;228(4705):1315-7.
Smith, Phage-encoded Serine Integrases and Other Large Serine Recombinases. Microbiol Spectr. Aug. 2015;3(4). doi: 10.1128/microbiolspec.MDNA3-0059-2014.
Smolen and Ball, Controlled Drug Bioavailability, Drug Product Design and Performance. 1984. Wiley, New York.
Somanathan et al., AAV vectors expressing LDLR gain-of-function variants demonstrate increased efficacy in mouse models of familial hypercholesterolemia. Circ Res. Aug. 29, 2014;115(6):591-9. doi: 10.1161/CIRCRESAHA.115.304008. Epub Jul. 14, 2014.
Sommerfelt et al., Receptor interference groups of 20 retroviruses plating on human cells. Virology. May 1990;176(1):58-69. doi: 10.1016/0042-6822(90)90230-0.
Song et al., Antibody mediated in vivo delivery of small interfering RNAs via cell-surface receptors. Nat Biotechnol. Jun. 2005;23(6):709-17. Epub May 22, 2005.
Song et al., RS-1 enhances CRISPR/Cas9- and TALEN-mediated knock-in efficiency. Nat Commun. Jan. 28, 2016;7:10548. doi: 10.1038/ncomms10548.
Sorusch et al., Characterization of the ternary Usher syndrome SANS/ush2a/whirlin protein complex. Hum Mol Genet. Mar. 15, 2017;26(6):1157-1172. doi: 10.1093/hmg/ddx027.
Southworth et al., Control of protein splicing by intein fragment reassembly. EMBO J. Feb. 16, 1998;17(4):918-26. doi: 10.1093/emboj/17.4.918.
Southworth et al., Purification of proteins fused to either the amino or carboxy terminus of the *Mycobacterium xenopi* gyrase A intein. Biotechniques. Jul. 1999;27(1):110-4, 116, 118-20. doi: 10.2144/99271st04.
Spencer et al., A general strategy for producing conditional alleles of Src-like tyrosine kinases. Proc Natl Acad Sci U S A. Oct. 10, 1995;92(21):9805-9. doi: 10.1073/pnas.92.21.9805.
Spencer et al., Controlling signal transduction with synthetic ligands. Science. Nov. 12, 1993;262(5136):1019-24. doi: 10.1126/science.7694365.
Spencer et al., Functional analysis of Fas signaling in vivo using synthetic inducers of dimerization. Curr Biol. Jul. 1, 1996;6(7):839-47. doi: 10.1016/s0960-9822(02)00607-3.
Srivastava et al., An inhibitor of nonhomologous end-joining abrogates double-strand break repair and impedes cancer progression. Cell. Dec. 21, 2012;151(7):1474-87. doi: 10.1016/j.cell.2012.11.054.
Stadtman, Selenocysteine. Annu Rev Biochem. 1996;65:83-100.
Stark et al., ATP hydrolysis by mammalian RAD51 has a key role during homology-directed DNA repair. J Biol Chem. Jun. 7, 2002;277(23):20185-94. doi: 10.1074/jbc.M112132200. Epub Mar. 28, 2002.
Steele et al., The prion protein knockout mouse: a phenotype under challenge. Prion. Apr.-Jun. 2007;1(2):83-93. doi: 10.4161/pri.1.2.4346. Epub Apr. 25, 2007.
Steiner et al., The neurotropic herpes viruses: herpes simplex and varicella-zoster. Lancet Neurol. Nov. 2007;6(11):1015-28. doi: 10.1016/S1474-4422(07)70267-3.
Stella et al., Structure of the Cpf1 endonuclease R-loop complex after target DNA cleavage. Nature. Jun. 22, 2017;546(7659):559-563. doi: 10.1038/nature22398. Epub May 31, 2017.
Stenglein et al., APOBEC3 proteins mediate the clearance of foreign DNA from human cells. Nat Struct Mol Biol. Feb. 2010;17(2):222-9. doi: 10.1038/nsmb.1744. Epub Jan. 10, 2010.
Stenson et al., The Human Gene Mutation Database: towards a comprehensive repository of inherited mutation data for medical research, genetic diagnosis and next-generation sequencing studies. Hum Genet. Jun. 2017;136(6):665-677. doi: 10.1007/s00439-017-1779-6. Epub Mar. 27, 2017.
Stephens et al., The landscape of cancer genes and mutational processes in breast cancer. Nature Jun. 2012;486:400-404. doi: 10.1038/nature11017.
Sternberg et al., Conformational control of DNA target cleavage by CRISPR-Cas9. Nature. Nov. 5, 2015;527(7576):110-3. doi: 10.1038/nature15544. Epub Oct. 28, 2015.
Sternberg et al., DNA interrogation by the CRISPR RNA-guided endonuclease Cas9. Nature.Mar. 6, 2014;507(7490):62-7. doi: 10.1038/nature13011. Epub Jan. 29, 2014.
Sterne-Weiler et al., Exon identity crisis: disease-causing mutations that disrupt the splicing code. Genome Biol. Jan. 23, 2014;15(1):201. doi: 10.1186/gb4150.
Stevens et al., A promiscuous split intein with expanded protein engineering applications. Proc Natl Acad Sci U S A. Aug. 8, 2017;114(32):8538-8543. doi: 10.1073/pnas.1701083114. Epub Jul. 24, 2017.
Stevens et al., Design of a Split Intein with Exceptional Protein-Splicing Activity. J Am Chem Soc. Feb. 24, 2016;138(7):2162-5. doi: 10.1021/jacs.5b13528. Epub Feb. 8, 2016.
Stockwell et al., Probing the role of homomeric and heteromeric receptor interactions in TGF-beta signaling using small molecule dimerizers. Curr Biol. Jun. 18, 1998;8(13):761-70. doi: 10.1016/s0960-9822(98)70299-4.
Sudarsan et al., An mRNA structure in bacteria that controls gene expression by binding lysine. Genes Dev. Nov. 1, 2003;17(21):2688-97.
Sudarsan et al., Riboswitches in eubacteria sense the second messenger cyclic di-GMP. Science. Jul. 18, 2008;321(5887):411-3. doi: 10.1126/science.1159519.
Suess et al., A theophylline responsive riboswitch based on helix slipping controls gene expression in vivo. Nucleic Acids Res. Mar. 5, 2004;32(4):1610-4.
Sullenger et al., Ribozyme-mediated repair of defective mRNA by targeted, trans-splicing. Nature. Oct. 13, 1994;371(6498):619-22. doi: 10.1038/371619a0.
Sun et al., Optimized TAL effector nucleases (TALENs) for use in treatment of sickle cell disease. Mol Biosyst. Apr. 2012;8(4):1255-63. doi: 10.1039/c2mb05461b. Epub Feb. 3, 2012.
Sun et al., The CRISPR/Cas9 system for gene editing and its potential application in pain research. Transl Periop & Pain Med. Aug. 3, 2016;1(3):22-33.
Suzuki et al., In vivo genome editing via CRISPR/Cas9 mediated homology-independent targeted integration. Nature. Dec. 1, 2016;540(7631):144-149. doi: 10.1038/nature20565. Epub Nov. 16, 2016.
Suzuki et al., VCre/VloxP and SCre/SloxP: new site-specific recombination systems for genome engineering. Nucleic Acids Res. Apr. 2011;39(8):e49. doi: 10.1093/nar/gkq1280. Epub Feb. 1, 2011.
Swarts et al., Argonaute of the archaeon Pyrococcus furiosus is a DNA-guided nuclease that targets cognate DNA. Nucleic Acids Res. May 26, 2015;43(10):5120-9. doi: 10.1093/nar/gkv415. Epub Apr. 29, 2015.
Swarts et al., DNA-guided DNA interference by a prokaryotic Argonaute. Nature. Mar. 13, 2014;507(7491):258-61. doi: 10.1038/nature12971. Epub Feb. 16, 2014.

(56) References Cited

OTHER PUBLICATIONS

Swarts et al., The evolutionary journey of Argonaute proteins. Nat Struct Mol Biol. Sep. 2014;21(9):743-53. doi: 10.1038/nsmb.2879.
Szczepek et al., Structure-based redesign of the dimerization interface reduces the toxicity of zinc-finger nucleases. Nat Biotechnol. Jul. 2007;25(7):786-93. Epub Jul. 1, 2007.
Tabebordbar et al., In vivo gene editing in dystrophic mouse muscle and muscle stem cells. Science. Jan. 22, 2016;351(6271):407-411. doi: 10.1126/science.aad5177. Epub Dec. 31, 2015.
Tagalakis et al., Lack of RNA-DNA oligonucleotide (chimeraplast) mutagenic activity in mouse embryos. Mol Reprod Dev. Jun. 2005;71(2):140-4.
Tajiri et al., Functional cooperation of MutT, MutM and MutY proteins in preventing mutations caused by spontaneous oxidation of guanine nucleotide in *Escherichia coli*. Mutat Res. May 1995;336(3):257-67. doi: 10.1016/0921-8777(94)00062-b.
Takimoto et al., Stereochemical basis for engineered pyrrolysyl-tRNA synthetase and the efficient in vivo incorporation of structurally divergent non-native amino acids. ACS Chem Biol. Jul. 15, 2011;6(7):733-43. doi: 10.1021/cb200057a. Epub May 5, 2011.
Talbot et al., Spinal muscular atrophy. Semin Neurol. Jun. 2001;21(2):189-97. doi: 10.1055/s-2001-15264.
Tambunan et al., Vaccine Design for H5N1 Based on B- and T-cell Epitope Predictions. Bioinform Biol Insights. Apr. 28, 2016;10:27-35. doi: 10.4137/BBI.S38378.
Tanenbaum et al., A protein-tagging system for signal amplification in gene expression and fluorescence imaging. Cell. Oct. 23, 2014;159(3):635-46. doi: 10.1016/j.cell.2014.09.039. Epub Oct. 9, 2014.
Tanese et al., Expression of enzymatically active reverse transcriptase in *Escherichia coli*. Proc Natl Acad Sci U S A. Aug. 1985;82(15):4944-8. doi: 10.1073/pnas.82.15.4944.
Tang et al., Aptazyme-embedded guide RNAs enable ligand-responsive genome editing and transcriptional activation. Nat Commun. Jun. 28, 2017;8:15939. doi: 10.1038/ncomms15939.
Tang et al., Evaluation of Bioinformatic Programmes for the Analysis of Variants within Splice Site Consensus Regions. Adv Bioinformatics. 2016;2016:5614058. doi: 10.1155/2016/5614058. Epub May 24, 2016.
Tassabehji, Williams-Beuren syndrome: a challenge for genotype-phenotype correlations. Hum Mol Genet. Oct. 15, 2003;12 Spec No. 2:R229-37. doi: 10.1093/hmg/ddg299. Epub Sep. 2, 2003.
Taube et al., Reverse transcriptase of mouse mammary tumour virus: expression in bacteria, purification and biochemical characterization. Biochem J. Feb. 1, 1998;329 ( Pt 3)(Pt 3):579-87. doi: 10.1042/bj3290579. Erratum in: Biochem J Jun. 15, 1998;332(Pt 3):808.
Tebas et al., Gene editing of CCR5 in autologous CD4 T cells of persons infected with Hiv. N Engl J Med. Mar. 6, 2014;370(10):901-10. doi: 10.1056/NEJMoa1300662.
Tee et al., Polishing the craft of genetic diversity creation in directed evolution. Biotechnol Adv. Dec. 2013;31(8):1707-21. doi: 10.1016/j.biotechadv.2013.08.021. Epub Sep. 6, 2013.
Telenti et al., The Mycobacterium xenopi GyrA protein splicing element: characterization of a minimal intein. J Bacteriol. Oct. 1997;179(20):6378-82. doi: 10.1128/jb.179.20.6378-6382.1997.
Telesnitsky et al., RNase H domain mutations affect the interaction between Moloney murine leukemia virus reverse transcriptase and its primer-template. Proc Natl Acad Sci U S A. Feb. 15, 1993;90(4):1276-80. doi: 10.1073/pnas.90.4.1276.
Teng et al., Mutational analysis of apolipoprotein B mRNA editing enzyme (APOBEC1). structure-function relationships of RNA editing and dimerization. J Lipid Res. Apr. 1999;40(4):623-35.
Tessarollo et al., Targeted mutation in the neurotrophin-3 gene results in loss of muscle sensory neurons. Proc Natl Acad Sci U S A. Dec. 6, 1994;91(25):11844-8.
Tesson et al., Knockout rats generated by embryo microinjection of TALENs. Nat Biotechnol. Aug. 5, 2011;29(8):695-6. doi: 10.1038/nbt.1940.
Thompson et al., Cellular uptake mechanisms and endosomal trafficking of supercharged proteins. Chem Biol. Jul. 27, 2012;19(7):831-43. doi: 10.1016/j.chembiol.2012.06.014.
Thompson et al., Engineering and identifying supercharged proteins for macromolecule delivery into mammalian cells. Methods Enzymol. 2012;503:293-319. doi: 10.1016/B978-0-12-396962-0.00012-4.
Thomson et al., Mutational analysis of loxP sites for efficient Cre-mediated insertion into genomic DNA. Genesis. Jul. 2003;36(3):162-7. doi: 10.1002/gene. 10211.
Thorpe et al., Functional correction of episomal mutations with short DNA fragments and RNA-DNA oligonucleotides. J Gene Med. Mar.-Apr. 2002;4(2):195-204.
Thyagarajan et al., Creation of engineered human embryonic stem cell lines using phiC31 integrase. Stem Cells. Jan. 2008;26(1):119-26. doi: 10.1634/stemcells.2007-0283. Epub Oct. 25, 2007.
Thyagarajan et al., Mammalian genomes contain active recombinase recognition sites. Gene. Feb. 22, 2000;244(1-2):47-54.
Thyagarajan et al., Site-specific genomic integration in mammalian cells mediated by phage phiC31 integrase. Mol Cell Biol. Jun. 2001;21(12):3926-34.
Tinland et al., The T-DNA-linked VirD2 protein contains two distinct functional nuclear localization signals. Proc Natl Acad Sci U S A. Aug. 15, 1992;89(16):7442-6. doi: 10.1073/pnas.89.16.7442.
Tirumalai et al., Recognition of core-type DNA sites by lambda integrase. J Mol Biol. Jun. 12, 1998;279(3):513-27.
Tom et al., Mechanism whereby proliferating cell nuclear antigen stimulates flap endonuclease 1. J Biol Chem. Apr. 7, 2000;275(14):10498-505. doi: 10.1074/jbc.275.14.10498.
Tone et al., Single-stranded DNA binding protein Gp5 of Bacillus subtilis phage Ø29 is required for viral DNA replication in growth-temperature dependent fashion. Biosci Biotechnol Biochem. 2012;76(12):2351-3. doi: 10.1271/bbb.120587. Epub Dec. 7, 2012.
Toor et al., Crystal structure of a self-spliced group II intron. Science. Apr. 4, 2008;320(5872):77-82. doi: 10.1126/science. 1153803.
Toro et al., The Reverse Transcriptases Associated with CRISPR-Cas Systems. Sci Rep. Aug. 2, 2017;7(1):7089. doi: 10.1038/s41598-017-07828-y.
Torres et al., Non-integrative lentivirus drives high-frequency cre-mediated cassette exchange in human cells. PLoS One. 2011;6(5):e19794. doi: 10.1371/journal.pone.0019794. Epub May 23, 2011.
Tourdot et al., A general strategy to enhance immunogenicity of low-affinity HLA-A2. 1-associated peptides: implication in the identification of cryptic tumor epitopes. Eur J Immunol. Dec. 2000;30(12):3411-21.
Townsend et al., Role of HFE in iron metabolism, hereditary haemochromatosis, anaemia of chronic disease, and secondary iron overload. Lancet. Mar. 2, 2002;359(9308):786-90. doi: 10.1016/S0140-6736(02)07885-6.
Tracewell et al., Directed enzyme evolution: climbing fitness peaks one amino acid at a time. Curr Opin Chem Biol. Feb. 2009;13(1):3-9. doi: 10.1016/j.cbpa.2009.01.017. Epub Feb. 25, 2009.
Tratschin et al., A human parvovirus, adeno-associated virus, as a eucaryotic vector: transient expression and encapsidation of the procaryotic gene for chloramphenicol acetyltransferase. Mol Cell Biol. Oct. 1984;4(10):2072-81. doi: 10.1128/mcb.4.10.2072.
Tratschin et al., Adeno-associated virus vector for high-frequency integration, expression, and rescue of genes in mammalian cells. Mol Cell Biol. Nov. 1985;5(11):3251-60. doi: 10.1128/mcb.5.11.3251.
Trausch et al., The structure of a tetrahydrofolate-sensing riboswitch reveals two ligand binding sites in a single aptamer. Structure. Oct. 12, 2011;19(10):1413-23. doi: 10.1016/j.str.2011.06.019. Epub Sep. 8, 2011.
Traxler et al., A genome-editing strategy to treat β-hemoglobinopathies that recapitulates a mutation associated with a benign genetic condition. Nat Med. Sep. 2016;22(9):987-90. doi: 10.1038/nm.4170. Epub Aug. 15, 2016.
Trojan et al., Functional analysis of hMLH1 variants and HNPCC-related mutations using a human expression system. Gastroenterology. Jan. 2002;122(1):211-9. doi: 10.1053/gast.2002.30296.

(56) References Cited

OTHER PUBLICATIONS

Trouet et al., A covalent linkage between daunorubicin and proteins that is stable in serum and reversible by lysosomal hydrolases, as required for a lysosomotropic drug-carrier conjugate: in vitro and in vivo studies.
Trudeau et al., On the Potential Origins of the High Stability of Reconstructed Ancestral Proteins. Mol Biol Evol. Oct. 2016;33(10):2633-41. doi: 10.1093/molbev/msw138. Epub Jul. 12, 2016.
Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015. With Supplementary Data.
Tsai et al., CIRCLE-seq: a highly sensitive in vitro screen for genome-wide CRISPR-Cas9 nuclease off-targets. Nat Methods. Jun. 2017; 14(6):607-614. doi: 10.1038/nmeth.4278. Epub May 1, 2017.
Tsai et al., Dimeric CRISPR RNA-guided FokI nucleases for highly specific genome editing. Nat Biotechnol. Jun. 2014;32(6):569-76. doi: 10.1038/nbt.2908. Epub Apr. 25, 2014.
Tsai et al., GUIDE-seq enables genome-wide profiling of off-target cleavage by CRISPR-Cas nucleases. Nat Biotechnol. Feb. 2015;33(2):187-97. doi: 10.1038/nbt.3117. Epub Dec. 16, 2014.
Tsang et al., Specialization of the DNA-cleaving activity of a group I ribozyme through in vitro evolution. J Mol Biol. Sep. 13, 1996;262(1):31-42. doi: 10.1006/jmbi.1996.0496.
Tsutakawa et al., Human flap endonuclease structures, DNA double-base flipping, and a unified understanding of the FEN1 superfamily. Cell. Apr. 15, 2011;145(2): 198-211. doi: 10.1016/j.cell.2011.03.004.
Turan et al., Recombinase-mediated cassette exchange (RMCE)—a rapidly-expanding toolbox for targeted genomic modifications. Gene. Feb. 15, 2013;515(1):1-27. doi: 10.1016/j.gene.2012.11.016. Epub Nov. 29, 2012.
Turan et al., Recombinase-mediated cassette exchange (RMCE): traditional concepts and current challenges. J Mol Biol. Mar. 25, 2011;407(2):193-221. doi: 10.1016/j.jmb.2011.01.004. Epub Jan. 15, 2011.
Turan et al., Site-specific recombinases: from tag-and-target- to tag-and-exchange-based genomic modifications. FASEB J. Dec. 2011;25(12):4088-107. doi: 10.1096/fj.11-186940. Epub Sep. 2, 2011. Review.
Tyszkiewicz et al., Activation of protein splicing with light in yeast. Nat Methods. Apr. 2008;5(4):303-5. doi: 10.1038/nmeth.1189. Epub Feb. 13, 2008.
UniProt Submission; UniProt, Accession No. P01011. Last modified Jun. 11, 2014, version 2. 15 pages.
UniProt Submission; UniProt, Accession No. P01011. Last modified Sep. 18, 2013, version 2. 15 pages.
UniProt Submission; UniProt, Accession No. P04264. Last modified Jun. 11, 2014, version 6. 15 pages.
UniProt Submission; UniProt, Accession No. P04275. Last modified Jul. 9, 2014, version 107. 29 pages.
UniProtKB Submission; Accession No. F0NH53. May 3, 2011. 4 pages.
UniProtKB Submission; Accession No. F0NN87. May 3, 2011. 4 pages.
UniProtKB Submission; Accession No. P0DOC6. No Author Listed., Oct. 5, 2016. 5 pages.
UniProtKB Submission; Accession No. T0D7A2. Oct. 16, 2013. 10 pages.
Urasaki et al., Functional dissection of the Tol2 transposable element identified the minimal cis-sequence and a highly repetitive sequence in the subterminal region essential for transposition. Genetics. Oct. 2006;174(2):639-49. doi: 10.1534/genetics.106.060244. Epub Sep. 7, 2006.
Urnov et al., Genome editing with engineered zinc finger nucleases. Nat Rev Genet. Sep. 2010;11(9):636-46. doi: 10.1038/nrg2842.
Urnov et al., Highly efficient endogenous human gene correction using designed zinc-finger nucleases. Nature. Jun. 2, 2005;435(7042):646-51. Epub Apr. 3, 2005.
Urrutia, KRAB-containing zinc-finger repressor proteins. Genome Biol. 2003;4(10):231. Epub Sep. 23, 2003.
Usman et al., Exploiting the chemical synthesis of RNA. Trends Biochem Sci. Sep. 1992;17(9):334-9. doi: 10.1016/0968-0004(92)90306-t.
Vagner et al., Efficiency of homologous DNA recombination varies along the Bacillus subtilis chromosome. J Bacteriol. Sep. 1988;170(9):3978-82.
Van Brunt et al., Genetically Encoded Azide Containing Amino Acid in Mammalian Cells Enables Site-Specific Antibody-Drug Conjugates Using Click Cycloaddition Chemistry. Bioconjug Chem. Nov. 18, 2015;26(11):2249-60. doi: 10.1021/acs.bioconjchem.5b00359. Epub Sep. 11, 2015.
Van Brunt et al., Molecular Farming: Transgenic Animals as Bioreactors. Biotechnology (NY). 1988;6(10):1149-1154. doi: 10.1038/nbt1088-1149.
Van Den Oord et al., Pixel Recurrent Neural Networks. Proceedings of the 33rd International Conference on Machine Learning. Journal of Machine Learning Research. Aug. 19, 2016. vol. 48. 11 pages.
Van Duyne et al., Teaching Cre to follow directions. Proc Natl Acad Sci U S A. Jan. 6, 2009;106(1):4-5. doi: 10.1073/pnas.0811624106. Epub Dec. 31, 2008.
Van Overbeek et al., DNA Repair Profiling Reveals Nonrandom Outcomes at Cas9- Mediated Breaks. Mol Cell. Aug. 18, 2016;63(4):633-646. doi: 10.1016/j.molcel.2016.06.037. Epub Aug. 4, 2016.
Van Swieten et al., A mutation in the fibroblast growth factor 14 gene is associated with autosomal dominant cerebellar ataxia [corrected]. Am J Hum Genet. Jan. 2003;72(1):191-9. Epub Dec. 13, 2002.
Van Wijk et al., Identification of 51 novel exons of the Usher syndrome type 2A (USH2A) gene that encode multiple conserved functional domains and that are mutated in patients with Usher syndrome type II. Am J Hum Genet. Apr. 2004;74(4):738-44. doi: 10.1086/383096. Epub Mar. 10, 2004.
Vanamee et al., FokI requires two specific DNA sites for cleavage. J Mol Biol. May 25, 2001;309(1):69-78.
Varga et al., Progressive vascular smooth muscle cell defects in a mouse model of Hutchinson-Gilford progeria syndrome. Proc Natl Acad Sci U S A. Feb. 28, 2006;103(9):3250-5. doi: 10.1073/pnas.0600012103. Epub Feb. 21, 2006.
Vasey et al., Phase I clinical and pharmacokinetic study of PK1 [N-(2-hydroxypropyl)methacrylamide copolymer doxorubicin]: first member of a new class of chemotherapeutic agents-drug-polymer conjugates. Cancer Research Campaign Phase I/II Committee.
Vellore et al., A group II intron-type open reading frame from the thermophile Bacillus (Geobacillus) stearothermophilus encodes a heat-stable reverse transcriptase. Appl Environ Microbiol. Dec. 2004;70(12):7140-7. doi: 10.1128/AEM.70.12.7140-7147.2004.
Venken et al., Genome-wide manipulations of *Drosophila melanogaster* with transposons, Flp recombinase, and ?C31 integrase. Methods Mol Biol. 2012;859:203-28. doi: 10.1007/978-1- 61779-603-6_12.
Verma, The reverse transcriptase. Biochim Biophys Acta. Mar. 21, 1977;473(1):1-38. doi: 10.1016/0304-419x(77)90005-1.
Vidal et al., Yeast forward and reverse 'n'-hybrid systems. Nucleic Acids Res. Feb. 15, 1999;27(4):919-29. doi: 10.1093/nar/27.4.919.
Vigne et al., Third-generation adenovectors for gene therapy. Restor Neurol Neurosci. Jan. 1, 1995;8(1):35-6. doi: 10.3233/RNN-1995-81208.
Vik et al., Endonuclease V cleaves at inosines in RNA. Nat Commun. 2013;4:2271. doi: 10.1038/ncomms3271.
Vilenchik et al., Endogenous DNA double-strand breaks: production, fidelity of repair, and induction of cancer. Proc Natl Acad Sci U S A. Oct. 28, 2003;100(22):12871-6. doi: 10.1073/pnas.2135498100. Epub Oct. 17, 2003.
Vitreschak et al., Regulation of the vitamin B12 metabolism and transport in bacteria by a conserved RNA structural element. RNA. Sep. 2003;9(9):1084-97.
Voigt et al., Rational evolutionary design: the theory of in vitro protein evolution. Adv Protein Chem. 2000;55:79-160.

(56) References Cited

OTHER PUBLICATIONS

Vriend et al., Nick-initiated homologous recombination: Protecting the genome, one strand at a time. DNA Repair (Amst). Feb. 2017;50:1-13. doi: 10.1016/j.dnarep.2016.12.005. Epub Dec. 29, 2016.
Wacey et al., Disentangling the perturbational effects of amino acid substitutions in the DNA-binding domain of p53. Hum Genet. Jan. 1999;104(1):15-22.
Wadia et al., Modulation of cellular function by TAT mediated transduction of full length proteins. Curr Protein Pept Sci. Apr. 2003;4(2):97-104.
Wadia et al., Transducible TAT-HA fusogenic peptide enhances escape of TAT-fusion proteins after lipid raft macropinocytosis. Nat Med. Mar. 2004;10(3):310-5. Epub Feb. 8, 2004.
Wah et al., Structure of FokI has implications for DNA cleavage. Proc Natl Acad Sci U S A. Sep. 1, 1998;95(18):10564-9.
Wals et al., Unnatural amino acid incorporation in *E. coli*: current and future applications in the design of therapeutic proteins. Front Chem. Apr. 1, 2014;2:15. doi: 10.3389/fchem.2014.00015. eCollection 2014.
Wang et al. CRISPR-Cas9 and CRISPR-Assisted Cytidine Deaminase Enable Precise and Efficient Genome Editing in Klebsiella pneumoniae. Appl Environ Microbiol. 2018;84(23):e01834-18. Published Nov. 15, 2018. doi:10.1128/AEM.01834-18.
Wang et al., AID upmutants isolated using a high-throughput screen highlight the immunity/cancer balance limiting DNA deaminase activity. Nat Struct Mol Biol. Jul. 2009;16(7):769-76. doi: 10.1038/nsmb.1623. Epub Jun. 21, 2009.
Wang et al., CRISPR-Cas9 Targeting of PCSK9 in Human Hepatocytes In Vivo-Brief Report. Arterioscler Thromb Vasc Biol. May 2016;36(5):783-6. doi: 10.1161/ATVBAHA.116.307227. Epub Mar. 3, 2016.
Wang et al., Efficient delivery of genome-editing proteins using bioreducible lipid nanoparticles. Proc Natl Acad Sci U S A. Feb. 29, 2016. pii: 201520244. [Epub ahead of print].
Wang et al., Enhanced base editing by co-expression of free uracil DNA glycosylase inhibitor. Cell Res. Oct. 2017;27(1):1289-92. doi: 10.1038/cr.2017.111. Epub Aug. 29, 2017.
Wang et al., Evolution of new nonantibody proteins via iterative somatic hypermutation. Proc Natl Acad Sci U S A. Nov. 30, 2004;101(48):16745-9. Epub Nov. 19, 2004.
Wang et al., Expanding the genetic code. Annu Rev Biophys Biomol Struct. 2006;35:225-49. Review.
Wang et al., Genetic screens in human cells using the CRISPR-Cas9 system. Science. Jan. 3, 2014;343(6166):80-4. doi: 10.1126/science.1246981. Epub Dec. 12, 2013.
Wang et al., Highly efficient CRISPR/HDR-mediated knock-in for mouse embryonic stem cells and zygotes. Biotechniques. 2015:59,201-2;204;206-8.
Wang et al., N(6)-methyladenosine Modulates Messenger RNA Translation Efficiency. Cell. Jun. 4, 2015;161(6):1388-99. doi: 10.1016/j.cell.2015.05.014.
Wang et al., N6-methyladenosine-dependent regulation of messenger RNA stability. Nature. Jan. 2, 2014;505(7481):117-20. doi: 10.1038/nature12730. Epub Nov. 27, 2013.
Wang et al., Neutralizing antibodies to therapeutic enzymes: considerations for testing, prevention and treatment. Nat Biotechnol. Aug. 2008;26(8):901-8. doi: 10.1038/nbt.1484.
Wang et al., Nucleation, propagation and cleavage of target RNAs in Ago silencing complexes. Nature. Oct. 8, 2009;461(7265):754-61. doi: 10.1038/nature08434.
Wang et al., One-step generation of mice carrying mutations in multiple genes by CRISPR/Cas-mediated genome engineering. Cell. May 9, 2013;153(4):910-8. doi: 10.1016/j.cell.2013.04.025. Epub May 2, 2013.
Wang et al., Programming cells by multiplex genome engineering and accelerated evolution. Nature. Aug. 13, 2009;460(7257):894-8. Epub Jul. 26, 2009.
Wang et al., Reading RNA methylation codes through methyl-specific binding proteins. RNA Biol. 2014;11(6):669-72. doi: 10.4161/rna.28829. Epub Apr. 24, 2014.
Wang et al., Recombinase technology: applications and possibilities. Plant Cell Rep. Mar. 2011;30(3):267-85. doi: 10.1007/s00299-010-0938-1. Epub Oct. 24, 2010.
Wang et al., Riboswitches that sense S-adenosylhomocysteine and activate genes involved in coenzyme recycling. Mol Cell. Mar. 25, 2008;29(6):691-702. doi: 10.1016/j.molcel.2008.01.012.
Wang et al., *Staphylococcus aureus* protein SAUGI acts as a uracil-DNA glycosylase inhibitor. Nucleic Acids Res. Jan. 2014;42(2):1354-64. doi: 10.1093/nar/gkt964. Epub Oct. 22, 2013.
Wang et al., Structural basis of N(6)-adenosine methylation by the METTL3-METTL14 complex. Nature. Jun. 23, 2016;534(7608):575-8. doi: 10.1038/nature18298. Epub May 25, 2016.
Wang et al., Targeted gene addition to a predetermined site in the human genome using a ZFN-based nicking enzyme. Genome Res. Jul. 2012;22(7):1316-26. doi: 10.1101/gr.122879.111. Epub Mar. 20, 2012.
Wang et al., Uracil-DNA glycosylase inhibitor gene of bacteriophage PBS2 encodes a binding protein specific for uracil-DNA glycosylase. J Biol Chem. Jan. 15, 1989;264(2):1163-71.
Warren et al., A chimeric Cre recombinase with regulated directionality. Proc Natl Acad Sci USA. Nov. 25, 2008;105(47):18278-83. doi: 10.1073/pnas.0809949105. Epub Nov. 14, 2008.
Warren et al., Mutations in the amino-terminal domain of lambda-integrase have differential effects on integrative and excisive recombination. Mol Microbiol. Feb. 2005;55(4):1104-12.
Watowich, The erythropoietin receptor: molecular structure and hematopoietic signaling pathways. J Investig Med. Oct. 2011;59(7):1067-72. doi: 10.2310/JIM.0b013e31820fb28c.
Waxman et al., Regulating excitability of peripheral afferents: emerging ion channel targets. Nat Neurosci. Feb. 2014;17(2):153-63. doi: 10.1038/nn.3602. Epub Jan. 28, 2014.
Weber et al., Assembly of designer TAL effectors by Golden Gate cloning. PLoS One. 2011;6(5):e19722. doi: 10.1371/journal.pone.0019722. Epub May 19, 2011.
Weill et al., DNA polymerases in adaptive immunity. Nat Rev Immunol. Apr. 2008;8(4):302-12. doi: 10.1038/nri2281. Epub Mar. 14, 2008.
Weinberg et al., New Classes of Self-Cleaving Ribozymes Revealed by Comparative Genomics Analysis. Nat Chem Biol. Aug. 2015;11(8):606-10. doi: 10.1038/nchembio.1846. Epub Jul. 13, 2015.
Weinberg et al., The aptamer core of SAM-IV riboswitches mimics the ligand-binding site of SAM-I riboswitches. RNA. May 2008;14(5):822-8. doi: 10.1261/rna.988608. Epub Mar. 27, 2008.
Weinberger et al., Disease-causing mutations C277R and C277Y modify gating of human CIC-1 chloride channels in myotonia congenita. J Physiol. Aug. 1, 2012;590(Pt 15):3449-64. doi: 0.1113/jphysiol.2012.232785. Epub May 28, 2012.
Weiss et al., Loss-of-function mutations in sodium channel Nav1.7 cause anosmia. Nature. Apr. 14, 2011;472(7342):186-90. doi: 10.1038/nature09975. Epub Mar. 23, 2011.
Wen et al., Inclusion of a universal tetanus toxoid CD4(+) T cell epitope P2 significantly enhanced the immunogenicity of recombinant rotavirus AVP8* subunit parenteral vaccines. Vaccine. Jul. 31, 2014;32(35):4420-4427. doi: 10.1016/j.vaccine.2014.06.060. Epub Jun. 21, 2014.
West et al., Gene expression in adeno-associated virus vectors: the effects of chimeric mRNA structure, helper virus, and adenovirus VA1 RNA. Virology. Sep. 1987;160(1):38-47. doi: 10.1016/0042-6822(87)90041-9.
Wharton et al., A new-specificity mutant of 434 repressor that defines an amino acid-base pair contact. Nature. Apr. 30-May 6, 1987;326(6116):888-91.
Wharton et al., Changing the binding specificity of a repressor by redesigning an alpha-helix. Nature. Aug. 15-21, 1985;316(6029):601-5.
Wheeler et al., The thermostability and specificity of ancient proteins. Curr Opin Struct Biol. Jun. 2016;38:37-43. doi: 10.1016/j.sbi.2016.05.015. Epub Jun. 9, 2016.

(56) References Cited

OTHER PUBLICATIONS

Wiedenheft et al., RNA-guided genetic silencing systems in bacteria and archaea. Nature. Feb. 15, 2012;482(7385):331-8. doi: 10.1038/nature10886. Review.
Wienert et al., KLF1 drives the expression of fetal hemoglobin in British HPFH. Blood. Aug. 10, 2017;130(6):803-807. doi: 10.1182/blood-2017-02-767400. Epub Jun. 28, 2017.
Wijesinghe et al., Efficient deamination of 5-methylcytosines in DNA by human APOBEC3A, but not by AID or APOBEC3G. Nucleic Acids Res. Oct. 2012;40(18):9206-17. doi: 10.1093/nar/gks685. Epub Jul. 13, 2012.
Wijnker et al., Managing meiotic recombination in plant breeding. Trends Plant Sci. Dec. 2008; 13(12):640-6. doi: 10.1016/j.tplants.2008.09.004. Epub Oct. 22, 2008.
Williams et al., Assessing the accuracy of ancestral protein reconstruction methods. PLoS Comput Biol. Jun. 23, 2006;2(6):e69. doi: 10.1371/journal.pcbi.0020069. Epub Jun. 23, 2006.
Wills et al., Pseudoknot-dependent read-through of retroviral gag termination codons: importance of sequences in the spacer and loop 2. EMBO J. Sep. 1, 1994;13(17):4137-44. doi: 10.1002/j.1460-2075.1994.tb06731.x.
Wilson et al., Assessing annotation transfer for genomics: quantifying the relations between protein sequence, structure and function through traditional and probabilistic scores. J Mol Biol 2000;297:233-49.
Wilson et al., Formation of infectious hybrid virions with gibbon ape leukemia virus and human T-cell leukemia virus retroviral envelope glycoproteins and the gag and pol proteins of Moloney murine leukemia virus. J Virol. May 1989;63(5):2374-8. doi: 10.1128/JVI.63.5.2374-2378.1989.
Wilson et al., In Vitro Selection of Functional Nucleic Acids. Annu Rev Biochem. 1999;68:611-47. doi: 10.1146/annurev.biochem.68.1.611.
Wilson et al., Kinase dynamics. Using ancient protein kinases to unravel a modern cancer drug's mechanism. Science. Feb. 20, 2015;347(6224):882-6. doi: 10.1126/science.aaa1823.
Winkler et al., An mRNA structure that controls gene expression by binding FMN. Proc Natl Acad Sci U S A. Dec. 10, 2002;99(25):15908-13. Epub Nov. 27, 2002.
Winkler et al., An mRNA structure that controls gene expression by binding S-adenosylmethionine. Nat Struct Biol.Sep. 2003;10(9):701-7. Epub Aug. 10, 2003.
Winkler et al., Control of gene expression by a natural metabolite-responsive ribozyme. Nature. Mar. 18, 2004;428(6980):281-6.
Winkler et al., Thiamine derivatives bind messenger RNAs directly to regulate bacterial gene expression. Nature. Oct. 31, 2002;419(6910):952-6. Epub Oct. 16, 2002.
Winoto et al., A novel, inducible and T cell-specific enhancer located at the 3' end of the T cell receptor alpha locus. Embo J. Mar. 1989;8(3):729-33.
Winter et al., Drug Development. Phthalimide conjugation as a strategy for in vivo target protein degradation. Science. Jun. 19, 2015;348(6241):1376-81. doi:; 10.1126/science.aab1433. Epub May 21, 2015.
Wirth et al., Mildly affected patients with spinal muscular atrophy are partially protected by an increased SMN2 copy number Hum Genet. May 2006;119(4):422-8. doi: 10.1007/s00439-006-0156-7. Epub Mar. 1, 2006.
Wold, Replication protein A: a heterotrimeric, single-stranded DNA-binding protein required for eukaryotic DNA metabolism. Annu Rev Biochem. 1997;66:61-92. doi: 10.1146/annurev.biochem.66.1.61.
Wolf et al., tadA, an essential tRNA-specific adenosine deaminase from *Escherichia coli*. EMBO J. Jul. 15, 2002;21(14):3841-51.
Wolfe et al., Analysis of zinc fingers optimized via phage display: evaluating the utility of a recognition code. J Mol Biol. Feb. 5, 1999;285(5):1917-34.
Wong et al., A statistical analysis of random mutagenesis methods used for directed protein evolution. J Mol Biol. Jan. 27, 2006;355(4):858-71. Epub Nov. 17, 2005.
Wong et al., The Diversity Challenge in Directed Protein Evolution. Comb Chem High Throughput Screen. May 2006;9(4):271-88.
Woo et al., Gene activation of SMN by selective disruption of IncRNA-mediated recruitment of PRC2 for the treatment of spinal muscular atrophy. Proc Natl Acad Sci U S A. Feb. 21, 2017;114(8):E1509-E1518. doi:10.1073/pnas.1616521114. Epub Feb. 13, 2017.
Wood et al., A genetic system yields self-cleaving inteins for bioseparations. Nat Biotechnol. Sep. 1999;17(9):889-92. doi: 10.1038/12879.
Wood et al., Targeted genome editing across species using ZFNs and TALENs. Science. Jul. 15, 2011;333(6040):307. doi: 10.1126/science.1207773. Epub Jun. 23, 2011.
Woods et al., The phenotype of congenital insensitivity to pain due to the NaV1.9 variant p.L811P. Eur J Hum Genet. May 2015;23(5):561-3. doi: 10.1038/ejhg.2014.166. Epub Aug. 13, 2014.
Wright et al., Continuous in vitro evolution of catalytic function. Science. Apr. 25, 1997;276(5312):614-7.
Wright et al., Rational design of a split-Cas9 enzyme complex. Proc Natl Acad Sci U S A. Mar. 10, 2015;112(10):2984-9. doi: 10.1073/pnas. 1501698112. Epub Feb. 23, 2015.
Wu et al., A novel SCN9A mutation responsible for primary erythromelalgia and is resistant to the treatment of sodium channel blockers. PLoS One. 2013;8(1):e55212. doi: 10.1371/journal.pone.0055212. Epub Jan. 31, 2013. 15 pages.
Wu et al., Correction of a genetic disease in mouse via use of CRISPR-Cas9. Cell Stem Cell. Dec. 5, 2013;13(6):659-62. doi: 10.1016/j.stem.2013.10.016.
Wu et al., Genome-wide binding of the CRISPR endonuclease Cas9 in mammalian cells. Nat Biotechnol. Jul. 2014;32(7):670-6. doi: 10.1038/nbt.2889. Epub Apr. 20, 2014.
Wu et al., Human single-stranded DNA binding proteins: guardians of genome stability. Acta Biochim Biophys Sin (Shanghai). Jul. 2016;48(7):671-7. doi: 10.1093/abbs/gmw044. Epub May 23, 2016.
Wu et al., Protein trans-splicing and functional mini-inteins of a cyanobacterial dnaB intein. Biochim Biophys Acta. Sep. 8, 1998;1387(1-2):422-32. doi: 10.1016/s0167-4838(98)00157-5.
Wu et al., Protein trans-splicing by a split intein encoded in a split DnaE gene of *Synechocystis* sp. PCC6803. Proc Natl Acad Sci U S A. Aug. 4, 1998;95(16):9226-31. doi: 10.1073/pnas.95.16.9226.
Wu et al., Readers, writers and erasers of N6-methylated adenosine modification. Curr Opin Struct Biol. Dec. 2017;47:67-76. doi: 10.1016/j.sbi.2017.05.011. Epub Jun. 16, 2017.
Xiang et al., RNA m6A methylation regulates the ultraviolet-induced DNA damage response. Nature. Mar. 23, 2017;543(7646):573-576. doi: 10.1038/nature21671. Epub Mar. 15, 2017.
Xiao et al., Genetic incorporation of multiple unnatural amino acids into proteins in mammalian cells. Angew Chem Int Ed Engl. Dec. 23, 2013;52(52):14080-3. doi: 10.1002/anie.201308137. Epub Nov. 8, 2013.
Xiao et al., Nuclear m(6)A Reader YTHDC1 Regulates mRNA Splicing. Mol Cell. Feb. 18, 2016;61(4):507-519. doi: 10.1016/j.molcel.2016.01.012. Epub Feb. 11, 2016.
Xie et al., Adjusting the attB site in donor plasmid improves the efficiency of ΦC31 integrase system. DNA Cell Biol. Jul. 2012;31(7):1335-40. doi: 10.1089/dna.2011.1590. Epub Apr. 10, 2012.
Xiong et al., Origin and evolution of retroelements based upon their reverse transcriptase sequences. EMBO J. Oct. 1990;9(10):3353-62.
Xu et al., Accuracy and efficiency define Bxb1 integrase as the best of fifteen candidate serine recombinases for the integration of DNA into the human genome. BMC Biotechnol. Oct. 20, 2013;13:87. doi: 10.1186/1472-6750-13-87.
Xu et al., Chemical ligation of folded recombinant proteins: segmental isotopic labeling of domains for NMR studies. Proc Natl Acad Sci U S A. Jan. 19, 1999;96(2):388-93. doi: 10.1073/pnas.96.2.388.
Xu et al., Protein splicing: an analysis of the branched intermediate and its resolution by succinimide formation. EMBO J. Dec. 1, 1994;13(23):5517-22.
Xu et al., Sequence determinants of improved CRISPR sgRNA design. Genome Res. Aug. 2015;25(8): 1147-57. doi: 10.1101/gr.191452.115. Epub Jun. 10, 2015.

(56) References Cited

OTHER PUBLICATIONS

Xu et al., Structures of human ALKBH5 demethylase reveal a unique binding mode for specific single-stranded N6-methyladenosine RNA demethylation. J Biol Chem. Jun. 20, 2014;289(25):17299-311. doi: 10.1074/jbc.M114.550350. Epub Apr. 28, 2014.

Xu et al., The mechanism of protein splicing and its modulation by mutation. EMBO J. Oct. 1, 1996;15(19):5146-53.

Yahata et al., Unified, Efficient, and Scalable Synthesis of Halichondrins: Zirconium/Nickel-Mediated One-Pot Ketone Synthesis as the Final Coupling Reaction. Angew Chem Int Ed Engl. Aug. 28, 2017;56(36):10796-10800. doi: 10.1002/anie.201705523. Epub Jul. 28, 2017.

Yamada et al., Crystal Structure of the Minimal Cas9 from Campylobacter jejuni Reveals the Molecular Diversity in the CRISPR-Cas9 Systems. Mol Cell. Mar. 16, 2017;65(6):P1109-1121. /doi.org/10.1016/j.molcel.2017.02.007.

Yamamoto et al., The ons and offs of inducible transgenic technology: a review. Neurobiol Dis. Dec. 2001;8(6):923-32.

Yamamoto et al., Virological and immunological bases for HIV-1 vaccine design. Uirusu 2007;57(2):133-139. https://doi.org/10.2222/jsv.57.133.

Yamane et al., Deep-sequencing identification of the genomic targets of the cytidine deaminase AID and its cofactor RPA in B lymphocytes. Nat Immunol. Jan. 2011;12(1):62-9. doi: 10.1038/ni.1964. Epub Nov. 28, 2010.

Yamano et al., Crystal Structure of Cpf1 in Complex with Guide RNA and Target DNA. Cell. May 5, 2016;165(4):949-62 and Supplemental Info. doi: 10.1016/j.cell.2016.04.003. Epub Apr. 21, 2016.

Yamano et al., Crystal Structure of Cpf1 in Complex with Guide RNA and Target DNA. Cell. May 5, 2016;165(4):949-62. doi: 10.1016/j.cell.2016.04.003. Epub Apr. 21, 2016.

Yamazaki et al., Segmental Isotope Labeling for Protein NMR Using Peptide Splicing. J. Am. Chem. Soc. May 22, 1998; 120(22):5591-2. https://doi.org/10.1021/ja9807760.

Yang et al., APOBEC: From mutator to editor. J Genet Genomics. Sep. 20, 2017;44(9):423-437. doi: 10.1016/j.jgg.2017.04.009. Epub Aug. 7, 2017.

Yang et al., BRCA2 function in DNA binding and recombination from a BRCA2-DSS1- ssDNA structure. Science. Sep. 13, 2002;297(5588):1837-48. doi: 10.1126/science.297.5588.1837.

Yang et al., Construction of an integration-proficient vector based on the site-specific recombination mechanism of enterococcal temperate phage phiFC1. J Bacteriol. Apr. 2002; 184(7):1859-64. doi: 10.1128/jb.184.7.1859-1864.2002.

Yang et al., Engineering and optimising deaminase fusions for genome editing. Nat Commun. Nov. 2, 2016;7:13330. doi: 10.1038/ncomms13330.

Yang et al., Genome editing with targeted deaminases. BioRxiv. Preprint. First posted online Jul. 28, 2016.

Yang et al., Genome-wide inactivation of porcine endogenous retroviruses (PERVs). Science. Nov. 27, 2015;350(6264):1101-4. doi: 10.1126/science.aad1191. Epub Oct. 11, 2015.

Yang et al., Mutations in SCN9A, encoding a sodium channel alpha subunit, in patients with primary erythermalgia. J Med Genet. Mar. 2004;41(3):171-4. doi: 10.1136/jmg.2003.012153.

Yang et al., New CRISPR-Cas systems discovered. Cell Res. Mar. 2017;27(3):313-314. doi: 10.1038/cr.2017.21. Epub Feb. 21, 2017.

Yang et al., One-step generation of mice carrying reporter and conditional alleles by CRISPR/Cas-mediated genome engineering. Cell. Sep. 12, 2013;154(6):1370-9. doi: 10.1016/j.cell.2013.08.022. Epub Aug. 29, 2013.

Yang et al., PAM-dependent Target DNA Recognition and Cleavage by C2C1 CRISPR-Cas endonuclease. Cell Dec. 2016;167(7):1814-28.

Yang et al., Permanent genetic memory with >1-byte capacity. Nat Methods. Dec. 2014;11(12):1261-6. doi: 10.1038/nmeth.3147. Epub Oct. 26, 2014.

Yang et al., Preparation of RNA-directed DNA polymerase from spleens of Balb-c mice infected with Rauscher leukemia virus. Biochem Biophys Res Commun. Apr. 28, 1972;47(2):505-11. doi: 10.1016/0006-291x(72)90743-7.

Yang et al., Small-molecule control of insulin and PDGF receptor signaling and the role of membrane attachment. Curr Biol. Jan. 1, 1998;8(1):11-8. doi: 10.1016/s0960-9822(98)70015-6.

Yang et al., The BRCA2 homologue Brh2 nucleates RAD51 filament formation at a dsDNA-ssDNA junction. Nature. Feb. 10, 2005;433(7026):653-7. doi: 10.1038/nature03234.

Yang, Development of Human Genome Editing Tools for the Study of Genetic Variations and Gene Therapies. Doctoral Dissertation. Harvard University. 2013. Accessible via nrs.harvard.edu/urn-3:HUL.InstRepos: 11181072. 277 pages.

Yang, Nucleases: diversity of structure, function and mechanism. Q Rev Biophys. Feb. 2011;44(1):1-93. doi: 10.1017/S0033583510000181. Epub Sep. 21, 2010.

Yang, Paml 4: phylogenetic analysis by maximum likelihood. Mol Biol Evol. Aug. 2007;24(8): 1586-91. doi: 10.1093/molbev/msm088. Epub May 4, 2007.

Yanover et al., Extensive protein and DNA backbone sampling improves structure-based specificity prediction for C2H2 zinc fingers. Nucleic Acids Res. Jun. 2011;39(11):4564-76. doi: 10.1093/nar/gkr048. Epub Feb. 22, 2011.

Yasui et al., Miscoding Properties of 2'-Deoxyinosine, a Nitric Oxide-Derived DNA Adduct, during Translesion Synthesis Catalyzed by Human DNA Polymerases. J Molec Biol. Apr. 4, 2008;377(4):1015-23.

Yasui, Alternative excision repair pathways. Cold Spring Harb Perspect Biol. Jun. 1, 2013;5(6):a012617. doi: 10.1101/cshperspect.a012617.

Yasukawa et al., Characterization of Moloney murine leukaemia virus/avian myeloblastosis virus chimeric reverse transcriptases. J Biochem. Mar. 2009;145(3):315-24. doi: 10.1093/jb/mvn166. Epub Dec. 6, 2008.

Yazaki et al., Hereditary systemic amyloidosis associated with a new apolipoprotein AII stop codon mutation Stop78Arg. Kidney Int. Jul. 2003;64(1):11-6.

Yin et al., Genome editing with Cas9 in adult mice corrects a disease mutation and phenotype. Nat Biotechnol. Jun. 2014;32(6):551-3. doi: 10.1038/nbt.2884. Epub Mar. 30, 2014.

Yokoe et al., Spatial dynamics of GFP-tagged proteins investigated by local fluorescence enhancement. Nat Biotechnol. Oct. 1996; 14(10):1252-6. doi: 10.1038/nbt1096-1252.

Young et al., Beyond the canonical 20 amino acids: expanding the genetic lexicon. J Biol Chem. Apr. 9, 2010;285(15):11039-44. doi: 10.1074/jbc.R109.091306. Epub Feb. 10, 2010.

Yu et al., Circular permutation: a different way to engineer enzyme structure and function. Trends Biotechnol. Jan. 2011;29(1):18-25. doi: 10.1016/j.tibtech.2010.10.004. Epub Nov. 17, 2010.

Yu et al., Dynamic control of Rad51 recombinase by self-association and interaction with BRCA2. Mol Cell. Oct. 2003;12(4):1029-41. doi: 10.1016/s1097-2765(03)00394-0.

Yu et al., Liposome-mediated in vivo ELA gene transfer suppressed dissemination of ovarian cancer cells that overexpress HER-2/neu. Oncogene. Oct. 5, 1995;11(7):1383-8.

Yu et al., Progress towards gene therapy for HIV infection. Gene Ther. Jan. 1994;1(1):13-26.

Yu et al., Small molecules enhance CRISPR genome editing in pluripotent stem cells. Cell Stem Cell. Feb. 5, 2015;16(2):142-7. doi: 10.1016/j.stem.2015.01.003.

Yu et al., Synthesis-dependent microhomology-mediated end joining accounts for multiple types of repair junctions. Nucleic Acids Res. Sep. 2010;38(17):5706-17. doi: 10.1093/nar/gkq379. Epub May 11, 2010.

Yuan et al., Laboratory-directed protein evolution. Microbiol Mol Biol Rev. 2005; 69(3):373-92. PMID: 16148303.

Yuan et al., Tetrameric structure of a serine integrase catalytic domain. Structure. Aug. 6, 2008;16(8):1275-86. doi: 10.1016/j.str.2008.04.018.

Yuen et al., Control of transcription factor activity and osteoblast differentiation in mammalian cells using an evolved small-molecule-dependent intein. J Am Chem Soc. Jul. 12, 2006;128(27):8939-46.

(56) References Cited

OTHER PUBLICATIONS

Zakas et al., Enhancing the pharmaceutical properties of protein drugs by ancestral sequence reconstruction. Nat Biotechnol. Jan. 2017;35(1):35-37. doi: 10.1038/nbt.3677. Epub Sep. 26, 2016.
Zalatan et al., Engineering complex synthetic transcriptional programs with Crispr Rna scaffolds. Cell. Jan. 15, 2015;160(1-2):339-50. doi: 10.1016/j.cell.2014.11.052. Epub Dec. 18, 2014.
Zangi et al., Modified mRNA directs the fate of heart progenitor cells and induces vascular regeneration after myocardial infarction. Nat Biotechnol. Oct. 2013;31(10):898-907. doi: 10.1038/nbt.2682. Epub Sep. 8, 2013.
Zelphati et al., Intracellular delivery of proteins with a new lipid-mediated delivery system. J Biol Chem. Sep. 14, 2001;276(37):35103-10. Epub Jul. 10, 2001.
Zetsche et al., A split-Cas9 architecture for inducible genome editing and transcription modulation. Nat Biotechnol. Feb. 2015;33(2):139-42. doi: 10.1038/nbt.3149.
Zetsche et al., Cpf1 is a single RNA-guided endonuclease of a class 2 CRISPR-Cas system. Cell. Oct. 22, 2015;163(3):759-71 and Supplemental Info. doi: 10.1016/j.cell.2015.09.038. Epub Sep. 25, 2015.
Zetsche et al., Cpf1 is a single RNA-guided endonuclease of a class 2 CRISPR-Cas system. Cell. Oct. 22, 2015;163(3):759-71. doi: 10.1016/j.cell.2015.09.038. Epub Sep. 25, 2015.
Zettler et al., The naturally split Npu DnaE intein exhibits an extraordinarily high rate in the protein trans-splicing reaction. FEBS Lett. Mar. 4, 2009;583(5):909-14. doi: 10.1016/j.febslet.2009.02.003. Epub Feb. 10, 2009.
Zhang et al., II-Clamp-mediated cysteine conjugation. Nat Chem. Feb. 2016;8(2):120-8. doi: 10.1038/nchem.2413. Epub Dec. 21, 2015.
Zhang et al., A new strategy for the site-specific modification of proteins in vivo. Biochemistry. Jun. 10, 2003;42(22):6735-46.
Zhang et al., Circular intronic long noncoding RNAs. Mol Cell. Sep. 26, 2013;51(6):792-806. doi: 10.1016/j.molcel.2013.08.017. Epub Sep. 12, 2013.
Zhang et al., Comparison of non-canonical PAMs for CRISPR/Cas9-mediated DNA cleavage in human cells. Sci Rep. Jun. 2014;4:5405.
Zhang et al., Conditional gene manipulation: Cre-ating a new biological era. J Zhejiang Univ Sci B. Jul. 2012;13(7):511-24. doi: 10.1631/jzus.B1200042. Review.
Zhang et al., Copy number variation in human health, disease, and evolution. Annu Rev Genomics Hum Genet. 2009;10:451-81. doi: 10.1146/annurev.genom.9.081307.164217.
Zhang et al., CRISPR/Cas9 for genome editing: progress, implications and challenges. Hum Mol Genet. Sep. 15, 2014;23(R1):R40-6. doi: 10.1093/hmg/ddu125. Epub Mar. 20, 2014.
Zhang et al., Efficient construction of sequence-specific TAL effectors for modulating mammalian transcription. Nat Biotechnol. Feb. 2011;29(2):149-53. doi: 10.1038/nbt. 1775. Epub Jan. 19, 2011.
Zhang et al., Efficient precise knockin with a double cut HDR donor after CRISPR/Cas9-mediated double-stranded DNA cleavage. Genome Biol. Feb. 20, 2017;18(1):35. doi: 10.1186/s13059-017-1164-8.
Zhang et al., Global analysis of small RNA and mRNA targets of Hfq. Mol Microbiol. Nov. 2003;50(4):1111-24. doi: 10.1046/j.1365-2958.2003.03734.x.
Zhang et al., Large genomic fragment deletions and insertions in mouse using CRISPR/Cas9. PLoS One. Mar. 24, 2015;10(3):e0120396. doi: 10.1371/journal.pone.0120396. 14 pages.
Zhang et al., Programmable base editing of zebrafish genome using a modified CRISPR-Cas9 system. Nat Commun. Jul. 25, 2017;8(1):118. doi: 10.1038/s41467-017-00175-6.
Zhang et al., Ribozymes and Riboswitches: Modulation of RNA Function by Small Molecules. Biochemistry. Nov. 2, 2010;49(43):9123-31. doi: 10.1021/bi1012645.
Zhang et al., Stabilized plasmid-lipid particles for regional gene therapy: formulation and transfection properties. Gene Ther. Aug. 1999;6(8):1438-47.
Zhao et al., Crystal structures of a group II intron maturase reveal a missing link in spliceosome evolution. Nat Struct Mol Biol. Jun. 2016;23(6):558-65. doi: 10.1038/nsmb.3224. Epub May 2, 2016.
Zhao et al., Post-transcriptional gene regulation by mRNA modifications. Nat Rev Mol Cell Biol. Jan. 2017;18(1):31-42. doi: 10.1038/nrm.2016.132. Epub Nov. 3, 2016.
Zheng et al., ALKBH5 is a mammalian RNA demethylase that impacts RNA metabolism and mouse fertility. Mol Cell. Jan. 10, 2013;49(1):18-29. doi: 10.1016/j.molcel.2012.10.015. Epub Nov. 21, 2012.
Zheng et al., DNA editing in DNA/RNA hybrids by adenosine deaminases that act on RNA. Nucleic Acids Res. Apr. 7, 2017;45(6):3369-3377. doi: 10.1093/nar/gkx050.
Zhong et al., Rational Design of Aptazyme Riboswitches for Efficient Control of Gene Expression in Mammalian Cells. Elife. Nov. 2, 2016;5:e18858. doi: 10.7554/eLife.18858.
Zhou et al., Dynamic m(6)A mRNA methylation directs translational control of heat shock response. Nature. Oct. 22, 2015;526(7574):591-4. doi: 10.1038/nature15377. Epub Oct. 12, 2015.
Zhou et al., Generation of induced pluripotent stem cells using recombinant proteins. Cell Stem Cell. May 8, 2009;4(5):381-4. doi: 10.1016/j.stem.2009.04.005. Epub Apr. 23, 2009.
Zhou et al., GISSD: Group I Intron Sequence and Structure Database. Nucleic Acids Res. Jan. 2008;36(Database issue):D31-7. doi: 10.1093/nar/gkm766. Epub Oct. 16, 2007.
Zhou et al., Protective V127 prion variant prevents prion disease by interrupting the formation of dimer and fibril from molecular dynamics simulations. Sci Rep. Feb. 24, 2016;6:21804. doi: 10.1038/srep21804.
Zhu et al., Novel Thrombotic Function of a Human SNP in STXBP5 Revealed by CRISPR/Cas9 Gene Editing in Mice. Arterioscler Thromb Vasc Biol. Feb. 2017;37(2):264-270. doi: 10.1161/ATVBAHA.116.308614. Epub Dec. 29, 2016.
Zielenski, Genotype and phenotype in cystic fibrosis. Respiration. 2000;67(2):117-33. doi: 10.1159/000029497.
Zimmerly et al., An Unexplored Diversity of Reverse Transcriptases in Bacteria. Microbiol Spectr. Apr. 2015;3(2):MDNA3-0058-2014. doi: 10.1128/microbiolspec.MDNA3-0058-2014.
Zimmerly et al., Group II intron mobility occurs by target DNA-primed reverse transcription. Cell. Aug. 25, 1995;82(4):545-54. doi: 10.1016/0092-8674(95)90027-6.
Zimmermann et al., Molecular interactions and metal binding in the theophylline-binding core of an RNA aptamer. RNA. May 2000;6(5):659-67.
Zolotukhin et al., Production and purification of serotype 1, 2, and 5 recombinant adeno- associated viral vectors. Methods. Oct. 2002;28(2):158-67. doi: 10.1016/s1046-2023(02)00220-7.
Zong et al., Precise base editing in rice, wheat and maize with a Cas9-cytidine deaminase fusion. Nat Biotechnol. May 2017;35(5):438-440. doi: 10.1038/nbt.3811. Epub Feb. 27, 2017.
Zorko et al., Cell-penetrating peptides: mechanism and kinetics of cargo delivery. Adv Drug Deliv Rev. Feb. 28, 2005;57(4):529-45. Epub Jan. 22, 2005.
Zou et al., Gene targeting of a disease-related gene in human induced pluripotent stem and embryonic stem cells. Cell Stem Cell. Jul. 2, 2009;5(1):97-110. doi: 10.1016/j.stem.2009.05.023. Epub Jun. 18, 2009.
Zufferey et al., Woodchuck hepatitis virus posttranscriptional regulatory element enhances expression of transgenes delivered by retroviral vectors. J Virol. Apr. 1999;73(4):2886-92. doi: 10.1128/JVI.73.4.2886-2892.1999.
Zuker et al., Optimal computer folding of large RNA sequences using thermodynamics and auxiliary information. Nucleic Acids Res. Jan. 10, 1981;9(1):133-48. doi: 10.1093/nar/9.1.133.
Zuris et al., Cationic lipid-mediated delivery of proteins enables efficient protein-based genome editing in vitro and in vivo. Nat Biotechnol. 2015;33:73-80.
†U.S. Appl. No. 17/289,665, filed Apr. 28, 2021, Liu et al.
†U.S. Appl. No. 16/756,432, filed Apr. 15, 2020, Liu et al.
†U.S. Appl. No. 16/772,747, filed Jun. 12, 2020, Shen et al.
†U.S. Appl. No. 17/425,261, filed Jul. 22, 2021, Kim et al.
†U.S. Appl. No. 17/057,398, filed Nov. 20, 2020, Liu et al.

(56) References Cited

OTHER PUBLICATIONS

†U.S. Appl. No. 17/259,147, filed Jan. 8, 2021, Liu et al.
†U.S. Appl. No. 17/270,396, filed Feb. 22, 2021, Liu et al.
†U.S. Appl. No. 17/273,688, filed Mar. 4, 2021, Liu et al.
†U.S. Appl. No. 17/294,287, filed May 14, 2021, Liu et al.
†U.S. Appl. No. 17/288,504, filed Apr. 23, 2021, Liu et al.
†U.S. Appl. No. 17/633,573, filed Feb. 7, 2022, Liu et al.
†U.S. Appl. No. 17/910,552, filed Sep. 9, 2022, Liu et al.
†U.S. Appl. No. 17/436,048, filed Sep. 2, 2021, Liu et al.
†U.S. Appl. No. 17/219,590, filed Mar. 31, 2021, Liu et al.
†U.S. Appl. No. 17/603,917, filed Oct. 14, 2021, Liu et al.
†U.S. Appl. No. 17/797,700, filed Aug. 4, 2022, Liu et al.
†U.S. Appl. No. 17/602,738, filed Oct. 8, 2021, Liu et al.
†U.S. Appl. No. 17/613,025, filed Nov. 19, 2021, Liu et al.
†U.S. Appl. No. 17/300,668, filed Sep. 17, 2021, Liu et al.
†U.S. Appl. No. 17/795,819, filed Jul. 27, 2022, Liu et al.
†U.S. Appl. No. 17/779,953, filed May 25, 2022, Liu et al.
†U.S. Appl. No. 17/767,777, filed Apr. 8, 2022, Liu et al.
†U.S. Appl. No. 17/797,701, filed Aug. 4, 2022, Liu et al.
†U.S. Appl. No. 18/053,269, filed Nov. 7, 2022, Liu et al.
†U.S. Appl. No. 17/797,697, filed Aug. 4, 2022, Liu et al.
†U.S. Appl. No. 17/921,971, filed Oct. 27, 2022, Liu et al.
†U.S. Appl. No. 17/219,635, filed Mar. 31, 2021, Liu et al.
†U.S. Appl. No. 18/064,738, filed Dec. 12, 2022, Liu et al.
†U.S. Appl. No. 17/219,672, filed Mar. 31, 2021, Liu et al.
†U.S. Appl. No. 17/751,599, filed May 23, 2022, Liu et al.
†U.S. Appl. No. 17/440,682, filed Sep. 17, 2021, Liu et al.
†U.S. Appl. No. 14/234,031, filed Mar. 24, 2014, Liu et al.
†U.S. Appl. No. 14/320,271, filed Jun. 30, 2014, Liu et al.
†U.S. Appl. No. 16/441,751, filed Jun. 14, 2019, Liu et al.
†U.S. Appl. No. 14/320,519, filed Jun. 30, 2014, Liu et al.
†U.S. Appl. No. 14/913,458, filed Feb. 22, 2016, Liu et al.
†U.S. Appl. No. 16/266,937, filed Feb. 4, 2019, Liu et al.
†U.S. Appl. No. 14/320,370, filed Jun. 30, 2014, Liu et al.
†U.S. Appl. No. 14/320,413, filed Jun. 30, 2014, Liu et al.
†U.S. Appl. No. 14/874,123, filed Oct. 2, 2015, Liu et al.
†U.S. Appl. No. 14/911,117, filed Feb. 9, 2016, Liu et al.
†U.S. Appl. No. 17/160,329, filed Jan. 27, 2021, Liu et al.
†U.S. Appl. No. 15/029,602, filed Apr. 14, 2016, Ritter et al.
†U.S. Appl. No. 14/462,163, filed Aug. 18, 2014, Liu et al.
†U.S. Appl. No. 14/462,189, filed Aug. 18, 2014, Liu et al.
†U.S. Appl. No. 14/916,679, filed Mar. 4, 2016, Liu et al.
†U.S. Appl. No. 16/860,639, filed Apr. 28, 2020, Liu et al.
†U.S. Appl. No. 14/320,498, filed Jun. 30, 2014, Liu et al.
†U.S. Appl. No. 14/320,467, filed Jun. 30, 2014, Liu et al.
†U.S. Appl. No. 14/916,681, filed Mar. 4, 2016, Liu et al.
†U.S. Appl. No. 17/103,233, filed Nov. 24, 2020, Liu et al.
†U.S. Appl. No. 17/937,203, filed Sep. 30, 2022, Liu et al.
†U.S. Appl. No. 14/326,329, filed Jul. 8, 2014, Liu et al.
†U.S. Appl. No. 14/326,340, filed Jul. 8, 2014, Liu et al.
†U.S. Appl. No. 14/326,361, filed Jul. 8, 2014, Liu et al.
†U.S. Appl. No. 14/916,683, filed Mar. 4, 2016, Liu et al.
†U.S. Appl. No. 16/796,323, filed Feb. 20, 2020, Liu et al.
†U.S. Appl. No. 17/688,416, filed Mar. 7, 2022, Liu et al.
†U.S. Appl. No. 14/325,815, filed Jul. 8, 2014, Liu et al.
†U.S. Appl. No. 14/326,109, filed Jul. 8, 2014, Liu et al.
†U.S. Appl. No. 14/326,140, filed Jul. 8, 2014, Liu et al.
†U.S. Appl. No. 14/326,269, filed Jul. 8, 2014, Liu et al.
†U.S. Appl. No. 14/326,290, filed Jul. 8, 2014, Liu et al.
†U.S. Appl. No. 14/326,318, filed Jul. 8, 2014, Liu et al.
†U.S. Appl. No. 14/326,303, filed Jul. 8, 2014, Liu et al.
†U.S. Appl. No. 15/103,608, filed Jun. 10, 2016, Liu et al.
†U.S. Appl. No. 16/374,634, filed Apr. 3, 2019, Liu et al.
†U.S. Appl. No. 17/408,306, filed Aug. 20, 2021, Liu et al.
†U.S. Appl. No. 15/329,925, filed Jan. 27, 2017, Liu et al.
†U.S. Appl. No. 16/132,276, filed Sep. 14, 2018, Liu et al.
†U.S. Appl. No. 16/888,646, filed May 29, 2020, Liu et al.
†U.S. Appl. No. 14/529,010, filed Oct. 30, 2014, Liu et al.
†U.S. Appl. No. 15/958,721, filed Apr. 20, 2018, Liu et al.
†U.S. Appl. No. 17/130,812, filed Dec. 22, 2020, Liu et al.
†U.S. Appl. No. 15/331,852, filed Oct. 22, 2016, Liu et al.
†U.S. Appl. No. 15/960,171, filed Apr. 23, 2018, Liu et al.
†U.S. Appl. No. 17/527,011, filed Nov. 15, 2021, Liu et al.
†U.S. Appl. No. 15/770,076, filed Apr. 20, 2018, Liu et al.
†U.S. Appl. No. 16/327,744, filed Feb. 22, 2019, Maianti et al.
†U.S. Appl. No. 18/055,274, filed Nov. 14, 2022, Maianti et al.
†U.S. Appl. No. 15/852,891, filed Dec. 22, 2017, Maianti et al.
†U.S. Appl. No. 16/926,436, filed Jul. 10, 2020, Maianti et al.
†U.S. Appl. No. 15/852,526, filed Dec. 22, 2017, Maianti et al.
†U.S. Appl. No. 16/492,534, filed Sep. 9, 2019, Liu et al.
†U.S. Appl. No. 16/324,476, filed Feb. 8, 2019, Liu et al.
†U.S. Appl. No. 15/791,085, filed Oct. 23, 2017, Liu et al.
†U.S. Appl. No. 16/143,370, filed Sep. 26, 2018, Liu et al.
†U.S. Appl. No. 17/148,059, filed Jan. 13, 2021, Liu et al.
†U.S. Appl. No. 16/492,548, filed Sep. 9, 2019, Maianti et al.
†U.S. Appl. No. 15/784,033, filed Oct. 13, 2017, Liu et al.
†U.S. Appl. No. 17/692,925, filed Mar. 11, 2022, Liu et al.
†U.S. Appl. No. 16/492,553, filed Sep. 9, 2019, Liu et al.
†U.S. Appl. No. 18/059,308, filed Nov. 28, 2022, Liu et al.
†U.S. Appl. No. 15/934,945, filed Mar. 23, 2018, Liu et al.
†U.S. Appl. No. 17/586,688, filed Jan. 27, 2022, Liu et al.
†U.S. Appl. No. 18/066,878, filed Dec. 15, 2022, Liu et al.
†U.S. Appl. No. 16/643,376, filed Feb. 28, 2020, Liu et al.
†U.S. Appl. No. 17/700,109, filed Mar. 21, 2022, Liu et al.
†U.S. Appl. No. 16/612,988, filed Nov. 12, 2019, Liu et al.
†U.S. Appl. No. 16/634,405, filed Jan. 27, 2020, Liu et al.
†U.S. Appl. No. 16/976,047, filed Aug. 26, 2020, Liu et al.
†U.S. Appl. No. 17/593,020, filed Sep. 3, 2021, Church et al.
EP 15830407.1, Mar. 2, 2018, Extended European Search Report.
EP 22156453.7, Sep. 26, 2022, Extended European Search Report.
PCT/US2015/042770, Feb. 23, 2016, International Search Report and Written Opinion.
PCT/U82015/042770, Dec. 19, 2016, *nternational Preliminary Report on Patentability.
[No. Author Listed] NCBI Reference Sequence: WP_032188360.1. Apr. 6, 2015. 1 page.
[No. Author Listed], MutL homolog 1. UniProtKB Acc. No. F1MPG0. May 3, 2011. Accessible at https://rest.uniprot.org/unisave/F1MPG0?format=txt&versions=1. 1 page.
[No. Author Listed], tRNA-specific adenosine deaminase [*Escherichia coli*]. GenBank Acc. No. CTS26096.1. Accessible at https://www.ncbi.nlm.nih.gov/protein/CTS26096.1. Aug. 22, 2015. 1 page.
Acharya et al., hMSH2 forms specific mispair-binding complexes with hMSH3 and hMSH6. Proc Natl Acad Sci U S A. Nov. 26, 1996;93(24):13629-34. doi: 10.1073/pnas.93.24.13629.
Avidan et al., Expression and characterization of a recombinant novel reverse transcriptase of a porcine endogenous retrovirus. Virology. Mar. 15, 2003;307(2):341-57. doi: 10.1016/s0042-6822(02)00131-9.
Bae et al., Heteroclitic CD33 peptide with enhanced anti-acute myeloid leukemic immunogenicity. Clin Cancer Res. Oct. 15, 2004;10(20):7043-52. doi: 10.1158/1078-0432.CCR-04-0322.
Baños-Sanz et al., Crystal structure and functional insights into uracil-DNA glycosylase inhibition by phage Φ29 DNA mimic protein p56. Nucleic Acids Res. Jul. 2013;41(13):6761-73. doi: 10.1093/nar/gkt395. Epub May 13, 2013.
Cheriyan et al., Faster protein splicing with the Nostoc punctiforme DnaE intein using non- native extein residues. J Biol Chem. Mar. 1, 2013;288(9):6202-11. doi: 10.1074/jbc.M112.433094. Epub Jan. 10, 2013.
Choi et al., Optimization of AAV expression cassettes to improve packaging capacity and transgene expression in neurons. Mol Brain. Mar. 11, 2014;7:17. doi: 10.1186/1756-6606-7-17.
Damdindorj et al., A comparative analysis of constitutive promoters located in adeno- associated viral vectors. PLoS One. Aug. 29, 2014;9(8):e106472. doi: 10.1371/journal.pone.0106472.
Ding et al., Gene therapy for cardiovascular disease. Journal of Shanghai University (Natural Science Edition). 2016;3:270-9 . DOI: 10.3969/j.issn.1007-2861.2016.03.013.
Eriksen et al., Occlusion of the Ribosome Binding Site Connects the Translational Initiation Frequency, mRNA Stability and Premature Transcription Termination. Front Microbiol. Mar. 14, 2017;8:362. doi: 10.3389/fmicb.2017.00362.

(56) References Cited

OTHER PUBLICATIONS

Fang et al., Human strand-specific mismatch repair occurs by a bidirectional mechanism similar to that of the bacterial reaction. J Biol Chem. Jun. 5, 1993;268(16):11838-44.
Feng et al., Efficient genome editing in plants using a CRISPR/Cas system. Cell Res. Oct. 2013;23(10):1229-32. doi: 10.1038/cr.2013.114. Epub Aug. 20, 2013.
Fikes et al., Design of multi-epitope, analogue-based cancer vaccines. Expert Opin Biol Ther. Sep. 2003;3(6):985-93. doi: 10.1517/14712598.3.6.985.
Fishel et al., The human mutator gene homolog MSH2 and its association with hereditary nonpolyposis colon cancer. Cell. Dec. 3, 1993;75(5):1027-38. doi: 10.1016/0092-8674(93)90546-3. Erratum in: Cell. Apr. 8, 1994;77(1):1 p following 166.
Fu et al., Targeted genome editing in human cells using CRISPR/Cas nucleases and truncated guide RNAs. Methods Enzymol. 2014;546:21-45. doi: 10.1016/B978-0-12-801185-0.00002-7.
Genbank Submission; NIH/NCBI, Accession No. NP_060228.2. Bi et al., Dec. 21, 2005. 1 page.
Genbank Submission; NIH/NCBI, Accession No. NP_062826.2. Bokar et al., Sep. 18, 2004. 2 pages.
Genbank Submission; NIH/NCBI, Accession No. NP_066012.1. Ota et al., Apr. 3, 2005. 2 pages.
Genbank Submission; NIH/NCBI, Accession No. WP_042518169.1. No Author, Feb. 10, 2015. 1 page.
Geng et al., In vitro studies of DNA mismatch repair proteins. Anal Biochem. Jun. 15, 2011;413(2):179-84. doi: 10.1016/j.ab.2011.02.017. Epub Feb. 15, 2011.
Genschel et al., Human exonuclease I is required for 5' and 3' mismatch repair. J Biol Chem. Apr. 12, 2002;277(15):13302-11. doi: 10.1074/jbc.M111854200. Epub Jan. 24, 2002.
Genschel et al., Isolation of MutSbeta from human cells and comparison of the mismatch repair specificities of MutSbeta and MutSalpha. J Biol Chem. Jul. 31, 1998;273(31):19895-901. doi: 10.1074/jbc.273.31.19895. Erratum in: J Biol Chem Oct. 9, 1998;273(41):27034.
Gueneau et al., Structure of the MutLa C-terminal domain reveals how Mlh1 contributes to Pms1 endonuclease site. Nat Struct Mol Biol. Apr. 2013;20(4):461-8. doi: 10.1038/nsmb.2511. Epub Feb. 24, 2013.
Guerrette et al., The interaction of the human MutL homologues in hereditary nonpolyposis colon cancer. J Biol Chem. Mar. 5, 1999;274(10):6336-41. doi: 10.1074/jbc.274.10.6336.
Gupta et al., Mechanism of mismatch recognition revealed by human MutSβ bound to unpaired DNA loops. Nat Struct Mol Biol. Dec. 18, 2011;19(1):72-8. doi: 10.1038/nsmb.2175.
Hizi et al., Retroviral reverse transcriptases (other than those of HIV-1 and murine leukemia virus): a comparison of their molecular and biochemical properties. Virus Res. Jun. 2008;134(1-2):203-20. doi: 10.1016/j.virusres.2007.12.008. Epub Mar. 3, 2008.
Houghton et al., Immunological validation of the EpitOptimizer program for streamlined design of heteroclitic epitopes. Vaccine. Jul. 20, 2007;25(29):5330-42. doi: 10.1016/j.vaccine.2007.05.008. Epub Jun. 4, 2007.
Hwang et al., Heritable and precise zebrafish genome editing using a CRISPR-Cas system. PLoS One. Jul. 9, 2013;8(7):e68708. doi: 10.1371/journal.pone.0068708.
Iaccarino et al., hMSH2 and hMSH6 play distinct roles in mismatch binding and contribute differently to the ATPase activity of hMutSalpha. EMBO J. May 1, 1998;17(9):2677-86. doi: 10.1093/emboj/17.9.2677.
Iyer et al., DNA mismatch repair: functions and mechanisms. Chem Rev. Feb. 2006;106(2):302-23. doi: 10.1021/cr0404794.
Kadyrov et al., Endonucleolytic function of MutLalpha in human mismatch repair. Cell. Jul. 28, 2006;126(2):297-308. doi: 10.1016/j.cell.2006.05.039.
Kirshenboim et al., Expression and characterization of a novel reverse transcriptase of the LTR retrotransposon Tf1. Virology. Sep. 30, 2007;366(2):263-76. doi: 10.1016/j.virol.2007.04.002. Epub May 23, 2007.
Kunkel et al., DNA mismatch repair. Annu Rev Biochem. 2005;74:681-710. doi: 10.1146/annurev.biochem.74.082803.133243.
Lahue et al., DNA mismatch correction in a defined system. Science. Jul. 14, 1989;245(4914):160-4. doi: 10.1126/science.2665076.
Leach et al., Mutations of a mutS homolog in hereditary nonpolyposis colorectal cancer. Cell. Dec. 17, 1993;75(6):1215-25. doi: 10.1016/0092-8674(93)90330-s.
Lujan et al., Heterogeneous polymerase fidelity and mismatch repair bias genome variation and composition. Genome Res. Nov. 2014;24(11):1751-64. doi: 10.1101/gr.178335.114. Epub Sep. 12, 2014.
Mahoney et al., The Next Immune-Checkpoint Inhibitors: PD-1/PD-L1 Blockade in Melanoma. Clin Ther. Apr. 1, 2015;37(4):764-82. doi: 10.1016/j.clinthera.2015.02.018. Epub Mar. 29, 2015.
Mariani et al., Species-specific exclusion of APOBEC3G from HIV-1 virions by Vif. Cell. Jul. 11, 2003;114(1):21-31. doi: 10.1016/s0092-8674(03)00515-4.
Misra et al., An enzymatically active chimeric HIV-1 reverse transcriptase (RT) with the RNase-H domain of murine leukemia virus RT exists as a monomer. J Biol Chem. Apr. 17, 1998;273(16):9785-9. doi: 10.1074/jbc.273.16.9785.
Niemeyer, C.M., Semisynthetic DNA-protein conjugates for biosensing and nanofabrication. Angew Chem Int Ed Engl. Feb. 8, 2010;49(7):1200-16. doi: 10.1002/anie.200904930.
Nowak et al., Ty3 reverse transcriptase complexed with an RNA-DNA hybrid shows structural and functional asymmetry. Nat Struct Mol Biol. Apr. 2014;21(4):389-96. doi: 10.1038/nsmb.2785. Epub Mar. 9, 2014. Author Manuscript, 22 pages.
Parsons et al., Hypermutability and mismatch repair deficiency in RER+ tumor cells. Cell. Dec. 17, 1993;75(6):1227-36. doi: 10.1016/0092-8674(93)90331-j.
Petit et al., Powerful mutators lurking in the genome. Philos Trans R Soc Lond B Biol Sci. Mar. 12, 2009;364(1517):705-15. doi: 10.1098/rstb.2008.0272.
Plotz et al., N-terminus of hMLH1 confers interaction of hMutLalpha and hMutLbeta with hMutSalpha. Nucleic Acids Res. Jun. 15, 2003;31(12):3217-26. doi: 10.1093/nar/gkg420.
Räschle et al., Mutations within the hMLH1 and hPMS2 subunits of the human MutLalpha mismatch repair factor affect its ATPase activity, but not its ability to interact with hMutSalpha. J Biol Chem. Jun. 14, 2002;277(24):21810-20. doi: 10.1074/jbc.M108787200. Epub Apr. 10, 2002.
Riddle et al., Frameshift suppression: a nucleotide addition in the anticodon of a glycine transfer RNA. Nat New Biol. Apr. 25, 1973;242(121):230-4. doi: 10.1038/newbio242230a0.
Riddle et al., Frameshift suppressors. II. Genetic mapping and dominance studies. J Mol Biol. May 28, 1972;66(3):483-93. doi: 10.1016/0022-2836(72)90428-7.
Riddle et al., Suppressors of frameshift mutations in Salmonella typhimurium. J Mol Biol. Nov. 28, 1970;54(1):131-44. doi: 10.1016/0022-2836(70)90451-1.
Sadowski et al., The sequence-structure relationship and protein function prediction. Curr Opin Struct Biol. Jun. 2009;19(3):357-62. doi: 10.1016/j.sbi.2009.03.008. Epub May 4, 2009.
Score Results for US 2014-0186919 A1 to Zhang et al. Aug. 28, 2014. 3 pages.
Seffernick et al., Melamine deaminase and atrazine chlorohydrolase: 98 percent identical but functionally different. J Bacteriol. Apr. 2001;183(8):2405-10. doi: 10.1128/JB.183.8.2405-2410.2001.
Shcherbakova et al., Mutator phenotypes conferred by MLH1 overexpression and by heterozygosity for mlh1 mutations. Mol Cell Biol. Apr. 1999;19(4):3177-83. doi: 10.1128/MCB.19.4.3177.
Strand et al., Destabilization of tracts of simple repetitive DNA in yeast by mutations affecting DNA mismatch repair. Nature. Sep. 16, 1993;365(6443):274-6. doi: 10.1038/365274a0. Erratum in: Nature Apr. 7, 1994;368(6471);569.
Studebaker et al., Depletion of uracil-DNA glycosylase activity is associated with decreased cell proliferation. Biochem Biophys Res Commun. Aug. 26, 2005;334(2):509-15. doi: 10.1016/j.bbrc.2005.06.118.

(56) References Cited

OTHER PUBLICATIONS

Su et al., Mispair specificity of methyl-directed DNA mismatch correction in vitro. J Biol Chem. May 15, 1988;263(14):6829-35. Erratum in: J Biol Chem Aug. 5, 1988;263(22):11015.

Sugawara et al., Heteroduplex rejection during single-strand annealing requires Sgs1 helicase and mismatch repair proteins Msh2 and Msh6 but not Pms1. Proc Natl Acad Sci U S A. Jun. 22, 2004;101(25):9315-20. doi: 10.1073/pnas.0305749101. Epub Jun. 15, 2004.

Supek et al., Differential DNA mismatch repair underlies mutation rate variation across the human genome. Nature. May 7, 2015;521(7550):81-4. doi: 10.1038/nature14173. Epub Feb. 23, 2015.

Svitashev et al., Targeted Mutagenesis, Precise Gene Editing, and Site-Specific Gene Insertion in Maize Using Cas9 and Guide RNA. Plant Physiol. Oct. 2015; 169(2):931-45. doi: 10.1104/p. 15.00793. Epub Aug. 12, 2015.

Tang et al., Identification of Dehalobacter reductive dehalogenases that catalyse dechlorination of chloroform, 1,1,1-trichloroethane and 1,1-dichloroethane. Philos Trans R Soc Lond B Biol Sci. Mar. 11, 2013;368(1616):20120318. doi: 10.1098/rstb.2012.0318.

Thomas et al., Heteroduplex repair in extracts of human HeLa cells. J Biol Chem. Feb. 25, 1991;266(6):3744-51.

Tomer et al., Contribution of human mlh1 and pms2 ATPase activities to DNA mismatch repair. J Biol Chem. Jun. 14, 2002;277(24):21801-9. doi: 10.1074/jbc.M111342200. Epub Mar. 15, 2002.

Toro et al., Comprehensive phylogenetic analysis of bacterial reverse transcriptases. PLoS One. Nov. 25, 2014;9(11):e114083. doi: 10.1371/journal.pone.0114083.

Tran et al., Hypermutability of homonucleotide runs in mismatch repair and DNA polymerase proofreading yeast mutants. Mol Cell Biol. May 1997;17(5):2859-65. doi: 10.1128/MCB.17.5.2859.

Umar et al., DNA loop repair by human cell extracts. Science. Nov. 4, 1994;266(5186):814-6. doi: 10.1126/science.7973637.

Warren et al., Structure of the human MutSalpha DNA lesion recognition complex. Mol Cell. May 25, 2007;26(4):579-92. doi: 10.1016/j.molcel.2007.04.018.

Witkowski et al., Conversion of a beta-ketoacyl synthase to a malonyl decarboxylase by replacement of the active-site cysteine with glutamine. Biochemistry. Sep. 7, 1999;38(36):11643-50. doi: 10.1021/bi990993h.

Xi et al., C-terminal Loop Mutations Determine Folding and Secretion Properties of PCSK9. Biochem Mol Biol J. 2016;2(3):17. doi: 10.21767/2471-8084.100026. 12 pages.

Zhang et al., Reconstitution of 5'-directed human mismatch repair in a purified system. Cell. Sep. 9, 2005;122(5):693-705. doi: 10.1016/j.cell.2005.06.027.

[No Author Listed], dCas9-5xPlat2AfID-P2A-scFvGCN4sfGFPTET1CD [Cloning vector pPlatTET-gRNA2]. GenBank No. BAV54124. Apr. 18, 2017. 5 pages.

Alves et al., Immunogenicity of the carcinoembryonic antigen derived peptide 694 in HLA-A2 healthy donors and colorectal carcinoma patients. Cancer Immunol Immunother. Nov. 2007;56(11):1795-805. doi: 10.1007/s00262-007-0323-2. Epub Apr. 20, 2007.

Asemissen et al., Identification of a highly immunogenic HLA-A*01-binding T cell epitope of WT1. Clin Cancer Res. Dec. 15, 2006;12(24):7476-82. doi: 10.1158/1078-0432.CCR-06-1337.

Attia et al., Autoimmunity correlates with tumor regression in patients with metastatic melanoma treated with anti-cytotoxic T-lymphocyte antigen-4. J Clin Oncol. Sep. 1, 2005;23(25):6043-53. doi: 10.1200/JCO.2005.06.205. Epub Aug. 8, 2005.

Aurisicchio et al., A novel minigene scaffold for therapeutic cancer vaccines. Oncoimmunology. Jan. 1, 2014;3(1):e27529. doi: 10.4161/onci.27529. Epub Jan. 16, 2014.

Bae et al., Identification of novel CD33 antigen-specific peptides for the generation of cytotoxic T lymphocytes against acute myeloid leukemia. Cell Immunol. Jan. 2004;227(1):38-50. doi: 10.1016/j.cellimm.2004.01.002.

Bakker et al., Analogues of CTL epitopes with improved MHC class-I binding capacity elicit anti-melanoma CTL recognizing the wild-type epitope. Int J Cancer. Jan. 27, 1997;70(3):302-9. doi: 10.1002/(sici)1097-0215(19970127)70:3<302::aid-ijc10>3.0.co;2-h.

Banerjee et al., Viral glycoproteins: biological role and application in diagnosis. Virusdisease. Mar. 2016;27(1):1-11. doi: 10.1007/s13337-015-0293-5. Epub Jan. 18, 2016.

Barve et al., Induction of immune responses and clinical efficacy in a phase II trial of IDM-2101, a 10-epitope cytotoxic T-lymphocyte vaccine, in metastatic non-small-cell lung cancer. J Clin Oncol. Sep. 20, 2008;26(27):4418-25. doi: 10.1200/JCO.2008.16.6462.

Benlalam et al., Identification of five new HLA-B*3501-restricted epitopes derived from common melanoma-associated antigens, spontaneously recognized by tumor-infiltrating lymphocytes. J Immunol. Dec. 1, 2003;171(11):6283-9. doi: 10.4049/jimmunol.171.11.6283.

Bernatchez et al., Altered decamer and nonamer from an HLA-A0201-restricted epitope of Survivin differentially stimulate T-cell responses in different individuals. Vaccine. Apr. 5, 2011;29(16):3021-30. doi: 10.1016/j.vaccine.2011.01.115. Epub Feb. 12, 2011.

Bioley et al., Melan-A/MART-1-specific CD4 T cells in melanoma patients: identification of new epitopes and ex vivo visualization of specific T cells by MHC class II tetramers. J Immunol. Nov. 15, 2006;177(10):6769-79. doi: 10.4049/jimmunol.177.10.6769.

Blanchet et al., A new generation of Melan-A/MART-1 peptides that fulfill both increased immunogenicity and high resistance to biodegradation: implication for molecular anti-melanoma immunotherapy. J Immunol. Nov. 15, 2001;167(10):5852-61. doi: 10.4049/jimmunol.167.10.5852.

Borbulevych et al., Increased immunogenicity of an anchor-modified tumor-associated antigen is due to the enhanced stability of the peptide/MHC complex: implications for vaccine design. J Immunol. Apr. 15, 2005;174(8):4812-20. doi: 10.4049/jimmunol.174.8.4812.

Brichard et al., A tyrosinase nonapeptide presented by HLA-B44 is recognized on a human melanoma by autologous cytolytic T lymphocytes. Eur J Immunol. Jan. 1996;26(1):224-30. doi: 10.1002/eji.1830260135.

Campi et al., CD4(+) T cells from healthy subjects and colon cancer patients recognize a carcinoembryonic antigen-specific immunodominant epitope. Cancer Res. Dec. 1, 2003;63(23):8481-6.

Casnici et al., Immunologic evaluation of peptides derived from BCR/ABL-out-of-frame fusion protein in Hla A2.1 transgenic mice. J Immunother. May 2012;35(4):321-8. doi: 10.1097/CJI.0b013e3182562d37.

Casnici et al., Out of frame peptides from BCR/ABL alternative splicing are immunogenic in HLA A2.1 transgenic mice. Cancer Lett. Apr. 8, 2009;276(1):61-7. doi: 10.1016/j.canlet.2008.10.032. Epub Dec. 4, 2008.

Castelli et al., Mass spectrometric identification of a naturally processed melanoma peptide recognized by CD8+ cytotoxic T lymphocytes. J Exp Med. Jan. 1, 1995;181(1):363-8. doi: 10.1084/jem.181.1.363.

Castelli et al., Novel HLA-Cw8-restricted T cell epitopes derived from tyrosinase-related protein-2 and gp100 melanoma antigens. J Immunol. Feb. 1, 1999;162(3):1739-48.

Castle et al., Exploiting the mutanome for tumor vaccination. Cancer Res. Mar. 1, 2012;72(5):1081-91. doi: 10.1158/0008-5472.CAN-11-3722. Epub Jan. 11, 2012.

Cervera et al., Generation of HIV-1 Gag VLPs by transient transfection of HEK 293 suspension cell cultures using an optimized animal-derived component free medium. J Biotechnol. Jul. 20, 2013;166(4):152-65. doi: 10.1016/j.jbiotec.2013.05.001. Epub May 17, 2013.

Chen et al., Identification of NY-ESO-1 peptide analogues capable of improved stimulation of tumor-reactive Ctl. J Immunol. Jul. 15, 2000;165(2):948-55. doi: 10.4049/jimmunol.165.2.948.

Cho et al., Optimized peptide vaccines eliciting extensive CD8 T-cell responses with therapeutic antitumor effects. Cancer Res. Dec. 1, 2009;69(23):9012-9. doi: 10.1158/0008- 5472.CAN-Sep. 2019. Epub Nov. 10, 2009.

(56) References Cited

OTHER PUBLICATIONS

Choi et al., Lentivirus pre-packed with Cas9 protein for safer gene editing. Gene Ther. Jul. 2016;23(7):627-33. doi: 10.1038/gt.2016.27. Epub Apr. 7, 2016.
Christensen et al., Melan-A/MART1 analog peptide triggers anti-myeloma T-cells through crossreactivity with HM1.24. J Immunother. Jul.-Aug. 2009;32(6):613-21. doi: 10.1097/CJI.0b013e3181a95198.
Correale et al., In vitro generation of human cytotoxic T lymphocytes specific for peptides derived from prostate-specific antigen. J Natl Cancer Inst. Feb. 19, 1997;89(4):293-300. doi: 10.1093/jnci/89.4.293.
Courtney et al., CRISPR/Cas9 DNA cleavage at SNP-derived PAM enables both in vitro and in vivo KRT12 mutation-specific targeting. Gene Ther. Jan. 2016;23(1):108-12. doi: 10.1038/gt.2015.82. Epub Aug. 20, 2015.
Cox et al., Identification of a peptide recognized by five melanoma-specific human cytotoxic T cell lines. Science. Apr. 29, 1994;264(5159):716-9. doi: 10.1126/science.7513441.
Cronin et al., Altering the tropism of lentiviral vectors through pseudotyping. Curr Gene Ther. Aug. 2005;5(4):387-98. doi: 10.2174/1566523054546224. Erratum in: Curr Gene Ther. Oct. 2005;5(5):531. Author Manuscript, 19 pages.
Crosti et al., Identification of novel subdominant epitopes on the carcinoembryonic antigen recognized by CD4+ T cells of lung cancer patients. J Immunol. Apr. 15, 2006;176(8):5093-9. doi: 10.4049/jimmunol.176.8.5093.
Dalet et al., An antigenic peptide produced by reverse splicing and double asparagine deamidation. Proc Natl Acad Sci U S A. Jul. 19, 2011;108(29):E323-31. doi: 10.1073/pnas.1101892108. Epub Jun. 13, 2011.
David et al., Viral Vectors: The Road to Reducing Genotoxicity. Toxicol Sci. Feb. 2017;155(2):315-325. doi: 10.1093/toxsci/kfw220. Epub Nov. 1, 2016.
Depontieu et al., Identification of tumor-associated, MHC class II-restricted phosphopeptides as targets for immunotherapy. Proc Natl Acad Sci U S A. Jul. 21, 2009;106(29):12073-8. doi: 10.1073/pnas.0903852106. Epub Jul. 6, 2009.
Di Stasi et al., Review of the Results of WT1 Peptide Vaccination Strategies for Myelodysplastic Syndromes and Acute Myeloid Leukemia from Nine Different Studies. Front Immunol. Feb. 4, 2015;6:36. doi: 10.3389/fimmu.2015.00036.
Duan et al., Immune rejection of mouse tumors expressing mutated self. Cancer Res. Apr. 15, 2009;69(8):3545-53. doi: 10.1158/0008-5472.CAN-08-2779. Epub Apr. 7, 2009. Author Manuscript. 18 pages.
Duportet et al., A platform for rapid prototyping of synthetic gene networks in mammalian cells. Nucleic Acids Res. Dec. 1, 2014;42(21):13440-51. doi: 10.1093/nar/gku1082. Epub Nov. 5, 2014.
Fontana et al., Rabies virus-like particles expressed in HEK293 cells. Vaccine. May 19, 2014;32(24):2799-804. doi: 10.1016/j.vaccine.2014.02.031. Epub Mar. 12, 2014.
Fonteneau et al., The Tumor Antigen NY-ESO-1 Mediates Direct Recognition of Melanoma Cells by CD4+ T Cells after Intercellular Antigen Transfer. J Immunol. Jan. 1, 2016;196(1):64- 71. doi: 10.4049/jimmunol. 1402664. Epub Nov. 25, 2015.
Fourcade et al., PD-1 and Tim-3 regulate the expansion of tumor antigen-specific CD8? T cells induced by melanoma vaccines. Cancer Res. Feb. 15, 2014;74(4): 1045-55. doi: 10.1158/0008-5472.CAN-13-2908. Epub Dec. 16, 2013.
Fridman et al., An efficient T-cell epitope discovery strategy using in silico prediction and the iTopia assay platform. Oncoimmunology. Nov. 1, 2012;1(8):1258-1270. doi: 10.4161/onci.21355.
Fujiki et al., Identification and characterization of a WT1 (Wilms Tumor Gene) protein-derived HLA-DRB1*0405-restricted 16-mer helper peptide that promotes the induction and activation of WT1-specific cytotoxic T lymphocytes. J Immunother. Apr. 2007;30(3):282-93. doi: 10.1097/01.cji.0000211337.91513.94.
GenBank Access No. BAP64357. Aug 1, 2013. 1 page.
Geynisman et al., A randomized pilot phase I study of modified carcinoembryonic antigen (CEA) peptide (CAP1-6D)/montanide/GM-CSF-vaccine in patients with pancreatic adenocarcinoma. J Immunother Cancer. Jun. 27, 2013;1:8. doi: 10.1186/2051-1426-1-8.
Ghosh et al., Synapsis in phage Bxb1 integration: selection mechanism for the correct pair of recombination sites. J Mol Biol. Jun. 3, 2005;349(2):331-48. doi: 10.1016/j.jmb.2005.03.043. Epub Apr. 7, 2005.
Girard-Gagnepain et al., Baboon envelope pseudotyped LVs outperform VSV-G-LVs for gene transfer into early-cytokine-stimulated and resting HSCs. Blood. Aug. 21, 2014;124(8):1221-31. doi: 10.1182/blood-2014-02-558163. Epub Jun. 20, 2014.
Godefroy et al., Identification of two Melan-A CD4+ T cell epitopes presented by frequently expressed MHC class II alleles. Clin Immunol. Oct. 2006; 121(1):54-62. doi: 10.1016/j.clim.2006.05.007. Epub Jun. 30, 2006.
Graff-Dubois et al., Generation of CTL recognizing an HLA-A*0201-restricted epitope shared by MAGE-A1, -A2, -A3, -A4, -A6, -A10, and -A12 tumor antigens: implication in a broad-spectrum tumor immunotherapy. J Immunol. Jul. 1, 2002;169(1):575-80. doi: 10.4049/jimmunol.169.1.575.
Gross et al., High vaccination efficiency of low-affinity epitopes in antitumor immunotherapy. J Clin Invest. Feb. 2004;113(3):425-33. doi: 10.1172/JCI19418.
Guevara-patiño et al., Optimization of a self antigen for presentation of multiple epitopes in cancer immunity. J Clin Invest. May 2006;116(5):1382-90. doi: 10.1172/JCI25591. Epub Apr. 13, 2006.
Guibinga et al., Cell surface heparan sulfate is a receptor for attachment of envelope protein- free retrovirus-like particles and VSV-G pseudotyped MLV-derived retrovirus vectors to target cells. Mol Ther. May 2002;5(5 Pt 1):538-46. doi: 10.1006/mthe.2002.0578.
Gulley et al., Combining a Recombinant Cancer Vaccine with Standard Definitive Radiotherapy in Patients with Localized Prostate Cancer. Clin Cancer Res. May 2, 2005;11(9):3353-62. doi: 10.1158/1078-0432.CCR-04-2062.
Guo et al., Direct recognition and lysis of leukemia cells by WT1-specific CD4+ T lymphocytes in an HLA class II-restricted manner. Blood. Aug. 15, 2005;106(4): 1415-8. doi: 10.1182/blood-2005-01-0413. Epub Apr. 21, 2005.
Haeussler et al., Genome Editing with CRISPR-Cas9: Can It Get Any Better? J Genet Genomics. May 20, 2016;43(5):239-50. doi: 10.1016/j.jgg.2016.04.008. Epub Apr. 24, 2016. Author Manuscript. 22 pages.
Herbst-Kralovetz et al., Norwalk virus-like particles as vaccines. Expert Rev Vaccines. Mar. 2010;9(3):299-307. doi: 10.1586/erv.09.163. Author Manuscript, 16 pages.
Hirohashi et al., An HLA-A24-restricted cytotoxic T lymphocyte epitope of a tumor- associated protein, survivin. Clin Cancer Res. Jun. 2002;8(6):1731-9.
Hong et al., Novel recombinant hepatitis B virus vectors efficiently deliver protein and RNA encoding genes into primary hepatocytes. J Virol. Jun. 2013;87(12):6615-24. doi: 10.1128/JVI.03328-12. Epub Apr. 3, 2013.
Jalaguier et al., Efficient production of HIV-1 virus-like particles from a mammalian expression vector requires the N-terminal capsid domain. PLoS One. 2011;6(11):e28314. doi: 10.1371/journal.pone.0028314. Epub Nov. 30, 2011.
Jaramillo et al., Identification of HLA-A3-restricted CD8+ T cell epitopes derived from mammaglobin-A, a tumor-associated antigen of human breast cancer. Int J Cancer. Dec. 10, 2002;102(5):499-506. doi: 10.1002/ijc.10736.
Kaczmarczyk et al., Protein delivery using engineered virus-like particles. Proc Natl Acad Sci U S A. Oct. 11, 2011;108(41):16998-7003. doi: 10.1073/pnas.1101874108. Epub Sep. 26, 2011.
Kang et al., Chimeric rabies virus-like particles containing membrane-anchored GM-CSF enhances the immune response against rabies virus. Viruses. Mar. 11, 2015;7(3):1134-52. doi: 10.3390/v7031134.
Kang et al., Identification of a tyrosinase epitope recognized by HLA-A24-restricted, tumor- infiltrating lymphocytes. J Immunol. Aug. 1, 1995;155(3):1343-8.

(56) References Cited

OTHER PUBLICATIONS

Karbach et al., Long-term complete remission following radiosurgery and immunotherapy in a melanoma patient with brain metastasis: immunologic correlates. Cancer Immunol Res. May 2014;2(5):404-9. doi: 10.1158/2326-6066.CIR-13-0200. Epub Feb. 5, 2014.

Kato et al., A lentiviral strategy for highly efficient retrograde gene transfer by pseudotyping with fusion envelope glycoprotein. Hum Gene Ther. Feb. 2011;22(2):197-206. doi: 10.1089/hum.2009.179. Epub Jan. 27, 2011.

Kato et al., Selective neural pathway targeting reveals key roles of thalamostriatal projection in the control of visual discrimination. J Neurosci. Nov. 23, 2011;31(47):17169-79. doi: 10.1523/JNEUROSCI.4005-11.2011.

Kawakami et al., Identification of a human melanoma antigen recognized by tumor- infiltrating lymphocytes associated with in vivo tumor rejection. Proc Natl Acad Sci U S A. Jul. 5, 1994;91(14):6458-62. doi: 10.1073/pnas.91.14.6458.

Kawakami et al., Identification of new melanoma epitopes on melanosomal proteins recognized by tumor infiltrating T lymphocytes restricted by HLA-A1, -A2, and -A3 alleles. J Immunol. Dec. 15, 1998;161(12):6985-92.

Kawakami et al., Identification of the immunodominant peptides of the MART-1 human melanoma antigen recognized by the majority of HLA-A2-restricted tumor infiltrating lymphocytes. J Exp Med. Jul. 1, 1994;180(1):347-52. doi: 10.1084/jem.180.1.347.

Kawakami et al., Recognition of multiple epitopes in the human melanoma antigen gp100 by tumor-infiltrating T lymphocytes associated with in vivo tumor regression. J Immunol. Apr. 15, 1995;154(8):3961-8.

Kawashima et al., Identification of gp100-derived, melanoma-specific cytotoxic T- lymphocyte epitopes restricted by HLA-A3 supertype molecules by primary in vitro immunization with peptide-pulsed dendritic cells. Int J Cancer. Nov. 9, 1998;78(4):518-24. doi: 10.1002/(sici)1097-0215(19981109)78:4<518::aid-ijc20>3.0.co;2-0.

Kawashima et al., Identification of HLA-A3-restricted cytotoxic T lymphocyte epitopes from carcinoembryonic antigen and HER-2/neu by primary in vitro immunization with peptide-pulsed dendritic cells. Cancer Res. Jan. 15, 1999;59(2):431-5.

Kawashima et al., The multi-epitope approach for immunotherapy for cancer: identification of several CTL epitopes from various tumor-associated antigens expressed on solid epithelial tumors. Hum Immunol. Jan. 1998;59(1):1-14. doi: 10.1016/s0198-8859(97)00255-3.

Kemmler et al., Elevated tumor-associated antigen expression suppresses variant peptide vaccine responses. J Immunol. Nov. 1, 2011;187(9):4431-9. doi: 10.4049/jimmunol.1101555. Epub Sep. 21, 2011.

Kittlesen et al., Human melanoma patients recognize an HLA-A1-restricted CTL epitope from tyrosinase containing two cysteine residues: implications for tumor vaccine development. J Immunol. Mar. 1, 1998;160(5):2099-106. Erratum in: J Immunol Mar. 1, 1999;162(5):3106. Shabanowitz JA [corrected to Shabanowitz J].

Kizer et al., Application of functional genomics to pathway optimization for increased isoprenoid production. Appl Environ Microbiol. May 2008;74(10):3229-41. doi: 10.1128/AEM.02750-07. Epub Mar. 14, 2008.

Kobayashi et al., CD4+ T cells from peripheral blood of a melanoma patient recognize peptides derived from nonmutated tyrosinase. Cancer Res. Jan. 15, 1998;58(2):296-301.

Kobayashi et al., Identification of an antigenic epitope for helper T lymphocytes from carcinoembryonic antigen. Clin Cancer Res. Oct. 2002;8(10):3219-25.

Kobayashi et al., Identification of helper T-cell epitopes that encompass or lie proximal to cytotoxic T-cell epitopes in the gp100 melanoma tumor antigen. Cancer Res. Oct. 15, 2001;61(20): 7577-84.

Kotterman et al., Engineering adeno-associated viruses for clinical gene therapy. Nat Rev Genet. Jul. 2014;15(7):445-51. doi: 10.1038/nrg3742. Epub May 20, 2014.

Kueh et al., The new editor-targeted genome engineering in the absence of homology-directed repair. Cell Death Discov. Jun. 13, 2016;2:16042. doi: 10.1038/cddiscovery.2016.42.

Kushnir et al., Virus-like particles as a highly efficient vaccine platform: diversity of targets and production systems and advances in clinical development. Vaccine. Dec. 17, 2012;31(1):58- 83. doi: 10.1016/j.vaccine.2012.10.083. Epub Nov. 6, 2012.

Lally et al., Unmasking cryptic epitopes after loss of immunodominant tumor antigen expression through epitope spreading. Int J Cancer. Sep. 2001;93(6):841-7. doi: 10.1002/ijc.1420.

Lapointe et al., Retrovirally transduced human dendritic cells can generate T cells recognizing multiple MHC class I and class II epitopes from the melanoma antigen glycoprotein 100. J Immunol. Oct. 15, 2001;167(8):4758-64. doi: 10.4049/jimmunol.167.8.4758.

Larrieu et al., A HLA-Cw*0701 restricted Melan-A/MART1 epitope presented by melanoma tumor cells to CD8+ tumor infiltrating lymphocytes. Cancer Immunol Immunother. May 2008;57(5):745-52. doi: 10.1007/s00262-007-0436-7. Epub Dec. 21, 2007.

Latham et al., Formation of wild-type and chimeric influenza virus-like particles following simultaneous expression of only four structural proteins. J Virol. Jul. 2001;75(13):6154-65. doi: 10.1128/JVI.75.13.6154-6165.2001.

Lennerz et al., The response of autologous T cells to a human melanoma is dominated by mutated neoantigens. Proc Natl Acad Sci U S A. Nov. 1, 2005;102(44):16013-8. doi: 10.1073/pnas.0500090102. Epub Oct. 24, 2005.

Li et al., Expression and self-assembly of empty virus-like particles of hepatitis E virus. J Virol. Oct. 1997;71(10):7207-13. doi: 10.1128/JVI.71.10.7207-7213.1997.

Lin et al., HLA-DPB1*05: 01-restricted WT1332-specific TCR-transduced CD4+ T lymphocytes display a helper activity for WT1-specific CTL induction and a cytotoxicity against leukemia cells. J Immunother. Apr. 2013;36(3):159-70. doi: 10.1097/CJI.0b013e3182873581.

Lu, Periodic Chart of Amino Acid PDF. Accessed on the internet at https://figshare.com/articles/figure/periodic_chart_of_amino_acid_pdf/3445001/1. Posted 2016-06-21. www.bachem.com. 1 page.

Ludwig et al., Virus-like particles-universal molecular toolboxes. Curr Opin Biotechnol. Dec. 2007;18(6):537-45. doi: 10.1016/j.copbio.2007.10.013.

Lupetti et al., Translation of a retained intron in tyrosinase-related protein (TRP) 2 mRNA generates a new cytotoxic T lymphocyte (CTL)-defined and shared human melanoma antigen not expressed in normal cells of the melanocytic lineage. J Exp Med. Sep. 21, 1998;188(6): 1005- 16. doi: 10.1084/jem.188.6.1005.

Maetzig et al., Retroviral protein transfer: falling apart to make an impact. Curr Gene Ther. Oct. 2012;12(5):389-409. doi: 10.2174/156652312802762581.

Mandic et al., The alternative open reading frame of LAGE-1 gives rise to multiple promiscuous HLA-DR-restricted epitopes recognized by T-helper 1-type tumor-reactive CD4+ T cells. Cancer Res. Oct. 1, 2003;63(19):6506-15.

Mangeot et al., A universal transgene silencing method based on RNA interference. Nucleic Acids Res. Jul. 12, 2004;32(12):e102. doi: 10.1093/nar/gnh105.

Mangeot et al., Development of minimal lentivirus vectors derived from simian immunodeficiency virus (SIVmac251) and their use for gene transfer into human dendritic cells. J Virol. Sep. 2000;74(18):8307-15. doi: 10.1128/jvi.74.18.8307-8315.2000.

Mangeot et al., Protein transfer into human cells by VSV-G-induced nanovesicles. Mol Ther. Sep. 2011;19(9):1656-66. doi: 10.1038/mt.2011.138. Epub Jul. 12, 2011.

Meng et al., Identification of an HLA-DPB1*0501 restricted Melan-A/MART-1 epitope recognized by CD4+ T lymphocytes: prevalence for immunotherapy in Asian populations. J Immunother. Sep. 2011;34(7):525-34. doi: 10.1097/CJI.0b013e318226bd45. Author Manuscript. 16 pages.

Michaux et al., A spliced antigenic peptide comprising a single spliced amino acid is produced in the proteasome by reverse splicing of a longer peptide fragment followed by trimming. J Immunol. Feb. 15, 2014;192(4):1962-71. doi: 10.4049/jimmunol.1302032. Epub Jan. 22, 2014.

(56) References Cited

OTHER PUBLICATIONS

Momose et al., Diving into marine genomics with CRISPR/Cas9 systems. Mar Genomics. Dec. 2016;30:55-65. doi: 10.1016/j.margen.2016.10.003. Epub Oct. 12, 2016.

Morel et al., A tyrosinase peptide presented by HLA-B35 is recognized on a human melanoma by autologous cytotoxic T lymphocytes. Int J Cancer. Dec. 10, 1999;83(6):755-9. doi: 10.1002/(sici)1097-0215(19991210)83:6<755::aid-ijc10>3.0.co;2-s.

Mselli-Lakhal et al., Gene transfer system derived from the caprine arthritis-encephalitis lentivirus. J Virol Methods. Sep. 2006;136(1-2):177-84. doi: 10.1016/j.jviromet.2006.05.006. Epub Jun. 21, 2006.

Murawski et al., Newcastle disease virus-like particles containing respiratory syncytial virus G protein induced protection in BALB/c mice, with No. evidence of immunopathology. J Virol. Jan. 2010;84(2):1110-23. doi: 10.1128/JVI.01709-09. Epub Nov. 4, 2009.

Naskalska et al., Virus Like Particles as Immunogens and Universal Nanocarriers. Pol J Microbiol. 2015;64(1):3-13.

Negre et al., Characterization of novel safe lentiviral vectors derived from simian immunodeficiency virus (SIVmac251) that efficiently transduce mature human dendritic cells. Gene Ther. Oct. 2000;7(19):1613-23. doi: 10.1038/sj.gt.3301292.

Noppen et al., Naturally processed and concealed HLA-A2.1-restricted epitopes from tumor- associated antigen tyrosinase-related protein-2. Int J Cancer. Jul. 15, 2000;87(2):241-6.

Nukaya et al., Identification of HLA-A24 epitope peptides of carcinoembryonic antigen which induce tumor-reactive cytotoxic T lymphocyte. Int J Cancer. Jan. 5, 1999;80(1):92-7. doi: 10.1002/(sici)1097-0215(19990105)80:1<92::aid-ijc18>3.0.co;2-m.

Ogasawara et al., Recombinant viral-like particles of parvovirus B19 as antigen carriers of anthrax protective antigen. In Vivo. May-Jun. 2006;20(3):319-24.

Ohminami et al., HLA class I-restricted lysis of leukemia cells by a CD8(+) cytotoxic T- lymphocyte clone specific for WT1 peptide. Blood. Jan. 1, 2000;95(1):286-93.

Oka et al., WT1 peptide vaccine for the treatment of cancer. Curr Opin Immunol. Apr. 2008;20(2):211-20. doi: 10.1016/j.coi.2008.04.009. Epub May 24, 2008.

Olsen, J.C., Gene transfer vectors derived from equine infectious anemia virus. Gene Ther. Nov. 1998;5(11):1481-7. doi: 10.1038/sj.gt.3300768.

Olson et al., HLA-A2-restricted T-cell epitopes specific for prostatic acid phosphatase. Cancer Immunol Immunother. Jun. 2010;59(6):943-53. doi: 10.1007/s00262-010-0820-6. Epub Feb. 6, 2010.

Osen et al., Screening of human tumor antigens for CD4 T cell epitopes by combination of HLA-transgenic mice, recombinant adenovirus and antigen peptide libraries. PLoS One. Nov. 30, 2010;5(11):e14137. doi: 10.1371/journal.pone.0014137.

Parkhurst et al., Identification of a shared HLA-A*0201-restricted T-cell epitope from the melanoma antigen tyrosinase-related protein 2 (TRP2). Cancer Res. Nov. 1, 1998;58(21):4895-901.

Parkhurst et al., Induction of CD4+ Th1 lymphocytes that recognize known and novel class II MHC restricted epitopes from the melanoma antigen gp100 by stimulation with recombinant protein. J Immunother. Mar.-Apr. 2004;27(2):79-91. doi: 10.1097/00002371-200403000-00001. Author Manuscript. 22 pages.

Paschen et al., Detection of spontaneous CD4+ T-cell responses in melanoma patients against a tyrosinase-related protein-2-derived epitope identified in HLA-DRB1*0301 transgenic mice. Clin Cancer Res. Jul. 15, 2005;11(14):5241-7. doi: 10.1158/1078-0432.CCR-05-0170.

Pinilla et al., Combinatorial peptide libraries as an alternative approach to the identification of ligands for tumor-reactive cytolytic T lymphocytes. Cancer Res. Jul. 1, 2001;61(13):5153-60.

Pinilla-Ibarz et al., Improved human T-cell responses against synthetic HLA-0201 analog peptides derived from the WT1 oncoprotein. Leukemia. Nov. 2006;20(11):2025-33. doi: 10.1038/sj.leu.2404380. Epub Aug. 31, 2006.

Prather et al., De novo biosynthetic pathways: rational design of microbial chemical factories. Curr Opin Biotechnol. Oct. 2008; 19(5):468-74. doi: 10.1016/j.copbio.2008.07.009. Epub Sep. 5, 2008.

Quan et al., Influenza M1 VLPs containing neuraminidase induce heterosubtypic cross- protection. Virology. Sep. 1, 2012;430(2):127-35. doi: 10.1016/j.virol.2012.05.006. Epub Jun. 2, 2012.

Rasmussen et al., Characterization of virus-like particles produced by a recombinant baculovirus containing the gag gene of the bovine immunodeficiency-like virus. Virology. Oct. 1990; 178(2):435-51. doi: 10.1016/0042-6822(90)90341-n.

Riley et al., Identification of a new shared HLA-A2.1 restricted epitope from the melanoma antigen tyrosinase. J Immunother. May-Jun. 2001;24(3):212-20.

Rimoldi et al., Efficient simultaneous presentation of NY-ESO-1/LAGE-1 primary and nonprimary open reading frame-derived CTL epitopes in melanoma. J Immunol. Dec. 15, 2000;165(12):7253-61. doi: 10.4049/jimmunol.165.12.7253.

Robbins et al., Multiple HLA class II-restricted melanocyte differentiation antigens are recognized by tumor-infiltrating lymphocytes from a patient with melanoma. J Immunol. Nov. 15, 2002;169(10):6036-47. doi: 10.4049/jimmunol.169.10.6036.

Robbins et al., The intronic region of an incompletely spliced gp100 gene transcript encodes an epitope recognized by melanoma-reactive tumor-infiltrating lymphocytes. J Immunol. Jul. 1, 1997;159(1):303-8.

Rohovie et al., Virus-like particles: Next-generation nanoparticles for targeted therapeutic delivery. Bioeng Transl Med. Jan. 19, 2017;2(1):43-57. doi: 10.1002/btm2.10049.

Rosenberg et al., Immunologic and therapeutic evaluation of a synthetic peptide vaccine for the treatment of patients with metastatic melanoma. Nat Med. Mar. 1998;4(3):321-7. doi: 10.1038/nm0398-321.

Rubio-Godoy et al., Toward synthetic combinatorial peptide libraries in positional scanning format (PS-SCL)-based identification of CD8+ Tumor-reactive T-Cell Ligands: a comparative analysis of PS-SCL recognition by a single tumor-reactive CD8+ cytolytic T-lymphocyte clone. Cancer Res. Apr. 1, 2002;62(7):2058-63.

Ruiz et al., Identification and characterization of a T-helper peptide from carcinoembryonic antigen. Clin Cancer Res. Apr. 15, 2004;10(8):2860-7. doi: 10.1158/1078-0432.ccr-03-0476.

Rusk, Cas9 and the importance of asymmetry. Nat Methods. Apr. 2016;13(4):286-7. doi: 10.1038/nmeth.3826.

Saenger et al., Improved tumor immunity using anti-tyrosinase related protein-1 monoclonal antibody combined with DNA vaccines in murine melanoma. Cancer Res. Dec. 1, 2008;68(23):9884-91. doi: 10.1158/0008-5472.CAN-08-2233. Author Manuscript. 19 pages.

Saenz et al., Feline immunodeficiency virus-based lentiviral vectors. Cold Spring Harb Protoc. Jan. 1, 2012;2012(1):71-6. doi: 10.1101/pdb.ip067579.

Saenz et al., Production, harvest, and concentration of feline immunodeficiency virus-based lentiviral vector from cells grown in CF10 or CF2 devices. Cold Spring Harb Protoc. Jan. 1, 2012;2012(1):118-23. doi: 10.1101/pdb.prot067546.

Schneider et al., Overlapping peptides of melanocyte differentiation antigen Melan- A/MART-1 recognized by autologous cytolytic T lymphocytes in association with HLA-B45.1 and HLA-A2.1. Int J Cancer. Jan. 30, 1998;75(3):451-8. doi: 10.1002/(sici)1097-0215(19980130)75:3<451::aid-ijc20>3.0.co;2-a.

Sensi et al., Identification of a novel gp100/pMel17 peptide presented by HLA-A*6801 and recognized on human melanoma by cytolytic T cell clones. Tissue Antigens. Apr. 2002;59(4):273-9. doi: 10.1034/j.1399-0039.2002.590404.x.

Shang et al., The spontaneous CD8+ T-cell response to HLA-A2-restricted NY-ESO-1b peptide in hepatocellular carcinoma patients. Clin Cancer Res. Oct. 15, 2004;10(20):6946-55. doi: 10.1158/1078-0432.CCR-04-0502.

Sharma et al., Noninfectious virus-like particles produced by Moloney murine leukemia virus-based retrovirus packaging cells deficient in viral envelope become infectious in the presence of lipofection reagents. Proc Natl Acad Sci U S A. Sep. 30, 1997;94(20):10803-8. doi: 10.1073/pnas.94.20.10803.

Shellenberger et al., A recombinant polypeptide extends the in vivo half-life of peptides and proteins in a tunable manner. Nat Biotechnol. Dec. 2009;27(12):1186-90. doi: 10.1038/nbt.1588.

(56) References Cited

OTHER PUBLICATIONS

Shen et al., Identification of a MHC class-II restricted epitope in carcinoembryonic antigen. Cancer Immunol Immunother. May 2004;53(5):391-403. doi: 10.1007/s00262-003-0455-y. Epub Nov. 18, 2003.
Skipper et al., An HLA-A2-restricted tyrosinase antigen on melanoma cells results from posttranslational modification and suggests a novel pathway for processing of membrane proteins. J Exp Med. Feb. 1, 1996;183(2):527-34. doi: 10.1084/jem.183.2.527.
Skipper et al., Shared epitopes for HLA-A3-restricted melanoma-reactive human CTL include a naturally processed epitope from Pmel-17/gp100. J Immunol. Dec. 1, 1996;157(11):5027-33.
Slansky et al., Enhanced antigen-specific antitumor immunity with altered peptide ligands that stabilize the MHC-peptide-TCR complex. Immunity. Oct. 2000;13(4):529-38. doi: 10.1016/s1074-7613(00)00052-2.
Slingluff et al., Clinical and immunologic results of a randomized phase II trial of vaccination using four melanoma peptides either administered in granulocyte-macrophage colony-stimulating factor in adjuvant or pulsed on dendritic cells. J Clin Oncol. Nov. 1, 2003;21(21):4016-26. doi: 10.1200/JCO.2003.10.005.
Slingluff et al., Immunologic and clinical outcomes of vaccination with a multiepitope melanoma peptide vaccine plus low-dose interleukin-2 administered either concurrently or on a delayed schedule. J Clin Oncol. Nov. 15, 2004;22(22):4474-85. doi: 10.1200/JCO.2004.10.212.
Tangri et al., Structural features of peptide analogs of human histocompatibility leukocyte antigen class I epitopes that are more potent and immunogenic than wild-type peptide. J Exp Med. Sep. 17, 2001;194(6):833-46. doi: 10.1084/jem.194.6.833.
Tomé-Amat et al., Secreted production of assembled Norovirus virus-like particles from Pichia pastoris. Microb Cell Fact. Sep. 10, 2014;13:134. doi: 10.1186/s12934-014-0134-z.
Topalian et al., Melanoma-specific CD4+ T cells recognize nonmutated HLA-DR-restricted tyrosinase epitopes. J Exp Med. May 1, 1996;183(5):1965-71. doi: 10.1084/jem.183.5.1965.
Touloukian et al., Expression of a "self-"antigen by human tumor cells enhances tumor antigen-specific CD4(+) T-cell function. Cancer Res. Sep. 15, 2002;62(18):5144-7. Author Manuscript. 11 pages.
Touloukian et al., Identification of a MHC class II-restricted human gp100 epitope using DR4-IE transgenic mice. J Immunol. Apr. 1, 2000;164(7):3535-42. doi: 10.4049/jimmunol.164.7.3535.
Touloukian et al., Normal tissue depresses while tumor tissue enhances human T cell responses in vivo to a novel self/tumor melanoma antigen, OA1. J Immunol. Feb. 1, 2003;170(3):1579-85. doi: 10.4049/jimmunol.170.3.1579.
Trojan et al., Generation of cytotoxic T lymphocytes against native and altered peptides of human leukocyte antigen-A*0201 restricted epitopes from the human epithelial cell adhesion molecule. Cancer Res. Jun. 15, 2001;61(12):4761-5.
Tsai et al., Identification of subdominant CTL epitopes of the GP100 melanoma-associated tumor antigen by primary in vitro immunization with peptide-pulsed dendritic cells. J Immunol. Feb. 15, 1997;158(4):1796-802.
Tsang et al., A human cytotoxic T-lymphocyte epitope and its agonist epitope from the nonvariable No. of tandem repeat sequence of MUC-1. Clin Cancer Res. Mar. 15, 2004;10(6):2139-49. doi: 10.1158/1078-0432.ccr-1011-03.
Tsang et al., Generation of human cytotoxic T cells specific for human carcinoembryonic antigen epitopes from patients immunized with recombinant vaccinia-CEA vaccine. J Natl Cancer Inst. Jul. 5, 1995;87(13):982-90. doi: 10.1093/jnci/87.13.982.
Tsuboi et al., Enhanced induction of human WT1-specific cytotoxic T lymphocytes with a 9- mer WT1 peptide modified at HLA-A*2402-binding residues. Cancer Immunol Immunother. Dec. 2002;51(11-12):614-20. doi: 10.1007/s00262-002-0328-9. Epub Oct. 18, 2002.
Tuorto et al., Genome recoding by tRNA modifications. Open Biol. Dec. 2016;6(12):160287. doi: 10.1098/rsob.160287.
Tycko et al., Methods for Optimizing CRISPR-Cas9 Genome Editing Specificity. Mol Cell. Aug. 4, 2016;63(3):355-70. doi: 10.1016/j.molcel.2016.07.004.
Valmori et al., Analysis of the cytolytic T lymphocyte response of melanoma patients to the naturally HLA-A*0201-associated tyrosinase peptide 368-376. Cancer Res. Aug. 15, 1999;59(16):4050-5.
Valmori et al., Enhanced generation of specific tumor-reactive CTL in vitro by selected Melan-A/MART-1 immunodominant peptide analogues. J Immunol. Feb. 15, 1998;160(4):1750-8.
Valmori et al., Naturally occurring human lymphocyte antigen-A2 restricted CD8+ T-cell response to the cancer testis antigen NY-ESO-1 in melanoma patients. Cancer Res. Aug. 15, 2000;60(16):4499-506.
Vigneron et al., A peptide derived from melanocytic protein gp100 and presented by HLA-B35 is recognized by autologous cytolytic T lymphocytes on melanoma cells. Tissue Antigens. Feb. 2005;65(2):156-62. doi: 10.1111/j.1399-0039.2005.00365.x.
Vigneron et al., An antigenic peptide produced by peptide splicing in the proteasome. Science. Apr. 23, 2004;304(5670):587-90. doi: 10.1126/science.1095522.
Visseren et al., Affinity, specificity and T-cell-receptor diversity of melanoma-specific CTL generated in vitro against a single tyrosinase epitope. Int J Cancer. Sep. 17, 1997;72(6):1122-8. doi: 10.1002/(sici)1097-0215(19970917)72:6<1122::aid-ijc30>3.0.co;2-3.
Voelkel et al., Protein transduction from retroviral Gag precursors. Proc Natl Acad Sci U S A. Apr. 27, 2010;107(17):7805-10. doi: 10.1073/pnas.0914517107. Epub Apr. 12, 2010.
Volpe et al., Alternative BCR/ABL splice variants in Philadelphia chromosome-positive leukemias result in novel tumor-specific fusion proteins that may represent potential targets for immunotherapy approaches. Cancer Res. Jun. 1, 2007;67(11):5300-7. doi: 10.1158/0008-5472.CAN-06-3737.
Voutev et al., Bxb1 phage recombinase assists genome engineering in Drosophila melanogaster. Biotechniques. Jan. 1, 2017;62(1):37-38. doi: 10.2144/000114494.
Walpita et al., Mammalian Cell-Derived Respiratory Syncytial Virus-Like Particles Protect the Lower as well as the Upper Respiratory Tract. PLoS One. Jul. 14, 2015;10(7):e0130755. doi: 10.1371/journal.pone.0130755.
Walton et al., Spontaneous CD8 T cell responses against the melanocyte differentiation antigen RAB38/NY-MEL-1 in melanoma patients. J Immunol. Dec. 1, 2006;177(11):8212-8. doi: 10.4049/jimmunol.177.11.8212.
Wang et al., CRISPR/Cas9 in Genome Editing and Beyond. Annu Rev Biochem. Jun. 2, 2016;85:227-64. doi: 10.1146/annurev-biochem-060815-014607. Epub Apr. 25, 2016.
Wang et al., Recognition of an antigenic peptide derived from tyrosinase-related protein-2 by CTL in the context of HLA-A31 and -A33. J Immunol. Jan. 15, 1998;160(2):890-7.
Wang et al., Recognition of breast cancer cells by CD8+ cytotoxic T-cell clones specific for NY-BR-1. Cancer Res. Jul. 1, 2006;66(13):6826-33. doi: 10.1158/0008-5472.CAN-05-3529.
Wang et al., Utilization of an alternative open reading frame of a normal gene in generating a novel human cancer antigen. J Exp Med. Mar. 1, 1996;183(3):1131-40. doi: 10.1084/jem.183.3.1131.
Wang et al., Virus-like particles for the prevention of human papillomavirus-associated malignancies. Expert Rev Vaccines. Feb. 2013; 12(2):129-41. doi: 10.1586/erv.12.151. Author Manuscript, 22 pages.
Wölfel et al., Two tyrosinase nonapeptides recognized on HLA-A2 melanomas by autologous cytolytic T lymphocytes. Eur J Immunol. Mar. 1994;24(3):759-64. doi: 10.1002/eji.1830240340.
Yang et al., HIV-1 virus-like particles produced by stably transfected Drosophila S2 cells: a desirable vaccine component. J Virol. Jul. 2012;86(14):7662-76. doi: 10.1128/JVI.07164-11. Epub May 2, 2012.
Yee et al., A general method for the generation of high-titer, pantropic retroviral vectors: highly efficient infection of primary hepatocytes. Proc Natl Acad Sci U S A. Sep. 27, 1994;91(20):9564-8. doi: 10.1073/pnas.91.20.9564.
Yu et al., Poor immunogenicity of a self/tumor antigen derives from peptide-MHC-I instability and is independent of tolerance. J Clin Invest. Aug. 2004; 114(4):551-9. doi: 10.1172/JCI21695.

(56) References Cited

OTHER PUBLICATIONS

Zarour et al., Melan-A/MART-1(51-73) represents an immunogenic HLA-DR4-restricted epitope recognized by melanoma-reactive CD4(+) T cells. Proc Natl Acad Sci U S A. Jan. 4, 2000;97(1):400-5. doi: 10.1073/pnas.97.1.400.
Zeltins, A., Construction and characterization of virus-like particles: a review. Mol Biotechnol. Jan. 2013;53(1):92-107. doi: 10.1007/s12033-012-9598-4.
Zhang et al., CRISPR-Cpf1 correction of muscular dystrophy mutations in human cardiomyocytes and mice. Sci Adv. Apr. 12, 2017;3(4):e1602814. doi: 10.1126/sciadv.1602814.
Zhao et al., Study on p21 gene knock out in G401 cell line by using CRISPR/Cas9 system. Tianjin Med J. Oct. 2016;44(10):1190-1194.

* cited by examiner

SEQUENCE LISTING

```
Sequence total quantity: 203
SEQ ID NO: 1           moltype = DNA  length = 4104
FEATURE                Location/Qualifiers
source                 1..4104
                       mol_type = genomic DNA
                       organism = Streptococcus pyogenes
SEQUENCE: 1
atggataaga aatactcaat aggcttagat atcggcacaa atagcgtcgg atgggcggtg  60
atcactgatg attataaggt tccgtctaaa aagttcaagg ttctgggaaa tacagaccgc  120
cacagtatca aaaaaaatct tataggggct cttttatttg gcagtggaga gacagcggaa  180
gcgactcgtc tcaaacggac agctcgtaga aggtatacac gtcggaagaa tcgtatttgt  240
tatctacagg agattttttc aaatgagatg gcgaaagtag atgatagttt ctttcatcga  300
cttgaagagt ctttttggt ggaagaagac aagaagcatg aacgtcatcc tatttttgga  360
aatatagtag atgaagttgc ttatcatgag aaatatccaa ctatctatca tctgcgaaaa  420
aaattggcag attctactga taaagcggat ttgcgcttaa tctatttggc cttagcgcat  480
atgattaagt ttcgtggtca tttttgatt gagggagatt taaatcctga taatagtgat  540
gtggacaaac tatttatcca gttggtacaa atctacaatc aattatttga agaaaaccct  600
attaacgcaa gtagagtaga tgctaaagcg attctttctg cacgattgag taaatcaaga  660
cgattagaaa atctcattgc tcagctcccc ggtgagaaga gaaatggctt gtttgggaat  720
ctcattgctt tgtcattggg attgacccct aattttaaat caaattttga tttggcagaa  780
gatgctaaat tacagctttc aaaagatact tacgatgatg atttagataa tttattggcg  840
caaattggag atcaatatgc tgatttgttt ttggcagcta agaatttatc agatgctatt  900
ttactttcag atatcctaag agtaaatagt gaaataacta aggctcccct atcagcttca  960
atgattaagc gctacgatga acatcatcaa gacttgactc ttttaaaagc tttagttcga  1020
caacaacttc cagaaaagta taaagaaatc tttttgatc aatcaaaaaa cggatatgca  1080
ggttatattg atgggggagc tagccaagaa gaattttata aatttatcaa accaatttta  1140
gaaaaaatgg atggtactga ggaattattg gtgaaactaa atcgtgaaga tttgctgcgc  1200
aagcaacgga cctttgacaa cggctctatt ccccatcaaa ttcacttggg tgagctgcat  1260
gctattttga gaagacaaga agacttttat ccatttttaa aagacaatcg tgagaagatt  1320
gaaaaaatct tgacttttcg aattccttat tatgttggtc cattggcgcg tggcaatagt  1380
cgttttgcat ggatgactcg gaagtctgaa gaaacaatta ccccatggaa ttttgaagaa  1440
gttgtcgata aaggtgcttc agctcaatca tttattgaac gcatgacaaa ctttgataaa  1500
aatcttccaa atgaaaaagt actaccaaaa catagtttgc tttatgagta ttttacggtt  1560
tataacgaat tgacaaaggt caaatatgtt actgagggaa tgcgaaaacc agcatttctt  1620
tcaggtgaac agaagaaagc cattgttgat ttactcttca aaacaaatcg aaaagtaacc  1680
gttaagcaat taaaagaaga ttatttcaaa aaaatagaat gttttgatag tgttgaaatt  1740
tcaggagttg aagatagatt taatgcttca ttaggcgcct accatgattt gctaaaaatt  1800
attaaagata aagatttttt ggataatgaa gaaaatgaag atatcttaga ggatattgtt  1860
ttaacattga ccttatttga agataggggg atgattgagg aaagacttaa aacatatgct  1920
cacctctttg atgataaggt gatgaaacag cttaaacgtc gccgttatac tggttgggga  1980
cgtttgtctc gaaaattgat taatggtatt agggataagc aatctggcaa aacaatatta  2040
gatttttga aatcagatgg ttttgccaat cgcaatttta tgcagctgat ccatgatgat  2100
agtttgacat ttaaagaaga tattcaaaaa gcacaggtgt ctggacaagg ccatagttta  2160
catgaacaga ttgctaactt agctggcagt cctgctatta aaaaaggtat tttacagact  2220
gtaaaaattg ttgatgaact ggtcaaagta atggggcata agccagaaaa tatcgttatt  2280
gaaatggcac gtgaaaatca gacaactcaa aagggccaga aaaattcgcg agagcgtatg  2340
aaacgaatcg aagaaggtat caaagaatta ggaagtcaga ttcttaaaga gcatcctgtt  2400
gaaaatactc aattgcaaaa tgaaaagctc tatctctatt atctacaaaa tggaagagac  2460
atgtatgtgg accaagaatt agatattaat cgtttaagtg attatgatgt cgatcacatt  2520
gttccacaaa gtttcattaa agacgattca atagacaata aggtactaac gcgttctgat  2580
aaaaatcgtg gtaaatcgga taacgttcca agtgaagaag tagtcaaaaa gatgaaaaac  2640
tattggagac aacttctaaa cgccaagtta atcactcaac gtaagtttga taatttaacg  2700
aaagctgaac gtggaggttt gagtgaactt gataaagctg gttttatcaa acgccaattg  2760
gttgaaactc gccaaatcac taagcatgtg gcacaaattt tggatagtcg catgaatact  2820
aaatacgatg aaaatgataa acttattcga gaggttaaag tgattacctt aaaatctaaa  2880
ttagtttctg acttccgaaa agatttccaa ttctataaag tacgtgagat taacaattac  2940
catcatgccc atgatgcgta tctaaatgcc gtcgttggaa ctgctttgat taagaaatat  3000
ccaaaacttg aatcggagtt tgtctatggt gattataaag tttatgatgt tcgtaaaatg  3060
attgctaagt ctgagcaaga aataggcaaa gcaaccgcaa aatatttctt ttactctaat  3120
atcatgaact tcttcaaaac agaaattaca cttgcaaatg gagagattcg caaacgccct  3180
ctaatcgaaa ctaatgggga aactggagaa attgtctggg ataaagggcg agattttgcc  3240
acagtgcgca aagtattgtc catgccccaa gtcaatattg tcaagaaaac agaagtacag  3300
acaggcggat tctccaagga gtcaatttta ccaaaaagaa attcggacaa gcttattgct  3360
cgtaaaaaag actgggatcc aaaaaaatat ggtggttttg atagtccaac ggtagcttat  3420
tcagtcctag tggttgctaa ggtggaaaaa gggaaatcga agaagttaaa atccgttaaa  3480
gagttactag ggatcacaat tatggaaaga agttcctttg aaaaaaatcc gattgacttt  3540
ttagaagcta aaggatataa ggaagttaaa aaagacttaa tcattaaact acctaaatat  3600
agtcttttg agttagaaaa cggtcgtaaa cggatgctgg ctagtgccgg agaattacaa  3660
aaaggaaatg agctggctct gccaagcaaa tatgtgaatt ttttatattt agctagtcat  3720
tatgaaaagt tgaagggtag tccagaagat aacgaacaaa aacaattgtt tgtggagcag  3780
cataagcatt atttagatga gattattgag caaatcagtg aattttctaa gcgtgttatt  3840
ttagcagatg ccaatttaga taaagttctt agtgcatata acaaacatag agacaaacca  3900
atacgtgaac aagcagaaaa tattattcat ttatttacgt tgacgaatct tggagctccc  3960
gctgctttta aatattttga tacaacaatt gatcgtaaac gatatacgtc tacaaaagaa  4020
gttttagatg ccactcttat ccatcaatcc atcactggtc tttatgaaac acgcattgat  4080
ttgagtcagc taggaggtga ctga                                        4104
```

-continued

```
SEQ ID NO: 2            moltype = AA  length = 1368
FEATURE                 Location/Qualifiers
source                  1..1368
                        mol_type = protein
                        organism = Streptococcus pyogenes
SEQUENCE: 2
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD              1368

SEQ ID NO: 3            moltype = DNA  length = 4104
FEATURE                 Location/Qualifiers
source                  1..4104
                        mol_type = genomic DNA
                        organism = Homo sapiens
SEQUENCE: 3
atggataaaa agtattctat tggtttagac atcggcacta attccgttgg atgggctgtc  60
ataaccgatg aatacaaagt accttcaaag aaatttaagg tgttggggaa cacagaccgt  120
cattcgatta aaaagaatct tatcggtgcc ctcctattcg atagtggcga aacggcagag  180
gcgactcgcc tgaaacgaac cgctcggaga aggtatacac gtcgcaagaa ccgaatatgt  240
tacttacaag aaatttttag caatgagatg gccaaagttg acgattcttt ctttcaccgt  300
ttggaagagt ccttccttgt cgaagaggac aagaaacatg aacggcaccc catctttgga  360
aacatagtag atgaggtggc atatcatgaa aagtacccaa cgatttatca cctcagaaaa  420
aagctagttg actcaactga taaagcggac ctgaggttaa tctacttggc tcttgcccat  480
atgataaagt tccgtgggca ctttctcatt gagggtgatc taaatccgga caactcggat  540
gtcgacaaac tgttcatcca gttagtacaa acctataatc agttgtttga agagaaccct  600
ataaatgcaa gtggcgtgga tgcgaaggct attcttagcg cccgcctctc taaatcccga  660
cggctagaaa acctgatcgc acaattaccc ggagagaaga aaaatgggtt gttcggtaac  720
cttatagcgc tctcactagg cctgacacca aattttaagt cgaacttcga cttagctgaa  780
gatgccaaat tgcagcttag taaggacacg tacgatgacg atctcgacaa tctactggca  840
caaattggag atcagtatgc ggacttattt ttggctgcca aaaaccttag cgatgcaatc  900
ctcctatctg acatactgag agttaatact gagattacca aggcgccgtt atccgcttca  960
atgatcaaaa ggtacgatga acatcaccaa gacttgacac ttctcaaggc cctagtccgt  1020
cagcaactgc ctgagaaata taaggaaata ttctttgatc agtcgaaaaa cgggtacgca  1080
ggttatattg acggcggagc gagtcaagag gaattctaca agtttatcaa acccatatta  1140
gagaagatgg atgggacgga agagttgctt gtaaaactca atcgcgaaga tctactgcga  1200
aagcagcgga ctttcgacaa cggtagcatt ccacatcaaa tccacttagg cgaattgcat  1260
gctatactta gaaggcagga ggatttttat ccgttcctca aagacaatcg tgaaaagatt  1320
gagaaaatcc taacctttcg cataccttac tatgtgggac ccctggcccg agggaactct  1380
cggttcgcat ggatgacaag aaagtccgaa gaaacgatta ctccatggaa ttttgaggaa  1440
gttgtcgata aaggtgcgtc agctcaatcg ttcatcgaga ggatgaccaa ctttgacaag  1500
aatttaccga acgaaaaagt attgcctaag cacagtttac tttacgagta tttcacagtg  1560
tacaatgaac tcacgaaagt taagtatgtc actgagggca tgcgtaaacc cgcctttcta  1620
agcggagaac agaagaaagc aatagtagat ctgttattca agaccaaccg caaagtgaca  1680
gttaagcaat tgaaagagga ctactttaag aaaattgaat gcttcgattc tgtcgagatc  1740
tccggggtag aagatcgatt taatgcgtca cttggtacgt atcatgacct cctaaagata  1800
attaaagata aggacttcct ggataacgaa gagaatgaag atatcttaga agatatagtg  1860
ttgactctta ccctctttga agatcgggaa atgattgagg aaagactaaa aacatacgct  1920
cacctgttcg acgataaggt tatgaaacag ttaaagaggc gtcgctatac gggctgggga  1980
cgattgtcgc ggaaacttat caacgggata agagacaagc aaagtggtaa aactattctc  2040
gattttctaa agagcgacgg cttcgccaat aggaacttta tgcagctgat ccatgatgac  2100
tctttaacct tcaaagagga tatacaaaag gcacaggttt ccggacaagg ggactcattg  2160
cacgaacata ttgcgaatct tgctggttcg ccagccatca aaaagggcat actccagaca  2220
gtcaaagtag tggatgagct agttaaggtc atgggacgtc acaaaccgga aaacattgta  2280
atcgagatgg cacgcgaaaa tcaaacgact cagaaggggc aaaaaaacag tcgagagcgg  2340
atgaagagaa tagaagaggg tattaaagaa ctgggcagcc agatcttaaa ggagcatcct  2400
gtggaaaata cccaattgca gaacgagaaa ctttacctct attacctaca aaatggaagg  2460
gacatgtatg ttgatcagga actggacata aaccgtttat ctgattacga cgtcgatcac  2520
```

-continued

```
attgtacccc aatccttttt gaaggacgat tcaatcgaca ataaagtgct tacacgctcg  2580
gataagaacc gagggaaaag tgacaatgtt ccaagcgagg aagtcgtaaa gaaaatgaag  2640
aactattggc ggcagctcct aaatgcgaaa ctgataacgc aaagaaagtt cgataactta  2700
actaaagctg agaggggtgg cttgtctgaa cttgacaagg ccggatttat taaacgtcag  2760
ctcgtggaaa cccgccaaat cacaaagcat gttgcacaga tactagattc ccgaatgaat  2820
acgaaatacg acgagaacga taagctgatt cgggaagtca aagtaatcac tttaaagtca  2880
aaattggtgt cggacttcag aaaggatttt caattctata aagttaggga gataaataac  2940
taccaccatg cgcacgacgc ttatcttaat gccgtcgtag ggaccgcact cattaagaaa  3000
tacccgaagc tagaaagtga gtttgtgtat ggtgattaca aagtttatga cgtccgtaag  3060
atgatcgcga aaagcgaaca ggagataggc aaggctacag ccaaatactt cttttattct  3120
aacattatga atttctttaa gacggaaatc actctggcaa acggagagat acgcaaacga  3180
cctttaattg aaaccaatgg ggagacaggt gaaatcgtat gggataaggg ccgggacttc  3240
gcgacggtga gaaaagtttt gtccatgccc caagtcaaca tagtaaagaa aactgaggtg  3300
cagaccggag ggttttcaaa ggaatcgatt cttccaaaaa ggaatagtga taagctcatc  3360
gctcgtaaaa aggactggga cccgaaaaag tacggtggct tcgatagccc tacagttgcc  3420
tattctgtcc tagtagtggc aaaagttgag aagggaaaat ccaagaaact gaagtcagtc  3480
aaagaattat tggggataac gattatggag cgctcgtctt ttgaaaagaa ccccatcgac  3540
ttccttgagg cgaaaggtta caaggaagta aaaaaggatc tcataattaa actaccaaag  3600
tatagtctgt ttgagttaga aaatggccga aaacggatgt tggctagcgc cggagagctt  3660
caaaagggga acgaactcgc actaccgtct aaatacgtga atttcctgta tttagcgtcc  3720
cattacgaga agttgaaagg ttcacctgaa gataacgaac agaagcaact tttgttgag  3780
cagcacaaac attatctcga cgaaatcata gagcaaattt cggaattcag taagagagtc  3840
atcctagctg atgccaatct ggacaaagta ttaagcgcat acaacaagca cagggataaa  3900
cccatacgtg agcaggcgga aaatattatc catttgttta ctcttaccaa cctcggcgct  3960
ccagccgcat tcaagtattt tgacacaacg atagatcgca aacgatacac ttctaccaag  4020
gaggtgctag acgcgacact gattcaccaa tccatcacgg gattatatga aactcggata  4080
gatttgtcac agcttggggg tgac                                         4104

SEQ ID NO: 4           moltype = AA  length = 1368
FEATURE                Location/Qualifiers
REGION                 1..1368
                       note = Synthetic Polypeptide
source                 1..1368
                       mol_type = protein
                       organism = synthetic construct
SEQUENCE: 4
MDKKYSIGLA IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD               1368

SEQ ID NO: 5           moltype = AA  length = 1368
FEATURE                Location/Qualifiers
REGION                 1..1368
                       note = Synthetic Polypeptide
source                 1..1368
                       mol_type = protein
                       organism = synthetic construct
SEQUENCE: 5
MDKKYSIGLA IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
```

```
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDA  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD              1368

SEQ ID NO: 6            moltype = AA  length = 198
FEATURE                 Location/Qualifiers
REGION                  1..198
                        note = Synthetic Polypeptide
source                  1..198
                        mol_type = protein
                        organism = synthetic construct
SEQUENCE: 6
GSQLVKSELE EKKSELRHKL KYVPHEYIEL IEIARNSTQD RILEMKVMEF FMKVYGYRGK  60
HLGGSRKPDG AIYTVGSPID YGVIVDTKAY SGGYNLPIGQ ADEMQRYVEE NQTRNKHINP  120
NEWWKVYPSS VTEFKFLFVS GHFKGNYKAQ LTRLNHITNC NGAVLSVEEL LIGGEMIKAG  180
TLTLEEVRRK FNNGEINF                                                198

SEQ ID NO: 7            moltype = AA  length = 413
FEATURE                 Location/Qualifiers
REGION                  1..413
                        note = Synthetic Polypeptide
source                  1..413
                        mol_type = protein
                        organism = synthetic construct
SEQUENCE: 7
CLAEGTRIFD PVTGTTHRIE DVVDGRKPIH VVAAAKDGTL LARPVVSWFD QGTRDVIGLR  60
IAGGAIVWAT PDHKVLTEYG WRAAGELRKG DRVAGPGGSG NSLALSLTAD QMVSALLDAE  120
PPILYSEYDP TSPFSEASMM GLLTNLADRE LVHMINWAKR VPGFVDLTLH DQAHLLECAW  180
LEILMIGLVW RSMEHPGKLL FAPNLLLDRN QGKCVEGMVE IFDMLLATSS RFRMMNLQGE  240
EFVCLKSIIL LNSGVYTFLS STLKSLEEKD HIHRALDKIT DTLIHLMAKA GLTLQQQHQR  300
LAQLLLILSH IRHMSNKGME HLYSMKYKNV VPLYDLLLEM LDAHRLHAGG SGASRVQAFA  360
DALDDKFLHD MLAEELRYSV IREVLPTRRA RTFDLEVEEL HTLVAEGVVV HNC         413

SEQ ID NO: 8            moltype = AA  length = 413
FEATURE                 Location/Qualifiers
REGION                  1..413
                        note = Synthetic Polypeptide
source                  1..413
                        mol_type = protein
                        organism = synthetic construct
SEQUENCE: 8
CLAEGTRIFD PVTGTTHRIE DVVDGRKPIH VVAVAKDGTL LARPVVSWFD QGTRDVIGLR  60
IAGGAIVWAT PDHKVLTEYG WRAAGELRKG DRVAGPGGSG NSLALSLTAD QMVSALLDAE  120
PPILYSEYDP TSPFSEASMM GLLTNLADRE LVHMINWAKR VPGFVDLTLH DQAHLLECAW  180
LEILMIGLVW RSMEHPGKLL FAPNLLLDRN QGKCVEGMVE IFDMLLATSS RFRMMNLQGE  240
EFVCLKSIIL LNSGVYTFLS STLKSLEEKD HIHRALDKIT DTLIHLMAKA GLTLQQQHQR  300
LAQLLLILSH IRHMSNKGME HLYSMKYTNV VPLYDLLLEM LDAHRLHAGG SGASRVQAFA  360
DALDDKFLHD MLAEELRYSV IREVLPTRRA RTFDLEVEEL HTLVAEGVVV HNC         413

SEQ ID NO: 9            moltype = AA  length = 413
FEATURE                 Location/Qualifiers
REGION                  1..413
                        note = Synthetic Polypeptide
source                  1..413
                        mol_type = protein
                        organism = synthetic construct
SEQUENCE: 9
CLAEGTRIFD PVTGTTHRIE DVVDGRKPIH VVAAAKDGTL LARPVVSWFD QGTRDVIGLR  60
IAGGATVWAT PDHKVLTEYG WRAAGELRKG DRVAGPGGSG NSLALSLTAD QMVSALLDAE  120
PPIPYSEYDP TSPFSEASMM GLLTNLADRE LVHMINWAKR VPGFVDLTLH DQAHLLECAW  180
LEILMIGLVW RSMEHPGKLL FAPNLLLDRN QGKCVEGMVE IFDMLLATSS RFRMMNLQGE  240
EFVCLKSIIL LNSGVYTFLS STLKSLEEKD HIHRALDKIT DTLIHLMAKA GLTLQQQHQR  300
LAQLLLILSH IRHMSNKGME HLYSMKYTNV VPLYDLLLEM LDAHRLHAGG SGASRVQAFA  360
DALDDKFLHD MLAEGLRYSV IREVLPTRRA RTFDLEVEEL HTLVAEGVVV HNC         413

SEQ ID NO: 10           moltype = AA  length = 413
FEATURE                 Location/Qualifiers
REGION                  1..413
                        note = Synthetic Polypeptide
```

```
source                  1..413
                        mol_type = protein
                        organism = synthetic construct
SEQUENCE: 10
CLAEGTRIFD PVTGTTHRIE DVVDGRKPIH VVAAAKDGTL LARPVVSWFD QGTRDVIGLR  60
IAGGATVWAT PDHKVLTEYG WRAAGELRKG DRVAGPGGSG NSLALSLTAD QMVSALLDAE  120
PPILYSEYDP TSPFSEASMM GLLTNLADRE LVHMINWAKR VPGFVDLTLH DQAHLLECAW  180
LEILMIGLVW RSMEHPGKLL FAPNLLLDRN QGKCVEGMVE IFDMLLATSS RFRMMNLQGE  240
EFVCLKSIIL LNSGVYTFLS STLKSLEEKD HIHRALDKIT DTLIHLMAKA GLTLQQQHQR  300
LAQLLLILSH IRHMSNKGME HLYSMKYKNV VPLYDLLLEM LDAHRLHAGG SGASRVQAFA  360
DALDDKFLHD MLAEELRYSV IREVLPTRRA RTFDLEVEEL HTLVAEGVVV HNC         413

SEQ ID NO: 11           moltype = AA  length = 413
FEATURE                 Location/Qualifiers
REGION                  1..413
                        note = Synthetic Polypeptide
source                  1..413
                        mol_type = protein
                        organism = synthetic construct
SEQUENCE: 11
CLAEGTRIFD PVTGTTHRIE DVVDGRKPIH VVAAAKDGTL LARPVVSWFD QGTRDVIGLR  60
IAGGATVWAT PDHKVLTEYG WRAAGELRKG DRVAGPGGSG NSLALSLTAD QMVSALLDAE  120
PPIPYSEYDP TSPFSEASMM GLLTNLADRE LVHMINWAKR VPGFVDLTLH DQAHLLECAW  180
LEILMIGLVW RSMEHPGKLL FAPNLLLDRN QGKCVEGMVE IFDMLLATSS RFRMMNLQGE  240
EFVCLKSIIL LNSGVYTFLS STLKSLEEKD HIHRALDKIT DTLIHLMAKA GLTLQQQHQR  300
LAQLLLILSH IRHMSNKGME HLYSMKYKNV VPLYDLLLEM LDAHRLHAGG SGASRVQAFA  360
DALDDKFLHD MLAEELRYSV IREVLPTRRA RTFDLEVEEL HTLVAEGVVV HNC         413

SEQ ID NO: 12           moltype = AA  length = 413
FEATURE                 Location/Qualifiers
REGION                  1..413
                        note = Synthetic Polypeptide
source                  1..413
                        mol_type = protein
                        organism = synthetic construct
SEQUENCE: 12
CLAEGTRIFD PVTGTTHRIE DVVDGRKPIH VVAAAKDGTL LARPVVSWFD QGTRDVIGLR  60
IAGGATVWAT PDHKVLTEYG WRAAGELRKG DRVAGPGGSG NSLALSLTAD QMVSALLDAE  120
PPILYSEYNP TSPFSEASMM GLLTNLADRE LVHMINWAKR VPGFVDLTLH DQAHLLERAW  180
LEILMIGLVW RSMEHPGKLL FAPNLLLDRN QGKCVEGMVE IFDMLLATSS RFRMMNLQGE  240
EFVCLKSIIL LNSGVYTFLS STLKSLEEKD HIHRALDKIT DTLIHLMAKA GLTLQQQHQR  300
LAQLLLILSH IRHMSNKGME HLYSMKYKNV VPLYDLLLEM LDAHRLHAGG SGASRVQAFA  360
DALDDKFLHD MLAEGLRYSV IREVLPTRRA RTFDLEVEEL HTLVAEGVVV HNC         413

SEQ ID NO: 13           moltype = AA  length = 413
FEATURE                 Location/Qualifiers
REGION                  1..413
                        note = Synthetic Polypeptide
source                  1..413
                        mol_type = protein
                        organism = synthetic construct
SEQUENCE: 13
CLAEGTRIFD PVTGTTHRIE DVVDGRKPIH VVAAAKDGTL LARPVVSWFD QGTRDVIGLR  60
IAGGAIVWAT PDHKVLTEYG WRAAGELRKG DRVAGPGGSG NSLALSLTAD QMVSALLDAE  120
PPILYSEYDP TSPFSEASMM GLLTNLADRE LVHMINWAKR VPGFVDLTLH DQAHLLERAW  180
LEILMIGLVW RSMEHPGKLL FAPNLLLDRN QGKCVEGMVE IFDMLLATSS RFRMMNLQGE  240
EFVCLKSIIL LNSGVYTFLS STLKSLEEKD HIHRALDKIT DTLIHLMAKA GLTLQQQHQR  300
LAQLLLILSH IRHMSNKGME HLYSMKYKNV VPLYDLLLEM LDAHRLHAGG SGASRVQAFA  360
DALDDKFLHD MLAEGLRYSV IREVLPTRRA RTFDLEVEEL HTLVAEGVVV HNC         413

SEQ ID NO: 14           moltype = AA  length = 413
FEATURE                 Location/Qualifiers
REGION                  1..413
                        note = Synthetic Polypeptide
source                  1..413
                        mol_type = protein
                        organism = synthetic construct
SEQUENCE: 14
CLAEGTRIFD PVTGTTHRIE DVVDGRKPIH VVAVAKDGTL LARPVVSWFD QGTRDVIGLR  60
IAGGATVWAT PDHKVLTEYG WRAAGELRKG DRVAGPGGSG NSLALSLTAD QMVSALLDAE  120
PPILYSEYDP TSPFSEASMM GLLTNLADRE LVHMINWAKR VPGFVDLTLH DQAHLLERAW  180
LEILMIGLVW RSMEHPGKLL FAPNLLLDRN QGKCVEGMVE IFDMLLATSS RFRMMNLQGE  240
EFVCLKSIIL LNSGVYTFLS STLKSLEEKD HIHRALDKIT DTLIHLMAKA GLTLQQQHQR  300
LAQLLLILSH IRHMSNKGME HLYSMKYKNV VPLYDLLLEM LDAHRLHAGG SGASRVQAFA  360
DALDDKFLHD MLAEELRYSV IREVLPTRRA RTFDLEVEEL HTLVAEGVVV HNC         413
```

```
SEQ ID NO: 15           moltype = AA  length = 18
FEATURE                 Location/Qualifiers
REGION                  1..18
                        note = Synthetic Polypeptide
source                  1..18
                        mol_type = protein
                        organism = synthetic construct
SEQUENCE: 15
GGSGGSGGSG GSGGSGGS                                             18

SEQ ID NO: 16           moltype = AA  length = 16
FEATURE                 Location/Qualifiers
REGION                  1..16
                        note = Synthetic Polypeptide
source                  1..16
                        mol_type = protein
                        organism = synthetic construct
SEQUENCE: 16
SGSETPGTSE SATPES                                               16

SEQ ID NO: 17           moltype = AA  length = 12
FEATURE                 Location/Qualifiers
REGION                  1..12
                        note = Synthetic Polypeptide
source                  1..12
                        mol_type = protein
                        organism = synthetic construct
SEQUENCE: 17
SGSETPGTSE SA                                                   12

SEQ ID NO: 18           moltype = AA  length = 21
FEATURE                 Location/Qualifiers
REGION                  1..21
                        note = Synthetic Polypeptide
source                  1..21
                        mol_type = protein
                        organism = synthetic construct
SEQUENCE: 18
SGSETPGTSE SATPEGGSGG S                                         21

SEQ ID NO: 19           moltype = AA  length = 15
FEATURE                 Location/Qualifiers
REGION                  1..15
                        note = Synthetic Polypeptide
source                  1..15
                        mol_type = protein
                        organism = synthetic construct
SEQUENCE: 19
VPFLLEPDNI NGKTC                                                15

SEQ ID NO: 20           moltype = AA  length = 12
FEATURE                 Location/Qualifiers
REGION                  1..12
                        note = Synthetic Polypeptide
source                  1..12
                        mol_type = protein
                        organism = synthetic construct
SEQUENCE: 20
GSAGSAAGSG EF                                                   12

SEQ ID NO: 21           moltype = AA  length = 12
FEATURE                 Location/Qualifiers
REGION                  1..12
                        note = Synthetic Polypeptide
source                  1..12
                        mol_type = protein
                        organism = synthetic construct
SEQUENCE: 21
SIVAQLSRPD PA                                                   12

SEQ ID NO: 22           moltype = AA  length = 10
FEATURE                 Location/Qualifiers
REGION                  1..10
                        note = Synthetic Polypeptide
source                  1..10
                        mol_type = protein
                        organism = synthetic construct
```

```
SEQUENCE: 22
MKIIEQLPSA                                                    10

SEQ ID NO: 23          moltype = AA  length = 10
FEATURE                Location/Qualifiers
REGION                 1..10
                       note = Synthetic Polypeptide
source                 1..10
                       mol_type = protein
                       organism = synthetic construct
SEQUENCE: 23
VRHKLKRVGS                                                    10

SEQ ID NO: 24          moltype = AA  length = 12
FEATURE                Location/Qualifiers
REGION                 1..12
                       note = Synthetic Polypeptide
source                 1..12
                       mol_type = protein
                       organism = synthetic construct
SEQUENCE: 24
GHGTGSTGSG SS                                                 12

SEQ ID NO: 25          moltype = AA  length = 7
FEATURE                Location/Qualifiers
REGION                 1..7
                       note = Synthetic Polypeptide
source                 1..7
                       mol_type = protein
                       organism = synthetic construct
SEQUENCE: 25
MSRPDPA                                                       7

SEQ ID NO: 26          moltype = AA  length = 4
FEATURE                Location/Qualifiers
REGION                 1..4
                       note = Synthetic Polypeptide
source                 1..4
                       mol_type = protein
                       organism = synthetic construct
SEQUENCE: 26
GGSM                                                          4

SEQ ID NO: 27          moltype = AA  length = 1780
FEATURE                Location/Qualifiers
REGION                 1..1780
                       note = Synthetic Polypeptide
source                 1..1780
                       mol_type = protein
                       organism = synthetic construct
SEQUENCE: 27
MDKKYSIGLD IGTNSVGWAV ITDEYKVPSK KFKVLGNTDR HSIKKNLIGA LLFDSGETAE  60
ATRLKRTARR RYTRRKNRIC LAEGTRIFDP VTGTTHRIED VVDGRKPIHV VAAAKDGTLL  120
ARPVVSWFDQ GTRDVIGLRI AGGAIVWATP DHKVLTEYGW RAAGELRKGD RVAGPGGSGN  180
SLALSLTADQ MVSALLDAEP PILYSEYDPT SPFSEASMMG LLTNLADREL VHMINWAKRV  240
PGFVDLTLHD QAHLLERAWL EILMIGLVWR SMEHPGKLLF APNLLLDRNQ GKCVEGMVEI  300
FDMLLATSSR FRMMNLQGEE FVCLKSIILL NSGVYTFLSS TLKSLEEKDH IHRALDKITD  360
TLIHLMAKAG LTLQQQHQRL AQLLLILSHI RHMSNKGMEH LYSMKYKNVV PLYDLLLEML  420
DAHRLHAGGS GASRVQAFAD ALDDKFLHDM LAEGLRYSVI REVLPTRRAR TFDLEVEELH  480
TLVAEGVVVH NCYLQEIFSN EMAKVDDSFF HRLEESFLVE EDKKHERHPI FGNIVDEVAY  540
HEKYPTIYHL RKKLVDSTDK ADLRLIYLAL AHMIKFRGHF LIEGDLNPDN SDVDKLFIQL  600
VQTYNQLFEE NPINASGVDA KAILSARLSK SRRLENLIAQ LPGEKKNGLF GNLIALSLGL  660
TPNFKSNFDL AEDAKLQLSK DTYDDDLDNL LAQIGDQYAD LFLAAKNLSD AILLSDILRV  720
NTEITKAPLS ASMIKRYDEH HQDLTLLKAL VRQQLPEKYK EIFFDQSKNG YAGYIDGGAS  780
QEEFYKFIKP ILEKMDGTEE LLVKLNREDL LRKQRTFDNG SIPHQIHLGE LHAILRRQED  840
FYPFLKDNRE KIEKILTFRI PYYVGPLARG NSRFAWMTRK SEETITPWNF EEVVDKGASA  900
QSFIERMTNF DKNLPNEKVL PKHSLLYEYF TVYNELTKVK YVTEGMRKPA FLSGEQKKAI  960
VDLLFKTNRK VTVKQLKEDY FKKIECFDSV EISGVEDRFN ASLGTYHDLL KIIKDKDFLD  1020
NEENEDILED IVLTLTLFED REMIEERLKT YAHLFDDKVM KQLKRRRYTG WGRLSRKLIN  1080
GIRDKQSGKT ILDFLKSDGF ANRNFMQLIH DDSLTFKEDI QKAQVSGQGD SLHEHIANLA  1140
GSPAIKKGIL QTVKVVDELV KVMGRHKPEN IVIEMARENQ TTQKGQKNSR ERMKRIEEGI  1200
KELGSQILKE HPVENTQLQN EKLYLYYLQN GRDMYVDQEL DINRLSDYDV DHIVPQSFLK  1260
DDSIDNKVLT RSDKNRGKSD NVPSEEVVKK MKNYWRQLLN AKLITQRKFD NLTKAERGGL  1320
SELDKAGFIK RQLVETRQIT KHVAQILDSR MNTKYDENDK LIREVKVITL KSKLVSDFRK  1380
DFQFYKVREI NNYHHAHDAY LNAVVGTALI KKYPKLESEF VYGDYKVYDV RKMIAKSEQE  1440
IGKATAKYFF YSNIMNFFKT EITLANGEIR KRPLIETNGE TGEIVWDKGR DFATVRKVLS  1500
MPQVNIVKKT EVQTGGFSKE SILPKRNSDK LIARKKDWDP KKYGGFDSPT VAYSVLVVAK  1560
VEKGKSKKLK SVKELLGITI MERSSFEKNP IDFLEAKGYK EVKKDLIIKL PKYSLFELEN  1620
```

```
GRKRMLASAG ELQKGNELAL PSKYVNFLYL ASHYEKLKGS PEDNEQKQLF VEQHKHYLDE  1680
IIEQISEFSK RVILADANLD KVLSAYNKHR DKPIREQAEN IIHLFTLTNL GAPAAFKYFD  1740
TTIDRKRYTS TKEVLDATLI HQSITGLYET RIDLSQLGGD                        1780

SEQ ID NO: 28          moltype = AA  length = 1780
FEATURE                Location/Qualifiers
REGION                 1..1780
                       note = Synthetic Polypeptide
source                 1..1780
                       mol_type = protein
                       organism = synthetic construct
SEQUENCE: 28
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVCLAE GTRIFDPVTG TTHRIEDVVD GRKPIHVVAA AKDGTLLARP VVSWFDQGTR  180
DVIGLRIAGG AIVWATPDHK VLTEYGWRAA GELRKGDRVA GPGGSGNSLA LSLTADQMVS  240
ALLDAEPPIL YSEYDPTSPF SEASMMGLLT NLADRELVHM INWAKRVPGF VDLTLHDQAH  300
LLERAWLEIL MIGLVWRSME HPGKLLFAPN LLLDRNQGKC VEGMVEIFDM LLATSSRFRM  360
MNLQGEEFVC LKSIILLNSG VYTFLSSTLK SLEEKDHIHR ALDKITDTLI HLMAKAGLTL  420
QQQHQRLAQL LLILSHIRHM SNKGMEHLYS MKYKNVVPLY DLLLEMLDAH RLHAGGSGAS  480
RVQAFADALD DKFLHDMLAE GLRYSVIREV LPTRRARTFD LEVEELHTLV AEGVVVHNCY  540
HEKYPTIYHL RKKLVDSTDK ADLRLIYLAL AHMIKFRGHF LIEGDLNPDN SDVDKLFIQL  600
VQTYNQLFEE NPINASGVDA KAILSARLSK SRRLENLIAQ LPGEKKNGLF GNLIALSLGL  660
TPNFKSNFDL AEDAKLQLSK DTYDDDLDNL LAQIGDQYAD LFLAAKNLSD AILLSDILRV  720
NTEITKAPLS ASMIKRYDEH HQDLTLLKAL VRQQLPEKYK EIFFDQSKNG YAGYIDGGAS  780
QEEFYKFIKP ILEKMDGTEE LLVKLNREDL LRKQRTFDNG SIPHQIHLGE LHAILRRQED  840
FYPFLKDNRE KIEKILTFRI PYYVGPLARG NSRFAWMTRK SEETITPWNF EEVVDKGASA  900
QSFIERMTNF DKNLPNEKVL PKHSLLYEYF TVYNELTKVK YVTEGMRKPA FLSGEQKKAI  960
VDLLFKTNRK VTVKQLKEDY FKKIECFDSV EISGVEDRFN ASLGTYHDLL KIIKDKDFLD  1020
NEENEDILED IVLTLTLFED REMIEERLKT YAHLFDDKVM KQLKRRRYTG WGRLSRKLIN  1080
GIRDKQSGKT ILDFLKSDGF ANRNFMQLIH DDSLTFKEDI QKAQVSGQGD SLHEHIANLA  1140
GSPAIKKGIL QTVKVVDELV KVMGRHKPEN IVIEMARENQ TTQKGQKNSR ERMKRIEEGI  1200
KELGSQILKE HPVENTQLQN EKLYLYYLQN GRDMYVDQEL DINRLSDYDV DHIVPQSFLK  1260
DDSIDNKVLT RSDKNRGKSD NVPSEEVVKK MKNYWRQLLN AKLITQRKFD NLTKAERGGL  1320
SELDKAGFIK RQLVETRQIT KHVAQILDSR MNTKYDENDK LIREVKVITL KSKLVSDFRK  1380
DFQFYKVREI NNYHHAHDAY LNAVVGTALI KKYPKLESEF VYGDYKVYDV RKMIAKSEQE  1440
IGKATAKYFF YSNIMNFFKT EITLANGEIR KRPLIETNGE TGEIVWDKGR DFATVRKVLS  1500
MPQVNIVKKT EVQTGGFSKE SILPKRNSDK LIARKKDWDP KKYGGFDSPT VAYSVLVVAK  1560
VEKGKSKKLK SVKELLGITI MERSSFEKNP IDFLEAKGYK EVKKDLIIKL PKYSLFELEN  1620
GRKRMLASAG ELQKGNELAL PSKYVNFLYL ASHYEKLKGS PEDNEQKQLF VEQHKHYLDE  1680
IIEQISEFSK RVILADANLD KVLSAYNKHR DKPIREQAEN IIHLFTLTNL GAPAAFKYFD  1740
TTIDRKRYTS TKEVLDATLI HQSITGLYET RIDLSQLGGD                        1780

SEQ ID NO: 29          moltype = AA  length = 1780
FEATURE                Location/Qualifiers
REGION                 1..1780
                       note = Synthetic Polypeptide
source                 1..1780
                       mol_type = protein
                       organism = synthetic construct
SEQUENCE: 29
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSCLAEG TRIFDPVTGT THRIEDVVDG RKPIHVVAAA  180
KDGTLLARPV VSWFDQGTRD VIGLRIAGGA IVWATPDHKV LTEYGWRAAG ELRKGDRVAG  240
PGGSGNSLAL SLTADQMVSA LLDAEPPILY SEYDPTSPFS EASMMGLLTN LADRELVHMI  300
NWAKRVPGFV DLTLHDQAHL LERAWLEILM IGLVWRSMEH PGKLLFAPNL LLDRNQGKCV  360
EGMVEIFDML LATSSRFRMM NLQGEEFVCL KSIILLNSGV YTFLSSTLKS LEEKDHIHRA  420
LDKITDTLIH LMAKAGLTLQ QQHQRLAQLL LILSHIRHMS NKGMEHLYSM KYKNVVPLYD  480
LLLEMLDAHR LHAGGSGASR VQAFADALDD KFLHDMLAEG LRYSVIREVL PTRRARTFDL  540
EVEELHTLVA EGVVVHNCDK ADLRLIYLAL AHMIKFRGHF LIEGDLNPDN SDVDKLFIQL  600
VQTYNQLFEE NPINASGVDA KAILSARLSK SRRLENLIAQ LPGEKKNGLF GNLIALSLGL  660
TPNFKSNFDL AEDAKLQLSK DTYDDDLDNL LAQIGDQYAD LFLAAKNLSD AILLSDILRV  720
NTEITKAPLS ASMIKRYDEH HQDLTLLKAL VRQQLPEKYK EIFFDQSKNG YAGYIDGGAS  780
QEEFYKFIKP ILEKMDGTEE LLVKLNREDL LRKQRTFDNG SIPHQIHLGE LHAILRRQED  840
FYPFLKDNRE KIEKILTFRI PYYVGPLARG NSRFAWMTRK SEETITPWNF EEVVDKGASA  900
QSFIERMTNF DKNLPNEKVL PKHSLLYEYF TVYNELTKVK YVTEGMRKPA FLSGEQKKAI  960
VDLLFKTNRK VTVKQLKEDY FKKIECFDSV EISGVEDRFN ASLGTYHDLL KIIKDKDFLD  1020
NEENEDILED IVLTLTLFED REMIEERLKT YAHLFDDKVM KQLKRRRYTG WGRLSRKLIN  1080
GIRDKQSGKT ILDFLKSDGF ANRNFMQLIH DDSLTFKEDI QKAQVSGQGD SLHEHIANLA  1140
GSPAIKKGIL QTVKVVDELV KVMGRHKPEN IVIEMARENQ TTQKGQKNSR ERMKRIEEGI  1200
KELGSQILKE HPVENTQLQN EKLYLYYLQN GRDMYVDQEL DINRLSDYDV DHIVPQSFLK  1260
DDSIDNKVLT RSDKNRGKSD NVPSEEVVKK MKNYWRQLLN AKLITQRKFD NLTKAERGGL  1320
SELDKAGFIK RQLVETRQIT KHVAQILDSR MNTKYDENDK LIREVKVITL KSKLVSDFRK  1380
DFQFYKVREI NNYHHAHDAY LNAVVGTALI KKYPKLESEF VYGDYKVYDV RKMIAKSEQE  1440
IGKATAKYFF YSNIMNFFKT EITLANGEIR KRPLIETNGE TGEIVWDKGR DFATVRKVLS  1500
MPQVNIVKKT EVQTGGFSKE SILPKRNSDK LIARKKDWDP KKYGGFDSPT VAYSVLVVAK  1560
```

-continued

```
VEKGKSKKLK SVKELLGITI MERSSFEKNP IDFLEAKGYK EVKKDLIIKL PKYSLFELEN  1620
GRKRMLASAG ELQKGNELAL PSKYVNFLYL ASHYEKLKGS PEDNEQKQLF VEQHKHYLDE  1680
IIEQISEFSK RVILADANLD KVLSAYNKHR DKPIREQAEN IIHLFTLTNL GAPAAFKYFD  1740
TTIDRKRYTS TKEVLDATLI HQSITGLYET RIDLSQLGGD                        1780

SEQ ID NO: 30          moltype = AA  length = 1780
FEATURE                Location/Qualifiers
REGION                 1..1780
                       note = Synthetic Polypeptide
source                 1..1780
                       mol_type = protein
                       organism = synthetic construct
SEQUENCE: 30
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKCL AEGTRIFDPV TGTTHRIEDV  240
VDGRKPIHVV AAAKDGTLLA RPVVSWFDQG TRDVIGLRIA GGAIVWATPD HKVLTEYGWR  300
AAGELRKGDR VAGPGGSGNS LALSLTADQM VSALLDAEPP ILYSEYDPTS PFSEASMMGL  360
LTNLADRELV HMINWAKRVP GFVDLTLHDQ AHLLERAWLE ILMIGLVWRS MEHPGKLLFA  420
PNLLLDRNQG KCVEGMVEIF DMLLATSSRF RMMNLQGEEF VCLKSIILLN SGVYTFLSST  480
LKSLEEKDHI HRALDKITDT LIHLMAKAGL TLQQQHQRLA QLLLILSHIR HMSNKGMEHL  540
YSMKYKNVVP LYDLLLEMLD AHRLHAGGSG ASRVQAFADA LDDKFLHDML AEGLRYSVIR  600
EVLPTRRART FDLEVEELHT LVAEGVVVHN CRRLENLIAQ LPGEKKNGLF GNLIALSLGL  660
TPNFKSNFDL AEDAKLQLSK DTYDDDLDNL LAQIGDQYAD LFLAAKNLSD AILLSDILRV  720
NTEITKAPLS ASMIKRYDEH HQDLTLLKAL VRQQLPEKYK EIFFDQSKNG YAGYIDGGAS  780
QEEFYKFIKP ILEKMDGTEE LLVKLNREDL LRKQRTFDNG SIPHQIHLGE LHAILRRQED  840
FYPFLKDNRE KIEKILTFRI PYYVGPLARG NSRFAWMTRK SEETITPWNF EEVVDKGASA  900
QSFIERMTNF DKNLPNEKVL PKHSLLYEYF TVYNELTKVK YVTEGMRKPA FLSGEQKKAI  960
VDLLFKTNRK VTVKQLKEDY FKKIECFDSV EISGVEDRFN ASLGTYHDLL KIIKDKDFLD  1020
NEENEDILED IVLTLTLFED REMIEERLKT YAHLFDDKVM KQLKRRRYTG WGRLSRKLIN  1080
GIRDKQSGKT ILDFLKSDGF ANRNFMQLIH DDSLTFKEDI QKAQVSGQGD SLHEHIANLA  1140
GSPAIKKGIL QTVKVVDELV KVMGRHKPEN IVIEMARENQ TTQKGQKNSR ERMKRIEEGI  1200
KELGSQILKE HPVENTQLQN EKLYLYYLQN GRDMYVDQEL DINRLSDYDV DHIVPQSFLK  1260
DDSIDNKVLT RSDKNRGKSD NVPSEEVVKK MKNYWRQLLN AKLITQRKFD NLTKAERGGL  1320
SELDKAGFIK RQLVETRQIT KHVAQILDSR MNTKYDENDK LIREVKVITL KSKLVSDFRK  1380
DFQFYKVREI NNYHHAHDAY LNAVVGTALI KKYPKLESEF VYGDYKVYDV RKMIAKSEQE  1440
IGKATAKYFF YSNIMNFFKT EITLANGEIR KRPLIETNGE TGEIVWDKGR DFATVRKVLS  1500
MPQVNIVKKT EVQTGGFSKE SILPKRNSDK LIARKKDWDP KKYGGFDSPT VAYSVLVVAK  1560
VEKGKSKKLK SVKELLGITI MERSSFEKNP IDFLEAKGYK EVKKDLIIKL PKYSLFELEN  1620
GRKRMLASAG ELQKGNELAL PSKYVNFLYL ASHYEKLKGS PEDNEQKQLF VEQHKHYLDE  1680
IIEQISEFSK RVILADANLD KVLSAYNKHR DKPIREQAEN IIHLFTLTNL GAPAAFKYFD  1740
TTIDRKRYTS TKEVLDATLI HQSITGLYET RIDLSQLGGD                        1780

SEQ ID NO: 31          moltype = AA  length = 1780
FEATURE                Location/Qualifiers
REGION                 1..1780
                       note = Synthetic Polypeptide
source                 1..1780
                       mol_type = protein
                       organism = synthetic construct
SEQUENCE: 31
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLCLAEGTRI FDPVTGTTHR IEDVVDGRKP  360
IHVVAAAKDG TLLARPVVSW FDQGTRDVIG LRIAGGAIVW ATPDHKVLTE YGWRAAGELR  420
KGDRVAGPGG SGNSLALSLT ADQMVSALLD AEPPILYSEY DPTSPFSEAS MMGLLTNLAD  480
RELVHMINWA KRVPGFVDLT LHDQAHLLER AWLEILMIGL VWRSMEHPGK LLFAPNLLLD  540
RNQGKCVEGM VEIFDMLLAT SSRFRMMNLQ GEEFVCLKSI ILLNSGVYTF LSSTLKSLEE  600
KDHIHRALDK ITDTLIHLMA KAGLTLQQQH QRLAQLLLIL SHIRHMSNKG MEHLYSMKYK  660
NVVPLYDLLL EMLDAHRLHA GGSGASRVQA FADALDDKFL HDMLAEGLRY SVIREVLPTR  720
RARTFDLEVE ELHTLVAEGV VVHNCLLKAL VRQQLPEKYK EIFFDQSKNG YAGYIDGGAS  780
QEEFYKFIKP ILEKMDGTEE LLVKLNREDL LRKQRTFDNG SIPHQIHLGE LHAILRRQED  840
FYPFLKDNRE KIEKILTFRI PYYVGPLARG NSRFAWMTRK SEETITPWNF EEVVDKGASA  900
QSFIERMTNF DKNLPNEKVL PKHSLLYEYF TVYNELTKVK YVTEGMRKPA FLSGEQKKAI  960
VDLLFKTNRK VTVKQLKEDY FKKIECFDSV EISGVEDRFN ASLGTYHDLL KIIKDKDFLD  1020
NEENEDILED IVLTLTLFED REMIEERLKT YAHLFDDKVM KQLKRRRYTG WGRLSRKLIN  1080
GIRDKQSGKT ILDFLKSDGF ANRNFMQLIH DDSLTFKEDI QKAQVSGQGD SLHEHIANLA  1140
GSPAIKKGIL QTVKVVDELV KVMGRHKPEN IVIEMARENQ TTQKGQKNSR ERMKRIEEGI  1200
KELGSQILKE HPVENTQLQN EKLYLYYLQN GRDMYVDQEL DINRLSDYDV DHIVPQSFLK  1260
DDSIDNKVLT RSDKNRGKSD NVPSEEVVKK MKNYWRQLLN AKLITQRKFD NLTKAERGGL  1320
SELDKAGFIK RQLVETRQIT KHVAQILDSR MNTKYDENDK LIREVKVITL KSKLVSDFRK  1380
DFQFYKVREI NNYHHAHDAY LNAVVGTALI KKYPKLESEF VYGDYKVYDV RKMIAKSEQE  1440
IGKATAKYFF YSNIMNFFKT EITLANGEIR KRPLIETNGE TGEIVWDKGR DFATVRKVLS  1500
MPQVNIVKKT EVQTGGFSKE SILPKRNSDK LIARKKDWDP KKYGGFDSPT VAYSVLVVAK  1560
VEKGKSKKLK SVKELLGITI MERSSFEKNP IDFLEAKGYK EVKKDLIIKL PKYSLFELEN  1620
```

```
GRKRMLASAG ELQKGNELAL PSKYVNFLYL ASHYEKLKGS PEDNEQKQLF VEQHKHYLDE  1680
IIEQISEFSK RVILADANLD KVLSAYNKHR DKPIREQAEN IIHLFTLTNL GAPAAFKYFD  1740
TTIDRKRYTS TKEVLDATLI HQSITGLYET RIDLSQLGGD                        1780

SEQ ID NO: 32          moltype = AA  length = 1780
FEATURE                Location/Qualifiers
REGION                 1..1780
                       note = Synthetic Polypeptide
source                 1..1780
                       mol_type = protein
                       organism = synthetic construct
SEQUENCE: 32
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFCL AEGTRIFDPV TGTTHRIEDV  540
VDGRKPIHVV AAAKDGTLLA RPVVSWFDQG TRDVIGLRIA GGAIVWATPD HKVLTEYGWR  600
AAGELRKGDR VAGPGGSGNS LALSLTADQM VSALLDAEPP ILYSEYDPTS PFSEASMMGL  660
LTNLADRELV HMINWAKRVP GFVDLTLHDQ AHLLERAWLE ILMIGLVWRS MEHPGKLLFA  720
PNLLLDRNQG KCVEGMVEIF DMLLATSSRF RMMNLQGEEF VCLKSIILLN SGVYTFLSST  780
LKSLEEKDHI HRALDKITDT LIHLMAKAGL TLQQQHQRLA QLLLILSHIR HMSNKGMEHL  840
YSMKYKNVVP LYDLLLEMLD AHRLHAGGSG ASRVQAFADA LDDKFLHDML AEGLRYSVIR  900
EVLPTRRART FDLEVEELHT LVAEGVVVHN CVYNELTKVK YVTEGMRKPA FLSGEQKKAI  960
VDLLFKTNRK VTVKQLKEDY FKKIECFDSV EISGVEDRFN ASLGTYHDLL KIIKDKDFLD  1020
NEENEDILED IVLTLTLFED REMIEERLKT YAHLFDDKVM KQLKRRRYTG WGRLSRKLIN  1080
GIRDKQSGKT ILDFLKSDGF ANRNFMQLIH DDSLTFKEDI QKAQVSGQGD SLHEHIANLA  1140
GSPAIKKGIL QTVKVVDELV KVMGRHKPEN IVIEMARENQ TTQKGQKNSR ERMKRIEEGI  1200
KELGSQILKE HPVENTQLQN EKLYLYYLQN GRDMYVDQEL DINRLSDYDV DHIVPQSFLK  1260
DDSIDNKVLT RSDKNRGKSD NVPSEEVVKK MKNYWRQLLN AKLITQRKFD NLTKAERGGL  1320
SELDKAGFIK RQLVETRQIT KHVAQILDSR MNTKYDENDK LIREVKVITL KSKLVSDFRK  1380
DFQFYKVREI NNYHHAHDAY LNAVVGTALI KKYPKLESEF VYGDYKVYDV RKMIAKSEQE  1440
IGKATAKYFF YSNIMNFFKT EITLANGEIR KRPLIETNGE TGEIVWDKGR DFATVRKVLS  1500
MPQVNIVKKT EVQTGGFSKE SILPKRNSDK LIARKKDWDP KKYGGFDSPT VAYSVLVVAK  1560
VEKGKSKKLK SVKELLGITI MERSSFEKNP IDFLEAKGYK EVKKDLIIKL PKYSLFELEN  1620
GRKRMLASAG ELQKGNELAL PSKYVNFLYL ASHYEKLKGS PEDNEQKQLF VEQHKHYLDE  1680
IIEQISEFSK RVILADANLD KVLSAYNKHR DKPIREQAEN IIHLFTLTNL GAPAAFKYFD  1740
TTIDRKRYTS TKEVLDATLI HQSITGLYET RIDLSQLGGD                        1780

SEQ ID NO: 33          moltype = AA  length = 1780
FEATURE                Location/Qualifiers
REGION                 1..1780
                       note = Synthetic Polypeptide
source                 1..1780
                       mol_type = protein
                       organism = synthetic construct
SEQUENCE: 33
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECLAEGTR IFDPVTGTTH RIEDVVDGRK  600
PIHVVAAAKD GTLLARPVVS WFDQGTRDVI GLRIAGGAIV WATPDHKVLT EYGWRAAGEL  660
RKGDRVAGPG GSGNSLALSL TADQMVSALL DAEPPILYSE YDPTSPFSEA SMMGLLTNLA  720
DRELVHMINW AKRVPGFVDL TLHDQAHLLE RAWLEILMIG LVWRSMEHPG KLLFAPNLLL  780
DRNQGKCVEG MVEIFDMLLA TSSRFRMMNL QGEEFVCLKS IILLNSGVYT FLSSTLKSLE  840
EKDHIHRALD KITDTLIHLM AKAGLTLQQQ HQRLAQLLLI LSHIRHMSNK GMEHLYSMKY  900
KNVVPLYDLL LEMLDAHRLH AGGSGASRVQ AFADALDDKF LHDMLAEGLR YSVIREVLPT  960
RRARTFDLEV EELHTLVAEG VVVHNCFDSV EISGVEDRFN ASLGTYHDLL KIIKDKDFLD  1020
NEENEDILED IVLTLTLFED REMIEERLKT YAHLFDDKVM KQLKRRRYTG WGRLSRKLIN  1080
GIRDKQSGKT ILDFLKSDGF ANRNFMQLIH DDSLTFKEDI QKAQVSGQGD SLHEHIANLA  1140
GSPAIKKGIL QTVKVVDELV KVMGRHKPEN IVIEMARENQ TTQKGQKNSR ERMKRIEEGI  1200
KELGSQILKE HPVENTQLQN EKLYLYYLQN GRDMYVDQEL DINRLSDYDV DHIVPQSFLK  1260
DDSIDNKVLT RSDKNRGKSD NVPSEEVVKK MKNYWRQLLN AKLITQRKFD NLTKAERGGL  1320
SELDKAGFIK RQLVETRQIT KHVAQILDSR MNTKYDENDK LIREVKVITL KSKLVSDFRK  1380
DFQFYKVREI NNYHHAHDAY LNAVVGTALI KKYPKLESEF VYGDYKVYDV RKMIAKSEQE  1440
IGKATAKYFF YSNIMNFFKT EITLANGEIR KRPLIETNGE TGEIVWDKGR DFATVRKVLS  1500
MPQVNIVKKT EVQTGGFSKE SILPKRNSDK LIARKKDWDP KKYGGFDSPT VAYSVLVVAK  1560
VEKGKSKKLK SVKELLGITI MERSSFEKNP IDFLEAKGYK EVKKDLIIKL PKYSLFELEN  1620
```

```
GRKRMLASAG ELQKGNELAL PSKYVNFLYL ASHYEKLKGS PEDNEQKQLF VEQHKHYLDE  1680
IIEQISEFSK RVILADANLD KVLSAYNKHR DKPIREQAEN IIHLFTLTNL GAPAAFKYFD  1740
TTIDRKRYTS TKEVLDATLI HQSITGLYET RIDLSQLGGD                        1780

SEQ ID NO: 34          moltype = AA  length = 1780
FEATURE                Location/Qualifiers
REGION                 1..1780
                       note = Synthetic Polypeptide
source                 1..1780
                       mol_type = protein
                       organism = synthetic construct
SEQUENCE: 34
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LCLAEGTRIF DPVTGTTHRI EDVVDGRKPI HVVAAAKDGT  660
LLARPVVSWF DQGTRDVIGL RIAGGAIVWA TPDHKVLTEY GWRAAGELRK GDRVAGPGGS  720
GNSLALSLTA DQMVSALLDA EPPILYSEYD PTSPFSEASM MGLLTNLADR ELVHMINWAK  780
RVPGFVDLTL HDQAHLLERA WLEILMIGLV WRSMEHPGKL LFAPNLLLDR NQGKCVEGMV  840
EIFDMLLATS SRFRMMNLQG EEFVCLKSII LLNSGVYTFL SSTLKSLEEK DHIHRALDKI  900
TDTLIHLMAK AGLTLQQQHQ RLAQLLLILS HIRHMSNKGM EHLYSMKYKN VVPLYDLLLE  960
MLDAHRLHAG GSGASRVQAF ADALDDKFLH DMLAEGLRYS VIREVLPTRR ARTFDLEVEE  1020
LHTLVAEGVV VHNCLTLFED REMIEERLKT YAHLFDDKVM KQLKRRRYTG WGRLSRKLIN  1080
GIRDKQSGKT ILDFLKSDGF ANRNFMQLIH DDSLTFKEDI QKAQVSGQGD SLHEHIANLA  1140
GSPAIKKGIL QTVKVVDELV KVMGRHKPEN IVIEMARENQ TTQKGQKNSR ERMKRIEEGI  1200
KELGSQILKE HPVENTQLQN EKLYLYYLQN GRDMYVDQEL DINRLSDYDV DHIVPQSFLK  1260
DDSIDNKVLT RSDKNRGKSD NVPSEEVVKK MKNYWRQLLN AKLITQRKFD NLTKAERGGL  1320
SELDKAGFIK RQLVETRQIT KHVAQILDSR MNTKYDENDK LIREVKVITL KSKLVSDFRK  1380
DFQFYKVREI NNYHHAHDAY LNAVVGTALI KKYPKLESEF VYGDYKVYDV RKMIAKSEQE  1440
IGKATAKYFF YSNIMNFFKT EITLANGEIR KRPLIETNGE TGEIVWDKGR DFATVRKVLS  1500
MPQVNIVKKT EVQTGGFSKE SILPKRNSDK LIARKKDWDP KKYGGFDSPT VAYSVLVVAK  1560
VEKGKSKKLK SVKELLGITI MERSSFEKNP IDFLEAKGYK EVKKDLIIKL PKYSLFELEN  1620
GRKRMLASAG ELQKGNELAL PSKYVNFLYL ASHYEKLKGS PEDNEQKQLF VEQHKHYLDE  1680
IIEQISEFSK RVILADANLD KVLSAYNKHR DKPIREQAEN IIHLFTLTNL GAPAAFKYFD  1740
TTIDRKRYTS TKEVLDATLI HQSITGLYET RIDLSQLGGD                        1780

SEQ ID NO: 35          moltype = AA  length = 1780
FEATURE                Location/Qualifiers
REGION                 1..1780
                       note = Synthetic Polypeptide
source                 1..1780
                       mol_type = protein
                       organism = synthetic construct
SEQUENCE: 35
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD CLAEGTRIFD PVTGTTHRIE  720
DVVDGRKPIH VVAAAKDGTL LARPVVSWFD QGTRDVIGLR IAGGAIVWAT PDHKVLTEYG  780
WRAAGELRKG DRVAGPGGSG NSLALSLTAD QMVSALLDAE PPILYSEYDP TSPFSEASMM  840
GLLTNLADRE LVHMINWAKR VPGFVDLTLH DQAHLLERAW LEILMIGLVW RSMEHPGKLL  900
FAPNLLLDRN QGKCVEGMVE IFDMLLATSS RFRMMNLQGE EFVCLKSIIL LNSGVYTFLS  960
STLKSLEEKD HIHRALDKIT DTLIHLMAKA GLTLQQQHQR LAQLLLILSH IRHMSNKGME  1020
HLYSMKYKNV VPLYDLLLEM LDAHRLHAGG SGASRVQAFA DALDDKFLHD MLAEGLRYSV  1080
IREVLPTRRA RTFDLEVEEL HTLVAEGVVV HNCLTFKEDI QKAQVSGQGD SLHEHIANLA  1140
GSPAIKKGIL QTVKVVDELV KVMGRHKPEN IVIEMARENQ TTQKGQKNSR ERMKRIEEGI  1200
KELGSQILKE HPVENTQLQN EKLYLYYLQN GRDMYVDQEL DINRLSDYDV DHIVPQSFLK  1260
DDSIDNKVLT RSDKNRGKSD NVPSEEVVKK MKNYWRQLLN AKLITQRKFD NLTKAERGGL  1320
SELDKAGFIK RQLVETRQIT KHVAQILDSR MNTKYDENDK LIREVKVITL KSKLVSDFRK  1380
DFQFYKVREI NNYHHAHDAY LNAVVGTALI KKYPKLESEF VYGDYKVYDV RKMIAKSEQE  1440
IGKATAKYFF YSNIMNFFKT EITLANGEIR KRPLIETNGE TGEIVWDKGR DFATVRKVLS  1500
MPQVNIVKKT EVQTGGFSKE SILPKRNSDK LIARKKDWDP KKYGGFDSPT VAYSVLVVAK  1560
```

-continued

```
VEKGKSKKLK SVKELLGITI MERSSFEKNP IDFLEAKGYK EVKKDLIIKL PKYSLFELEN  1620
GRKRMLASAG ELQKGNELAL PSKYVNFLYL ASHYEKLKGS PEDNEQKQLF VEQHKHYLDE  1680
IIEQISEFSK RVILADANLD KVLSAYNKHR DKPIREQAEN IIHLFTLTNL GAPAAFKYFD  1740
TTIDRKRYTS TKEVLDATLI HQSITGLYET RIDLSQLGGD                        1780

SEQ ID NO: 36          moltype = AA  length = 1780
FEATURE                Location/Qualifiers
REGION                 1..1780
                       note = Synthetic Polypeptide
source                 1..1780
                       mol_type = protein
                       organism = synthetic construct
SEQUENCE: 36
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLCLA EGTRIFDPVT GTTHRIEDVV DGRKPIHVVA AAKDGTLLAR PVVSWFDQGT  780
RDVIGLRIAG GAIVWATPDH KVLTEYGWRA AGELRKGDRV AGPGGSGNSL ALSLTADQMV  840
SALLDAEPPI LYSEYDPTSP FSEASMMGLL TNLADRELVH MINWAKRVPG FVDLTLHDQA  900
HLLERAWLEI LMIGLVWRSM EHPGKLLFAP NLLLDRNQGK CVEGMVEIFD MLLATSSRFR  960
MMNLQGEEFV CLKSIILLNS GVYTFLSSTL KSLEEKDHIH RALDKITDTL IHLMAKAGLT  1020
LQQQHQRLAQ LLLILSHIRH MSNKGMEHLY SMKYKNVVPL YDLLLEMLDA HRLHAGGSGA  1080
SRVQAFADAL DDKFLHDMLA EGLRYSVIRE VLPTRRARTF DLEVEELHTL VAEGVVVHNC  1140
GSPAIKKGIL QTVKVVDELV KVMGRHKPEN IVIEMARENQ TTQKGQKNSR ERMKRIEEGI  1200
KELGSQILKE HPVENTQLQN EKLYLYYLQN GRDMYVDQEL DINRLSDYDV DHIVPQSFLK  1260
DDSIDNKVLT RSDKNRGKSD NVPSEEVVKK MKNYWRQLLN AKLITQRKFD NLTKAERGGL  1320
SELDKAGFIK RQLVETRQIT KHVAQILDSR MNTKYDENDK LIREVKVITL KSKLVSDFRK  1380
DFQFYKVREI NNYHHAHDAY LNAVVGTALI KKYPKLESEF VYGDYKVYDV RKMIAKSEQE  1440
IGKATAKYFF YSNIMNFFKT EITLANGEIR KRPLIETNGE TGEIVWDKGR DFATVRKVLS  1500
MPQVNIVKKT EVQTGGFSKE SILPKRNSDK LIARKKDWDP KKYGGFDSPT VAYSVLVVAK  1560
VEKGKSKKLK SVKELLGITI MERSSFEKNP IDFLEAKGYK EVKKDLIIKL PKYSLFELEN  1620
GRKRMLASAG ELQKGNELAL PSKYVNFLYL ASHYEKLKGS PEDNEQKQLF VEQHKHYLDE  1680
IIEQISEFSK RVILADANLD KVLSAYNKHR DKPIREQAEN IIHLFTLTNL GAPAAFKYFD  1740
TTIDRKRYTS TKEVLDATLI HQSITGLYET RIDLSQLGGD                        1780

SEQ ID NO: 37          moltype = AA  length = 1780
FEATURE                Location/Qualifiers
REGION                 1..1780
                       note = Synthetic Polypeptide
source                 1..1780
                       mol_type = protein
                       organism = synthetic construct
SEQUENCE: 37
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGCLAEGT RIFDPVTGTT HRIEDVVDGR  1020
KPIHVVAAAK DGTLLARPVV SWFDQGTRDV IGLRIAGGAI VWATPDHKVL TEYGWRAAGE  1080
LRKGDRVAGP GGSGNSLALS LTADQMVSAL LDAEPPILYS EYDPTSPFSE ASMMGLLTNL  1140
ADRELVHMIN WAKRVPGFVD LTLHDQAHLL ERAWLEILMI GLVWRSMEHP GKLLFAPNLL  1200
LDRNQGKCVE GMVEIFDMLL ATSSRFRMMN LQGEEFVCLK SIILLNSGVY TFLSSTLKSL  1260
EEKDHIHRAL DKITDTLIHL MAKAGLTLQQ QHQRLAQLLL ILSHIRHMSN KGMEHLYSMK  1320
YKNVVPLYDL LLEMLDAHRL HAGGSGASRV QAFADALDDK FLHDMLAEGL RYSVIREVLP  1380
TRRARTFDLE VEELHTLVAE GVVVHNCALI KKYPKLESEF VYGDYKVYDV RKMIAKSEQE  1440
IGKATAKYFF YSNIMNFFKT EITLANGEIR KRPLIETNGE TGEIVWDKGR DFATVRKVLS  1500
MPQVNIVKKT EVQTGGFSKE SILPKRNSDK LIARKKDWDP KKYGGFDSPT VAYSVLVVAK  1560
VEKGKSKKLK SVKELLGITI MERSSFEKNP IDFLEAKGYK EVKKDLIIKL PKYSLFELEN  1620
```

-continued

```
GRKRMLASAG ELQKGNELAL PSKYVNFLYL ASHYEKLKGS PEDNEQKQLF VEQHKHYLDE  1680
IIEQISEFSK RVILADANLD KVLSAYNKHR DKPIREQAEN IIHLFTLTNL GAPAAFKYFD  1740
TTIDRKRYTS TKEVLDATLI HQSITGLYET RIDLSQLGGD                        1780

SEQ ID NO: 38          moltype = AA  length = 1780
FEATURE                Location/Qualifiers
REGION                 1..1780
                       note = Synthetic Polypeptide
source                 1..1780
                       mol_type = protein
                       organism = synthetic construct
SEQUENCE: 38
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLECLAEG TRIFDPVTGT  1020
THRIEDVVDG RKPIHVVAAA KDGTLLARPV VSWFDQGTRD VIGLRIAGGA IVWATPDHKV  1080
LTEYGWRAAG ELRKGDRVAG PGGSGNSLAL SLTADQMVSA LLDAEPPILY SEYDPTSPFS  1140
EASMMGLLTN LADRELVHMI NWAKRVPGFV DLTLHDQAHL LERAWLEILM IGLVWRSMEH  1200
PGKLLFAPNL LLDRNQGKCV EGMVEIFDML LATSSRFRMM NLQGEEFVCL KSIILLNSGV  1260
YTFLSSTLKS LEEKDHIHRA LDKITDTLIH LMAKAGLTLQ QQHQRLAQLL LILSHIRHMS  1320
NKGMEHLYSM KYKNVVPLYD LLLEMLDAHR LHAGGSGASR VQAFADALDD KFLHDMLAEG  1380
LRYSVIREVL PTRRARTFDL EVEELHTLVA EGVVVHNCEF VYGDYKVYDV RKMIAKSEQE  1440
IGKATAKYFF YSNIMNFFKT EITLANGEIR KRPLIETNGE TGEIVWDKGR DFATVRKVLS  1500
MPQVNIVKKT EVQTGGFSKE SILPKRNSDK LIARKKDWDP KKYGGFDSPT VAYSVLVVAK  1560
VEKGKSKKLK SVKELLGITI MERSSFEKNP IDFLEAKGYK EVKKDLIIKL PKYSLFELEN  1620
GRKRMLASAG ELQKGNELAL PSKYVNFLYL ASHYEKLKGS PEDNEQKQLF VEQHKHYLDE  1680
IIEQISEFSK RVILADANLD KVLSAYNKHR DKPIREQAEN IIHLFTLTNL GAPAAFKYFD  1740
TTIDRKRYTS TKEVLDATLI HQSITGLYET RIDLSQLGGD                        1780

SEQ ID NO: 39          moltype = AA  length = 1780
FEATURE                Location/Qualifiers
REGION                 1..1780
                       note = Synthetic Polypeptide
source                 1..1780
                       mol_type = protein
                       organism = synthetic construct
SEQUENCE: 39
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKCLAEGTR IFDPVTGTTH RIEDVVDGRK PIHVVAAAKD GTLLARPVVS  1200
WFDQGTRDVI GLRIAGGAIV WATPDHKVLT EYGWRAAGEL RKGDRVAGPG GSGNSLALSL  1260
TADQMVSALL DAEPPILYSE YDPTSPFSEA SMMGLLTNLA DRELVHMINW AKRVPGFVDL  1320
TLHDQAHLLE RAWLEILMIG LVWRSMEHPG KLLFAPNLLL DRNQGKCVEG MVEIFDMLLA  1380
TSSRFRMMNL QGEEFVCLKS IILLNSGVYT FLSSTLKSLE EKDHIHRALD KITDTLIHLM  1440
AKAGLTLQQQ HQRLAQLLLI LSHIRHMSNK GMEHLYSMKY KNVVPLYDLL LEMLDAHRLH  1500
AGGSGASRVQ AFADALDDKF LHDMLAEGLR YSVIREVLPT RRARTFDLEV EELHTLVAEG  1560
VVVHNCKKLK SVKELLGITI MERSSFEKNP IDFLEAKGYK EVKKDLIIKL PKYSLFELEN  1620
GRKRMLASAG ELQKGNELAL PSKYVNFLYL ASHYEKLKGS PEDNEQKQLF VEQHKHYLDE  1680
```

```
IIEQISEFSK RVILADANLD KVLSAYNKHR DKPIREQAEN IIHLFTLTNL GAPAAFKYFD  1740
TTIDRKRYTS TKEVLDATLI HQSITGLYET RIDLSQLGGD                        1780

SEQ ID NO: 40          moltype = AA  length = 1780
FEATURE                Location/Qualifiers
REGION                 1..1780
                       note = Synthetic Polypeptide
source                 1..1780
                       mol_type = protein
                       organism = synthetic construct
SEQUENCE: 40
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKCL AEGTRIFDPV TGTTHRIEDV VDGRKPIHVV AAAKDGTLLA  1200
RPVVSWFDQG TRDVIGLRIA GGAIVWATPD HKVLTEYGWR AAGELRKGDR VAGPGGSGNS  1260
LALSLTADQM VSALLDAEPP ILYSEYDPTS PFSEASMMGL LTNLADRELV HMINWAKRVP  1320
GFVDLTLHDQ AHLLERAWLE ILMIGLVWRS MEHPGKLLFA PNLLLDRNQG KCVEGMVEIF  1380
DMLLATSSRF RMMNLQGEEF VCLKSIILLN SGVYTFLSST LKSLEEKDHI HRALDKITDT  1440
LIHLMAKAGL TLQQQHQRLA QLLLILSHIR HMSNKGMEHL YSMKYKNVVP LYDLLLEMLD  1500
AHRLHAGGSG ASRVQAFADA LDDKFLHDML AEGLRYSVIR EVLPTRRART FDLEVEELHT  1560
LVAEGVVVHN CVKELLGITI MERSSFEKNP IDFLEAKGYK EVKKDLIIKL PKYSLFELEN  1620
GRKRMLASAG ELQKGNELAL PSKYVNFLYL ASHYEKLKGS PEDNEQKQLF VEQHKHYLDE  1680
IIEQISEFSK RVILADANLD KVLSAYNKHR DKPIREQAEN IIHLFTLTNL GAPAAFKYFD  1740
TTIDRKRYTS TKEVLDATLI HQSITGLYET RIDLSQLGGD                        1780

SEQ ID NO: 41          moltype = AA  length = 1780
FEATURE                Location/Qualifiers
REGION                 1..1780
                       note = Synthetic Polypeptide
source                 1..1780
                       mol_type = protein
                       organism = synthetic construct
SEQUENCE: 41
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQICLAEGTR IFDPVTGTTH RIEDVVDGRK PIHVVAAAKD GTLLARPVVS  1320
WFDQGTRDVI GLRIAGGAIV WATPDHKVLT EYGWRAAGEL RKGDRVAGPG GSGNSLALSL  1380
TADQMVSALL DAEPPILYSE YDPTSPFSEA SMMGLLTNLA DRELVHMINW AKRVPGFVDL  1440
TLHDQAHLLE RAWLEILMIG LVWRSMEHPG KLLFAPNLLL DRNQGKCVEG MVEIFDMLLA  1500
TSSRFRMMNL QGEEFVCLKS IILLNSGVYT FLSSTLKSLE EKDHIHRALD KITDTLIHLM  1560
AKAGLTLQQQ HQRLAQLLLI LSHIRHMSNK GMEHLYSMKY KNVVPLYDLL LEMLDAHRLH  1620
```

-continued

```
AGGSGASRVQ AFADALDDKF LHDMLAEGLR YSVIREVLPT RRARTFDLEV EELHTLVAEG  1680
VVVHNCEFSK RVILADANLD KVLSAYNKHR DKPIREQAEN IIHLFTLTNL GAPAAFKYFD  1740
TTIDRKRYTS TKEVLDATLI HQSITGLYET RIDLSQLGGD                        1780

SEQ ID NO: 42          moltype = AA  length = 16
FEATURE                Location/Qualifiers
REGION                 1..16
                       note = Synthetic Polypeptide
source                 1..16
                       mol_type = protein
                       organism = synthetic construct
SEQUENCE: 42
MAPKKKRKVG IHRGVP                                                  16

SEQ ID NO: 43          moltype = AA  length = 23
FEATURE                Location/Qualifiers
REGION                 1..23
                       note = Synthetic Polypeptide
source                 1..23
                       mol_type = protein
                       organism = synthetic construct
SEQUENCE: 43
MDYKDHDGDY KDHDIDYKDD DDK                                          23

SEQ ID NO: 44          moltype = DNA  length = 432
FEATURE                Location/Qualifiers
misc_feature           1..432
                       note = Synthetic Polynucleotide
source                 1..432
                       mol_type = other DNA
                       organism = synthetic construct
SEQUENCE: 44
atggccctgt ttggctacgc acgcgtgtct accagtcaac agtcactcga tttgcaagtg  60
agggctctta aagatgccgg agtgaaggca aacagaattt ttactgataa ggccagcgga  120
agcagcacag acagagaggg gctggatctc ctgagaatga aggtaaagga gggtgatgtg  180
atcttggtca aaaaattgga tcgactgggg agagacacag ctgatatgct tcagcttatt  240
aaagagtttg acgctcaggg tgttgccgtg aggtttatcg atgacggcat ctcaaccgac  300
tcctacattg gtcttatgtt tgtgacaatt ttgtccgctg tggctcaggc tgagcggaga  360
aggattctcg aaaggacgaa tgagggacgg caagcagcta agttgaaagg tatcaaattt  420
ggcagacgaa gg                                                      432

SEQ ID NO: 45          moltype = AA  length = 144
FEATURE                Location/Qualifiers
REGION                 1..144
                       note = Synthetic Polypeptide
source                 1..144
                       mol_type = protein
                       organism = synthetic construct
SEQUENCE: 45
MALFGYARVS TSQQSLDLQV RALKDAGVKA NRIFTDKASG SSTDREGLDL LRMKVKEGDV  60
ILVKKLDRLG RDTADMLQLI KEFDAQGVAV RFIDDGISTD SYIGLMFVTI LSAVAQAERR  120
RILERTNEGR QAAKLKGIKF GRRR                                         144

SEQ ID NO: 46          moltype = DNA  length = 414
FEATURE                Location/Qualifiers
misc_feature           1..414
                       note = Synthetic Polynucleotide
source                 1..414
                       mol_type = other DNA
                       organism = synthetic construct
SEQUENCE: 46
atggcaacca ttggctacat aagggtgtct accatcgacc aaaatatcga cctgcagcgc  60
aacgctctga catccgccaa ctgcgatcgg atcttcgagg ataggatcag tggcaagatc  120
gccaaccggc ccggtctgaa gcgggctctg aagtacgtga ataagggcga tactctggtt  180
gtgtggaagt tggatcgctt gggtagatca gtgaagaatc tcgtagccct gataagcgag  240
ctgcacgaga ggggtgcaca tttccattct ctgaccgatt ccatcgatac gtctagcgcc  300
atgggccgat tcttctttta cgtcatgtcc gccctcgctg aaatggagcg cgaacttatt  360
gttgaacgga ctttggctgg actggcagcg gctagagcac agggccgact tgga        414

SEQ ID NO: 47          moltype = AA  length = 138
FEATURE                Location/Qualifiers
REGION                 1..138
                       note = Synthetic Polypeptide
source                 1..138
                       mol_type = protein
                       organism = synthetic construct
```

```
SEQUENCE: 47
MATIGYIRVS TIDQNIDLQR NALTSANCDR IFEDRISGKI ANRPGLKRAL KYVNKGDTLV  60
VWKLDRLGRS VKNLVALISE LHERGAHFHS LTDSIDTSSA MGRFFFYVMS ALAEMERELI  120
VERTLAGLAA ARAQGRLG                                               138

SEQ ID NO: 48          moltype = DNA  length = 432
FEATURE                Location/Qualifiers
misc_feature           1..432
                       note = Synthetic Polynucleotide
source                 1..432
                       mol_type = other DNA
                       organism = synthetic construct
SEQUENCE: 48
atgctcattg gctatgtaag ggtcagcacc aatgaccaaa acacagactt gcaacgcaat  60
gctttggttt gcgccggatg tgaacagata tttgaagata aactgagcgg cactcggaca  120
gacagacctg ggcttaagag agcactgaaa agactgcaga agggggacac cctggtcgtc  180
tggaaactgg atcgcctcgg acgcagcatg aaacatctga ttagcctggt tggtgagctt  240
agggagagag gaatcaactt cagaagcctg accgactcca tcgacaccag tagcccccatg  300
ggacgattct tcttctatgt gatgggagca cttgctgaga tggaaagaga gcttattatc  360
gaaagaacta tggctggtat cgctgctgcc cggaacaaag gcagacggtt cggcagaccg  420
ccgaagagcg gc                                                     432

SEQ ID NO: 49          moltype = AA  length = 144
FEATURE                Location/Qualifiers
REGION                 1..144
                       note = Synthetic Polypeptide
source                 1..144
                       mol_type = protein
                       organism = synthetic construct
SEQUENCE: 49
MLIGYVRVST NDQNTDLQRN ALVCAGCEQI FEDKLSGTRT DRPGLKRALK RLQKGDTLVV  60
WKLDRLGRSM KHLISLVGEL RERGINFRSL TDSIDTSSPM GRFFFYVMGA LAEMERELII  120
ERTMAGIAAA RNKGRRFGRP PKSG                                        144

SEQ ID NO: 50          moltype = AA  length = 198
FEATURE                Location/Qualifiers
source                 1..198
                       mol_type = protein
                       organism = Homo sapiens
SEQUENCE: 50
MDSLLMNRRK FLYQFKNVRW AKGRRETYLC YVVKRRDSAT SFSLDFGYLR NKNGCHVELL  60
FLRYISDWDL DPGRCYRVTW FTSWSPCYDC ARHVADFLRG NPNLSLRIFT ARLYFCEDRK  120
AEPEGLRRLH RAGVQIAIMT FKDYFYCWNT FVENHERTFK AWEGLHENSV RLSRQLRRIL  180
LPLYEVDDLR DAFRTLGL                                               198

SEQ ID NO: 51          moltype = AA  length = 198
FEATURE                Location/Qualifiers
source                 1..198
                       mol_type = protein
                       organism = Mus musculus
SEQUENCE: 51
MDSLLMKQKK FLYHFKNVRW AKGRHETYLC YVVKRRDSAT SCSLDFGHLR NKSGCHVELL  60
FLRYISDWDL DPGRCYRVTW FTSWSPCYDC ARHVAEFLRW NPNLSLRIFT ARLYFCEDRK  120
AEPEGLRRLH RAGVQIGIMT FKDYFYCWNT FVENRERTFK AWEGLHENSV RLTRQLRRIL  180
LPLYEVDDLR DAFRMLGF                                               198

SEQ ID NO: 52          moltype = AA  length = 198
FEATURE                Location/Qualifiers
source                 1..198
                       mol_type = protein
                       note = sub-species familiaris
                       organism = Canis lupus
SEQUENCE: 52
MDSLLMKQRK FLYHFKNVRW AKGRHETYLC YVVKRRDSAT SFSLDFGHLR NKSGCHVELL  60
FLRYISDWDL DPGRCYRVTW FTSWSPCYDC ARHVADFLRG YPNLSLRIFA ARLYFCEDRK  120
AEPEGLRRLH RAGVQIAIMT FKDYFYCWNT FVENREKTFK AWEGLHENSV RLSRQLRRIL  180
LPLYEVDDLR DAFRTLGL                                               198

SEQ ID NO: 53          moltype = AA  length = 199
FEATURE                Location/Qualifiers
source                 1..199
                       mol_type = protein
                       organism = Bos taurus
SEQUENCE: 53
MDSLLKKQRQ FLYQFKNVRW AKGRHETYLC YVVKRRDSPT SFSLDFGHLR NKAGCHVELL  60
FLRYISDWDL DPGRCYRVTW FTSWSPCYDC ARHVADFLRG YPNLSLRIFT ARLYFCDKER  120
KAEPEGLRRL HRAGVQIAIM TFKDYFYCWN TFVENHERTF KAWEGLHENS VRLSRQLRRI  180
LLPLYEVDDL RDAFRTLGL                                              199
```

-continued

```
SEQ ID NO: 54          moltype = AA  length = 429
FEATURE                Location/Qualifiers
source                 1..429
                       mol_type = protein
                       organism = Mus musculus
SEQUENCE: 54
MGPFCLGCSH RKCYSPIRNL ISQETFKFHF KNLGYAKGRK DTFLCYEVTR KDCDSPVSLH  60
HGVFKNKDNI HAEICFLYWF HDKVLKVLSP REEFKITWYM SWSPCFECAE QIVRFLATHH  120
NLSLDIFSSR LYNVQDPETQ QNLCRLVQEG AQVAAMDLYE FKKCWKKFVD NGGRRFRPWK  180
RLLTNFRYQD SKLQEILRPC YIPVPSSSSS TLSNICLTKG LPETRFCVEG RRMDPLSEEE  240
FYSQFYNQRV KHLCYYHRMK PYLCYQLEQF NGQAPLKGCL LSEKGKQHAE ILFLDKIRSM  300
ELSQVTITCY LTWSPCPNCA WQLAAFKRDR PDLILHIYTS RLYFHWKRPF QKGLCSLWQS  360
GILVDVMDLP QFTDCWTNFV NPKRPFWPWK GLEIISRRTQ RRLRRIKESW GLQDLVNDFG  420
NLQLGPPMS                                                        429

SEQ ID NO: 55          moltype = AA  length = 429
FEATURE                Location/Qualifiers
source                 1..429
                       mol_type = protein
                       organism = Rattus rattus
SEQUENCE: 55
MGPFCLGCSH RKCYSPIRNL ISQETFKFHF KNLRYAIDRK DTFLCYEVTR KDCDSPVSLH  60
HGVFKNKDNI HAEICFLYWF HDKVLKVLSP REEFKITWYM SWSPCFECAE QVLRFLATHH  120
NLSLDIFSSR LYNIRDPENQ QNLCRLVQEG AQVAAMDLYE FKKCWKKFVD NGGRRFRPWK  180
KLLTNFRYQD SKLQEILRPC YIPVPSSSSS TLSNICLTKG LPETRFCVER RRVHLLSEEE  240
FYSQFYNQRV KHLCYYHGVK PYLCYQLEQF NGQAPLKGCL LSEKGKQHAE ILFLDKIRSM  300
ELSQVIITCY LTWSPCPNCA WQLAAFKRDR PDLILHIYTS RLYFHWKRPF QKGLCSLWQS  360
GILVDVMDLP QFTDCWTNFV NPKRPFWPWK GLEIISRRTQ RRLHRIKESW GLQDLVNDFG  420
NLQLGPPMS                                                        429

SEQ ID NO: 56          moltype = AA  length = 370
FEATURE                Location/Qualifiers
source                 1..370
                       mol_type = protein
                       organism = Macaca mulatta
SEQUENCE: 56
MVEPMDPRTF VSNFNNRPIL SGLNTVWLCC EVKTKDPSGP PLDAKIFQGK VYSKAKYHPE  60
MRFLRWFHKW RQLHHDQEYK VTWYVSWSPC TRCANSVATF LAKDPKVTLT IFVARLYYFW  120
KPDYQQALRI LCQKRGGPHA TMKIMNYNEF QDCWNKFVDG RGKPFKPRNN LPKHYTLLQA  180
TLGELLRHLM DPGTFTSNFN NKPWVSGQHE TYLCYKVERL HNDTWVPLNQ HRGFLRNQAP  240
NIHGFPKGRH AELCFLDLIP FWKLDGQQYR VTCFTSWSPC FSCAQEMAKF ISNNEHVSLC  300
IFAARIYDDQ GRYQEGLRAL HRDGAKIAMM NYSEFEYCWD TFVDRQGRPF QPWDGLDEHS  360
QALSGRLRAI                                                       370

SEQ ID NO: 57          moltype = AA  length = 384
FEATURE                Location/Qualifiers
source                 1..384
                       mol_type = protein
                       organism = Pan troglodytes
SEQUENCE: 57
MKPHFRNPVE RMYQDTFSDN FYNRPILSHR NTVWLCYEVK TKGPSRPPLD AKIFRGQVYS  60
KLKYHPEMRF FHWFSKWRKL HRDQEYEVTW YISWSPCTKC TRDVATFLAE DPKVTLTIFV  120
ARLYYFWDPD YQEALRSLCQ KRDGPRATMK IMNYDEFQHC WSKFVYSQRE LFEPWNNLPK  180
YYILLHIMLG EILRHSMDPP TFTSNFNNEL WVRGRHETYL CYEVERLHND TWVLLNQRRG  240
FLCNQAPHKH GFLEGRHAEL CFLDVIPFWK LDLHQDYRVT CFTSWSPCFS CAQEMAKFIS  300
NNKHVSLCIF AARIYDDQGR CQEGLRTLAK AGAKISIMTY SEFKHCWDTF VDHQGCPFQP  360
WDGLEEHSQA LSGRLRAILQ NQGN                                       384

SEQ ID NO: 58          moltype = AA  length = 377
FEATURE                Location/Qualifiers
source                 1..377
                       mol_type = protein
                       organism = Chlorocebus sabaeus
SEQUENCE: 58
MNPQIRNMVE QMEPDIFVYY FNNRPILSGR NTVWLCYEVK TKDPSGPPLD ANIFQGKLYP  60
EAKDHPEMKF LHWFRKWRQL HRDQEYEVTW YVSWSPCTRC ANSVATFLAE DPKVTLTIFV  120
ARLYYFWKPD YQQALRILCQ ERGGPHATMK IMNYNEFQHC WNEFVDGQGK PFKPRKNLPK  180
HYTLLHATLG ELLRHVMDPG TFTSNFNNKP WVSGQRETYL CYKVERSHND TWVLLNQHRG  240
FLRNQAPDRH GFPKGRHAEL CFLDLIPFWK LDDQQYRVTC FTSWSPCFSC AQKMAKFISN  300
NKHVSLCIFA ARIYDDQGRC QEGLRTLHRD GAKIAVMNYS EFEYCWDTFV DRQGRPFQPW  360
DGLDEHSQAL SGRLRAI                                               377

SEQ ID NO: 59          moltype = AA  length = 384
FEATURE                Location/Qualifiers
source                 1..384
                       mol_type = protein
                       organism = Homo sapiens
```

```
SEQUENCE: 59
MKPHFRNTVE RMYRDTFSYN FYNRPILSRR NTVWLCYEVK TKGPSRPPLD AKIFRGQVYS  60
ELKYHPEMRF FHWFSKWRKL HRDQEYEVTW YISWSPCTKC TRDMATFLAE DPKVTLTIFV  120
ARLYYFWDPD YQEALRSLCQ KRDGPRATMK IMNYDEFQHC WSKFVYSQRE LFEPWNNLPK  180
YYILLHIMLG EILRHSMDPP TFTFNFNNEP WVRGRHETYL CYEVERMHND TWVLLNQRRG  240
FLCNQAPHKH GFLEGRHAEL CFLDVIPFWK LDLDQDYRVT CFTSWSPCFS CAQEMAKFIS  300
KNKHVSLCIF TARIYDDQGR CQEGLRTLAE AGAKISIMTY SEFKHCWDTF VDHQGCPFQP  360
WDGLDEHSQD LSGRLRAILQ NQEN                                         384

SEQ ID NO: 60          moltype = AA  length = 373
FEATURE                Location/Qualifiers
source                 1..373
                       mol_type = protein
                       organism = Homo sapiens
SEQUENCE: 60
MKPHFRNTVE RMYRDTFSYN FYNRPILSRR NTVWLCYEVK TKGPSRPRLD AKIFRGQVYS  60
QPEHHAEMCF LSWFCGNQLP AYKCFQITWF VSWTPCPDCV AKLAEFLAEH PNVTLTISAA  120
RLYYYWERDY RRALCRLSQA GARVKIMDDE EFAYCWENFV YSEGQPFMPW YKFDDNYAFL  180
HRTLKEILRN PMEAMYPHIF YFHFKNLRKA YGRNESWLCF TMEVVKHHSP VSWKRGVFRN  240
QVDPETHCHA ERCFLSWFCD DILSPNTNYE VTWYTSWSPC PECAGEVAEF LARHSNVNLT  300
IFTARLYYFW DTDYQEGLRS LSQEGASVEI MGYKDFKYCW ENFVYNDDEP FKPWKGLKYN  360
FLFLDSKLQE ILE                                                     373

SEQ ID NO: 61          moltype = AA  length = 382
FEATURE                Location/Qualifiers
source                 1..382
                       mol_type = protein
                       organism = Homo sapiens
SEQUENCE: 61
MNPQIRNPME RMYRDTFYDN FENEPILYGR SYTWLCYEVK IKRGRSNLLW DTGVFRGQVY  60
FKPQYHAEMC FLSWFCGNQL PAYKCFQITW FVSWTPCPDC VAKLAEFLSE HPNVTLTISA  120
ARLYYYWERD YRRALCRLSQ AGARVTIMDY EEFAYCWENF VYNEGQQFMP WYKFDENYAF  180
LHRTLKEILR YLMDPDTFTF NFNNDPLVLR RRQTYLCYEV ERLDNGTWVL MDQHMGFLCN  240
EAKNLLCGFY GRHAELRFLD LVPSLQLDPA QIYRVTWFIS WSPCFSWGCA GEVRAFLQEN  300
THVRLRIFAA RIYDYDPLYK EALQMLRDAG AQVSIMTYDE FEYCWDTFVY RQGCPFQPWD  360
GLEEHSQALS GRLRAILQNQ GN                                           382

SEQ ID NO: 62          moltype = AA  length = 190
FEATURE                Location/Qualifiers
source                 1..190
                       mol_type = protein
                       organism = Homo sapiens
SEQUENCE: 62
MNPQIRNPMK AMYPGTFYFQ FKNLWEANDR NETWLCFTVE GIKRRSVVSW KTGVFRNQVD  60
SETHCHAERC FLSWFCDDIL SPNTKYQVTW YTSWSPCPDC AGEVAEFLAR HSNVNLTIFT  120
ARLYYFQYPC YQEGLRSLSQ EGVAVEIMDY EDFKYCWENF VYNDNEPFKP WKGLKTNFRL  180
LKRRLRESLQ                                                         190

SEQ ID NO: 63          moltype = AA  length = 199
FEATURE                Location/Qualifiers
source                 1..199
                       mol_type = protein
                       organism = Homo sapiens
SEQUENCE: 63
MEASPASGPR HLMDPHIFTS NFNNGIGRHK TYLCYEVERL DNGTSVKMDQ HRGFLHNQAK  60
NLLCGFYGRH AELRFLDLVP SLQLDPAQIY RVTWFISWSP CFSWGCAGEV RAFLQENTHV  120
RLRIFAARIY DYDPLYKEAL QMLRDAGAQV SIMTYDEFKH CWDTFVDHQG CPFQPWDGLD  180
EHSQALSGRL RAILQNQGN                                               199

SEQ ID NO: 64          moltype = AA  length = 200
FEATURE                Location/Qualifiers
source                 1..200
                       mol_type = protein
                       organism = Homo sapiens
SEQUENCE: 64
MALLTAETFR LQFNNKRRLR RPYYPRKALL CYQLTPQNGS TPTRGYFENK KKCHAEICFI  60
NEIKSMGLDE TQCYQVTCYL TWSPCSSCAW ELVDFIKAHD HLNLGIFASR LYYHWCKPQQ  120
KGLRLLCGSQ VPVEVMGFPK FADCWENFVD HEKPLSFNPY KMLEELDKNS RAIKRRLERI  180
KIPGVRAQGR YMDILCDAEV                                              200

SEQ ID NO: 65          moltype = AA  length = 386
FEATURE                Location/Qualifiers
source                 1..386
                       mol_type = protein
                       organism = Homo sapiens
SEQUENCE: 65
MNPQIRNPME RMYRDTFYDN FENEPILYGR SYTWLCYEVK IKRGRSNLLW DTGVFRGPVL  60
PKRQSNHRQE VYFRFENHAE MCFLSWFCGN RLPANRRFQI TWFVSWNPCL PCVVKVTKFL  120
AEHPNVTLTI SAARLYYYRD RDWRWVLLRL HKAGARVKIM DYEDFAYCWE NFVCNEGQPF  180
```

-continued

```
MPWYKFDDNY ASLHRTLKEI LRNPMEAMYP HIFYFHFKNL LKACGRNESW LCFTMEVTKH  240
HSAVFRKRGV FRNQVDPETH CHAERCFLSW FCDDILSPNT NYEVTWYTSW SPCPECAGEV  300
AEFLARHSNV NLTIFTARLC YFWDTDYQEG LCSLSQEGAS VKIMGYKDFV SCWKNFVYSD  360
DEPFKPWKGL QTNFRLLKRR LREILQ                                       386

SEQ ID NO: 66          moltype = AA  length = 236
FEATURE                Location/Qualifiers
source                 1..236
                       mol_type = protein
                       organism = Homo sapiens
SEQUENCE: 66
MTSEKGPSTG DPTLRRRIEP WEFDVFYDPR ELRKEACLLY EIKWGMSRKI WRSSGKNTTN  60
HVEVNFIKKF TSERDFHPSM SCSITWFLSW SPCWECSQAI REFLSRHPGV TLVIYVARLF  120
WHMDQQNRQG LRDLVNSGVT IQIMRASEYY HCWRNFVNYP PGDEAHWPQY PPLWMMLYAL  180
ELHCIILSLP PCLKISRRWQ NHLTFFRLHL QNCHYQTIPP HILLATGLIH PSVAWR      236

SEQ ID NO: 67          moltype = AA  length = 229
FEATURE                Location/Qualifiers
source                 1..229
                       mol_type = protein
                       organism = Mus musculus
SEQUENCE: 67
MSSETGPVAV DPTLRRRIEP HEFEVFFDPR ELRKETCLLY EINWGGRHSV WRHTSQNTSN  60
HVEVNFLEKF TTERYFRPNT RCSITWFLSW SPCGECSRAI TEFLSRHPYV TLFIYIARLY  120
HHTDQRNRQG LRDLISSGVT IQIMTEQEYC YCWRNFVNYP PSNEAYWPRY PHLWVKLYVL  180
ELYCIILGLP PCLKILRRKQ PQLTFFTITL QTCHYQRIPP HLLWATGLK             229

SEQ ID NO: 68          moltype = AA  length = 229
FEATURE                Location/Qualifiers
source                 1..229
                       mol_type = protein
                       organism = Rattus rattus
SEQUENCE: 68
MSSETGPVAV DPTLRRRIEP HEFEVFFDPR ELRKETCLLY EINWGGRHSI WRHTSQNTNK  60
HVEVNFIEKF TTERYFCPNT RCSITWFLSW SPCGECSRAI TEFLSRYPHV TLFIYIARLY  120
HHADPRNRQG LRDLISSGVT IQIMTEQESG YCWRNFVNYS PSNEAHWPRY PHLWVRLYVL  180
ELYCIILGLP PCLNILRRKQ PQLTFFTIAL QSCHYQRLPP HILWATGLK             229

SEQ ID NO: 69          moltype = AA  length = 191
FEATURE                Location/Qualifiers
source                 1..191
                       mol_type = protein
                       organism = Homo sapiens
SEQUENCE: 69
MEAKAAPKPA ASGACSVSAE ETEKWMEEAM HMAKEALENT EVPVGCLMVY NNEVVGKGRN  60
EVNQTKNATR HAEMVAIDQV LDWCRQSGKS PSEVFEHTVL YVTVEPCIMC AAALRLMKIP  120
LVVYGCQNER FGGCGSVLNI ASADLPNTGR PFQCIPGYRA EEAVEMLKTF YKQENPNAPK  180
SKVRKKECQK S                                                       191

SEQ ID NO: 70          moltype = AA  length = 191
FEATURE                Location/Qualifiers
source                 1..191
                       mol_type = protein
                       organism = Mus musculus
SEQUENCE: 70
MEEKVESTTT PDGPCVVSVQ ETEKWMEEAM RMAKEALENI EVPVGCLMVY NNEVVGKGRN  60
EVNQTKNATR HAEMVAIDQV LDWCHQHGQS PSTVFEHTVL YVTVEPCIMC AAALRLMKIP  120
LVVYGCQNER FGGCGSVLNI ASADLPNTGR PFQCIPGYRA EEAVELLKTF YKQENPNAPK  180
SKVRKKDCQK S                                                       191

SEQ ID NO: 71          moltype = AA  length = 499
FEATURE                Location/Qualifiers
source                 1..499
                       mol_type = protein
                       organism = Mus musculus
SEQUENCE: 71
MWTADEIAQL CYAHYNVRLP KQGKPEPNRE WTLLAAVVKI QASANQACDI PEKEVQVTKE  60
VVSMGTGTKC IGQSKMRESG DILNDSHAEI IARRSFQRYL LHQLHLAAVL KEDSIFVPGT  120
QRGLWRLRPD LSFVFFSSHT PCGDASIIPM LEFEEQPCCP VIRSWANNSP VQETENLEDS  180
KDKRNCEDPA SPVAKKMRLG TPARSLSNCV AHHGTQESGP VKPDVSSSDL TKEEPDAANG  240
IASGSFRVVD VYRTGAKCVP GETGDLREPG AAYHQVGLLR VKPGRGDRTC SMSCSDKMAR  300
WNVLGCQGAL LMHFLEKPIY LSAVVIGKCP YSQEAMRRAL TGRCEETLVL PRGFGVQELE  360
IQQSGLLFEQ SRCAVHRKRG DSPGRLVPCG AAISWSAVPQ QPLDVTANGF PQGTTKKEIG  420
SPRARSRISK VELFRSFQKL LSSIADDEQP DSIRVTKKLD TYQEYKDAAS AYQEAWGALR  480
RIQPFASWIR NPPDYHQFK                                               499
```

```
SEQ ID NO: 72          moltype = AA  length = 502
FEATURE                Location/Qualifiers
source                 1..502
                       mol_type = protein
                       organism = Homo sapiens
SEQUENCE: 72
MWTADEIAQL CYEHYGIRLP KKGKPEPNHE WTLLAAVVKI QSPADKACDT PDKPVQVTKE  60
VVSMGTGTKC IGQSKMRKNG DILNDSHAEV IARRSFQRYL LHQLQLAATL KEDSIFVPGT  120
QKGVWKLRRD LIFVFFSSHT PCGDASIIPM LEFEDQPCCP VFRNWAHNSS VEASSNLEAP  180
GNERKCEDPD SPVTKKMRLE PGTAAREVTN GAAHHQSFGK QKSGPISPGI HSCDLTVEGL  240
ATVTRIAPGS AKVIDVYRTG AKCVPGEAGD SGKPGAAFHQ VGLLRVKPGR GDRTRSMSCS  300
DKMARWNVLG CQGALLMHLL EEPIYLSAVV IGKCPYSQEA MQRALIGRCQ NVSALPKGFG  360
VQELKILQSD LLFEQSRSAV QAKRADSPGR LVPCGAAISW SAVPEQPLDV TANGFPQGTT  420
KKTIGSLQAR SQISKVELFR SFQKLLSRIA RDKWPHSLRV QKLDTYQEYK EAASSYQEAW  480
STLRKQVFGS WIRNPPDYHQ FK                                          502

SEQ ID NO: 73          moltype = AA  length = 57
FEATURE                Location/Qualifiers
REGION                 1..57
                       note = Synthetic Polypeptide
source                 1..57
                       mol_type = protein
                       organism = synthetic construct
SEQUENCE: 73
GSGRADALDD FDLDMLGSDA LDDFDLDMLG SDALDDFDLD MLGSDALDDF DLDMLIN     57

SEQ ID NO: 74          moltype = AA  length = 85
FEATURE                Location/Qualifiers
REGION                 1..85
                       note = Synthetic Polypeptide
source                 1..85
                       mol_type = protein
                       organism = synthetic construct
SEQUENCE: 74
APPTDVSLGD ELHLDGEDVA MAHADALDDF DLDMLGDGDS PGPGFTPHDS APYGALDMAD  60
FEFEQMFTDA LGIDEYGGEF PGIRR                                       85

SEQ ID NO: 75          moltype = AA  length = 184
FEATURE                Location/Qualifiers
REGION                 1..184
                       note = Synthetic Polypeptide
source                 1..184
                       mol_type = protein
                       organism = synthetic construct
SEQUENCE: 75
PSGQISNQAL ALAPSSAPVL AQTMVPSSAM VPLAQPPAPA PVLTPGPPQS LSAPVPKSTQ  60
AGEGTLSEAL LHLQFDADED LGALLGNSTD PGVFTDLASV DNSEFQQLLN QGVSMSHSTA  120
EPMLMEYPEA ITRLVTGSQR PPDPAPTPLG TSGLPNGLSG DEDFSSIADM DFSALLSQIS  180
SSGQ                                                              184

SEQ ID NO: 76          moltype = AA  length = 94
FEATURE                Location/Qualifiers
source                 1..94
                       mol_type = protein
                       organism = Homo sapiens
SEQUENCE: 76
MNMFKEAVTF KDVAVAFTEE ELGLLGPAQR KLYRDVMVEN FRNLLSVGHP PFKQDVSPIE  60
RNEQLWIMTT ATRRQGNLDT LPVKALLLYD LAQT                             94

SEQ ID NO: 77          moltype = AA  length = 74
FEATURE                Location/Qualifiers
source                 1..74
                       mol_type = protein
                       organism = Homo sapiens
SEQUENCE: 77
EQVSFKDVCV DFTQEEWYLL DPAQKILYRD VILENYSNLV SVGYCITKPE VIFKIEQGEE  60
PWILEKGFPS QCHP                                                   74

SEQ ID NO: 78          moltype = AA  length = 42
FEATURE                Location/Qualifiers
source                 1..42
                       mol_type = protein
                       organism = Homo sapiens
SEQUENCE: 78
EAVTFKDVAV VFTEEELGLL DPAQRKLYRD VMLENFRNLL SV                    42

SEQ ID NO: 79          moltype = AA  length = 69
FEATURE                Location/Qualifiers
```

```
source                  1..69
                        mol_type = protein
                        organism = Mus musculus
SEQUENCE: 79
MDLVTYDDVH VNFTQDEWAL LDPSQKSLYK GVMLETYKNL TAIGYIWEEH TIEDHFQTSR  60
SHGSNKKTH                                                         69

SEQ ID NO: 80           moltype = AA  length = 32
FEATURE                 Location/Qualifiers
REGION                  1..32
                        note = Synthetic Polypeptide
source                  1..32
                        mol_type = protein
                        organism = synthetic construct
SEQUENCE: 80
GSGMNIQMLL EAADYLERRE REAEHGYASM LP                               32

SEQ ID NO: 81           moltype = AA  length = 130
FEATURE                 Location/Qualifiers
REGION                  1..130
                        note = Synthetic Polypeptide
source                  1..130
                        mol_type = protein
                        organism = synthetic construct
SEQUENCE: 81
GSGMNIQMLL EAADYLERRE REAEHGYASM LPGSGMNIQM LLEAADYLER REREAEHGYA  60
SMLPGSGMNI QMLLEAADYL ERREREAEHG YASMLPGSGM NIQMLLEAAD YLERREREAE  120
HGYASMLPSR                                                        130

SEQ ID NO: 82           moltype = AA  length = 876
FEATURE                 Location/Qualifiers
source                  1..876
                        mol_type = protein
                        organism = Homo sapiens
SEQUENCE: 82
MLSGKKAAAA AAAAAAAATG TEAGPGTAGG SENGSEVAAQ PAGLSGPAEV GPGAVGERTP  60
RKKEPPRASP PGGLAEPPGS AGPQAGPTVV PGSATPMETG IAETPEGRRT SRRKRAKVEY  120
REMDESLANL SEDEYYSEEE RNAKAEKEKK LPPPPPQAPP EEENESEPEE PSGQAGGLQD  180
DSSGGYGDGQ ASGVEGAAFQ SRLPHDRMTS QEAACFPDII SGPQQTQKVF LFIRNRTLQL  240
WLDNPKIQLT FEATLQQLEA PYNSDTVLVH RVHSYLERHG LINFGIYKRI KPLPTKKTGK  300
VIIIGSGVSG LAAARQLQSF GMDVTLLEAR DRVGGRVATF RKGNYVADLG AMVVTGLGGN  360
PMAVVSKQVN MELAKIKQKC PLYEANGQAD TVKVPKEKDE MVEQEFNRLL EATSYLSHQL  420
DFNVLNNKPV SLGQALEVVI QLQEKHVKDE QIEHWKKIVK TQEELKELLN KMVNLKEKIK  480
ELHQQYKEAS EVKPPRDITA EFLVKSKHRD LTALCKEYDE LAETQGKLEE KLQELEANPP  540
SDVYLSSRDR QILDWHFANL EFANATPLST LSLKHWDQDD DFEFTGSHLT VRNGYSCVPV  600
ALAEGLDIKL NTAVRQVRYT ASGCEVIAVN TRSTSQTFIY KCDAVLCTLP LGVLKQQPPA  660
VQFVPPLPEW KTSAVQRMGF GNLNKVVLCF DRVFWDPSVN LFGHVGSTTA SRGELFLFWN  720
LYKAPILLAL VAGEAAGIME NISDDVIVGR CLAILKGIFG SSAVPQPKET VVSRWRADPW  780
ARGSYSYVAA GSSGNDYDLM AQPITPGPSI PGAPQPIPRL FFAGEHTIRN YPATVHGALL  840
SGLREAGRIA DQFLGAMYTL PRQATPGVPA QQSPSM                           876

SEQ ID NO: 83           moltype = AA  length = 852
FEATURE                 Location/Qualifiers
source                  1..852
                        mol_type = protein
                        organism = Homo sapiens
SEQUENCE: 83
MLSGKKAAAA AAAAAAAATG TEAGPGTAGG SENGSEVAAQ PAGLSGPAEV GPGAVGERTP  60
RKKEPPRASP PGGLAEPPGS AGPQAGPTVV PGSATPMETG IAETPEGRRT SRRKRAKVEY  120
REMDESLANL SEDEYYSEEE RNAKAEKEKK LPPPPPQAPP EEENESEPEE PSGVEGAAFQ  180
SRLPHDRMTS QEAACFPDII SGPQQTQKVF LFIRNRTLQL WLDNPKIQLT FEATLQQLEA  240
PYNSDTVLVH RVHSYLERHG LINFGIYKRI KPLPTKKTGK VIIIGSGVSG LAAARQLQSF  300
GMDVTLLEAR DRVGGRVATF RKGNYVADLG AMVVTGLGGN PMAVVSKQVN MELAKIKQKC  360
PLYEANGQAV PKEKDEMVEQ EFNRLLEATS YLSHQLDFNV LNNKPVSLGQ ALEVVIQLQE  420
KHVKDEQIEH WKKIVKTQEE LKELLNKMVN LKEKIKELHQ QYKEASEVKP PRDITAEFLV  480
KSKHRDLTAL CKEYDELAET QGKLEEKLQE LEANPPSDVY LSSRDRQILD WHFANLEFAN  540
ATPLSTLSLK HWDQDDDFEF TGSHLTVRNG YSCVPVALAE GLDIKLNTAV RQVRYTASGC  600
EVIAVNTRST SQTFIYKCDA VLCTLPLGVL KQQPPAVQFV PPLPEWKTSA VQRMGFGNLN  660
KVVLCFDRVF WDPSVNLFGH VGSTTASRGE LFLFWNLYKA PILLALVAGE AAGIMENISD  720
DVIVGRCLAI LKGIFGSSAV PQPKETVVSR WRADPWARGS YSYVAAGSSG NDYDLMAQPI  780
TPGPSIPGAP QPIPRLFFAG EHTIRNYPAT VHGALLSGLR EAGRIADQFL GAMYTLPRQA  840
TPGVPAQQSP SM                                                     852

SEQ ID NO: 84           moltype = AA  length = 817
FEATURE                 Location/Qualifiers
REGION                  1..817
                        note = Synthetic Polypeptide
```

-continued

```
source                  1..817
                        mol_type = protein
                        organism = synthetic construct
SEQUENCE: 84
SIVAQLSRPD PALAALTNDH LVALACLGGR PALDAVKKGL PHAPALIKRT NRRIPERTSH  60
RVADHAQVVR VLGFFQCHSH PAQAFDDAMT QFGMSGGGSL PTCSCLDRVI QKDKGPYYTH  120
LGAGPSVAAV REIMENRYGQ KGNAIRIEIV VYTGKEGKSS HGCPIAKWVL RRSSDEEKVL  180
CLVRQRTGHH CPTAVMVVLI MVWDGIPLPM ADRLYTELTE NLKSYNGHPT DRRCTLNENR  240
TCTCQGIDPE TCGASFSFGC SWSMYFNGCK FGRSPSPRRF RIDPSSPLHE KNLEDNLQSL  300
ATRLAPIYKQ YAPVAYQNQV EYENVARECR LGSKEGRPFS GVTACLDFCA HPHRDIHNMN  360
NGSTVVCTLT REDNRSLGVI PQDEQLHVLP LYKLSDTDEF GSKEGMEAKI KSGAIEVLAP  420
RRKKRTCFTQ PVPRSGKKRA AMMTEVLAHK IRAVEKKPIP RIKRKNNSTT TNNSKPSSLP  480
TLGSNTETVQ PEVKSETEPH FILKSSDNTK TYSLMPSAPH PVKEASPGFS WSPKTASATP  540
APLKNDATAS CGFSERSSTP HCTMPSGRLS GANAAAADGP GISQLGEVAP LPTLSAPVME  600
PLINSEPSTG VTEPLTPHQP NHQPSFLTSP QDLASSPMEE DEQHSEADEP PSDEPLSDDP  660
LSPAEEKLPH IDEYWSDSEH IFLDANIGGV AIAPAHGSVL IECARRELHA TTPVEHPNRN  720
HPTRLSLVFY QHKNLNKPQH GFELNKIKFE AKEAKNKKMK ASEQKDQAAN EGPEQSSEVN  780
ELNQIPSHKA LTLTHDNVVT VSPYALTHVA GPYNHWV                          817

SEQ ID NO: 85           moltype = AA  length = 340
FEATURE                 Location/Qualifiers
source                  1..340
                        mol_type = protein
                        organism = Xenopus laevis
SEQUENCE: 85
ASSPKKKRKV EASMSRVVKP KVASMEEMAA FHTDAYLQHL HKVSEEGDND DPETLEYGLG  60
YDCPITEGIY DYAAAVGGAT LTAAEQLIEG KTRIAVNWPG GWHHAKKDEA SGFCYLNDAV  120
LGILKLREKF DRVLYVDMDL HHGDGVEDAF SFTSKVMTVS LHKFSPGFFP GTGDVSDIGL  180
GKGRYYSINV PLQDGIQDDK YYQICEGVLK EVFTTFNPEA VVLQLGADTI AGDPMCSFNM  240
TPEGIGKCLK YVLQWQLPTL ILGGGGYHLP NTARCWTYLT ALIVGRTLSS EIPDHEFFTE  300
YGPDYVLEIT PSCRPDRNDT QKVQEILQSI KGNLKRVVEF                       340

SEQ ID NO: 86           moltype = AA  length = 337
FEATURE                 Location/Qualifiers
source                  1..337
                        mol_type = protein
                        organism = Saccharomyces cerevisiae
SEQUENCE: 86
ASSPKKKRKV EASRRVAYFY DADVGNYAYG AGHPMKPHRI RMAHSLIMNY GLYKKMEIYR  60
AKPATKQEMC QFHTDEYIDF LSRVTPDNLE MFKRESVKFN VGDDCPVFDG LYEYCSISGG  120
GSMEGAARLN RGKCDVAVNY AGGLHHAKKS EASGFCYLND IVLGIIELLR YHPRVLYIDI  180
DVHHGDGVEE AFYTTDRVMT CSFHKYGEFF PGTGELRDIG VGAGKNYAVN VPLRDGIDDA  240
TYRSVFEPVI KKIMEWYQPS AVVLQCGGDS LSGDRLGCFN LSMEGHANCV NYVKSFGIPM  300
MVVGGGGYTM RNVARTWCFE TGLLNNVVLD KDLPYEF                          337

SEQ ID NO: 87           moltype = AA  length = 315
FEATURE                 Location/Qualifiers
source                  1..315
                        mol_type = protein
                        organism = Mesorhizobium loti
SEQUENCE: 87
ASSPKKKRKV EASMPLQIVH HPDYDAGFAT NHRFPMSKYP LLMEALRARG LASPDALNTT  60
EPAPASWLKL AHAADYVDQV ISCSVPEKIE REIGFPVGPR VSLRAQLATG GTILAARLAL  120
RHGIACNTAG GSHHARRAQG AGFCTFNDVA VASLVLLDEG AAQNILVVDL DVHQGDGTAD  180
ILSDEPGVFT FSMHGERNYP VRKIASDLDI ALPDGTGDAA YLRRLATILP ELSARARWDI  240
VFYNAGVDVH AEDRLGRLAL SNGGLRARDE MVIGHFRALG IPVCGVIGGG YSTDVPALAS  300
RHAILFEVAS TYAEF                                                  315

SEQ ID NO: 88           moltype = AA  length = 362
FEATURE                 Location/Qualifiers
source                  1..362
                        mol_type = protein
                        organism = Homo sapiens
SEQUENCE: 88
ASSPKKKRKV EASMLHTTQL YQHVPETRWP IVYSPRYNIT FMGLEKLHPF DAGKWGKVIN  60
FLKEEKLLSD SMLVEAREAS EEDLLVVHTR RYLNELKWSF AVATITEIPP VIFLPNFLVQ  120
RKVLRPLRTQ TGGTIMAGKL AVERGWAINV GGGFHHCSSD RGGGFCAYAD ITLAIKFLFE  180
RVEGISRATI IDLDAHQGNG HERDFMDDKR VYIMDVYNRH IYPGDRFAKQ AIRRKVELEW  240
GTEDDEYLDK VERNIKKSLQ EHLPDVVVYN AGTDILEGDR LGGLSISPAG IVKRDELVFR  300
MVRGRRVPIL MVTSGGYQKR TARIIADSIL NLFGLGLIGP ESPSVSAQNS DTPLLPPAVP  360
EF                                                                362

SEQ ID NO: 89           moltype = AA  length = 226
FEATURE                 Location/Qualifiers
source                  1..226
                        mol_type = protein
                        organism = Arabidopsis thaliana
```

```
SEQUENCE: 89
ASSPKKKRKV EASMEFWGIE VKSGKPVTVT PEEGILIHVS QASLGECKNK KGEFVPLHVK  60
VGNQNLVLGT LSTENIPQLF CDLVFDKEFE LSHTWGKGSV YFVGYKTPNI EPQGYSEEEE  120
EEEEEVPAGN AAKAVAKPKA KPAEVKPAVD DEEDESDSDG MDEDDSDGED SEEEEPTPKK  180
PASSKKRANE TTPKAPVSAK KAKVAVTPQK TDEKKKGGKA ANQSEF                226

SEQ ID NO: 90          moltype = AA  length = 272
FEATURE                Location/Qualifiers
source                 1..272
                       mol_type = protein
                       organism = Homo sapiens
SEQUENCE: 90
ASSPKKKRKV EASMVGAGIS TPSGIPDFRS PGSGLYSNLQ QYDLPYPEAI FELPFFFHNP  60
KPFFTLAKEL YPGNYKPNVT HYFLRLLHDK GLLLRLYTQN IDGLERVSGI PASKLVEAHG  120
TFASATCTVC QRPFPGEDIR ADVMADRVPR CPVCTGVVKP DIVFFGEPLP QRFLLHVVDF  180
PMADLLLILG TSLEVEPFAS LTEAVRSSVP RLLINRDLVG PLAWHPRSRD VAQLGDVVHG  240
VESLVELLGW TEEMRDLVQR ETGKLDGPDK EF                               272

SEQ ID NO: 91          moltype = AA  length = 306
FEATURE                Location/Qualifiers
source                 1..306
                       mol_type = protein
                       organism = Saccharomyces cerevisiae
SEQUENCE: 91
ASSPKKKRKV EASTEMSVRK IAAHMKSNPN AKVIFMVGAG ISTSCGIPDF RSPGTGLYHN  60
LARLKLPYPE AVFDVDFFQS DPLPFYTLAK ELYPGNFRPS KFHYLLKLFQ DKDVLKRVYT  120
QNIDTLERQA GVKDDLIIEA HGSFAHCHCI GCGKVYPPQV FKSKLAEHPI KDFVKCDVCG  180
ELVKPAIVFF GEDLPDSFSE TWLNDSEWLR EKITTSGKHP QQPLVIVVGT SLAVYPFASL  240
PEEIPRKVKR VLCNLETVGD FKANKRPTDL IVHQYSDEFA EQLVEELGWQ EDFEKILTAQ  300
GGMGEF                                                            306

SEQ ID NO: 92          moltype = AA  length = 257
FEATURE                Location/Qualifiers
source                 1..257
                       mol_type = protein
                       organism = Escherichia coli
SEQUENCE: 92
ASSPKKKRKV EASMEKPRVL VLTGAGISAE SGIRTFRAAD GLWEEHRVED VATPEGFDRD  60
PELVQAFYNA RRRQLQQPEI QPNAAHLALA KLQDALGDRF LLVTQNIDNL HERAGNTNVI  120
HMHGELLKVR CSQSGQVLDW TGDVTPEDKC HCCQFPAPLR PHVVWFGEMP LGMDEIYMAL  180
SMADIFIAIG TSGHVYPAAG FVHEAKLHGA HTVELNLEPS QVGNEFAEKY YGPASQVVPE  240
FVEKLLKGLK AGSIAEF                                                257

SEQ ID NO: 93          moltype = AA  length = 346
FEATURE                Location/Qualifiers
source                 1..346
                       mol_type = protein
                       organism = Candida albicans
SEQUENCE: 93
ASSPKKKRKV EASMPSLDDI LKPVAEAVKN GKKVTFFNGA GISTGAGIPD FRSPDTGLYA  60
NLAKLNLPFA EAVFDIDFFK EDPKPFYTLA EELYPGNFAP TKFHHFIKLL QDQGSLKRVY  120
TQNIDTLERL AGVEDKYIVE AHGSFASNHC VDCHKEMTTE TLKTYMKDKK IPSCQHCEGY  180
VKPDIVFFGE GLPVKFFDLW EDDCEDVEVA IVAGTSLTVF PFASLPGEVN KKCLRVLVNK  240
EKVGTFKHEP RKSDIIALHD CDIVAERLCT LLGLDDKLNE VYEKEKIKYS KAETKEIKMH  300
EIEDKLKEEA HLKEDKHTTK VDKKEKQNDA NDKELEQLID KAKAEF                346

SEQ ID NO: 94          moltype = AA  length = 289
FEATURE                Location/Qualifiers
source                 1..289
                       mol_type = protein
                       organism = Homo sapiens
SEQUENCE: 94
ASSPKKKRKV EASSSSMADF RKFFAKAKHI VIISGAGVSA ESGVPTFRGA GGYWRKWQAQ  60
DLATPLAFAH NPSRVWEFYH YRREVMGSKE PNAGHRAIAE CETRLGKQGR RVVVITQNID  120
ELHRKAGTKN LLEIHGSLFK TRCTSCGVVA ENYKSPICPA LSGKGAPEPG TQDASIPVEK  180
LPRCEEAGCG GLLRPHVVWF GENLDPAILE EVDRELAHCD LCLVVGTSSV VYPAAMFAPQ  240
VAARGVPVAE FNTETTPATN RFRFHFQGPC GTTLPEALAC HENETVSEF             289

SEQ ID NO: 95          moltype = AA  length = 288
FEATURE                Location/Qualifiers
source                 1..288
                       mol_type = protein
                       organism = Plasmodium falciparum
SEQUENCE: 95
ASSPKKKRKV EASMGNLMIS FLKKDTQSIT LEELAKIIKK CKHVVALTGS GTSAESNIPS  60
FRGSSNSIWS KYDPRIYGTI WGFWKYPEKI WEVIRDISSD YEIEINNGHV ALSTLESLGY  120
LKSVVTQNVD GLHEASGNTK VISLHGNVFE AVCCTCNKIV KLNKIMLQKT SHFMHQLPPE  180
CPCGGIFKPN IILFGEVVSS DLLKEAEEEI AKCDLLLVIG TSSTVSTATN LCHFACKKKK  240
KIVEINISKT YITNKMSDYH VCAKFSELTK VANILKGSSE KNKKIMEF               288
```

```
SEQ ID NO: 96          moltype = AA  length = 304
FEATURE                Location/Qualifiers
source                 1..304
                       mol_type = protein
                       organism = Homo sapiens
SEQUENCE: 96
ASSPKKKRKV EASMSVNYAA GLSPYADKGK CGLPEIFDPP EELERKVWEL ARLVWQSSSV  60
VFHTGAGIST ASGIPDFRGP HGVWTMEERG LAPKFDTTFE SARPTQTHMA LVQLERVGLL  120
RFLVSQNVDG LHVRSGFPRD KLAELHGNMF VEECAKCKTQ YVRDTVVGTM GLKATGRLCT  180
VAKARGLRAC RGELRDTILD WEDSLPDRDL ALADEASRNA DLSITLGTSL QIRPSGNLPL  240
ATKRRGGRLV IVNLQPTKHD RHADLRIHGY VDEVMTRLMK HLGLEIPAWD GPRVLERALP  300
PLEF                                                              304

SEQ ID NO: 97          moltype = AA  length = 234
FEATURE                Location/Qualifiers
source                 1..234
                       mol_type = protein
                       organism = Chlamydia trachomatis
SEQUENCE: 97
ASSPKKKRKV EASMTTNSTQ DTLYLSLHGG IDSAIPYPVR RVEQLLQFSF LPELQFQNAA  60
VKQRIQRLCY REEKRLAVSS LAKWLGQLHK QRLRAPKNPP VAICWINSYV GYGVFARESI  120
PAWSYIGEYT GILRRRQALW LDENDYCFRY PVPRYSFRYF TIDSGMQGNV TRFINHSDNP  180
NLEAIGAFEN GIFHIIIRAI KDILPGEELC YHYGPLYWKH RKKREEFVPQ EEEF        234

SEQ ID NO: 98          moltype = AA  length = 134
FEATURE                Location/Qualifiers
source                 1..134
                       mol_type = protein
                       organism = Paramecium bursaria
SEQUENCE: 98
ASSPKKKRKV EASMFNDRVI VKKSPLGGYG VFARKSFEKG ELVEECLCIV RHNDDWGTAL  60
EDYLFSRKNM SAMALGFGAI FNHSKDPNAR HELTAGLKRM RIFTIKPIAI GEEITISYGD  120
DYWLSRPRLT QNEF                                                   134

SEQ ID NO: 99          moltype = AA  length = 349
FEATURE                Location/Qualifiers
source                 1..349
                       mol_type = protein
                       organism = Homo sapiens
SEQUENCE: 99
ASSPKKKRKV EASNLKCVRI LKQFHKDLER ELLRRHHRSK TPRHLDPSLA NYLVQKAKQR  60
RALRRWEQEL NAKRSHLGRI TVENEVDLDG PPRAFVYINE YRVGEGITLN QVAVGCECQD  120
CLWAPTGGCC PGASLHKFAY NDQGQVRLRA GLPIYECNSR CRCGYDCPNR VVQKGIRYDL  180
CIFRTDDGRG WGVRTLEKIR KNSFVMEYVG EIITSEEAER RGQIYDRQGA TYLFDLDYVE  240
DVYTVDAAYY GNISHFVNHS CDPNLQVYNV FIDNLDERLP RIAFFATRTI RAGEELTFDY  300
NMQVDPVDME STRMDSNFGL AGLPGSPKKR VRIECKCGTE SCRKYLFEF             349

SEQ ID NO: 100         moltype = AA  length = 346
FEATURE                Location/Qualifiers
source                 1..346
                       mol_type = protein
                       organism = Neurospora crassa
SEQUENCE: 100
ASSPKKKRKV EASMEKAFRP HFFNHGKPDA NPKEKKNCHW CQIRSFATHA QLPISIVNRE  60
DDAFLNPNFR FIDHSIIGKN VPVADQSFRV GCSCASDEEC MYSTCQCLDE MAPDSDEEAD  120
PYTRKKRFAY YSQGAKKGLL RDRVLQSQEP IYECHQGCAC SKDCPNRVVE RGRTVPLQIF  180
RTKDRGWGVK CPVNIKRGQF VDRYLGEIIT SEEADRRRAE STIARRKDVY LFALDKFSDP  240
DSLDPLLAGQ PLEVDGEYMS GPTRFINHSC DPNMAIFARV GDHADKHIHD LALFAIKDIP  300
KGTELTFDYV NGLTGLESDA HDPSKISEMT KCLCGTAKCR GYLWEF                346

SEQ ID NO: 101         moltype = AA  length = 282
FEATURE                Location/Qualifiers
source                 1..282
                       mol_type = protein
                       organism = Arabidopsis thaliana
SEQUENCE: 101
ASSPKKKRKV EASDISGGLE FKGIPATNRV DDSPVSPTSG FTYIKSLIIE PNVIIPKSST  60
GCNCRGSCTD SKKCACAKLN GGNFPYVDLN DGRLIESRDV VFECGPHCGC GPKCVNRTSQ  120
KRLRFNLEVF RSAKKGWAVR SWEYIPAGSP VCEYIGVVRR TADVDTISDN EYIFEIDCQQ  180
TMQGLGGRQR RLRDVAVPMN NGVSQSSEDE NAPEFCIDAG STGNFARFIN HSCEPNLFVQ  240
CVLSSHQDIR LARVVLFAAD NISPMQELTY DYGYALDSVH EF                    282

SEQ ID NO: 102         moltype = AA  length = 328
FEATURE                Location/Qualifiers
source                 1..328
                       mol_type = protein
                       organism = Arabidopsis thaliana
```

```
SEQUENCE: 102
ASSPKKKRKV EASQSAYLHV SLARISDEDC CANCKGNCLS ADFPCTCARE TSGEYAYTKE  60
GLLKEKFLDT CLKMKKEPDS FPKVYCKDCP LERDHDKGTY GKCDGHLIRK FIKECWRKCG  120
CDMQCGNRVV QRGIRCQLQV YFTQEGKGWG LRTLQDLPKG TFICEYIGEI LTNTELYDRN  180
VRSSSERHTY PVTLDADWGS EKDLKDEEAL CLDATICGNV ARFINHRCED ANMIDIPIEI  240
ETPDRHYYHI AFFTLRDVKA MDELTWDYMI DFNDKSHPVK AFRCCCGSES CRDRKIKGSQ  300
GKSIERRKIV SAKKQQGSKE VSKKRKEF                                    328

SEQ ID NO: 103         moltype = AA  length = 303
FEATURE                Location/Qualifiers
source                 1..303
                       mol_type = protein
                       organism = Caenorhabditis elegans
SEQUENCE: 103
ASSPKKKRKV EASMQLHEQI ANISVTFNDI PRSDHSMTPT ELCYFDDFAT TLVVDSVLNF  60
TTHKMSKKRR YLYQDEYRTA RTVMKTFREQ RDWTNAIYGL LTLRSVSHFL SKLPPNKLFE  120
FRDHIVRFLN MFILDSGYTI QECKRYSQEG HQGAKLVSTG VWSRGDKIER LSGVVCLLSS  180
EDEDSILAQE GSDFSVMYST RKRCSTLWLG PGAYINHDCR PTCEFVSHGS TAHIRVLRDM  240
VPGDEITCFY GSEFFGPNNI DCECCTCEKN MNGAFSYLRG NENAEPIISE KKTKYELRSR  300
SEF                                                               303

SEQ ID NO: 104         moltype = AA  length = 257
FEATURE                Location/Qualifiers
source                 1..257
                       mol_type = protein
                       organism = Caenorhabditis elegans
SEQUENCE: 104
ASSPKKKRKV EASMKVAAKK LATSRMRKDR AAAASPSSDI ENSENPSSLA SHSSSSGRMT  60
PSKNTRSRKG VSVKDVSNHK ITEFFQVRRS NRKTSKQISD EAKHALRDTV LKGTNERLLE  120
VYKDVVKGRG IRTKVNFEKG DFVVEYRGVM MEYSEAKVIE EQYSNDEEIG SYMYFFEHNN  180
KKWCIDATKE SPWKGRLINH SVLRPNLKTK VVEIDGSHHL ILVARRQIAQ GEELLYDYGD  240
RSAETIAKNP WLVNTEF                                                257

SEQ ID NO: 105         moltype = AA  length = 224
FEATURE                Location/Qualifiers
source                 1..224
                       mol_type = protein
                       organism = Homo sapiens
SEQUENCE: 105
ASSPKKKRKV EASSCDSTNA AIAKQALKKP IKGKQAPRKK AQGKTQQNRK LTDFYPVRRS  60
SRKSKAELQS EERKRIDELI ESGKEEGMKI DLIDGKGRGV IATKQFSRGD FVVEYHGDLI  120
EITDAKKREA LYAQDPSTGC YMYYFQYLSK TYCVDATRET NRLGRLINHS KCGNCQTKLH  180
DIDGVPHLIL IASRDIAAGE ELLYDYGDRS KASIEAFPWL KHEF                  224

SEQ ID NO: 106         moltype = AA  length = 319
FEATURE                Location/Qualifiers
source                 1..319
                       mol_type = protein
                       organism = Toxoplasma gondii
SEQUENCE: 106
ASSPKKKRKV EASASRRTGE FLRDAQAPSR WLKRSKTGQD DGAFCLETWL AGAGDDAAGG  60
ERGRDREGAA DKAKQREERR QKELEERFEE MKVEFEEKAQ RMIARRAALT GEIYSDGKGS  120
KKPRVPSLPE NDDDALIEII IDPEQGILKW PLSVMSIRQR TVIYQECLRR DLTACIHLTK  180
VPGKGRAVFA ADTILKDDFV VEYKGELCSE REAREREQRY NRSKVPMGSF MFYFKNGSRM  240
MAIDATDEKQ DFGPARLINH SRRNPNMTPR AITLGDFNSE PRLIFVARRN IEKGEELLVD  300
YGERDPDVIK EHPWLNSEF                                              319

SEQ ID NO: 107         moltype = DNA  length = 23
FEATURE                Location/Qualifiers
misc_feature           1..23
                       note = Synthetic Polynucleotide
source                 1..23
                       mol_type = other DNA
                       organism = synthetic construct
SEQUENCE: 107
gagtccgagc agaagaagaa ggg                                         23

SEQ ID NO: 108         moltype = DNA  length = 23
FEATURE                Location/Qualifiers
misc_feature           1..23
                       note = Synthetic Polynucleotide
source                 1..23
                       mol_type = other DNA
                       organism = synthetic construct
SEQUENCE: 108
gaggccgagc agaagaaaga cgg                                         23

SEQ ID NO: 109         moltype = DNA  length = 23
FEATURE                Location/Qualifiers
```

```
misc_feature            1..23
                        note = Synthetic Polynucleotide
source                  1..23
                        mol_type = other DNA
                        organism = synthetic construct
SEQUENCE: 109
gagtcctagc aggagaagaa gag                                          23

SEQ ID NO: 110          moltype = DNA  length = 23
FEATURE                 Location/Qualifiers
misc_feature            1..23
                        note = Synthetic Polynucleotide
source                  1..23
                        mol_type = other DNA
                        organism = synthetic construct
SEQUENCE: 110
gagtctaagc agaagaagaa gag                                          23

SEQ ID NO: 111          moltype = DNA  length = 23
FEATURE                 Location/Qualifiers
misc_feature            1..23
                        note = Synthetic Polynucleotide
source                  1..23
                        mol_type = other DNA
                        organism = synthetic construct
SEQUENCE: 111
gagttagagc agaagaagaa agg                                          23

SEQ ID NO: 112          moltype = DNA  length = 23
FEATURE                 Location/Qualifiers
misc_feature            1..23
                        note = Synthetic Polynucleotide
source                  1..23
                        mol_type = other DNA
                        organism = synthetic construct
SEQUENCE: 112
gggtgggggg agtttgctcc tgg                                          23

SEQ ID NO: 113          moltype = DNA  length = 23
FEATURE                 Location/Qualifiers
misc_feature            1..23
                        note = Synthetic Polynucleotide
source                  1..23
                        mol_type = other DNA
                        organism = synthetic construct
SEQUENCE: 113
ggatggaggg agtttgctcc tgg                                          23

SEQ ID NO: 114          moltype = DNA  length = 23
FEATURE                 Location/Qualifiers
misc_feature            1..23
                        note = Synthetic Polynucleotide
source                  1..23
                        mol_type = other DNA
                        organism = synthetic construct
SEQUENCE: 114
gggagggtgg agtttgctcc tgg                                          23

SEQ ID NO: 115          moltype = DNA  length = 23
FEATURE                 Location/Qualifiers
misc_feature            1..23
                        note = Synthetic Polynucleotide
source                  1..23
                        mol_type = other DNA
                        organism = synthetic construct
SEQUENCE: 115
cgggggaggg agtttgctcc tgg                                          23

SEQ ID NO: 116          moltype = DNA  length = 23
FEATURE                 Location/Qualifiers
misc_feature            1..23
                        note = Synthetic Polynucleotide
source                  1..23
                        mol_type = other DNA
                        organism = synthetic construct
SEQUENCE: 116
ggggagggga agtttgctcc tgg                                          23

SEQ ID NO: 117          moltype = DNA  length = 23
```

```
FEATURE               Location/Qualifiers
misc_feature          1..23
                      note = Synthetic Polynucleotide
source                1..23
                      mol_type = other DNA
                      organism = synthetic construct
SEQUENCE: 117
gcagatgtag tgtttccaca ggg                                         23

SEQ ID NO: 118        moltype = DNA  length = 23
FEATURE               Location/Qualifiers
misc_feature          1..23
                      note = Synthetic Polynucleotide
source                1..23
                      mol_type = other DNA
                      organism = synthetic construct
SEQUENCE: 118
acatatgtag tatttccaca ggg                                         23

SEQ ID NO: 119        moltype = DNA  length = 23
FEATURE               Location/Qualifiers
misc_feature          1..23
                      note = Synthetic Polynucleotide
source                1..23
                      mol_type = other DNA
                      organism = synthetic construct
SEQUENCE: 119
ccagatgtag tattcccaca ggg                                         23

SEQ ID NO: 120        moltype = DNA  length = 23
FEATURE               Location/Qualifiers
misc_feature          1..23
                      note = Synthetic Polynucleotide
source                1..23
                      mol_type = other DNA
                      organism = synthetic construct
SEQUENCE: 120
ctagatgaag tgcttccaca tgg                                         23

SEQ ID NO: 121        moltype = DNA  length = 20
FEATURE               Location/Qualifiers
misc_feature          1..20
                      note = Synthetic Polynucleotide
source                1..20
                      mol_type = other DNA
                      organism = synthetic construct
SEQUENCE: 121
agctggagga ggaagggcct                                             20

SEQ ID NO: 122        moltype = DNA  length = 20
FEATURE               Location/Qualifiers
misc_feature          1..20
                      note = Synthetic Polynucleotide
source                1..20
                      mol_type = other DNA
                      organism = synthetic construct
SEQUENCE: 122
ccccttcttc tgcaaatgag                                             20

SEQ ID NO: 123        moltype = DNA  length = 20
FEATURE               Location/Qualifiers
misc_feature          1..20
                      note = Synthetic Polynucleotide
source                1..20
                      mol_type = other DNA
                      organism = synthetic construct
SEQUENCE: 123
ggctggggcc agcatgacct                                             20

SEQ ID NO: 124        moltype = DNA  length = 20
FEATURE               Location/Qualifiers
misc_feature          1..20
                      note = Synthetic Polynucleotide
source                1..20
                      mol_type = other DNA
                      organism = synthetic construct
SEQUENCE: 124
cctttattca tagtagacaa                                             20
```

-continued

```
SEQ ID NO: 125          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 125
catggcaaga cagattgtca                                              20

SEQ ID NO: 126          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 126
gggaatgggc tttggaaagg                                              20

SEQ ID NO: 127          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 127
catctaagga cggatttgtg                                              20

SEQ ID NO: 128          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 128
ctggtcagcc cattatgata                                              20

SEQ ID NO: 129          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 129
ctggagagag gctcccatca                                              20

SEQ ID NO: 130          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 130
catttttgct gtcacaactc                                              20

SEQ ID NO: 131          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 131
ctgagtagga ttaagatatt                                              20

SEQ ID NO: 132          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 132
gttgggaaga gatgcataca                                              20
```

```
SEQ ID NO: 133          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 133
gcctccttga ttgaggtgtc                                              20

SEQ ID NO: 134          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 134
ctcatctaga gttctttcca                                              20

SEQ ID NO: 135          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 135
ctcccatcac atcaaccggt                                              20

SEQ ID NO: 136          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 136
cgacagatgt tgggggagg                                               20

SEQ ID NO: 137          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 137
gcagcctaga gtcttctgtg                                              20

SEQ ID NO: 138          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 138
agccactacc caaccatcta                                              20

SEQ ID NO: 139          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 139
catggagtaa aggcaatctt                                              20

SEQ ID NO: 140          moltype = DNA  length = 20
FEATURE                 Location/Qualifiers
misc_feature            1..20
                        note = Synthetic Polynucleotide
source                  1..20
                        mol_type = other DNA
                        organism = synthetic construct
```

```
SEQUENCE: 140
accccctatt tctgacctcc                                              20

SEQ ID NO: 141          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 141
ggtgtcagaa tgtcctgtct                                              20

SEQ ID NO: 142          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 142
ggatggaagg gccggctccg                                              20

SEQ ID NO: 143          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 143
ggaacctgtg atccccacag                                              20

SEQ ID NO: 144          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 144
cattcagtgg gtagagtcca                                              20

SEQ ID NO: 145          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 145
tggctcttca gtgcaccagc                                              20

SEQ ID NO: 146          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 146
aatacaatgg acaaataacc                                              20

SEQ ID NO: 147          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 147
gtctggcagg cccctcctgt                                              20

SEQ ID NO: 148          moltype = DNA  length = 20
FEATURE                 Location/Qualifiers
misc_feature            1..20
                        note = Synthetic Polynucleotide
```

```
source                 1..20
                       mol_type = other DNA
                       organism = synthetic construct
SEQUENCE: 148
ctttcattag agtttagtcc                                              20

SEQ ID NO: 149         moltype = DNA  length = 1239
FEATURE                Location/Qualifiers
misc_feature           1..1239
                       note = Synthetic Polynucleotide
source                 1..1239
                       mol_type = other DNA
                       organism = synthetic construct
SEQUENCE: 149
tgccttgccg agggtacccg aatcttcgat ccggtcactg gtacaacgca tcgcatcgag  60
gatgttgtcg atgggcgcaa gcctattcat gtcgtggctg ctgccaagga cggaacgctg  120
ctcgcgcggc ccgtggtgtc ctggttcgac cagggaacgc gggatgtgat cgggttgcgg  180
atcgccggtg gcgccatcgt gtgggcgaca cccgatcaca aggtgctgac agagtacggc  240
tggcgtgccg ccggggaact ccgcaaggga gacagggtgg ccggaccggg tggttctggt  300
aacagcctgg ccttgtccct gacggccgac cagatggtca gtgccttgtt ggatgctgag  360
ccccccatac tctattccga gtatgatcct accagtccct tcagtgaagc ttcgatgatg  420
ggcttactga ccaacctggc agacagggag ctggttcaca tgatcaactg ggcgaagagg  480
gtgccaggct ttgtggattt gaccctccat gatcaggccc accttctaga acgtgcctgg  540
ctagagatcc tgatgattgg tctcgtctgg cgctccatgg agcacccagg gaagctactg  600
tttgctccta acttgctctt ggacaggaac cagggaaaat gtgtagaggg catggtggag  660
atcttcgaca tgctgctggc tacatcatct cggttccgca tgatgaatct gcagggagag  720
gagtttgtgt gcctcaaatc tattattttg cttaattctg gagtgtacac atttctgtcc  780
agcaccctga agtctctgga agagaaggac catatccacc gagccctgga caagatcacg  840
gacactttga tccacctgat ggccaaggca ggcctgaccc tgcagcagca gcaccagcgg  900
ctggcccagc tcctcctcat cctctcccac atcaggcaca tgagtaacaa aggaatggag  960
catctgtaca gcatgaagta caagaacgtg gtgcccctct atgacctgct gctggagatg  1020
ctggacgccc accgcctaca tgcgggtggt tctggtgcta gccgcgtgca ggcgttcgcg  1080
gatgccctgg atgacaaatt cctgcacgac atgctggcgg aaggactccg ctattccgtg  1140
atccgagaag tgctgccaac gcggcgggca cgaacgttcg acctcgaggt cgaggaactg  1200
cacaccctcg tcgccgaagg ggttgtcgtg cacaactgc                         1239

SEQ ID NO: 150         moltype = AA  length = 1404
FEATURE                Location/Qualifiers
REGION                 1..1404
                       note = Synthetic Polypeptide
source                 1..1404
                       mol_type = protein
                       organism = synthetic construct
SEQUENCE: 150
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGDGS PKKKRKVSSD  1380
YKDHDGDYKD HDIDYKDDDD KAAG                                         1404

SEQ ID NO: 151         moltype = AA  length = 1816
FEATURE                Location/Qualifiers
REGION                 1..1816
                       note = Synthetic Polypeptide
source                 1..1816
                       mol_type = protein
                       organism = synthetic construct
SEQUENCE: 151
MDKKYSIGLD IGTNSVGWAV ITDEYKVPSK KFKVLGNTDR HSIKKNLIGA LLFDSGETAE  60
ATRLKRTARR RYTRRKNRIC LAEGTRIFDP VTGTTHRIED VVDGRKPIHV VAAAKDGTLL  120
```

-continued

```
ARPVVSWFDQ GTRDVIGLRI AGGAIVWATP DHKVLTEYGW RAAGELRKGD RVAGPGGSGN  180
SLALSLTADQ MVSALLDAEP PILYSEYDPT SPFSEASMMG LLTNLADREL VHMINWAKRV  240
PGFVDLTLHD QAHLLERAWL EILMIGLVWR SMEHPGKLLF APNLLLDRNQ GKCVEGMVEI  300
FDMLLATSSR FRMMNLQGEE FVCLKSIILL NSGVYTFLSS TLKSLEEKDH IHRALDKITD  360
TLIHLMAKAG LTLQQQHQRL AQLLLILSHI RHMSNKGMEH LYSMKYKNVV PLYDLLLEML  420
DAHRLHAGGS GASRVQAFAD ALDDKFLHDM LAEGLRYSVI REVLPTRRAR TFDLEVEELH  480
TLVAEGVVVH NCYLQEIFSN EMAKVDDSFF HRLEESFLVE EDKKHERHPI FGNIVDEVAY  540
HEKYPTIYHL RKKLVDSTDK ADLRLIYLAL AHMIKFRGHF LIEGDLNPDN SDVDKLFIQL  600
VQTYNQLFEE NPINASGVDA KAILSARLSK SRRLENLIAQ LPGEKKNGLF GNLIALSLGL  660
TPNFKSNFDL AEDAKLQLSK DTYDDDLDNL LAQIGDQYAD LFLAAKNLSD AILLSDILRV  720
NTEITKAPLS ASMIKRYDEH HQDLTLLKAL VRQQLPEKYK EIFFDQSKNG YAGYIDGGAS  780
QEEFYKFIKP ILEKMDGTEE LLVKLNREDL LRKQRTFDNG SIPHQIHLGE LHAILRRQED  840
FYPFLKDNRE KIEKILTFRI PYYVGPLARG NSRFAWMTRK SEETITPWNF EEVVDKGASA  900
QSFIERMTNF DKNLPNEKVL PKHSLLYEYF TVYNELTKVK YVTEGMRKPA FLSGEQKKAI  960
VDLLFKTNRK VTVKQLKEDY FKKIECFDSV EISGVEDRFN ASLGTYHDLL KIIKDKDFLD  1020
NEENEDILED IVLTLTLFED REMIEERLKT YAHLFDDKVM KQLKRRRYTG WGRLSRKLIN  1080
GIRDKQSGKT ILDFLKSDGF ANRNFMQLIH DDSLTFKEDI QKAQVSGQGD SLHEHIANLA  1140
GSPAIKKGIL QTVKVVDELV KVMGRHKPEN IVIEMARENQ TTQKGQKNSR ERMKRIEEGI  1200
KELGSQILKE HPVENTQLQN EKLYLYYLQN GRDMYVDQEL DINRLSDYDV DHIVPQSFLK  1260
DDSIDNKVLT RSDKNRGKSD NVPSEEVVKK MKNYWRQLLN AKLITQRKFD NLTKAERGGL  1320
SELDKAGFIK RQLVETRQIT KHVAQILDSR MNTKYDENDK LIREVKVITL KSKLVSDFRK  1380
DFQFYKVREI NNYHHAHDAY LNAVVGTALI KKYPKLESEF VYGDYKVYDV RKMIAKSEQE  1440
IGKATAKYFF YSNIMNFFKT EITLANGEIR KRPLIETNGE TGEIVWDKGR DFATVRKVLS  1500
MPQVNIVKKT EVQTGGFSKE SILPKRNSDK LIARKKDWDP KKYGGFDSPT VAYSVLVVAK  1560
VEKGKSKKLK SVKELLGITI MERSSFEKNP IDFLEAKGYK EVKKDLIIKL PKYSLFELEN  1620
GRKRMLASAG ELQKGNELAL PSKYVNFLYL ASHYEKLKGS PEDNEQKQLF VEQHKHYLDE  1680
IIEQISEFSK RVILADANLD KVLSAYNKHR DKPIREQAEN IIHLFTLTNL GAPAAFKYFD  1740
TTIDRKRYTS TKEVLDATLI HQSITGLYET RIDLSQLGGD GSPKKKRKVS SDYKDHDGDY  1800
KDHDIDYKDD DDKAAG                                                 1816

SEQ ID NO: 152          moltype = AA  length = 1816
FEATURE                 Location/Qualifiers
REGION                  1..1816
                        note = Synthetic Polypeptide
source                  1..1816
                        mol_type = protein
                        organism = synthetic construct
SEQUENCE: 152
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVCLAE GTRIFDPVTG TTHRIEDVVD GRKPIHVVAA AKDGTLLARP VVSWFDQGTR  180
DVIGLRIAGG AIVWATPDHK VLTEYGWRAA GELRKGDRVA GPGGSGNSLA LSLTADQMVS  240
ALLDAEPPIL YSEYDPTSPF SEASMMGLLT NLADRELVHM INWAKRVPGF VDLTLHDQAH  300
LLERAWLEIL MIGLVWRSME HPGKLLFAPN LLLDRNQGKC VEGMVEIFDM LLATSSRFRM  360
MNLQGEEFVC LKSIILLNSG VYTFLSSTLK SLEEKDHIHR ALDKITDTLI HLMAKAGLTL  420
QQQHQRLAQL LLILSHIRHM SNKGMEHLYS MKYKNVVPLY DLLLEMLDAH RLHAGGSGAS  480
RVQAFADALD DKFLHDMLAE GLRYSVIREV LPTRRARTFD LEVEELHTLV AEGVVVHNCY  540
HEKYPTIYHL RKKLVDSTDK ADLRLIYLAL AHMIKFRGHF LIEGDLNPDN SDVDKLFIQL  600
VQTYNQLFEE NPINASGVDA KAILSARLSK SRRLENLIAQ LPGEKKNGLF GNLIALSLGL  660
TPNFKSNFDL AEDAKLQLSK DTYDDDLDNL LAQIGDQYAD LFLAAKNLSD AILLSDILRV  720
NTEITKAPLS ASMIKRYDEH HQDLTLLKAL VRQQLPEKYK EIFFDQSKNG YAGYIDGGAS  780
QEEFYKFIKP ILEKMDGTEE LLVKLNREDL LRKQRTFDNG SIPHQIHLGE LHAILRRQED  840
FYPFLKDNRE KIEKILTFRI PYYVGPLARG NSRFAWMTRK SEETITPWNF EEVVDKGASA  900
QSFIERMTNF DKNLPNEKVL PKHSLLYEYF TVYNELTKVK YVTEGMRKPA FLSGEQKKAI  960
VDLLFKTNRK VTVKQLKEDY FKKIECFDSV EISGVEDRFN ASLGTYHDLL KIIKDKDFLD  1020
NEENEDILED IVLTLTLFED REMIEERLKT YAHLFDDKVM KQLKRRRYTG WGRLSRKLIN  1080
GIRDKQSGKT ILDFLKSDGF ANRNFMQLIH DDSLTFKEDI QKAQVSGQGD SLHEHIANLA  1140
GSPAIKKGIL QTVKVVDELV KVMGRHKPEN IVIEMARENQ TTQKGQKNSR ERMKRIEEGI  1200
KELGSQILKE HPVENTQLQN EKLYLYYLQN GRDMYVDQEL DINRLSDYDV DHIVPQSFLK  1260
DDSIDNKVLT RSDKNRGKSD NVPSEEVVKK MKNYWRQLLN AKLITQRKFD NLTKAERGGL  1320
SELDKAGFIK RQLVETRQIT KHVAQILDSR MNTKYDENDK LIREVKVITL KSKLVSDFRK  1380
DFQFYKVREI NNYHHAHDAY LNAVVGTALI KKYPKLESEF VYGDYKVYDV RKMIAKSEQE  1440
IGKATAKYFF YSNIMNFFKT EITLANGEIR KRPLIETNGE TGEIVWDKGR DFATVRKVLS  1500
MPQVNIVKKT EVQTGGFSKE SILPKRNSDK LIARKKDWDP KKYGGFDSPT VAYSVLVVAK  1560
VEKGKSKKLK SVKELLGITI MERSSFEKNP IDFLEAKGYK EVKKDLIIKL PKYSLFELEN  1620
GRKRMLASAG ELQKGNELAL PSKYVNFLYL ASHYEKLKGS PEDNEQKQLF VEQHKHYLDE  1680
IIEQISEFSK RVILADANLD KVLSAYNKHR DKPIREQAEN IIHLFTLTNL GAPAAFKYFD  1740
TTIDRKRYTS TKEVLDATLI HQSITGLYET RIDLSQLGGD GSPKKKRKVS SDYKDHDGDY  1800
KDHDIDYKDD DDKAAG                                                 1816

SEQ ID NO: 153          moltype = AA  length = 1816
FEATURE                 Location/Qualifiers
REGION                  1..1816
                        note = Synthetic Polypeptide
source                  1..1816
                        mol_type = protein
                        organism = synthetic construct
```

```
SEQUENCE: 153
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSCLAEG TRIFDPVTGT THRIEDVVDG RKPIHVVAAA  180
KDGTLLARPV VSWFDQGTRD VIGLRIAGGA IVWATPDHKV LTEYGWRAAG ELRKGDRVAG  240
PGGSGNSLAL SLTADQMVSA LLDAEPPILY SEYDPTSPFS EASMMGLLTN LADRELVHMI  300
NWAKRVPGFV DLTLHDQAHL LERAWLEILM IGLVWRSMEH PGKLLFAPNL LLDRNQGKCV  360
EGMVEIFDML LATSSRFRMM NLQGEEFVCL KSIILLNSGV YTFLSSTLKS LEEKDHIHRA  420
LDKITDTLIH LMAKAGLTLQ QQHQRLAQLL LILSHIRHMS NKGMEHLYSM KYKNVVPLYD  480
LLLEMLDAHR LHAGGSGASR VQAFADALDD KFLHDMLAEG LRYSVIREVL PTRRARTFDL  540
EVEELHTLVA EGVVVHNCDK ADLRLIYLAL AHMIKFRGHF LIEGDLNPDN SDVDKLFIQL  600
VQTYNQLFEE NPINASGVDA KAILSARLSK SRRLENLIAQ LPGEKKNGLF GNLIALSLGL  660
TPNFKSNFDL AEDAKLQLSK DTYDDDLDNL LAQIGDQYAD LFLAAKNLSD AILLSDILRV  720
NTEITKAPLS ASMIKRYDEH HQDLTLLKAL VRQQLPEKYK EIFFDQSKNG YAGYIDGGAS  780
QEEFYKFIKP ILEKMDGTEE LLVKLNREDL LRKQRTFDNG SIPHQIHLGE LHAILRRQED  840
FYPFLKDNRE KIEKILTFRI PYYVGPLARG NSRFAWMTRK SEETITPWNF EEVVDKGASA  900
QSFIERMTNF DKNLPNEKVL PKHSLLYEYF TVYNELTKVK YVTEGMRKPA FLSGEQKKAI  960
VDLLFKTNRK VTVKQLKEDY FKKIECFDSV EISGVEDRFN ASLGTYHDLL KIIKDKDFLD  1020
NEENEDILED IVLTLTLFED REMIEERLKT YAHLFDDKVM KQLKRRRYTG WGRLSRKLIN  1080
GIRDKQSGKT ILDFLKSDGF ANRNFMQLIH DDSLTFKEDI QKAQVSGQGD SLHEHIANLA  1140
GSPAIKKGIL QTVKVVDELV KVMGRHKPEN IVIEMARENQ TTQKGQKNSR ERMKRIEEGI  1200
KELGSQILKE HPVENTQLQN EKLYLYYLQN GRDMYVDQEL DINRLSDYDV DHIVPQSFLK  1260
DDSIDNKVLT RSDKNRGKSD NVPSEEVVKK MKNYWRQLLN AKLITQRKFD NLTKAERGGL  1320
SELDKAGFIK RQLVETRQIT KHVAQILDSR MNTKYDENDK LIREVKVITL KSKLVSDFRK  1380
DFQFYKVREI NNYHHAHDAY LNAVVGTALI KKYPKLESEF VYGDYKVYDV RKMIAKSEQE  1440
IGKATAKYFF YSNIMNFFKT EITLANGEIR KRPLIETNGE TGEIVWDKGR DFATVRKVLS  1500
MPQVNIVKKT EVQTGGFSKE SILPKRNSDK LIARKKDWDP KKYGGFDSPT VAYSVLVVAK  1560
VEKGKSKKLK SVKELLGITI MERSSFEKNP IDFLEAKGYK EVKKDLIIKL PKYSLFELEN  1620
GRKRMLASAG ELQKGNELAL PSKYVNFLYL ASHYEKLKGS PEDNEQKQLF VEQHKHYLDE  1680
IIEQISEFSK RVILADANLD KVLSAYNKHR DKPIREQAEN IIHLFTLTNL GAPAAFKYFD  1740
TTIDRKRYTS TKEVLDATLI HQSITGLYET RIDLSQLGGD GSPKKKRKVS SDYKDHDGDY  1800
KDHDIDYKDD DDKAAG                                                 1816

SEQ ID NO: 154         moltype = AA  length = 1816
FEATURE                Location/Qualifiers
REGION                 1..1816
                       note = Synthetic Polypeptide
source                 1..1816
                       mol_type = protein
                       organism = synthetic construct
SEQUENCE: 154
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKCL AEGTRIFDPV TGTTHRIEDV  240
VDGRKPIHVV AAAKDGTLLA RPVVSWFDQG TRDVIGLRIA GGAIVWATPD HKVLTEYGWR  300
AAGELRKGDR VAGPGGSGNS LALSLTADQM VSALLDAEPP ILYSEYDPTS PFSEASMMGL  360
LTNLADRELV HMINWAKRVP GFVDLTLHDQ AHLLERAWLE ILMIGLVWRS MEHPGKLLFA  420
PNLLLDRNQG KCVEGMVEIF DMLLATSSRF RMMNLQGEEF VCLKSIILLN SGVYTFLSST  480
LKSLEEKDHI HRALDKITDT LIHLMAKAGL TLQQQHQRLA QLLLILSHIR HMSNKGMEHL  540
YSMKYKNVVP LYDLLLEMLD AHRLHAGGSG ASRVQAFADA LDDKFLHDML AEGLRYSVIR  600
EVLPTRRART FDLEVEELHT LVAEGVVVHN CRRLENLIAQ LPGEKKNGLF GNLIALSLGL  660
TPNFKSNFDL AEDAKLQLSK DTYDDDLDNL LAQIGDQYAD LFLAAKNLSD AILLSDILRV  720
NTEITKAPLS ASMIKRYDEH HQDLTLLKAL VRQQLPEKYK EIFFDQSKNG YAGYIDGGAS  780
QEEFYKFIKP ILEKMDGTEE LLVKLNREDL LRKQRTFDNG SIPHQIHLGE LHAILRRQED  840
FYPFLKDNRE KIEKILTFRI PYYVGPLARG NSRFAWMTRK SEETITPWNF EEVVDKGASA  900
QSFIERMTNF DKNLPNEKVL PKHSLLYEYF TVYNELTKVK YVTEGMRKPA FLSGEQKKAI  960
VDLLFKTNRK VTVKQLKEDY FKKIECFDSV EISGVEDRFN ASLGTYHDLL KIIKDKDFLD  1020
NEENEDILED IVLTLTLFED REMIEERLKT YAHLFDDKVM KQLKRRRYTG WGRLSRKLIN  1080
GIRDKQSGKT ILDFLKSDGF ANRNFMQLIH DDSLTFKEDI QKAQVSGQGD SLHEHIANLA  1140
GSPAIKKGIL QTVKVVDELV KVMGRHKPEN IVIEMARENQ TTQKGQKNSR ERMKRIEEGI  1200
KELGSQILKE HPVENTQLQN EKLYLYYLQN GRDMYVDQEL DINRLSDYDV DHIVPQSFLK  1260
DDSIDNKVLT RSDKNRGKSD NVPSEEVVKK MKNYWRQLLN AKLITQRKFD NLTKAERGGL  1320
SELDKAGFIK RQLVETRQIT KHVAQILDSR MNTKYDENDK LIREVKVITL KSKLVSDFRK  1380
DFQFYKVREI NNYHHAHDAY LNAVVGTALI KKYPKLESEF VYGDYKVYDV RKMIAKSEQE  1440
IGKATAKYFF YSNIMNFFKT EITLANGEIR KRPLIETNGE TGEIVWDKGR DFATVRKVLS  1500
MPQVNIVKKT EVQTGGFSKE SILPKRNSDK LIARKKDWDP KKYGGFDSPT VAYSVLVVAK  1560
VEKGKSKKLK SVKELLGITI MERSSFEKNP IDFLEAKGYK EVKKDLIIKL PKYSLFELEN  1620
GRKRMLASAG ELQKGNELAL PSKYVNFLYL ASHYEKLKGS PEDNEQKQLF VEQHKHYLDE  1680
IIEQISEFSK RVILADANLD KVLSAYNKHR DKPIREQAEN IIHLFTLTNL GAPAAFKYFD  1740
TTIDRKRYTS TKEVLDATLI HQSITGLYET RIDLSQLGGD GSPKKKRKVS SDYKDHDGDY  1800
KDHDIDYKDD DDKAAG                                                 1816

SEQ ID NO: 155         moltype = AA  length = 1816
FEATURE                Location/Qualifiers
REGION                 1..1816
                       note = Synthetic Polypeptide
```

-continued

```
source                 1..1816
                       mol_type = protein
                       organism = synthetic construct
SEQUENCE: 155
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLCLAEGTRI FDPVTGTTHR IEDVVDGRKP  360
IHVVAAAKDG TLLARPVVSW FDQGTRDVIG LRIAGGAIVW ATPDHKVLTE YGWRAAGELR  420
KGDRVAGPGG SGNSLALSLT ADQMVSALLD AEPPILYSEY DPTSPFSEAS MMGLLTNLAD  480
RELVHMINWA KRVPGFVDLT LHDQAHLLER AWLEILMIGL VWRSMEHPGK LLFAPNLLLD  540
RNQGKCVEGM VEIFDMLLAT SSRFRMMNLQ GEEFVCLKSI ILLNSGVYTF LSSTLKSLEE  600
KDHIHRALDK ITDTLIHLMA KAGLTLQQQH QRLAQLLLIL SHIRHMSNKG MEHLYSMKYK  660
NVVPLYDLLL EMLDAHRLHA GGSGASRVQA FADALDDKFL HDMLAEGLRY SVIREVLPTR  720
RARTFDLEVE ELHTLVAEGV VVHNCLLKAL VRQQLPEKYK EIFFDQSKNG YAGYIDGGAS  780
QEEFYKFIKP ILEKMDGTEE LLVKLNREDL LRKQRTFDNG SIPHQIHLGE LHAILRRQED  840
FYPFLKDNRE KIEKILTFRI PYYVGPLARG NSRFAWMTRK SEETITPWNF EEVVDKGASA  900
QSFIERMTNF DKNLPNEKVL PKHSLLYEYF TVYNELTKVK YVTEGMRKPA FLSGEQKKAI  960
VDLLFKTNRK VTVKQLKEDY FKKIECFDSV EISGVEDRFN ASLGTYHDLL KIIKDKDFLD  1020
NEENEDILED IVLTLTLFED REMIEERLKT YAHLFDDKVM KQLKRRRYTG WGRLSRKLIN  1080
GIRDKQSGKT ILDFLKSDGF ANRNFMQLIH DDSLTFKEDI QKAQVSGQGD SLHEHIANLA  1140
GSPAIKKGIL QTVKVVDELV KVMGRHKPEN IVIEMARENQ TTQKGQKNSR ERMKRIEEGI  1200
KELGSQILKE HPVENTQLQN EKLYLYYLQN GRDMYVDQEL DINRLSDYDV DHIVPQSFLK  1260
DDSIDNKVLT RSDKNRGKSD NVPSEEVVKK MKNYWRQLLN AKLITQRKFD NLTKAERGGL  1320
SELDKAGFIK RQLVETRQIT KHVAQILDSR MNTKYDENDK LIREVKVITL KSKLVSDFRK  1380
DFQFYKVREI NNYHHAHDAY LNAVVGTALI KKYPKLESEF VYGDYKVYDV RKMIAKSEQE  1440
IGKATAKYFF YSNIMNFFKT EITLANGEIR KRPLIETNGE TGEIVWDKGR DFATVRKVLS  1500
MPQVNIVKKT EVQTGGFSKE SILPKRNSDK LIARKKDWDP KKYGGFDSPT VAYSVLVVAK  1560
VEKGKSKKLK SVKELLGITI MERSSFEKNP IDFLEAKGYK EVKKDLIIKL PKYSLFELEN  1620
GRKRMLASAG ELQKGNELAL PSKYVNFLYL ASHYEKLKGS PEDNEQKQLF VEQHKHYLDE  1680
IIEQISEFSK RVILADANLD KVLSAYNKHR DKPIREQAEN IIHLFTLTNL GAPAAFKYFD  1740
TTIDRKRYTS TKEVLDATLI HQSITGLYET RIDLSQLGGD GSPKKKRKVS SDYKDHDGDY  1800
KDHDIDYKDD DDKAAG                                                 1816

SEQ ID NO: 156         moltype = AA  length = 1816
FEATURE                Location/Qualifiers
REGION                 1..1816
                       note = Synthetic Polypeptide
source                 1..1816
                       mol_type = protein
                       organism = synthetic construct
SEQUENCE: 156
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFCL AEGTRIFDPV TGTTHRIEDV  540
VDGRKPIHVV AAAKDGTLLA RPVVSWFDQG TRDVIGLRIA GGAIVWATPD HKVLTEYGWR  600
AAGELRKGDR VAGPGGSGNS LALSLTADQM VSALLDAEPP ILYSEYDPTS PFSEASMMGL  660
LTNLADRELV HMINWAKRVP GFVDLTLHDQ AHLLERAWLE ILMIGLVWRS MEHPGKLLFA  720
PNLLLDRNQG KCVEGMVEIF DMLLATSSRF RMMNLQGEEF VCLKSIILLN SGVYTFLSST  780
LKSLEEKDHI HRALDKITDT LIHLMAKAGL TLQQQHQRLA QLLLILSHIR HMSNKGMEHL  840
YSMKYKNVVP LYDLLLEMLD AHRLHAGGSG ASRVQAFADA LDDKFLHDML AEGLRYSVIR  900
EVLPTRRART FDLEVEELHT LVAEGVVVHN CVYNELTKVK YVTEGMRKPA FLSGEQKKAI  960
VDLLFKTNRK VTVKQLKEDY FKKIECFDSV EISGVEDRFN ASLGTYHDLL KIIKDKDFLD  1020
NEENEDILED IVLTLTLFED REMIEERLKT YAHLFDDKVM KQLKRRRYTG WGRLSRKLIN  1080
GIRDKQSGKT ILDFLKSDGF ANRNFMQLIH DDSLTFKEDI QKAQVSGQGD SLHEHIANLA  1140
GSPAIKKGIL QTVKVVDELV KVMGRHKPEN IVIEMARENQ TTQKGQKNSR ERMKRIEEGI  1200
KELGSQILKE HPVENTQLQN EKLYLYYLQN GRDMYVDQEL DINRLSDYDV DHIVPQSFLK  1260
DDSIDNKVLT RSDKNRGKSD NVPSEEVVKK MKNYWRQLLN AKLITQRKFD NLTKAERGGL  1320
SELDKAGFIK RQLVETRQIT KHVAQILDSR MNTKYDENDK LIREVKVITL KSKLVSDFRK  1380
DFQFYKVREI NNYHHAHDAY LNAVVGTALI KKYPKLESEF VYGDYKVYDV RKMIAKSEQE  1440
IGKATAKYFF YSNIMNFFKT EITLANGEIR KRPLIETNGE TGEIVWDKGR DFATVRKVLS  1500
MPQVNIVKKT EVQTGGFSKE SILPKRNSDK LIARKKDWDP KKYGGFDSPT VAYSVLVVAK  1560
VEKGKSKKLK SVKELLGITI MERSSFEKNP IDFLEAKGYK EVKKDLIIKL PKYSLFELEN  1620
GRKRMLASAG ELQKGNELAL PSKYVNFLYL ASHYEKLKGS PEDNEQKQLF VEQHKHYLDE  1680
IIEQISEFSK RVILADANLD KVLSAYNKHR DKPIREQAEN IIHLFTLTNL GAPAAFKYFD  1740
TTIDRKRYTS TKEVLDATLI HQSITGLYET RIDLSQLGGD GSPKKKRKVS SDYKDHDGDY  1800
KDHDIDYKDD DDKAAG                                                 1816
```

```
SEQ ID NO: 157          moltype = AA  length = 1816
FEATURE                 Location/Qualifiers
REGION                  1..1816
                        note = Synthetic Polypeptide
source                  1..1816
                        mol_type = protein
                        organism = synthetic construct
SEQUENCE: 157
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECLAEGTR IFDPVTGTTH RIEDVVDGRK  600
PIHVVAAAKD GTLLARPVVS WFDQGTRDVI GLRIAGGAIV WATPDHKVLT EYGWRAAGEL  660
RKGDRVAGPG GSGNSLALSL TADQMVSALL DAEPPILYSE YDPTSPFSEA SMMGLLTNLA  720
DRELVHMINW AKRVPGFVDL TLHDQAHLLE RAWLEILMIG LVWRSMEHPG KLLFAPNLLL  780
DRNQGKCVEG MVEIFDMLLA TSSRFRMMNL QGEEFVCLKS IILLNSGVYT FLSSTLKSLE  840
EKDHIHRALD KITDTLIHLM AKAGLTLQQQ HQRLAQLLLI LSHIRHMSNK GMEHLYSMKY  900
KNVVPLYDLL LEMLDAHRLH AGGSGASRVQ AFADALDDKF LHDMLAEGLR YSVIREVLPT  960
RRARTFDLEV EELHTLVAEG VVVHNCFDSV EISGVEDRFN ASLGTYHDLL KIIKDKDFLD  1020
NEENEDILED IVLTLTLFED REMIEERLKT YAHLFDDKVM KQLKRRRYTG WGRLSRKLIN  1080
GIRDKQSGKT ILDFLKSDGF ANRNFMQLIH DDSLTFKEDI QKAQVSGQGD SLHEHIANLA  1140
GSPAIKKGIL QTVKVVDELV KVMGRHKPEN IVIEMARENQ TTQKGQKNSR ERMKRIEEGI  1200
KELGSQILKE HPVENTQLQN EKLYLYYLQN GRDMYVDQEL DINRLSDYDV DHIVPQSFLK  1260
DDSIDNKVLT RSDKNRGKSD NVPSEEVVKK MKNYWRQLLN AKLITQRKFD NLTKAERGGL  1320
SELDKAGFIK RQLVETRQIT KHVAQILDSR MNTKYDENDK LIREVKVITL KSKLVSDFRK  1380
DFQFYKVREI NNYHHAHDAY LNAVVGTALI KKYPKLESEF VYGDYKVYDV RKMIAKSEQE  1440
IGKATAKYFF YSNIMNFFKT EITLANGEIR KRPLIETNGE TGEIVWDKGR DFATVRKVLS  1500
MPQVNIVKKT EVQTGGFSKE SILPKRNSDK LIARKKDWDP KKYGGFDSPT VAYSVLVVAK  1560
VEKGKSKKLK SVKELLGITI MERSSFEKNP IDFLEAKGYK EVKKDLIIKL PKYSLFELEN  1620
GRKRMLASAG ELQKGNELAL PSKYVNFLYL ASHYEKLKGS PEDNEQKQLF VEQHKHYLDE  1680
IIEQISEFSK RVILADANLD KVLSAYNKHR DKPIREQAEN IIHLFTLTNL GAPAAFKYFD  1740
TTIDRKRYTS TKEVLDATLI HQSITGLYET RIDLSQLGGD GSPKKKRKVS SDYKDHDGDY  1800
KDHDIDYKDD DDKAAG                                                 1816

SEQ ID NO: 158          moltype = AA  length = 1816
FEATURE                 Location/Qualifiers
REGION                  1..1816
                        note = Synthetic Polypeptide
source                  1..1816
                        mol_type = protein
                        organism = synthetic construct
SEQUENCE: 158
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LCLAEGTRIF DPVTGTTHRI EDVVDGRKPI HVVAAAKDGT  660
LLARPVVSWF DQGTRDVIGL RIAGGAIVWA TPDHKVLTEY GWRAAGELRK GDRVAGPGGS  720
GNSLALSLTA DQMVSALLDA EPPILYSEYD PTSPFSEASM MGLLTNLADR ELVHMINWAK  780
RVPGFVDLTL HDQAHLLERA WLEILMIGLV WRSMEHPGKL LFAPNLLLDR NQGKCVEGMV  840
EIFDMLLATS SRFRMMNLQG EEFVCLKSII LLNSGVYTFL SSTLKSLEEK DHIHRALDKI  900
TDTLIHLMAK AGLTLQQQHQ RLAQLLLILS HIRHMSNKGM EHLYSMKYKN VVPLYDLLLE  960
MLDAHRLHAG GSGASRVQAF ADALDDKFLH DMLAEGLRYS VIREVLPTRR ARTFDLEVEE  1020
LHTLVAEGVV VHNCLTLFED REMIEERLKT YAHLFDDKVM KQLKRRRYTG WGRLSRKLIN  1080
GIRDKQSGKT ILDFLKSDGF ANRNFMQLIH DDSLTFKEDI QKAQVSGQGD SLHEHIANLA  1140
GSPAIKKGIL QTVKVVDELV KVMGRHKPEN IVIEMARENQ TTQKGQKNSR ERMKRIEEGI  1200
KELGSQILKE HPVENTQLQN EKLYLYYLQN GRDMYVDQEL DINRLSDYDV DHIVPQSFLK  1260
DDSIDNKVLT RSDKNRGKSD NVPSEEVVKK MKNYWRQLLN AKLITQRKFD NLTKAERGGL  1320
SELDKAGFIK RQLVETRQIT KHVAQILDSR MNTKYDENDK LIREVKVITL KSKLVSDFRK  1380
DFQFYKVREI NNYHHAHDAY LNAVVGTALI KKYPKLESEF VYGDYKVYDV RKMIAKSEQE  1440
IGKATAKYFF YSNIMNFFKT EITLANGEIR KRPLIETNGE TGEIVWDKGR DFATVRKVLS  1500
MPQVNIVKKT EVQTGGFSKE SILPKRNSDK LIARKKDWDP KKYGGFDSPT VAYSVLVVAK  1560
VEKGKSKKLK SVKELLGITI MERSSFEKNP IDFLEAKGYK EVKKDLIIKL PKYSLFELEN  1620
GRKRMLASAG ELQKGNELAL PSKYVNFLYL ASHYEKLKGS PEDNEQKQLF VEQHKHYLDE  1680
```

```
IIEQISEFSK RVILADANLD KVLSAYNKHR DKPIREQAEN IIHLFTLTNL GAPAAFKYFD  1740
TTIDRKRYTS TKEVLDATLI HQSITGLYET RIDLSQLGGD GSPKKKRKVS SDYKDHDGDY  1800
KDHDIDYKDD DDKAAG                                                 1816

SEQ ID NO: 159          moltype = AA  length = 1816
FEATURE                 Location/Qualifiers
REGION                  1..1816
                        note = Synthetic Polypeptide
source                  1..1816
                        mol_type = protein
                        organism = synthetic construct
SEQUENCE: 159
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD CLAEGTRIFD PVTGTTHRIE  720
DVVDGRKPIH VVAAAKDGTL LARPVVSWFD QGTRDVIGLR IAGGAIVWAT PDHKVLTEYG  780
WRAAGELRKG DRVAGPGGSG NSLALSLTAD QMVSALLDAE PPILYSEYDP TSPFSEASMM  840
GLLTNLADRE LVHMINWAKR VPGFVDLTLH DQAHLLERAW LEILMIGLVW RSMEHPGKLL  900
FAPNLLLDRN QGKCVEGMVE IFDMLLATSS RFRMMNLQGE EFVCLKSIIL LNSGVYTFLS  960
STLKSLEEKD HIHRALDKIT DTLIHLMAKA GLTLQQQHQR LAQLLLILSH IRHMSNKGME  1020
HLYSMKYKNV VPLYDLLLEM LDAHRLHAGG SGASRVQAFA DALDDKFLHD MLAEGLRYSV  1080
IREVLPTRRA RTFDLEVEEL HTLVAEGVVV HNCLTFKEDI QKAQVSGQGD SLHEHIANLA  1140
GSPAIKKGIL QTVKVVDELV KVMGRHKPEN IVIEMARENQ TTQKGQKNSR ERMKRIEEGI  1200
KELGSQILKE HPVENTQLQN EKLYLYYLQN GRDMYVDQEL DINRLSDYDV DHIVPQSFLK  1260
DDSIDNKVLT RSDKNRGKSD NVPSEEVVKK MKNYWRQLLN AKLITQRKFD NLTKAERGGL  1320
SELDKAGFIK RQLVETRQIT KHVAQILDSR MNTKYDENDK LIREVKVITL KSKLVSDFRK  1380
DFQFYKVREI NNYHHAHDAY LNAVVGTALI KKYPKLESEF VYGDYKVYDV RKMIAKSEQE  1440
IGKATAKYFF YSNIMNFFKT EITLANGEIR KRPLIETNGE TGEIVWDKGR DFATVRKVLS  1500
MPQVNIVKKT EVQTGGFSKE SILPKRNSDK LIARKKDWDP KKYGGFDSPT VAYSVLVVAK  1560
VEKGKSKKLK SVKELLGITI MERSSFEKNP IDFLEAKGYK EVKKDLIIKL PKYSLFELEN  1620
GRKRMLASAG ELQKGNELAL PSKYVNFLYL ASHYEKLKGS PEDNEQKQLF VEQHKHYLDE  1680
IIEQISEFSK RVILADANLD KVLSAYNKHR DKPIREQAEN IIHLFTLTNL GAPAAFKYFD  1740
TTIDRKRYTS TKEVLDATLI HQSITGLYET RIDLSQLGGD GSPKKKRKVS SDYKDHDGDY  1800
KDHDIDYKDD DDKAAG                                                 1816

SEQ ID NO: 160          moltype = AA  length = 1816
FEATURE                 Location/Qualifiers
REGION                  1..1816
                        note = Synthetic Polypeptide
source                  1..1816
                        mol_type = protein
                        organism = synthetic construct
SEQUENCE: 160
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLCLA EGTRIFDPVT GTTHRIEDVV DGRKPIHVVA AAKDGTLLAR PVVSWFDQGT  780
RDVIGLRIAG GAIVWATPDH KVLTEYGWRA AGELRKGDRV AGPGGSGNSL ALSLTADQMV  840
SALLDAEPPI LYSEYDPTSP FSEASMMGLL TNLADRELVH MINWAKRVPG FVDLTLHDQA  900
HLLERAWLEI LMIGLVWRSM EHPGKLLFAP NLLLDRNQGK CVEGMVEIFD MLLATSSRFR  960
MMNLQGEEFV CLKSIILLNS GVYTFLSSTL KSLEEKDHIH RALDKITDTL IHLMAKAGLT  1020
LQQQHQRLAQ LLLILSHIRH MSNKGMEHLY SMKYKNVVPL YDLLLEMLDA HRLHAGGSGA  1080
SRVQAFADAL DDKFLHDMLA EGLRYSVIRE VLPTRRARTF DLEVEELHTL VAEGVVVHNC  1140
GSPAIKKGIL QTVKVVDELV KVMGRHKPEN IVIEMARENQ TTQKGQKNSR ERMKRIEEGI  1200
KELGSQILKE HPVENTQLQN EKLYLYYLQN GRDMYVDQEL DINRLSDYDV DHIVPQSFLK  1260
DDSIDNKVLT RSDKNRGKSD NVPSEEVVKK MKNYWRQLLN AKLITQRKFD NLTKAERGGL  1320
SELDKAGFIK RQLVETRQIT KHVAQILDSR MNTKYDENDK LIREVKVITL KSKLVSDFRK  1380
DFQFYKVREI NNYHHAHDAY LNAVVGTALI KKYPKLESEF VYGDYKVYDV RKMIAKSEQE  1440
IGKATAKYFF YSNIMNFFKT EITLANGEIR KRPLIETNGE TGEIVWDKGR DFATVRKVLS  1500
MPQVNIVKKT EVQTGGFSKE SILPKRNSDK LIARKKDWDP KKYGGFDSPT VAYSVLVVAK  1560
VEKGKSKKLK SVKELLGITI MERSSFEKNP IDFLEAKGYK EVKKDLIIKL PKYSLFELEN  1620
```

-continued

```
GRKRMLASAG ELQKGNELAL PSKYVNFLYL ASHYEKLKGS PEDNEQKQLF VEQHKHYLDE  1680
IIEQISEFSK RVILADANLD KVLSAYNKHR DKPIREQAEN IIHLFTLTNL GAPAAFKYFD  1740
TTIDRKRYTS TKEVLDATLI HQSITGLYET RIDLSQLGGD GSPKKKRKVS SDYKDHDGDY  1800
KDHDIDYKDD DDKAAG                                                  1816

SEQ ID NO: 161          moltype = AA  length = 1816
FEATURE                 Location/Qualifiers
REGION                  1..1816
                        note = Synthetic Polypeptide
source                  1..1816
                        mol_type = protein
                        organism = synthetic construct
SEQUENCE: 161
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGCLAEGT RIFDPVTGTT HRIEDVVDGR  1020
KPIHVVAAAK DGTLLARPVV SWFDQGTRDV IGLRIAGGAI VWATPDHKVL TEYGWRAAGE  1080
LRKGDRVAGP GGSGNSLALS LTADQMVSAL LDAEPPILYS EYDPTSPFSE ASMMGLLTNL  1140
ADRELVHMIN WAKRVPGFVD LTLHDQAHLL ERAWLEILMI GLVWRSMEHP GKLLFAPNLL  1200
LDRNQGKCVE GMVEIFDMLL ATSSRFRMMN LQGEEFVCLK SIILLNSGVY TFLSSTLKSL  1260
EEKDHIHRAL DKITDTLIHL MAKAGLTLQQ QHQRLAQLLL ILSHIRHMSN KGMEHLYSMK  1320
YKNVVPLYDL LLEMLDAHRL HAGGSGASRV QAFADALDDK FLHDMLAEGL RYSVIREVLP  1380
TRRARTFDLE VEELHTLVAE GVVVHNCALI KKYPKLESEF VYGDYKVYDV RKMIAKSEQE  1440
IGKATAKYFF YSNIMNFFKT EITLANGEIR KRPLIETNGE TGEIVWDKGR DFATVRKVLS  1500
MPQVNIVKKT EVQTGGFSKE SILPKRNSDK LIARKKDWDP KKYGGFDSPT VAYSVLVVAK  1560
VEKGKSKKLK SVKELLGITI MERSSFEKNP IDFLEAKGYK EVKKDLIIKL PKYSLFELEN  1620
GRKRMLASAG ELQKGNELAL PSKYVNFLYL ASHYEKLKGS PEDNEQKQLF VEQHKHYLDE  1680
IIEQISEFSK RVILADANLD KVLSAYNKHR DKPIREQAEN IIHLFTLTNL GAPAAFKYFD  1740
TTIDRKRYTS TKEVLDATLI HQSITGLYET RIDLSQLGGD GSPKKKRKVS SDYKDHDGDY  1800
KDHDIDYKDD DDKAAG                                                  1816

SEQ ID NO: 162          moltype = AA  length = 1816
FEATURE                 Location/Qualifiers
REGION                  1..1816
                        note = Synthetic Polypeptide
source                  1..1816
                        mol_type = protein
                        organism = synthetic construct
SEQUENCE: 162
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLECLAEG TRIFDPVTGT  1020
THRIEDVVDG RKPIHVVAAA KDGTLLARPV VSWFDQGTRD VIGLRIAGGA IVWATPDHKV  1080
LTEYGWRAAG ELRKGDRVAG PGGSGNSLAL SLTADQMVSA LLDAEPPILY SEYDPTSPFS  1140
EASMMGLLTN LADRELVHMI NWAKRVPGFV DLTLHDQAHL LERAWLEILM IGLVWRSMEH  1200
PGKLLFAPNL LLDRNQGKCV EGMVEIFDML LATSSRFRMM NLQGEEFVCL KSIILLNSGV  1260
YTFLSSTLKS LEEKDHIHRA LDKITDTLIH LMAKAGLTLQ QQHQRLAQLL LILSHIRHMS  1320
NKGMEHLYSM KYKNVVPLYD LLLEMLDAHR LHAGGSGASR VQAFADALDD KFLHDMLAEG  1380
LRYSVIREVL PTRRARTFDL EVEELHTLVA EGVVVHNCEF VYGDYKVYDV RKMIAKSEQE  1440
IGKATAKYFF YSNIMNFFKT EITLANGEIR KRPLIETNGE TGEIVWDKGR DFATVRKVLS  1500
MPQVNIVKKT EVQTGGFSKE SILPKRNSDK LIARKKDWDP KKYGGFDSPT VAYSVLVVAK  1560
```

```
VEKGKSKKLK SVKELLGITI MERSSFEKNP IDFLEAKGYK EVKKDLIIKL PKYSLFELEN  1620
GRKRMLASAG ELQKGNELAL PSKYVNFLYL ASHYEKLKGS PEDNEQKQLF VEQHKHYLDE  1680
IIEQISEFSK RVILADANLD KVLSAYNKHR DKPIREQAEN IIHLFTLTNL GAPAAFKYFD  1740
TTIDRKRYTS TKEVLDATLI HQSITGLYET RIDLSQLGGD GSPKKKRKVS SDYKDHDGDY  1800
KDHDIDYKDD DDKAAG                                                  1816

SEQ ID NO: 163          moltype = AA  length = 1816
FEATURE                 Location/Qualifiers
REGION                  1..1816
                        note = Synthetic Polypeptide
source                  1..1816
                        mol_type = protein
                        organism = synthetic construct
SEQUENCE: 163
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKCLAEGTR IFDPVTGTTH RIEDVVDGRK PIHVVAAAKD GTLLARPVVS  1200
WFDQGTRDVI GLRIAGGAIV WATPDHKVLT EYGWRAAGEL RKGDRVAGPG GSGNSLALSL  1260
TADQMVSALL DAEPPILYSE YDPTSPFSEA SMMGLLTNLA DRELVHMINW AKRVPGFVDL  1320
TLHDQAHLLE RAWLEILMIG LVWRSMEHPG KLLFAPNLLL DRNQGKCVEG MVEIFDMLLA  1380
TSSRFRMMNL QGEEFVCLKS IILLNSGVYT FLSSTLKSLE EKDHIHRALD KITDTLIHLM  1440
AKAGLTLQQQ HQRLAQLLLI LSHIRHMSNK GMEHLYSMKY KNVVPLYDLL LEMLDAHRLH  1500
AGGSGASRVQ AFADALDDKF LHDMLAEGLR YSVIREVLPT RRARTFDLEV EELHTLVAEG  1560
VVVHNCKKLK SVKELLGITI MERSSFEKNP IDFLEAKGYK EVKKDLIIKL PKYSLFELEN  1620
GRKRMLASAG ELQKGNELAL PSKYVNFLYL ASHYEKLKGS PEDNEQKQLF VEQHKHYLDE  1680
IIEQISEFSK RVILADANLD KVLSAYNKHR DKPIREQAEN IIHLFTLTNL GAPAAFKYFD  1740
TTIDRKRYTS TKEVLDATLI HQSITGLYET RIDLSQLGGD GSPKKKRKVS SDYKDHDGDY  1800
KDHDIDYKDD DDKAAG                                                  1816

SEQ ID NO: 164          moltype = AA  length = 1816
FEATURE                 Location/Qualifiers
REGION                  1..1816
                        note = Synthetic Polypeptide
source                  1..1816
                        mol_type = protein
                        organism = synthetic construct
SEQUENCE: 164
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKCL AEGTRIFDPV TGTTHRIEDV VDGRKPIHVV AAAKDGTLLA  1200
RPVVSWFDQG TRDVIGLRIA GGAIVWATPD HKVLTEYGWR AAGELRKGDR VAGPGGSGNS  1260
LALSLTADQM VSALLDAEPP ILYSEYDPTS PFSEASMMGL LTNLADRELV HMINWAKRVP  1320
GFVDLTLHDQ AHLLERAWLE ILMIGLVWRS MEHPGKLLFA PNLLLDRNQG KCVEGMVEIF  1380
DMLLATSSRF RMMNLQGEEF VCLKSIILLN SGVYTFLSST LKSLEEKDHI HRALDKITDT  1440
LIHLMAKAGL TLQQQHQRLA QLLLILSHIR HMSNKGMEHL YSMKYKNVVP LYDLLLEMLD  1500
```

```
AHRLHAGGSG ASRVQAFADA LDDKFLHDML AEGLRYSVIR EVLPTRRART FDLEVEELHT  1560
LVAEGVVVHN CVKELLGITI MERSSFEKNP IDFLEAKGYK EVKKDLIIKL PKYSLFELEN  1620
GRKRMLASAG ELQKGNELAL PSKYVNFLYL ASHYEKLKGS PEDNEQKQLF VEQHKHYLDE  1680
IIEQISEFSK RVILADANLD KVLSAYNKHR DKPIREQAEN IIHLFTLTNL GAPAAFKYFD  1740
TTIDRKRYTS TKEVLDATLI HQSITGLYET RIDLSQLGGD GSPKKKRKVS SDYKDHDGDY  1800
KDHDIDYKDD DDKAAG                                                  1816

SEQ ID NO: 165          moltype = AA  length = 1816
FEATURE                 Location/Qualifiers
REGION                  1..1816
                        note = Synthetic Polypeptide
source                  1..1816
                        mol_type = protein
                        organism = synthetic construct
SEQUENCE: 165
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQICLAEGTR IFDPVTGTTH RIEDVVDGRK PIHVVAAAKD GTLLARPVVS  1320
WFDQGTRDVI GLRIAGGAIV WATPDHKVLT EYGWRAAGEL RKGDRVAGPG GSGNSLALSL  1380
TADQMVSALL DAEPPILYSE YDPTSPFSEA SMMGLLTNLA DRELVHMINW AKRVPGFVDL  1440
TLHDQAHLLE RAWLEILMIG LVWRSMEHPG KLLFAPNLLL DRNQGKCVEG MVEIFDMLLA  1500
TSSRFRMMNL QGEEFVCLKS IILLNSGVYT FLSSTLKSLE EKDHIHRALD KITDTLIHLM  1560
AKAGLTLQQQ HQRLAQLLLI LSHIRHMSNK GMEHLYSMKY KNVVPLYDLL LEMLDAHRLH  1620
AGGSGASRVQ AFADALDDKF LHDMLAEGLR YSVIREVLPT RRARTFDLEV EELHTLVAEG  1680
VVVHNCEFSK RVILADANLD KVLSAYNKHR DKPIREQAEN IIHLFTLTNL GAPAAFKYFD  1740
TTIDRKRYTS TKEVLDATLI HQSITGLYET RIDLSQLGGD GSPKKKRKVS SDYKDHDGDY  1800
KDHDIDYKDD DDKAAG                                                  1816

SEQ ID NO: 166          moltype = AA  length = 1816
FEATURE                 Location/Qualifiers
REGION                  1..1816
                        note = Synthetic Polypeptide
source                  1..1816
                        mol_type = protein
                        organism = synthetic construct
SEQUENCE: 166
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKCL AEGTRIFDPV TGTTHRIEDV  240
VDGRKPIHVV AAAKDGTLLA RPVVSWFDQG TRDVIGLRIA GGAIVWATPD HKVLTEYGWR  300
AAGELRKGDR VAGPGGSGNS LALSLTADQM VSALLDAEPP ILYSEYDPTS PFSEASMMGL  360
LTNLADRELV HMINWAKRVP GFVDLTLHDQ AHLLERAWLE ILMIGLVWRS MEHPGKLLFA  420
PNLLLDRNQG KCVEGMVEIF DMLLATSSRF RMMNLQGEEF VCLKSIILLN SGVYTFLSST  480
LKSLEEKDHI HRALDKITDT LIHLMAKAGL TLQQQHQRLA QLLLILSHIR HMSNKRMEHL  540
YSMKYKNVVP LYDLLLEMLD AHRLHAGGSG ASRVQAFADA LDDKFLHDML AEGLRYSVIR  600
EVLPTRRART FDLEVEELHT LVAEGVVVHN CRRLENLIAQ LPGEKKNGLF GNLIALSLGL  660
TPNFKSNFDL AEDAKLQLSK DTYDDDLDNL LAQIGDQYAD LFLAAKNLSD AILLSDILRV  720
NTEITKAPLS ASMIKRYDEH HQDLTLLKAL VRQQLPEKYK EIFFDQSKNG YAGYIDGGAS  780
QEEFYKFIKP ILEKMDGTEE LLVKLNREDL LRKQRTFDNG SIPHQIHLGE LHAILRRQED  840
FYPFLKDNRE KIEKILTFRI PYYVGPLARG NSRFAWMTRK SEETITPWNF EEVVDKGASA  900
QSFIERMTNF DKNLPNEKVL PKHSLLYEYF TVYNELTKVK YVTEGMRKPA FLSGEQKKAI  960
VDLLFKTNRK VTVKQLKEDY FKKIECFDSV EISGVEDRFN ASLGTYHDLL KIIKDKDFLD  1020
NEENEDILED IVLTLTLFED REMIEERLKT YAHLFDDKVM KQLKRRRYTG WGRLSRKLIN  1080
GIRDKQSGKT ILDFLKSDGF ANRNFMQLIH DDSLTFKEDI QKAQVSGQGD SLHEHIANLA  1140
GSPAIKKGIL QTVKVVDELV KVMGRHKPEN IVIEMARENQ TTQKGQKNSR ERMKRIEEGI  1200
KELGSQILKE HPVENTQLQN EKLYLYYLQN GRDMYVDQEL DINRLSDYDV DHIVPQSFLK  1260
DDSIDNKVLT RSDKNRGKSD NVPSEEVVKK MKNYWRQLLN AKLITQRKFD NLTKAERGGL  1320
SELDKAGFIK RQLVETRQIT KHVAQILDSR MNTKYDENDK LIREVKVITL KSKLVSDFRK  1380
DFQFYKVREI NNYHHAHDAY LNAVVGTALI KKYPKLESEF VYGDYKVYDV RKMIAKSEQE  1440
```

-continued

```
IGKATAKYFF YSNIMNFFKT EITLANGEIR KRPLIETNGE TGEIVWDKGR DFATVRKVLS  1500
MPQVNIVKKT EVQTGGFSKE SILPKRNSDK LIARKKDWDP KKYGGFDSPT VAYSVLVVAK  1560
VEKGKSKKLK SVKELLGITI MERSSFEKNP IDFLEAKGYK EVKKDLIIKL PKYSLFELEN  1620
GRKRMLASAG ELQKGNELAL PSKYVNFLYL ASHYEKLKGS PEDNEQKQLF VEQHKHYLDE  1680
IIEQISEFSK RVILADANLD KVLSAYNKHR DKPIREQAEN IIHLFTLTNL GAPAAFKYFD  1740
TTIDRKRYTS TKEVLDATLI HQSITGLYET RIDLSQLGGD GSPKKKRKVS SDYKDHDGDY  1800
KDHDIDYKDD DDKAAG                                                  1816

SEQ ID NO: 167         moltype = DNA  length = 153
FEATURE                Location/Qualifiers
misc_feature           1..153
                       note = Synthetic Polynucleotide
source                 1..153
                       mol_type = other DNA
                       organism = synthetic construct
SEQUENCE: 167
tgcagtctca tgacttggcc tttgtaggaa aacaccatta gaagagtaga tggttgggta  60
gtggctctct tctgcttaga ctcttgtcta ctatgaataa agggctctat ttgcaaaggc  120
cgtgatgggt tgaagcacat tgagaaagag gct                               153

SEQ ID NO: 168         moltype = DNA  length = 155
FEATURE                Location/Qualifiers
misc_feature           1..155
                       note = Synthetic Polynucleotide
source                 1..155
                       mol_type = other DNA
                       organism = synthetic construct
SEQUENCE: 168
ctcacctggg cgagaaaggt aacttatgtt tcagtagcct ctttctcaat gtgcttcaac  60
ccatcacggc ctttgcaaat agagcccttt attcatagta gacaagagtc taagcagaag  120
agagccacta cccaaccatc tactcttcta atggt                             155

SEQ ID NO: 169         moltype = DNA  length = 17
FEATURE                Location/Qualifiers
misc_feature           1..17
                       note = Synthetic Polynucleotide
source                 1..17
                       mol_type = other DNA
                       organism = synthetic construct
SEQUENCE: 169
ctcttctgct tagactc                                                 17

SEQ ID NO: 170         moltype = DNA  length = 17
FEATURE                Location/Qualifiers
misc_feature           1..17
                       note = Synthetic Polynucleotide
source                 1..17
                       mol_type = other DNA
                       organism = synthetic construct
SEQUENCE: 170
gagtctaagc agaagag                                                 17

SEQ ID NO: 171         moltype = DNA  length = 17
FEATURE                Location/Qualifiers
misc_feature           1..17
                       note = Synthetic Polynucleotide
source                 1..17
                       mol_type = other DNA
                       organism = synthetic construct
SEQUENCE: 171
gagtctaagc agaagag                                                 17

SEQ ID NO: 172         moltype = AA  length = 248
FEATURE                Location/Qualifiers
source                 1..248
                       mol_type = protein
                       organism = Homo sapiens
SEQUENCE: 172
NSLALSLTAD QMVSALLDAE PPILYSEYDP TSPFSEASMM GLLTNLADRE LVHMINWAKR  60
VPGFVDLTLH DQAHLLECAW LEILMIGLVW RSMEHPGKLL FAPNLLLDRN QGKCVEGMVE  120
IFDMLLATSS RFRMMNLQGE EFVCLKSIIL LNSGVYTFLS STLKSLEEKD HIHRALDKIT  180
DTLIHLMAKA GLTLQQQHQR LAQLLLILSH IRHMSNKGME HLYSMKYTNV VPLYDLLLEM  240
LDAHRLHA                                                           248

SEQ ID NO: 173         moltype = AA  length = 248
FEATURE                Location/Qualifiers
REGION                 1..248
                       note = Synthetic Polypeptide
```

```
VARIANT                24
                       note = Xaa can be any amino acid
VARIANT                29
                       note = Xaa can be any amino acid
VARIANT                78
                       note = Xaa can be any amino acid
VARIANT                228
                       note = Xaa can be any amino acid
source                 1..248
                       mol_type = protein
                       organism = synthetic construct
SEQUENCE: 173
NSLALSLTAD QMVSALLDAE PPIXYSEYXP TSPFSEASMM GLLTNLADRE LVHMINWAKR  60
VPGFVDLTLH DQAHLLEXAW LEILMIGLVW RSMEHPGKLL FAPNLLLDRN QGKCVEGMVE  120
IFDMLLATSS RFRMMNLQGE EFVCLKSIIL LNSGVYTFLS STLKSLEEKD HIHRALDKIT  180
DTLIHLMAKA GLTLQQQHQR LAQLLLILSH IRHMSNKGME HLYSMKYXNV VPLYDLLLEM  240
LDAHRLHA                                                           248

SEQ ID NO: 174         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 174
agctggagga ggaagggcct                                              20

SEQ ID NO: 175         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 175
ccccttcttc tgcaaatgag                                              20

SEQ ID NO: 176         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 176
ggctggggcc agcatgacct                                              20

SEQ ID NO: 177         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 177
cctttattca tagtagacaa                                              20

SEQ ID NO: 178         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 178
catggcaaga cagattgtca                                              20

SEQ ID NO: 179         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 179
gggaatgggc tttggaaagg                                              20

SEQ ID NO: 180         moltype = DNA  length = 20
```

```
FEATURE                Location/Qualifiers
misc_feature           1..20
                       note = Synthetic Polynucleotide
source                 1..20
                       mol_type = other DNA
                       organism = synthetic construct
SEQUENCE: 180
catctaagga cggatttgtg                                                20

SEQ ID NO: 181         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 181
ctggtcagcc cattatgata                                                20

SEQ ID NO: 182         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 182
ctggagagag gctcccatca                                                20

SEQ ID NO: 183         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 183
catttttgct gtcacaactc                                                20

SEQ ID NO: 184         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 184
ctgagtagga ttaagatatt                                                20

SEQ ID NO: 185         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 185
gttgggaaga gatgcataca                                                20

SEQ ID NO: 186         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 186
gcctccttga ttgaggtgtc                                                20

SEQ ID NO: 187         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 187
ctcatctaga gttctttcca                                                20
```

```
SEQ ID NO: 188          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 188
ctcccatcac atcaaccggt                                              20

SEQ ID NO: 189          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 189
cgacagatgt tgggggagg                                               20

SEQ ID NO: 190          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 190
gcagcctaga gtcttctgtg                                              20

SEQ ID NO: 191          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 191
agccactacc caaccatcta                                              20

SEQ ID NO: 192          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 192
catggagtaa aggcaatctt                                              20

SEQ ID NO: 193          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 193
accccctatt tctgacctcc                                              20

SEQ ID NO: 194          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 194
ggtgtcagaa tgtcctgtct                                              20

SEQ ID NO: 195          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 195
ggatggaagg gccggctccg                                              20
```

```
SEQ ID NO: 196          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 196
ggaacctgtg atccccacag                                              20

SEQ ID NO: 197          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 197
cattcagtgg gtagagtcca                                              20

SEQ ID NO: 198          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 198
tggctcttca gtgcaccagc                                              20

SEQ ID NO: 199          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 199
aatacaatgg acaaataacc                                              20

SEQ ID NO: 200          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 200
gtctggcagg cccctcctgt                                              20

SEQ ID NO: 201          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 201
ctttcattag agtttagtcc                                              20

SEQ ID NO: 202          moltype = DNA  length = 17
FEATURE                 Location/Qualifiers
misc_feature            1..17
                        note = Synthetic Polynucleotide
source                  1..17
                        mol_type = other DNA
                        organism = synthetic construct
SEQUENCE: 202
gagtctaagc agaagag                                                 17

SEQ ID NO: 203          moltype =   length =
SEQUENCE: 203
000
```

CAS9 PROTEINS INCLUDING LIGAND-DEPENDENT INTEINS

RELATED APPLICATIONS

This application is a continuation of and claims priority under 35 U.S.C. § 120 to U.S. non-provisional patent application U.S. Ser. No. 16/888,646, filed May 29, 2020, which is a continuation of and claims priority under 35 U.S.C. § 120 to U.S. non-provisional patent application U.S. Ser. No. 16/132,276, filed Sep. 14, 2018, which is a continuation of U.S. non-provisional patent application U.S. Ser. No. 15/329,925, filed Jan. 27, 2017, which is a national stage filing under 35 U.S.C. § 371 of international PCT application, PCT/US2015/042770, filed Jul. 30, 2015, which claims priority under 35 U.S.C. § 119(e) to U.S. provisional patent application, U.S. Ser. No. 62/030,943, filed Jul. 30, 2014, and to U.S. provisional patent application, U.S. Ser. No. 62/135,629, filed Mar. 19, 2015, the entire contents of each of which are incorporated herein by reference.

GOVERNMENT SUPPORT

This invention was made with government support under HR0011-11-2-0003 awarded by the Department of Defense/Defense Advanced Research Projects Agency; GM095501 and GM106601 awarded by the National Institutes of Health; and N66001-12-C-4207 awarded by the Space and Naval Warfare Systems Command. The government has certain rights in the invention.

REFERENCE TO AN ELECTRONIC SEQUENCE LISTING

The contents of the electronic sequence listing (H082470183US05-SUBSEQ-JQM.xml; Size: 328,367 bytes; and Date of Creation: Jan. 1, 2023) is herein incorporated by reference in its entirety.

BACKGROUND OF THE INVENTION

Site-specific enzymes theoretically allow for the targeted manipulation of a single site within a genome and are useful in the context of gene targeting as well as for therapeutic applications. In a variety of organisms, including mammals, site-specific enzymes such as endonucleases have been used for genome engineering by stimulating either non-homologous end joining or homologous recombination. In addition to providing powerful research tools, site-specific nucleases also have potential as gene therapy agents, and two site-specific endonucleases have recently entered clinical trials: one, CCR5-2246, targeting a human CCR-5 allele as part of an anti-HIV therapeutic approach (clinical trials NCT00842634, NCT01044654, NCT01252641), and the other one, VF24684, targeting the human VEGF-A promoter as part of an anti-cancer therapeutic approach (clinical trial NCT01082926).

Specific manipulation of the intended target site without or with only minimal off-target activity is a prerequisite for clinical applications of site-specific enzymes, and also for high-efficiency genomic manipulations in basic research applications. For example, imperfect specificity of engineered site-specific binding domains of certain nucleases has been linked to cellular toxicity and undesired alterations of genomic loci other than the intended target. Most nucleases available today, however, exhibit significant off-target activity, and thus may not be suitable for clinical applications. An emerging nuclease platform for use in clinical and research settings are the RNA-guided nucleases, such as Cas9. While these nucleases are able to bind guide RNAs (gRNAs) that direct cleavage of specific target sites, off-target activity is still observed for certain Cas9:gRNA complexes (Pattanayak et al., "High-throughput profiling of off-target DNA cleavage reveals RNA-programmed Cas9 nuclease specificity." *Nat Biotechnol.* 2013; doi: 10.1038/nbt.2673). Technology for engineering site-specific enzymes with reduced off-target effects is therefore needed.

SUMMARY OF THE INVENTION

The reported toxicity of some engineered site-specific enzymes such as endonucleases is thought to be based on off-target DNA cleavage. Further, the activity of existing RNA-guided nucleases generally cannot be controlled at the molecular level, for example, to switch a nuclease from an "off" to an "on" state. Controlling the activity of nucleases and other site-specific enzymes suitable for nucleic acid manipulations or modifications could decrease the likelihood of incurring off-target effects. Some aspects of this disclosure provide strategies, compositions, systems, and methods to control the binding and/or enzymatic activity of RNA-programmable enzymes, such as Cas9 endonuclease, nickases, deaminases, recombinases, transcriptional activators and repressors, epigenetic modifiers variants and fusions thereof.

Accordingly, one aspect of the present disclosure provides Cas9 proteins (including fusions of Cas9 proteins and functional domains) comprising inteins, for example, ligand-dependent inteins. The presence of the intein inhibits one or more activities of the Cas9 proteins, for example, nucleic acid binding activity (e.g., target nucleic acid binding activity and/or gRNA binding activity), a nuclease activity, or another enzymatic activity (e.g., nucleic acid modifying activity, transcriptional activation and repression, etc.) for which the Cas9 protein (e.g., Cas9 fusion protein) is engineered to undertake (e.g., nuclease activity, nickase activity, recombinase activity, deaminase activity, transcriptional activator/repressor activity, epigenetic modification, etc.). In some embodiments, the Cas9 protein is a Cas9 nickase. The Cas9 fusions are typically between a nuclease inactivated Cas9 ("dCas") and one or more functional domains. The intein may be inserted into any location of a Cas9 protein, including one or more domains of a Cas9 protein or Cas9 fusion (including in a functional domain), such as the HNH nuclease domain or the RuvC nuclease domain. In some embodiments, the intein replaces amino acid residue Cys80, Ala127, Thr146, Ser219, Thr333, Thr519, Cys574, Thr622, Ser701, Ala728, Thr995, Ser1006, Ser1154, Ser1159, or Ser1274 in the Cas9 polypeptide sequence set forth as SEQ ID NO:2, in the dCas9 polypeptide sequence set forth as SEQ ID NO:5, or in the Cas9 nickase polypeptide sequence set forth as SEQ ID NO:4. In some embodiments, the intein replaces or is inserted at an amino acid residue that is within 5, within 10, within 15, or within 20 amino acid residues of Cys80, Ala127, Thr146, Ser219, Thr333, Thr519, Cys574, Thr622, Ser701, Ala728, Thr995, Ser1006, Ser1154, Ser1159, or Ser1274 in the Cas9 polypeptide sequence set forth as SEQ ID NO:2, in the dCas9 polypeptide sequence set forth as SEQ ID NO:5, or in the Cas9 nickase polypeptide sequence set forth as SEQ ID NO:4. the intein replaces amino acid residue Ala127, Thr146, Ser219, Thr519, or Cys574 in the Cas9 polypeptide sequence set forth as SEQ ID NO:2, in the dCas9 polypeptide sequence set forth as SEQ ID NO:5, or in the Cas9 nickase polypeptide sequence set forth as SEQ ID NO:4. Typically the intein is a ligand-dependent intein which exhibits no or minimal protein splicing activity in the absence of ligand (e.g., small molecules such as 4-hydroxytamoxifen, peptides, proteins, polynucleotides, amino acids, and nucleotides). Ligand-dependent inteins are known, and include those described in U.S. patent application U.S. Ser. No. 14/004,280, published as U.S. 2014/0065711 A1, the entire contents of which are incorporated herein by reference. In some embodiments, the intein comprises an amino acid sequence selected from the group consisting of SEQ ID NO:7-14.

In one aspect, a Cas9 protein is provided that comprises: (i) a nuclease-inactivated Cas9 (e.g., dCas9 (SEQ ID NO:5)) domain; (ii) a ligand-dependent intein; and (iii) a recombinase catalytic domain. In some embodiments, the ligand-dependent intein domain is inserted into the dCas9 domain as described herein. Typically, the presence of the intein in the Cas9 protein inhibits one or more activities of the Cas9 protein, such as gRNA binding activity, target nucleic acid binding activity, and/or recombinase activity. Accordingly, upon self-excision of the intein (e.g., induced by ligand binding the intein) the one or more activities of the Cas9 protein is/are restored. In some embodiments, the recombinase catalytic domain is a monomer of the recombinase catalytic domain of Hin recombinase, Gin recombinase, or Tn3 recombinase.

According to another aspect, a Cas9 protein is provided that comprises: (i) a nuclease-inactivated Cas9 (e.g., dCas9 (SEQ ID NO:5)) domain; (ii) a ligand-dependent intein; and (iii) a deaminase catalytic domain. In some embodiments, the ligand-dependent intein domain is inserted into the dCas9 domain as described herein. Typically, the presence of the intein in the Cas9 protein inhibits one or more activities of the Cas9 protein, such as gRNA binding activity, target nucleic acid binding activity, and/or deaminase activity. Accordingly, upon self-excision of the intein (e.g., induced by ligand binding of the intein) the one or more activities of the Cas9 protein is/are restored. In some embodiments, the deaminase catalytic domain comprises a cytidine deaminase (e.g., of apolipoprotein B mRNA-editing complex (APOBEC) family deaminases such as APOBEC1 or activation-induced cytidine deaminase (AID)). In some embodiments, the deaminase catalytic domain comprises a ACF1/ASE deaminase or an adenosine deaminase, such as a ADAT family deaminase.

According to another aspect, a Cas9 protein is provided that comprises: (i) a nuclease-inactivated Cas9 (e.g., dCas9 (SEQ ID NO:5)) domain; (ii) a ligand-dependent intein; and (iii) a transcriptional activator domain. In some embodiments, the ligand-dependent intein domain is inserted into the dCas9 domain as described herein. Typically, the presence of the intein in the Cas9 protein inhibits one or more activities of the Cas9 protein, such as gRNA binding activity, target nucleic acid binding activity, and/or transcriptional activation. Accordingly, upon self-excision of the intein (e.g., induced by ligand binding the intein) the one or more activities of the Cas9 protein is/are restored. In some embodiments, the transcriptional activator domain is VP64, CP16, and p65.

According to yet another aspect, a Cas9 protein is provided that comprises: (i) a nuclease-inactivated Cas9 (e.g., dCas9 (SEQ ID NO:5)) domain; (ii) a ligand-dependent intein; and (iii) a transcriptional repressor domain. In some embodiments, the ligand-dependent intein domain is inserted into the dCas9 domain as described herein. Typically, the presence of the intein in the Cas9 protein inhibits one or more activities of the Cas9 protein, such as gRNA binding activity, target nucleic acid binding activity, and/or transcriptional repression. Accordingly, upon self-excision of the intein (e.g., induced by ligand binding the intein) the one or more activities of the Cas9 protein is/are restored. In some embodiments, the transcriptional repressor domain is KRAB, SID, or SID4x. According to yet another aspect, a Cas9 protein is provided that comprises: (i) a nuclease-inactivated Cas9 (e.g., dCas9 (SEQ ID NO:5)) domain; (ii) a ligand-dependent intein; and (iii) an epigenetic modifier domain. In some embodiments, the ligand-dependent intein domain is inserted into the dCas9 domain as described herein. Typically, the presence of the intein in the Cas9 protein inhibits one or more activities of the Cas9 protein, such as gRNA binding activity, target nucleic acid binding activity, and/or epigenetic modification activity. Accordingly, upon self-excision of the intein (e.g., induced by ligand binding the intein) the one or more activities of the Cas9 protein is/are restored. In some embodiments, the epigenetic modifier domain is epigenetic modifier is selected from the group consisting of histone demethylase, histone methyltransferase, hydroxylase, histone deacetylase, and histone acetyltransferase. In some embodiments, the epigenetic modifier comprises the LSD1 histone demethylase or TET1 hydroxylase.

According to another aspect, methods of using Cas9 proteins are provided. In some embodiments involving site-specific DNA cleavage, the methods comprise (a) contacting a Cas9 protein (e.g., having nuclease activity) comprising a ligand-dependent intein with a ligand, wherein binding of the ligand to the intein induces self-excision of the intein; and (b) contacting a DNA with the Cas9 protein, wherein the Cas9 protein is associated with a gRNA; whereby self-excision of the intein from the Cas9 protein in step (a) allows the Cas9 protein to cleave the DNA, thereby producing cleaved DNA. In some embodiments, the Cas9 protein first binds a gRNA and optionally the target DNA prior to excision of the intein, but is unable to cleave the DNA until excision of the intein occurs. Any of the Cas9 proteins having nuclease activity and comprising a ligand-dependent intein, as described herein, can be used in the inventive methods.

According to another aspect, methods of using any of the ligand-dependent intein-containing Cas9 proteins comprising a recombinase catalytic domain are provided. In some embodiments, the method is useful for recombining two nucleic acids, such as two DNAs, and comprises (a) contacting a first DNA with a first ligand-dependent dCas9-recombinase fusion protein (e.g., any of those described herein), wherein the dCas9 domain of the first fusion protein binds a first gRNA that hybridizes to a region of the first DNA; (b) contacting the first DNA with a second ligand-dependent dCas9-recombinase fusion protein, wherein the dCas9 domain of the second fusion protein binds a second gRNA that hybridizes to a second region of the first DNA; (c) contacting a second DNA with a third ligand-dependent dCas9-recombinase fusion protein, wherein the dCas9 domain of the third fusion protein binds a third gRNA that hybridizes to a region of the second DNA; and (d) contacting the second DNA with a fourth ligand-dependent dCas9-recombinase fusion protein, wherein the dCas9 domain of the fourth fusion protein binds a fourth gRNA that hybridizes to a second region of the second DNA; whereby the binding of the fusion proteins in steps (a)-(d) results in the tetramerization of the recombinase catalytic domains of the fusion proteins, under conditions such that the DNAs are recombined. In some embodiments, the methods are useful for site-specific recombination between two regions of a single DNA molecule, and comprise (a) contacting the DNA with a first ligand-dependent dCas9-recombinase fusion protein, wherein the dCas9 domain if the first fusion protein binds a first gRNA that hybridizes to a region of the DNA; (b) contacting the DNA with a second ligand-dependent dCas9-recombinase fusion protein, wherein the dCas9 domain of the second fusion protein binds a second gRNA that hybridizes to a second region of the DNA; (c) contacting the DNA with a third ligand-dependent dCas9-recombinase fusion protein, wherein the dCas9 domain of the third fusion protein binds a third gRNA that hybridizes to a third region of the DNA; (d) contacting the DNA with a fourth ligand-dependent dCas9-recombinase fusion protein, wherein the dCas9 domain of the fourth fusion protein binds a fourth gRNA that hybridizes to a fourth region of the DNA; whereby the binding of the fusion proteins in steps (a)-(d) results in the tetramerization of the recombinase catalytic domains of the fusion proteins, under conditions such that the DNA is recombined. In some embodiment, any of the methods first comprise contacting the fusion proteins with a ligand that induces self-excision of the intein. In some embodiments, the fusion proteins are contacted with the ligand after: (i) the fusion proteins bind a gRNA; (ii) the fusion proteins bind the DNA; or (iii) after the recombinase domains form a tetramer. In some embodiments, the gRNAs in any step (a)-(d) of the inventive methods hybridize to the same strand or to opposing strands in the DNA(s). In some embodiments, the gRNAs hybridize to regions of their respective DNAs that are no more than 10, no more than 15, no more than 20, no more than 25, no more than 30, no more than 40, no more than 50, no more than 60, no more than 70, no more than 80, no more than 90, or no more than 100 base pairs apart.

According to yet another aspect, methods of using any of the ligand-dependent intein Cas9 proteins comprising deaminase catalytic domains are provided. The methods comprise contacting a DNA molecule with (a) a ligand-dependent Cas9 protein comprising deaminase catalytic domain as provided herein; and (b) a gRNA targeting the Cas9 protein of step (a) to a target nucleotide sequence of the DNA strand; wherein the DNA molecule is contacted with the Cas9 protein, and the gRNA in an amount effective and under conditions suitable for the deamination of a nucleotide base. In some embodiments, the methods comprise contacting the Cas9 protein with a ligand that induces self-excision of the intein either before or after the Cas9 protein binds the gRNA. In some embodiments, the target DNA sequence comprises a sequence associated with a disease or disorder, and wherein the deamination of the nucleotide base results in a sequence that is not associated with a disease or disorder. In some embodiments, the DNA sequence to be modified comprises a T→C or A→G point mutation associated with a disease or disorder, and the deamination of the mutant C or G base results in a sequence that is not associated with a disease or disorder (e.g., the deamination corrects the mutation the caused the disease or disorder). In some embodiments, the deamination corrects a point mutation in the sequence associated with the disease or disorder. In some embodiments, the sequence associated with the disease or disorder encodes a protein, and wherein the deamination introduces a stop codon into the sequence associated with the disease or disorder, resulting in a truncation of the encoded protein. In some embodiments, the deamination corrects a point mutation in the PI3KCA gene, thus correcting an H1047R and/or a A3140G mutation. In some embodiments, the contacting is performed in vivo in a subject susceptible to having or diagnosed with the disease or disorder. In some embodiments, the disease or disorder is a disease associated with a point mutation, or a single-base mutation, in the genome. In some embodiments, the disease is a genetic disease, a cancer, a metabolic disease, or a lysosomal storage disease.

According to another aspect, methods for transcriptional activation of a gene are provided. In some embodiments, the methods comprise contacting a DNA molecule comprising a gene with (a) a ligand-dependent dCas9 fusion protein comprising a transcriptional activator (e.g., any of those provided herein) and (b) a gRNA targeting the fusion protein of (a) to a target nucleotide sequence of the DNA strand; wherein the DNA molecule is contacted with the fusion protein and the gRNA in an amount effective and under conditions suitable for the transcriptional activation of the gene. In some embodiments, the method further comprises contacting the fusion protein with a ligand that induces self-excision of the intein. In some embodiments, the fusion protein is contacted with the ligand prior to forming a complex with a gRNA. In some embodiments, the fusion protein is contacted with the ligand after forming a complex with a gRNA. In some embodiments, the gRNA targets the promoter region of a gene.

According to another aspect, methods for transcriptional repression of a gene are provided. In some embodiments, the methods comprise contacting a DNA molecule comprising a gene with (a) a ligand-dependent dCas9 fusion protein comprising a transcriptional repressor (e.g., any of those provided herein) and (b) a gRNA targeting the fusion protein of (a) to a target nucleotide sequence of the DNA strand; wherein the DNA molecule is contacted with the fusion protein and the gRNA in an amount effective and under conditions suitable for the transcriptional repression of the gene. In some embodiments, the method further comprises contacting the fusion protein with a ligand that induces self-excision of the intein. In some embodiments, the fusion protein is contacted with the ligand prior to forming a complex with a gRNA. In some embodiments, the fusion protein is contacted with the ligand after forming a complex with a gRNA. In some embodiments, the gRNA targets the promoter region of a gene.

According to another aspect, methods for epigenetic modification of DNA are provided. In some embodiments, the DNA is chromosomal DNA. In some embodiments, the methods comprise contacting a DNA molecule with (a) a ligand-dependent dCas9 fusion protein comprising a epigenetic modifier (e.g., any of those provided herein) and (b) a gRNA targeting the fusion protein of (a) to a target nucleotide sequence of the DNA strand; wherein the DNA molecule is contacted with the fusion protein and the gRNA in an amount effective and under conditions suitable for the epigenetic modification of the DNA. In some embodiments, the method further comprises contacting the fusion protein with a ligand that induces self-excision of the intein. In some embodiments, the fusion protein is contacted with the ligand prior to forming a complex with a gRNA. In some embodiments, the fusion protein is contacted with the ligand after forming a complex with a gRNA. In some embodiments, the gRNA targets the promoter region of a gene in the DNA.

Any of the methods provided herein can be performed on DNA in a cell, for example, a cell in vitro or in vivo. In some embodiments, any of the methods provided herein are performed on DNA in a eukaryotic cell. In some embodiments, the eukaryotic cell is in an individual, for example, a human.

According to some embodiments, polynucleotides are provided, for example, that encode any of the proteins (e.g., proteins comprising ligand-dependent Cas9 proteins or variants) described herein. In some embodiments, vectors that comprise a polynucleotide described herein are provided. In some embodiments, vectors for recombinant expression of any of the proteins (e.g., comprising ligand-dependent Cas9 proteins or variants) described herein are provided. In some embodiments, cells comprising genetic constructs for expressing any of the proteins (e.g., comprising ligand-dependent Cas9 proteins or variants) described herein are provided.

In some embodiments, kits useful in using, producing, or creating any of the ligand-dependent Cas9 proteins or variants thereof, as described herein, are provided. For example, kits comprising any of the proteins (e.g., ligand-dependent Cas9 proteins or variants) described herein are provided. In some embodiments, kits comprising any of the polynucleotides described herein are provided. In some embodiments, kits comprising a vector for recombinant expression, wherein the vectors comprise a polynucleotide encoding any of the proteins (e.g., ligand-dependent Cas9 proteins or variants) described herein, are provided. In some embodiments, kits comprising a cell comprising genetic constructs for expressing any of the proteins (e.g., ligand-dependent Cas9 proteins or variants) described herein are provided.

Other advantages, features, and uses of the invention will be apparent from the Detailed Description of Certain Embodiments of the Invention; the Drawings, which are schematic and not intended to be drawn to scale; and the Claims.

BRIEF DESCRIPTION OF THE DRAWINGS

(FIG. 3A) Intein insertion renders Cas9 inactive. Upon 4-HT binding, the intein undergoes conformational changes that trigger protein splicing and restore Cas9 activity. (FIG. 3B) The evolved intein was inserted to replace each of the colored residues. Intein-inserted Cas9 variants at S219 and C574 (green) were used in subsequent experiments. (FIG. 3C) Genomic EGFP disruption activity of wild-type Cas9 and intein-Cas9 variants in the absence or presence of 4-HT. Intein-Cas9 variants are identified by the residue replaced by the intein. Error bars reflect the standard deviation of three biological replicates.

(FIG. 4A) Indel frequency from high-throughput DNA sequencing of amplified genomic on-target sites in the absence or presence of 4-HT. Note that a significant number of indels were observed at the CLTA on-target site even in the absence of a targeting sgRNA (Table 9). (FIGS. 4B-4D) DNA modification specificity, defined as on-target:off-target indel frequency ratio[4-6], normalized to wild-type Cas9. Cells were transfected with 500 ng of the Cas9 expression plasmid. P-values are $<10^{-15}$ for the Fisher exact test (one-sided up) on comparisons of indel modification frequency in the presence versus the absence of 4-HT for intein-Cas9(S219) and intein-Cas9(C574). P-values were adjusted for multiple comparisons using the Benjamini-Hochberg method, and are listed in Table 5. Error bars reflect the range of two independent experiments conducted on different days.

(FIGS. 8A-8C) On-target:off-target indel frequency ratio following the transfection of 500 ng of intein-Cas9(S219), intein-Cas9(C574), or wild-type Cas9 expression plasmid.

(FIGS. 11A-11C) On-target:off-target indel frequency ratio normalized to wild-type Cas9 (500 ng). Five different amounts of wild-type Cas9 expression plasmid, specified in parenthesis, were transfected.

DEFINITIONS

Figure 1:
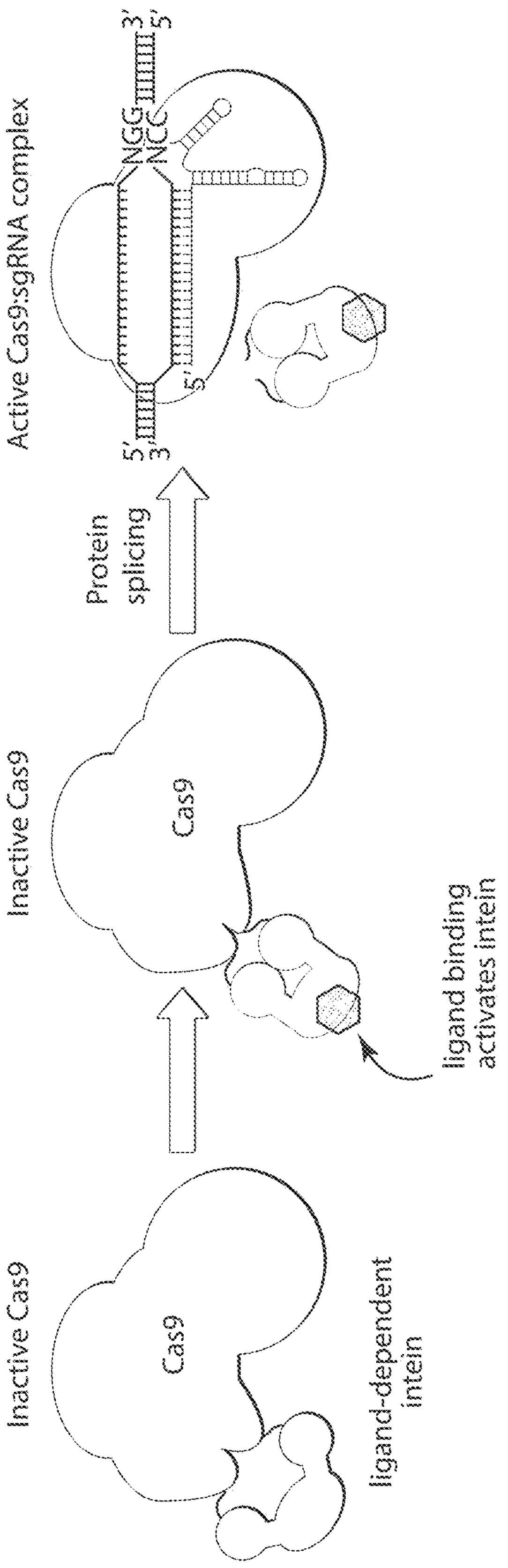
FIG. 1 shows a schematic depicting an exemplary embodiment of the disclosure. A Cas9 protein comprising a ligand-dependent intein, remains inactive in the absence of a ligand that binds the intein domain. Upon addition of the ligand, the intein is self-excised, restoring the activity of the Cas9 protein. Cas9 is then able to mediate RNA-guided cleavage of a DNA target sequence.

As used herein and in the claims, the singular forms "a," "an," and "the" include the singular and the plural reference unless the context clearly indicates otherwise. Thus, for example, a reference to "an agent" includes a single agent and a plurality of such agents.

The term "Cas9" or "Cas9 nuclease" refers to an RNA-guided nuclease comprising a Cas9 protein, or a fragment thereof. A Cas9 nuclease is also referred to sometimes as a casn1 nuclease or a CRISPR (clustered regularly interspaced short palindromic repeat)—associated nuclease. CRISPR is a prokaryotic adaptive immune system that provides protection against mobile genetic elements (e.g., viruses, transposable elements, and conjugative plasmids). CRISPR clusters contain spacers, sequences complementary to antecedent mobile elements, and target invading nucleic acids. CRISPR clusters are transcribed and processed into CRISPR RNA (crRNA). In type II CRISPR systems correct processing of pre-crRNA requires a trans-encoded small RNA (tracrRNA), endogenous ribonuclease 3 (rnc), and a Cas9 protein. The tracrRNA serves as a guide for ribonuclease 3-aided processing of pre-crRNA. Subsequently, Cas9/crRNA/tracrRNA endonucleolytically cleaves linear or circular dsDNA target complementary to the spacer. The target strand not complementary to crRNA is first cut endonucleolytically, then trimmed 3'→5' exonucleolytically. In nature, DNA-binding and cleavage typically requires protein and both RNA species. However, single guide RNAs ("sgRNA", or simply "gNRA") can be engineered so as to incorporate aspects of both the crRNA and tracrRNA into a single RNA molecule. See, e.g., Jinek M., Chylinski K., Fonfara I., Hauer M., Doudna J. A., Charpentier E. *Science* 337:816-821(2012), the entire contents of which is hereby incorporated by reference. Cas9 recognizes a short motif in the CRISPR repeat sequences (the PAM or protospacer adjacent motif) to help distinguish self versus non-self. Cas9 nuclease sequences and structures are well known to those of skill in the art (see, e.g., "Complete genome sequence of an M1 strain of *Streptococcus pyogenes*." Ferretti J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L. expand/collapse author list McLaughlin R. E., *Proc. Natl. Acad. Sci. U.S.A.* 98:4658-4663(2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., *Nature* 471:602-607(2011); and "A programmable dual-RNA-guided DNA endonuclease in adaptive bacterial immunity." Jinek M., Chylinski K., Fonfara I., Hauer M., Doudna J. A., Charpentier E. *Science* 337:816-821(2012), the entire contents of each of which are incorporated herein by reference). Cas9 orthologs have been described in various species, including, but not limited to, *S. pyogenes* and *S. thermophilus*. Additional suitable Cas9 nucleases and sequences will be apparent to those of skill in the art based on this disclosure, and such Cas9 nucleases and sequences include Cas9 sequences from the organisms and loci disclosed in Chylinski, Rhun, and Charpentier, "The tracrRNA and Cas9 families of type II CRISPR-Cas immunity systems" (2013) *RNA Biology* 10:5, 726-737; the entire contents of which are incorporated herein by reference. In some embodiments, proteins comprising Cas9 proteins or fragments thereof are referred to as "Cas9 variants." A Cas9 variant shares homology to Cas9, or a fragment thereof. For example, a Cas9 variant may be at least about 70% identical, at least about 80% identical, at least about 90% identical, at least about 95% identical, at least about 98% identical, at least about 99% identical, at least about 99.5% identical, or at least about 99.9% to wild type Cas9. In some embodiments, the Cas9 variant comprises a fragment of Cas9 (e.g., a gRNA binding domain or a DNA-cleavage domain, an N-terminal domain or a C-terminal domain, etc.), such that the fragment is at least about 70% identical, at least about 80% identical, at least about 90% identical, at least about 95% identical, at least about 98% identical, at least about 99% identical, at least about 99.5% identical, or at least about 99.9% to the corresponding fragment of wild type Cas9. In some embodiments, wild type Cas9 corresponds to Cas9 from *Streptococcus pyogenes* (NCBI Reference Sequences: NC_017053.1 and NC_002737.1). In some embodiments, wild type Cas9 corresponds to SEQ ID NO:1 (nucleotide); SEQ ID NO:2 (amino acid)). In some embodiments, Cas9 corresponds to a human codon optimized sequence of Cas9 (e.g., SEQ ID NO:3; See, e.g., Fu et al. High-frequency off-target mutagenesis induced by CRISPR-Cas nucleases in human cells. *Nat. Biotechnol.* 2013; 31, 822-826). In some embodiments, a Cas9 nuclease has an inactive (e.g., an inactivated) DNA cleavage domain. A nuclease-inactivated Cas9 protein may also be referred to as a "dCas9" protein (for nuclease "dead" Cas9). In some embodiments, dCas9 corresponds to, or comprises in part or in whole, the amino acid set forth as SEQ ID NO:5, below. In some embodiments, variants of dCas9 (e.g., variants of SEQ ID NO:5) are provided. For example, in some embodiments, variants having mutations other than D10A and H840A are provided, which e.g., result in a nuclease inactivated Cas9 (dCas9). Such mutations, by way of example, include other amino acid substitutions at D10 and H840, or other substitutions within the nuclease domains of Cas9 (e.g., substitutions in the HNH nuclease subdomain and/or the RuvC1 subdomain). In some embodiments, a Cas9 protein variant is a Cas9 nickase, which includes a mutation which abolishes the nuclease activity of one of the two nuclease domains of the protein. In some embodiments, a Cas9 nickase has one, but not both of a D10A and H840A substitution. In some embodiments, a Cas9 nickase corresponds to, or comprises in part or in whole, the amino acid set forth as SEQ ID NO:4, below. In some embodiments, variants or homologues of dCas9 or Cas9 nickase are provided which are at least about 70% identical, at least about 80% identical, at least about 90% identical, at least about 95% identical, at least about 98% identical, at least about 99% identical, at least about 99.5% identical, or at least about 99.9% to SEQ ID NO:5 or SEQ ID NO:4, respectively. In some embodiments, variants of dCas9 or Cas9 nickase (e.g., variants of SEQ ID NO:5 and SEQ ID NO:4, respectively) are provided having amino acid sequences which are shorter, or longer than SEQ ID NO:5 or SEQ ID NO:4, by about 5 amino acids, by about 10 amino acids, by about 15 amino acids, by about 20 amino acids, by about 25 amino acids, by about 30 amino acids, by about 40 amino acids, by about 50 amino acids, by about 75 amino acids, by about 100 amino acids or more.

Cas9; nucleotide (*Streptococcus pyogenes*)

(SEQ ID NO: 1)

ATGGATAAGAAATACTCAATAGGCTTAGATATCGGCACAAATAGCGTCGGATGGGCGGTGATCACTGATGATTAT

AAGGTTCCGTCTAAAAAGTTCAAGGTTCTGGGAAATACAGACCGCCACAGTATCAAAAAAAATCTTATAGGGGCT

CTTTTATTTGGCAGTGGAGAGACAGCGGAAGCGACTCGTCTCAAACGGACAGCTCGTAGAAGGTATACACGTCGG

AAGAATCGTATTTGTTATCTACAGGAGATTTTTTCAAATGAGATGGCGAAAGTAGATGATAGTTTCTTTCATCGA

CTTGAAGAGTCTTTTTTGGTGGAAGAAGACAAGAAGCATGAACGTCATCCTATTTTTGGAAATATAGTAGATGAA

GTTGCTTATCATGAGAAATATCCAACTATCTATCATCTGCGAAAAAAATTGGCAGATTCTACTGATAAAGCGGAT

TTGCGCTTAATCTATTTGGCCTTAGCGCATATGATTAAGTTTCGTGGTCATTTTTTGATTGAGGGAGATTTAAAT

CCTGATAATAGTGATGTGGACAAACTATTTATCCAGTTGGTACAAATCTACAATCAATTATTTGAAGAAAACCCT

ATTAACGCAAGTAGAGTAGATGCTAAAGCGATTCTTTCTGCACGATTGAGTAAATCAAGACGATTAGAAAATCTC

ATTGCTCAGCTCCCCGGTGAGAAGAGAAATGGCTTGTTTGGGAATCTCATTGCTTTGTCATTGGGATTGACCCCT

AATTTTAAATCAAATTTTGATTTGGCAGAAGATGCTAAATTACAGCTTTCAAAAGATACTTACGATGATGATTTA

GATAATTTATTGGCGCAAATTGGAGATCAATATGCTGATTTGTTTTTGGCAGCTAAGAATTTATCAGATGCTATT

TTACTTTCAGATATCCTAAGAGTAAATAGTGAAATAACTAAGGCTCCCCTATCAGCTTCAATGATTAAGCGCTAC

GATGAACATCATCAAGACTTGACTCTTTTAAAAGCTTTAGTTCGACAACAACTTCCAGAAAAGTATAAAGAAATC

TTTTTTGATCAATCAAAAAACGGATATGCAGGTTATATTGATGGGGGAGCTAGCCAAGAAGAATTTTATAAATTT

ATCAAACCAATTTTAGAAAAAATGGATGGTACTGAGGAATTATTGGTGAAACTAAATCGTGAAGATTTGCTGCGC

AAGCAACGGACCTTTGACAACGGCTCTATTCCCCATCAAATTCACTTGGGTGAGCTGCATGCTATTTTGAGAAGA

CAAGAAGACTTTTATCCATTTTTAAAAGACAATCGTGAGAAGATTGAAAAAATCTTGACTTTTCGAATTCCTTAT

TATGTTGGTCCATTGGCGCGTGGCAATAGTCGTTTTGCATGGATGACTCGGAAGTCTGAAGAAACAATTACCCCA

TGGAATTTTGAAGAAGTTGTCGATAAAGGTGCTTCAGCTCAATCATTTATTGAACGCATGACAAACTTTGATAAA

AATCTTCCAAATGAAAAAGTACTACCAAAACATAGTTTGCTTTATGAGTATTTTACGGTTTATAACGAATTGACA

AAGGTCAAATATGTTACTGAGGGAATGCGAAAACCAGCATTTCTTTCAGGTGAACAGAAGAAAGCCATTGTTGAT

TTACTCTTCAAAACAAATCGAAAAGTAACCGTTAAGCAATTAAAAGAAGATTATTTCAAAAAAATAGAATGTTTT

GATAGTGTTGAAATTTCAGGAGTTGAAGATAGATTTAATGCTTCATTAGGCGCCTACCATGATTTGCTAAAAATT

ATTAAAGATAAAGATTTTTTGGATAATGAAGAAAATGAAGATATCTTAGAGGATATTGTTTTAACATTGACCTTA

TTTGAAGATAGGGGGATGATTGAGGAAAGACTTAAAACATATGCTCACCTCTTTGATGATAAGGTGATGAAACAG

CTTAAACGTCGCCGTTATACTGGTTGGGGACGTTTGTCTCGAAAATTGATTAATGGTATTAGGGATAAGCAATCT

GGCAAAACAATATTAGATTTTTTGAAATCAGATGGTTTTGCCAATCGCAATTTTATGCAGCTGATCCATGATGAT

AGTTTGACATTTAAAGAAGATATTCAAAAAGCACAGGTGTCTGGACAAGGCCATAGTTTACATGAACAGATTGCT

AACTTAGCTGGCAGTCCTGCTATTAAAAAAGGTATTTTACAGACTGTAAAAATTGTTGATGAACTGGTCAAAGTA

ATGGGGCATAAGCCAGAAAATATCGTTATTGAAATGGCACGTGAAAATCAGACAACTCAAAAGGGCCAGAAAAAT

TCGCGAGAGCGTATGAAACGAATCGAAGAAGGTATCAAAGAATTAGGAAGTCAGATTCTTAAAGAGCATCCTGTT

GAAAATACTCAATTGCAAAATGAAAAGCTCTATCTCTATTATCTACAAAATGGAAGAGACATGTATGTGGACCAA

GAATTAGATATTAATCGTTTAAGTGATTATGATGTCGATCACATTGTTCCACAAAGTTTCATTAAAGACGATTCA

ATAGACAATAAGGTACTAACGCGTTCTGATAAAAATCGTGGTAAATCGGATAACGTTCCAAGTGAAGAAGTAGTC

AAAAAGATGAAAAACTATTGGAGACAACTTCTAAACGCCAAGTTAATCACTCAACGTAAGTTTGATAATTTAACG

AAAGCTGAACGTGGAGGTTTGAGTGAACTTGATAAAGCTGGTTTTATCAAACGCCAATTGGTTGAAACTCGCCAA

-continued

ATCACTAAGCATGTGGCACAAATTTTGGATAGTCGCATGAATACTAAATACGATGAAAATGATAAACTTATTCGA

GAGGTTAAAGTGATTACCTTAAAATCTAAATTAGTTTCTGACTTCCGAAAAGATTTCCAATTCTATAAAGTACGT

GAGATTAACAATTACCATCATGCCCATGATGCGTATCTAAATGCCGTCGTTGGAACTGCTTTGATTAAGAAATAT

CCAAAACTTGAATCGGAGTTTGTCTATGGTGATTATAAAGTTTATGATGTTCGTAAAATGATTGCTAAGTCTGAG

CAAGAAATAGGCAAAGCAACCGCAAAATATTTCTTTTACTCTAATATCATGAACTTCTTCAAAACAGAAATTACA

CTTGCAAATGGAGAGATTCGCAAACGCCCTCTAATCGAAACTAATGGGGAAACTGGAGAAATTGTCTGGGATAAA

GGGCGAGATTTTGCCACAGTGCGCAAAGTATTGTCCATGCCCCAAGTCAATATTGTCAAGAAAACAGAAGTACAG

ACAGGCGGATTCTCCAAGGAGTCAATTTTACCAAAAAGAAATTCGGACAAGCTTATTGCTCGTAAAAAAGACTGG

GATCCAAAAAAATATGGTGGTTTTGATAGTCCAACGGTAGCTTATTCAGTCCTAGTGGTTGCTAAGGTGGAAAAA

GGGAAATCGAAGAAGTTAAAATCCGTTAAAGAGTTACTAGGGATCACAATTATGGAAAGAAGTTCCTTTGAAAAA

AATCCGATTGACTTTTTAGAAGCTAAAGGATATAAGGAAGTTAAAAAAGACTTAATCATTAAACTACCTAAATAT

AGTCTTTTTGAGTTAGAAAACGGTCGTAAACGGATGCTGGCTAGTGCCGGAGAATTACAAAAAGGAAATGAGCTG

GCTCTGCCAAGCAAATATGTGAATTTTTTATATTTAGCTAGTCATTATGAAAAGTTGAAGGGTAGTCCAGAAGAT

AACGAACAAAAACAATTGTTTGTGGAGCAGCATAAGCATTATTTAGATGAGATTATTGAGCAAATCAGTGAATTT

TCTAAGCGTGTTATTTTAGCAGATGCCAATTTAGATAAAGTTCTTAGTGCATATAACAAACATAGAGACAAACCA

ATACGTGAACAAGCAGAAAATATTATTCATTTATTTACGTTGACGAATCTTGGAGCTCCCGCTGCTTTTAAATAT

TTTGATACAACAATTGATCGTAAACGATATACGTCTACAAAAGAAGTTTTAGATGCCACTCTTATCCATCAATCC

ATCACTGGTCTTTATGAAACACGCATTGATTTGAGTCAGCTAGGAGGTGACTGA

Cas9 (human codon optimized)

(SEQ ID NO: 3)

ATGGATAAAAAGTATTCTATTGGTTTAGACATCGGCACTAATTCCGTTGGATGGGCTGTCATAACCGATGAATAC

AAAGTACCTTCAAAGAAATTTAAGGTGTTGGGGAACACAGACCGTCATTCGATTAAAAAGAATCTTATCGGTGCC

CTCCTATTCGATAGTGGCGAAACGGCAGAGGCGACTCGCCTGAAACGAACCGCTCGGAGAAGGTATACACGTCGC

AAGAACCGAATATGTTACTTACAAGAAATTTTTAGCAATGAGATGGCCAAAGTTGACGATTCTTTCTTTCACCGT

TTGGAAGAGTCCTTCCTTGTCGAAGAGGACAAGAAACATGAACGGCACCCCATCTTTGGAAACATAGTAGATGAG

GTGGCATATCATGAAAAGTACCCAACGATTTATCACCTCAGAAAAAAGCTAGTTGACTCAACTGATAAAGCGGAC

CTGAGGTTAATCTACTTGGCTCTTGCCCATATGATAAAGTTCCGTGGGCACTTTCTCATTGAGGGTGATCTAAAT

CCGGACAACTCGGATGTCGACAAACTGTTCATCCAGTTAGTACAAACCTATAATCAGTTGTTTGAAGAGAACCCT

ATAAATGCAAGTGGCGTGGATGCGAAGGCTATTCTTAGCGCCCGCCTCTCTAAATCCCGACGGCTAGAAAACCTG

ATCGCACAATTACCCGGAGAGAAGAAAAATGGGTTGTTCGGTAACCTTATAGCGCTCTCACTAGGCCTGACACCA

AATTTTAAGTCGAACTTCGACTTAGCTGAAGATGCCAAATTGCAGCTTAGTAAGGACACGTACGATGACGATCTC

GACAATCTACTGGCACAAATTGGAGATCAGTATGCGGACTTATTTTTGGCTGCCAAAAACCTTAGCGATGCAATC

CTCCTATCTGACATACTGAGAGTTAATACTGAGATTACCAAGGCGCCGTTATCCGCTTCAATGATCAAAAGGTAC

GATGAACATCACCAAGACTTGACACTTCTCAAGGCCCTAGTCCGTCAGCAACTGCCTGAGAAATATAAGGAAATA

TTCTTTGATCAGTCGAAAAACGGGTACGCAGGTTATATTGACGGCGGAGCGAGTCAAGAGGAATTCTACAAGTTT

ATCAAACCCATATTAGAGAAGATGGATGGGACGGAAGAGTTGCTTGTAAAACTCAATCGCGAAGATCTACTGCGA

AAGCAGCGGACTTTCGACAACGGTAGCATTCCACATCAAATCCACTTAGGCGAATTGCATGCTATACTTAGAAGG

CAGGAGGATTTTTATCCGTTCCTCAAAGACAATCGTGAAAAGATTGAGAAAATCCTAACCTTTCGCATACCTTAC

TATGTGGGACCCCTGGCCCGAGGGAACTCTCGGTTCGCATGGATGACAAGAAAGTCCGAAGAAACGATTACTCCA

TGGAATTTTGAGGAAGTTGTCGATAAAGGTGCGTCAGCTCAATCGTTCATCGAGAGGATGACCAACTTTGACAAG

AATTTACCGAACGAAAAAGTATTGCCTAAGCACAGTTTACTTTACGAGTATTTCACAGTGTACAATGAACTCACG

-continued

AAAGTTAAGTATGTCACTGAGGGCATGCGTAAACCCGCCTTTCTAAGCGGAGAACAGAAGAAAGCAATAGTAGAT

CTGTTATTCAAGACCAACCGCAAAGTGACAGTTAAGCAATTGAAAGAGGACTACTTTAAGAAAATTGAATGCTTC

GATTCTGTCGAGATCTCCGGGGTAGAAGATCGATTTAATGCGTCACTTGGTACGTATCATGACCTCCTAAAGATA

ATTAAAGATAAGGACTTCCTGGATAACGAAGAGAATGAAGATATCTTAGAAGATATAGTGTTGACTCTTACCCTC

TTTGAAGATCGGGAAATGATTGAGGAAAGACTAAAAACATACGCTCACCTGTTCGACGATAAGGTTATGAAACAG

TTAAAGAGGCGTCGCTATACGGGCTGGGGACGATTGTCGCGGAAACTTATCAACGGGATAAGAGACAAGCAAAGT

GGTAAAACTATTCTCGATTTTCTAAAGAGCGACGGCTTCGCCAATAGGAACTTTATGCAGCTGATCCATGATGAC

TCTTTAACCTTCAAAGAGGATATACAAAAGGCACAGGTTTCCGGACAAGGGGACTCATTGCACGAACATATTGCG

AATCTTGCTGGTTCGCCAGCCATCAAAAAGGGCATACTCCAGACAGTCAAAGTAGTGGATGAGCTAGTTAAGGTC

ATGGGACGTCACAAACCGGAAAACATTGTAATCGAGATGGCACGCGAAAATCAAACGACTCAGAAGGGGCAAAAA

AACAGTCGAGAGCGGATGAAGAGAATAGAAGAGGGTATTAAAGAACTGGGCAGCCAGATCTTAAAGGAGCATCCT

GTGGAAAATACCCAATTGCAGAACGAGAAACTTTACCTCTATTACCTACAAAATGGAAGGGACATGTATGTTGAT

CAGGAACTGGACATAAACCGTTTATCTGATTACGACGTCGATCACATTGTACCCCAATCCTTTTTGAAGGACGAT

TCAATCGACAATAAAGTGCTTACACGCTCGGATAAGAACCGAGGGAAAAGTGACAATGTTCCAAGCGAGGAAGTC

GTAAAGAAAATGAAGAACTATTGGCGGCAGCTCCTAAATGCGAAACTGATAACGCAAAGAAAGTTCGATAACTTA

ACTAAAGCTGAGAGGGGTGGCTTGTCTGAACTTGACAAGGCCGGATTTATTAAACGTCAGCTCGTGGAAACCCGC

CAAATCACAAAGCATGTTGCACAGATACTAGATTCCCGAATGAATACGAAATACGACGAGAACGATAAGCTGATT

CGGGAAGTCAAAGTAATCACTTTAAAGTCAAAATTGGTGTCGGACTTCAGAAAGGATTTTCAATTCTATAAAGTT

AGGGAGATAAATAACTACCACCATGCGCACGACGCTTATCTTAATGCCGTCGTAGGGACCGCACTCATTAAGAAA

TACCCGAAGCTAGAAAGTGAGTTTGTGTATGGTGATTACAAAGTTTATGACGTCCGTAAGATGATCGCGAAAAGC

GAACAGGAGATAGGCAAGGCTACAGCCAAATACTTCTTTTATTCTAACATTATGAATTTCTTTAAGACGGAAATC

ACTCTGGCAAACGGAGAGATACGCAAACGACCTTTAATTGAAACCAATGGGGAGACAGGTGAAATCGTATGGGAT

AAGGGCCGGGACTTCGCGACGGTGAGAAAAGTTTTGTCCATGCCCCAAGTCAACATAGTAAAGAAAACTGAGGTG

CAGACCGGAGGGTTTTCAAAGGAATCGATTCTTCCAAAAAGGAATAGTGATAAGCTCATCGCTCGTAAAAAGGAC

TGGGACCCGAAAAAGTACGGTGGCTTCGATAGCCCTACAGTTGCCTATTCTGTCCTAGTAGTGGCAAAAGTTGAG

AAGGGAAAATCCAAGAAACTGAAGTCAGTCAAAGAATTATTGGGGATAACGATTATGGAGCGCTCGTCTTTTGAA

AAGAACCCCATCGACTTCCTTGAGGCGAAAGGTTACAAGGAAGTAAAAAAGGATCTCATAATTAAACTACCAAAG

TATAGTCTGTTTGAGTTAGAAAATGGCCGAAAACGGATGTTGGCTAGCGCCGGAGAGCTTCAAAAGGGGAACGAA

CTCGCACTACCGTCTAAATACGTGAATTTCCTGTATTTAGCGTCCCATTACGAGAAGTTGAAAGGTTCACCTGAA

GATAACGAACAGAAGCAACTTTTTGTTGAGCAGCACAAACATTATCTCGACGAAATCATAGAGCAAATTTCGGAA

TTCAGTAAGAGAGTCATCCTAGCTGATGCCAATCTGGACAAAGTATTAAGCGCATACAACAAGCACAGGGATAAA

CCCATACGTGAGCAGGCGGAAAATATTATCCATTTGTTTACTCTTACCAACCTCGGCGCTCCAGCCGCATTCAAG

TATTTTGACACAACGATAGATCGCAAACGATACACTTCTACCAAGGAGGTGCTAGACGCGACACTGATTCACCAA

TCCATCACGGGATTATATGAAACTCGGATAGATTTGTCACAGCTTGGGGGTGAC

Cas9; amino acid (*Streptococcus pyogenes*)

(SEQ ID NO: 2)

MDKKYSIGLDIGTNSVGWAVITDEYKVPSKKFKVLGNTDRHSIKKNLIGALLFDSGETAEATRLKRTARRRYTRR

KNRICYLQEIFSNEMAKVDDSFFHRLEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENPINASGVDAKAILSARLSKSRRLENL

IAQLPGEKKNGLFGNLIALSLGLTPNFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEIFFDQSKNGYAGYIDGGASQEEFYKF

IKPILEKMDGTEELLVKLNREDLLRKQRTFDNGSIPHQIHLGELHAILRRQEDFYPFLKDNREKIEKILTFRIPY

-continued

YVGPLARGNSRFAWMTRKSEETITPWNFEEVVDKGASAQSFIERMTNFDKNLPNEKVLPKHSLLYEYFTVYNELT

KVKYVTEGMRKPAFLSGEQKKAIVDLLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQLKRRRYTGWGRLSRKLINGIRDKQS

GKTILDFLKSDGFANRNFMQLIHDDSLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHPVENTQLQNEKLYLYYLQNGRDMYVD

QELDINRLSDYDVDHIVPQSFLKDDSIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLIREVKVITLKSKLVSDFRKDFQFYKV

REINNYHHAHDAYLNAVVGTALIKKYPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEVQTGGFSKESILPKRNSDKLIARKKD

WDPKKYGGFDSPTVAYSVLVVAKVEKGKSKKLKSVKELLGITIMERSSFEKNPIDFLEAKGYKEVKKDLIIKLPK

YSLFELENGRKRMLASAGELQKGNELALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAFKYFDTTIDRKRYTSTKEVLDATLIHQ

SITGLYETRIDLSQLGGD
(single underline: HNH domain; double underline: RuvC domain)

dCas9 (D10A and H840A)

(SEQ ID NO: 5)
MDKKYSIGLAIGTNSVGWAVITDEYKVPSKKFKVLGNTDRHSIKKNLIGALLFDSGETAEATRLKRTARRRYTRR

KNRICYLQEIFSNEMAKVDDSFFHRLEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENPINASGVDAKAILSARLSKSRRLENL

IAQLPGEKKNGLFGNLIALSLGLTPNFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEIFFDQSKNGYAGYIDGGASQEEFYKF

IKPILEKMDGTEELLVKLNREDLLRKQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDKNLPNEKVLPKHSLLYEYFTVYNELT

KVKYVTEGMRKPAFLSGEQKKAIVDLLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQLKRRRYTGWGRLSRKLINGIRDKQS

GKTILDFLKSDGFANRNFMQLIHDDSLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHPVENTQLQNEKLYLYYLQNGRDMYVD

QELDINRLSDYDVDAIVPQSFLKDDSIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLIREVKVITLKSKLVSDFRKDFQFYKV

REINNYHHAHDAYLNAVVGTALIKKYPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEVQTGGFSKESILPKRNSDKLIARKKD

WDPKKYGGFDSPTVAYSVLVVAKVEKGKSKKLKSVKELLGITIMERSSFEKNPIDFLEAKGYKEVKKDLIIKLPK

YSLFELENGRKRMLASAGELQKGNELALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAFKYFDTTIDRKRYTSTKEVLDATLIHQ

SITGLYETRIDLSQLGGD
(single underline: HNH domain; double underline: RuvC domain)

Cas9 nickase (D10A)(amino acid sequence)

(SEQ ID NO: 4)
MDKKYSIGLAIGTNSVGWAVITDEYKVPSKKFKVLGNTDRHSIKKNLIGALLFDSGETAEATRLKRTARRRYTRR

KNRICYLQEIFSNEMAKVDDSFFHRLEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENPINASGVDAKAILSARLSKSRRLENL

IAQLPGEKKNGLFGNLIALSLGLTPNFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEIFFDQSKNGYAGYIDGGASQEEFYKF

-continued

IKPILEKMDGTEELLVKLNREDLLRKQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDKNLPNEKVLPKHSLLYEYFTVYNELT

KVKYVTEGMRKPAFLSGEQKKAIVDLLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQLKRRRYTGWGRLSRKLINGIRDKQS

GKTILDFLKSDGFANRNFMQLIHDDSLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHPVENTQLQNEKLYLYYLQNGRDMYVD

QELDINRLSDYDVDHIVPQSFLKDDSIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLIREVKVITLKSKLVSDFRKDFQFYKV

REINNYHHAHDAYLNAVVGTALIKKYPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEVQTGGFSKESILPKRNSDKLIARKKD

WDPKKYGGFDSPTVAYSVLVVAKVEKGKSKKLKSVKELLGITIMERSSFEKNPIDFLEAKGYKEVKKDLIIKLPK

YSLFELENGRKRMLASAGELQKGNELALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAFKYFDTTIDRKRYTSTKEVLDATLIHQ

SITGLYETRIDLSQLGGD

Cas9 variants are provided comprising an intein (e.g., a ligand-dependent intein) inserted within the Cas9 sequence and may be referred to as small-molecule-controlled Cas9 or ligand-dependent Cas9. In some embodiments, the intein is inserted into any location (e.g., at any amino acid position) in Cas9. In some embodiments, the inserted intein sequence replaces one or more amino acids in Cas9. For example, in some embodiments the inserted intein sequence replaces any cysteine, any alanine, any threonine, or any serine in Cas9 or a Cas9 variant such as dCas9 or Cas9 nickase. In some embodiments the inserted intein sequence replaces Cys80, Ala127, Thr146, Ser219, Thr333, Thr519, Cys574, Thr622, Ser701, Ala728, Thr995, Ser1006, Ser1154, Ser1159, or Ser1274 in Cas9 (SEQ ID NO:2), dCas9 (SEQ ID NO:5), or Cas9 nickase (SEQ ID NO:4).

The terms "conjugating," "conjugated," and "conjugation" refer to an association of two entities, for example, of two molecules such as two proteins, two domains (e.g., a binding domain and a cleavage domain), or a protein and an agent, e.g., a ligand binding domain and a small molecule. In some aspects, the association is between a protein (e.g., RNA-programmable nuclease) and a nucleic acid (e.g., a guide RNA). The association can be, for example, via a direct or indirect (e.g., via a linker) covalent linkage. In some aspects, the association is between two or more proteins, for example, an RNA-programmable nuclease (e.g., Cas9) and an intein protein. In some embodiments, the association is covalent. In some embodiments, two molecules are conjugated via a linker connecting both molecules.

The term "consensus sequence," as used herein in the context of nucleic acid sequences, refers to a calculated sequence representing the most frequent nucleotide residues found at each position in a plurality of similar sequences. Typically, it represents the results of a multiple sequence alignments in which related sequences are compared to each other and similar sequence motifs are calculated. Methods and software for determining a consensus sequence are known in the art (See, e.g., JalCiew (jalview.org); and UGENE; Okonechnikov, K.; Golosova, O.; Fursov, M.; the UGENE team. "Unipro UGENE: a unified bioinformatics toolkit". *Bioinformatics.* 2012; doi:10.1093/bioinformatics/bts091).

The term "deaminase" refers to an enzyme that catalyzes a deamination reaction. In some embodiments, the deaminase is a cytidine deaminase, catalyzing the hydrolytic deamination of cytidine or deoxycytidine to uracil or deoxyuracil, respectively.

The term "effective amount," as used herein, refers to an amount of a biologically active agent (e.g., a ligand-dependent Cas9) that is sufficient to elicit a desired biological response. For example, in some embodiments, an effective amount of a nuclease may refer to the amount of the nuclease that is sufficient to induce cleavage of a desired target site-specifically bound and cleaved by the nuclease, preferably with minimal or no off-target cleavage. In some embodiments, an effective amount of another ligand-dependent Cas9 protein having other nucleic acid modifying activities may refer to the amount of the protein that is sufficient to induce the nucleic acid modification. As will be appreciated by the skilled artisan, the effective amount of an agent, e.g., a ligand-dependent nuclease, deaminase, recombinase, nickase, or a hybrid protein, a fusion protein, a protein dimer, a complex of a protein (or protein dimer) and a polynucleotide, or a polynucleotide, may vary depending on various factors as, for example, on the desired biological response, the specific allele, genome, target site, cell, or tissue being targeted, and the agent being used.

The term "engineered," as used herein, refers to a nucleic acid molecule, a protein molecule, complex, substance, or entity that has been designed, produced, prepared, synthesized, and/or manufactured by a human. Accordingly, an engineered product is a product that does not occur in nature.

The term "epigenetic modifier," as used herein, refers to a protein or catalytic domain thereof having enzymatic activity that results in the epigenetic modification of DNA, for example, chromosomal DNA. Epigenetic modifications include, but are not limited to, DNA methylation and demethylation; histone modifications including methylation and demethylation (e.g., mono-, di- and tri-methylation), histone acetylation and deacetylation, as well as histone ubiquitylation, phosphorylation, and sumoylation.

The term "extein," as used herein, refers to an polypeptide sequence that is flanked by an intein and is ligated to another extein during the process of protein splicing to form a mature, spliced protein. Typically, an intein is flanked by two extein sequences that are ligated together when the intein catalyzes its own excision. Exteins, accordingly, are the protein analog to exons found in mRNA. For example, a polypeptide comprising an intein may be of the structure extein(N)—intein—extein(C). After excision of the intein and splicing of the two exteins, the resulting structures are extein(N)—extein(C) and a free intein.

The term "hybrid protein," as used herein, refers to a protein that comprises the amino acid sequence of a target protein (e.g., a Cas9 protein) and, embedded in that amino acid sequence, a ligand-dependent intein as described herein. Accordingly, a hybrid protein generally comprises the structure: target protein(N)—intein—target protein(C). Typically, a hybrid protein comprises a Cas9 protein (e.g., Cas9, Cas9 variants such as dCas9, fragments of Cas9 or Cas9 variants, etc.) and a ligand-dependent intein. In some embodiments, a hybrid protein is encoded by a recombinant nucleic acid, in which a nucleic acid sequence encoding an intein is inserted in frame into a nucleic acid sequence encoding a target protein. In certain embodiments, the target protein exhibits a desired activity or property that is absent or reduced in the hybrid protein. In some embodiments, excision of the intein from the hybrid protein results in a restoration of the desired activity or property in the mature, spliced target protein. Non-limiting examples of desired activities or properties of target proteins are binding activities, enzymatic activities (e.g., nuclease activities, gene editing activities, deaminase activities, recombinase activities), reporter activities (e.g., fluorescent activity), therapeutic activities, size, charge, hydrophobicity, hydrophilicity, or 3D-structure. In some embodiments, excision of the intein from a hybrid protein results in a mature, spliced target protein that exhibits the same or similar levels of a desired activity as the native target protein. A hybrid protein may be created from any target protein by embedding an intein sequence into the amino acid sequence of the target protein, for example, by generating a recombinant, hybrid protein-encoding nucleic acid molecule and subsequent transcription and translation, or by protein synthesis methods known to those of skill in the art.

The term "intein," as used herein, refers to an amino acid sequence that is able to excise itself from a protein and to rejoin the remaining protein segments (the exteins) via a peptide bond in a process termed protein splicing. Inteins are analogous to the introns found in mRNA. Many naturally occurring and engineered inteins and hybrid proteins comprising such inteins are known to those of skill in the art, and the mechanism of protein splicing has been the subject of extensive research. As a result, methods for the generation of hybrid proteins from naturally occurring and engineered inteins are well known to the skilled artisan. For an overview, see pages 1-10, 193-207, 211-229, 233-252, and 325-341 of Gross, Belfort, Derbyshire, Stoddard, and Wood (Eds.) *Homing Endonucleases and Inteins* Springer Verlag Heidelberg, 2005; ISBN 9783540251064; the contents of which are incorporated herein by reference for disclosure of inteins and methods of generating hybrid proteins comprising natural or engineered inteins. As will be apparent to those of skill in the art, an intein may catalyze protein splicing in a variety of extein contexts. Accordingly, an intein can be introduced into virtually any target protein sequence to create a desired hybrid protein, and the invention is not limited in the choice of target proteins.

The term "intein domain," as used herein, refers to the amino acid sequence of an intein that is essential for self-excision and extein ligation. For example, in some inteins, the entire intein amino acid sequence, or part(s) thereof, may constitute the intein domain, while in ligand-dependent inteins, the ligand-binding domain is typically embedded into the intein domain, resulting in the structure: intein domain (N)—ligand-binding domain—intein domain (C).

The term "ligand binding domain," as used herein, refers to a peptide or protein domain that binds a ligand. A ligand binding domain may be a naturally occurring domain or an engineered domain. Examples of ligand-binding domains referred to herein are the ligand binding domain of a native estrogen receptor, e.g., the ligand-binding domain of the native human estrogen receptor, and engineered, evolved, or mutated derivatives thereof. Other suitable ligand binding domains include the human thyroid hormone receptor (see, e.g., Skretas et al., "Regulation of protein activity with small-molecule-controlled inteins." *Protein Sci.* 2005; 14, 523-532) and members of the ribose-binding protein family (see, e.g., Björkman et al., "Multiple open forms of ribose-binding protein trace the path of its conformational change." *J Mol Biol.* 1998 12; 279(3):651-64). Typically, a ligand-binding domain useful in the context of ligand-dependent inteins, as provided herein, exhibits a specific three-dimensional structure in the absence of the ligand, which inhibits intein self-excision, and undergoes a conformational change upon binding of the ligand, which promotes intein self-excision. Some of the ligand-dependent inteins provided herein comprise a ligand-binding domain derived from the estrogen receptor that can bind 4-HT and other estrogen-receptor ligands, e.g., ligands described in more detail elsewhere herein, and undergo a conformational change upon binding of the ligand. An appropriate ligand may be any chemical compound that binds the ligand-binding domain and induces a desired conformational change. In some embodiments, an appropriate ligand is a molecule that is bound by the ligand-binding domain with high specificity and affinity. In some embodiments, the ligand is a small molecule. In some embodiments, the ligand is a molecule that does not naturally occur in the context (e.g., in a cell or tissue) that a ligand-dependent intein is used in. For example, in some embodiments, the ligand-binding domain is a ligand-binding domain derived from an estrogen receptor, and the ligand is tamoxifen, or a derivative or analog thereof (e.g., 4-hydroxytamoxifen, 4-HT).

The term "ligand-dependent intein," as used herein refers to an intein that comprises a ligand-binding domain. Typically, the ligand-binding domain is inserted into the amino acid sequence of the intein, resulting in a structure intein (N)—ligand-binding domain—intein (C). Typically, ligand-dependent inteins exhibit no or only minimal protein splicing activity in the absence of an appropriate ligand, and a marked increase of protein splicing activity in the presence of the ligand. In some embodiments, the ligand-dependent intein does not exhibit observable splicing activity in the absence of ligand but does exhibit splicing activity in the presence of the ligand. In some embodiments, the ligand-dependent intein exhibits an observable protein splicing activity in the absence of the ligand, and a protein splicing activity in the presence of an appropriate ligand that is at least 5 times, at least 10 times, at least 50 times, at least 100 times, at least 150 times, at least 200 times, at least 250 times, at least 500 times, at least 1000 times, at least 1500 times, at least 2000 times, at least 2500 times, at least 5000 times, at least 10000 times, at least 20000 times, at least 25000 times, at least 50000 times, at least 100000 times, at least 500000 times, or at least 1000000 times greater than the activity observed in the absence of the ligand. In some embodiments, the increase in activity is dose dependent over at least 1 order of magnitude, at least 2 orders of magnitude, at least 3 orders of magnitude, at least 4 orders of magnitude, or at least 5 orders of magnitude, allowing for fine-tuning of intein activity by adjusting the concentration of the ligand. Suitable ligand-dependent inteins are known in the art, and in include those provided below and those described in published U.S. Patent Application U.S. 2014/0065711 A1; Mootz et al., "Protein splicing triggered by a small molecule." *J. Am. Chem. Soc.* 2002; 124, 9044-9045; Mootz et al., "Conditional protein splicing: a new tool to control protein structure and function in vitro and in vivo." *J. Am. Chem. Soc.* 2003; 125, 10561-10569; Buskirk et al., *Proc. Natl. Acad. Sci. USA.* 2004; 101, 10505-10510); Skretas & Wood, "Regulation of protein activity with small-molecule-controlled inteins." *Protein Sci.* 2005; 14, 523-532; Schwartz, et al., "Post-translational enzyme activation in an animal via optimized conditional protein splicing." *Nat. Chem. Biol.* 2007; 3, 50-54; Peck et al., *Chem. Biol.* 2011; 18 (5), 619-630; the entire contents of each are hereby incorporated by reference.

```
2-4 intein:
                                                           (SEQ ID NO: 7)
CLAEGTRIFDPVTGTTHRIEDVVDGRKPIHVVAAAKDGTLLARPVVSWFDQGTRDVIGLRIAGGAIVWATPDHKV

LTEYGWRAAGELRKGDRVAGPGGSGNSLALSLTADQMVSALLDAEPPILYSEYDPTSPFSEASMMGLLTNLADRE

LVHMINWAKRVPGFVDLTLHDQAHLLECAWLEILMIGLVWRSMEHPGKLLFAPNLLLDRNQGKCVEGMVEIFDML

LATSSRFRMMNLQGEEFVCLKSIILLNSGVYTFLSSTLKSLEEKDHIHRALDKITDTLIHLMAKAGLTLQQQHQR

LAQLLLILSHIRHMSNKGMEHLYSMKYKNVVPLYDLLLEMLDAHRLHAGGSGASRVQAFADALDDKFLHDMLAEE

LRYSVIREVLPTRRARTFDLEVEELHTLVAEGVVVHNC

3-2 intein:
                                                           (SEQ ID NO: 8)
CLAEGTRIFDPVTGTTHRIEDVVDGRKPIHVVAVAKDGTLLARPVVSWFDQGTRDVIGLRIAGGAIVWATPDHKV

LTEYGWRAAGELRKGDRVAGPGGSGNSLALSLTADQMVSALLDAEPPILYSEYDPTSPFSEASMMGLLTNLADRE

LVHMINWAKRVPGFVDLTLHDQAHLLECAWLEILMIGLVWRSMEHPGKLLFAPNLLLDRNQGKCVEGMVEIFDML

LATSSRFRMMNLQGEEFVCLKSIILLNSGVYTFLSSTLKSLEEKDHIHRALDKITDTLIHLMAKAGLTLQQQHQR

LAQLLLILSHIRHMSNKGMEHLYSMKYTNVVPLYDLLLEMLDAHRLHAGGSGASRVQAFADALDDKFLHDMLAEE

LRYSVIREVLPTRRARTFDLEVEELHTLVAEGVVVHNC

30R3-1 intein:
                                                           (SEQ ID NO: 9)
CLAEGTRIFDPVTGTTHRIEDVVDGRKPIHVVAAAKDGTLLARPVVSWFDQGTRDVIGLRIAGGATVWATPDHKV

LTEYGWRAAGELRKGDRVAGPGGSGNSLALSLTADQMVSALLDAEPPIPYSEYDPTSPFSEASMMGLLTNLADRE

LVHMINWAKRVPGFVDLTLHDQAHLLECAWLEILMIGLVWRSMEHPGKLLFAPNLLLDRNQGKCVEGMVEIFDML

LATSSRFRMMNLQGEEFVCLKSIILLNSGVYTFLSSTLKSLEEKDHIHRALDKITDTLIHLMAKAGLTLQQQHQR

LAQLLLILSHIRHMSNKGMEHLYSMKYKNVVPLYDLLLEMLDAHRLHAGGSGASRVQAFADALDDKFLHDMLAEG

LRYSVIREVLPTRRARTFDLEVEELHTLVAEGVVVHNC

30R3-2 intein:
                                                          (SEQ ID NO: 10)
CLAEGTRIFDPVTGTTHRIEDVVDGRKPIHVVAAAKDGTLLARPVVSWFDQGTRDVIGLRIAGGATVWATPDHKV

LTEYGWRAAGELRKGDRVAGPGGSGNSLALSLTADQMVSALLDAEPPILYSEYDPTSPFSEASMMGLLTNLADRE

LVHMINWAKRVPGFVDLTLHDQAHLLECAWLEILMIGLVWRSMEHPGKLLFAPNLLLDRNQGKCVEGMVEIFDML

LATSSRFRMMNLQGEEFVCLKSIILLNSGVYTFLSSTLKSLEEKDHIHRALDKITDTLIHLMAKAGLTLQQQHQR

LAQLLLILSHIRHMSNKGMEHLYSMKYKNVVPLYDLLLEMLDAHRLHAGGSGASRVQAFADALDDKFLHDMLAEE

LRYSVIREVLPTRRARTFDLEVEELHTLVAEGVVVHNC

30R3-3 intein:
                                                          (SEQ ID NO: 11)
CLAEGTRIFDPVTGTTHRIEDVVDGRKPIHVVAAAKDGTLLARPVVSWFDQGTRDVIGLRIAGGATVWATPDHKV

LTEYGWRAAGELRKGDRVAGPGGSGNSLALSLTADQMVSALLDAEPPIPYSEYDPTSPFSEASMMGLLTNLADRE

LVHMINWAKRVPGFVDLTLHDQAHLLECAWLEILMIGLVWRSMEHPGKLLFAPNLLLDRNQGKCVEGMVEIFDML

LATSSRFRMMNLQGEEFVCLKSIILLNSGVYTFLSSTLKSLEEKDHIHRALDKITDTLIHLMAKAGLTLQQQHQR
```

-continued

LAQLLLILSHIRHMSNKGMEHLYSMKYKNVVPLYDLLLEMLDAHRLHAGGSGASRVQAFADALDDKFLHDMLAEE

LRYSVIREVLPTRRARTFDLEVEELHTLVAEGVVVHNC

37R3-1 intein:

(SEQ ID NO: 12)
CLAEGTRIFDPVTGTTHRIEDVVDGRKPIHVVAAAKDGTLLARPVVSWFDQGTRDVIGLRIAGGATVWATPDHKV

LTEYGWRAAGELRKGDRVAGPGGSGNSLALSLTADQMVSALLDAEPPILYSEYNPTSPFSEASMMGLLTNLADRE

LVHMINWAKRVPGFVDLTLHDQAHLLERAWLEILMIGLVWRSMEHPGKLLFAPNLLLDRNQGKCVEGMVEIFDML

LATSSRFRMMNLQGEEFVCLKSIILLNSGVYTFLSSTLKSLEEKDHIHRALDKITDTLIHLMAKAGLTLQQQHQR

LAQLLLILSHIRHMSNKGMEHLYSMKYKNVVPLYDLLLEMLDAHRLHAGGSGASRVQAFADALDDKFLHDMLAEG

LRYSVIREVLPTRRARTFDLEVEELHTLVAEGVVVHNC

37R3-2 intein:

(SEQ ID NO: 13)
CLAEGTRIFDPVTGTTHRIEDVVDGRKPIHVVAAAKDGTLLARPVVSWFDQGTRDVIGLRIAGGAIVWATPDHKV

LTEYGWRAAGELRKGDRVAGPGGSGNSLALSLTADQMVSALLDAEPPILYSEYDPTSPFSEASMMGLLTNLADRE

LVHMINWAKRVPGFVDLTLHDQAHLLERAWLEILMIGLVWRSMEHPGKLLFAPNLLLDRNQGKCVEGMVEIFDML

LATSSRFRMMNLQGEEFVCLKSIILLNSGVYTFLSSTLKSLEEKDHIHRALDKITDTLIHLMAKAGLTLQQQHQR

LAQLLLILSHIRHMSNKGMEHLYSMKYKNVVPLYDLLLEMLDAHRLHAGGSGASRVQAFADALDDKFLHDMLAEG

LRYSVIREVLPTRRARTFDLEVEELHTLVAEGVVVHNC

37R3-3 intein:

(SEQ ID NO: 14)
CLAEGTRIFDPVTGTTHRIEDVVDGRKPIHVVAVAKDGTLLARPVVSWFDQGTRDVIGLRIAGGATVWATPDHKV

LTEYGWRAAGELRKGDRVAGPGGSGNSLALSLTADQMVSALLDAEPPILYSEYDPTSPFSEASMMGLLTNLADRE

LVHMINWAKRVPGFVDLTLHDQAHLLERAWLEILMIGLVWRSMEHPGKLLFAPNLLLDRNQGKCVEGMVEIFDML

LATSSRFRMMNLQGEEFVCLKSIILLNSGVYTFLSSTLKSLEEKDHIHRALDKITDTLIHLMAKAGLTLQQQHQR

LAQLLLILSHIRHMSNKGMEHLYSMKYKNVVPLYDLLLEMLDAHRLHAGGSGASRVQAFADALDDKFLHDMLAEE

LRYSVIREVLPTRRARTFDLEVEELHTLVAEGVVVHNC

The term "linker," as used herein, refers to a chemical group or a molecule linking two adjacent molecules or moieties, e.g., two polypeptides. Typically, the linker is positioned between, or flanked by, two groups, molecules, or other moieties and connected to each one via a covalent bond, thus connecting the two. In some embodiments, the linker is an amino acid linker. In some embodiments, the amino acid linker comprises at least 1, at least 2, at least 3, at least 4, at least 5, at least 6, at least 7, at least 8, at least 9, at least 10, at least 15, at least 20, at least 25, or at least 30 amino acids. In some embodiments, the linker is a divalent organic molecule, group, polymer, or chemical moiety. In some embodiments, the peptide linker comprises repeats of the tri-peptide Gly-Gly-Ser, e.g., comprising the sequence $(GGS)_n$ (SEQ ID NO: 203), wherein n represents at least 1, 2, 3, 4, 5, 6, 7, 8, 9, 10, or more repeats. In some embodiments, the linker comprises the sequence $(GGS)_6$ (SEQ ID NO:15). In some embodiments, the peptide linker is the 16 residue "XTEN" linker, or a variant thereof (See, e.g., Schellenberger et al. A recombinant polypeptide extends the in vivo half-life of peptides and proteins in a tunable manner. *Nat. Biotechnol.* 27, 1186-1190 (2009)). In some embodiments, the XTEN linker comprises the sequence SGSETPGTSESATPES (SEQ ID NO:16), SGSETPGTSESA (SEQ ID NO:17), or SGSETPGTSESATPEGGSGGS (SEQ ID NO:18). In some embodiments, the peptide linker is one or more selected from VPFLLEPDNINGKTC (SEQ ID NO:19), GSAGSAAGSGEF (SEQ ID NO:20), SIVAQLSRPDPA (SEQ ID NO:21), MKIIEQLPSA (SEQ ID NO:22), VRHKLKRVGS (SEQ ID NO:23), GHGTGSTGSGSS (SEQ ID NO:24), MSRPDPA (SEQ ID NO:25); or GGSM (SEQ ID NO:26).

The term "mutation," as used herein, refers to a substitution of a residue within a sequence, e.g., a nucleic acid or amino acid sequence, with another residue, or a deletion or insertion of one or more residues within a sequence. Mutations are typically described herein by identifying the original residue followed by the position of the residue within the sequence and by the identity of the newly substituted residue. Methods for making the amino acid substitutions (mutations) provided herein are known in the art and are provided by, for example, Green and Sambrook, *Molecular Cloning: A Laboratory Manual* (4th ed., Cold Spring Harbor Laboratory Press, Cold Spring Harbor, N.Y. (2012)).

The term "nuclease," as used herein, refers to an agent, for example, a protein, capable of cleaving a phosphodiester bond connecting two nucleotide residues in a nucleic acid molecule. In some embodiments, "nuclease" refers to a protein having an inactive DNA cleavage domain, such that the nuclease is incapable of cleaving a phosphodiester bond. In some embodiments, the nuclease is a protein, e.g., an enzyme that can bind a nucleic acid molecule and cleave a phosphodiester bond connecting nucleotide residues within the nucleic acid molecule. A nuclease may be an endonuclease, cleaving a phosphodiester bonds within a polynucleotide chain, or an exonuclease, cleaving a phosphodiester bond at the end of the polynucleotide chain. In some embodiments, a nuclease is a site-specific nuclease, binding and/or cleaving a specific phosphodiester bond within a specific nucleotide sequence, which is also referred to herein as the "recognition sequence," the "nuclease target site," or the "target site." In some embodiments, a nuclease is an RNA-guided (i.e., RNA-programmable) nuclease, which is associated with (e.g., binds to) an RNA (e.g., a guide RNA, "gRNA") having a sequence that complements a target site, thereby providing the sequence specificity of the nuclease. In some embodiments, a nuclease recognizes a single stranded target site. In some embodiments, a nuclease recognizes a double-stranded target site, for example, a double-stranded DNA target site. The target sites of many naturally occurring nucleases, for example, many naturally occurring DNA restriction nucleases, are well known to those of skill in the art. In many cases, a DNA nuclease, such as EcoRI, HindIII, or BamHI, recognize a palindromic, double-stranded DNA target site of 4 to 10 base pairs in length, and cut each of the two DNA strands at a specific position within the target site. Some endonucleases cut a double-stranded nucleic acid target site symmetrically, i.e., cutting both strands at the same position so that the ends comprise base-paired nucleotides, also referred to herein as blunt ends. Other endonucleases cut a double-stranded nucleic acid target site asymmetrically, i.e., cutting each strand at a different position so that the ends include unpaired nucleotides. Unpaired nucleotides at the end of a double-stranded DNA molecule are also referred to as "overhangs," e.g., as "5'-overhang" or as "3'-overhang," depending on whether the unpaired nucleotide(s) form(s) the 5' or the 5' end of the respective DNA strand. Double-stranded DNA molecule ends ending with unpaired nucleotide(s) are also referred to as sticky ends, as they can "stick to" other double-stranded DNA molecule ends comprising complementary unpaired nucleotide(s). A nuclease protein typically comprises a "binding domain" that mediates the interaction of the protein with the nucleic acid substrate, and also, in some cases, specifically binds to a target site, and a "cleavage domain" that catalyzes the cleavage of the phosphodiester bond within the nucleic acid backbone. In some embodiments, a nuclease protein can bind and cleave a nucleic acid molecule in a monomeric form. In some embodiments, a nuclease protein has to dimerize or multimerize in order to cleave a target nucleic acid. Binding domains and cleavage domains of naturally occurring nucleases, as well as modular binding domains and cleavage domains that can be fused to create nucleases binding specific target sites, are well known to those of skill in the art. For example, the binding domain of RNA-programmable nucleases (e.g., Cas9), or a Cas9 protein having an inactive DNA cleavage domain (e.g., dCas9), can be used as a binding domain (e.g., that binds a gRNA to direct binding to a target site) to specifically bind a desired target site, and fused or conjugated to a cleavage domain, for example, the cleavage domain of FokI, to create an engineered nuclease cleaving the target site. In some embodiments, Cas9 fusion proteins provided herein comprise the cleavage domain of FokI, and are therefore referred to as "fCas9" proteins. In some embodiments, the cleavage domain of FokI, e.g., in a fCas9 protein corresponds to, or comprises in part or whole, the amino acid sequence (or variants thereof) set forth as SEQ ID NO:6, below. In some embodiments, variants or homologues of the FokI cleavage domain include any variant or homologue capable of dimerizing (e.g., as part of fCas9 fusion protein) with another FokI cleavage domain at a target site in a target nucleic acid, thereby resulting in cleavage of the target nucleic acid. In some embodiments, variants of the FokI cleavage domain (e.g., variants of SEQ ID NO:6) are provided which are at least about 70% identical, at least about 80% identical, at least about 90% identical, at least about 95% identical, at least about 98% identical, at least about 99% identical, at least about 99.5% identical, or at least about 99.9% to SEQ ID NO:6. In some embodiments, variants of the FokI cleavage domain (e.g., variants of SEQ ID NO:6) are provided having an amino acid sequence which is shorter, or longer than SEQ ID NO:6, by about 5 amino acids, by about 10 amino acids, by about 15 amino acids, by about 20 amino acids, by about 25 amino acids, by about 30 amino acids, by about 40 amino acids, by about 50 amino acids, by about 75 amino acids, by about 100 amino acids, or more.

```
Cleavage domain of FokI:
                                              (SEQ ID NO: 6)
GSQLVKSELEEKKSELRHKLKYVPHEYIELIEIARNSTQDRILEMKVMEF

FMKVYGYRGKHLGGSRKPDGAIYTVGSPIDYGVIVDTKAYSGGYNLPIGQ

ADEMQRYVEENQTRNKHINPNEWWKVYPSSVTEFKFLFVSGHFKGNYKAQ

LTRLNHITNCNGAVLSVEELLIGGEMIKAGTLTLEEVRRKFNNGEINF
```

The terms "nucleic acid" and "nucleic acid molecule," as used herein, refer to a compound comprising a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, the term "nucleic acid" refers to individual nucleic acid residues (e.g. nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. Nucleic acids may be naturally occurring, for example, in the context of a genome, a transcript, an mRNA, tRNA, rRNA, siRNA, snRNA, a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or including non-naturally occurring nucleotides or nucleosides. Furthermore, the terms "nucleic acid," "DNA," "RNA," and/or similar terms include nucleic acid analogs, i.e. analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications. A nucleic acid sequence is presented in the 5' to 3' direction unless otherwise indicated. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine);

nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

The term "pharmaceutical composition," as used herein, refers to a composition that can be administrated to a subject in the context of treatment of a disease or disorder. In some embodiments, a pharmaceutical composition comprises an active ingredient, e.g., a nuclease or a nucleic acid encoding a nuclease, and a pharmaceutically acceptable excipient.

The term "proliferative disease," as used herein, refers to any disease in which cell or tissue homeostasis is disturbed in that a cell or cell population exhibits an abnormally elevated proliferation rate. Proliferative diseases include hyperproliferative diseases, such as pre-neoplastic hyperplastic conditions and neoplastic diseases. Neoplastic diseases are characterized by an abnormal proliferation of cells and include both benign and malignant neoplasias. Malignant neoplasia is also referred to as cancer.

The terms "protein," "peptide," and "polypeptide" are used interchangeably herein and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof.

The term "fusion protein" as used herein refers to a hybrid polypeptide which comprises protein domains from at least two different proteins. One protein may be located at the amino-terminal (N-terminal) portion of the fusion protein or at the carboxy-terminal (C-terminal) protein thus forming an "amino-terminal fusion protein" or a "carboxy-terminal fusion protein," respectively. A protein may comprise different domains, for example, a nucleic acid binding domain (e.g., the gRNA binding domain of Cas9 that directs the binding of the protein to a target site or a dCas9 protein) and a nucleic acid cleavage domain(s). In some embodiments, a protein is in a complex with, or is in association with, a nucleic acid, e.g., DNA or RNA. Any of the proteins provided herein may be produced by any method known in the art. For example, the proteins provided herein may be produced via recombinant protein expression and purification, which is especially suited for fusion proteins comprising a peptide linker. Methods for recombinant protein expression and purification are well known and include those described by Green and Sambrook, *Molecular Cloning: A Laboratory Manual* (4th ed., Cold Spring Harbor Laboratory Press, Cold Spring Harbor, N.Y. (2012)), the entire contents of which are incorporated herein by reference.

The term "protein splicing," as used herein, refers to a process in which a sequence, an intein, is excised from within an amino acid sequence, and the remaining fragments of the amino acid sequence, the exteins, are ligated via an amide bond to form a continuous amino acid sequence.

The term "RNA-programmable nuclease" and "RNA-guided nuclease" are used interchangeably herein and refer to a nuclease that forms a complex with (e.g., binds or associates with) one or more RNAs that is not a target for cleavage. In some embodiments, an RNA-programmable nuclease, when in a complex with an RNA, may be referred to as a nuclease:RNA complex. Typically, the bound RNA(s) is referred to as a guide RNA (gRNA). gRNAs can exist as an association of two or more RNAs, or as a single RNA molecule. gRNAs that exist as a single RNA molecule may be referred to as single-guide RNAs (sgRNAs), though "gRNA" is used interchangeably to refer to guide RNAs that exist as either a single molecule or as a complex of two or more molecules. Typically, gRNAs that exist as single RNA species comprise at least two domains: (1) a domain that shares homology to a target nucleic acid and may direct binding of a Cas9 complex to the target; and (2) a domain that binds a Cas9 protein. In some embodiments, domain (2) corresponds to a sequence known as a tracrRNA and comprises a stem-loop structure. For example, in some embodiments, domain (2) is homologous to a tracrRNA as depicted in FIG. 1E of Jinek et al., *Science* 337:816-821(2012), the entire contents of which is incorporated herein by reference. In some embodiments, domain 2 is at least 90%, at least 95%, at least 98%, or at least 99% identical to the tracrRNA as described by Jinek et al., *Science* 337:816-821(2012). The gRNA comprises a nucleotide sequence that complements a target site, which mediates binding of the nuclease/RNA complex to said target site and the sequence specificity of the nuclease:RNA complex. The sequence of a gRNA that binds a target nucleic acid can comprise any sequence that complements a region of the target and is suitable for a nuclease: RNA complex to bind. In some embodiments, the RNA-programmable nuclease is the (CRISPR-associated system) Cas9 endonuclease, for example, Cas9 (Csn1) from *Streptococcus pyogenes* (see, e.g., "Complete genome sequence of an M1 strain of *Streptococcus pyogenes*." Ferretti J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L. expand/collapse author list McLaughlin R. E., *Proc. Natl. Acad. Sci. U.S.A.* 98:4658-4663(2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., *Nature* 471:602-607(2011); and "A programmable dual-RNA-guided DNA endonuclease in adaptive bacterial immunity." Jinek M., Chylinski K., Fonfara I., Hauer M., Doudna J. A., Charpentier E. *Science* 337:816-821(2012), the entire contents of each of which are incorporated herein by reference.

Because RNA-programmable nucleases (e.g., Cas9) use RNA:DNA hybridization to determine target DNA cleavage sites, these proteins are able to cleave, in principle, any sequence specified by the guide RNA. Methods of using RNA-programmable nucleases, such as Cas9, for site-specific cleavage (e.g., to modify a genome) are known in the art (see e.g., Cong et al. Multiplex genome engineering using CRISPR/Cas systems. *Science* 339, 819-823 (2013);

Mali et al. RNA-guided human genome engineering via Cas9. *Science* 339, 823-826 (2013); Hwang et al. Efficient genome editing in zebrafish using a CRISPR-Cas system. *Nature biotechnology* 31, 227-229 (2013); Jinek et al. RNA-programmed genome editing in human cells. *eLife* 2, e00471 (2013); Dicarlo et al. Genome engineering in *Saccharomyces cerevisiae* using CRISPR-Cas systems. *Nucleic acids research* (2013); Jiang et al. RNA-guided editing of bacterial genomes using CRISPR-Cas systems. *Nature biotechnology* 31, 233-239 (2013); the entire contents of each of which are incorporated herein by reference).

The term "recombinase," as used herein, refers to a site-specific enzyme that mediates the recombination of DNA between recombinase recognition sequences, which results in the excision, integration, inversion, or exchange (e.g., translocation) of DNA fragments between the recombinase recognition sequences. Recombinases can be classified into two distinct families: serine recombinases (e.g., resolvases and invertases) and tyrosine recombinases (e.g., integrases). Examples of serine recombinases include, without limitation, Hin, Gin, Tn3, β-six, CinH, ParA, γδ, Bxb1, ϕC31, TP901, TG1, φBT1, R4, φRV1, φFC1, MR11, A118, U153, and gp29. Examples of tyrosine recombinases include, without limitation, Cre, FLP, R, Lambda, HK101, HK022, and pSAM2. The serine and tyrosine recombinase names stem from the conserved nucleophilic amino acid residue that the recombinase uses to attack the DNA and which becomes covalently linked to the DNA during strand exchange. Recombinases have numerous applications, including the creation of gene knockouts/knock-ins and gene therapy applications. See, e.g., Brown et al., "Serine recombinases as tools for genome engineering." *Methods.* 2011; 53(4):372-9; Hirano et al., "Site-specific recombinases as tools for heterologous gene integration." *Appl. Microbiol. Biotechnol.* 2011; 92(2):227-39; Chavez and Calos, "Therapeutic applications of the ΦC31 integrase system." *Curr. Gene Ther.* 2011; 11(5):375-81; Turan and Bode, "Site-specific recombinases: from tag-and-target- to tag-and-exchange-based genomic modifications." *FASEB J.* 2011; 25(12):4088-107; Venken and Bellen, "Genome-wide manipulations of Drosophila melanogaster with transposons, Flp recombinase, and ΦC31 integrase." *Methods Mol. Biol.* 2012; 859:203-28; Murphy, "Phage recombinases and their applications." *Adv. Virus Res.* 2012; 83:367-414; Zhang et al., "Conditional gene manipulation: Cre-ating a new biological era." *J. Zhejiang Univ. Sci. B.* 2012; 13(7):511-24; Karpenshif and Bernstein, "From yeast to mammals: recent advances in genetic control of homologous recombination." DNA Repair (Amst). 2012; 1; 11(10):781-8; the entire contents of each are hereby incorporated by reference in their entirety. The recombinases provided herein are not meant to be exclusive examples of recombinases that can be used in embodiments of the invention. The methods and compositions of the invention can be expanded by mining databases for new orthogonal recombinases or designing synthetic recombinases with defined DNA specificities (See, e.g., Groth et al., "Phage integrases: biology and applications." *J. Mol. Biol.* 2004; 335, 667-678; Gordley et al., "Synthesis of programmable integrases." *Proc. Natl. Acad. Sci. USA.* 2009; 106, 5053-5058; the entire contents of each are hereby incorporated by reference in their entirety). Other examples of recombinases that are useful in the methods and compositions described herein are known to those of skill in the art, and any new recombinase that is discovered or generated is expected to be able to be used in the different embodiments of the invention. In some embodiments, the catalytic domains of a recombinase are fused to a nuclease-inactivated RNA-programmable nuclease (e.g., dCas9, or a fragment thereof), such that the recombinase domain does not comprise a nucleic acid binding domain or is unable to bind to a target nucleic acid (e.g., the recombinase domain is engineered such that it does not have specific DNA binding activity). Recombinases lacking DNA binding activity and methods for engineering such are known, and include those described by Klippel et al., "Isolation and characterisation of unusual gin mutants." *EMBO J.* 1988; 7: 3983-3989: Burke et al., "Activating mutations of Tn3 resolvase marking interfaces important in recombination catalysis and its regulation. *Mol Microbiol.* 2004; 51: 937-948; Olorunniji et al., "Synapsis and catalysis by activated Tn3 resolvase mutants." *Nucleic Acids Res.* 2008; 36: 7181-7191; Rowland et al., "Regulatory mutations in Sin recombinase support a structure-based model of the synaptosome." *Mol Microbiol.* 2009; 74: 282-298; Akopian et al., "Chimeric recombinases with designed DNA sequence recognition." *Proc Natl Acad Sci USA.* 2003; 100: 8688-8691; Gordley et al., "Evolution of programmable zinc finger-recombinases with activity in human cells. *J Mol Biol.* 2007; 367: 802-813; Gordley et al., "Synthesis of programmable integrases." *Proc Natl Acad Sci USA.* 2009; 106: 5053-5058; Arnold et al., "Mutants of Tn3 resolvase which do not require accessory binding sites for recombination activity." *EMBO J.* 1999;18: 1407-1414; Gaj et al., "Structure-guided reprogramming of serine recombinase DNA sequence specificity." *Proc Natl Acad Sci USA.* 2011; 108(2):498-503; and Proudfoot et al., "Zinc finger recombinases with adaptable DNA sequence specificity." *PLoS One.* 2011; 6(4):e19537; the entire contents of each are hereby incorporated by reference. For example, serine recombinases of the resolvase-invertase group, e.g., Tn3 and γδ resolvases and the Hin and Gin invertases, have modular structures with autonomous catalytic and DNA-binding domains (See, e.g., Grindley et al., "Mechanism of site-specific recombination." *Ann Rev Biochem.* 2006; 75: 567-605, the entire contents of which are incorporated by reference). The catalytic domains of these recombinases are thus amenable to being recombined with nuclease-inactivated RNA-programmable nucleases (e.g., dCas9, or a fragment thereof) as described herein, e.g., following the isolation of 'activated' recombinase mutants which do not require any accessory factors (e.g., DNA binding activities) (See, e.g., Klippel et al., "Isolation and characterisation of unusual gin mutants." *EMBO J.* 1988; 7: 3983-3989: Burke et al., "Activating mutations of Tn3 resolvase marking interfaces important in recombination catalysis and its regulation. *Mol Microbiol.* 2004; 51: 937-948; Olorunniji et al., "Synapsis and catalysis by activated Tn3 resolvase mutants." *Nucleic Acids Res.* 2008; 36: 7181-7191; Rowland et al., "Regulatory mutations in Sin recombinase support a structure-based model of the synaptosome." *Mol Microbiol.* 2009; 74: 282-298; Akopian et al., "Chimeric recombinases with designed DNA sequence recognition." *Proc Natl Acad Sci USA.* 2003;100: 8688-8691). Additionally, many other natural serine recombinases having an N-terminal catalytic domain and a C-terminal DNA binding domain are known (e.g., phiC31 integrase, TnpX transposase, IS607 transposase), and their catalytic domains can be co-opted to engineer programmable site-specific recombinases as described herein (See, e.g., Smith et al., "Diversity in the serine recombinases." *Mol Microbiol.* 2002;44: 299-307, the entire contents of which are incorporated by reference). Similarly, the core catalytic domains of tyrosine recombinases (e.g., Cre, λ integrase) are known, and can be similarly co-opted to engineer programmable site-specific recombinases as described herein (See, e.g., Guo et al., "Structure of Cre recombinase complexed with DNA in a site-specific recombination synapse." *Nature.* 1997; 389:40-46; Hartung et al., "Cre mutants with altered DNA binding properties." *J Biol Chem* 1998; 273:22884-22891; Shaikh et al., "Chimeras of the Flp and Cre recombinases: Tests of the mode of cleavage by Flp and Cre. *J Mol Biol.* 2000; 302:27-48; Rongrong et al., "Effect of deletion mutation on the recombination activity of Cre recombinase." *Acta Biochim Pol.* 2005; 52:541-544; Kilbride et al., "Determinants of product topology in a hybrid Cre-Tn3 resolvase site-specific recombination system." *J Mol Biol.* 2006; 355:185-195; Warren et al., "A chimeric cre recombinase with regulated directionality." *Proc Natl Acad Sci USA.* 2008 105:18278-18283; Van Duyne, "Teaching Cre to follow directions." *Proc Natl Acad Sci USA.* 2009 Jan. 6; 106(1):4-5; Numrych et al., "A comparison of the effects of single-base and triple-base changes in the integrase arm-type binding sites on the site-specific recombination of bacteriophage λ." *Nucleic Acids Res.* 1990; 18:3953-3959; Tirumalai et al., "The recognition of core-type DNA sites by k integrase." *J Mol Biol.* 1998; 279:513-527; Aihara et al., "A conformational switch controls the DNA cleavage activity of λ integrase." *Mol Cell.* 2003; 12:187-198; Biswas et al., "A structural basis for allosteric control of DNA recombination by λ integrase." *Nature.* 2005; 435:1059-1066; and Warren et al., "Mutations in the amino-terminal domain of λ-integrase have differential effects on integrative and excisive recombination." *Mol Microbiol.* 2005; 55:1104-1112; the entire contents of each are incorporated by reference).

The term "recombine," or "recombination," in the context of a nucleic acid modification (e.g., a genomic modification), is used to refer to the process by which two or more nucleic acid molecules, or two or more regions of a single nucleic acid molecule, are modified by the action of a recombinase protein (e.g., an inventive recombinase fusion protein provided herein). Recombination can result in, inter alia, the insertion, inversion, excision, or translocation of nucleic acids, e.g., in or between one or more nucleic acid molecules.

The term "site-specific enzyme," as used herein, refers to any enzyme capable of binding a nucleic acid at a target site to mediate a modification of the nucleic acid. Typically, the site-specific enzymes provided herein comprise an intein (e.g., a ligand-dependent intein). In some embodiments, the site-specific enzyme is unable to bind a target site prior to excision of the intein. In some embodiments, the site-specific enzyme is able to bind a target site prior to excision of the intein but remains enzymatically inactive (e.g., cannot cleave, recombine, edit, or otherwise modify a nucleic acid) until excision of the intein.

The term "small molecule," as used herein, refers to a non-peptidic, non-oligomeric organic compound either prepared in the laboratory or found in nature. Small molecules, as used herein, can refer to compounds that are "natural product-like", however, the term "small molecule" is not limited to "natural product-like" compounds. Rather, a small molecule is typically a non-polymeric, non-oligomeric molecule that is characterized in that it contains several carbon-carbon bonds, and has a molecular weight of less than 2000 g/mol, preferably less than 1500 g/mol, although this characterization is not intended to be limiting for the purposes of the present invention. In certain embodiments, the ligand of a ligand-dependent inteins used in the present invention is a small molecule.

The term "subject," as used herein, refers to an individual organism. In some embodiments, the subject is a human. In some embodiments, the subject is a non-human mammal. In some embodiments, the subject is a non-human primate. In some embodiments, the subject is a rodent. In some embodiments, the subject is a sheep, a goat, a cattle, a cat, or a dog. In some embodiments, the subject is a vertebrate, an amphibian, a reptile, a fish, an insect, a fly, or a nematode. In some embodiments, the subject is a research animal. In some embodiments, the subject is genetically engineered, e.g., a genetically engineered non-human subject. The subject may be of either sex and at any stage of development.

The terms "target nucleic acid," and "target genome," as used herein in the context of nucleases, refer to a nucleic acid molecule or a genome, respectively, that comprises at least one target site of a given nuclease.

The term "target site," refers to a sequence within a nucleic acid molecule that is bound and (1) cleaved; (2) recombined; (3) edited; or (4) otherwise modified by a site-specific enzyme. In some embodiments, a target site refers to a "nuclease target site," which is a sequence within a nucleic acid molecule that is bound and cleaved by a nuclease. A target site may be single-stranded or double-stranded. In the context of RNA-guided (i.e., RNA-programmable) nucleases (e.g., a Cas9 protein, a Cas9 variant, fragments of Cas9 or fragments of Cas9 variants, etc.), a target site typically comprises a nucleotide sequence that is complementary to a gRNA of the RNA-guided nuclease, and a protospacer adjacent motif (PAM) at the 3' end adjacent to the gRNA-complementary sequence. For the RNA-guided nuclease Cas9, the target site may be, in some embodiments, 20 base pairs plus a 3 base pair PAM (e.g., NNN, wherein N represents any nucleotide). Typically, the first nucleotide of a PAM can be any nucleotide, while the two downstream nucleotides are specified depending on the specific RNA-guided nuclease. Exemplary target sites for RNA-guided nucleases, such as Cas9, are known to those of skill in the art and include, without limitation, NNG, NGN, NAG, and NGG, wherein N represents any nucleotide. In addition, Cas9 nucleases from different species (e.g., *S. thermophilus* instead of *S. pyogenes*) recognize a PAM that comprises the sequence: NGGNG. Additional PAM sequences are known, including, but not limited to, NNAGAAW and NAAR (see, e.g., Esvelt and Wang, *Molecular Systems Biology,* 9:641 (2013), the entire contents of which are incorporated herein by reference). For example, the target site of an RNA-guided nuclease, such as, e.g., Cas9, may comprise the structure $[N_z]$-[PAM], where each N is, independently, any nucleotide, and z is an integer between 1 and 50. In some embodiments, z is at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, or at least 50. In some embodiments, z is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48,49, or 50. In some embodiments, Z is 20. In some embodiments, "target site" may also refer to a sequence within a nucleic acid molecule that is bound but not cleaved by a nuclease.

The terms "transcriptional activator" and "transcriptional repressor," refer to agents which activate and repress the transcription of a gene, respectively. Typically, such activators and repressors are proteins, e.g., as provided herein.

The terms "treatment," "treat," and "treating," refer to a clinical intervention aimed to reverse, alleviate, delay the onset of, or inhibit the progress of a disease or disorder, or one or more symptoms thereof, as described herein. As used herein, the terms "treatment," "treat," and "treating" refer to a clinical intervention aimed to reverse, alleviate, delay the onset of, or inhibit the progress of a disease or disorder, or one or more symptoms thereof, as described herein. In some embodiments, treatment may be administered after one or more symptoms have developed and/or after a disease has been diagnosed. In some embodiments, treatment may be administered in the absence of symptoms, e.g., to prevent or delay onset of a symptom or inhibit onset or progression of a disease. For example, treatment may be administered to a susceptible individual prior to the onset of symptoms (e.g., in light of a history of symptoms and/or in light of genetic or other susceptibility factors). Treatment may also be continued after symptoms have resolved, for example, to prevent or delay their recurrence.

The term "vector" refers to a polynucleotide comprising one or more recombinant polynucleotides of the present invention, e.g., those encoding or a Cas9 protein (e.g., a Cas9 protein comprising an intein) and/or a gRNA provided herein. Vectors include, but are not limited to, plasmids, viral vectors, cosmids, artificial chromosomes, and phagemids. The vector is one which is able to replicate in a host cell, and which is further characterized by one or more endonuclease restriction sites at which the vector may be cut and into which a desired nucleic acid sequence may be inserted. Vectors may contain one or more marker sequences suitable for use in the identification and/or selection of cells which have or have not been transformed or genomically modified with the vector. Markers include, for example, genes encoding proteins which increase or decrease either resistance or sensitivity to antibiotics (e.g., kanamycin, ampicillin) or other compounds, genes which encode enzymes whose activities are detectable by standard assays known in the art (e.g., (β-galactosidase, alkaline phosphatase or luciferase), and genes which visibly affect the phenotype of transformed or transfected cells, hosts, colonies, or plaques. Any vector suitable for the transformation of a host cell, (e.g., *E. coli*, mammalian cells such as CHO cell, insect cells, etc.) as embraced by the present invention, for example vectors belonging to the pUC series, pGEM series, pET series, pBAD series, pTET series, or pGEX series. In some embodiments, the vector is suitable for transforming a host cell for recombinant protein production. Methods for selecting and engineering vectors and host cells for expressing gRNAs and/or proteins (e.g., those provided herein), transforming cells, and expressing/purifying recombinant proteins are well known in the art, and are provided by, for example, Green and Sambrook, *Molecular Cloning: A Laboratory Manual* (4th ed., Cold Spring Harbor Laboratory Press, Cold Spring Harbor, N.Y. (2012)).

DETAILED DESCRIPTION OF CERTAIN EMBODIMENTS OF THE INVENTION

Site-specific enzymes which catalyze nucleic acid modifications are powerful tools for targeted genome modification in vitro and in vivo. Some site-specific enzymes can theoretically achieve a level of specificity for a target site that would allow one to target a single unique site in a genome for modification without affecting any other genomic site. In the case of site-specific nucleases, it has been reported that nuclease cleavage in living cells triggers a DNA repair mechanism that frequently results in a modification of the cleaved and repaired genomic sequence, for example, via homologous recombination or non-homologous end-joining. Accordingly, the targeted cleavage of a specific unique sequence within a genome opens up new avenues for gene targeting and gene modification in living cells, including cells that are hard to manipulate with conventional gene targeting methods, such as many human somatic cells or embryonic stem cells. Nuclease-mediated modification of disease-related sequences, e.g., the CCR-5 allele in HIV/AIDS patients, or of genes necessary for tumor neovascularization, can be used in the clinical context, and two site-specific nucleases are currently in clinical trials (Perez, E. E. et al., "Establishment of HIV-1 resistance in CD4+ T cells by genome editing using zinc-finger nucleases." *Nature Biotechnology*. 26, 808-816 (2008); ClinicalTrials.gov identifiers: NCT00842634, NCT01044654, NCT01252641, NCT01082926). Other diseases that can be treated using site-specific nucleases or other site-specific DNA modifying enzymes include, for example, diseases associated with triplet expansion (e.g., Huntington's disease, myotonic dystrophy, spinocerebellar atatxias, etc.), cystic fibrosis (by targeting the CFTR gene), cancer, autoimmune diseases, and viral infections.

One important problem with site-specific modification is off-target effects, e.g., the modification of genomic sequences that differ from the intended target sequence by one or more nucleotides. Undesired side effects of off-target modification range from insertion into unwanted loci during a gene targeting event to severe complications in a clinical scenario. For example, off-target modification of sequences encoding essential gene functions or tumor suppressor genes may result in disease or even the death of a subject. Accordingly, it is desirable to employ new strategies in designing site-specific enzymes having the greatest chance of minimizing off-target effects.

The systems, methods, and compositions of the present disclosure represent, in some aspects, an improvement over previous methods and compositions by providing means to control the spatiotemporal activity of site-specific enzymes, for example, RNA-guided nucleases and engineered RNA-guided nucleic acid modifying enzymes. For example, RNA-guided nucleases known in the art, both naturally occurring and those engineered, typically bind to and cleave DNA upon forming a complex with an RNA (e.g., a gRNA) that complements the target. Aspects of the present invention relate to the recognition that having spatiotemporal control of the enzymatic or nucleic acid binding properties of an RNA-guided nuclease and RNA-guided nucleic acid modifying enzymes by engineering variants to include an intein will decrease the likelihood of off-target effects by minimizing or controlling the time a RNA-guided nuclease or engineered RNA-guided nucleic acid modifying enzymes is active. Accordingly, the strategies, methods, compositions, kits, and systems provided herein can be used to control the activity of any site-specific enzyme (both naturally occurring and those engineered) such as RNA-guided nucleases (e.g., Cas9, Cas9 variants, fragments of Cas9 or Cas9 variants, etc.) or engineered nucleic acid modifying enzymes comprising a variant of an RNA-guided nuclease (e.g., dCas9).

Inteins are protein splicing elements that are able to catalyze their excision out of a single polypeptide and leave behind the flanking sequences, or exteins, precisely ligated together through a native peptide bond. Inteins are attractive tools for modulating protein structure and function because they do not require any other cellular components, are able to splice out of a wide variety of extein contexts, and can undergo splicing in minutes. Although natural inteins splice spontaneously, inteins that undergo splicing in a small molecule-dependent or ligand-dependent manner have been developed by fusing intein halves with proteins that dimerize in the presence of a small molecule, or by directed evolution in which a library of intact inteins fused to a ligand-binding domain was screened to splice in the presence, but not the absence, of a small molecule or ligand. These ligand-dependent inteins have enabled protein function in cells to be controlled post-translationally by the addition of an exogenous, cell-permeable molecule (See e.g., published U.S. Patent Application US 2014/0065711 A1, the entire contents of which are hereby incorporated by reference). The inventors have found that the targeted insertion of ligand-dependent inteins into site-specific enzymes renders the enzymes, in some instances, inactive prior to the controlled excision of the intein through binding of a ligand specific for the intein. For example, the targeted insertion of a ligand-dependent intein into Cas9 at fifteen different positions resulted in a subset of Cas9 variants that were inactive in the absence of ligand, but upon addition of the ligand the intein self-excised resulting in an active Cas9 protein capable of site-specific cleavage of a target gene.

Some aspects of this disclosure are based on the surprising discovery that Cas9 proteins comprising an intein, for example, a ligand-dependent intein as described herein, exhibit an increased specificity as compared to constitutively active Cas9 proteins. For example, it was found that the conditionally active Cas9 proteins comprising an intein exhibit an activity in the "on" state that is comparable to wild-type Cas9 activity or only slightly decreased as compared to wild-type Cas9 activity, while exhibiting decreased off-target activity.

In addition, some aspects of this disclosure relate to the recognition that Cas9 off-target activity is at least in part related to the concentration of active Cas9 proteins, and that the off-target activity of the provided conditionally active Cas9 proteins, e.g., the provided ligand-dependent Cas9 proteins, can be modulated, e.g., further decreased, by contacting the Cas9 proteins with a minimal amount of ligand effecting the desired result, e.g., the minimal amount effecting intein excision from a Cas9 protein, or the minimal amount resulting in a desired level of Cas9 protein activity.

While of particular relevance to DNA and DNA-cleaving nucleases such as Cas9 and variants thereof, the inventive concepts, methods, compositions, strategies, kits, and systems provided herein are not limited in this respect, but can be applied to any nuclease or nucleic acid:enzyme system utilizing nucleic acid templates such as RNA to direct binding to a target nucleic acid. For example, the inventive concepts provided herein can be applied to RNA-guided nucleic acid-targeting protein, e.g., to RNA-guided nucleases, and to fusion proteins comprising nucleic acid-targeting domains of such nucleases, e.g., to fusion proteins comprising a Cas9 targeting domain (e.g., dCas9 domain), and a functional (effector) domain, such as, for example, a heterologous nuclease domain, recombinase domain, or other nucleic acid-editing domain.

Small Molecule Controlled Site-Specific Enzymes

Some aspects of this disclosure provide site-specific enzymes engineered to have both an "on" and "off" state which depends on the presence of a ligand such as a small molecule. The ligand binds and activates the enzyme through binding a ligand-dependent intein in the enzyme, whereby ligand binding induces self-excision of the intein thereby activating the enzyme (e.g., the presence of the intein in the enzyme disrupted one or more activities of the enzyme). In some aspects then, the enzymes may collectively be referred to as "small molecule controlled" or "ligand-dependent" site-specific enzymes. In some embodiments, the site-specific enzyme that has been modified to include a ligand-dependent intein comprises Cas9, or a variant of Cas9.

Accordingly, in the absence of a ligand that binds the intein, the intein is not excised, and the protein comprising Cas9 or variant of Cas9 remains inactive. By "inactive" it is meant that the protein has no or minimal activity with respect to one or more activities described herein. In some embodiments, prior to intein excision, the protein has (i) no or minimal enzymatic activity; (ii) no or minimal gRNA binding activity; (iii) no or minimal target nucleic acid binding activity; or any combination of (i)-(iii), e.g., the protein has (i) and (ii); (i) and (iii); (ii) and (iii); or (i), (ii) and (iii). Enzymatic activities for (i), include, for example, nuclease activity, nickase activity, recombinase activity, nucleic acid editing (e.g., deaminase) activity, transcriptional activation, transcriptional repression, and epigenetic modification activity.

In some embodiments, by "minimal" activity, it is meant that the protein, prior to excision of the intein, exhibits less than 50%, less than 45%, less than 40%, less than 35%, less than 30%, less than 25%, less than 24%, less than 23%, less than 22%, less than 21%, less than 20, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% of a particular activity (e.g., nuclease activity, nickase activity, recombinase activity, deaminase activity, transcriptional activation, transcriptional repression, epigenetic modification activity, gRNA binding activity, and/or target nucleic acid binding activity) as compared to either the wild type counterpart of the protein or the intein-excised form of the protein. In some embodiments, following excision of the intein, the protein exhibits at least a 1.25-fold increase, at least a 1.5-fold increase, at least 1.75-fold increase, at least a 2.0-fold increase, at least a 2.25-fold increase, at least a 2.5-fold increase, at least a 2.75-fold increase, at least a 3.0-fold increase, at least a 3.25-fold increase, at least a 3.5-fold increase, at least a 3.75-fold increase, at least a 4.0-fold increase, at least a 4.5-fold increase, at least a 5.0-fold increase, at least a 5.5-fold increase, at least a 6.0-fold increase, at least a 6.5-fold increase, at least a 7.0-fold increase, at least a 7.5-fold increase, at least a 8.0-fold increase, at least a 8.5-fold increase, at least a 9.0-fold increase, at least a 9.5-fold increase, or at least a 10.0-fold or more increase in activity (e.g., nuclease activity, nickase activity, recombinase activity, or deaminase activity) as compared to the intein-intact form of the protein. Methods for assessing the activity of any ligand-dependent site-specific Cas9-containing enzyme provided herein are well known to those of ordinary skill in the art, and in the context of nuclease activity include those described in the Examples.

In some embodiments, upon excision, the intein leaves a cysteine residue. Thus, if the intein is inserted such that it replaces a cysteine, the Cas9 protein, upon intein excision, will be unmodified as compared to the original protein. If the intein replaces any other amino acid, the Cas9 protein, upon intein excision, will contain a cysteine in place of the amino acid that was replaced. In some embodiments, the intein does not replace an amino acid residue in a Cas9 protein, but is inserted into the Cas9 protein (e.g., in addition to the amino acid residues of the Cas9 protein). In this aspect, upon excision, the protein will comprise an additional cysteine residue. While the presence of an additional cysteine residue (or the substitution of a residue for a cysteine upon excision)

is unlikely to affect the function of the Cas9 protein, in some embodiments where the intein does not replace a cysteine, the intein replaces an alanine, serine, or threonine amino acid, as these residues are similar in size and/or polarity to cysteine.

Accordingly, in some embodiments, the intein is inserted into one or both of the nuclease domains of Cas9 or a Cas9 variant (e.g., dCas9, Cas9 nickase), such as the HNH domain and/or the RuvC domain. In some embodiments, the intein is inserted into one or more other domains of Cas9 or a Cas9 variant (e.g., dCas9, Cas9 nickase), such as, REC1, REC2, PAM-interacting (PI), and/or bridge helix (BH) domain. The sequences and structure corresponding to these domains are known, and in some aspects are represented by the underlined segments of SEQ ID NO:2 (Cas9) and SEQ ID NO:5 (dCas9) above (See also, Nishimasu et al., "Crystal structure of Cas9 in complex with guide RNA and target DNA." Cell. 2014; 156(5), 935-949). In some embodiments, the intein is inserted into any location of Cas9, e.g., any location that disrupts one or more activities of Cas9 (e.g., enzymatic activity, gRNA binding activity, and/or DNA binding activity). In some embodiments, the intein is inserted into a sequence of Cas9 or a Cas9 variant such that the intein sequence replaces one or more amino acids in the protein. In some embodiments, the intein replaces any cysteine, any alanine, any threonine, or any serine residue in Cas9 or a Cas9 variant including Cas9 nickase and dCas9 (and fusions thereof). In some embodiments the inserted intein sequence replaces Cys80, Ala127, Thr146, Ser219, Thr333, Thr519, Cys574, Thr622, Ser701, Ala728, Thr995, Ser1006, Ser1154, Ser1159, or Ser1274 in Cas9 (SEQ ID NO:2), dCas9 (SEQ ID NO:5), or Cas9 nickase (SEQ ID NO:4). In some embodiments, the intein is inserted within 5, within 10, within 15, or within 20 amino acids of Cys80, Ala127, Thr146, Ser219, Thr333, Thr519, Cys574, Thr622, Ser701, Ala728, Thr995, Ser1006, Ser1154, Ser1159, or Ser1274 in Cas9 (SEQ ID NO:2), dCas9 (SEQ ID NO:5), or Cas9 nickase (SEQ ID NO:4). In some embodiments, the inserted intein sequence replaces Ala127, Thr146, Ser219, Thr519, or Cys574 in Cas9 (SEQ ID NO:2), dCas9 (SEQ ID NO:5), or Cas9 nickase (SEQ ID NO:4). In some embodiments, a Cas9 protein comprising an intein comprises an amino acid sequence selected from the group consisting of SEQ ID NOs:27-41, or comprises an amino acid sequence that has at least 80%, at least 85%, at least 90%, at least 95%, or at least 99% sequence identity to any one of SEQ ID NOs:27-41. In some embodiments, the intein is inserted into the protein such that it does not replace any amino acid, but is added in addition to the amino acids of the protein. The intein that is inserted into the protein can be any ligand-dependent intein, e.g., those described herein. For example, in some embodiments, the intein that is inserted into the protein comprises, in part or in whole, a sequence that is at least 80%, at least 85%, at least 90%, at least 95%, at least 99%, or 100% identical to any one of SEQ ID NO:27-41.

```
Cas9:Intein (37R3-2; in double underline) replacing Cys80
                                                    (SEQ ID NO: 27)
MDKKYSIGLDIGTNSVGWAVITDEYKVPSKKFKVLGNTDRHSIKKNLIGALLFDSGETAEATRLKRTA

RRRYTRRKNRICLAEGTRIFDPVTGTTHRIEDVVDGRKPIHVVAAAKDGTLLARPVVSWFDQGTRDVI

GLRIAGGAIVWATPDHKVLTEYGWRAAGELRKGDRVAGPGGSGNSLALSLTADQMVSALLDAEPPILY

SEYDPTSPFSEASMMGLLTNLADRELVHMINWAKRVPGFVDLTLHDQAHLLERAWLEILMIGLVWRSM

EHPGKLLFAPNLLLDRNQGKCVEGMVEIFDMLLATSSRFRMMNLQGEEFVCLKSIILLNSGVYTFLSS

TLKSLEEKDHIHRALDKITDTLIHLMAKAGLTLQQQHQRLAQLLLILSHIRHMSNKGMEHLYSMKYKN

VVPLYDLLLEMLDAHRLHAGGSGASRVQAFADALDDKFLHDMLAEGLRYSVIREVLPTRRARTFDLEV

EELHTLVAEGVVVHNCYLQEIFSNEMAKVDDSFFHRLEESFLVEEDKKHERHPIFGNIVDEVAYHEKY

PTIYHLRKKLVDSTDKADLRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTPNFKSNFDLAEDAKLQLSK

DTYDDDLDNLLAQIGDQYADLFLAAKNLSDAILLSDILRVNTEITKAPLSASMIKRYDEHHQDLTLLK

ALVRQQLPEKYKEIFFDQSKNGYAGYIDGGASQEEFYKFIKPILEKMDGTEELLVKLNREDLLRKQRT

FDNGSIPHQIHLGELHAILRRQEDFYPFLKDNREKIEKILTFRIPYYVGPLARGNSRFAWMTRKSEET

ITPWNFEEVVDKGASAQSFIERMTNFDKNLPNEKVLPKHSLLYEYFTVYNELTKVKYVTEGMRKPAFL

SGEQKKAIVDLLFKTNRKVTVKQLKEDYFKKIECFDSVEISGVEDRFNASLGTYHDLLKIIKDKDFLD

NEENEDILEDIVLTLTLFEDREMIEERLKTYAHLFDDKVMKQLKRRRYTGWGRLSRKLINGIRDKQSG

KTILDFLKSDGFANRNFMQLIHDDSLTFKEDIQKAQVSGQGDSLHEHIANLAGSPAIKKGILQTVKVV

DELVKVMGRHKPENIVIEMARENQTTQKGQKNSRERMKRIEEGIKELGSQILKEHPVENTQLQNEKLY

LYYLQNGRDMYVDQELDINRLSDYDVDHIVPQSFLKDDSIDNKVLTRSDKNRGKSDNVPSEEVVKKMK

NYWRQLLNAKLITQRKFDNLTKAERGGLSELDKAGFIKRQLVETRQITKHVAQILDSRMNTKYDENDK

LIREVKVITLKSKLVSDFRKDFQFYKVREINNYHHAHDAYLNAVVGTALIKKYPKLESEFVYGDYKVY

DVRKMIAKSEQEIGKATAKYFFYSNIMNFFKTEITLANGEIRKRPLIETNGETGEIVWDKGRDFATVR
```

-continued

KVLSMPQVNIVKKTEVQTGGFSKESILPKRNSDKLIARKKDWDPKKYGGFDSPTVAYSVLVVAKVEKG

KSKKLKSVKELLGITIMERSSFEKNPIDFLEAKGYKEVKKDLIIKLPKYSLFELENGRKRMLASAGEL

QKGNELALPSKYVNFLYLASHYEKLKGSPEDNEQKQLFVEQHKHYLDEIIEQISEFSKRVILADANLD

KVLSAYNKHRDKPIREQAENIIHLFTLTNLGAPAAFKYFDTTIDRKRYTSTKEVLDATLIHQSITGLY

ETRIDLSQLGGD

Cas9:Intein (37R3-2; in double underline) replacing Ala127

(SEQ ID NO: 28)

MDKKYSIGLDIGTNSVGWAVITDEYKVPSKKFKVLGNTDRHSIKKNLIGALLFDSGETAEATRLKRTA

RRRYTRRKNRICYLQEIFSNEMAKVDDSFFHRLEESFLVEEDKKHERHPIFGNIVDEVCLAEGTRIFD

PVTGTTHRIEDVVDGRKPIHVVAAAKDGTLLARPVVSWFDQGTRDVIGLRIAGGAIVWATPDHKVLTE

YGWRAAGELRKGDRVAGPGGSGNSLALSLTADQMVSALLDAEPPILYSEYDPTSPFSEASMMGLLTNL

ADRELVHMINWAKRVPGFVDLTLHDQAHLLERAWLEILMIGLVWRSMEHPGKLLFAPNLLLDRNQGKC

VEGMVEIFDMLLATSSRFRMMNLQGEEFVCLKSIILLNSGVYTFLSSTLKSLEEKDHIHRALDKITDT

LIHLMAKAGLTLQQQHQRLAQLLLILSHIRHMSNKGMEHLYSMKYKNVVPLYDLLLEMLDAHRLHAGG

SGASRVQAFADALDDKFLHDMLAEGLRYSVIREVLPTRRARTFDLEVEELHTLVAEGVVVHNCYHEKY

PTIYHLRKKLVDSTDKADLRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTPNFKSNFDLAEDAKLQLSK

DTYDDDLDNLLAQIGDQYADLFLAAKNLSDAILLSDILRVNTEITKAPLSASMIKRYDEHHQDLTLLK

ALVRQQLPEKYKEIFFDQSKNGYAGYIDGGASQEEFYKFIKPILEKMDGTEELLVKLNREDLLRKQRT

FDNGSIPHQIHLGELHAILRRQEDFYPFLKDNREKIEKILTFRIPYYVGPLARGNSRFAWMTRKSEET

ITPWNFEEVVDKGASAQSFIERMTNFDKNLPNEKVLPKHSLLYEYFTVYNELTKVKYVTEGMRKPAFL

SGEQKKAIVDLLFKTNRKVTVKQLKEDYFKKIECFDSVEISGVEDRFNASLGTYHDLLKIIKDKDFLD

NEENEDILEDIVLTLTLFEDREMIEERLKTYAHLFDDKVMKQLKRRRYTGWGRLSRKLINGIRDKQSG

KTILDFLKSDGFANRNFMQLIHDDSLTFKEDIQKAQVSGQGDSLHEHIANLAGSPAIKKGILQTVKVV

DELVKVMGRHKPENIVIEMARENQTTQKGQKNSRERMKRIEEGIKELGSQILKEHPVENTQLQNEKLY

LYYLQNGRDMYVDQELDINRLSDYDVDHIVPQSFLKDDSIDNKVLTRSDKNRGKSDNVPSEEVVKKMK

NYWRQLLNAKLITQRKFDNLTKAERGGLSELDKAGFIKRQLVETRQITKHVAQILDSRMNTKYDENDK

LIREVKVITLKSKLVSDFRKDFQFYKVREINNYHHAHDAYLNAVVGTALIKKYPKLESEFVYGDYKVY

DVRKMIAKSEQEIGKATAKYFFYSNIMNFFKTEITLANGEIRKRPLIETNGETGEIVWDKGRDFATVR

KVLSMPQVNIVKKTEVQTGGFSKESILPKRNSDKLIARKKDWDPKKYGGFDSPTVAYSVLVVAKVEKG

KSKKLKSVKELLGITIMERSSFEKNPIDFLEAKGYKEVKKDLIIKLPKYSLFELENGRKRMLASAGEL

QKGNELALPSKYVNFLYLASHYEKLKGSPEDNEQKQLFVEQHKHYLDEIIEQISEFSKRVILADANLD

KVLSAYNKHRDKPIREQAENIIHLFTLTNLGAPAAFKYFDTTIDRKRYTSTKEVLDATLIHQSITGLY

ETRIDLSQLGGD

Cas9:Intein (37R3-2; in double underline) replacing Thr146

(SEQ ID NO: 29)

MDKKYSIGLDIGTNSVGWAVITDEYKVPSKKFKVLGNTDRHSIKKNLIGALLFDSGETAEATRLKRTA

RRRYTRRKNRICYLQEIFSNEMAKVDDSFFHRLEESFLVEEDKKHERHPIFGNIVDEVAYHEKYPTIY

HLRKKLVDSCLAEGTRIFDPVTGTTHRIEDVVDGRKPIHVVAAAKDGTLLARPVVSWFDQGTRDVIGL

RIAGGAIVWATPDHKVLTEYGWRAAGELRKGDRVAGPGGSGNSLALSLTADQMVSALLDAEPPILYSE

YDPTSPFSEASMMGLLTNLADRELVHMINWAKRVPGFVDLTLHDQAHLLERAWLEILMIGLVWRSMEH

PGKLLFAPNLLLDRNQGKCVEGMVEIFDMLLATSSRFRMMNLQGEEFVCLKSIILLNSGVYTFLSSTL

-continued

KSLEEKDHIHRALDKITDTLIHLMAKAGLTLQQQHQRLAQLLLILSHIRHMSNKGMEHLYSMKYKNVV
PLYDLLLEMLDAHRLHAGGSGASRVQAFADALDDKFLHDMLAEGLRYSVIREVLPTRRARTFDLEVEE
LHTLVAEGVVVHNCDKADLRLIYLALAHMIKFRGHFLIEGDLNPDNSDVDKLFIQLVQTYNQLFEENP
INASGVDAKAILSARLSKSRRLENLIAQLPGEKKNGLFGNLIALSLGLTPNFKSNFDLAEDAKLQLSK
DTYDDDLDNLLAQIGDQYADLFLAAKNLSDAILLSDILRVNTEITKAPLSASMIKRYDEHHQDLTLLK
ALVRQQLPEKYKEIFFDQSKNGYAGYIDGGASQEEFYKFIKPILEKMDGTEELLVKLNREDLLRKQRT
FDNGSIPHQIHLGELHAILRRQEDFYPFLKDNREKIEKILTFRIPYYVGPLARGNSRFAWMTRKSEET
ITPWNFEEVVDKGASAQSFIERMTNFDKNLPNEKVLPKHSLLYEYFTVYNELTKVKYVTEGMRKPAFL
SGEQKKAIVDLLFKTNRKVTVKQLKEDYFKKIECFDSVEISGVEDRFNASLGTYHDLLKIIKDKDFLD
NEENEDILEDIVLTLTLFEDREMIEERLKTYAHLFDDKVMKQLKRRRYTGWGRLSRKLINGIRDKQSG
KTILDFLKSDGFANRNFMQLIHDDSLTFKEDIQKAQVSGQGDSLHEHIANLAGSPAIKKGILQTVKVV
DELVKVMGRHKPENIVIEMARENQTTQKGQKNSRERMKRIEEGIKELGSQILKEHPVENTQLQNEKLY
LYYLQNGRDMYVDQELDINRLSDYDVDHIVPQSFLKDDSIDNKVLTRSDKNRGKSDNVPSEEVVKKMK
NYWRQLLNAKLITQRKFDNLTKAERGGLSELDKAGFIKRQLVETRQITKHVAQILDSRMNTKYDENDK
LIREVKVITLKSKLVSDFRKDFQFYKVREINNYHHAHDAYLNAVVGTALIKKYPKLESEFVYGDYKVY
DVRKMIAKSEQEIGKATAKYFFYSNIMNFFKTEITLANGEIRKRPLIETNGETGEIVWDKGRDFATVR
KVLSMPQVNIVKKTEVQTGGFSKESILPKRNSDKLIARKKDWDPKKYGGFDSPTVAYSVLVVAKVEKG
KSKKLKSVKELLGITIMERSSFEKNPIDFLEAKGYKEVKKDLIIKLPKYSLFELENGRKRMLASAGEL
QKGNELALPSKYVNFLYLASHYEKLKGSPEDNEQKQLFVEQHKHYLDEIIEQISEFSKRVILADANLD
KVLSAYNKHRDKPIREQAENIIHLFTLTNLGAPAAFKYFDTTIDRKRYTSTKEVLDATLIHQSITGLY
ETRIDLSQLGGD

Cas9:Intein (37R3-2; in double underline) replacing Ser219
(SEQ ID NO: 30)

MDKKYSIGLDIGTNSVGWAVITDEYKVPSKKFKVLGNTDRHSIKKNLIGALLFDSGETAEATRLKRTA
RRRYTRRKNRICYLQEIFSNEMAKVDDSFFHRLEESFLVEEDKKHERHPIFGNIVDEVAYHEKYPTIY
HLRKKLVDSTDKADLRLIYLALAHMIKFRGHFLIEGDLNPDNSDVDKLFIQLVQTYNQLFEENPINAS
GVDAKAILSARLSKCLAEGTRIFDPVTGTTHRIEDVVDGRKPIHVVAAAKDGTLLARPVVSWFDQGTR
DVIGLRIAGGAIVWATPDHKVLTEYGWRAAGELRKGDRVAGPGGSGNSLALSLTADQMVSALLDAEPP
ILYSEYDPTSPFSEASMMGLLTNLADRELVHMINWAKRVPGFVDLTLHDQAHLLERAWLEILMIGLVW
RSMEHPGKLLFAPNLLLDRNQGKCVEGMVEIFDMLLATSSRFRMMNLQGEEFVCLKSIILLNSGVYTF
LSSTLKSLEEKDHIHRALDKITDTLIHLMAKAGLTLQQQHQRLAQLLLILSHIRHMSNKGMEHLYSMK
YKNVVPLYDLLLEMLDAHRLHAGGSGASRVQAFADALDDKFLHDMLAEGLRYSVIREVLPTRRARTFD
LEVEELHTLVAEGVVVHNCRRLENLIAQLPGEKKNGLFGNLIALSLGLTPNFKSNFDLAEDAKLQLSK
DTYDDDLDNLLAQIGDQYADLFLAAKNLSDAILLSDILRVNTEITKAPLSASMIKRYDEHHQDLTLLK
ALVRQQLPEKYKEIFFDQSKNGYAGYIDGGASQEEFYKFIKPILEKMDGTEELLVKLNREDLLRKQRT
FDNGSIPHQIHLGELHAILRRQEDFYPFLKDNREKIEKILTFRIPYYVGPLARGNSRFAWMTRKSEET
ITPWNFEEVVDKGASAQSFIERMTNFDKNLPNEKVLPKHSLLYEYFTVYNELTKVKYVTEGMRKPAFL
SGEQKKAIVDLLFKTNRKVTVKQLKEDYFKKIECFDSVEISGVEDRFNASLGTYHDLLKIIKDKDFLD
NEENEDILEDIVLTLTLFEDREMIEERLKTYAHLFDDKVMKQLKRRRYTGWGRLSRKLINGIRDKQSG
KTILDFLKSDGFANRNFMQLIHDDSLTFKEDIQKAQVSGQGDSLHEHIANLAGSPAIKKGILQTVKVV
DELVKVMGRHKPENIVIEMARENQTTQKGQKNSRERMKRIEEGIKELGSQILKEHPVENTQLQNEKLY
LYYLQNGRDMYVDQELDINRLSDYDVDHIVPQSFLKDDSIDNKVLTRSDKNRGKSDNVPSEEVVKKMK

-continued

NYWRQLLNAKLITQRKFDNLTKAERGGLSELDKAGFIKRQLVETRQITKHVAQILDSRMNTKYDENDK
LIREVKVITLKSKLVSDFRKDFQFYKVREINNYHHAHDAYLNAVVGTALIKKYPKLESEFVYGDYKVY
DVRKMIAKSEQEIGKATAKYFFYSNIMNFFKTEITLANGEIRKRPLIETNGETGEIVWDKGRDFATVR
KVLSMPQVNIVKKTEVQTGGFSKESILPKRNSDKLIARKKDWDPKKYGGFDSPTVAYSVLVVAKVEKG
KSKKLKSVKELLGITIMERSSFEKNPIDFLEAKGYKEVKKDLIIKLPKYSLFELENGRKRMLASAGEL
QKGNELALPSKYVNFLYLASHYEKLKGSPEDNEQKQLFVEQHKHYLDEIIEQISEFSKRVILADANLD
KVLSAYNKHRDKPIREQAENIIHLFTLTNLGAPAAFKYFDTTIDRKRYTSTKEVLDATLIHQSITGLY
ETRIDLSQLGGD

Cas9:Intein (37R3-2; in double underline) replacing Thr333
(SEQ ID NO: 31)

MDKKYSIGLDIGTNSVGWAVITDEYKVPSKKFKVLGNTDRHSIKKNLIGALLFDSGETAEATRLKRTA
RRRYTRRKNRICYLQEIFSNEMAKVDDSFFHRLEESFLVEEDKKHERHPIFGNIVDEVAYHEKYPTIY
HLRKKLVDSTDKADLRLIYLALAHMIKFRGHFLIEGDLNPDNSDVDKLFIQLVQTYNQLFEENPINAS
GVDAKAILSARLSKSRRLENLIAQLPGEKKNGLFGNLIALSLGLTPNFKSNFDLAEDAKLQLSKDTYD
DDLDNLLAQIGDQYADLFLAAKNLSDAILLSDILRVNTEITKAPLSASMIKRYDEHHQDLCLAEGTRI
FDPVTGTTHRIEDVVDGRKPIHVVAAAKDGTLLARPVVSWFDQGTRDVIGLRIAGGAIVWATPDHKVL
TEYGWRAAGELRKGDRVAGPGGSGNSLALSLTADQMVSALLDAEPPILYSEYDPTSPFSEASMMGLLT
NLADRELVHMINWAKRVPGFVDLTLHDQAHLLERAWLEILMIGLVWRSMEHPGKLLFAPNLLLDRNQG
KCVEGMVEIFDMLLATSSRFRMMNLQGEEFVCLKSIILLNSGVYTFLSSTLKSLEEKDHIHRALDKIT
DTLIHLMAKAGLTLQQQHQRLAQLLLILSHIRHMSNKGMEHLYSMKYKNVVPLYDLLLEMLDAHRLHA
GGSGASRVQAFADALDDKFLHDMLAEGLRYSVIREVLPTRRARTFDLEVEELHTLVAEGVVVHNCLLK
ALVRQQLPEKYKEIFFDQSKNGYAGYIDGGASQEEFYKFIKPILEKMDGTEELLVKLNREDLLRKQRT
FDNGSIPHQIHLGELHAILRRQEDFYPFLKDNREKIEKILTFRIPYYVGPLARGNSRFAWMTRKSEET
ITPWNFEEVVDKGASAQSFIERMTNFDKNLPNEKVLPKHSLLYEYFTVYNELTKVKYVTEGMRKPAFL
SGEQKKAIVDLLFKTNRKVTVKQLKEDYFKKIECFDSVEISGVEDRFNASLGTYHDLLKIIKDKDFLD
NEENEDILEDIVLTLTLFEDREMIEERLKTYAHLFDDKVMKQLKRRRYTGWGRLSRKLINGIRDKQSG
KTILDFLKSDGFANRNFMQLIHDDSLTFKEDIQKAQVSGQGDSLHEHIANLAGSPAIKKGILQTVKVV
DELVKVMGRHKPENIVIEMARENQTTQKGQKNSRERMKRIEEGIKELGSQILKEHPVENTQLQNEKLY
LYYLQNGRDMYVDQELDINRLSDYDVDHIVPQSFLKDDSIDNKVLTRSDKNRGKSDNVPSEEVVKKMK
NYWRQLLNAKLITQRKFDNLTKAERGGLSELDKAGFIKRQLVETRQITKHVAQILDSRMNTKYDENDK
LIREVKVITLKSKLVSDFRKDFQFYKVREINNYHHAHDAYLNAVVGTALIKKYPKLESEFVYGDYKVY
DVRKMIAKSEQEIGKATAKYFFYSNIMNFFKTEITLANGEIRKRPLIETNGETGEIVWDKGRDFATVR
KVLSMPQVNIVKKTEVQTGGFSKESILPKRNSDKLIARKKDWDPKKYGGFDSPTVAYSVLVVAKVEKG
KSKKLKSVKELLGITIMERSSFEKNPIDFLEAKGYKEVKKDLIIKLPKYSLFELENGRKRMLASAGEL
QKGNELALPSKYVNFLYLASHYEKLKGSPEDNEQKQLFVEQHKHYLDEIIEQISEFSKRVILADANLD
KVLSAYNKHRDKPIREQAENIIHLFTLTNLGAPAAFKYFDTTIDRKRYTSTKEVLDATLIHQSITGLY
ETRIDLSQLGGD

Cas9:Intein (37R3-2; in double underline) replacing Thr519
(SEQ ID NO: 32)

MDKKYSIGLDIGTNSVGWAVITDEYKVPSKKFKVLGNTDRHSIKKNLIGALLFDSGETAEATRLKRTA
RRRYTRRKNRICYLQEIFSNEMAKVDDSFFHRLEESFLVEEDKKHERHPIFGNIVDEVAYHEKYPTIY
HLRKKLVDSTDKADLRLIYLALAHMIKFRGHFLIEGDLNPDNSDVDKLFIQLVQTYNQLFEENPINAS

-continued

GVDAKAILSARLSKSRRLENLIAQLPGEKKNGLFGNLIALSLGLTPNFKSNFDLAEDAKLQLSKDTYD

DDLDNLLAQIGDQYADLFLAAKNLSDAILLSDILRVNTEITKAPLSASMIKRYDEHHQDLTLLKALVR

QQLPEKYKEIFFDQSKNGYAGYIDGGASQEEFYKFIKPILEKMDGTEELLVKLNREDLLRKQRTFDNG

SIPHQIHLGELHAILRRQEDFYPFLKDNREKIEKILTFRIPYYVGPLARGNSRFAWMTRKSEETITPW

NFEEVVDKGASAQSFIERMTNFDKNLPNEKVLPKHSLLYEYFCLAEGTRIFDPVTGTTHRIEDVVDGR

KPIHVVAAAKDGTLLARPVVSWFDQGTRDVIGLRIAGGAIVWATPDHKVLTEYGWRAAGELRKGDRVA

GPGGSGNSLALSLTADQMVSALLDAEPPILYSEYDPTSPFSEASMMGLLTNLADRELVHMINWAKRVP

GFVDLTLHDQAHLLERAWLEILMIGLVWRSMEHPGKLLFAPNLLLDRNQGKCVEGMVEIFDMLLATSS

RFRMMNLQGEEFVCLKSIILLNSGVYTFLSSTLKSLEEKDHIHRALDKITDTLIHLMAKAGLTLQQQH

QRLAQLLLILSHIRHMSNKGMEHLYSMKYKNVVPLYDLLLEMLDAHRLHAGGSGASRVQAFADALDDK

FLHDMLAEGLRYSVIREVLPTRRARTFDLEVEELHTLVAEGVVVHNCVYNELTKVKYVTEGMRKPAFL

SGEQKKAIVDLLFKTNRKVTVKQLKEDYFKKIECFDSVEISGVEDRFNASLGTYHDLLKIIKDKDFLD

NEENEDILEDIVLTLTLFEDREMIEERLKTYAHLFDDKVMKQLKRRRYTGWGRLSRKLINGIRDKQSG

KTILDFLKSDGFANRNFMQLIHDDSLTFKEDIQKAQVSGQGDSLHEHIANLAGSPAIKKGILQTVKVV

DELVKVMGRHKPENIVIEMARENQTTQKGQKNSRERMKRIEEGIKELGSQILKEHPVENTQLQNEKLY

LYYLQNGRDMYVDQELDINRLSDYDVDHIVPQSFLKDDSIDNKVLTRSDKNRGKSDNVPSEEVVKKMK

NYWRQLLNAKLITQRKFDNLTKAERGGLSELDKAGFIKRQLVETRQITKHVAQILDSRMNTKYDENDK

LIREVKVITLKSKLVSDFRKDFQFYKVREINNYHHAHDAYLNAVVGTALIKKYPKLESEFVYGDYKVY

DVRKMIAKSEQEIGKATAKYFFYSNIMNFFKTEITLANGEIRKRPLIETNGETGEIVWDKGRDFATVR

KVLSMPQVNIVKKTEVQTGGFSKESILPKRNSDKLIARKKDWDPKKYGGFDSPTVAYSVLVVAKVEKG

KSKKLKSVKELLGITIMERSSFEKNPIDFLEAKGYKEVKKDLIIKLPKYSLFELENGRKRMLASAGEL

QKGNELALPSKYVNFLYLASHYEKLKGSPEDNEQKQLFVEQHKHYLDEIIEQISEFSKRVILADANLD

KVLSAYNKHRDKPIREQAENIIHLFTLTNLGAPAAFKYFDTTIDRKRYTSTKEVLDATLIHQSITGLY

ETRIDLSQLGGD

Cas9:Intein (37R3-2; in double underline) replacing Cys574

(SEQ ID NO: 33)

MDKKYSIGLDIGTNSVGWAVITDEYKVPSKKFKVLGNTDRHSIKKNLIGALLFDSGETAEATRLKRTA

RRRYTRRKNRICYLQEIFSNEMAKVDDSFFHRLEESFLVEEDKKHERHPIFGNIVDEVAYHEKYPTIY

HLRKKLVDSTDKADLRLIYLALAHMIKFRGHFLIEGDLNPDNSDVDKLFIQLVQTYNQLFEENPINAS

GVDAKAILSARLSKSRRLENLIAQLPGEKKNGLFGNLIALSLGLTPNFKSNFDLAEDAKLQLSKDTYD

DDLDNLLAQIGDQYADLFLAAKNLSDAILLSDILRVNTEITKAPLSASMIKRYDEHHQDLTLLKALVR

QQLPEKYKEIFFDQSKNGYAGYIDGGASQEEFYKFIKPILEKMDGTEELLVKLNREDLLRKQRTFDNG

SIPHQIHLGELHAILRRQEDFYPFLKDNREKIEKILTFRIPYYVGPLARGNSRFAWMTRKSEETITPW

NFEEVVDKGASAQSFIERMTNFDKNLPNEKVLPKHSLLYEYFTVYNELTKVKYVTEGMRKPAFLSGEQ

KKAIVDLLFKTNRKVTVKQLKEDYFKKIECLAEGTRIFDPVTGTTHRIEDVVDGRKPIHVVAAAKDGT

LLARPVVSWFDQGTRDVIGLRIAGGAIVWATPDHKVLTEYGWRAAGELRKGDRVAGPGGSGNSLALSL

TADQMVSALLDAEPPILYSEYDPTSPFSEASMMGLLTNLADRELVHMINWAKRVPGFVDLTLHDQAHL

LERAWLEILMIGLVWRSMEHPGKLLFAPNLLLDRNQGKCVEGMVEIFDMLLATSSRFRMMNLQGEEFV

CLKSIILLNSGVYTFLSSTLKSLEEKDHIHRALDKITDTLIHLMAKAGLTLQQQHQRLAQLLLILSHI

RHMSNKGMEHLYSMKYKNVVPLYDLLLEMLDAHRLHAGGSGASRVQAFADALDDKFLHDMLAEGLRYS

VIREVLPTRRARTFDLEVEELHTLVAEGVVVHNCFDSVEISGVEDRFNASLGTYHDLLKIIKDKDFLD

NEENEDILEDIVLTLTLFEDREMIEERLKTYAHLFDDKVMKQLKRRRYTGWGRLSRKLINGIRDKQSG

-continued

KTILDFLKSDGFANRNFMQLIHDDSLTFKEDIQKAQVSGQGDSLHEHIANLAGSPAIKKGILQTVKVV

DELVKVMGRHKPENIVIEMARENQTTQKGQKNSRERMKRIEEGIKELGSQILKEHPVENTQLQNEKLY

LYYLQNGRDMYVDQELDINRLSDYDVDHIVPQSFLKDDSIDNKVLTRSDKNRGKSDNVPSEEVVKKMK

NYWRQLLNAKLITQRKFDNLTKAERGGLSELDKAGFIKRQLVETRQITKHVAQILDSRMNTKYDENDK

LIREVKVITLKSKLVSDFRKDFQFYKVREINNYHHAHDAYLNAVVGTALIKKYPKLESEFVYGDYKVY

DVRKMIAKSEQEIGKATAKYFFYSNIMNFFKTEITLANGEIRKRPLIETNGETGEIVWDKGRDFATVR

KVLSMPQVNIVKKTEVQTGGFSKESILPKRNSDKLIARKKDWDPKKYGGFDSPTVAYSVLVVAKVEKG

KSKKLKSVKELLGITIMERSSFEKNPIDFLEAKGYKEVKKDLIIKLPKYSLFELENGRKRMLASAGEL

QKGNELALPSKYVNFLYLASHYEKLKGSPEDNEQKQLFVEQHKHYLDEIIEQISEFSKRVILADANLD

KVLSAYNKHRDKPIREQAENIIHLFTLTNLGAPAAFKYFDTTIDRKRYTSTKEVLDATLIHQSITGLY

ETRIDLSQLGGD

Cas9:Intein (37R3-2; in double underline) replacing Thr622

(SEQ ID NO: 34)

MDKKYSIGLDIGTNSVGWAVITDEYKVPSKKFKVLGNTDRHSIKKNLIGALLFDSGETAEATRLKRTA

RRRYTRRKNRICYLQEIFSNEMAKVDDSFFHRLEESFLVEEDKKHERHPIFGNIVDEVAYHEKYPTIY

HLRKKLVDSTDKADLRLIYLALAHMIKFRGHFLIEGDLNPDNSDVDKLFIQLVQTYNQLFEENPINAS

GVDAKAILSARLSKSRRLENLIAQLPGEKKNGLFGNLIALSLGLTPNFKSNFDLAEDAKLQLSKDTYD

DDLDNLLAQIGDQYADLFLAAKNLSDAILLSDILRVNTEITKAPLSASMIKRYDEHHQDLTLLKALVR

QQLPEKYKEIFFDQSKNGYAGYIDGGASQEEFYKFIKPILEKMDGTEELLVKLNREDLLRKQRTFDNG

SIPHQIHLGELHAILRRQEDFYPFLKDNREKIEKILTFRIPYYVGPLARGNSRFAWMTRKSEETITPW

NFEEVVDKGASAQSFIERMTNFDKNLPNEKVLPKHSLLYEYFTVYNELTKVKYVTEGMRKPAFLSGEQ

KKAIVDLLFKTNRKVTVKQLKEDYFKKIECFDSVEISGVEDRFNASLGTYHDLLKIIKDKDFLDNEEN

EDILEDIVLCLAEGTRIFDPVTGTTHRIEDVVDGRKPIHVVAAAKDGTLLARPVVSWFDQGTRDVIGL

RIAGGAIVWATPDHKVLTEYGWRAAGELRKGDRVAGPGGSGNSLALSLTADQMVSALLDAEPPILYSE

YDPTSPFSEASMMGLLTNLADRELVHMINWAKRVPGFVDLTLHDQAHLLERAWLEILMIGLVWRSMEH

PGKLLFAPNLLLDRNQGKCVEGMVEIFDMLLATSSRFRMMNLQGEEFVCLKSIILLNSGVYTFLSSTL

KSLEEKDHIHRALDKITDTLIHLMAKAGLTLQQQHQRLAQLLLILSHIRHMSNKGMEHLYSMKYKNVV

PLYDLLLEMLDAHRLHAGGSGASRVQAFADALDDKFLHDMLAEGLRYSVIREVLPTRRARTFDLEVEE

LHTLVAEGVVVHNCLTLFEDREMIEERLKTYAHLFDDKVMKQLKRRRYTGWGRLSRKLINGIRDKQSG

KTILDFLKSDGFANRNFMQLIHDDSLTFKEDIQKAQVSGQGDSLHEHIANLAGSPAIKKGILQTVKVV

DELVKVMGRHKPENIVIEMARENQTTQKGQKNSRERMKRIEEGIKELGSQILKEHPVENTQLQNEKLY

LYYLQNGRDMYVDQELDINRLSDYDVDHIVPQSFLKDDSIDNKVLTRSDKNRGKSDNVPSEEVVKKMK

NYWRQLLNAKLITQRKFDNLTKAERGGLSELDKAGFIKRQLVETRQITKHVAQILDSRMNTKYDENDK

LIREVKVITLKSKLVSDFRKDFQFYKVREINNYHHAHDAYLNAVVGTALIKKYPKLESEFVYGDYKVY

DVRKMIAKSEQEIGKATAKYFFYSNIMNFFKTEITLANGEIRKRPLIETNGETGEIVWDKGRDFATVR

KVLSMPQVNIVKKTEVQTGGFSKESILPKRNSDKLIARKKDWDPKKYGGFDSPTVAYSVLVVAKVEKG

KSKKLKSVKELLGITIMERSSFEKNPIDFLEAKGYKEVKKDLIIKLPKYSLFELENGRKRMLASAGEL

QKGNELALPSKYVNFLYLASHYEKLKGSPEDNEQKQLFVEQHKHYLDEIIEQISEFSKRVILADANLD

KVLSAYNKHRDKPIREQAENIIHLFTLTNLGAPAAFKYFDTTIDRKRYTSTKEVLDATLIHQSITGLY

ETRIDLSQLGGD

-continued

Cas9:Intein (37R3-2; in double underline) replacing Ser701

(SEQ ID NO: 35)

MDKKYSIGLDIGTNSVGWAVITDEYKVPSKKFKVLGNTDRHSIKKNLIGALLFDSGETAEATRLKRTA

RRRYTRRKNRICYLQEIFSNEMAKVDDSFFHRLEESFLVEEDKKHERHPIFGNIVDEVAYHEKYPTIY

HLRKKLVDSTDKADLRLIYLALAHMIKFRGHFLIEGDLNPDNSDVDKLFIQLVQTYNQLFEENPINAS

GVDAKAILSARLSKSRRLENLIAQLPGEKKNGLFGNLIALSLGLTPNFKSNFDLAEDAKLQLSKDTYD

DDLDNLLAQIGDQYADLFLAAKNLSDAILLSDILRVNTEITKAPLSASMIKRYDEHHQDLTLLKALVR

QQLPEKYKEIFFDQSKNGYAGYIDGGASQEEFYKFIKPILEKMDGTEELLVKLNREDLLRKQRTFDNG

SIPHQIHLGELHAILRRQEDFYPFLKDNREKIEKILTFRIPYYVGPLARGNSRFAWMTRKSEETITPW

NFEEVVDKGASAQSFIERMTNFDKNLPNEKVLPKHSLLYEYFTVYNELTKVKYVTEGMRKPAFLSGEQ

KKAIVDLLFKTNRKVTVKQLKEDYFKKIECFDSVEISGVEDRFNASLGTYHDLLKIIKDKDFLDNEEN

EDILEDIVLTLTLFEDREMIEERLKTYAHLFDDKVMKQLKRRRYTGWGRLSRKLINGIRDKQSGKTIL

DFLKSDGFANRNFMQLIHDDCLAEGTRIFDPVTGTTHRIEDVVDGRKPIHVVAAAKDGTLLARPVVSW

FDQGTRDVIGLRIAGGAIVWATPDHKVLTEYGWRAAGELRKGDRVAGPGGSGNSLALSLTADQMVSAL

LDAEPPILYSEYDPTSPFSEASMMGLLTNLADRELVHMINWAKRVPGFVDLTLHDQAHLLERAWLEIL

MIGLVWRSMEHPGKLLFAPNLLLDRNQGKCVEGMVEIFDMLLATSSRFRMMNLQGEEFVCLKSIILLN

SGVYTFLSSTLKSLEEKDHIHRALDKITDTLIHLMAKAGLTLQQQHQRLAQLLLILSHIRHMSNKGME

HLYSMKYKNVVPLYDLLLEMLDAHRLHAGGSGASRVQAFADALDDKFLHDMLAEGLRYSVIREVLPTR

RARTFDLEVEELHTLVAEGVVVHNCLTFKEDIQKAQVSGQGDSLHEHIANLAGSPAIKKGILQTVKVV

DELVKVMGRHKPENIVIEMARENQTTQKGQKNSRERMKRIEEGIKELGSQILKEHPVENTQLQNEKLY

LYYLQNGRDMYVDQELDINRLSDYDVDHIVPQSFLKDDSIDNKVLTRSDKNRGKSDNVPSEEVVKKMK

NYWRQLLNAKLITQRKFDNLTKAERGGLSELDKAGFIKRQLVETRQITKHVAQILDSRMNTKYDENDK

LIREVKVITLKSKLVSDFRKDFQFYKVREINNYHHAHDAYLNAVVGTALIKKYPKLESEFVYGDYKVY

DVRKMIAKSEQEIGKATAKYFFYSNIMNFFKTEITLANGEIRKRPLIETNGETGEIVWDKGRDFATVR

KVLSMPQVNIVKKTEVQTGGFSKESILPKRNSDKLIARKKDWDPKKYGGFDSPTVAYSVLVVAKVEKG

KSKKLKSVKELLGITIMERSSFEKNPIDFLEAKGYKEVKKDLIIKLPKYSLFELENGRKRMLASAGEL

QKGNELALPSKYVNFLYLASHYEKLKGSPEDNEQKQLFVEQHKHYLDEIIEQISEFSKRVILADANLD

KVLSAYNKHRDKPIREQAENIIHLFTLTNLGAPAAFKYFDTTIDRKRYTSTKEVLDATLIHQSITGLY

ETRIDLSQLGGD

Cas9:Intein (37R3-2; in double underline) replacing Ala728

(SEQ ID NO: 36)

MDKKYSIGLDIGTNSVGWAVITDEYKVPSKKFKVLGNTDRHSIKKNLIGALLFDSGETAEATRLKRTA

RRRYTRRKNRICYLQEIFSNEMAKVDDSFFHRLEESFLVEEDKKHERHPIFGNIVDEVAYHEKYPTIY

HLRKKLVDSTDKADLRLIYLALAHMIKFRGHFLIEGDLNPDNSDVDKLFIQLVQTYNQLFEENPINAS

GVDAKAILSARLSKSRRLENLIAQLPGEKKNGLFGNLIALSLGLTPNFKSNFDLAEDAKLQLSKDTYD

DDLDNLLAQIGDQYADLFLAAKNLSDAILLSDILRVNTEITKAPLSASMIKRYDEHHQDLTLLKALVR

QQLPEKYKEIFFDQSKNGYAGYIDGGASQEEFYKFIKPILEKMDGTEELLVKLNREDLLRKQRTFDNG

SIPHQIHLGELHAILRRQEDFYPFLKDNREKIEKILTFRIPYYVGPLARGNSRFAWMTRKSEETITPW

NFEEVVDKGASAQSFIERMTNFDKNLPNEKVLPKHSLLYEYFTVYNELTKVKYVTEGMRKPAFLSGEQ

KKAIVDLLFKTNRKVTVKQLKEDYFKKIECFDSVEISGVEDRFNASLGTYHDLLKIIKDKDFLDNEEN

EDILEDIVLTLTLFEDREMIEERLKTYAHLFDDKVMKQLKRRRYTGWGRLSRKLINGIRDKQSGKTIL

DFLKSDGFANRNFMQLIHDDSLTFKEDIQKAQVSGQGDSLHEHIANLCLAEGTRIFDPVTGTTHRIED

-continued

VVDGRKPIHVVAAAKDGTLLARPVVSWFDQGTRDVIGLRIAGGAIVWATPDHKVLTEYGWRAAGELRK

GDRVAGPGGSGNSLALSLTADQMVSALLDAEPPILYSEYDPTSPFSEASMMGLLTNLADRELVHMINW

AKRVPGFVDLTLHDQAHLLERAWLEILMIGLVWRSMEHPGKLLFAPNLLLDRNQGKCVEGMVEIFDML

LATSSRFRMMNLQGEEFVCLKSIILLNSGVYTFLSSTLKSLEEKDHIHRALDKITDTLIHLMAKAGLT

LQQQHQRLAQLLLILSHIRHMSNKGMEHLYSMKYKNVVPLYDLLLEMLDAHRLHAGGSGASRVQAFAD

ALDDKFLHDMLAEGLRYSVIREVLPTRRARTFDLEVEELHTLVAEGVVVHNCGSPAIKKGILQTVKVV

DELVKVMGRHKPENIVIEMARENQTTQKGQKNSRERMKRIEEGIKELGSQILKEHPVENTQLQNEKLY

LYYLQNGRDMYVDQELDINRLSDYDVDHIVPQSFLKDDSIDNKVLTRSDKNRGKSDNVPSEEVVKKMK

NYWRQLLNAKLITQRKFDNLTKAERGGLSELDKAGFIKRQLVETRQITKHVAQILDSRMNTKYDENDK

LIREVKVITLKSKLVSDFRKDFQFYKVREINNYHHAHDAYLNAVVGTALIKKYPKLESEFVYGDYKVY

DVRKMIAKSEQEIGKATAKYFFYSNIMNFFKTEITLANGEIRKRPLIETNGETGEIVWDKGRDFATVR

KVLSMPQVNIVKKTEVQTGGFSKESILPKRNSDKLIARKKDWDPKKYGGFDSPTVAYSVLVVAKVEKG

KSKKLKSVKELLGITIMERSSFEKNPIDFLEAKGYKEVKKDLIIKLPKYSLFELENGRKRMLASAGEL

QKGNELALPSKYVNFLYLASHYEKLKGSPEDNEQKQLFVEQHKHYLDEIIEQISEFSKRVILADANLD

KVLSAYNKHRDKPIREQAENIIHLFTLTNLGAPAAFKYFDTTIDRKRYTSTKEVLDATLIHQSITGLY

ETRIDLSQLGGD

Cas9:Intein (37R3-2; in double underline) replacing Thr995

(SEQ ID NO: 37)

MDKKYSIGLDIGTNSVGWAVITDEYKVPSKKFKVLGNTDRHSIKKNLIGALLFDSGETAEATRLKRTA

RRRYTRRKNRICYLQEIFSNEMAKVDDSFFHRLEESFLVEEDKKHERHPIFGNIVDEVAYHEKYPTIY

HLRKKLVDSTDKADLRLIYLALAHMIKFRGHFLIEGDLNPDNSDVDKLFIQLVQTYNQLFEENPINAS

GVDAKAILSARLSKSRRLENLIAQLPGEKKNGLFGNLIALSLGLTPNFKSNFDLAEDAKLQLSKDTYD

DDLDNLLAQIGDQYADLFLAAKNLSDAILLSDILRVNTEITKAPLSASMIKRYDEHHQDLTLLKALVR

QQLPEKYKEIFFDQSKNGYAGYIDGGASQEEFYKFIKPILEKMDGTEELLVKLNREDLLRKQRTFDNG

SIPHQIHLGELHAILRRQEDFYPFLKDNREKIEKILTFRIPYYVGPLARGNSRFAWMTRKSEETITPW

NFEEVVDKGASAQSFIERMTNFDKNLPNEKVLPKHSLLYEYFTVYNELTKVKYVTEGMRKPAFLSGEQ

KKAIVDLLFKTNRKVTVKQLKEDYFKKIECFDSVEISGVEDRFNASLGTYHDLLKIIKDKDFLDNEEN

EDILEDIVLTLTLFEDREMIEERLKTYAHLFDDKVMKQLKRRRYTGWGRLSRKLINGIRDKQSGKTIL

DFLKSDGFANRNFMQLIHDDSLTFKEDIQKAQVSGQGDSLHEHIANLAGSPAIKKGILQTVKVVDELV

KVMGRHKPENIVIEMARENQTTQKGQKNSRERMKRIEEGIKELGSQILKEHPVENTQLQNEKLYLYYL

QNGRDMYVDQELDINRLSDYDVDHIVPQSFLKDDSIDNKVLTRSDKNRGKSDNVPSEEVVKKMKNYWR

QLLNAKLITQRKFDNLTKAERGGLSELDKAGFIKRQLVETRQITKHVAQILDSRMNTKYDENDKLIRE

VKVITLKSKLVSDFRKDFQFYKVREINNYHHAHDAYLNAVVGCLAEGTRIFDPVTGTTHRIEDVVDGR

KPIHVVAAAKDGTLLARPVVSWFDQGTRDVIGLRIAGGAIVWATPDHKVLTEYGWRAAGELRKGDRVA

GPGGSGNSLALSLTADQMVSALLDAEPPILYSEYDPTSPFSEASMMGLLTNLADRELVHMINWAKRVP

GFVDLTLHDQAHLLERAWLEILMIGLVWRSMEHPGKLLFAPNLLLDRNQGKCVEGMVEIFDMLLATSS

RFRMMNLQGEEFVCLKSIILLNSGVYTFLSSTLKSLEEKDHIHRALDKITDTLIHLMAKAGLTLQQQH

QRLAQLLLILSHIRHMSNKGMEHLYSMKYKNVVPLYDLLLEMLDAHRLHAGGSGASRVQAFADALDDK

FLHDMLAEGLRYSVIREVLPTRRARTFDLEVEELHTLVAEGVVVHNCALIKKYPKLESEFVYGDYKVY

DVRKMIAKSEQEIGKATAKYFFYSNIMNFFKTEITLANGEIRKRPLIETNGETGEIVWDKGRDFATVR

KVLSMPQVNIVKKTEVQTGGFSKESILPKRNSDKLIARKKDWDPKKYGGFDSPTVAYSVLVVAKVEKG

KSKKLKSVKELLGITIMERSSFEKNPIDFLEAKGYKEVKKDLIIKLPKYSLFELENGRKRMLASAGEL

-continued

QKGNELALPSKYVNFLYLASHYEKLKGSPEDNEQKQLFVEQHKHYLDEIIEQISEFSKRVILADANLD

KVLSAYNKHRDKPIREQAENIIHLFTLTNLGAPAAFKYFDTTIDRKRYTSTKEVLDATLIHQSITGLY

ETRIDLSQLGGD

Cas9:Intein (37R3-2; in double underline) replacing Ser1006
(SEQ ID NO: 38)

MDKKYSIGLDIGTNSVGWAVITDEYKVPSKKFKVLGNTDRHSIKKNLIGALLFDSGETAEATRLKRTA

RRRYTRRKNRICYLQEIFSNEMAKVDDSFFHRLEESFLVEEDKKHERHPIFGNIVDEVAYHEKYPTIY

HLRKKLVDSTDKADLRLIYLALAHMIKFRGHFLIEGDLNPDNSDVDKLFIQLVQTYNQLFEENPINAS

GVDAKAILSARLSKSRRLENLIAQLPGEKKNGLFGNLIALSLGLTPNFKSNFDLAEDAKLQLSKDTYD

DDLDNLLAQIGDQYADLFLAAKNLSDAILLSDILRVNTEITKAPLSASMIKRYDEHHQDLTLLKALVR

QQLPEKYKEIFFDQSKNGYAGYIDGGASQEEFYKFIKPILEKMDGTEELLVKLNREDLLRKQRTFDNG

SIPHQIHLGELHAILRRQEDFYPFLKDNREKIEKILTFRIPYYVGPLARGNSRFAWMTRKSEETITPW

NFEEVVDKGASAQSFIERMTNFDKNLPNEKVLPKHSLLYEYFTVYNELTKVKYVTEGMRKPAFLSGEQ

KKAIVDLLFKTNRKVTVKQLKEDYFKKIECFDSVEISGVEDRFNASLGTYHDLLKIIKDKDFLDNEEN

EDILEDIVLTLTLFEDREMIEERLKTYAHLFDDKVMKQLKRRRYTGWGRLSRKLINGIRDKQSGKTIL

DFLKSDGFANRNFMQLIHDDSLTFKEDIQKAQVSGQGDSLHEHIANLAGSPAIKKGILQTVKVVDELV

KVMGRHKPENIVIEMARENQTTQKGQKNSRERMKRIEEGIKELGSQILKEHPVENTQLQNEKLYLYYL

QNGRDMYVDQELDINRLSDYDVDHIVPQSFLKDDSIDNKVLTRSDKNRGKSDNVPSEEVVKKMKNYWR

QLLNAKLITQRKFDNLTKAERGGLSELDKAGFIKRQLVETRQITKHVAQILDSRMNTKYDENDKLIRE

VKVITLKSKLVSDFRKDFQFYKVREINNYHHAHDAYLNAVVGTALIKKYPKLECLAEGTRIFDPVTGT

THRIEDVVDGRKPIHVVAAAKDGTLLARPVVSWFDQGTRDVIGLRIAGGAIVWATPDHKVLTEYGWRA

AGELRKGDRVAGPGGSGNSLALSLTADQMVSALLDAEPPILYSEYDPTSPFSEASMMGLLTNLADREL

VHMINWAKRVPGFVDLTLHDQAHLLERAWLEILMIGLVWRSMEHPGKLLFAPNLLLDRNQGKCVEGMV

EIFDMLLATSSRFRMMNLQGEEFVCLKSIILLNSGVYTFLSSTLKSLEEKDHIHRALDKITDTLIHLM

AKAGLTLQQQHQRLAQLLLILSHIRHMSNKGMEHLYSMKYKNVVPLYDLLLEMLDAHRLHAGGSGASR

VQAFADALDDKFLHDMLAEGLRYSVIREVLPTRRARTFDLEVEELHTLVAEGVVVHNCEFVYGDYKVY

DVRKMIAKSEQEIGKATAKYFFYSNIMNFFKTEITLANGEIRKRPLIETNGETGEIVWDKGRDFATVR

KVLSMPQVNIVKKTEVQTGGFSKESILPKRNSDKLIARKKDWDPKKYGGFDSPTVAYSVLVVAKVEKG

KSKKLKSVKELLGITIMERSSFEKNPIDFLEAKGYKEVKKDLIIKLPKYSLFELENGRKRMLASAGEL

QKGNELALPSKYVNFLYLASHYEKLKGSPEDNEQKQLFVEQHKHYLDEIIEQISEFSKRVILADANLD

KVLSAYNKHRDKPIREQAENIIHLFTLTNLGAPAAFKYFDTTIDRKRYTSTKEVLDATLIHQSITGLY

ETRIDLSQLGGD

Cas9:Intein (37R3-2; in double underline) replacing Ser1154
(SEQ ID NO: 39)

MDKKYSIGLDIGTNSVGWAVITDEYKVPSKKFKVLGNTDRHSIKKNLIGALLFDSGETAEATRLKRTA

RRRYTRRKNRICYLQEIFSNEMAKVDDSFFHRLEESFLVEEDKKHERHPIFGNIVDEVAYHEKYPTIY

HLRKKLVDSTDKADLRLIYLALAHMIKFRGHFLIEGDLNPDNSDVDKLFIQLVQTYNQLFEENPINAS

GVDAKAILSARLSKSRRLENLIAQLPGEKKNGLFGNLIALSLGLTPNFKSNFDLAEDAKLQLSKDTYD

DDLDNLLAQIGDQYADLFLAAKNLSDAILLSDILRVNTEITKAPLSASMIKRYDEHHQDLTLLKALVR

QQLPEKYKEIFFDQSKNGYAGYIDGGASQEEFYKFIKPILEKMDGTEELLVKLNREDLLRKQRTFDNG

SIPHQIHLGELHAILRRQEDFYPFLKDNREKIEKILTFRIPYYVGPLARGNSRFAWMTRKSEETITPW

NFEEVVDKGASAQSFIERMTNFDKNLPNEKVLPKHSLLYEYFTVYNELTKVKYVTEGMRKPAFLSGEQ

-continued

KKAIVDLLFKTNRKVTVKQLKEDYFKKIECFDSVEISGVEDRFNASLGTYHDLLKIIKDKDFLDNEEN
EDILEDIVLTLTLFEDREMIEERLKTYAHLFDDKVMKQLKRRRYTGWGRLSRKLINGIRDKQSGKTIL
DFLKSDGFANRNFMQLIHDDSLTFKEDIQKAQVSGQGDSLHEHIANLAGSPAIKKGILQTVKVVDELV
KVMGRHKPENIVIEMARENQTTQKGQKNSRERMKRIEEGIKELGSQILKEHPVENTQLQNEKLYLYYL
QNGRDMYVDQELDINRLSDYDVDHIVPQSFLKDDSIDNKVLTRSDKNRGKSDNVPSEEVVKKMKNYWR
QLLNAKLITQRKFDNLTKAERGGLSELDKAGFIKRQLVETRQITKHVAQILDSRMNTKYDENDKLIRE
VKVITLKSKLVSDFRKDFQFYKVREINNYHHAHDAYLNAVVGTALIKKYPKLESEFVYGDYKVYDVRK
MIAKSEQEIGKATAKYFFYSNIMNFFKTEITLANGEIRKRPLIETNGETGEIVWDKGRDFATVRKVLS
MPQVNIVKKTEVQTGGFSKESILPKRNSDKLIARKKDWDPKKYGGFDSPTVAYSVLVVAKVEKGKCLA
EGTRIFDPVTGTTHRIEDVVDGRKPIHVVAAAKDGTLLARPVVSWFDQGTRDVIGLRIAGGAIVWATP
DHKVLTEYGWRAAGELRKGDRVAGPGGSGNSLALSLTADQMVSALLDAEPPILYSEYDPTSPFSEASM
MGLLTNLADRELVHMINWAKRVPGFVDLTLHDQAHLLERAWLEILMIGLVWRSMEHPGKLLFAPNLLL
DRNQGKCVEGMVEIFDMLLATSSRFRMMNLQGEEFVCLKSIILLNSGVYTFLSSTLKSLEEKDHIHRA
LDKITDTLIHLMAKAGLTLQQQHQRLAQLLLILSHIRHMSNKGMEHLYSMKYKNVVPLYDLLLEMLDA
HRLHAGGSGASRVQAFADALDDKFLHDMLAEGLRYSVIREVLPTRRARTFDLEVEELHTLVAEGVVVH
NCKKLKSVKELLGITIMERSSFEKNPIDFLEAKGYKEVKKDLIIKLPKYSLFELENGRKRMLASAGEL
QKGNELALPSKYVNFLYLASHYEKLKGSPEDNEQKQLFVEQHKHYLDEIIEQISEFSKRVILADANLD
KVLSAYNKHRDKPIREQAENIIHLFTLTNLGAPAAFKYFDTTIDRKRYTSTKEVLDATLIHQSITGLY
ETRIDLSQLGGD

Cas9:Intein (37R3-2; in double underline) replacing Ser1159

(SEQ ID NO: 40)

MDKKYSIGLDIGTNSVGWAVITDEYKVPSKKFKVLGNTDRHSIKKNLIGALLFDSGETAEATRLKRTA
RRRYTRRKNRICYLQEIFSNEMAKVDDSFFHRLEESFLVEEDKKHERHPIFGNIVDEVAYHEKYPTIY
HLRKKLVDSTDKADLRLIYLALAHMIKFRGHFLIEGDLNPDNSDVDKLFIQLVQTYNQLFEENPINAS
GVDAKAILSARLSKSRRLENLIAQLPGEKKNGLFGNLIALSLGLTPNFKSNFDLAEDAKLQLSKDTYD
DDLDNLLAQIGDQYADLFLAAKNLSDAILLSDILRVNTEITKAPLSASMIKRYDEHHQDLTLLKALVR
QQLPEKYKEIFFDQSKNGYAGYIDGGASQEEFYKFIKPILEKMDGTEELLVKLNREDLLRKQRTFDNG
SIPHQIHLGELHAILRRQEDFYPFLKDNREKIEKILTFRIPYYVGPLARGNSRFAWMTRKSEETITPW
NFEEVVDKGASAQSFIERMTNFDKNLPNEKVLPKHSLLYEYFTVYNELTKVKYVTEGMRKPAFLSGEQ
KKAIVDLLFKTNRKVTVKQLKEDYFKKIECFDSVEISGVEDRFNASLGTYHDLLKIIKDKDFLDNEEN
EDILEDIVLTLTLFEDREMIEERLKTYAHLFDDKVMKQLKRRRYTGWGRLSRKLINGIRDKQSGKTIL
DFLKSDGFANRNFMQLIHDDSLTFKEDIQKAQVSGQGDSLHEHIANLAGSPAIKKGILQTVKVVDELV
KVMGRHKPENIVIEMARENQTTQKGQKNSRERMKRIEEGIKELGSQILKEHPVENTQLQNEKLYLYYL
QNGRDMYVDQELDINRLSDYDVDHIVPQSFLKDDSIDNKVLTRSDKNRGKSDNVPSEEVVKKMKNYWR
QLLNAKLITQRKFDNLTKAERGGLSELDKAGFIKRQLVETRQITKHVAQILDSRMNTKYDENDKLIRE
VKVITLKSKLVSDFRKDFQFYKVREINNYHHAHDAYLNAVVGTALIKKYPKLESEFVYGDYKVYDVRK
MIAKSEQEIGKATAKYFFYSNIMNFFKTEITLANGEIRKRPLIETNGETGEIVWDKGRDFATVRKVLS
MPQVNIVKKTEVQTGGFSKESILPKRNSDKLIARKKDWDPKKYGGFDSPTVAYSVLVVAKVEKGKSKK
LKCLAEGTRIFDPVTGTTHRIEDVVDGRKPIHVVAAAKDGTLLARPVVSWFDQGTRDVIGLRIAGGAI
VWATPDHKVLTEYGWRAAGELRKGDRVAGPGGSGNSLALSLTADQMVSALLDAEPPILYSEYDPTSPF
SEASMMGLLTNLADRELVHMINWAKRVPGFVDLTLHDQAHLLERAWLEILMIGLVWRSMEHPGKLLFA
PNLLLDRNQGKCVEGMVEIFDMLLATSSRFRMMNLQGEEFVCLKSIILLNSGVYTFLSSTLKSLEEKD

-continued

HIHRALDKITDTLIHLMAKAGLTLQQQHQRLAQLLLILSHIRHMSNKGMEHLYSMKYKNVVPLYDLLL

EMLDAHRLHAGGSGASRVQAFADALDDKFLHDMLAEGLRYSVIREVLPTRRARTFDLEVEELHTLVAE

GVVVHNCVKELLGITIMERSSFEKNPIDFLEAKGYKEVKKDLIIKLPKYSLFELENGRKRMLASAGEL

QKGNELALPSKYVNFLYLASHYEKLKGSPEDNEQKQLFVEQHKHYLDEIIEQISEFSKRVILADANLD

KVLSAYNKHRDKPIREQAENIIHLFTLTNLGAPAAFKYFDTTIDRKRYTSTKEVLDATLIHQSITGLY

ETRIDLSQLGGD

Cas9:Intein (37R3-2; in double underline) replacing Ser1274

(SEQ ID NO: 41)

MDKKYSIGLDIGTNSVGWAVITDEYKVPSKKFKVLGNTDRHSIKKNLIGALLFDSGETAEATRLKRTA

RRRYTRRKNRICYLQEIFSNEMAKVDDSFFHRLEESFLVEEDKKHERHPIFGNIVDEVAYHEKYPTIY

HLRKKLVDSTDKADLRLIYLALAHMIKFRGHFLIEGDLNPDNSDVDKLFIQLVQTYNQLFEENPINAS

GVDAKAILSARLSKSRRLENLIAQLPGEKKNGLFGNLIALSLGLTPNFKSNFDLAEDAKLQLSKDTYD

DDLDNLLAQIGDQYADLFLAAKNLSDAILLSDILRVNTEITKAPLSASMIKRYDEHHQDLTLLKALVR

QQLPEKYKEIFFDQSKNGYAGYIDGGASQEEFYKFIKPILEKMDGTEELLVKLNREDLLRKQRTFDNG

SIPHQIHLGELHAILRRQEDFYPFLKDNREKIEKILTFRIPYYVGPLARGNSRFAWMTRKSEETITPW

NFEEVVDKGASAQSFIERMTNFDKNLPNEKVLPKHSLLYEYFTVYNELTKVKYVTEGMRKPAFLSGEQ

KKAIVDLLFKTNRKVTVKQLKEDYFKKIECFDSVEISGVEDRFNASLGTYHDLLKIIKDKDFLDNEEN

EDILEDIVLTLTLFEDREMIEERLKTYAHLFDDKVMKQLKRRRYTGWGRLSRKLINGIRDKQSGKTIL

DFLKSDGFANRNFMQLIHDDSLTFKEDIQKAQVSGQGDSLHEHIANLAGSPAIKKGILQTVKVVDELV

KVMGRHKPENIVIEMARENQTTQKGQKNSRERMKRIEEGIKELGSQILKEHPVENTQLQNEKLYLYYL

QNGRDMYVDQELDINRLSDYDVDHIVPQSFLKDDSIDNKVLTRSDKNRGKSDNVPSEEVVKKMKNYWR

QLLNAKLITQRKFDNLTKAERGGLSELDKAGFIKRQLVETRQITKHVAQILDSRMNTKYDENDKLIRE

VKVITLKSKLVSDFRKDFQFYKVREINNYHHAHDAYLNAVVGTALIKKYPKLESEFVYGDYKVYDVRK

MIAKSEQEIGKATAKYFFYSNIMNFFKTEITLANGEIRKRPLIETNGETGEIVWDKGRDFATVRKVLS

MPQVNIVKKTEVQTGGFSKESILPKRNSDKLIARKKDWDPKKYGGFDSPTVAYSVLVVAKVEKGKSKK

LKSVKELLGITIMERSSFEKNPIDFLEAKGYKEVKKDLIIKLPKYSLFELENGRKRMLASAGELQKGN

ELALPSKYVNFLYLASHYEKLKGSPEDNEQKQLFVEQHKHYLDEIIEQICLAEGTRIFDPVTGTTHRI

EDVVDGRKPIHVVAAAKDGTLLARPVVSWFDQGTRDVIGLRIAGGAIVWATPDHKVLTEYGWRAAGEL

RKGDRVAGPGGSGNSLALSLTADQMVSALLDAEPPILYSEYDPTSPFSEASMMGLLTNLADRELVHMI

NWAKRVPGFVDLTLHDQAHLLERAWLEILMIGLVWRSMEHPGKLLFAPNLLLDRNQGKCVEGMVEIFD

MLLATSSRFRMMNLQGEEFVCLKSIILLNSGVYTFLSSTLKSLEEKDHIHRALDKITDTLIHLMAKAG

LTLQQQHQRLAQLLLILSHIRHMSNKGMEHLYSMKYKNVVPLYDLLLEMLDAHRLHAGGSGASRVQAF

ADALDDKFLHDMLAEGLRYSVIREVLPTRRARTFDLEVEELHTLVAEGVVVHNCEFSKRVILADANLD

KVLSAYNKHRDKPIREQAENIIHLFTLTNLGAPAAFKYFDTTIDRKRYTSTKEVLDATLIHQSITGLY

ETRIDLSQLGGD

In some embodiments, the intein inserted into the Cas9 protein is ligand-dependent. In some embodiments, the ligand-dependent inteins comprise a modified ligand-binding domain of the estrogen receptor protein, embedded into a modified RecA intein from *M. tuberculosis*. In some embodiments, the ligand-binding domain is derived from an estrogen receptor protein, for example, from the human estrogen receptor. The sequence of the human estrogen receptor and the location of the ligand-binding domain within the human estrogen receptor are known to those of skill in the art. Non-limiting, exemplary sequences of the human estrogen receptor can be retrieved from RefSeq database entries NP_000116 (isoform 1); NP_001116212 (isoform 2); NP_001116213 (isoform 3); and NP_001116214 (isoform 4) from the National Center for Biotechnology Information (NCBI, ncbi.nlm.nih.gov). In some embodiments, the ligand-binding domain of a ligand-dependent intein provided herein comprises or is derived from a sequence comprising amino acid residues 304-551 of the human estrogen receptor.

It will be appreciated by those of skill in the art that other ligand-dependent inteins are also suitable and useful in connection with the Cas9 proteins and methods provided herein. For example, some aspects of this invention provide Cas9 proteins comprising ligand-dependent inteins that comprise a ligand-binding domain of a hormone-binding protein, e.g., of an androgen receptor, an estrogen receptor, an ecdysone receptor, a glucocorticoid receptor, a mineralocorticoid receptor, a progesterone receptor, a retinoic acid receptor, or a thyroid hormone receptor protein. Ligand-binding domains of hormone-binding receptors, inducible fusion proteins comprising such ligand-binding domains, and methods for the generation of such fusion proteins are known to those of skill in the art (see, e.g., Becker, D., Hollenberg, S., and Ricciardi, R. (1989). Fusion of adenovirus E1A to the glucocorticoid receptor by high-resolution deletion cloning creates a hormonally inducible viral transactivator. Mol. Cell. Biol. 9, 3878-3887; Boehmelt, G., Walker, A., Kabrun, N., Mellitzer, G., Beug, H., Zenke, M., and Enrietto, P. J. (1992). Hormone-regulated v-rel estrogen receptor fusion protein: reversible induction of cell transformation and cellular gene expression. EMBO J 11, 4641-4652; Braselmann, S., Graninger, P., and Busslinger, M. (1993). A selective transcriptional induction system for mammalian cells based on Gal4-estrogen receptor fusion proteins. Proc Natl Acad Sci USA 90, 1657-1661; Furga G, Busslinger M (1992). Identification of Fos target genes by the use of selective induction systems. J. Cell Sci. Suppl 16, 97-109; Christopherson, K. S., Mark, M. R., Bajaj, V., and Godowski, P. J. (1992). Ecdysteroid-dependent regulation of genes in mammalian cells by a Drosophila ecdysone receptor and chimeric transactivators. Proc Natl Acad Sci USA 89, 6314-8; Eilers, M., Picard, D., Yamamoto, K., and Bishop, J. (1989). Chimaeras of Myc oncoprotein and steriod receptors cause hormone-dependent transformation of cells. Nature 340, 66-68; Fankhauser, C. P., Briand, P. A., and Picard, D. (1994). The hormone binding domain of the mineralocorticoid receptor can regulate heterologous activities in cis. Biochem Biophys Res Commun 200, 195-201; Godowski, P. J., Picard, D., and Yamamoto, K. R. (1988). Signal transduction and transcriptional regulation by glucocorticoid receptor-LexA fusion proteins. Science 241, 812-816; Kellendonk, C., Tronche, F., Monaghan, A., Angrand, P., Stewart, F., and Schütz, G. (1996). Regulation of Cre recombinase activity by the synthetic steroid RU486. Nuc. Acids Res. 24, 1404-1411; Lee, J. W., Moore, D. D., and Heyman, R. A. (1994). A chimeric thyroid hormone receptor constitutively bound to DNA requires retinoid X receptor for hormone-dependent transcriptional activation in yeast. Mol Endocrinol 8, 1245-1252; No, D., Yao, T. P., and Evans, R. M. (1996). Ecdysone-inducible gene expression in mammalian cells and transgenic mice. Proc Natl Acad Sci USA 93, 3346-3351; and Smith, D., Mason, C., Jones, E., and Old, R. (1994). Expression of a dominant negative retinoic acid receptor g in *Xenopus* embryos leads to partial resistance to retinoic acid. Roux's Arch. Dev. Biol. 203, 254-265; all of which are incorporated herein by reference in their entirety). Additional ligand-binding domains useful for the generation of ligand-dependent inteins as provided herein will be apparent to those of skill in the art, and the invention is not limited in this respect.

Additional exemplary inteins, ligand-binding domains, and ligands suitable for use in the Cas9 proteins provided herein are described in International Patent Application, PCT/US2012/028435, entitled "Small Molecule-Dependent Inteins and Uses Thereof," filed Mar. 9, 2012, and published as WO 2012/125445 on Sep. 20, 2012, the entire contents of which are incorporated herein by reference. Additional suitable inteins, ligand-binding domains, and ligands will be apparent to the skilled artisan based on this disclosure.

The ligand-dependent inteins provided herein are inactive (or only minimally active) in the absence of the appropriate ligand, but can be induced to be active, and, thus, to self-excise, by contacting them with a ligand that binds the ligand-binding domain of the human estrogen receptor. Small molecule ligands binding the ligand-binding domain of the estrogen receptor (e.g., the human estrogen receptor), and thus useful to induce the activity of the ligand-dependent inteins described herein, are known to those of skill in the art. In some embodiments, the ligand used to induce the activity of the ligand-dependent inteins described herein specifically binds to the ligand-binding domain of the estrogen receptor. In some embodiments, the ligand binds the ligand-binding domain of a ligand-dependent intein provided herein with high affinity, for example, with an affinity of at least about $10^{-10}$ M, at least about $10^{-9}$ M, at least about $10^{-8}$ M, at least about $10^{-7}$ M, at least about $10^{-6}$ M, or at least about $10^{-5}$ M. Examples of appropriate estrogen receptor-binding ligands that are useful to induce the activity of the ligand-dependent inteins provided herein, for example, the ligand-dependent inteins provided in SEQ ID NOs 3-8, include, but are not limited to, 17β-estradiol, 17α-ethynyl estradiol, tamoxifen and tamoxifen analogs (e.g., 4-hydroxytamoxifen (4-HT, 4-OHT), 3-hydroxytamoxifen (droloxifene)), tamoxifen metabolites (e.g., hydroxytamoxifen, endoxifen), raloxifene, toremifene, ICI-182, and ICI-780. Other useful ligands will be apparent to those of skill in the art, and the invention is not limited in this respect.

In some embodiments, any of the Cas9 proteins comprising inteins (e.g., SEQ ID NOs:27-41) can be modified so as to generate a Cas9 nickase comprising an intein (e.g., by making one of a D10A or H840A mutation relative to the Cas9 sequence lacking an intein), or to generate a dCas9 protein comprising an intein (e.g., by making both D10A and H840A mutations relative to the Cas9 sequence lacking an intein). In some embodiments, any of the Cas9 proteins comprising inteins (e.g., SEQ ID NOs:27-41) have additional features, for example, one or more linker sequences, localization sequences, such as nuclear localization sequences (NLS; e.g., MAPKKKRKVGIHRGVP (SEQ ID NO:42)); cytoplasmic localization sequences; export sequences, such as nuclear export sequences; or other localization sequences, as well as sequence tags that are useful for solubilization, purification, or detection of the fusion proteins. Suitable localization signal sequences and sequences of protein tags are provided herein and are known in the art, and include, but are not limited to, biotin carboxylase carrier protein (BCCP) tags, myc-tags, calmodulin-tags, FLAG-tags (e.g., 3×FLAG TAG: MDYKDHDGDYKDHDIDYKDDDDK (SEQ ID NO:43)), hemagglutinin (HA) tags, polyhistidine tags, also referred to as histidine tags or His-tags, maltose binding protein (MBP)-tags, nus-tags, glutathione-S-transferase (GST) tags, green fluorescent protein (GFP) tags, thioredoxin-tags, S-tags, Softags (e.g., Softag 1, Softag 3), strep-tags, biotin ligase tags, FlAsH tags, V5 tags, and SBP-tags. Additional suitable sequences will be apparent to those of skill in the art.

In some embodiments, ligand-dependent site-specific enzymes (e.g., fusion proteins) are provided which comprise a Cas9 variant (e.g., dCas9), a ligand-dependent intein, and one or more other polypeptide domains having a particular enzymatic activity. In some embodiments, the fusion protein comprises a nuclease inactivated Cas9 domain (e.g., dCas9), wherein the dCas9 domain comprises an intein sequence inserted in place of or in addition to any amino acid in dCas9. In some embodiments the inserted intein sequence replaces Cys80, Ala127, Thr146, Ser219, Thr333, Thr519, Cys574, Thr622, Ser701, Ala728, Thr995, Ser1006, Ser1154, Ser1159, or Ser1274 of dCas9 (SEQ ID NO:5). In some embodiments, the inserted intein sequence replaces Ala127, Thr146, Ser219, Thr519, or Cys574 of dCas9 (SEQ ID NO:5). In some embodiments, the intein is inserted into another domain of the fusion protein (i.e., not in the Cas9 domain, e.g., not in the dCas9 domain), such as the domain having a particular enzymatic activity. In some embodiments, the domain having a particular enzymatic activity is a nuclease domain (e.g., FokI), a recombinase catalytic domain (e.g., Hin, Gin, or Tn3 recombinase domains), a nucleic acid-editing domain (e.g., a deaminase domain), a transcriptional activator domain (e.g., VP64, p65), a transcriptional repressor domain (e.g., KRAB, SID), or an epigenetic modifier (e.g., LSD1 histone demethylase, TET1 hydoxylase). The intein that is inserted into the fusion protein can be any ligand-dependent intein, e.g., those described herein. For example, in some embodiments, the intein that is inserted into a Cas9 protein comprises in part or in whole, a sequence that is at least 80%, at least 85%, at least 90%, at least 95%, at least 99%, or 100% percent identical to any one of SEQ ID NO:7-14.

In some embodiments, the general architecture of exemplary fusion proteins provided herein comprises the structure:

[$NH_2$]-[enzymatic domain]-[dCas9]-[COOH] or

[$NH_2$]-[dCas9]-[enzymatic domain]-[COOH];

wherein $NH_2$ is the N-terminus of the fusion protein, COOH is the C-terminus of the fusion protein, dCas9 comprises an intein as provided herein, and the enzymatic domain comprises a nuclease domain (e.g., FokI), a recombinase catalytic domain (e.g., Hin, Gin, or Tn3 recombinase domains), a nucleic acid-editing domain (e.g., a deaminase domain), a transcriptional activator domain (e.g., VP64, p65), a transcriptional repressor domain (e.g., KRAB, SID), or an epigenetic modifier (e.g., LSD1 histone demethylase, TET1 hydoxylase). In some embodiments, the intein is comprised in a domain other than dCas9 (e.g., in an enzymatic domain), or is located between two domains.

Additional features may be present, for example, one or more linker sequences between certain domains. Other exemplary features that may be present are localization sequences, such as nuclear localization sequences (NLS; e.g., MAPKKKRKVGIHRGVP (SEQ ID NO:42)); cytoplasmic localization sequences; export sequences, such as nuclear export sequences; or other localization sequences, as well as sequence tags that are useful for solubilization, purification, or detection of the fusion proteins. Suitable localization signal sequences and sequences of protein tags are provided herein and are known in the art, and include, but are not limited to, biotin carboxylase carrier protein (BCCP) tags, myc-tags, calmodulin-tags, FLAG-tags (e.g., 3×FLAG TAG: MDYKDHDGDYKDHDIDYKDDDDK (SEQ ID NO:43)), hemagglutinin (HA) tags, polyhistidine tags, also referred to as histidine tags or His-tags, maltose binding protein (MBP)-tags, nus-tags, glutathione-S-transferase (GST) tags, green fluorescent protein (GFP) tags, thioredoxin-tags, S-tags, Softags (e.g., Softag 1, Softag 3), strep-tags, biotin ligase tags, FlAsH tags, V5 tags, and SBP-tags. Additional suitable sequences will be apparent to those of skill in the art.

In some embodiments, the enzymatic domain comprises a nuclease or a catalytic domain thereof. For example, in some embodiments, the general architecture of exemplary ligand-dependent dCas9 fusion proteins with a nuclease domain comprises the structure:

[$NH_2$]-[NLS]-[dCas9]-[nuclease]-[COOH],

[$NH_2$]-[NLS]-[nuclease]-[dCas9]-[COOH],

[$NH_2$]-[dCas9]-[nuclease]-[COOH], or

[$NH_2$]-[nuclease]-[dCas9]-[COOH];

wherein NLS is a nuclear localization signal, dCas9 comprises an intein as provided herein, $NH_2$ is the N-terminus of the fusion protein, and COOH is the C-terminus of the fusion protein. In some embodiments, a linker is inserted between the dCas9 and the nuclease domain. In some embodiments, a linker is inserted between the NLS and the nuclease and/or dCas9 domain. In some embodiments, the NLS is located C-terminal of the nuclease and/or the dCas9 domain. In some embodiments, the NLS is located between the nuclease and the dCas9 domain. Additional features, such as sequence tags, may also be present. In some aspects, the nuclease domain is a nuclease requiring dimerization (e.g., the coming together of two monomers of the nuclease) in order to cleave a target nucleic acid (e.g., DNA). In some embodiments, the nuclease domain is a monomer of the FokI DNA cleavage domain. The FokI DNA cleavage domain is known, and in some aspects corresponds to amino acids 388-583 of FokI (NCBI accession number J04623). In some embodiments, the FokI DNA cleavage domain corresponds to amino acids 300-583,320-583, 340-583, or 360-583 of FokI. See also Wah et al., "Structure of FokI has implications for DNA cleavage" *Proc. Natl. Acad. Sci. USA.* 1998; 1; 95(18):10564-9; Li et al., "TAL nucleases (TALNs): hybrid proteins composed of TAL effectors and FokI DNA-cleavage domain" *Nucleic Acids Res.* 2011; 39(1):359-72; Kim et al., "Hybrid restriction enzymes: zinc finger fusions to FokI cleavage domain" *Proc. Natl Acad. Sci. USA.* 1996; 93:1156-1160; the entire contents of each are herein incorporated by reference). In some embodiments, the FokI DNA cleavage domain corresponds to, or comprises in part or whole, the amino acid sequence set forth as SEQ ID NO:6. In some embodiments, the FokI DNA cleavage domain is a variant of FokI (e.g., a variant of SEQ ID NO:6), as described herein. Other exemplary compositions and methods of using dCas9-nuclease fusion proteins can be found in U.S. patent application U.S. Ser. No. 14/320,498; titled "Cas9-FokI fusion Proteins and Uses Thereof," filed Jun. 30, 2014; the entire contents of which are incorporated herein by reference.

In some embodiments, the enzymatic domain comprises a recombinase or other catalytic domain thereof. For example, in some embodiments, the general architecture of exemplary ligand-dependent dCas9 fusion proteins with a recombinase domain comprises the structure:

[$NH_2$]-[NLS]-[dCas9]-[recombinase]-[COOH],

[$NH_2$]-[NLS]-[recombinase]-[dCas9]-[COOH],

[$NH_2$]-[dCas9]-[recombinase]-[COOH], or

[$NH_2$]-[recombinase]-[dCas9]-[COOH];

wherein NLS is a nuclear localization signal, dCas9 comprises an intein as provided herein, $NH_2$ is the N-terminus of the fusion protein, and COOH is the C-terminus of the fusion protein. In some embodiments, a linker is inserted between the dCas9 and the recombinase domain. In some embodiments, a linker is inserted between the NLS and the recombinase and/or dCas9 domain. In some embodiments, the NLS is located C-terminal of the recombinase domain and/or the dCas9 domain. In some embodiments, the NLS is located between the recombinase domain and the dCas9 domain. Additional features, such as sequence tags, may also be present. By "catalytic domain of a recombinase," it is meant that a fusion protein includes a domain comprising an amino acid sequence of (e.g., derived from) a recombinase, such that the domain is sufficient to induce recombination when contacted with a target nucleic acid (either alone or with additional factors including other recombinase catalytic domains which may or may not form part of the fusion protein). In some embodiments, a catalytic domain of a recombinase does not include the DNA binding domain of the recombinase. In some embodiments, the catalytic domain of a recombinase includes part or all of a recombinase, e.g., the catalytic domain may include a recombinase domain and a DNA binding domain, or parts thereof, or the catalytic domain may include a recombinase domain and a DNA binding domain that is mutated or truncated to abolish DNA binding activity. Recombinases and catalytic domains of recombinases are known to those of skill in the art, and include, for example, those described herein. In some embodiments, the catalytic domain is derived from any recombinase. In some embodiments, the recombinase catalytic domain is a catalytic domain of aTn3 resolvase, a Hin recombinase, or a Gin recombinase. In some embodiments, the catalytic domain comprises a Tn3 resolvase (e.g., Stark Tn3 recombinase) that is encoded by a nucleotide sequence comprising, in part or in whole, SEQ ID NO:44, as provided below. In some embodiments, a Tn3 catalytic domain is encoded by a variant of SEQ ID NO:44. In some embodiments, a Tn3 catalytic domain is encoded by a polynucleotide (or a variant thereof) that encodes the polypeptide corresponding to SEQ ID NO:45. In some embodiments, the catalytic domain comprises a Hin recombinase that is encoded by a nucleotide sequence comprising, in part or in whole, SEQ ID NO:46, as provided below. In some embodiments, a Hin catalytic domain is encoded by a variant of SEQ ID NO:46. In some embodiments, a Hin catalytic domain is encoded by a polynucleotide (or a variant thereof) that encodes the polypeptide corresponding to SEQ ID NO:47. In some embodiments, the catalytic domain comprises a Gin recombinase (e.g., Gin beta recombinase) that is encoded by a nucleotide sequence comprising, in part or in whole, SEQ ID NO:48, as provided below. In some embodiments, a Gin catalytic domain is encoded by a variant of SEQ ID NO:48. In some embodiments, a Gin catalytic domain is encoded by a polynucleotide (or a variant thereof) that encodes the polypeptide corresponding to SEQ ID NO:49. Other exemplary compositions and methods of using dCas9-recombinase fusion proteins can be found in U.S. patent application U.S. Ser. No. 14/320,467; titled "Cas9 Variants and Uses Thereof," filed Jun. 30, 2014; the entire contents of which are incorporated herein by reference.

```
Stark Tn3 recombinase (nucleotide: SEQ ID
NO: 44; amino acid: SEQ ID NO: 45):
                                     (SEQ ID NO: 44)
ATGGCCCTGTTTGGCTACGCACGCGTGTCTACCAGTCAACAGT

CACTCGATTTGCAAGTGAGGGCTCTTAAAGATGCCGGAGTGAA

GGCAAACAGAATTTTTACTGATAAGGCCAGCGGAAGCAGCACA

GACAGAGAGGGGCTGGATCTCCTGAGAATGAAGGTAAAGGAGG

GTGATGTGATCTTGGTCAAAAAATTGGATCGACTGGGGAGAGA

CACAGCTGATATGCTTCAGCTTATTAAAGAGTTTGACGCTCAG

GGTGTTGCCGTGAGGTTTATCGATGACGGCATCTCAACCGACT

CCTACATTGGTCTTATGTTTGTGACAATTTTGTCCGCTGTGGC

TCAGGCTGAGCGGAGAAGGATTCTCGAAAGGACGAATGAGGGA
```

-continued

```
CGGCAAGCAGCTAAGTTGAAAGGTATCAAATTTGGCAGACGAA

GG

                                     (SEQ ID NO: 45)
MALFGYARVSTSQQSLDLQVRALKDAGVKANRIFTDKASGSST

DREGLDLLRMKVKEGDVILVKKLDRLGRDTADMLQLIKEFDAQ

GVAVRFIDDGISTDSYIGLMFVTILSAVAQAERRRILERTNEG

RQAAKLKGIKFGRRR

Hin Recombinase (nucleotide: SEQ ID NO: 46;
amino acid: SEQ ID NO: 47):
                                     (SEQ ID NO: 46)
ATGGCAACCATTGGCTACATAAGGGTGTCTACCATCGACCAAA

ATATCGACCTGCAGCGCAACGCTCTGACATCCGCCAACTGCGA

TCGGATCTTCGAGGATAGGATCAGTGGCAAGATCGCCAACCGG

CCCGGTCTGAAGCGGGCTCTGAAGTACGTGAATAAGGGCGATA

CTCTGGTTGTGTGGAAGTTGGATCGCTTGGGTAGATCAGTGAA

GAATCTCGTAGCCCTGATAAGCGAGCTGCACGAGAGGGGTGCA

CATTTCCATTCTCTGACCGATTCCATCGATACGTCTAGCGCC

ATGGGCCGATTCTTCTTTTACGTCATGTCCGCCCTCGCTGAAA

TGGAGCGCGAACTTATTGTTGAACGGACTTTGGCTGGACTGGC

AGCGGCTAGAGCACAGGGCCGACTTGGA

                                     (SEQ ID NO: 47)
MATIGYIRVSTIDQNIDLQRNALTSANCDRIFEDRISGKIANR

PGLKRALKYVNKGDTLVVWKLDRLGRSVKNLVALISELHERGA

HFHSLTDSIDTSSAMGRFFFYVMSALAEMERELIVERTLAGLA

AARAQGRLG

Gin beta recombinase (nucleotide: SEQ ID
NO: 48; amino acid: SEQ ID NO: 49):
                                     (SEQ ID NO: 48)
ATGCTCATTGGCTATGTAAGGGTCAGCACCAATGACCAAAACA

CAGACTTGCAACGCAATGCTTTGGTTTGCGCCGGATGTGAACA

GATATTTGAAGATAAACTGAGCGGCACTCGGACAGACAGACCT

GGGCTTAAGAGAGCACTGAAAAGACTGCAGAAGGGGGACACCC

TGGTCGTCTGGAAACTGGATCGCCTCGGACGCAGCATGAAACA

TCTGATTAGCCTGGTTGGTGAGCTTAGGGAGAGAGGAATCAAC

TTCAGAAGCCTGACCGACTCCATCGACACCAGTAGCCCCATGG

GACGATTCTTCTTCTATGTGATGGGAGCACTTGCTGAGATGGA

AAGAGAGCTTATTATCGAAAGAACTATGGCTGGTATCGCTGCT

GCCCGGAACAAAGGCAGACGGTTCGGCAGACCGCCGAAGAGCG

GC

                                     (SEQ ID NO: 49)
MLIGYVRVSTNDQNTDLQRNALVCAGCEQIFEDKLSGTRTDRP

GLKRALKRLQKGDTLVVWKLDRLGRSMKHLISLVGELRERGIN

FRSLTDSIDTSSPMGRFFFYVMGALAEMERELIIERTMAGIAA

ARNKGRRFGRPPKSG
```

In some embodiments, the enzymatic domain comprises a deaminase or a catalytic domain thereof. For example, in some embodiments, the general architecture of exemplary dCas9 fusion proteins with a deaminase enzyme or domain comprises the structure:

[$NH_2$]-[NLS]-[Cas9]-[deaminase]-[COOH],

[$NH_2$]-[NLS][deaminase]-[Cas9]-[COOH],

[$NH_2$]-[Cas9]-[deaminase]-[COOH], or

[$NH_2$]-[deaminase]-[Cas9-[COOH];

wherein NLS is a nuclear localization signal, dCas9 comprises an intein as provided herein, $NH_2$ is the N-terminus of the fusion protein, and COOH is the C-terminus of the fusion protein. In some embodiments, a linker is inserted between the dCas9 and the deaminase domain. In some embodiments, a linker is inserted between the NLS and the deaminase and/or dCas9 domain. In some embodiments, the NLS is located C-terminal of the deaminase and/or the dCas9 domain. In some embodiments, the NLS is located between the deaminase domain and the dCas9 domain. Additional features, such as sequence tags, may also be present. One exemplary suitable type of nucleic acid-editing enzymes and domains are cytosine deaminases, for example, of the apolipoprotein B mRNA-editing complex (APOBEC) family of cytosine deaminase enzymes, including activation-induced cytidine deaminase (AID) and apolipoprotein B editing complex 3 (APOBEC3) enzyme. Another exemplary suitable type of nucleic acid-editing enzyme and domain thereof suitable for use in the present invention include adenosine deaminases. For example, an ADAT family adenosine deaminase can be fused to a dCas9 domain comprising an intein. Some exemplary suitable nucleic-acid editing enzymes and domains, e.g., deaminases and deaminase domains, that can be fused to dCas9 domains comprising inteins according to aspects of this disclosure are provided below. It will be understood that, in some embodiments, the active domain of the respective sequence can be used, e.g., the domain without a localizing signal (nuclear localizing signal, without nuclear export signal, cytoplasmic localizing signal). Other exemplary compositions and methods of using dCas9-nuclease fusion proteins can be found in U.S. patent application U.S. Ser. No. 14/325,815; titled "Fusions of Cas9 Domains and Nucleic Acid-Editing Domains," filed Jul. 8, 2014; the entire contents of which are incorporated herein by reference.

Human AID:

(SEQ ID NO: 50)

MDSLLMNRRKFLYQFKNVRWAKGRRETYLCYVVKRRDSATSFSLDFGYLRNKNGCHVELLFLRYISDWDLDPGRC

YRVTWFTSWSPCYDCARHVADFLRGNPNLSLRIFTARLYFCEDRKAEPEGLRRLHRAGVQIAIMTFKDYFYCWNT

FVENHERTFKAWEGLHENSVRLSRQLRRILLPLYEVDDLRDAFRTLGL (underline: nuclear localization signal; double underline: nuclear export signal)

Mouse AID:

(SEQ ID NO: 51)

MDSLLMKQKKFLYHFKNVRWAKGRHETYLCYVVKRRDSATSCSLDFGHLRNKSGCHVELLFLRYISDWDLDPGRC

YRVTWFTSWSPCYDCARHVAEFLRWNPNLSLRIFTARLYFCEDRKAEPEGLRRLHRAGVQIGIMTFKDYFYCWNT

FVENRERTFKAWEGLHENSVRLTRQLRRILLPLYEVDDLRDAFRMLGF (underline: nuclear localization signal; double underline: nuclear export signal)

Dog AID:

(SEQ ID NO: 52)

MDSLLMKQRKFLYHFKNVRWAKGRHETYLCYVVKRRDSATSFSLDFGHLRNKSGCHVELLFLRYISDWDLDPGRC

YRVTWFTSWSPCYDCARHVADFLRGYPNLSLRIFAARLYFCEDRKAEPEGLRRLHRAGVQIAIMTFKDYFYCWNT

FVENREKTFKAWEGLHENSVRLSRQLRRILLPLYEVDDLRDAFRTLGL (underline: nuclear localization signal; double underline: nuclear export signal)

Bovine AID:

(SEQ ID NO: 53)

MDSLLKKQRQFLYQFKNVRWAKGRHETYLCYVVKRRDSPTSFSLDFGHLRNKAGCHVELLFLRYISDWDLDPGRC

YRVTWFTSWSPCYDCARHVADFLRGYPNLSLRIFTARLYFCDKERKAEPEGLRRLHRAGVQIAIMTFKDYFYCWN

TFVENHERTFKAWEGLHENSVRLSRQLRRILLPLYEVDDLRDAFRTLGL (underline: nuclear localization signal; double underline: nuclear export signal)

Mouse APOBEC-3:

(SEQ ID NO: 54)

MGPFCLGCSHRKCYSPIRNLISQETFKFHFKNLGYAKGRKDTFLCYEVTRKDCDSPVSLHHGVFKNKDNIHAEIC

FLYWFHDKVLKVLSPREEFKITWYMSWSPCFECAEQIVRFLATHHNLSLDIFSSRLYNVQDPETQQNLCRLVQEG

AQVAAMDLYEFKKCWKKFVDNGGRRFRPWKRLLTNFRYQDSKLQEILRPCYIPVPSSSSSTLSNICLTKGLPETR

FCVEGRRMDPLSEEEFYSQFYNQRVKHLCYYHRMKPYLCYQLEQFNGQAPLKGCLLSEKGKQHAEILFLDKIRSM

ELSQVTITCYLTWSPCPNCAWQLAAFKRDRPDLILHIYTSRLYFHWKRPFQKGLCSLWQSGILVDVMDLPQFTDC

WTNFVNPKRPFWPWKGLEIISRRTQRRLRRIKESWGLQDLVNDFGNLQLGPPMS (underline: nucleic acid editing domain)

-continued

Rat APOBEC-3:

(SEQ ID NO: 55)

MGPFCLGCSHRKCYSPIRNLISQETFKFHFKNLRYAIDRKDTFLCYEVTRKDCDSPVSLHHGVFKNKDNIHAEIC

FLYWFHDKVLKVLSPREEFKITWYMSWSPCFECAEQVLRFLATHHNLSLDIFSSRLYNIRDPENQQNLCRLVQEG

AQVAAMDLYEFKKCWKKFVDNGGRRFRPWKKLLTNFRYQDSKLQEILRPCYIPVPSSSSSTLSNICLTKGLPETR

FCVERRRVHLLSEEEFYSQFYNQRVKHLCYYHGVKPYLCYQLEQFNGQAPLKGCLLSEKGKQHAEILFLDKIRSM

ELSQVIITCYLTWSPCPNCAWQLAAFKRDRPDLILHIYTSRLYFHWKRPFQKGLCSLWQSGILVDVMDLPQFTDC

WTNFVNPKRPFWPWKGLEIISRRTQRRLHRIKESWGLQDLVNDFGNLQLGPPMS
(underline: nucleic acid editing domain)

Rhesus macaque APOBEC-3G:

(SEQ ID NO: 56)

MVEPMDPRTFVSNFNNRPILSGLNTVWLCCEVKTKDPSGPPLDAKIFQGKVYSKAKY*HPEMRFLRWFHKWRQLHH*

*DQEYKVTWYVSWSPCTRC*ANSVATFLAKDPKVTLTIFVARLYYFWKPDYQQALRILCQKRGGPHATMKIMNYNEF

QDCWNKFVDGRGKPFKPRNNLPKHYTLLQATLGELLRHLMDPGTFTSNFNNKPWVSGQHETYLCYKVERLHNDTW

VPLNQHRGFLRNQAPNIHGFPKGR*HAELCFLDLIPFWKLDGQQYRVTCFTSWSPCFSC*AQEMAKFISNNEHVSLC

IFAARIYDDQGRYQEGLRALHRDGAKIAMMNYSEFEYCWDTFVDRQGRPFQPWDGLDEHSQALSGRLRAI
(bold italic: nucleic acid editing domain; underline: cytoplasmic localization signal)

Chimpanzee APOBEC-3G:

(SEQ ID NO: 57)

MKPHFRNPVERMYQDTFSDNFYNRPILSHRNTVWLCYEVKTKGPSRPPLDAKIFRGQVYSKLKYHPEMRFFHWFS

KWRKLHRDQEYEVTWYISWSPCTKCTRDVATFLAEDPKVTLTIFVARLYYFWDPDYQEALRSLCQKRDGPRATMK

IMNYDEFQHCWSKFVYSQRELFEPWNNLPKYYILLHIMLGEILRHSMDPPTFTSNFNNELWVRGRHETYLCYEVE

RLHNDTWVLLNQRRGFLCNQAPHKHGFLEGRHAELCFLDVIPFWKLDLHQDYRVTCFTSWSPCFSCAQEMAKFIS

NNKHVSLCIFAARIYDDQGRCQEGLRTLAKAGAKISIMTYSEFKHCWDTFVDHQGCPFQPWDGLEEHSQALSGRL

RAILQNQGN
(underline: nucleic acid editing domain; double underline: cytoplasmic localization signal)

Green monkey APOBEC-3G:

(SEQ ID NO: 58)

MNPQIRNMVEQMEPDIFVYYFNNRPILSGRNTVWLCYEVKTKDPSGPPLDANIFQGKLYPEAKDHPEMKFLHWFR

KWRQLHRDQEYEVTWYVSWSPCTKCANSVATFLAEDPKVTLTIFVARLYYFWKPDYQQALRILCQERGGPHATMK

IMNYNEFQHCWNEFVDGQGKPFKPRKNLPKHYTLLHATLGELLRHVMDPGTFTSNFNNKPWVSGQRETYLCYKVE

RSHNDTWVLLNQHRGFLRNQAPDRHGFPKGRHAELCFLDLIPFWKLDDQQYRVTCFTSWSPCFSCAQKMAKFISN

NKHVSLCIFAARIYDDQGRCQEGLRTLHRDGAKIAVMNYSEFEYCWDTFVDRQGRPFQPWDGLDEHSQALSGRLR

AI
(underline: nucleic acid editing domain; double underline: cytoplasmic localization signal)

Human APOBEC-3G:

(SEQ ID NO: 59)

MKPHFRNTVERMYRDTFSYNFYNRPILSRRNTVWLCYEVKTKGPSRPPLDAKIFRGQVYSELKYHPEMRFFHWFS

KWRKLHRDQEYEVTWYISWSPCTKCTRDMATFLAEDPKVTLTIFVARLYYFWDPDYQEALRSLCQKRDGPRATMK

IMNYDEFQHCWSKFVYSQRELFEPWNNLPKYYILLHIMLGEILRHSMDPPTFTFNFNNEPWVRGRHETYLCYEVE

RMHNDTWVLLNQRRGFLCNQAPHKHGFLEGRHAELCFLDVIPFWKLDLDQDYRVTCFTSWSPCFSCAQEMAKFIS

KNKHVSLCIFTARIYDDQGRCQEGLRTLAEAGAKISIMTYSEFKHCWDTFVDHQGCPFQPWDGLDEHSQDLSGRL

RAILQNQEN
(underline: nucleic acid editing domain; double underline: cytoplasmic localization signal)

-continued

Human APOBEC-3F:

(SEQ ID NO: 60)

MKPHFRNTVERMYRDTFSYNFYNRPILSRRNTVWLCYEVKTKGPSRPRLDAKIFRGQVYSQPEHHAEMCFLSWFC

GNQLPAYKCFQITWFVSWTPCPDCVAKLAEFLAEHPNVTLTISAARLYYYWERDYRRALCRLSQAGARVKIMDDE

EFAYCWENFVYSEGQPFMPWYKFDDNYAFLHRTLKEILRNPMEAMYPHIFYFHFKNLRKAYGRNESWLCFTMEVV

KHHSPVSWKRGVFRNQVDPETHCHAERCFLSWFCDDILSPNTNYEVTWYTSWSPCPECAGEVAEFLARHSNVNLT

IFTARLYYFWDTDYQEGLRSLSQEGASVEIMGYKDFKYCWENFVYNDDEPFKPWKGLKYNFLFLDSKLQEILE
(underline: nucleic acid editing domain)

Human APOBEC-3B:

(SEQ ID NO: 61)

MNPQIRNPMERMYRDTFYDNFENEPILYGRSYTWLCYEVKIKRGRSNLLWDTGVFRGQVYFKPQYHAEMCFLSWF

CGNQLPAYKCFQITWFVSWTPCPDCVAKLAEFLSEHPNVTLTISAARLYYYWERDYRRALCRLSQAGARVTIMDY

EEFAYCWENFVYNEGQQFMPWYKFDENYAFLHRTLKEILRYLMDPDTFTFNFNNDPLVLRRRQTYLCYEVERLDN

GTWVLMDQHMGFLCNEAKNLLCGFYGRHAELRFLDLVPSLQLDPAQIYRVTWFISWSPCFSWGCAGEVRAFLQEN

THVRLRIFAARIYDYDPLYKEALQMLRDAGAQVSIMTYDEFEYCWDTFVYRQGCPFQPWDGLEEHSQALSGRLRA

ILQNQGN
(underline: nucleic acid editing domain)

Human APOBEC-3C:

(SEQ ID NO: 62)

MNPQIRNPMKAMYPGTFYFQFKNLWEANDRNETWLCFTVEGIKRRSVVSWKTGVFRNQVDSETHCHAERCFLSWF

CDDILSPNTKYQVTWYTSWSPCPDCAGEVAEFLARHSNVNLTIFTARLYYFQYPCYQEGLRSLSQEGVAVEIMDY

EDFKYCWENFVYNDNEPFKPWKGLKTNFRLLKRRLRESLQ
(underline: nucleic acid editing domain)

Human APOBEC-3A:

(SEQ ID NO: 63)

MEASPASGPRHLMDPHIFTSNFNNGIGRHKTYLCYEVERLDNGTSVKMDQHRGFLHNQAKNLLCGFYGRHAELRF

LDLVPSLQLDPAQIYRVTWFISWSPCFSWGCAGEVRAFLQENTHVRLRIFAARIYDYDPLYKEALQMLRDAGAQV

SIMTYDEFKHCWDTFVDHQGCPFQPWDGLDEHSQALSGRLRAILQNQGN
(underline: nucleic acid editing domain)

Human APOBEC-3H:

(SEQ ID NO: 64)

MALLTAETFRLQFNNKRRLRRPYYPRKALLCYQLTPQNGSTPTRGYFENKKKCHAEICFINEIKSMGLDETQCYQ

VTCYLTWSPCSSCAWELVDFIKAHDHLNLGIFASRLYYHWCKPQQKGLRLLCGSQVPVEVMGFPKFADCWENFVD

HEKPLSFNPYKMLEELDKNSRAIKRRLERIKIPGVRAQGRYMDILCDAEV
(underline: nucleic acid editing domain)

Human APOBEC-3D:

(SEQ ID NO: 65)

MNPQIRNPMERMYRDTFYDNFENEPILYGRSYTWLCYEVKIKRGRSNLLWDTGVFRGPVLPKRQSNHRQEVYFRF

ENHAEMCFLSWFCGNRLPANRRFQITWFVSWNPCLPCVVKVTKFLAEHPNVTLTISAARLYYYRDRDWRWVLLRL

HKAGARVKIMDYEDFAYCWENFVCNEGQPFMPWYKFDDNYASLHRTLKEILRNPMEAMYPHIFYFHFKNLLKACG

RNESWLCFTMEVTKHHSAVFRKRGVFRNQVDPETHCHAERCFLSWFCDDILSPNTNYEVTWYTSWSPCPECAGEV

AEFLARHSNVNLTIFTARLCYFWDTDYQEGLCSLSQEGASVKIMGYKDFVSCWKNFVYSDDEPFKPWKGLQTNFR

LLKRRLREILQ
(underline: nucleic acid editing domain)

Human APOBEC-1:

(SEQ ID NO: 66)

MTSEKGPSTGDPTLRRRIEPWEFDVFYDPRELRKEACLLYEIKWGMSRKIWRSSGKNTTNHVEVNFIKKFTSERD

FHPSMSCSITWFLSWSPCWECSQAIREFLSRHPGVTLVIYVARLFWHMDQQNRQGLRDLVNSGVTIQIMRASEYY

HCWRNFVNYPPGDEAHWPQYPPLWMMLYALELHCIILSLPPCLKISRRWQNHLTFFRLHLQNCHYQTIPPHILLA

TGLIHPSVAWR

-continued

Mouse APOBEC-1:

(SEQ ID NO: 67)

MSSETGPVAVDPTLRRRIEPHEFEVFFDPRELRKETCLLYEINWGGRHSVWRHTSQNTSNHVEVNFLEKFTTERY
FRPNTRCSITWFLSWSPCGECSRAITEFLSRHPYVTLFIYIARLYHHTDQRNRQGLRDLISSGVTIQIMTEQEYC
YCWRNFVNYPPSNEAYWPRYPHLWVKLYVLELYCIILGLPPCLKILRRKQPQLTFFTITLQTCHYQRIPPHLLWA
TGLK

Rat APOBEC-1:

(SEQ ID NO: 68)

MSSETGPVAVDPTLRRRIEPHEFEVFFDPRELRKETCLLYEINWGGRHSIWRHTSQNTNKHVEVNFIEKFTTERY
FCPNTRCSITWFLSWSPCGECSRAITEFLSRYPHVTLFIYIARLYHHADPRNRQGLRDLISSGVTIQIMTEQESG
YCWRNFVNYSPSNEAHWPRYPHLWVRLYVLELYCIILGLPPCLNILRRKQPQLTFFTIALQSCHYQRLPPHILWA
TGLK

Human ADAT-2:

(SEQ ID NO: 69)

MEAKAAPKPAASGACSVSAEETEKWMEEAMHMAKEALENTEVPVGCLMVYNNEVVGKGRNEVNQTKNATRHAEMV
AIDQVLDWCRQSGKSPSEVFEHTVLYVTVEPCIMCAAALRLMKIPLVVYGCQNERFGGCGSVLNIASADLPNTGR
PFQCIPGYRAEEAVEMLKTFYKQENPNAPKSKVRKKECQKS

Mouse ADAT-2:

(SEQ ID NO: 70)

MEEKVESTTTPDGPCVVSVQETEKWMEEAMRMAKEALENIEVPVGCLMVYNNEVVGKGRNEVNQTKNATRHAEMV
AIDQVLDWCHQHGQSPSTVFEHTVLYVTVEPCIMCAAALRLMKIPLVVYGCQNERFGGCGSVLNIASADLPNTGR
PFQCIPGYRAEEAVELLKTFYKQENPNAPKSKVRKKDCQKS

Mouse ADAT-1:

(SEQ ID NO: 71)

MWTADEIAQLCYAHYNVRLPKQGKPEPNREWTLLAAVVKIQASANQACDIPEKEVQVTKEVVSMGTGTKCIGQSK
MRESGDILNDSHAEIIARRSFQRYLLHQLHLAAVLKEDSIFVPGTQRGLWRLRPDLSFVFFSSHTPCGDASIIPM
LEFEEQPCCPVIRSWANNSPVQETENLEDSKDKRNCEDPASPVAKKMRLGTPARSLSNCVAHHGTQESGPVKPDV
SSSDLTKEEPDAANGIASGSFRVVDVYRTGAKCVPGETGDLREPGAAYHQVGLLRVKPGRGDRTCSMSCSDKMAR
WNVLGCQGALLMHFLEKPIYLSAVVIGKCPYSQEAMRRALTGRCEETLVLPRGFGVQELEIQQSGLLFEQSRCAV
HRKRGDSPGRLVPCGAAISWSAVPQQPLDVTANGFPQGTTKKEIGSPRARSRISKVELFRSFQKLLSSIADDEQP
DSIRVTKKLDTYQEYKDAASAYQEAWGALRRIQPFASWIRNPPDYHQFK (underline: nucleic acid editing domain)

Human ADAT-1:

(SEQ ID NO: 72)

MWTADEIAQLCYEHYGIRLPKKGKPEPNHEWTLLAAVVKIQSPADKACDTPDKPVQVTKEVVSMGTGTKCIGQSK
MRKNGDILNDSHAEVIARRSFQRYLLHQLQLAATLKEDSIFVPGTQKGVWKLRRDLIFVFFSSHTPCGDASIIPM
LEFEDQPCCPVFRNWAHNSSVEASSNLEAPGNERKCEDPDSPVTKKMRLEPGTAAREVTNGAAHHQSFGKQKSGP
ISPGIHSCDLTVEGLATVTRIAPGSAKVIDVYRTGAKCVPGEAGDSGKPGAAFHQVGLLRVKPGRGDRTRSMSCS
DKMARWNVLGCQGALLMHLLEEPIYLSAVVIGKCPYSQEAMQRALIGRCQNVSALPKGFGVQELKILQSDLLFEQ
SRSAVQAKRADSPGRLVPCGAAISWSAVPEQPLDVTANGFPQGTTKKTIGSLQARSQISKVELFRSFQKLLSRIA
RDKWPHSLRVQKLDTYQEYKEAASSYQEAWSTLRKQVFGSWIRNPPDYHQFK (underline: nucleic acid editing domain)

In some embodiments, the enzymatic domain comprises one or more of a transcriptional activator. For example, in some embodiments, the general architecture of exemplary dCas9 fusion proteins with a transcriptional activator domain comprises the structure:

$[NH_2]$-[NLS]-[Cas9]-[(transcriptional activator)$_n$]-[COOH], $[NH_2]$-[NLS]-[(transcriptional activator)$_n$]-[Cas9]—[COOH], $[NH_2]$-[Cas9]-[(transcriptional activator)$_n$]-[COOH], or $[NH_2]$-[(transcriptional activator)$_n$]-[Cas9]-[COOH];

wherein NLS is a nuclear localization signal, dCas9 comprises an intein as provided herein, $NH_2$ is the N-terminus of the fusion protein, and COOH is the C-terminus of the fusion protein. In some embodiments, the fusion proteins comprises one or more repeats of the transcriptional activator, for example wherein n=1-10 (e.g., n is 1, 2, 3, 4, 5, 6, 7, 8, 9, or 10). In some embodiments, n=1-20. In some embodiments, a linker is inserted between the dCas9 and the transcriptional activator domain. In some embodiments, a linker is inserted between the NLS and the transcriptional activator and/or dCas9 domain. In some embodiments, the NLS is located C-terminal of the transcriptional activator and/or the dCas9 domain. In some embodiments, the NLS is located between the transcriptional activator domain and the dCas9 domain. Additional features, such as sequence tags, may also be present. In some embodiments, the transcriptional activator is selected from the group consisting of VP64, (SEQ ID NO:73), VP16 (SEQ ID NO:74), and p65 (SEQ ID NO:75).

```
VP64
                                        (SEQ ID NO: 73)
GSGRADALDDFDLDMLGSDALDDFDLDMLGSDALDDFDLDM

LGSDALDDFDLDMLIN

VP16
                                        (SEQ ID NO: 74)
APPTDVSLGDELHLDGEDVAMAHADALDDFDLDMLGDGDSP

GPGFTPHDSAPYGALDMADFEFEQMFTDALGIDEYGGEFPG

IRR

p65:
                                        (SEQ ID NO: 75)
PSGQISNQALALAPSSAPVLAQTMVPSSAMVPLAQPPAPAP

VLTPGPPQSLSAPVPKSTQAGEGTLSEALLHLQFDADEDLG

ALLGNSTDPGVFTDLASVDNSEFQQLLNQGVSMSHSTAEPM

LMEYPEAITRLVTGSQRPPDPAPTPLGTSGLPNGLSGDEDF

SSIADMDFSALLSQISSSGQ
```

In some embodiments, the enzymatic domain comprises one or more of a transcriptional repressor. For example, in some embodiments, the general architecture of exemplary dCas9 fusion proteins with a transcriptional repressor domain comprises the structure:

$[NH_2]$-[NLS][Cas9]-[(transcriptional repressor)$_n$]-[COOH], $[NH_2]$-[NLS]-[(transcriptional repressor)$_n$-]-[Cas9]—[COOH], $[NH_2]$-[Cas9]-[(transcriptional repressor)$_n$-]-[COOH], or $[NH_2]$-[(transcriptional repressor)$_n$]-[Cas9]-[COOH];

wherein NLS is a nuclear localization signal, dCas9 comprises an intein as provided herein, $NH_2$ is the N-terminus of the fusion protein, and COOH is the C-terminus of the fusion protein. In some embodiments, the fusion proteins comprises one or more repeats of the transcriptional repressor, for example wherein n=1-10 (e.g., n is 1, 2, 3, 4, 5, 6, 7, 8, 9, or 10). In some embodiments, n=1-20. In some embodiments, a linker is inserted between the dCas9 and the transcriptional repressor domain. In some embodiments, a linker is inserted between the NLS and the transcriptional repressor and/or dCas9 domain. In some embodiments, the NLS is located C-terminal of the transcriptional repressor and/or the dCas9 domain. In some embodiments, the NLS is located between the transcriptional repressor domain and the dCas9 domain. Additional features, such as sequence tags, may also be present. In some embodiments, the transcriptional repressor is selected from the group consisting of the KRAB (Krüppel associated box) domain of Kox1, SID (mSin3 interaction domain), the CS (Chromo Shadow) domain of HP1α, or the WRPW domain of Hes1. These and other repressor domains are known in the art, and in some embodiments correspond to those described in Urrutia, KRAB-containing zinc-finger repressor proteins. *Genome Biol.* 2003; 4(10):231; Gilbert et al. CRISPR-mediated modular RNA-guided regulation of transcription in eukaryotes. *Cell.* 2013; 154, 442-451; Konermann et al., Optical control of mammalian endogenous transcription and epigenetic states. *Nature.* 2013; 500, 472-476; and published U.S. patent application U.S. Ser. No. 14/105,017, published as U.S. 2014/0186958 A1, the entire contents of which are incorporated herein by reference. In some embodiments, the transcription repressor domain comprises one or more repeats (e.g., 2, 3, 4, 5, 6, 7, 8, 9, or 10 repeats) of a KRAB domain. In some embodiments, the KRAB domain comprises an amino acid sequence selected from the group consisting of SEQ ID NOs:76-79. In some embodiments, the transcriptional repressor domains comprises one or more repeats of a SID protein. In some embodiments, the SID protein comprises an amino acid sequence set forth as SEQ ID NO:80. In some embodiments, the repressor domain comprises 2, 3, 4, 5, 6, 7, 8, 9, or 10 repeats of a SID protein (e.g., SEQ ID NO:80). In some embodiments, the repressor domain comprises four repeats of SID (e.g., SID4x; SEQ ID NO:81).

```
KRAB (human; GenBank: AAD20972.1)
                                        (SEQ ID NO: 76)
MNMFKEAVTFKDVAVAFTEEELGLLGPAQRKLYRD

VMVENFRNLLSVGHPPFKQDVSPIERNEQLWIMTT

ATRRQGNLDTLPVKALLLYDLAQT

KRAB protein domain, partial
(human; GenBank: CAB52478.1):
                                        (SEQ ID NO: 77)
EQVSFKDVCVDFTQEEWYLLDPAQKILYRDVILEN

YSNLVSVGYCITKPEVIFKIEQGEEPWILEKGFPS

QCHP

KRAB A domain, partial
(human; GenBank: AAB03530.1):
                                        (SEQ ID NO: 78)
EAVTFKDVAVVFTEEELGLLDPAQRKLYRDVMLEN

FRNLLSV

KRAB (mouse; C2H2 type domain containing
protein; GenBank: CAM27971.1):
                                        (SEQ ID NO: 79)
MDLVTYDDVHVNFTQDEWALLDPSQKSLYKGVMLE

TYKNLTAIGYIWEEHTIEDHFQTSRSHGSNKKTH

SID repressor domain:
                                        (SEQ ID NO: 80)
GSGMNIQMLLEAADYLERREREAEHGYASMLP

SID4x repressor domain:
                                        (SEQ ID NO: 81)
GSGMNIQMLLEAADYLERREREAEHGYASMLPGSG

MNIQMLLEAADYLERREREAEHGYASMLPGSGMNI

QMLLEAADYLERREREAEHGYASMLPGSGMNIQML

LEAADYLERREREAEHGYASMLPSR
```

In some embodiments, the enzymatic domain comprises an epigenetic modifier or a catalytic domain thereof. For example, in some embodiments, the general architecture of exemplary dCas9 fusion proteins with an epigenetic modifier or domain comprises the structure:

$[NH_2]$-[NLS]-[Cas9]-[epigenetic modifier]-[COOH], $[NH_2]$-[NLS]-[epigenetic modifier]-[Cas9]-[COOH], $[NH_2]$-[Cas9]-[epigenetic modifier]-[COOH], or $[NH_2]$-[epigenetic modifier]-[Cas9]-[COOH];

wherein NLS is a nuclear localization signal, dCas9 comprises an intein as provided herein, $NH_2$ is the N-terminus of the fusion protein, and COOH is the C-terminus of the fusion protein. In some embodiments, a linker is inserted between the dCas9 and the epigenetic modifier domain. In some embodiments, a linker is inserted between the NLS and the epigenetic modifier and/or dCas9 domain. In some embodiments, the NLS is located C-terminal of the epigenetic modifier and/or the dCas9 domain. In some embodiments, the NLS is located between the epigenetic modifier domain and the dCas9 domain. Additional features, such as sequence tags, may also be present. Epigenetic modifiers are well known in the art, and typically catalyze DNA methylation (and demethylation) or histone modifications (e.g., histone methylation/demethylation, acetylation/deacetylation, ubiquitylation, phosphorylation, sumoylation, etc.). The presence of one more epigenetic modifications can affect the transcriptional activity of one or more genes, for example turning genes from an "on" state to an "off" state, and vice versa. Epigenetic modifiers include, but are not limited to, histone demethylase, histone methyltransferase, hydroxylase, histone deacetylase, and histone acetyltransferase. Exemplary epigenetic modifying proteins can be found in Konermann et al., Optical control of mammalian endogenous transcription and epigenetic states. *Nature.* 2013; 500, 472-476; Mendenhall et al., Locus-specific editing of histone modifications at endogenous enhancers. *Nat. Biotechnol.* 2013; 31, 1133-1136; and Maeder et al., Targeted DNA demethylation and activation of endogenous genes using programmable TALE-TET1 fusion proteins. *Nat. Biotechnol.* 2013; 31, 1137-1142; the entire contents of each are incorporated herein by reference. In some embodiments, the epigenetic modifier domain is LSD1 (Lysine (K)-specific demethylase 1A) histone demethylase, which in some embodiments, comprises in whole or in part, an amino acid sequence set forth as SEQ ID NO:82 or SEQ ID NO:83. In some embodiments, the epigenetic modifier domain is TET1 hydroxylase catalytic domain, which in some embodiments, comprises an amino acid sequence set forth as SEQ ID NO:84. In some embodiments, the epigenetic modifier is a histone deacetylase (HDAC) effector domain. In some embodiments, the HDAC effector domain comprises in whole in in part, an amino acid sequence corresponding to any of the HDAC effector proteins provided in Supplementary Table 2 of Konermann et al., Optical control of mammalian endogenous transcription and epigenetic states. *Nature.* 2013; 500, 472-476; SEQ ID NOs:85-96. In some embodiments, the epigenetic modifier is a histone methyltransferase (HMT) effector domain. In some embodiments, the HMT effector domain comprises in whole in in part, an amino acid sequence corresponding to any of the HDAC effector proteins provided in Supplementary Table 3 of Konermann et al., Optical control of mammalian endogenous transcription and epigenetic states. *Nature.* 2013; 500, 472-476; SEQ ID NOs:97-106.

LSD1, isoform a (human):

(SEQ ID NO: 82)

MLSGKKAAAAAAAAAAAATGTEAGPGTAGGSENGSEVAAQPAGLSGPAEVGPGAVGERTPRKKEPPRA

SPPGGLAEPPGSAGPQAGPTVVPGSATPMETGIAETPEGRRTSRRKRAKVEYREMDESLANLSEDEYY

SEEERNAKAEKEKKLPPPPPQAPPEEENESEPEEPSGQAGGLQDDSSGGYGDGQASGVEGAAFQSRLP

HDRMTSQEAACFPDIISGPQQTQKVFLFIRNRTLQLWLDNPKIQLTFEATLQQLEAPYNSDTVLVHRV

HSYLERHGLINFGIYKRIKPLPTKKTGKVIIIGSGVSGLAAARQLQSFGMDVTLLEARDRVGGRVATF

RKGNYVADLGAMVVTGLGGNPMAVVSKQVNMELAKIKQKCPLYEANGQADTVKVPKEKDEMVEQEFNR

LLEATSYLSHQLDFNVLNNKPVSLGQALEVVIQLQEKHVKDEQIEHWKKIVKTQEELKELLNKMVNLK

EKIKELHQQYKEASEVKPPRDITAEFLVKSKHRDLTALCKEYDELAETQGKLEEKLQELEANPPSDVY

LSSRDRQILDWHFANLEFANATPLSTLSLKHWDQDDDFEFTGSHLTVRNGYSCVPVALAEGLDIKLNT

AVRQVRYTASGCEVIAVNTRSTSQTFIYKCDAVLCTLPLGVLKQQPPAVQFVPPLPEWKTSAVQRMGF

GNLNKVVLCFDRVFWDPSVNLFGHVGSTTASRGELFLFWNLYKAPILLALVAGEAAGIMENISDDVIV

GRCLAILKGIFGSSAVPQPKETVVSRWRADPWARGSYSYVAAGSSGNDYDLMAQPITPGPSIPGAPQP

IPRLFFAGEHTIRNYPATVHGALLSGLREAGRIADQFLGAMYTLPRQATPGVPAQQSPSM

LSD1, isoform b (human):

(SEQ ID NO: 83)

MLSGKKAAAAAAAAAAAATGTEAGPGTAGGSENGSEVAAQPAGLSGPAEVGPGAVGERTPRKKEPPRA

SPPGGLAEPPGSAGPQAGPTVVPGSATPMETGIAETPEGRRTSRRKRAKVEYREMDESLANLSEDEYY

SEEERNAKAEKEKKLPPPPPQAPPEEENESEPEEPSGVEGAAFQSRLPHDRMTSQEAACFPDIISGPQ

QTQKVFLFIRNRTLQLWLDNPKIQLTFEATLQQLEAPYNSDTVLVHRVHSYLERHGLINFGIYKRIKP

LPTKKTGKVIIIGSGVSGLAAARQLQSFGMDVTLLEARDRVGGRVATFRKGNYVADLGAMVVTGLGGN

PMAVVSKQVNMELAKIKQKCPLYEANGQAVPKEKDEMVEQEFNRLLEATSYLSHQLDFNVLNNKPVSL

GQALEVVIQLQEKHVKDEQIEHWKKIVKTQEELKELLNKMVNLKEKIKELHQQYKEASEVKPPRDITA

-continued

EFLVKSKHRDLTALCKEYDELAETQGKLEEKLQELEANPPSDVYLSSRDRQILDWHFANLEFANATPL

STLSLKHWDQDDDFEFTGSHLTVRNGYSCVPVALAEGLDIKLNTAVRQVRYTASGCEVIAVNTRSTSQ

TFIYKCDAVLCTLPLGVLKQQPPAVQFVPPLPEWKTSAVQRMGFGNLNKVVLCFDRVFWDPSVNLFGH

VGSTTASRGELFLFWNLYKAPILLALVAGEAAGIMENISDDVIVGRCLAILKGIFGSSAVPQPKETVV

SRWRADPWARGSYSYVAAGSSGNDYDLMAQPITPGPSIPGAPQPIPRLFFAGEHTIRNYPATVHGALL

SGLREAGRIADQFLGAMYTLPRQATPGVPAQQSPSM

TET1 catalytic domain:

(SEQ ID NO: 84)

SIVAQLSRPDPALAALTNDHLVALACLGGRPALDAVKKGLPHAPALIKRTNRRIPERTSHRVADHAQV

VRVLGFFQCHSHPAQAFDDAMTQFGMSGGGSLPTCSCLDRVIQKDKGPYYTHLGAGPSVAAVREIMEN

RYGQKGNAIRIEIVVYTGKEGKSSHGCPIAKWVLRRSSDEEKVLCLVRQRTGHHCPTAVMVVLIMVWD

GIPLPMADRLYTELTENLKSYNGHPTDRRCTLNENRTCTCQGIDPETCGASFSFGCSWSMYFNGCKFG

RSPSPRRFRIDPSSPLHEKNLEDNLQSLATRLAPIYKQYAPVAYQNQVEYENVARECRLGSKEGRPFS

GVTACLDFCAHPHRDIHNMNNGSTVVCTLTREDNRSLGVIPQDEQLHVLPLYKLSDTDEFGSKEGMEA

KIKSGAIEVLAPRRKKRTCFTQPVPRSGKKRAAMMTEVLAHKIRAVEKKPIPRIKRKNNSTTTNNSKP

SSLPTLGSNTETVQPEVKSETEPHFILKSSDNTKTYSLMPSAPHPVKEASPGFSWSPKTASATPAPLK

NDATASCGFSERSSTPHCTMPSGRLSGANAAAADGPGISQLGEVAPLPTLSAPVMEPLINSEPSTGVT

EPLTPHQPNHQPSFLTSPQDLASSPMEEDEQHSEADEPPSDEPLSDDPLSPAEEKLPHIDEYWSDSEH

IFLDANIGGVAIAPAHGSVLIECARRELHATTPVEHPNRNHPTRLSLVFYQHKNLNKPQHGFELNKIK

FEAKEAKNKKMKASEQKDQAANEGPEQSSEVNELNQIPSHKALTLTHDNVVTVSPYALTHVAGPYNHW

V

HDAC effector domains:
HDAC8 (*X. laevis*):

(SEQ ID NO: 85)

ASSPKKKRKVEASMSRVVKPKVASMEEMAAFHTDAYLQHLHKVSEEGDNDDPETLEYGLGYDCPITEG

IYDYAAAVGGATLTAAEQLIEGKTRIAVNWPGGWHHAKKDEASGFCYLNDAVLGILKLREKFDRVLYV

DMDLHHGDGVEDAFSFTSKVMTVSLHKFSPGFFPGTGDVSDIGLGKGRYYSINVPLQDGIQDDKYYQI

CEGVLKEVFTTFNPEAVVLQLGADTIAGDPMCSFNMTPEGIGKCLKYVLQWQLPTLILGGGGYHLPNT

ARCWTYLTALIVGRTLSSEIPDHEFFTEYGPDYVLEITPSCRPDRNDTQKVQEILQSIKGNLKRVVEF

RPD3 (*S. cerevisiae*):

(SEQ ID NO: 86)

ASSPKKKRKVEASRRVAYFYDADVGNYAYGAGHPMKPHRIRMAHSLIMNYGLYKKMEIYRAKPATKQE

MCQFHTDEYIDFLSRVTPDNLEMFKRESVKFNVGDDCPVFDGLYEYCSISGGGSMEGAARLNRGKCDV

AVNYAGGLHHAKKSEASGFCYLNDIVLGIIELLRYHPRVLYIDIDVHHGDGVEEAFYTTDRVMTCSFH

KYGEFFPGTGELRDIGVGAGKNYAVNVPLRDGIDDATYRSVFEPVIKKIMEWYQPSAVVLQCGGDSLS

GDRLGCFNLSMEGHANCVNYVKSFGIPMMVVGGGGYTMRNVARTWCFETGLLNNVVLDKDLPYEF

MesoLo4 (*M. loti*):

(SEQ ID NO: 87)

ASSPKKKRKVEASMPLQIVHHPDYDAGFATNHRFPMSKYPLLMEALRARGLASPDALNTTEPAPASWL

KLAHAADYVDQVISCSVPEKIEREIGFPVGPRVSLRAQLATGGTILAARLALRHGIACNTAGGSHHAR

RAQGAGFCTFNDVAVASLVLLDEGAAQNILVVDLDVHQGDGTADILSDEPGVFTFSMHGERNYPVRKI

ASDLDIALPDGTGDAAYLRRLATILPELSARARWDIVFYNAGVDVHAEDRLGRLALSNGGLRARDEMV

IGHFRALGIPVCGVIGGGYSTDVPALASRHAILFEVASTYAEF

-continued

HDAC11 (human):
(SEQ ID NO: 88)
ASSPKKKRKVEASMLHTTQLYQHVPETRWPIVYSPRYNITFMGLEKLHPFDAGKWGKVINFLKEEKLL
SDSMLVEAREASEEDLLVVHTRRYLNELKWSFAVATITEIPPVIFLPNFLVQRKVLRPLRTQTGGTIM
AGKLAVERGWAINVGGGFHHCSSDRGGGFCAYADITLAIKFLFERVEGISRATIIDLDAHQGNGHERD
FMDDKRVYIMDVYNRHIYPGDRFAKQAIRRKVELEWGTEDDEYLDKVERNIKKSLQEHLPDVVVYNAG
TDILEGDRLGGLSISPAGIVKRDELVFRMVRGRRVPILMVTSGGYQKRTARIIADSILNLFGLGLIGP
ESPSVSAQNSDTPLLPPAVPEF HDT1 (*A. thaliana*):
(SEQ ID NO: 89)
ASSPKKKRKVEASMEFWGIEVKSGKPVTVTPEEGILIHVSQASLGECKNKKGEFVPLHVKVGNQNLVL
GTLSTENIPQLFCDLVFDKEFELSHTWGKGSVYFVGYKTPNIEPQGYSEEEEEEEEEVPAGNAAKAVA
KPKAKPAEVKPAVDDEEDESDSDGMDEDDSDGEDSEEEEPTPKKPASSKKRANETTPKAPVSAKKAKV
AVTPQKTDEKKKGGKAANQSEF SIRT3 (human):
(SEQ ID NO: 90)
ASSPKKKRKVEASMVGAGISTPSGIPDFRSPGSGLYSNLQQYDLPYPEAIFELPFFFHNPKPFFTLAK
ELYPGNYKPNVTHYFLRLLHDKGLLLRLYTQNIDGLERVSGIPASKLVEAHGTFASATCTVCQRPFPG
EDIRADVMADRVPRCPVCTGVVKPDIVFFGEPLPQRFLLHVVDFPMADLLLILGTSLEVEPFASLTEA
VRSSVPRLLINRDLVGPLAWHPRSRDVAQLGDVVHGVESLVELLGWTEEMRDLVQRETGKLDGPDKEF HST2 (*S. cerevisiae*):
(SEQ ID NO: 91)
ASSPKKKRKVEASTEMSVRKIAAHMKSNPNAKVIFMVGAGISTSCGIPDFRSPGTGLYHNLARLKLPY
PEAVFDVDFFQSDPLPFYTLAKELYPGNFRPSKFHYLLKLFQDKDVLKRVYTQNIDTLERQAGVKDDL
IIEAHGSFAHCHCIGCGKVYPPQVFKSKLAEHPIKDFVKCDVCGELVKPAIVFFGEDLPDSFSETWLN
DSEWLREKITTSGKHPQQPLVIVVGTSLAVYPFASLPEEIPRKVKRVLCNLETVGDFKANKRPTDLIV
HQYSDEFAEQLVEELGWQEDFEKILTAQGGMGEF CobB (*E. coli* (K12)):
(SEQ ID NO: 92)
ASSPKKKRKVEASMEKPRVLVLTGAGISAESGIRTFRAADGLWEEHRVEDVATPEGFDRDPELVQAFY
NARRRQLQQPEIQPNAAHLALAKLQDALGDRFLLVTQNIDNLHERAGNTNVIHMHGELLKVRCSQSGQ
VLDWTGDVTPEDKCHCCQFPAPLRPHVVWFGEMPLGMDEIYMALSMADIFIAIGTSGHVYPAAGFVHE
AKLHGAHTVELNLEPSQVGNEFAEKYYGPASQVVPEFVEKLLKGLKAGSIAEF HST2 (*C. albicans*):
(SEQ ID NO: 93)
ASSPKKKRKVEASMPSLDDILKPVAEAVKNGKKVTFFNGAGISTGAGIPDFRSPDTGLYANLAKLNLP
FAEAVFDIDFFKEDPKPFYTLAEELYPGNFAPTKFHHFIKLLQDQGSLKRVYTQNIDTLERLAGVEDK
YIVEAHGSFASNHCVDCHKEMTTETLKTYMKDKKIPSCQHCEGYVKPDIVFFGEGLPVKFFDLWEDDC
EDVEVAIVAGTSLTVFPFASLPGEVNKKCLRVLVNKEKVGTFKHEPRKSDIIALHDCDIVAERLCTLL
GLDDKLNEVYEKEKIKYSKAETKEIKMHEIEDKLKEEAHLKEDKHTTKVDKKEKQNDANDKELEQLID
KAKAEF SIRT5 (human):
(SEQ ID NO: 94)
ASSPKKKRKVEASSSSMADFRKFFAKAKHIVIISGAGVSAESGVPTFRGAGGYWRKWQAQDLATPLAF
AHNPSRVWEFYHYRREVMGSKEPNAGHRAIAECETRLGKQGRRVVVITQNIDELHRKAGTKNLLEIHG -continued

SLFKTRCTSCGVVAENYKSPICPALSGKGAPEPGTQDASIPVEKLPRCEEAGCGGLLRPHVVWFGENL

DPAILEEVDRELAHCDLCLVVGTSSVVYPAAMFAPQVAARGVPVAEFNTETTPATNRFRFHFQGPCGT

TLPEALACHENETVSEF

Sir2A (*P. falciparum*):

(SEQ ID NO: 95)

ASSPKKKRKVEASMGNLMISFLKKDTQSITLEELAKIIKKCKHVVALTGSGTSAESNIPSFRGSSNSI

WSKYDPRIYGTIWGFWKYPEKIWEVIRDISSDYEIEINNGHVALSTLESLGYLKSVVTQNVDGLHEAS

GNTKVISLHGNVFEAVCCTCNKIVKLNKIMLQKTSHFMHQLPPECPCGGIFKPNIILFGEVVSSDLLK

EAEEEIAKCDLLLVIGTSSTVSTATNLCHFACKKKKKIVEINISKTYITNKMSDYHVCAKFSELTKVA

NILKGSSEKNKKIMEF

SIRT6 (human):

(SEQ ID NO: 96)

ASSPKKKRKVEASMSVNYAAGLSPYADKGKCGLPEIFDPPEELERKVWELARLVWQSSSVVFHTGAGI

STASGIPDFRGPHGVWTMEERGLAPKFDTTFESARPTQTHMALVQLERVGLLRFLVSQNVDGLHVRSG

FPRDKLAELHGNMFVEECAKCKTQYVRDTVVGTMGLKATGRLCTVAKARGLRACRGELRDTILDWEDS

LPDRDLALADEASRNADLSITLGTSLQIRPSGNLPLATKRRGGRLVIVNLQPTKHDRHADLRIHGYVD

EVMTRLMKHLGLEIPAWDGPRVLERALPPLEF

HMT effector domains:

NUE (*C. trachomatis*):

(SEQ ID NO: 97)

ASSPKKKRKVEASMTTNSTQDTLYLSLHGGIDSAIPYPVRRVEQLLQFSFLPELQFQNAAVKQRIQRL

CYREEKRLAVSSLAKWLGQLHKQRLRAPKNPPVAICWINSYVGYGVFARESIPAWSYIGEYTGILRRR

QALWLDENDYCFRYPVPRYSFRYFTIDSGMQGNVTRFINHSDNPNLEAIGAFENGIFHIIIRAIKDIL

PGEELCYHYGPLYWKHRKKREEFVPQEEEF vSET (*P. bursaria chlorella* virus):

(SEQ ID NO: 98)

ASSPKKKRKVEASMFNDRVIVKKSPLGGYGVFARKSFEKGELVEECLCIVRHNDDWGTALEDYLFSRK

NMSAMALGFGAIFNHSKDPNARHELTAGLKRMRIFTIKPIAIGEEITISYGDDYWLSRPRLTQNEF

SUV39H1 (human):

(SEQ ID NO: 99)

ASSPKKKRKVEASNLKCVRILKQFHKDLERELLRRHHRSKTPRHLDPSLANYLVQKAKQRRALRRWEQ

ELNAKRSHLGRITVENEVDLDGPPRAFVYINEYRVGEGITLNQVAVGCECQDCLWAPTGGCCPGASLH

KFAYNDQGQVRLRAGLPIYECNSRCRCGYDCPNRVVQKGIRYDLCIFRTDDGRGWGVRTLEKIRKNSF

VMEYVGEIITSEEAERRGQIYDRQGATYLFDLDYVEDVYTVDAAYYGNISHFVNHSCDPNLQVYNVFI

DNLDERLPRIAFFATRTIRAGEELTFDYNMQVDPVDMESTRMDSNFGLAGLPGSPKKRVRIECKCGTE

SCRKYLFEF

DIM5 (*N. crassa*):

(SEQ ID NO: 100)

ASSPKKKRKVEASMEKAFRPHFFNHGKPDANPKEKKNCHWCQIRSFATHAQLPISIVNREDDAFLNPN

FRFIDHSIIGKNVPVADQSFRVGCSCASDEECMYSTCQCLDEMAPDSDEEADPYTRKKRFAYYSQGAK

KGLLRDRVLQSQEPIYECHQGCACSKDCPNRVVERGRTVPLQIFRTKDRGWGVKCPVNIKRGQFVDRY

LGEIITSEEADRRRAESTIARRKDVYLFALDKFSDPDSLDPLLAGQPLEVDGEYMSGPTRFINHSCDP

NMAIFARVGDHADKHIHDLALFAIKDIPKGTELTFDYVNGLTGLESDAHDPSKISEMTKCLCGTAKCR

GYLWEF

KYP (*A. thaliana*):

(SEQ ID NO: 101)

ASSPKKKRKVEASDISGGLEFKGIPATNRVDDSPVSPTSGFTYIKSLIIEPNVIIPKSSTGCNCRGSC

TDSKKCACAKLNGGNFPYVDLNDGRLIESRDVVFECGPHCGCGPKCVNRTSQKRLRFNLEVFRSAKKG

-continued

WAVRSWEYIPAGSPVCEYIGVVRRTADVDTISDNEYIFEIDCQQTMQGLGGRQRRLRDVAVPMNNGVS

QSSEDENAPEFCIDAGSTGNFARFINHSCEPNLFVQCVLSSHQDIRLARVVLFAADNISPMQELTYDY

GYALDSVHEF

SUVR4 (*A. thaliana*):

(SEQ ID NO: 102)

ASSPKKKRKVEASQSAYLHVSLARISDEDCCANCKGNCLSADFPCTCARETSGEYAYTKEGLLKEKFL

DTCLKMKKEPDSFPKVYCKDCPLERDHDKGTYGKCDGHLIRKFIKECWRKCGCDMQCGNRVVQRGIRC

QLQVYFTQEGKGWGLRTLQDLPKGTFICEYIGEILTNTELYDRNVRSSSERHTYPVTLDADWGSEKDL

KDEEALCLDATICGNVARFINHRCEDANMIDIPIEIETPDRHYYHIAFFTLRDVKAMDELTWDYMIDF

NDKSHPVKAFRCCCGSESCRDRKIKGSQGKSIERRKIVSAKKQQGSKEVSKKRKEF

Set4 (*C. elegans*):

(SEQ ID NO: 103)

ASSPKKKRKVEASMQLHEQIANISVTFNDIPRSDHSMTPTELCYFDDFATTLVVDSVLNFTTHKMSKK

RRYLYQDEYRTARTVMKTFREQRDWTNAIYGLLTLRSVSHFLSKLPPNKLFEFRDHIVRFLNMFILDS

GYTIQECKRYSQEGHQGAKLVSTGVWSRGDKIERLSGVVCLLSSEDEDSILAQEGSDFSVMYSTRKRC

STLWLGPGAYINHDCRPTCEFVSHGSTAHIRVLRDMVPGDEITCFYGSEFFGPNNIDCECCTCEKNMN

GAFSYLRGNENAEPIISEKKTKYELRSRSEF

Set1 (*C. elegans*):

(SEQ ID NO: 104)

ASSPKKKRKVEASMKVAAKKLATSRMRKDRAAAASPSSDIENSENPSSLASHSSSSGRMTPSKNTRSR

KGVSVKDVSNHKITEFFQVRRSNRKTSKQISDEAKHALRDTVLKGTNERLLEVYKDVVKGRGIRTKVN

FEKGDFVVEYRGVMMEYSEAKVIEEQYSNDEEIGSYMYFFEHNNKKWCIDATKESPWKGRLINHSVLR

PNLKTKVVEIDGSHHLILVARRQIAQGEELLYDYGDRSAETIAKNPWLVNTEF

SETD8 (human)

(SEQ ID NO: 105)

ASSPKKKRKVEASSCDSTNAAIAKQALKKPIKGKQAPRKKAQGKTQQNRKLTDFYPVRRSSRKSKAEL

QSEERKRIDELIESGKEEGMKIDLIDGKGRGVIATKQFSRGDFVVEYHGDLIEITDAKKREALYAQDP

STGCYMYYFQYLSKTYCVDATRETNRLGRLINHSKCGNCQTKLHDIDGVPHLILIASRDIAAGEELLY

DYGDRSKASIEAFPWLKHEF

TgSET8 (*T. gondii*):

(SEQ ID NO: 106)

ASSPKKKRKVEASASRRTGEFLRDAQAPSRWLKRSKTGQDDGAFCLETWLAGAGDDAAGGERGRDREG

AADKAKQREERRQKELEERFEEMKVEFEEKAQRMIARRAALTGEIYSDGKGSKKPRVPSLPENDDDAL

IEIIIDPEQGILKWPLSVMSIRQRTVIYQECLRRDLTACIHLTKVPGKGRAVFAADTILKDDFVVEYK

GELCSEREAREREQRYNRSKVPMGSFMFYFKNGSRMMAIDATDEKQDFGPARLINHSRRNPNMTPRAI

TLGDFNSEPRLIFVARRNIEKGEELLVDYGERDPDVIKEHPWLNSEF

In some embodiments, ligand-dependent Cas9-intein variants are provided herein that exhibit decreased off-target activity. For example, in some embodiment, Cas9-intein variants are provided herein that comprise a Cas9 nuclease domain, or a nuclease-deficient Cas9 domain and a heterologous nucleic acid-editing domain, such as, for example, a heterologous nuclease domain, a recombinase domain, or a deaminase domain. In some such embodiments, the ligand-dependent Cas9-inteins provided herein exhibit decreased, minimal, or no off-target activity in the presence of a ligand at a concentration effective to effect excision of the intein from the Cas9-intein variant, or at a concentration effective to induce a desired modification (e.g., cleavage, nicking, recombination, or deamination) of a target site. In some embodiments, the ligand-dependent Cas9-intein variants provided herein exhibit an off-target activity in their active state (e.g., in the presence of or after being contacted with a suitable ligand) that is decreased as compared to the off-target activity of wild-type Cas9. For example, in some embodiments, the off-target activity of a Cas9-intein variant provided herein is decreased to less than 80%, less than 75%, less than 50%, less than 45%, less than 40%, less than 35%, less than 30%, less than 25%, less than 24%, less than 23%, less than 22%, less than 21%, less than 20, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% of wild-type Cas9 under the same conditions.

Pharmaceutical Compositions

In some embodiments, any of the ligand-dependent site-specific enzymes described herein are provided as part of a pharmaceutical composition. For example, some embodiments provide pharmaceutical compositions comprising a Cas9 protein comprising an intein, or fusion proteins comprising a dCas9 protein with an intein fused to a nuclease, recombinase, deaminase, or a transcriptional activator as provided herein, or a nucleic acid encoding such a protein, and a pharmaceutically acceptable excipient. Pharmaceutical compositions may further comprise one or more gRNA(s).

In some embodiments, compositions provided herein are administered to a subject, for example, to a human subject, in order to effect a targeted genomic modification within the subject. In some embodiments, cells are obtained from the subject and are contacted with an inventive ligand-dependent site-specific enzyme ex vivo. In some embodiments, cells removed from a subject and contacted ex vivo with an inventive ligand-dependent site-specific enzyme are re-introduced into the subject, optionally after the desired genomic modification has been effected and/or detected in the cells. Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, domesticated animals, pets, and commercially relevant mammals such as cattle, pigs, horses, sheep, cats, dogs, mice, and/or rats; and/or birds, including commercially relevant birds such as chickens, ducks, geese, and/or turkeys.

Formulations of the pharmaceutical compositions described herein may be prepared by any method known or hereafter developed in the art of pharmacology. In general, such preparatory methods include the step of bringing the active ingredient into association with an excipient, and then, if necessary and/or desirable, shaping and/or packaging the product into a desired single- or multi-dose unit.

Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. *Remington's The Science and Practice of Pharmacy,* $21^{st}$ Edition, A. R. Gennaro (Lippincott, Williams & Wilkins, Baltimore, MD, 2006; incorporated in its entirety herein by reference) discloses various excipients used in formulating pharmaceutical compositions and known techniques for the preparation thereof. See also PCT application PCT/US2010/055131, incorporated in its entirety herein by reference, for additional suitable methods, reagents, excipients and solvents for producing pharmaceutical compositions comprising a nuclease. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this disclosure.

In some embodiments, compositions in accordance with the present invention may be used for treatment of any of a variety of diseases, disorders, and/or conditions, including, but not limited to, autoimmune disorders (e.g. diabetes, lupus, multiple sclerosis, psoriasis, rheumatoid arthritis); inflammatory disorders (e.g. arthritis, pelvic inflammatory disease); infectious diseases (e.g. viral infections (e.g., HIV, HCV, RSV), bacterial infections, fungal infections, sepsis); neurological disorders (e.g. Alzheimer's disease, Huntington's disease; autism; Duchenne muscular dystrophy); cardiovascular disorders (e.g. atherosclerosis, hypercholesterolemia, thrombosis, clotting disorders, angiogenic disorders such as macular degeneration); proliferative disorders (e.g. cancer, benign neoplasms); respiratory disorders (e.g. chronic obstructive pulmonary disease); gastrointestinal disorders (e.g. inflammatory bowel disease, ulcers); musculoskeletal disorders (e.g. fibromyalgia, arthritis); endocrine, metabolic, and nutritional disorders (e.g. diabetes, osteoporosis); genitourinary disorders (e.g. renal disease); psychological disorders (e.g. depression, schizophrenia); skin disorders (e.g. wounds, eczema); and blood and lymphatic disorders (e.g. anemia, hemophilia); etc.

Methods

In another aspect of this disclosure, methods for site-specific nucleic acid (e.g., DNA) modification are provided. In some embodiments, the methods comprise contacting a DNA with any of the ligand-dependent Cas9 proteins (complexed with a gRNA) described herein, either before or after contacting the protein with a ligand that induces self-excision of the ligand-dependent intein thereby activating the nuclease. For example, in some embodiments, the method comprises (a) contacting a RNA-guided nuclease (e.g., a Cas9 protein including Cas9 nickase) comprising a ligand-dependent intein with a ligand, wherein binding of the ligand to the intein induces self-excision of the intein; and (b); contacting a DNA with the RNA-guided nuclease, wherein the RNA-guided nuclease is associated with a gRNA; whereby self-excision of the intein from the RNA-guided nuclease in step (a) allows the RNA-guided nuclease to cleave the DNA, thereby producing cleaved DNA. In some embodiments, for examples those involving the use of an intein containing Cas9 nickase, the method produces a single strand break in the DNA. In some embodiments, the method produces a double strand break in the DNA. In some embodiments, the RNA-guided nuclease is able to bind a gRNA and optionally bind a target nucleic acid prior to being contacted with a ligand that induces self-excision of the intein, but the RNA-guided nuclease is unable to cleave the target nucleic acid until self-excision of the intein occurs. In some embodiments, the RNA-guided nuclease is unable to bind a gRNA and therefore is unable to bind a target nucleic acid until the RNA-guided nuclease is contacted with a ligand that induces self-excision of the intein. In some embodiments, the RNA-guided nuclease is any nuclease comprising Cas9 (or a variant or a fragment thereof) which comprises a ligand-dependent intein as provided herein.

In some embodiments, the method involves the use of fusion proteins comprising a nuclease-inactivated Cas9 (e.g., dCas9) fused to a nuclease domain (e.g., FokI), wherein the fusion protein comprises a ligand-dependent intein (e.g., in the dCas9 domain as provided herein), and the fusion protein lacks one or more activities (as described herein) prior to excision of the intein. In some embodiments, the fusion protein is any fusion protein described herein. In some embodiments, the method comprises contacting a target nucleic acid (e.g., DNA) with two such fusion proteins, each comprising a distinct gRNA that targets the nucleic acid, and the method comprises contacting the target nucleic acid with two such fusion proteins. The method increases the specificity of cleavage, and therefore decreases off target effects, as two fusions are required to bind the target site to elicit any nuclease activity as the nuclease domains fused to the dCas9 domain typically must dimerize at the target site to induce cleavage. In some embodiments, the method comprises contacting the fusion proteins with a ligand that induces self-excision of the intein, either before or after the gRNAs bind the fusion proteins, and/or before or after the fusion proteins bind the target nucleic acid. Once the fusion proteins are activated following excision of the intein, the nuclease domains (e.g., the FokI domains) dimerize and cleave and the target nucleic acid. Compositions and methods of using dCas9-FokI fusions are known to those of skill in the art (see, e.g., U.S. patent application Ser. No. 14/320,498, titled "CAS9 VARIANTS AND USES THEREOF" which was filed on Jun. 30, 2014; the entire contents of which are incorporated herein by reference). Those of skill in the art are routinely able to design appropriate gRNAs that target two of the fusion proteins to a target nucleic acid, and understand that in some aspects the gRNAs are designed to hybridize to regions of the target nucleic acid that are no more than 10, no more than 15, no more than 20, no more than 25, no more than 30, no more than 40, no more than 50, no more than 60, no more than 70, no more than 80, no more than 90, or no more than 100 base pairs apart.

In some embodiments, any of the methods provided herein can be performed on DNA in a cell. For example, in some embodiments the DNA contacted by any of the inventive ligand-dependent site-specific Cas9 enzymes provided herein is in a eukaryotic cell. In some embodiments, the eukaryotic cell is in an individual. In some embodiments, the individual is a human. In some embodiments, any of the methods provided herein are performed in vitro. In some embodiments, any of the methods provided herein are performed in vivo.

In some embodiments of this disclosure, methods for site-specific nucleic acid (e.g., DNA) recombination are provided. In some embodiments, the methods are useful for inducing recombination of or between two or more regions of two or more nucleic acids (e.g., DNA). In some embodiments, the methods are useful for inducing recombination of or between two or more regions in a single nucleic acid molecule (e.g., DNA). Because the recombinase fusion proteins used in the methods are ligand-dependent, the timing of recombination can be controlled to minimize off-target effects. In some embodiments, the recombination of one or more target nucleic acid molecules requires the formation of a tetrameric complex at the target site. Typically, the tetramer comprises four (4) inventive RNA-guided recombinase fusion proteins (e.g., a complex of any four inventive recombinase fusion proteins provided herein). In some embodiments, each recombinase fusion protein of the tetramer targets a particular DNA sequence via a distinct gRNA bound to each recombinase fusion protein. In some embodiments, the fusion proteins are first contacted with a ligand that induces self-excision of the intein, thereby allowing the fusion proteins to (i) bind a gRNA, (ii) bind a target nucleic acid(s), and (iii) form a complex to induce recombination between the target nucleic acid(s). In some embodiments, the fusion proteins are able to bind a gRNA prior to excision of the intein and optionally are able to bind the target nucleic acid(s) but are unable to induce recombination until the intein is excised (e.g., through the addition of a ligand that binds the ligand-dependent intein). Any of the ligand-dependent recombinase fusion proteins provided herein are useful for methods for site-specific recombination.

In some embodiments, the method for site-specific recombination between two DNA molecules comprises (a) contacting a first DNA with a first ligand-dependent RNA-guided recombinase fusion protein, wherein the nuclease-inactivated Cas9 domain binds a first gRNA that hybridizes to a region of the first DNA; (b) contacting the first DNA with a second ligand-dependent RNA-guided recombinase fusion protein, wherein the nuclease-inactivated Cas9 domain of the second fusion protein binds a second gRNA that hybridizes to a second region of the first DNA; (c) contacting a second DNA with a third ligand-dependent RNA-guided recombinase fusion protein, wherein the nuclease-inactivated Cas9 domain of the third fusion protein binds a third gRNA that hybridizes to a region of the second DNA; and (d) contacting the second DNA with a fourth ligand-dependent RNA-guided recombinase fusion protein, wherein the nuclease-inactivated Cas9 domain of the fourth fusion protein binds a fourth gRNA that hybridizes to a second region of the second DNA. In some embodiments, the fusion proteins are first contacted with a ligand that induces self-excision of the intein prior to forming a complex with a gRNA and/or prior to hybridizing with a target DNA. In some embodiments, the method comprises contacting the fusion proteins with the ligand after the fusion proteins form a complex and/or hybridizes to a target DNA. Typically, the binding of the fusion proteins in steps (a)-(d) results in the tetramerization of the recombinase catalytic domains of the fusion proteins, such that the DNAs are recombined (i.e., following excision of the intein). In some embodiments, the gRNAs of steps (a) and (b) hybridize to opposing strands of the first DNA, and the gRNAs of steps (c) and (d) hybridize to opposing strands of the second DNA. In some embodiments, the target sites of the gRNAs of steps (a)-(d) are spaced to allow for tetramerization of the recombinase catalytic domains. For example, in some embodiments, the target sites of the gRNAs of steps (a)-(d) are no more than 10, no more 15, no more than 20, no more than 25, no more than 30, no more than 40, no more than 50, no more than 60, no more than 70, no more than 80, no more than 90, or no more than 100 base pairs apart. In some embodiments, the two regions of the two DNA molecules being recombined share homology, such that the regions being recombined are at least 80%, at least 90%, at least 95%, at least 98%, or are 100% homologous.

In some embodiments, methods for site-specific recombination between two regions of a single DNA molecule are provided. In some embodiments, the methods comprise (a) contacting a DNA with a first dCas9-recombinase fusion protein, wherein the dCas9 domain binds a first gRNA that hybridizes to a region of the DNA; (b) contacting the DNA with a second dCas9-recombinase fusion protein, wherein the dCas9 domain of the second fusion protein binds a second gRNA that hybridizes to a second region of the DNA; (c) contacting the DNA with a third dCas9-recombinase fusion protein, wherein the dCas9 domain of the third fusion protein binds a third gRNA that hybridizes to a third region of the DNA; and (d) contacting the DNA with a fourth dCas9-recombinase fusion protein, wherein the dCas9 domain of the fourth fusion protein binds a fourth gRNA that hybridizes to a fourth region of the DNA. In some embodiments, the fusion proteins are first contacted with a ligand that induces self-excision of the intein prior to forming a complex with a gRNA and/or prior to hybridizing with a target DNA. In some embodiments, the method comprises contacting the fusion proteins with the ligand after the fusion proteins form a complex and/or hybridizes to a target DNA. Typically, the binding of the fusion proteins in steps (a)-(d) results in the tetramerization of the recombinase catalytic domains of the fusion proteins, such that the DNA is recombined (e.g. following the excision of the intein). In some embodiments, two of the gRNAs of steps (a)-(d) hybridize to the same strand of the DNA, and the other two gRNAs of steps (a)-(d) hybridize to the opposing strand of the DNA. In some embodiments, the gRNAs of steps (a) and (b) hybridize to regions of the DNA that are no more 10, no more than 15, no more than 20, no more than 25, no more than 30, no more than 40, no more than 50, no more than 60, no more than 70, no more than 80, no more than 90, or no more than 100 base pairs apart, and the gRNAs of steps (c) and (d) hybridize to regions of the DNA that are no more than 10, no more 15, no more than 20, no more than 25, no more than 30, no more than 40, no more than 50, no more than 60, no more than 70, no more than 80, no more than 90, or no more than 100 base pairs apart. In some embodiments, the two regions of the DNA molecule being recombined share homology, such that the regions being recombined are at least 80%, at least 90%, at least 95%, at least 98%, or are 100% homologous.

In some embodiments, any of the inventive methods for site-specific recombination are amenable for inducing recombination, such that the recombination results in excision (e.g., a segment of DNA is excised from a target DNA molecule), insertion (e.g., a segment of DNA is inserted into a target DNA molecule), inversion (e.g., a segment of DNA is inverted in a target DNA molecule), or translocation (e.g., the exchange of DNA segments between one or more target DNA molecule(s)). In some embodiments, the particular recombination event (e.g., excision, insertion, inversion, translocation, etc.) depends, inter alia, on the orientation (e.g., with respect to the target DNA molecule(s)) of the bound RNA-guided recombinase fusion protein(s). In some embodiments, the orientation, or direction, in which a RNA-guided recombinase fusion protein binds a target nucleic acid can be controlled, e.g., by the particular sequence of the gRNA bound to the RNA-guided recombinase fusion protein(s). Methods for controlling or directing a particular recombination event are known in the art, and include, for example, those described by Turan and Bode, "Site-specific recombinases: from tag-and-target- to tag-and-exchange-based genomic modifications." *FASEB J.* 2011; December; 25(12):4088-107, the entire contents of which are hereby incorporated by reference.

In some embodiments, any of the methods for site-specific recombination can be performed in vivo or in vitro. In some embodiments, any of the methods for site-specific recombination are performed in a cell (e.g., recombining genomic DNA in a cell). The cell can be prokaryotic or eukaryotic. The cell, such as a eukaryotic cell, can be in an individual, such as a subject, as described herein (e.g., a human subject). The methods described herein are useful for the genetic modification of cells in vitro and in vivo, for example, in the context of the generation of transgenic cells, cell lines, or animals, or in the alteration of genomic sequence, e.g., the correction of a genetic defect, in a cell in or obtained from a subject. In some embodiments, a cell obtained from a subject and modified according to the methods provided herein, is re-introduced into a subject (e.g., the same subject), e.g., to treat a disease, or for the production of genetically modified organisms in agricultural, medical, or biological research.

In applications in which it is desirable to recombine two or more nucleic acids so as to insert a nucleic acid sequence into a target nucleic acid, a nucleic acid comprising a donor sequence to be inserted is also provided, e.g., to a cell. By a "donor sequence" it is meant a nucleic acid sequence to be inserted at the target site induced by one or more RNA-guided recombinase fusion protein(s). In some embodiments, e.g., in the context of genomic modifications, the donor sequence will share homology to a genomic sequence at the target site, e.g., 1%, 2%, 3%, 4%, 5%, 10%, 20%, 30%, 40%, 50%, 60%, 70%, 80%, 85%, 90%, 95%, or 100% homology with the nucleotide sequences flanking the target site, e.g., within about 100 bases or less of the target site, e.g. within about 90 bases, within about 80 bases, within about 70 bases, within about 60 bases, within about 50 bases, within about 40 bases, within about 30 bases, within about 15 bases, within about 10 bases, within about 5 bases, or immediately flanking the target site. In some embodiments, the donor sequence does not share any homology with the target nucleic acid, e.g., does not share homology to a genomic sequence at the target site. Donor sequences can be of any length, e.g., 10 nucleotides or more, 50 nucleotides or more, 100 nucleotides or more, 250 nucleotides or more, 500 nucleotides or more, 1000 nucleotides or more, 5000 nucleotides or more, 10000 nucleotides or more, 100000 nucleotides or more, etc.

Typically, the donor sequence is not identical to the target sequence that it replaces or is inserted into. In some embodiments, the donor sequence contains at least one or more single base changes, insertions, deletions, inversions, or rearrangements with respect to the target sequence (e.g., target genomic sequence). In some embodiments, donor sequences also comprise a vector backbone containing sequences that are not homologous to the DNA region of interest and that are not intended for insertion into the DNA region of interest.

The donor sequence may comprise certain sequence differences as compared to the target (e.g., genomic) sequence, for example, restriction sites, nucleotide polymorphisms, selectable markers (e.g., drug resistance genes, fluorescent proteins, enzymes etc.), which can be used to assess successful insertion of the donor sequence at the target site or in some cases may be used for other purposes (e.g., to signify expression at the targeted genomic locus). In some embodiments, if located in a coding region, such nucleotide sequence differences will not change the amino acid sequence, or will make silent amino acid changes (e.g., changes which do not affect the structure or function of the protein). In some embodiments, these sequences differences may include flanking recombination sequences such as FLPs, loxP sequences, or the like, that can be activated at a later time for removal of e.g., a marker sequence. The donor sequence may be provided to the cell as single-stranded DNA, single-stranded RNA, double-stranded DNA, or double-stranded RNA. It may be introduced into a cell in linear or circular form. If introduced in linear form, the ends of the donor sequence may be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, e.g., Chang et al., *Proc. Natl. Acad Sci USA.* 1987; 84:4959-4963; Nehls et al., *Science.* 1996; 272:886-889. In some embodiments, a donor sequence is introduced into a cell as part of a vector molecule having additional sequences such as, for example, replication origins, promoters, and genes encoding antibiotic resistance. In some embodiments, donor sequences can be introduced as naked nucleic acid, as nucleic acid complexed with an agent such as a liposome or polymer (e.g., poloxamer), or can be delivered by viruses (e.g., adenovirus, AAV, etc.).

In some embodiments, any of the methods provided herein can be performed on DNA in a cell. For example, in some embodiments the DNA contacted by any RNA/gRNA-comprising complex provided herein is in a eukaryotic cell. In some embodiments, the eukaryotic cell is in an individual. In some embodiments, the individual is a human. In some embodiments, any of the methods provided herein are performed in vitro. In some embodiments, any of the methods provided herein are performed in vivo.

In some embodiments of this disclosure, methods for site-specific nucleic acid (e.g., DNA) editing are provided. In some embodiments, the fusion protein is used to introduce a point mutation into a nucleic acid by deaminating a target nucleobase, e.g., a cytidine (C) residue. In some embodiments, the method comprises contacting a DNA molecule with a ligand-dependent fusion protein comprising a nuclease inactivated RNA-guided nuclease (e.g., dCas9), which comprises a ligand dependent intein, fused to a deaminase, and (b) a gRNA targeting the fusion protein of step (a) to a target nucleotide sequence of the DNA strand; wherein the DNA molecule is contacted with the fusion protein and the gRNA in an amount effective and under conditions suitable for the deamination of a nucleotide base. Any of the fusion proteins comprising a gene editing domain as provided herein are amenable for use in the methods. In some embodiments, the method first comprises contacting the fusion protein with a ligand that induces self-excision of the intein prior to forming a complex with the gRNA. In some embodiments, the method comprises contacting the fusion protein with a ligand that induces self-excision of the intein after the fusion protein has formed a complex with the gRNA.

In some embodiments, the deamination of the target nucleobase results in the correction of a genetic defect, e.g., in the correction of a point mutation that leads to a loss of function in a gene product. In some embodiments, the genetic defect is associated with a disease or disorder, e.g., a lysosomal storage disorder or a metabolic disease, such as, for example, type I diabetes. In some embodiments, the methods provided herein are used to introduce a deactivating point mutation into a gene or allele that encodes a gene product that is associated with a disease or disorder. For example, in some embodiments, methods are provided herein that employ a DNA editing fusion protein to introduce a deactivating point mutation into an oncogene (e.g., in the treatment of a proliferative disease). A deactivating mutation may, in some embodiments, generate a premature stop codon in a coding sequence, which results in the expression of a truncated gene product, e.g., a truncated protein lacking the function of the full-length protein.

In some embodiments, the purpose of the methods provided herein is to restore the function of a dysfunctional gene via genome editing. Compositions and methods of using gene editing enzymes fused e.g., to Cas9 are known, and include those described in U.S. patent application Ser. No. 14/325,815 titled "FUSIONS OF CAS9 DOMAINS AND NUCLEIC ACID-EDITING DOMAINS," and filed on Jul. 8, 2014; the entire contents of which are incorporated herein by reference. The fusion proteins provided herein (comprising ligand-dependent inteins) can be validated for gene editing-based human therapeutics in vitro, e.g., by correcting a disease-associated mutation in human cell culture. It will be understood by the skilled artisan that the fusion proteins provided herein, e.g., the fusion proteins comprising a dCas9 domain (e.g., comprising a ligand-dependent intein) and a nucleic acid deaminase domain can be used to correct any single point T→C or A→G mutation. In the first case, deamination of the mutant C back to U corrects the mutation, and in the latter case, deamination of the C that is base-paired with the mutant G, followed by a round of replication, corrects the mutation.

An exemplary disease-relevant mutation that can be corrected by the provided fusion proteins in vitro or in vivo is the H1047R (A3140G) polymorphism in the PI3KCA protein. The phosphoinositide-3-kinase, catalytic alpha subunit (PI3KCA) protein acts to phosphorylate the 3-OH group of the inositol ring of phosphatidylinositol. The PI3KCA gene has been found to be mutated in many different carcinomas, and thus it is considered to be a potent oncogene (Lee et al., PIK3CA gene is frequently mutated in breast carcinomas and hepatocellular carcinomas. *Oncogene.* 2005; 24(8): 1477-80). In fact, the A3140G mutation is present in several NCI-60 cancer cell lines, such as, for example, the HCT116, SKOV3, and T47D cell lines, which are readily available from the American Type Culture Collection (ATCC)(Ikediobi et al., Mutation analysis of 24 known cancer genes in the NCI-60 cell line set. *Mol Cancer Ther.* 2006; 5(11): 2606-12.

In some embodiments, a cell carrying a mutation to be corrected, e.g., a cell carrying a point mutation, e.g., an A3140G point mutation in exon 20 of the PI3KCA gene, resulting in a H1047R substitution in the PI3KCA protein is contacted with an expression construct encoding a ligand-dependent Cas9 deaminase fusion protein and an appropriately designed gRNA targeting the fusion protein to the respective mutation site in the encoding PI3KCA gene. Control experiments can be performed where the gRNAs are designed to target the fusion enzymes to non-C residues that are within the PI3KCA gene. Genomic DNA of the treated cells can be extracted, and the relevant sequence of the PI3KCA genes PCR amplified and sequenced to assess the activities of the fusion proteins in human cell culture.

It will be understood that the example of correcting point mutations in PI3KCA is provided for illustration purposes and is not meant to limit the instant disclosure. The skilled artisan will understand that the instantly disclosed ligand-dependent DNA-editing fusion proteins can be used to correct other point mutations and mutations associated with other cancers and with diseases other than cancer including other proliferative diseases.

The successful correction of point mutations in disease-associated genes and alleles opens up new strategies for gene correction with applications in therapeutics and basic research. Site-specific single-base modification systems like the disclosed fusions of ligand-dependent Cas9 and deaminase enzymes or domains also have applications in "reverse" gene therapy, where certain gene functions are purposely suppressed or abolished. In these cases, site-specifically mutating Trp (TGG), Gln (CAA and CAG), or Arg (CGA) residues to premature stop codons (TAA, TAG, TGA) can be used to abolish protein function in vitro, ex vivo, or in vivo.

The instant disclosure provides methods for the treatment of a subject diagnosed with a disease associated with or caused by a point mutation that can be corrected by a ligand-dependent Cas9 DNA editing fusion protein provided herein. For example, in some embodiments, a method is provided that comprises administering to a subject having such a disease, e.g., a cancer associated with a PI3KCA point mutation as described above, an effective amount of a ligand-dependent Cas9 deaminase fusion protein that corrects the point mutation or introduces a deactivating mutation into the disease-associated gene, e.g., following subsequent administration of the small molecule (e.g., ligand) that activates the fusion protein. In some embodiments, the disease is a proliferative disease. In some embodiments, the disease is a genetic disease. In some embodiments, the disease is a neoplastic disease. In some embodiments, the disease is a metabolic disease. In some embodiments, the disease is a lysosomal storage disease. Other diseases that can be treated by correcting a point mutation or introducing a deactivating mutation into a disease-associated gene will be known to those of skill in the art, and the disclosure is not limited in this respect.

The instant disclosure provides methods for the treatment of additional diseases or disorders, e.g., diseases or disorders that are associated or caused by a point mutation that can be corrected by deaminase-mediated gene editing. Some such diseases are described herein, and additional suitable diseases that can be treated with the strategies and fusion proteins provided herein will be apparent to those of skill in the art based on the instant disclosure. Exemplary suitable diseases and disorders include, without limitation, cystic fibrosis (see, e.g., Schwank et al., Functional repair of CFTR by CRISPR/Cas9 in intestinal stem cell organoids of cystic fibrosis patients. *Cell stem cell.* 2013; 13: 653-658; and Wu et. al., Correction of a genetic disease in mouse via use of CRISPR-Cas9. *Cell stem cell.* 2013; 13: 659-662, neither of which uses a deaminase fusion protein to correct the genetic defect); phenylketonuria—e.g., phenylalanine to serine mutation at position 835 in phenylalanine hydroxylase gene (T>C mutation)—see, e.g., McDonald et al., *Genomics.* 1997; 39:402-405; Bernard-Soulier syndrome (BSS)—e.g., phenylalanine to serine mutation at position 55 in the platelet membrane glycoprotein IX (T>C mutation)—see, e.g., Noris et al., *British Journal of Haematology.* 1997; 97: 312-320; epidermolytic hyperkeratosis (EHK)—e.g., leucine to proline mutation at position 160 in keratin 1 (T>C mutation)—see, e.g., Chipev et al., *Cell.* 1992; 70: 821-828; chronic obstructive pulmonary disease (COPD)—e.g., leucine to proline mutation at position 55 in $\alpha_1$-antitrypsin (T>C mutation)—see, e.g., Poller et al., *Genomics.* 1993; 17: 740-743; Charcot-Marie-Toot disease type 4J—e.g., leucine to proline mutation at position 197 in FIG. 4 (T>C mutation)—see, e.g., Kundu et al., 3 *Biotech.* 2013; 3: 225-234; neuroblastoma (NB)—e.g., isoleucine to threonine mutation at position 41 in Caspase-9 (T>C mutation)—see, e.g., Lenk et al., *PLoS Genetics.* 2011; 7: e1002104; von Willebrand disease (vWD)—e.g., cysteine to arginine mutation at position 509 in von Willebrand factor (T>C mutation)—see, e.g., Lavergne et al., *Br. J. Haematol.* 1992; 82: 66-72; myotonia congenital—e.g., cysteine to arginine mutation at position 277 in the muscle chloride channel gene CLCN1 (T>C mutation)—see, e.g., Weinberger et al., *The J. of Physiology.* 2012; 590: 3449-3464; hereditary renal amyloidosis—e.g., stop codon to arginine mutation at position 78 in apolipoprotein AII (T>C mutation)—see, e.g., Yazaki et al., *Kidney Int.* 2003; 64: 11-16; dilated cardiomyopathy (DCM)—e.g., tryptophan to Arginine mutation at position 148 in the FOXD4 gene (T>C mutation), see, e.g., Minoretti et. al., *Int. J. of Mol. Med.* 2007; 19: 369-372; hereditary lymphedema—e.g., histidine to arginine mutation at position 1035 in tyrosine kinase (A>G mutation), see, e.g., Irrthum et al., *Am. J. Hum. Genet.* 2000; 67: 295-301; familial Alzheimer's disease—e.g., isoleucine to valine mutation at position 143 in presenilinl (A>G mutation), see, e.g., Gallo et. al., *J. Alzheimer's disease.* 2011; 25: 425-431; Prion disease—e.g., methionine to valine mutation at position 129 in prion protein (A>G mutation)—see, e.g., Lewis et. al., *J. of General Virology.* 2006; 87: 2443-2449; chronic infantile neurologic cutaneous articular syndrome (CINCA)—e.g., Tyrosine to Cysteine mutation at position 570 in cryopyrin (A>G mutation)—see, e.g., Fujisawa et. al. *Blood.* 2007; 109: 2903-2911; and desmin-related myopathy (DRM)—e.g., arginine to glycine mutation at position 120 in aB crystallin (A>G mutation)—see, e.g., Kumar et al., *J. Biol. Chem.* 1999; 274: 24137-24141. The entire contents of each of the foregoing references and database entries are incorporated herein by reference.

According to another aspect, methods for transcriptional activation of a gene are provided. In some embodiments, the methods comprise contacting a DNA molecule comprising a gene with (a) a ligand-dependent dCas9 fusion protein comprising a transcriptional activator (e.g., any of those provided herein) and (b) a gRNA targeting the fusion protein of (a) to a target nucleotide sequence of the DNA strand; wherein the DNA molecule is contacted with the fusion protein and the gRNA in an amount effective and under conditions suitable for the transcriptional activation of the gene. In some embodiments, the method further comprises contacting the fusion protein with a ligand that induces self-excision of the intein. In some embodiments, the fusion protein is contacted with the ligand prior to forming a complex with a gRNA. In some embodiments, the fusion protein is contacted with the ligand after forming a complex with a gRNA. In some embodiments, the gRNA targets the promoter region of a gene. Methods for inducing gene activation using fusion proteins comprising a transcriptional activator are known in the art, and include those described by Perex-Pinera et al., "RNA-guided gene activation by CRISPR-Cas9-based transcription factors." *Nature Methods.* 2013; 10, 973-976; the entire contents of which are incorporated herein by reference.

According to another aspect, methods for transcriptional repression of a gene are provided. In some embodiments, the methods comprise contacting a DNA molecule comprising a gene with (a) a ligand-dependent dCas9 fusion protein comprising a transcriptional repressor (e.g., any of those provided herein) and (b) a gRNA targeting the fusion protein of (a) to a target nucleotide sequence of the DNA strand; wherein the DNA molecule is contacted with the fusion protein and the gRNA in an amount effective and under conditions suitable for the transcriptional repression of the gene. In some embodiments, the method further comprises contacting the fusion protein with a ligand that induces self-excision of the intein. In some embodiments, the fusion protein is contacted with the ligand prior to forming a complex with a gRNA. In some embodiments, the fusion protein is contacted with the ligand after forming a complex with a gRNA. In some embodiments, the gRNA targets the promoter region of a gene. Methods for inducing gene repression using fusion proteins comprising a transcriptional repressor are known in the art, and include those described by Gilbert et al., CRISPR-mediated modular RNA-guided regulation of transcription in eukaryotes. *Cell.* 2013; 154, 442-451; the entire contents of which are incorporated herein by reference.

According to another aspect, methods for epigenetic modification of DNA are provided. In some embodiments, the methods comprise contacting a DNA molecule comprising with (a) a ligand-dependent dCas9 fusion protein comprising an epigenetic modifier (e.g., any of those provided herein) and (b) a gRNA targeting the fusion protein of (a) to a target nucleotide sequence of the DNA strand; wherein the DNA molecule is contacted with the fusion protein and the gRNA in an amount effective and under conditions suitable for the epigenetic modification of the DNA. In some embodiments, the DNA comprises one or more genes. In some embodiments, the method further comprises contacting the fusion protein with a ligand that induces self-excision of the intein. In some embodiments, the fusion protein is contacted with the ligand prior to forming a complex with a gRNA. In some embodiments, the fusion protein is contacted with the ligand after forming a complex with a gRNA. In some embodiments, the gRNA targets the promoter region of a gene. In some embodiments, the epigenetic modification that results is methylation od DNA. In some embodiments, the epigenetic modification that results is demethylation of DNA. In some embodiments, the epigenetic modification that results is methylation of histone protein. In some embodiments, the epigenetic modification that results is demethylation of histone protein. In some embodiments, the epigenetic modification that results is acetylation of histone protein. In some embodiments, the epigenetic modification that results is deacetylation of histone protein. Methods for inducing epigenetic modifications using fusion proteins comprising an epigenetic modifier are known in the art, and include those described by Konermann et al., Optical control of mammalian endogenous transcription and epigenetic states. *Nature.* 2013; 500, 472-476; Mendenhall et al., Locus-specific editing of histone modifications at endogenous enhancers. *Nat. Biotechnol.* 2013; 31, 1133-1136; and Maeder et al., Targeted DNA demethylation and activation of endogenous genes using programmable TALE-TET1 fusion proteins. *Nat. Biotechnol.* 2013; 31, 1137-1142; the entire contents of which are incorporated herein by reference.

In some embodiments, any of the methods provided herein can be performed on DNA in a cell. For example, in some embodiments the DNA contacted by any RNA/gRNA-comprising complex provided herein is in a eukaryotic cell. In some embodiments, the eukaryotic cell is in an individual. In some embodiments, the individual is a human. In some embodiments, any of the methods provided herein are performed in vitro. In some embodiments, any of the methods provided herein are performed in vivo.

In some embodiments of the methods provided herein, the ligand-dependent Cas9 protein, e.g., the Cas9-intein or the Cas9-intein fusion protein, is contacted with the ligand at a concentration effective to excise the intein from the Cas9-intein variant, or at a concentration effective to induce a desired modification (e.g., cleavage, nicking, recombination, or deamination) of a target site. In some embodiments, a ligand-dependent Cas9 protein provided herein is contacted with a suitable ligand at a concentration resulting in decreased off-target activity of the Cas9 protein as compared to the off-target activity of wild-type Cas9. For example, in some embodiments, a method provided herein comprises contacting a population of ligand-dependent Cas9 proteins in vitro or in vivo in the presence of a target nucleic acid to be modified with a suitable ligand at a concentration resulting in the desired modification of the target nucleic acid, and in either no off-target activity (i.e., no modification of any non-target nucleic acids) or in an off-target activity of less than 80%, less than 75%, less than 50%, less than 45%, less than 40%, less than 35%, less than 30%, less than 25%, less than 24%, less than 23%, less than 22%, less than 21%, less than 20, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% of the off-target activity observed or expected under the same conditions when using wild-type Cas9.

Polynucleotides, Vectors, Cells, Kits

In another aspect of this disclosure, polynucleotides encoding one or more of the inventive proteins and/or gRNAs are provided. For example, polynucleotides encoding any of the proteins described herein are provided, e.g., for recombinant expression and purification of isolated nucleases, recombinases, gene editing enzymes, and other nucleic acid modifying enzymes, e.g., comprising Cas9 variants (e.g., dCas9) comprising ligand-dependent inteins. In some embodiments, an isolated polynucleotide comprises one or more sequences encoding a ligand dependent RNA-guided nuclease (e.g., Cas9). In some embodiments, an isolated polynucleotide comprises one or more sequences encoding a Cas9 fusion protein, for example, any of the Cas9 fusion proteins described herein (e.g., those comprising a nuclease-inactivated Cas9 fused to a nuclease, recombinase, deaminase domain, or transcriptional activator). In some embodiments, an isolated polynucleotides comprises one or more sequences encoding a gRNA, alone or in combination with a sequence encoding any of the proteins described herein.

In some embodiments, vectors encoding any of the proteins described herein are provided, e.g., for recombinant expression and purification of Cas9 proteins, and/or fusions comprising Cas9 proteins (e.g., variants). In some embodiments, the vector comprises or is engineered to include an isolated polynucleotide, e.g., those described herein. In some embodiments, the vector comprises one or more sequences encoding a Cas9 protein (as described herein), a gRNA, or combinations thereof, as described herein. Typically, the vector comprises a sequence encoding an inventive protein operably linked to a promoter, such that the fusion protein is expressed in a host cell.

In some embodiments, cells are provided, e.g., for recombinant expression and purification of any of the Cas9 proteins provided herein. The cells include any cell suitable for recombinant protein expression, for example, cells comprising a genetic construct expressing or capable of expressing an inventive protein (e.g., cells that have been transformed with one or more vectors described herein, or cells having genomic modifications, for example, those that express a protein provided herein from an allele that has been incorporated into the cell's genome). Methods for transforming cells, genetically modifying cells, and expressing genes and proteins in such cells are well known in the art, and include those provided by, for example, Green and Sambrook, *Molecular Cloning: A Laboratory Manual* (4th ed., Cold Spring Harbor Laboratory Press, Cold Spring Harbor, N.Y. (2012)) and Friedman and Rossi, Gene Transfer: Delivery and Expression of DNA and RNA, *A Laboratory Manual* ($1^{st}$ ed., Cold Spring Harbor Laboratory Press, Cold Spring Harbor, N.Y. (2006)).

Some aspects of this disclosure provide kits comprising a ligand-dependent Cas9 variant (e.g., a ligand dependent Cas9 nuclease (or nickase), and/or a ligand-dependent dCas9 variant fused to a nuclease, recombinase, deaminase, or a transcriptional activator as provided herein. In some embodiments, the kit comprises a polynucleotide encoding an inventive Cas9 variant, nuclease, recombinase, and/or deaminase e.g., as provided herein. In some embodiments, the kit comprises a vector for recombinant protein expression, wherein the vector comprises a polynucleotide encoding any of the proteins provided herein. In some embodiments, the kit comprises a cell (e.g., any cell suitable for expressing Cas9 proteins or fusions comprising Cas9 proteins, such as bacterial, yeast, or mammalian cells) that comprises a genetic construct for expressing any of the proteins provided herein. In some embodiments, any of the kits provided herein further comprise one or more gRNAs and/or vectors for expressing one or more gRNAs. In some embodiments, the kit comprises an excipient and instructions for contacting the Cas9 proteins or dCas9 fusions with the excipient to generate a composition suitable for contacting a nucleic acid with the inventive protein. In some embodiments, the composition is suitable for delivering an inventive protein to a cell, or for delivering a nucleic acid encoding the protein to a cell. In some embodiments, the composition is suitable for delivering an inventive protein to a subject. In some embodiments, the excipient is a pharmaceutically acceptable excipient.

EXAMPLES

Example 1: Small Molecule-Controlled Cas9

Cas9 variants that can be activated in the presence of a small molecule were engineered, allowing spatiotemporal control over DNA cleavage. These engineered Cas9 variants contain a small-molecule-regulated intein (Buskirk et al., *Proc. Natl. Acad. Sci. USA*. 2004; 101, 10505-10510), which has been optimized for mammalian cells (Peck et al., *Chem. Biol.* 2011; 18 (5), 619-630), that renders the protein inactive as a nuclease. Upon addition of the cell-permeable molecule, 4-hydroxytamoxifen (4-HT), the intein excises itself from the protein and ligates the flanking extein sequences, restoring Cas9 activity. Because these Cas9 variants can be active over a smaller time window than wild-type Cas9, the likelihood of having off-target cleavage is reduced.

The 37R3-2 intein was inserted at 15 different positions into human codon-optimized *Streptococcus pyogenes* Cas9 (e.g., SEQ ID NO:2). The intein was inserted in place of a single cysteine, alanine, serine, or threonine residue. Upon excision, the intein leaves a cysteine residue. Thus, the primary structure generated following protein splicing is either identical to the unmodified version of Cas9 when the intein is inserted in place of cysteine, or it is one amino acid different when the intein is inserted in place of alanine, serine, or threonine.

Plasmid constructs were generated in which the intein replaced amino acid residues: Cys80, Ala127, Thr146, Ser219, Thr333, Thr519, Cys574, Thr622, Ser701, Ala728, Thr995, Ser1006, Ser1154, Ser1159, or Ser1274 (e.g., in the amino acid sequence set forth as SEQ ID NO:2). These plasmids express the Cas9 variant with a nuclear localization signal (NLS) and 3×FLAG tag from the CMV promoter.

HEK293-GFP stable cells were transfected with the Cas9 expression plasmid, a gRNA (targeting Emerald GFP; Guilinger et al., *Nature Biotechnology* (2014)), and iRFP670 (transfection control), using Lipofectamine 2000. Twelve hours after transfection, media, either containing 4-HT (1 μM) or without 4-HT, was added.

Five days after transfection, cells were trypsinized and analyzed on a flow cytometer. Cells lacking GFP indicated genome modification. Cas9 variants that induced minimal genome modification in the absence of 4-HT but induce significant genome modification in the presence of 4-HT were deemed small-molecule-regulated variants in this Example. Of fifteen targeted insertions, five demonstrated minimal genome modification in the absence of 4-HT. These variants are highlighted in bold in the Table I below.

Additionally, a time course was performed in which incubation with 4-HT was limited to 2, 4, 8, 12 or 24 hours, after which point the media was replaced. Presumably, the shorter time an "active" cas9 is present, the less off-target cleavage. As depicted in Table II below, treating with 4-HT for 2 hours is sufficient for on-target cleavage and longer treatment periods do not show significant increased cleavage in this assay.

To assess the ability of the ligand-dependent Cas9 proteins to affect genomic modifications in the presence of absence of ligand, HEK293-GFP stable cells (GenTarget) were transfected with Cas9 expression plasmids and sgRNAs targeting EMX, VEGF, or CLTA genomic sites using Lipofectamine 2000 as previously described (Guilinger et al., Fusion of catalytically inactive Cas9 to FokI nuclease improves the specificity of genome modification *Nature Biotechnology*. 2014; 32(6):577-82). 4-HT (1 μM) was added during transfection for +4-HT samples. 12 hours after transfection the media was replaced. 60 hours after transfection, cells were trypsinized and genomic DNA was isolated using the DNAdvance kit (Agencourt). 40-80 ng of genomic DNA was used as a template to PCR amplify the targeted genomic loci with flanking Survey primer pairs as previously described (Guilinger et al., Fusion of catalytically inactive Cas9 to FokI nuclease improves the specificity of genome modification *Nature Biotechnology*. 2014; 32(6): 577-82). PCR products were purified with a QIAquick PCR Purification Kit (Qiagen) and quantified with a Quant-iT PicoGreen dsDNA Kit (Life Technologies). 200 ng of purified PCR DNA was then combined with 2 μL of NEBuffer 2 (NEB) in a total volume of 19 μL and denatured then re-annealed with thermocycling at 95° C. for 5 min, 95-85° C. at 2° C./s, 85-20° C. at 0.2° C./s. The re-annealed DNA was incubated with 1 μL of T7 Endonuclease I (10U/μL, NEB) at 37° C. for 15 min. 10 μL of 50% glycerol was added to the T7 Endonuclease reaction and 15 μL was analyzed on a 5% TBE 18-well Criterion PAGE gel (Bio-Rad) electrophoresed for 30 min at 200V and stained with EtBr for 15 min.

Figure 2:
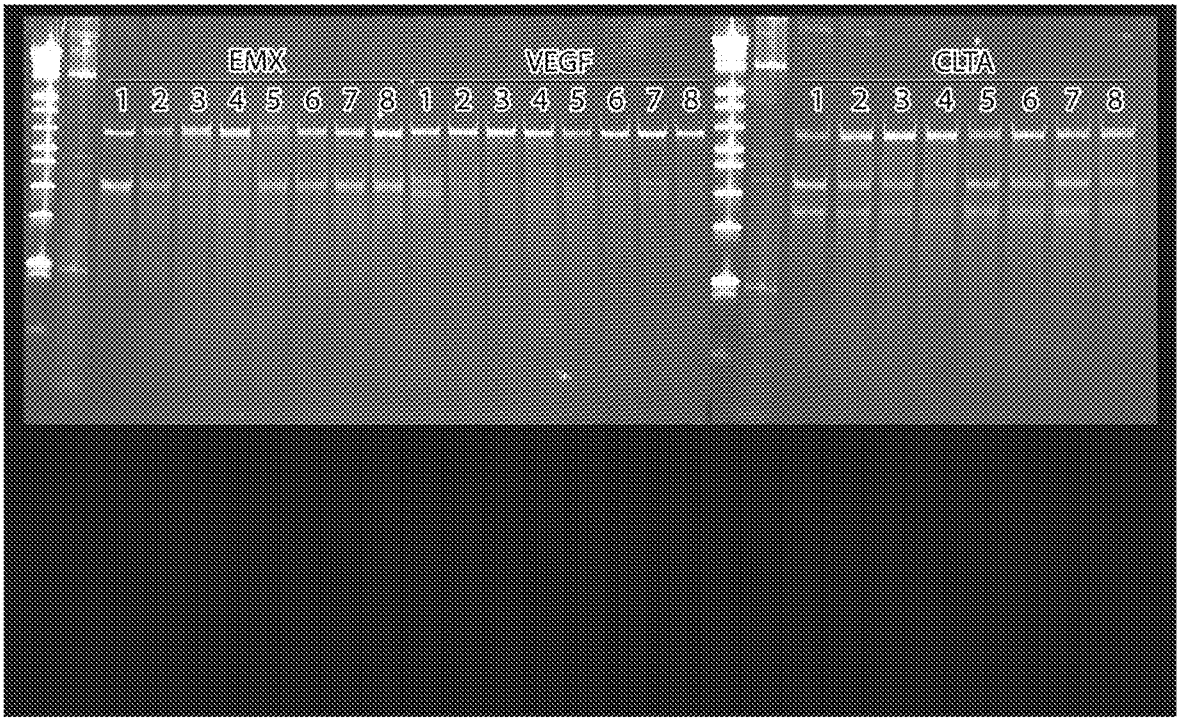
FIG. 2 shows the results of T7 Endonuclease I Surveyor assay used to assess ligand-dependent Cas9 gene modification at three target sites (EMX, VEGF, or CLTA). The presence of two bands corresponding to smaller DNA fragments (the fragments are approximately the same size for EMX) indicates genomic modification.

As shown in FIG. 2, the addition of 4-HT to ligand-dependent Cas9:Intein variants (Cas9:Intein with 37R3-2 replacing S219 (SEQ ID NO:30) and Cas9:Intein with 37R3-2 replacing C574 (SEQ ID NO:33)) resulted in genomic modification of the target sites, comparable to modification by wild-type Cas9. In the absence of 4-HT, the Cas9:Intein variants displayed minimal or no modification of the EMX and VEGF genomic target sites, while some background cleavage was observed for the CLTA genomic target site. Gene modification levels can be estimated by comparing the intensities of the cleaved (two smaller fragments) and uncleaved bands. These results demonstrate that Cas9 cleavage of genomic target sites can be controlled by the addition of ligand (here, 4-HT) which activates the proteins.

TABLE 1

| | Cells without GFP (%) | |
|---|---|---|
| Cas9 Variant | −4-HT | +4-HT |
| None | 4.65 | 3.42 |
| wild-type cas9 | 48.49 | 40.49 |
| intein(Cys80)-Cas9 (SEQ ID NO: 27) | 7.08 | 4.96 |
| **intein(Ala127)-Cas9** (SEQ ID NO: 28) | **7.97** | **19.73** |
| **intein(Thr146)-Cas9** (SEQ ID NO: 29) | **8.77** | **21.60** |
| **intein(Ser219)-Cas9** (SEQ ID NO: 30) | **6.53** | **23.98** |
| intein(Thr333)-Cas9 (SEQ ID NO: 31) | 4.96 | 9.17 |
| **intein(Thr519)-Cas9** (SEQ ID NO: 32) | **9.49** | **25.96** |
| **intein(Cys574)-Cas9** (SEQ ID NO: 33) | **5.74** | **21.44** |
| intein(Thr622)-Cas9 (SEQ ID NO: 34) | 5.67 | 3.96 |

TABLE 1-continued

| Cas9 Variant | Cells without GFP (%) −4-HT | +4-HT |
|---|---|---|
| intein(Ser701)-Cas9 (SEQ ID NO: 35) | 6.54 | 9.56 |
| intein(Ala728)-Cas9 (SEQ ID NO: 36) | 20.82 | 41.89 |
| intein(Thr995)-Cas9 (SEQ ID NO: 37) | 14.95 | 21.39 |
| intein(Ser1006)-Cas9 (SEQ ID NO: 38) | 6.80 | 12.61 |
| intein(Ser1154)-Cas9 (SEQ ID NO: 39) | 21.14 | 41.94 |
| intein(Ser1159)-Cas9 (SEQ ID NO: 40) | 5.65 | 13.21 |
| intein(Ser1274)-Cas9 (SEQ ID NO: 41) | 3.08 | 5.00 |

TABLE 2

| | Cells without GFP (%) | | | | | |
|---|---|---|---|---|---|---|
| | | +4-HT | | | | |
| Cas9 Variant | −4-HT | 2 hrs | 4 hrs | 8 hrs | 12 hrs | 24 hrs |
| None | 2.98 | 2.60 | 3.78 | 3.71 | 2.76 | 2.82 |
| wild-type cas9 | 34.65 | 42.28 | 37.68 | 33.89 | 33.81 | 37.26 |
| intein(Ala127)-Cas9 (SEQ ID NO: 28) | 5.03 | 18.95 | 18.57 | 18.64 | 18.35 | 16.83 |
| intein(Thr146)-Cas9 (SEQ ID NO: 29) | 4.28 | 16.29 | 15.07 | 13.65 | 14.44 | 19.57 |
| intein(Ser219)-Cas9 (SEQ ID NO: 30) | 3.92 | 17.25 | 17.07 | 15.12 | 15.28 | 24.39 |
| intein(Thr519)-Cas9 (SEQ ID NO: 32) | 4.29 | 14.55 | 13.98 | 14.74 | 13.93 | 18.04 |
| intein(Cys574)-Cas9 (SEQ ID NO: 33) | 2.91 | 14.57 | 13.11 | 16.91 | 16.10 | 14.52 |

Example 2: Small Molecule-Controlled Cas9 Protein with Improved Genome-Editing Specificity Cas9 nucleases that are activated by the presence of a cell-permeable small molecule were developed by inserting an evolved 4-hydroxytamoxifen (4-HT)-responsive intein at specific positions in Cas9. In human cells, conditionally active Cas9s modify target genomic sites with up to 25-fold higher specificity than wild-type Cas9.

The RNA-guided endonuclease Cas9 from the type II CRISPR-Cas system enables simple and efficient genome editing in a wide variety of organisms. Virtually any target DNA locus can be cleaved by programming Cas9 with a single guide RNA (sgRNA) that contains a stretch of ~20 nucleotides complementary to the target sequence[1-3]. Due to its simplicity and robustness, the Cas9 system has been widely adopted for biological research and therapeutic development. The DNA cleavage specificity of Cas9 is imperfect[4-8], however, raising concerns over off-target genome modification that may limit its usefulness in therapeutic or research applications. Cas9 off-target activity has been reduced through protein[9-12] and sgRNA[13] engineering, and by direct delivery of Cas9:sgRNA protein:RNA complexes into cells[14-16].

A complementary, underexplored strategy to improve Cas9 specificity is to reduce its activity once it has had sufficient opportunity to modify the target DNA locus. Indeed, higher concentrations of Cas9 in cells have been observed to degrade specificity[4-6] (defined as the ratio of on-target:off-target DNA cleavage activity), presumably because any Cas9 protein present after the target locus has been modified can only process off-target substrates. Unfortunately, wild-type Cas9 nucleases are not known to be regulated by other molecules and therefore are used in constitutively active form. While Cas9 can be regulated at the transcriptional level through the use of inducible promoters[17,18], transcriptional control cannot limit activity to the short temporal windows that may be necessary to maximize genome-editing specificity[16,19], in contrast with the high temporal resolution of post-translational strategies that directly control protein activity.

Figure 3A:
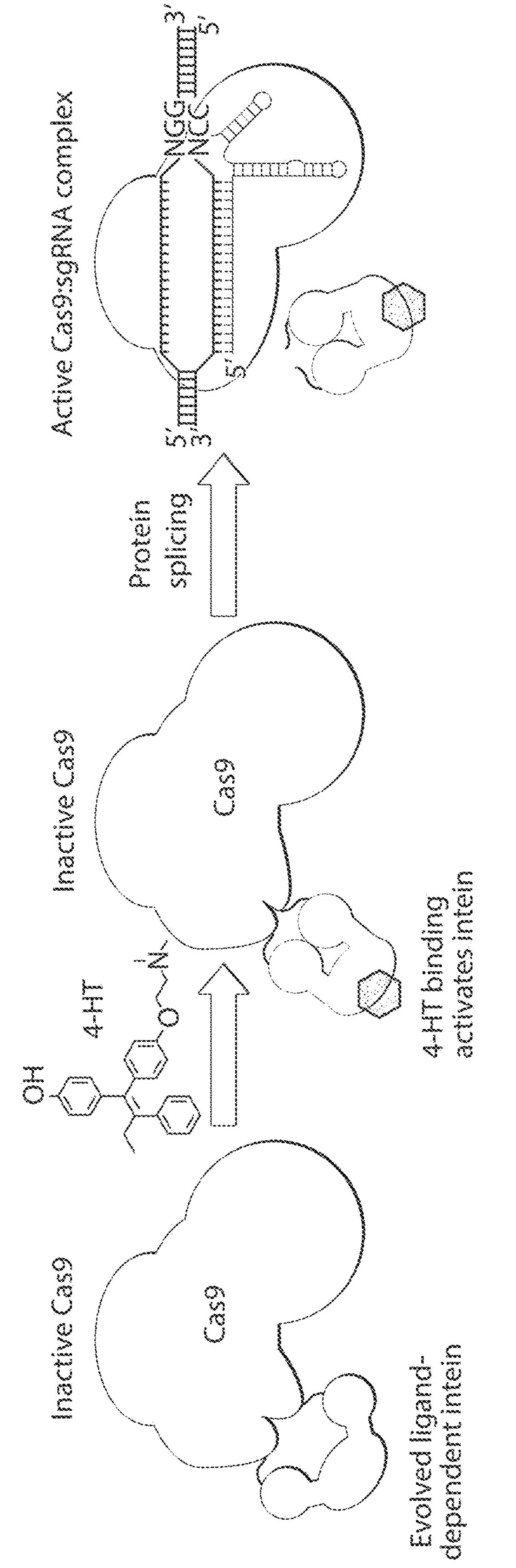
FIGS. 3A-3C. Insertion of an evolved ligand-dependent intein enables small-molecule control of Cas9.

Engineered variants of Cas9 that can be controlled with a readily available, cell-permeable small molecule were developed. We previously evolved inteins that undergo protein splicing only in the presence of 4-hydroxytamoxifen (4-HT)[20]. These inteins were developed by inserting the human estrogen receptor ligand-binding domain into the *M. tuberculosis* RecA intein and evolving the resulting inactive fusion protein into a conditionally active intein that requires the presence of 4-HT[20-22]. Subsequent evolution at 37° ° C. yielded a second-generation intein, 37R3-2, with improved splicing properties in mammalian cells[22]. We envisioned that inserting the 37R3-2 intein into Cas9 at a location that disrupts Cas9 activity until protein splicing has taken place could result in conditionally active Cas9 nucleases that are active only in the presence of 4-HT (FIG. 3*a*).

Figure 3C:
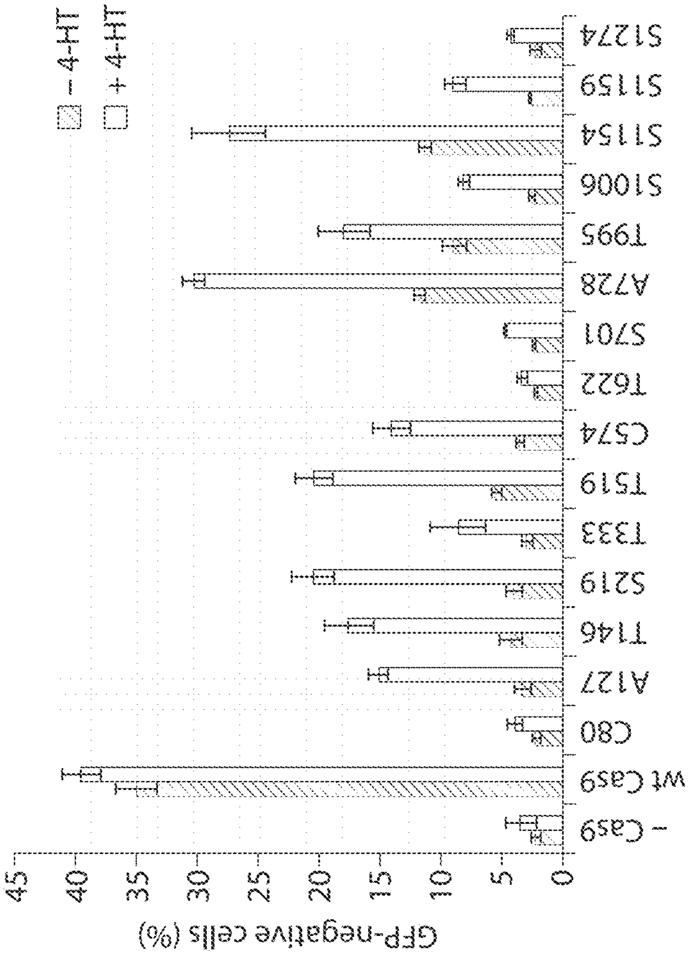
Figure 3B:

We genetically inserted the 4-HT-dependent intein at each of fifteen positions in Cas9 (Cys80, Ala127, Thr146, Ser219, Thr333, Thr519, Cys574, Thr622, Ser701, Ala728, Thr995, Ser1006, Ser1154, Ser1159, and Ser1274), chosen to distribute the location of the intein across the structural domains of Cas9[23] (FIG. 3*b* and Example 1). Because intein splicing leaves behind a single Cys residue, the intein was inserted in place of one Cas9 amino acid in each of the 15 candidate constructs. In addition to replacing natural Cys amino acids, we also favored replacing Ala, Ser, or Thr residues to minimize the likelihood that the resulting Cys point mutation resulting from protein splicing would disrupt Cas9 activity. The 15 intein-Cas9 candidates were expressed in HEK293-GFP cells together with a sgRNA that targets the genomic EGFP locus in these cells. Twelve hours post-transfection, cells were treated with or without 1 μM 4-HT. Five days post-transfection, cells were analyzed on a flow cytometer for loss of GFP expression from Cas9-mediated EGFP cleavage and subsequent non-homologous end joining.

Eight of the candidates, corresponding to intein insertion at A127, T146, S219, T333, T519, C574, S1006, and S1159, demonstrated 4-HT-dependent loss of GFP expression consistent with 4-HT-triggered Cas9 activity (FIG. 3*c*). Interestingly, three intein-Cas9 proteins (insertion at A728, T995, and S1154) showed high DNA modification rates both in the presence and absence of 4-HT, suggesting that large protein insertions at these positions do not significantly inhibit nuclease activity, or that the intein lost its 4-HT dependence due to context-dependent conformational perturbations. We speculate that it may be possible to engineer split Cas9 variants by dividing the protein at these locations, given their tolerance of a 413-residue insertion. The lack of nuclease activity of the remaining four Cas9-inteins (insertion at C80, T622, 5701, and S1274) in the presence or absence of 4-HT could result from the inability of the intein to splice in those contexts, the inability of Cas9 to refold properly following splicing, or intolerance of replacement of native Thr or Ser residues with Cys. We pursued two intein-Cas9 variants corresponding to insertion at S219 and C574 (FIG. 3*b*). These two variants combined high activity in the presence of 4-HT and low activity in the absence of 4-HT.

Figure 4A:
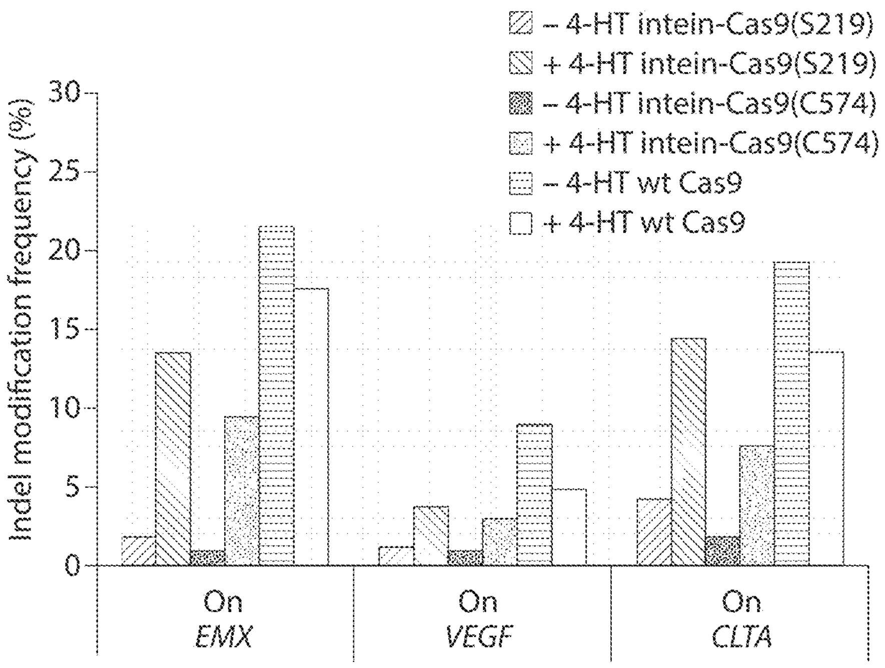
FIGS. 4A-4D. Genomic DNA modification by intein-Cas9(S219), intein-Cas9(C574), and wild-type Cas9.
Figure 5:
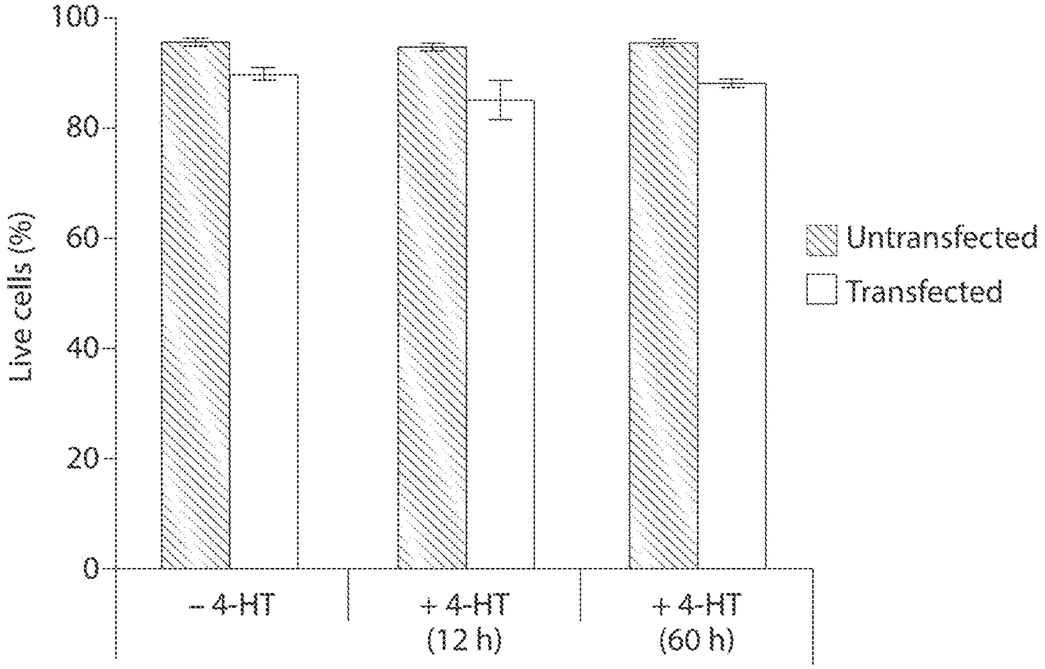
FIG. 5. Effect of 4-HT on cellular toxicity. Untransfected HEK293-GFP stable cells, and cells transfected with intein-Cas9(S219) and sgRNA expression plasmids, were treated with or without 4-HT (1 μM). 12 h after transfection, the media was replaced with full serum media, with or without 4-HT (1 μM). Cells were thus exposed to 4-HT for 0, 12, or 60 h. The live cell population was determined by flow cytometry 60 h after transfection using TO-PRO-3 stain (Life Technologies). Error bars reflect the standard deviation of six technical replicates.
Figure 6A:
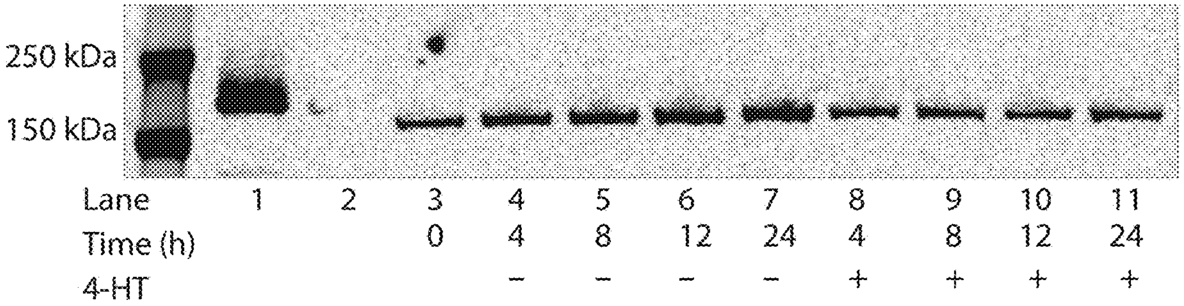
FIGS. 6A-6B. Western blot analysis of HEK293-GFP stable cells transfected with (FIG. 6A) wild-type Cas9 or (FIG. 6B) intein-Cas9(S219) expression plasmid. 12 h after transfection, cells were treated with or without 4-HT (1 μM). Cells were lysed and pooled from three technical replicates 4, 8, 12, or 24 h after 4-HT treatment. An anti-FLAG antibody (Sigma-Aldrich F1804) and an anti-mouse 800CW IRDye (LI-COR) were used to visualize the gel. Lanes 1 and 2 contain purified dCas9-VP64-3×FLAG protein and lysate from untransfected HEK293 cells, respectively.
Figure 6B:
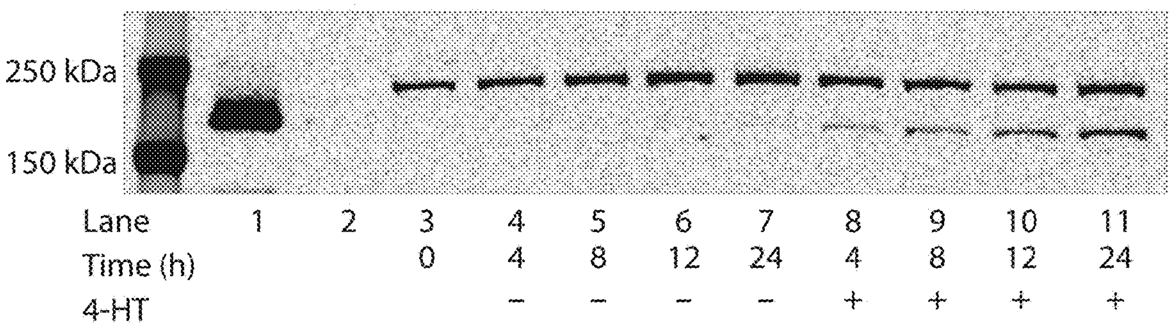

To evaluate the genome modification specificity of conditionally active Cas9 variants, we expressed intein-Cas9 (S219), intein-Cas9(C574), and wild-type Cas9 in HEK293-GFP cells together with each of three previously described[11] sgRNAs that target the well-studied EMX, VEGF, and CLTA genomic loci. We assayed these Cas9:sgRNA combinations in human cells for their ability to modify the three on-target loci as well as 11 known off-target genomic sites (Table 3)[4,5,10,13]. Cells were treated with or without 1 μM 4-HT during transfection, and after 12 h the media was replaced with fresh media lacking 4-HT. We observed no cellular toxicity arising from 12 or 60 h of treatment with 1 μM 4-HT in untransfected or transfected HEK293 cells (FIG. 5). Genomic DNA was isolated 60 h post-transfection and analyzed by high-throughput DNA sequencing Overall on-target genome modification frequency of intein-Cas9(S219) and intein-Cas9 (C574) in the presence of 1 μM 4-HT was similar to that of wild-type Cas9 (FIG. 4*a*, Tables 4 and 5). On-target modification frequency in the presence of 4-HT was 3.4-to 7.3-fold higher for intein-Cas9 (S219), and 3.6- to 9.6-fold higher for intein-Cas9(C574), than in the absence of 4-HT, whereas modification efficiency for wild-type Cas9 was 1.2- to 1.8-fold lower in the presence of 4-HT (FIG. 4*a*). Both intein-Cas9 variants exhibited a low level of background activity in the absence of 4-HT, consistent with previous reports[20-22]. Western blot analysis of intein-Cas9(S219) from transfected HEK293 cells confirmed the presence of spliced product at the earliest assayed time point (4 h) following 4-HT treatment; no spliced product was detected in the absence of 4-HT (FIG. 6). Together, these results indicate that intein-Cas9(S219) and intein-Cas9(C574) are slightly less active than wild-type Cas9 in the presence of 4-HT, likely due to incomplete splicing (FIG. 6), but much less active in the absence of 4-HT.

Figure 4B:
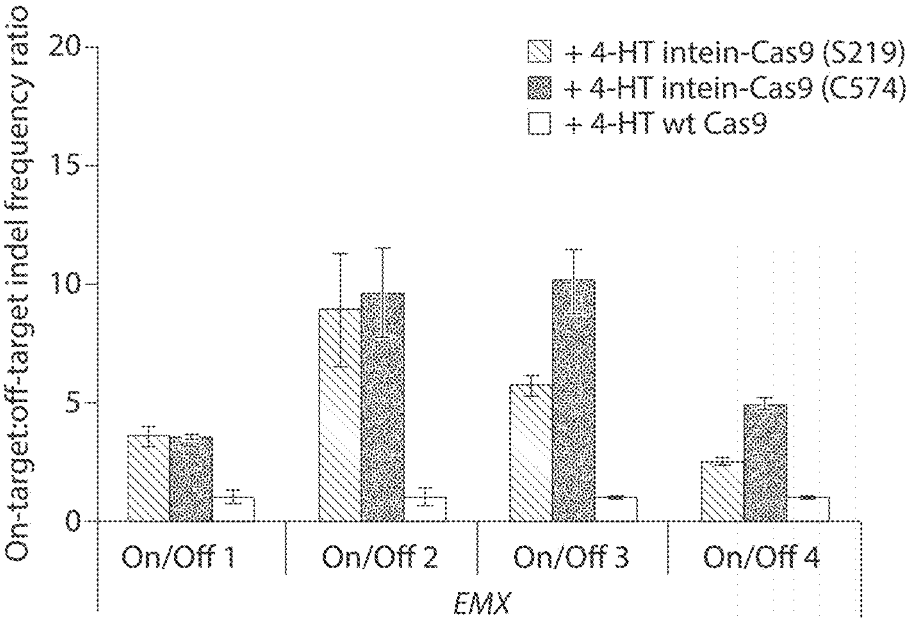
Figure 4C:
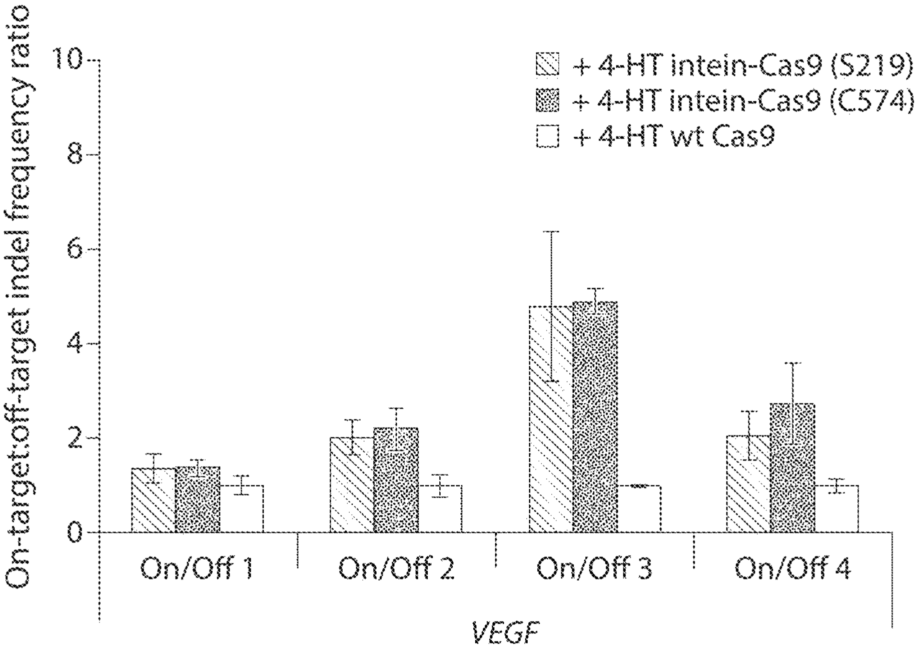
Figure 4D:
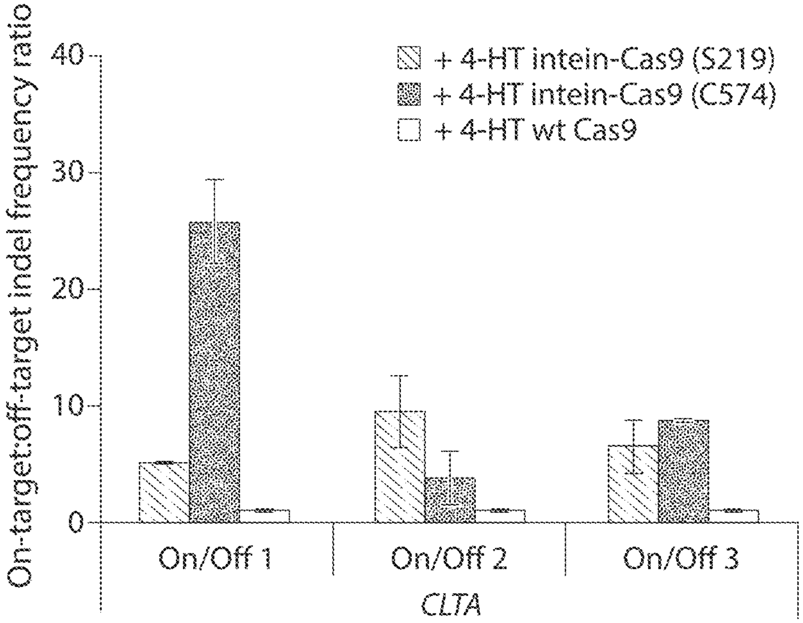
Figure 7:
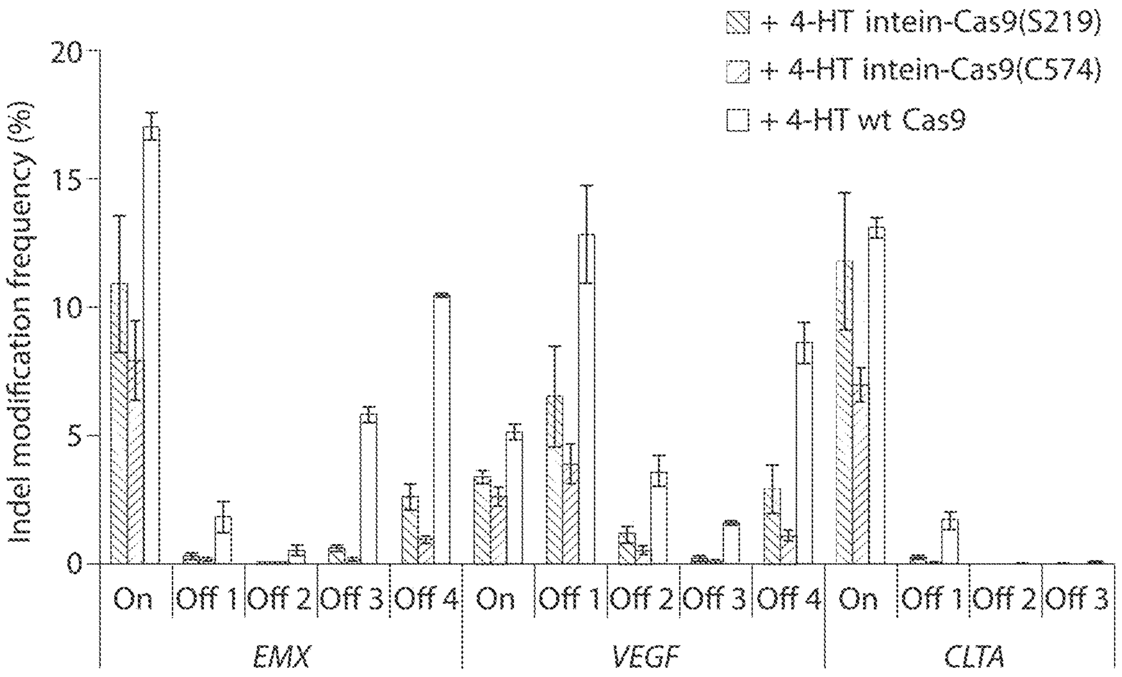
FIG. 7. Indel frequency from high-throughput DNA sequencing of amplified genomic on-target sites ("On") and off-target sites ("Off 1-Off 4") by intein-Cas9(S219), intein-Cas9(C574), and wild-type Cas9 in the presence of 4-HT. 500 ng of Cas9 expression plasmid was transfected. The higher observed efficiency of VEGF Off 1 modification than VEGF on-target modification is consistent with a previous report. P-values are <0.005 for the Fisher exact test (one-sided down) on all pairwise comparisons within each independent experiment of off-target modification frequency between either intein-Cas9 variant in the presence of 4-HT versus that of wild-type Cas9 in the presence of 4-HT. P-values were adjusted for multiple comparisons using the Benjamini-Hochberg method, and are listed in Table 7. Error bars reflect the range of two independent experiments conducted on different days. See also Fu, Y. et al. High-frequency off-target mutagenesis induced by CRISPR-Cas nucleases in human cells. *Nature biotechnology* 31, 822-826 (2013).

High-throughput sequencing of 11 previously described off-target sites that are modified by wild-type Cas9:sgRNA complexes targeting the EMX, VEGF, and CLTA loci revealed that both intein-Cas9 variants when treated with 4-HT for 12 h exhibit substantially improved specificity compared to that of wild-type Cas9 (FIG. 7, Tables 4, 6, and 7). On-target:off-target indel modification ratios for both intein-Cas9 variants were on average 6-fold higher, and as much as 25-fold higher, than that of wild-type Cas9 (FIG. 4*b*-*d*). In the absence of 4-HT, the genome modification specificity of both intein-Cas9 variants was on average 14-fold higher than that of wild-type Cas9 in the absence of 4-HT (FIG. 8), presumably resulting from the much lower activity of the intein-Cas9 variants in the absence of 4-HT[4-6].

Figure 9:
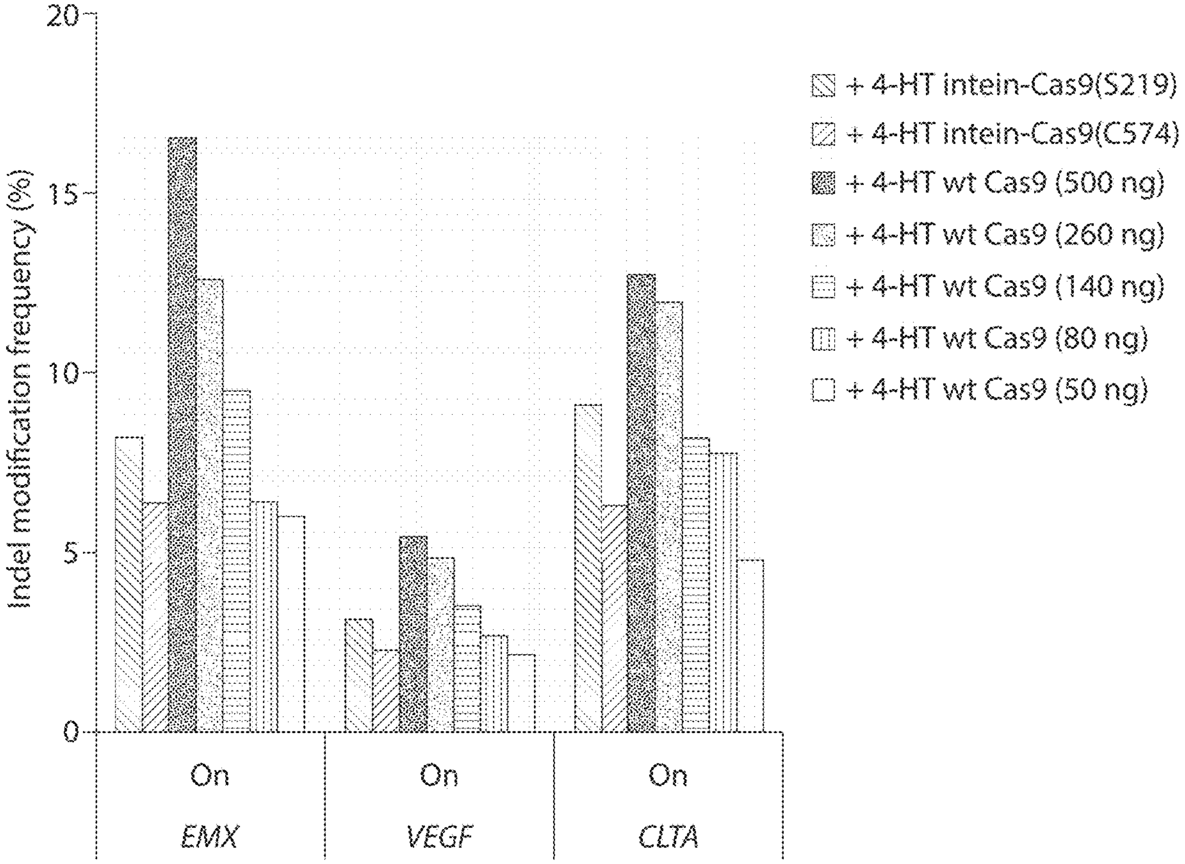
FIG. 9. Genomic on-target DNA modification by intein-Cas9(S219), intein-Cas9(C574), and wild-type Cas9 in the presence of 4-HT. Five different amounts of wild-type Cas9 expression plasmid, specified in parenthesis, were transfected. P-values for comparisons between conditions (Table 8) were obtained using the Fisher exact test and adjusted for multiple comparisons using the Benjamini-Hochberg Method.
Figure 10A:
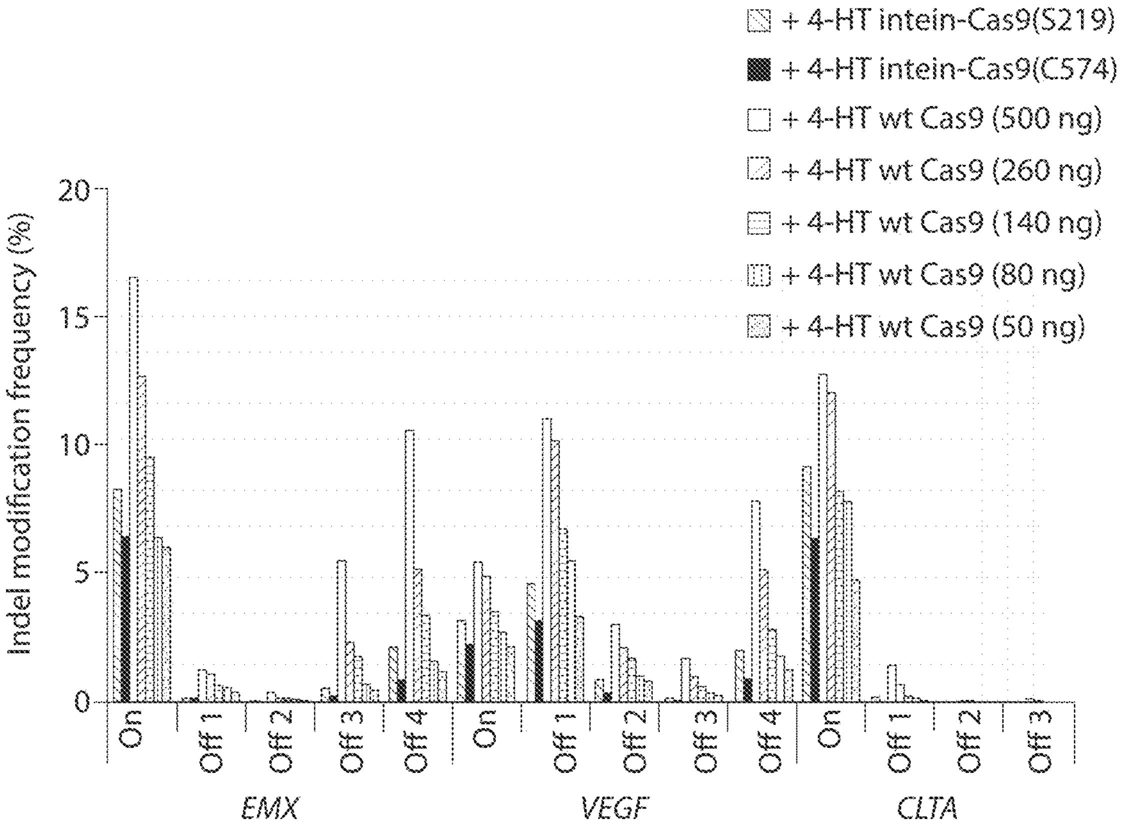
FIGS. 10A-10B. Indel frequency from high-throughput DNA sequencing of amplified genomic on-target sites ("On") and off-target sites ("Off 1-Off 4") by intein-Cas9 (S219), intein-Cas9(C574), and wild-type Cas9 in the presence of 4-HT. Five different amounts of wild-type Cas9 expression plasmid, specified in parenthesis, were transfected (FIG. 10A). Genomic sites with low modification frequencies are enlarged in (FIG. 10B). P-values for comparisons between conditions (Table 8) were obtained using the Fisher exact test and adjusted for multiple comparisons using the Benjamini-Hochberg Method.
Figure 10B:
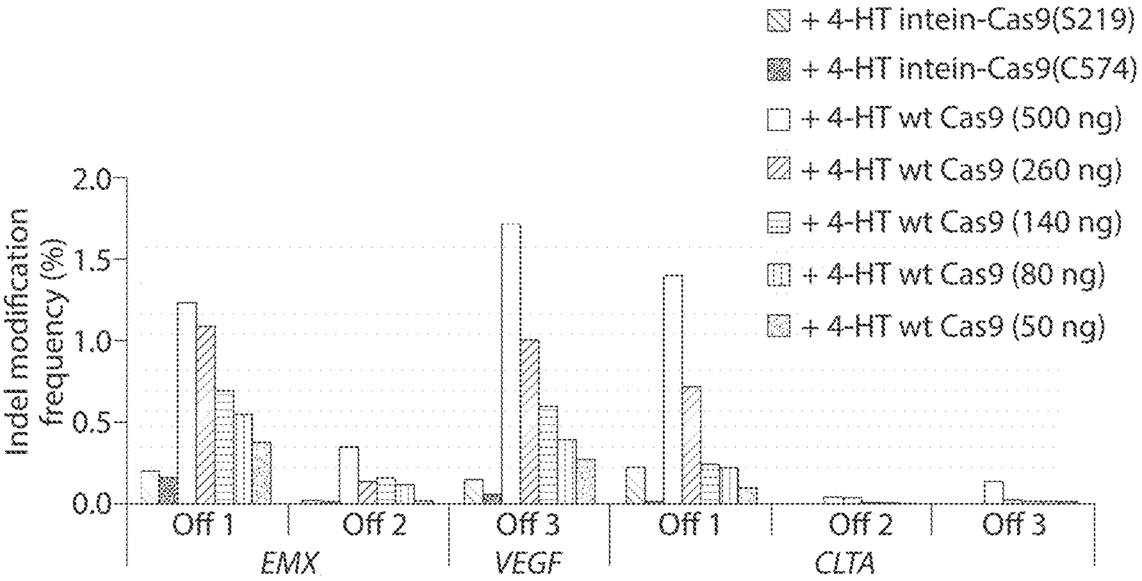
Figure 11A:
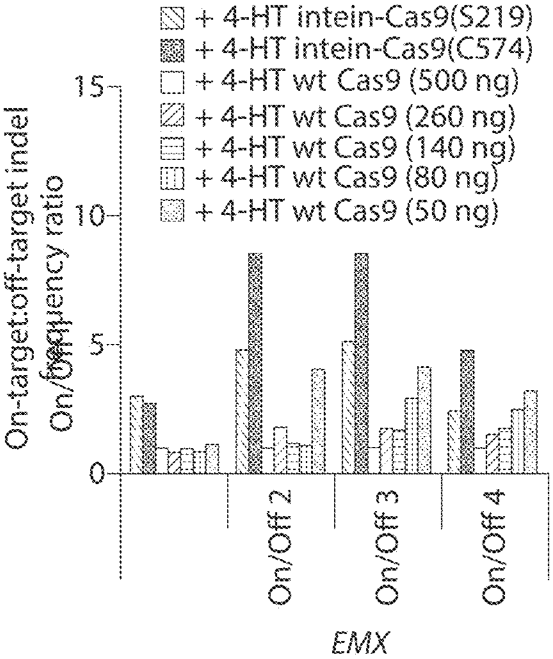
FIGS. 11A-11C. DNA modification specificity of intein-Cas9(S219), intein-Cas9(C574), and wild-type Cas9 in the presence of 4-HT.
Figure 11B:
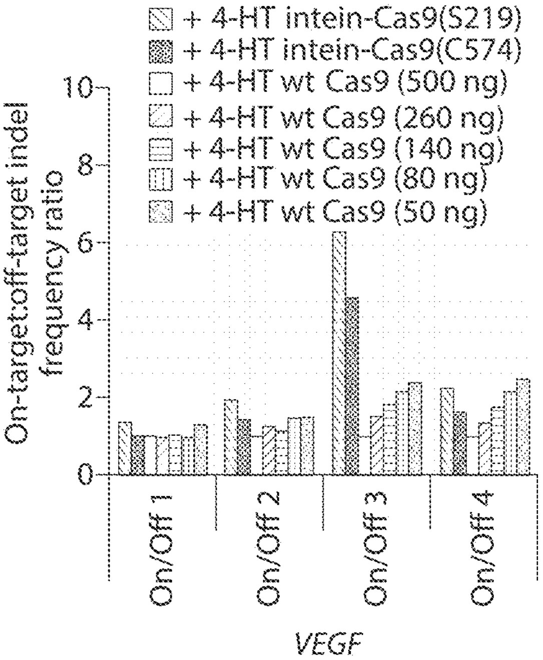
Figure 11C:
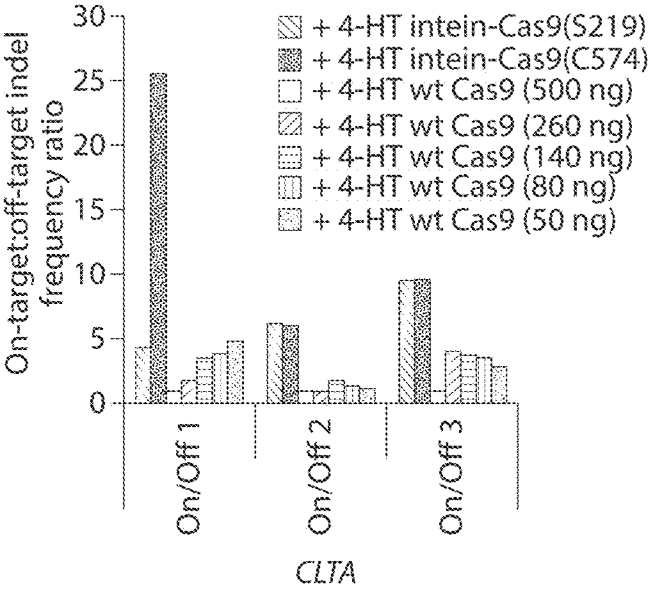

Since intein-Cas9s can result in slightly lower on-target modification rates compared to wild-type Cas9 (FIG. 4*a*), we sought to verify that the improvements in specificity among the intein-Cas9s were not simply a result of reduced activity. Both on- and off-target activity of Cas9 has been shown to be dependent on the amount of Cas9 expression plasmid transfected[4-6]. By transfecting lower amounts of the wild-type Cas9 expression plasmid, we compared intein-Cas9s with wild-type Cas9 under conditions that result in very similar levels of on-target modification. To minimize potential differences in transfection efficiency, we supplemented with a plasmid that does not express Cas9 so that the same total amount of plasmid DNA was transfected into each sample. High-throughput sequencing revealed that wild-type Cas9 shows slightly improved specificity, as expected, as the on-target cleavage rate is reduced. The intein-Cas9 variants, however, remain substantially more specific than wild-type Cas9 at similar on-target DNA cleavage rates (FIGS. 9-11, Tables 6 and 8). For example, intein-Cas9(C574) and wild-type Cas9 (80 ng) have virtually identical on-target DNA cleavage rates (both 6.4%) at the EMX locus but all four off-target sites are modified at an average of 4-fold lower frequencies ($P<1\times10^{-13}$) by intein-Cas9(C574) than by wild-type Cas9. These findings indicate that specificity improvements of intein-Cas9 variants do not simply arise from differences in overall genome editing activity.

Figure 12A:
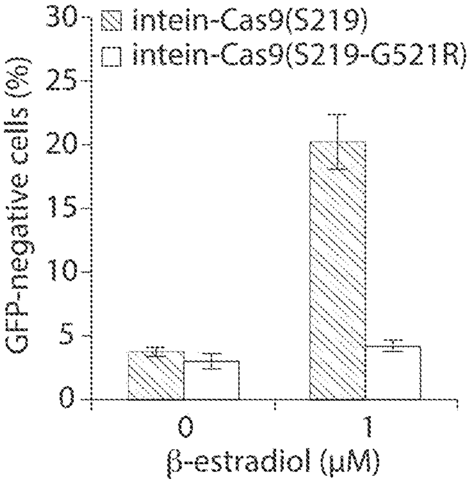
FIGS. 12A-12B. Genomic EGFP disruption activity of intein-Cas9(S219) and intein-Cas9(S219-G521R) in the presence of (FIG. 12A) β-estradiol or (FIG. 12B) 4-HT. Error bars reflect the standard deviation of three technical replicates.
Figure 12B:
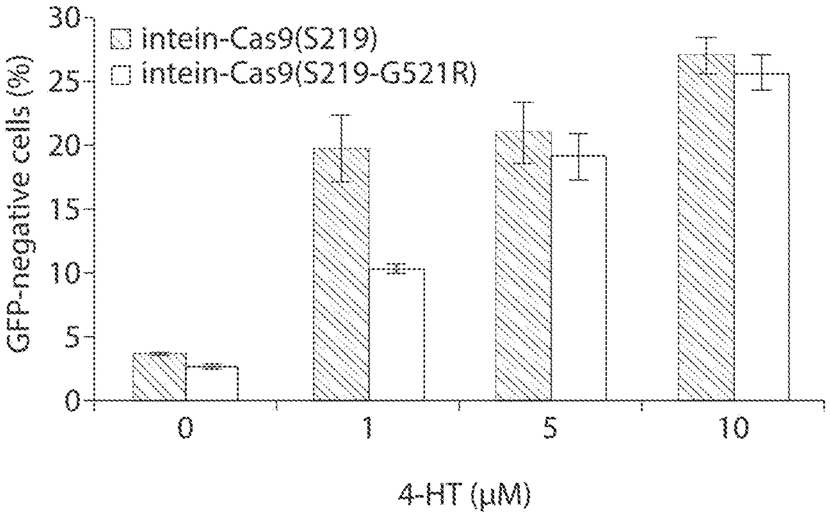

Intein 37R3-2 can be activated by other estrogen receptor modulators. To enable intein-Cas9 applications in which endogenous β-estradiol is present, we inserted into the estrogen receptor ligand-binding domain a point mutation (G521R) that renders the domain more specific for 4-HT[24]. This mutation slightly reduces affinity for 4-HT but almost abolishes affinity for β-estradiol. The addition of this mutation to intein-Cas9(S219) eliminates the ability of β-estradiol to trigger Cas9 activity (FIG. 12).

The intein-Cas9 variants developed here demonstrate small-molecule control of Cas9 function, thereby enhancing genome-modification specificity. The use of ligand-dependent Cas9 variants provides greater control over genomic modification efficiencies and specificities than is currently achievable with constitutively active or transcriptionally regulated genome editing. This approach can synergize with other specificity-augmenting strategies such as direct delivery of transient Cas9 protein into cells[16], using truncated guide RNAs[13], paired Cas9 nickases[9,10], or FokI-dCas9 fusions[11,12]. This approach could also be applied to other genome engineering proteins to enable, for example, small-molecule control of TALE-based or Cas9-mediated transcriptional regulators.

TABLE 3

On-target and 11 known off-target substrates of Cas9: sgRNAs that target sites in EMX, VEGF, and CLTA. List of genomic on-target and off-targets sites of the EMX, VEGF, and CLTA sites are shown with mutations from the on-target sequence shown in lower case. Protospacer-adjacent motifs (PAMs) are shown underlined.

| | | |
|---|---|---|
| EMX On | GAGTCCGAGCAGAAGAAGAAGGG | (SEQ ID NO: 107) |
| EMX Off 1 | GAGgCCGAGCAGAAGAAagACGG | (SEQ ID NO: 108) |
| EMX Off 2 | GAGTCCtAGCAGgAGAAGAAGaG | (SEQ ID NO: 109) |
| EMX Off 3 | GAGTCtaAGCAGAAGAAGAAGaG | (SEQ ID NO: 110) |
| EMX Off 4 | GAGTtaGAGCAGAAGAAGAAAGG | (SEQ ID NO: 111) |
| VEGF On | GGGTGGGGGGAGTTTGCTCCTGG | (SEQ ID NO: 112) |
| VEGF Off 1 | GGaTGGaGGGAGTTTGCTCCTGG | (SEQ ID NO: 113) |
| VEGF Off 2 | GGGaGGGtGGAGTTTGCTCCTGG | (SEQ ID NO: 114) |
| VEGF Off 3 | cGGgGGaGGGAGTTTGCTCCTGG | (SEQ ID NO: 115) |
| VEGF Off 4 | GGGgaGGGGaAGTTTGCTCCTGG | (SEQ ID NO: 116) |
| CLTA On | GCAGATGTAGTGTTTCCACAGGG | (SEQ ID NO: 117) |
| CLTA Off 1 | aCAtATGTAGTaTTTCCACAGGG | (SEQ ID NO: 118) |

TABLE 3-continued

On-target and 11 known off-target substrates of Cas9: sgRNAs that target sites in EMX, VEGF, and CLTA. List of genomic on-target and off-targets sites of the EMX, VEGF, and CLTA sites are shown with mutations from the on-target sequence shown in lower case. Protospacer-adjacent motifs (PAMs) are shown underlined.

| | |
|---|---|
| CLTA Off 2 | cCAGATGTAGTaTTcCCACAGGG (SEQ ID NO: 119) |
| CLTA Off 3 | ctAGATGaAGTGcTTCCACATGG (SEQ ID NO: 120) |

TABLE 4

Figure 8A:
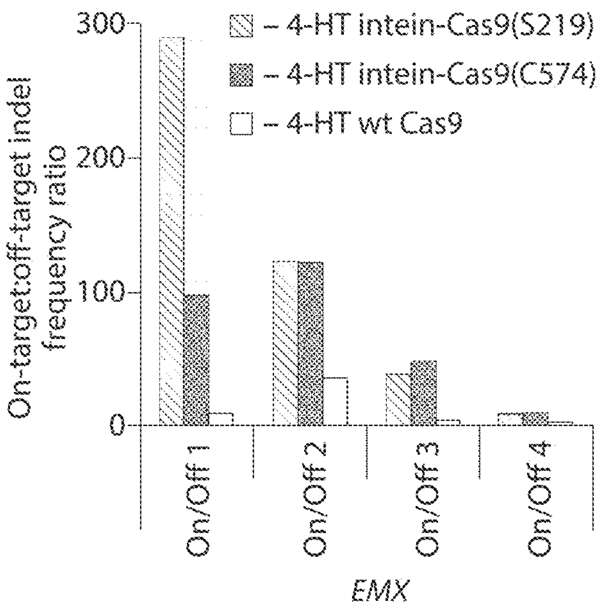
FIGS. 8A-8C. DNA modification specificity of intein-Cas9(S219), intein-Cas9(C574), and wild-type Cas9 in the absence of 4-HT.
Figure 8B:
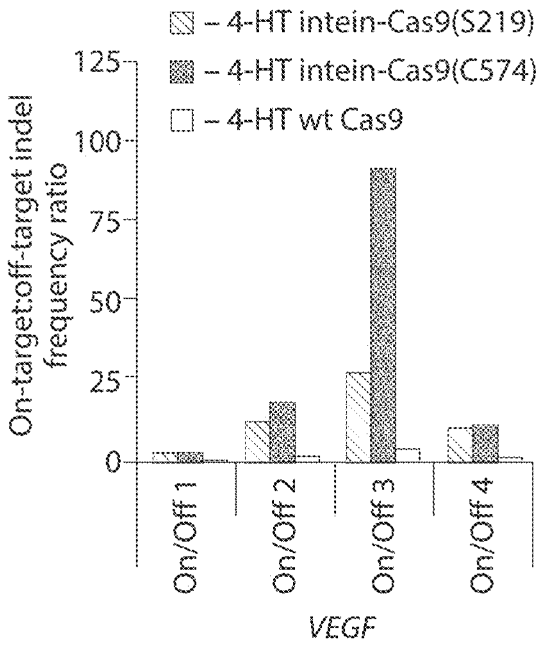
Figure 8C:
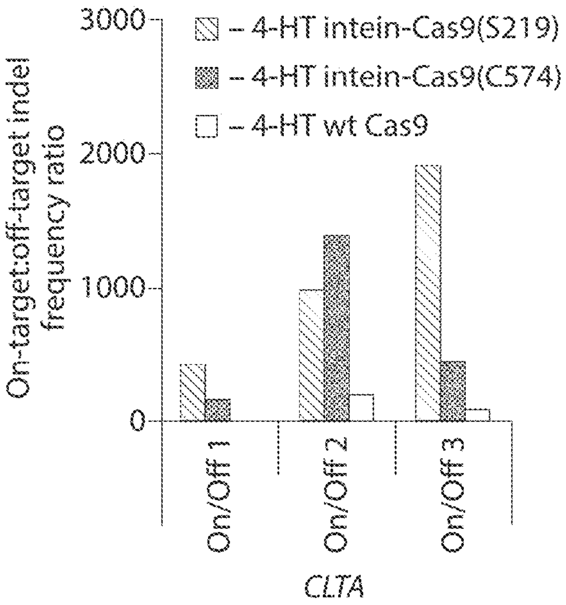

Raw sequence counts and modification frequencies for data plotted in FIGS. 4, 7, and 8. Total: total number of sequence counts. Modification frequency: number of indels divided by the total number of sequences listed as percentages.

| | −4-HT intein-Cas9 (S219) | | | −4-HT intein-Cas9 (C574) | | | −4-HT wt Cas9 (500 ng) | | |
|---|---|---|---|---|---|---|---|---|---|
| | Indels | Total | Mod. Freq | Indels | Total | Mod. Freq | Indels | Total | Mod. Freq |
| EMX On | 1123 | 59967 | 1.87% | 561 | 56700 | 0.99% | 15589 | 72127 | 21.61% |
| EMX Off 1 | 3 | 46360 | 0.01% | 4 | 39544 | 0.01% | 1143 | 55334 | 2.07% |
| EMX Off 2 | 8 | 52362 | 0.02% | 3 | 36983 | 0.01% | 540 | 89945 | 0.60% |
| EMX Off 3 | 32 | 66472 | 0.05% | 10 | 49582 | 0.02% | 5804 | 83231 | 6.97% |
| EMX Off 4 | 146 | 76633 | 0.19% | 57 | 60976 | 0.09% | 11817 | 86566 | 13.65% |
| VEGF On | 359 | 34089 | 1.05% | 379 | 44841 | 0.85% | 3815 | 42732 | 8.93% |
| VEGF Off 1 | 214 | 49383 | 0.43% | 117 | 40358 | 0.29% | 14578 | 71764 | 20.31% |
| VEGF Off 2 | 29 | 34582 | 0.08% | 10 | 21753 | 0.05% | 2551 | 43775 | 5.83% |
| VEGF Off 3 | 18 | 47664 | 0.04% | 4 | 43171 | 0.01% | 1743 | 82128 | 2.12% |
| VEGF Off 4 | 58 | 56732 | 0.10% | 33 | 44096 | 0.07% | 14114 | 116598 | 12.10% |
| CLTA On | 2087 | 48566 | 4.30% | 930 | 51240 | 1.81% | 16930 | 88447 | 19.14% |
| CLTA Off 1 | 8 | 79008 | 0.01% | 8 | 72536 | 0.01% | 3361 | 111154 | 3.02% |
| CLTA Off 2 | 3 | 69103 | 0.00% | 0 | 76788 | 0.00% | 75 | 78021 | 0.10% |
| CLTA Off 3 | 1 | 44342 | 0.00% | 2 | 49937 | 0.00% | 94 | 51070 | 0.18% |
| | +4-HT intein-Cas9 (S219) | | | +4-HT intein-Cas9 (C574) | | | +4-HT wt Cas9 (500 ng) | | |
| | Indels | Total | Mod. Freq | Indels | Total | Mod. Freq | Indels | Total | Mod. Freq |
| EMX On | 7434 | 54764 | 13.57% | 5209 | 54997 | 9.47% | 9820 | 55972 | 17.54% |
| EMX Off 1 | 185 | 43554 | 0.42% | 116 | 42432 | 0.27% | 1043 | 41387 | 2.52% |
| EMX Off 2 | 20 | 56997 | 0.04% | 22 | 61504 | 0.04% | 412 | 52780 | 0.78% |
| EMX Off 3 | 413 | 53819 | 0.77% | 160 | 56140 | 0.29% | 4149 | 67153 | 6.18% |
| EMX Off 4 | 2413 | 76405 | 3.16% | 574 | 50867 | 1.13% | 6561 | 62651 | 10.47% |
| VEGF On | 1285 | 35095 | 3.66% | 1179 | 38909 | 3.03% | 1120 | 23157 | 4.84% |
| VEGF Off 1 | 2951 | 34729 | 8.50% | 2272 | 48512 | 4.68% | 6262 | 42489 | 14.74% |
| VEGF Off 2 | 288 | 19326 | 1.49% | 273 | 35253 | 0.77% | 1199 | 28117 | 4.26% |
| VEGF Off 3 | 167 | 45573 | 0.37% | 107 | 56967 | 0.19% | 679 | 42675 | 1.59% |
| VEGF Off 4 | 1465 | 37619 | 3.89% | 1229 | 88062 | 1.40% | 3159 | 33446 | 9.45% |
| CLTA On | 5691 | 39290 | 14.48% | 4348 | 56815 | 7.65% | 7974 | 59031 | 13.51% |
| CLTA Off 1 | 286 | 79836 | 0.36% | 32 | 72909 | 0.04% | 1468 | 72166 | 2.03% |
| CLTA Off 2 | 0 | 25019 | 0.00% | 11 | 64317 | 0.02% | 18 | 36863 | 0.05% |
| CLTA Off 3 | 13 | 38264 | 0.03% | 4 | 42814 | 0.01% | 78 | 58340 | 0.13% |

TABLE 5

P-values for comparisons between conditions in FIG. 2a. P-values were obtained using the Fisher exact test and adjusted for multiple comparisons using the Benjamini-Hochberg Method.

| | intein-Cas9(S219) (+4-HT vs. −4-HT) | intein-Cas9(C574) (+4-HT vs. −4-HT) | wt Cas9 (+4-HT vs. −4-HT) |
|---|---|---|---|
| EMX On | $<3.3 \times 10^{-16}$ | $<3.3 \times 10^{-16}$ | 1 |
| VEGF On | $<3.3 \times 10^{-16}$ | $<3.3 \times 10^{-16}$ | 1 |
| CLTA On | $<3.3 \times 10^{-16}$ | $<3.3 \times 10^{-16}$ | 1 |

TABLE 6

Raw sequence counts and modification frequencies for data plotted in FIG. 4b-d, and 9-11. Total: total number of sequence counts. Modification frequency: number of indels divided by the total number of sequences listed as percentages.

| | +4-HT intein-Cas9 (S219) | | | +4-HT intein-Cas9 (C574) | | | +4-HT wt Cas9 (500 ng) | | | +4-HT wt Cas9 (260 ng) | |
|---|---|---|---|---|---|---|---|---|---|---|---|
| | Indels | Total | Mod Freq | Indels | Total | Mod Freq | Indels | Total | Mod Freq | Indels | Total |
| EMX On | 5446 | 66039 | 8.25% | 4125 | 64260 | 6.42% | 10453 | 63225 | 16.53% | 6836 | 54232 |
| EMX Off 1 | 134 | 65439 | 0.20% | 115 | 65758 | 0.17% | 466 | 37687 | 1.24% | 488 | 44817 |
| EMX Off 2 | 26 | 69924 | 0.04% | 10 | 61188 | 0.02% | 236 | 65936 | 0.36% | 94 | 62522 |
| EMX Off 3 | 438 | 81696 | 0.54% | 173 | 68783 | 0.25% | 4890 | 88690 | 5.51% | 1760 | 74807 |
| EMX Off 4 | 1907 | 87678 | 2.18% | 708 | 82863 | 0.85% | 6997 | 66384 | 10.54% | 4131 | 80091 |
| VEGF On | 1633 | 51546 | 3.17% | 1330 | 57690 | 2.31% | 2072 | 37912 | 5.47% | 1873 | 38181 |
| VEGF Off 1 | 3132 | 67908 | 4.61% | 1978 | 62133 | 3.18% | 8471 | 76941 | 11.01% | 5893 | 58006 |
| VEGF Off 2 | 347 | 38567 | 0.90% | 189 | 49925 | 0.38% | 1008 | 33299 | 3.03% | 668 | 31470 |
| VEGF Off 3 | 84 | 52871 | 0.16% | 44 | 58976 | 0.07% | 1088 | 63365 | 1.72% | 490 | 48793 |
| VEGF Off 4 | 1067 | 52667 | 2.03% | 845 | 92592 | 0.91% | 3712 | 47327 | 7.84% | 3838 | 74876 |
| CLTA On | 4230 | 46334 | 9.13% | 3097 | 48752 | 6.35% | 7586 | 59582 | 12.73% | 5747 | 47919 |
| CLTA Off 1 | 169 | 72881 | 0.23% | 20 | 72486 | 0.03% | 1247 | 88428 | 1.41% | 576 | 79763 |
| CLTA Off 2 | 2 | 40883 | 0.00% | 2 | 56739 | 0.00% | 27 | 63439 | 0.04% | 27 | 64354 |
| CLTA Off 3 | 5 | 45599 | 0.01% | 3 | 39745 | 0.01% | 72 | 49309 | 0.15% | 16 | 47504 |

| | +4-HT wt Cas9 (260 ng) | +4-HT wt Cas9 (140 ng) | | | +4-HT wt Cas9 (80 ng) | | | +4-HT wt Cas9 (50 ng) | | |
|---|---|---|---|---|---|---|---|---|---|---|
| | Mod Freq | Indels | Total | Mod Freq | Indels | Total | Mod Freq | Indels | Total | Mod Freq |
| EMX On | 12.61% | 6215 | 65222 | 9.53% | 3674 | 57146 | 6.43% | 3551 | 58687 | 6.05% |
| EMX Off 1 | 1.09% | 373 | 53270 | 0.70% | 280 | 49924 | 0.56% | 196 | 50343 | 0.39% |
| EMX Off 2 | 0.15% | 115 | 67406 | 0.17% | 76 | 61509 | 0.12% | 19 | 58791 | 0.03% |
| EMX Off 3 | 2.35% | 1400 | 77420 | 1.81% | 507 | 69582 | 0.73% | 312 | 63812 | 0.49% |
| EMX Off 4 | 5.16% | 3065 | 89659 | 3.42% | 1372 | 83194 | 1.65% | 933 | 78093 | 1.19% |
| VEGF On | 4.91% | 1651 | 46948 | 3.52% | 1209 | 44425 | 2.72% | 994 | 45715 | 2.17% |
| VEGF Off 1 | 10.16% | 4073 | 60556 | 6.73% | 2884 | 52518 | 5.49% | 1792 | 53739 | 3.33% |
| VEGF Off 2 | 2.12% | 522 | 30231 | 1.73% | 388 | 37944 | 1.02% | 282 | 34935 | 0.81% |
| VEGF Off 3 | 1.00% | 293 | 48740 | 0.60% | 183 | 46144 | 0.40% | 143 | 50504 | 0.28% |
| VEGF Off 4 | 5.13% | 1892 | 66578 | 2.84% | 1224 | 67397 | 1.82% | 693 | 54510 | 1.27% |
| CLTA On | 11.99% | 4593 | 56068 | 8.19% | 3864 | 49534 | 7.80% | 2243 | 46510 | 4.82% |
| CLTA Off 1 | 0.72% | 223 | 87021 | 0.26% | 177 | 78827 | 0.22% | 75 | 68762 | 0.11% |
| CLTA Off 2 | 0.04% | 11 | 74571 | 0.01% | 7 | 38162 | 0.02% | 6 | 46931 | 0.01% |
| CLTA Off 3 | 0.03% | 12 | 49085 | 0.02% | 12 | 48776 | 0.02% | 8 | 42490 | 0.02% |

TABLE 7

P-values for comparisons between conditions in FIG. 7. P-values were obtained using the Fisher exact test and adjusted for multiple comparisons using the Benjamini-Hochberg Method.

| | Independent Experiment 1 | | Independent Experiment 2 | |
|---|---|---|---|---|
| | +4-HT intein-Cas9(S219) vs. +4-HT wt Cas9 (500 ng) | +4-HT intein-Cas9(C574) vs. +4-HT wt Cas9 (500 ng) | +4-HT intein-Cas9(S219) vs. +4-HT wt Cas9 (500 ng) | +4-HT intein-Cas9(C574) vs. +4-HT wt Cas9 (500 ng) |
| EMX On | $<2.4 \times 10^{-16}$ | $<2.4 \times 10^{-16}$ | $<3.9 \times 10^{-16}$ | $<3.9 \times 10^{-16}$ |
| EMX Off 1 | $<2.4 \times 10^{-16}$ | $<2.4 \times 10^{-16}$ | $<3.9 \times 10^{-16}$ | $<3.9 \times 10^{-16}$ |
| EMX Off 2 | $<2.4 \times 10^{-16}$ | $<2.4 \times 10^{-16}$ | $<3.9 \times 10^{-16}$ | $<3.9 \times 10^{-16}$ |
| EMX Off 3 | $<2.4 \times 10^{-16}$ | $<2.4 \times 10^{-16}$ | $<3.9 \times 10^{-16}$ | $<3.9 \times 10^{-16}$ |
| EMX Off 4 | $<2.4 \times 10^{-16}$ | $<2.4 \times 10^{-16}$ | $<3.9 \times 10^{-16}$ | $<3.9 \times 10^{-16}$ |
| VEGF On | $2.8 \times 10^{-12}$ | $<2.4 \times 10^{-16}$ | $<3.9 \times 10^{-16}$ | $<3.9 \times 10^{-16}$ |
| VEGF Off 1 | $<2.4 \times 10^{-16}$ | $<2.4 \times 10^{-16}$ | $<3.9 \times 10^{-16}$ | $<3.9 \times 10^{-16}$ |
| VEGF Off 2 | $<2.4 \times 10^{-16}$ | $<2.4 \times 10^{-16}$ | $<3.9 \times 10^{-16}$ | $<3.9 \times 10^{-16}$ |
| VEGF Off 3 | $<2.4 \times 10^{-16}$ | $<2.4 \times 10^{-16}$ | $<3.9 \times 10^{-16}$ | $<3.9 \times 10^{-16}$ |
| VEGF Off 4 | $<2.4 \times 10^{-16}$ | $<2.4 \times 10^{-16}$ | $<3.9 \times 10^{-16}$ | $<3.9 \times 10^{-16}$ |
| CLTA On | 1 | $<2.4 \times 10^{-16}$ | $<3.9 \times 10^{-16}$ | $<3.9 \times 10^{-16}$ |
| CLTA Off 1 | $<2.4 \times 10^{-16}$ | $<2.4 \times 10^{-16}$ | $<3.9 \times 10^{-16}$ | $<3.9 \times 10^{-16}$ |
| CLTA Off 2 | $9.1 \times 10^{-5}$ | $4.4 \times 10^{-3}$ | $1.4 \times 10^{-4}$ | $4.6 \times 10^{-6}$ |
| CLTA Off 3 | $1.3 \times 10^{-7}$ | $1.5 \times 10^{-14}$ | $3.1 \times 10^{-15}$ | $3.5 \times 10^{-15}$ |

TABLE 8

P-values for comparisons between conditions in FIGS. 9 and 10. All conditions were treated with 4-HT. P-values were obtained using the Fisher exact test and adjusted tor multiple comparisons using the Benjamim-Hochberg Method.

| | intein-Cas9(S219) vs. wt Cas9 (500 ng) | intein-Cas9(S219) vs. wt Cas9 (260 ng) | intein-Cas9(S219) vs. wt Cas9 (140 ng) | intein-Cas9(S219) vs. wt Cas9 (80 ng) | intein-Cas9(S219) vs. wt Cas9 (50 ng) | intein-Cas9(C574) vs. wt Cas9 (500 ng) |
|---|---|---|---|---|---|---|
| EMX On | $<3.9 \times 10^{-16}$ | $<3.9 \times 10^{-16}$ | $<3.9 \times 10^{-16}$ | 1 | 1 | $<3.9 \times 10^{-16}$ |
| EMX Off 1 | $<3.9 \times 10^{-16}$ | $<3.9 \times 10^{-16}$ | $<3.9 \times 10^{-16}$ | $<3.9 \times 10^{-16}$ | $6.7 \times 10^{-9}$ | $<3.9 \times 10^{-16}$ |
| EMX Off 2 | $<3.9 \times 10^{-16}$ | $4.3 \times 10^{-12}$ | $2.4 \times 10^{-15}$ | $1.7 \times 10^{-8}$ | 0.84 | $<3.9 \times 10^{-16}$ |
| EMX Off 3 | $<3.9 \times 10^{-16}$ | $<3.9 \times 10^{-16}$ | $<3.9 \times 10^{-16}$ | $2.0 \times 10^{-6}$ | 1 | $<3.9 \times 10^{-16}$ |
| EMX Off 4 | $<3.9 \times 10^{-16}$ | $<3.9 \times 10^{-16}$ | $<3.9 \times 10^{-16}$ | 1 | 1 | $<3.9 \times 10^{-16}$ |
| VEGF On | $<3.9 \times 10^{-16}$ | $<3.9 \times 10^{-16}$ | $1.7 \times 10^{-3}$ | 1 | 1 | $<3.9 \times 10^{-16}$ |
| VEGF Off 1 | $<3.9 \times 10^{-16}$ | $<3.9 \times 10^{-16}$ | $<3.9 \times 10^{-16}$ | $3.8 \times 10^{-12}$ | 1 | $<3.9 \times 10^{-16}$ |
| VEGF Off 2 | $<3.9 \times 10^{-16}$ | $<3.9 \times 10^{-16}$ | $<3.9 \times 10^{-16}$ | $5.7 \times 10^{-2}$ | 1 | $<3.9 \times 10^{-16}$ |
| VEGF Off 3 | $<3.9 \times 10^{-16}$ | $<3.9 \times 10^{-16}$ | $<3.9 \times 10^{-16}$ | $5.9 \times 10^{-13}$ | $1.8 \times 10^{-5}$ | $<3.9 \times 10^{-16}$ |
| VEGF Off 4 | $<3.9 \times 10^{-16}$ | $<3.9 \times 10^{-16}$ | $<3.9 \times 10^{-16}$ | 1 | 1 | $<3.9 \times 10^{-16}$ |
| CLTA On | $<3.9 \times 10^{-16}$ | $<3.9 \times 10^{-16}$ | 1 | 1 | 1 | $<3.9 \times 10^{-16}$ |
| CLTA Off 1 | $<3.9 \times 10^{-16}$ | $<3.9 \times 10^{-16}$ | 0.21 | 0.74 | 1 | $<3.9 \times 10^{-16}$ |
| CLTA Off 2 | $1.4 \times 10^{-4}$ | $1.6 \times 10^{-4}$ | 0.13 | $9.4 \times 10^{-2}$ | 0.23 | $4.6 \times 10^{-6}$ |
| CLTA Off 3 | $3.1 \times 10^{-15}$ | $2.3 \times 10^{-2}$ | 0.12 | 0.11 | 0.29 | $3.5 \times 10^{-15}$ |

| | intein-Cas9(C574) vs. wt Cas9 (260 ng) | intein-Cas9(C574) vs. wt Cas9 (140 ng) | intein-Cas9(C574) vs. wt Cas9 (80 ng) | intein-Cas9(C574) vs. wt Cas9 (50 ng) |
|---|---|---|---|---|
| EMX On | $<3.9 \times 10^{-16}$ | $<3.9 \times 10^{-16}$ | 0.56 | 1 |
| EMX Off 1 | $<3.9 \times 10^{-16}$ | $<3.9 \times 10^{-16}$ | $<3.9 \times 10^{-16}$ | $3.7 \times 10^{-12}$ |
| EMX Off 2 | $<3.9 \times 10^{-16}$ | $<3.9 \times 10^{-16}$ | $1.0 \times 10^{-13}$ | $7.1 \times 10^{-2}$ |
| EMX Off 3 | $<3.9 \times 10^{-16}$ | $<3.9 \times 10^{-16}$ | $<3.9 \times 10^{-16}$ | $7.5 \times 10^{-13}$ |
| EMX Off 4 | $<3.9 \times 10^{-16}$ | $<3.9 \times 10^{-16}$ | $<3.9 \times 10^{-16}$ | $1.0 \times 10^{-11}$ |
| VEGF On | $<3.9 \times 10^{-16}$ | $<3.9 \times 10^{-16}$ | $1.9 \times 10^{-5}$ | 1 |
| VEGF Off 1 | $<3.9 \times 10^{-16}$ | $<3.9 \times 10^{-16}$ | $<3.9 \times 10^{-16}$ | $9.6 \times 10^{-2}$ |
| VEGF Off 2 | $<3.9 \times 10^{-16}$ | $<3.9 \times 10^{-16}$ | $<3.9 \times 10^{-16}$ | $<3.9 \times 10^{-16}$ |
| VEGF Off 3 | $<3.9 \times 10^{-16}$ | $<3.9 \times 10^{-16}$ | $<3.9 \times 10^{-16}$ | $<3.9 \times 10^{-16}$ |
| VEGF Off 4 | $<3.9 \times 10^{-16}$ | $<3.9 \times 10^{-16}$ | $<3.9 \times 10^{-16}$ | $9.9 \times 10^{-11}$ |
| CLTA On | $<3.9 \times 10^{-16}$ | $<3.9 \times 10^{-16}$ | $<3.9 \times 10^{-16}$ | 1 |
| CLTA Off 1 | $<3.9 \times 10^{-16}$ | $<3.9 \times 10^{-16}$ | $<3.9 \times 10^{-16}$ | $2.0 \times 10^{-9}$ |
| CLTA Off 2 | $5.4 \times 10^{-6}$ | $4.8 \times 10^{-2}$ | $3.5 \times 10^{-2}$ | 0.11 |
| CLTA Off 3 | $9.3 \times 10^{-3}$ | $5.7 \times 10^{-2}$ | $5.7 \times 10^{-2}$ | 0.16 |

TABLE 9

Raw sequence counts and modification frequencies (for cells transfected with wild-type Cas9 (500 ng) but without a targeting sgRNA, in the presence of 4-HT).

| | +4-HT wt Cas9 (500 ng) −sgRNA | | |
|---|---|---|---|
| | Indels | Total | Modification frequency |
| EMX On | 8 | 78943 | 0.01% |
| EMX Off 1 | 1 | 42232 | 0.00% |
| EMX Off 2 | 4 | 79008 | 0.01% |
| EMX Off 3 | 60 | 113629 | 0.05% |
| EMX Off 4 | 5 | 104159 | 0.00% |
| VEGF On | 0 | 60667 | 0.00% |
| VEGF Off 1 | 2 | 111409 | 0.00% |
| VEGF Off 2 | 0 | 52048 | 0.00% |
| VEGF Off 3 | 4 | 88105 | 0.00% |
| VEGF Off 4 | 2 | 123559 | 0.00% |

TABLE 9-continued

Raw sequence counts and modification frequencies (for cells transfected with wild-type Cas9 (500 ng) but without a targeting sgRNA, in the presence of 4-HT).

| | +4-HT wt Cas9 (500 ng) −sgRNA | | |
|---|---|---|---|
| | Indels | Total | Modification frequency |
| CLTA On | 491 | 68600 | 0.72% |
| CLTA Off 1 | 10 | 116033 | 0.01% |
| CLTA Off 2 | 6 | 75723 | 0.01% |
| CLTA Off 3 | 4 | 53885 | 0.01% |

Total: total number of sequence counts.

Modification frequency: number of indels divided by the total number of sequences listed as percentages.

Sequences

Intein 37R32:
TGCCTTGCCGAGGGTACCCGAATCTTCGATCCGGTCACTGGTACAACGCATCGCA
TCGAGGATGTTGTCGATGGGCGCAAGCCTATTCATGTCGTGGCTGCTGCCAAGGA
CGGAACGCTGCTCGCGCGGCCCGTGGTGTCCTGGTTCGACCAGGGAACGCGGGA
TGTGATCGGGTTGCGGATCGCCGGTGGCGCCATCGTGTGGGCGACACCCGATCAC
AAGGTGCTGACAGAGTACGGCTGGCGTGCCGCCGGGGAACTCCGCAAGGGAGAC
AGGGTGGCCGGACCGGGTGGTTCTGGTAACAGCCTGGCCTTGTCCCTGACGGCCG
ACCAGATGGTCAGTGCCTTGTTGGATGCTGAGCCCCCCATACTCTATTCCGAGTA
TGATCCTACCAGTCCCTTCAGTGAAGCTTCGATGATGGGCTTACTGACCAACCTG
GCAGACAGGGAGCTGGTTCACATGATCAACTGGGCGAAGAGGGTGCCAGGCTTT
GTGGATTTGACCCTCCATGATCAGGCCCACCTTCTAGAACGTGCCTGGCTAGAGA
TCCTGATGATTGGTCTCGTCTGGCGCTCCATGGAGCACCCAGGGAAGCTACTGTT
TGCTCCTAACTTGCTCTTGGACAGGAACCAGGGAAAATGTGTAGAGGGCATGGT
GGAGATCTTCGACATGCTGCTGGCTACATCATCTCGGTTCCGCATGATGAATCTG
CAGGGAGAGGAGTTTGTGTGCCTCAAATCTATTATTTTGCTTAATTCTGGAGTGT
ACACATTTCTGTCCAGCACCCTGAAGTCTCTGGAAGAGAAGGACCATATCCACCG
AGCCCTGGACAAGATCACGGACACTTTGATCCACCTGATGGCCAAGGCAGGCCT
GACCCTGCAGCAGCAGCACCAGCGGCTGGCCCAGCTCCTCCTCATCCTCTCCCAC
ATCAGGCACATGAGTAACAAAGGAATGGAGCATCTGTACAGCATGAAGTACAAG
AACGTGGTGCCCCTCTATGACCTGCTGCTGGAGATGCTGGACGCCCACCGCCTAC
ATGCGGGTGGTTCTGGTGCTAGCCGCGTGCAGGCGTTCGCGGATGCCCTGGATGA
CAAATTCCTGCACGACATGCTGGCGGAAGGACTCCGCTATTCCGTGATCCGAGAA
GTGCTGCCAACGCGGCGGGCACGAACGTTCGACCTCGAGGTCGAGGAACTGCAC
ACCCTCGTCGCCGAAGGGGTTGTCGTGCACAACTGC (SEQ ID NO: 149)

Cas9-NLS-3×FLAG:
MDKKYSIGLDIGTNSVGWAVITDEYKVPSKKFKVLGNTDRHSIKKNLIGALLFDSGE
TAEATRLKRTARRRYTRRKNRICYLQEIFSNEMAKVDDSFFHRLEESFLVEEDKKHE
RHPIFGNIVDEVAYHEKYPTIYHLRKKLVDSTDKADLRLIYLALAHMIKFRGHFLIEG
DLNPDNSDVDKLFIQLVQTYNQLFEENPINASGVDAKAILSARLSKSRRLENLIAQLP
GEKKNGLFGNLIALSLGLTPNFKSNFDLAEDAKLQLSKDTYDDDLDNLLAQIGDQYA
DLFLAAKNLSDAILLSDILRVNTEITKAPLSASMIKRYDEHHQDLTLLKALVRQQLPE
KYKEIFFDQSKNGYAGYIDGGASQEEFYKFIKPILEKMDGTEELLVKLNREDLLRKQR
TFDNGSIPHQIHLGELHAILRRQEDFYPFLKDNREKIEKILTFRIPYYVGPLARGNSRFA
WMTRKSEETITPWNFEEVVDKGASAQSFIERMTNFDKNLPNEKVLPKHSLLYEYFTV
YNELTKVKYVTEGMRKPAFLSGEQKKAIVDLLFKTNRKVTVKQLKEDYFKKIECFD
SVEISGVEDRFNASLGTYHDLLKIIKDKDFLDNEENEDILEDIVLTLTLFEDREMIEERL
KTYAHLFDDKVMKQLKRRRYTGWGRLSRKLINGIRDKQSGKTILDFLKSDGFANRN
FMQLIHDDSLTFKEDIQKAQVSGQGDSLHEHIANLAGSPAIKKGILQTVKVVDELVK
VMGRHKPENIVIEMARENQTTQKGQKNSRERMKRIEEGIKELGSQILKEHPVENTQL
QNEKLYLYYLQNGRDMYVDQELDINRLSDYDVDHIVPQSFLKDDSIDNKVLTRSDK
NRGKSDNVPSEEVVKKMKNYWRQLLNAKLITQRKFDNLTKAERGGLSELDKAGFIK
RQLVETRQITKHVAQILDSRMNTKYDENDKLIREVKVITLKSKLVSDFRKDFQFYKV
REINNYHHAHDAYLNAVVGTALIKKYPKLESEFVYGDYKVYDVRKMIAKSEQEIGK
ATAKYFFYSNIMNFFKTEITLANGEIRKRPLIETNGETGEIVWDKGRDFATVRKVLSM
PQVNIVKKTEVQTGGFSKESILPKRNSDKLIARKKDWDPKKYGGFDSPTVAYSVLVV
AKVEKGKSKKLKSVKELLGITIMERSSFEKNPIDFLEAKGYKEVKKDLIIKLPKYSLFE
LENGRKRMLASAGELQKGNELALPSKYVNFLYLASHYEKLKGSPEDNEQKQLFVEQ
PAAFKYFDTTIDRKRYTSTKEVLDATLIHQSITGLYETRIDLSQLGGDGSPKKKRKVSS
DYKDHDGDYKDHDIDYKDDDDKAAG (SEQ ID NO: 150)

Intein-Cas9(C80)-NLS-3×FLAG:
MDKKYSIGLDIGTNSVGWAVITDEYKVPSKKFKVLGNTDRHSIKKNLIGALLFDSGE
TAEATRLKRTARRRYTRRKNRICLAEGTRIFDPVTGTTHRIEDVVDGRKPIHVVAAA
KDGTLLARPVVSWFDQGTRDVIGLRIAGGAIVWATPDHKVLTEYGWRAAGELRKG
DRVAGPGGSGNSLALSLTADQMVSALLDAEPPILYSEYDPTSPFSEASMMGLLTNLA
DRELVHMINWAKRVPGFVDLTLHDQAHLLERAWLEILMIGLVWRSMEHPGKLLFAP
NLLLDRNQGKCVEGMVEIFDMLLATSSRFRMMNLQGEEFVCLKSIILLNSGVYTFLS
STLKSLEEKDHIHRALDKITDTLIHLMAKAGLTLQQQHQRLAQLLLILSHIRHMSNKG
MEHLYSMKYKNVVPLYDLLLEMLDAHRLHAGGSGASRVQAFADALDDKFLHDML
AEGLRYSVIREVLPTRRARTFDLEVEELHTLVAEGVVVHNCYLQEIFSNEMAKVDDS
FFHRLEESFLVEEDKKHERHPIFGNIVDEVAYHEKYPTIYHLRKKLVDSTDKADLRLI
YLALAHMIKFRGHFLIEGDLNPDNSDVDKLFIQLVQTYNQLFEENPINASGVDAKAIL
SARLSKSRRLENLIAQLPGEKKNGLFGNLIALSLGLTPNFKSNFDLAEDAKLQLSKDT
YDDDLDNLLAQIGDQYADLFLAAKNLSDAILLSDILRVNTEITKAPLSASMIKRYDEH
HQDLTLLKALVRQQLPEKYKEIFFDQSKNGYAGYIDGGASQEEFYKFIKPILEKMDG
TEELLVKLNREDLLRKQRTFDNGSIPHQIHLGELHAILRRQEDFYPFLKDNREKIEKIL
TFRIPYYVGPLARGNSRFAWMTRKSEETITPWNFEEVVDKGASAQSFIERMTNFDKN
LPNEKVLPKHSLLYEYFTVYNELTKVKYVTEGMRKPAFLSGEQKKAIVDLLFKTNRK
VTVKQLKEDYFKKIECFDSVEISGVEDRFNASLGTYHDLLKIIKDKDFLDNEENEDILE
DIVLTLTLFEDREMIEERLKTYAHLFDDKVMKQLKRRRYTGWGRLSRKLINGIRDKQ
SGKTILDFLKSDGFANRNFMQLIHDDSLTFKEDIQKAQVSGQGDSLHEHIANLAGSPA
IKKGILQTVKVVDELVKVMGRHKPENIVIEMARENQTTQKGQKNSRERMKRIEEGIK
ELGSQILKEHPVENTQLQNEKLYLYYLQNGRDMYVDQELDINRLSDYDVDHIVPQSF
LKDDSIDNKVLTRSDKNRGKSDNVPSEEVVKKMKNYWRQLLNAKLITQRKFDNLTK
AERGGLSELDKAGFIKRQLVETRQITKHVAQILDSRMNTKYDENDKLIREVKVITLKS
KLVSDFRKDFQFYKVREINNYHHAHDAYLNAVVGTALIKKYPKLESEFVYGDYKVY
DVRKMIAKSEQEIGKATAKYFFYSNIMNFFKTEITLANGEIRKRPLIETNGETGEIVWD
KGRDFATVRKVLSMPQVNIVKKTEVQTGGFSKESILPKRNSDKLIARKKDWDPKKY -continued

| Sequences |
| --- |

GGFDSPTVAYSVLVVAKVEKGKSKKLKSVKELLGITIMERSSFEKNPIDFLEAKGYKE
VKKDLIIKLPKYSLFELENGRKRMLASAGELQKGNELALPSKYVNFLYLASHYEKLK
QAENIIHLFTLTNLGAPAAFKYFDTTIDRKRYTSTKEVLDATLIHQSITGLYETRIDLSQ
LGGDGSPKKKRKVSSDYKDHDGDYKDHDIDYKDDDDKAAG (SEQ ID NO: 151)

Intein-Cas9(A127)-NLS-3×FLAG:
MDKKYSIGLDIGTNSVGWAVITDEYKVPSKKFKVLGNTDRHSIKKNLIGALLFDSGE
TAEATRLKRTARRRYTRRKNRICYLQEIFSNEMAKVDDSFFHRLEESFLVEEDKKHE
RHPIFGNIVDEVCLAEGTRIFDPVTGTTHRIEDVVDGRKPIHVVAAAKDGTLLARPVV
SWFDQGTRDVIGLRIAGGAIVWATPDHKVLTEYGWRAAGELRKGDRVAGPGGSGN
SLALSLTADQMVSALLDAEPPILYSEYDPTSPFSEASMMGLLTNLADRELVHMINWA
KRVPGFVDLTLHDQAHLLERAWLEILMIGLVWRSMEHPGKLLFAPNLLLDRNQGKC
VEGMVEIFDMLLATSSRFRMMNLQGEEFVCLKSIILLNSGVYTFLSSTLKSLEEKDHI
HRALDKITDTLIHLMAKAGLTLQQQHQRLAQLLLILSHIRHMSNKGMEHLYSMKYK
NVVPLYDLLLEMLDAHRLHAGGSGASRVQAFADALDDKFLHDMLAEGLRYSVIRE
VLPTRRARTFDLEVEELHTLVAEGVVVHNCYHEKYPTIYHLRKKLVDSTDKADLRLI
YLALAHMIKFRGHFLIEGDLNPDNSDVDKLFIQLVQTYNQLFEENPINASGVDAKAIL
SARLSKSRRLENLIAQLPGEKKNGLFGNLIALSLGLTPNFKSNFDLAEDAKLQLSKDT
YDDDLDNLLAQIGDQYADLFLAAKNLSDAILLSDILRVNTEITKAPLSASMIKRYDEH
HQDLTLLKALVRQQLPEKYKEIFFDQSKNGYAGYIDGGASQEEFYKFIKPILEKMDG
TEELLVKLNREDLLRKQRTFDNGSIPHQIHLGELHAILRRQEDFYPFLKDNREKIEKIL
TFRIPYYVGPLARGNSRFAWMTRKSEETITPWNFEEVVDKGASAQSFIERMTNFDKN
LPNEKVLPKHSLLYEYFTVYNELTKVKYVTEGMRKPAFLSGEQKKAIVDLLFKTNRK
VTVKQLKEDYFKKIECFDSVEISGVEDRFNASLGTYHDLLKIIKDKDFLDNEENEDILE
DIVLTLTLFEDREMIEERLKTYAHLFDDKVMKQLKRRRYTGWGRLSRKLINGIRDKQ
SGKTILDFLKSDGFANRNFMQLIHDDSLTFKEDIQKAQVSGQGDSLHEHIANLAGSPA
IKKGILQTVKVVDELVKVMGRHKPENIVIEMARENQTTQKGQKNSRERMKRIEEGIK
ELGSQILKEHPVENTQLQNEKLYLYYLQNGRDMYVDQELDINRLSDYDVDHIVPQSF
LKDDSIDNKVLTRSDKNRGKSDNVPSEEVVKKMKNYWRQLLNAKLITQRKFDNLTK
AERGGLSELDKAGFIKRQLVETRQITKHVAQILDSRMNTKYDENDKLIREVKVITLKS
KLVSDFRKDFQFYKVREINNYHHAHDAYLNAVVGTALIKKYPKLESEFVYGDYKVY
DVRKMIAKSEQEIGKATAKYFFYSNIMNFFKTEITLANGEIRKRPLIETNGETGEIVWD
KGRDFATVRKVLSMPQVNIVKKTEVQTGGFSKESILPKRNSDKLIARKKDWDPKKY
GGFDSPTVAYSVLVVAKVEKGKSKKLKSVKELLGITIMERSSFEKNPIDFLEAKGYKE
VKKDLIIKLPKYSLFELENGRKRMLASAGELQKGNELALPSKYVNFLYLASHYEKLK
GSPEDNEQKQLFVEQHKHYLDEIIEQISEFSKRVILADANLDKVLSAYNKHRDKPIRE
QAENIIHLFTLTNLGAPAAFKYFDTTIDRKRYTSTKEVLDATLIHQSITGLYETRIDLSQ
LGGDGSPKKKRKVSSDYKDHDGDYKDHDIDYKDDDDKAAG (SEQ ID NO: 152)

Intein-Cas9(T146)-NLS-3×FLAG:
MDKKYSIGLDIGTNSVGWAVITDEYKVPSKKFKVLGNTDRHSIKKNLIGALLFDSGE
TAEATRLKRTARRRYTRRKNRICYLQEIFSNEMAKVDDSFFHRLEESFLVEEDKKHE
RHPIFGNIVDEVAYHEKYPTIYHLRKKLVDSCLAEGTRIFDPVTGTTHRIEDVVDGRK
PIHVVAAAKDGTLLARPVVSWFDQGTRDVIGLRIAGGAIVWATPDHKVLTEYGWRA
AGELRKGDRVAGPGGSGNSLALSLTADQMVSALLDAEPPILYSEYDPTSPFSEASMM
GLLTNLADRELVHMINWAKRVPGFVDLTLHDQAHLLERAWLEILMIGLVWRSMEH
PGKLLFAPNLLLDRNQGKCVEGMVEIFDMLLATSSRFRMMNLQGEEFVCLKSIILLN
SGVYTFLSSTLKSLEEKDHIHRALDKITDTLIHLMAKAGLTLQQQHQRLAQLLLILSHI
RHMSNKGMEHLYSMKYKNVVPLYDLLLEMLDAHRLHAGGSGASRVQAFADALDD
KFLHDMLAEGLRYSVIREVLPTRRARTFDLEVEELHTLVAEGVVVHNCDKADLRLIY
LALAHMIKFRGHFLIEGDLNPDNSDVDKLFIQLVQTYNQLFEENPINASGVDAKAILS
ARLSKSRRLENLIAQLPGEKKNGLFGNLIALSLGLTPNFKSNFDLAEDAKLQLSKDTY
DDDLDNLLAQIGDQYADLFLAAKNLSDAILLSDILRVNTEITKAPLSASMIKRYDEHH
QDLTLLKALVRQQLPEKYKEIFFDQSKNGYAGYIDGGASQEEFYKFIKPILEKMDGTE
ELLVKLNREDLLRKQRTFDNGSIPHQIHLGELHAILRRQEDFYPFLKDNREKIEKILTF
RIPYYVGPLARGNSRFAWMTRKSEETITPWNFEEVVDKGASAQSFIERMTNFDKNLP
NEKVLPKHSLLYEYFTVYNELTKVKYVTEGMRKPAFLSGEQKKAIVDLLFKTNRKV
TVKQLKEDYFKKIECFDSVEISGVEDRFNASLGTYHDLLKIIKDKDFLDNEENEDILED
IVLTLTLFEDREMIEERLKTYAHLFDDKVMKQLKRRRYTGWGRLSRKLINGIRDKQS
GKTILDFLKSDGFANRNFMQLIHDDSLTFKEDIQKAQVSGQGDSLHEHIANLAGSPAI
KKGILQTVKVVDELVKVMGRHKPENIVIEMARENQTTQKGQKNSRERMKRIEEGIK
ELGSQILKEHPVENTQLQNEKLYLYYLQNGRDMYVDQELDINRLSDYDVDHIVPQSF
LKDDSIDNKVLTRSDKNRGKSDNVPSEEVVKKMKNYWRQLLNAKLITQRKFDNLTK
AERGGLSELDKAGFIKRQLVETRQITKHVAQILDSRMNTKYDENDKLIREVKVITLKS
KLVSDFRKDFQFYKVREINNYHHAHDAYLNAVVGTALIKKYPKLESEFVYGDYKVY
DVRKMIAKSEQEIGKATAKYFFYSNIMNFFKTEITLANGEIRKRPLIETNGETGEIVWD
KGRDFATVRKVLSMPQVNIVKKTEVQTGGFSKESILPKRNSDKLIARKKDWDPKKY
GGFDSPTVAYSVLVVAKVEKGKSKKLKSVKELLGITIMERSSFEKNPIDFLEAKGYKE
VKKDLIIKLPKYSLFELENGRKRMLASAGELQKGNELALPSKYVNFLYLASHYEKLK
QAENIIHLFTLTNLGAPAAFKYFDTTIDRKRYTSTKEVLDATLIHQSITGLYETRIDLSQ
LGGDGSPKKKRKVSSDYKDHDGDYKDHDIDYKDDDDKAAG (SEQ ID NO: 153)

Intein-Cas9(S219)-NLS-3×FLAG:
MDKKYSIGLDIGTNSVGWAVITDEYKVPSKKFKVLGNTDRHSIKKNLIGALLFDSGE
TAEATRLKRTARRRYTRRKNRICYLQEIFSNEMAKVDDSFFHRLEESFLVEEDKKHE
RHPIFGNIVDEVAYHEKYPTIYHLRKKLVDSTDKADLRLIYLALAHMIKFRGHFLIEG
DLNPDNSDVDKLFIQLVQTYNQLFEENPINASGVDAKAILSARLSKCLAEGTRIFDPV -continued

| Sequences |
|---|
| TGTTHRIEDVVDGRKPIHVVAAAKDGTLLARPVVSWFDQGTRDVIGLRIAGGAIVW<br>ATPDHKVLTEYGWRAAGELRKGDRVAGPGGSGNSLALSLTADQMVSALLDAEPPIL<br>YSEYDPTSPFSEASMMGLLTNLADRELVHMINWAKRVPGFVDLTLHDQAHLLERA<br>WLEILMIGLVWRSMEHPGKLLFAPNLLLDRNQGKCVEGMVEIFDMLLATSSRFRMM<br>NLQGEEFVCLKSIILLNSGVYTFLSSTLKSLEEKDHIHRALDKITDTLIHLMAKAGLTL<br>QQQHQRLAQLLLILSHIRHMSNKGMEHLYSMKYKNVVPLYDLLLEMLDAHRLHAG<br>GSGASRVQAFADALDDKFLHDMLAEGLRYSVIREVLPTRRARTFDLEVEELHTLVAE<br>GVVVHNCRRLENLIAQLPGEKKNGLFGNLIALSLGLTPNFKSNFDLAEDAKLQLSKD<br>TYDDDLDNLLAQIGDQYADLFLAAKNLSDAILLSDILRVNTEITKAPLSASMIKRYDE<br>HHQDLTLLKALVRQQLPEKYKEIFFDQSKNGYAGYIDGGASQEEFYKFIKPILEKMD<br>GTEELLVKLNREDLLRKQRTFDNGSIPHQIHLGELHAILRRQEDFYPFLKDNREKIEKI<br>LTFRIPYYVGPLARGNSRFAWMTRKSEETITPWNFEEVVDKGASAQSFIERMTNFDK<br>NLPNEKVLPKHSLLYEYFTVYNELTKVKYVTEGMRKPAFLSGEQKKAIVDLLFKTNR<br>KVTVKQLKEDYFKKIECFDSVEISGVEDRFNASLGTYHDLLKIIKDKDFLDNEENEDI<br>LEDIVLTLTLFEDREMIEERLKTYAHLFDDKVMKQLKRRRYTGWGRLSRKLINGIRD<br>KQSGKTILDFLKSDGFANRNFMQLIHDDSLTFKEDIQKAQVSGQGDSLHEHIANLAG<br>SPAIKKGILQTVKVVDELVKVMGRHKPENIVIEMARENQTTQKGQKNSRERMKRIEE<br>GIKELGSQILKEHPVENTQLQNEKLYLYYLQNGRDMYVDQELDINRLSDYDVDHIVP<br>QSFLKDDSIDNKVLTRSDKNRGKSDNVPSEEVVKKMKNYWRQLLNAKLITQRKFDN<br>LTKAERGGLSELDKAGFIKRQLVETRQITKHVAQILDSRMNTKYDENDKLIREVKVIT<br>LKSKLVSDFRKDFQFYKVREINNYHHAHDAYLNAVVGTALIKKYPKLESEFVYGDY<br>KVYDVRKMIAKSEQEIGKATAKYFFYSNIMNFFKTEITLANGEIRKRPLIETNGETGEI<br>VWDKGRDFATVRKVLSMPQVNIVKKTEVQTGGFSKESILPKRNSDKLIARKKDWDP<br>KKYGGFDSPTVAYSVLVVAKVEKGKSKKLKSVKELLGITIMERSSFEKNPIDFLEAK<br>GYKEVKKDLIIKLPKYSLFELENGRKRMLASAGELQKGNELALPSKYVNFLYLASHY<br>PIREQAENIIHLFTLTNLGAPAAFKYFDTTIDRKRYTSTKEVLDATLIHQSITGLYETRI<br>DLSQLGGDGSPKKKRKVSSDYKDHDGDYKDHDIDYKDDDDKAAG (SEQ ID NO: 154) |
| Intein-Cas9(T333)-NLS-3×FLAG:<br>MDKKYSIGLDIGTNSVGWAVITDEYKVPSKKFKVLGNTDRHSIKKNLIGALLFDSGE<br>TAEATRLKRTARRRYTRRKNRICYLQEIFSNEMAKVDDSFFHRLEESFLVEEDKKHE<br>RHPIFGNIVDEVAYHEKYPTIYHLRKKLVDSTDKADLRLIYLALAHMIKFRGHFLIEG<br>DLNPDNSDVDKLFIQLVQTYNQLFEENPINASGVDAKAILSARLSKSRRLENLIAQLP<br>GEKKNGLFGNLIALSLGLTPNFKSNFDLAEDAKLQLSKDTYDDDLDNLLAQIGDQYA<br>DLFLAAKNLSDAILLSDILRVNTEITKAPLSASMIKRYDEHHQDLCLAEGTRIFDPVTG<br>TTHRIEDVVDGRKPIHVVAAAKDGTLLARPVVSWFDQGTRDVIGLRIAGGAIVWATP<br>DHKVLTEYGWRAAGELRKGDRVAGPGGSGNSLALSLTADQMVSALLDAEPPILYSE<br>YDPTSPFSEASMMGLLTNLADRELVHMINWAKRVPGFVDLTLHDQAHLLERAWLEI<br>LMIGLVWRSMEHPGKLLFAPNLLLDRNQGKCVEGMVEIFDMLLATSSRFRMMNLQ<br>GEEFVCLKSIILLNSGVYTFLSSTLKSLEEKDHIHRALDKITDTLIHLMAKAGLTLQQQ<br>HQRLAQLLLILSHIRHMSNKGMEHLYSMKYKNVVPLYDLLLEMLDAHRLHAGGSG<br>ASRVQAFADALDDKFLHDMLAEGLRYSVIREVLPTRRARTFDLEVEELHTLVAEGV<br>VVHNCLLKALVRQQLPEKYKEIFFDQSKNGYAGYIDGGASQEEFYKFIKPILEKMDG<br>TEELLVKLNREDLLRKQRTFDNGSIPHQIHLGELHAILRRQEDFYPFLKDNREKIEKIL<br>TFRIPYYVGPLARGNSRFAWMTRKSEETITPWNFEEVVDKGASAQSFIERMTNFDKN<br>LPNEKVLPKHSLLYEYFTVYNELTKVKYVTEGMRKPAFLSGEQKKAIVDLLFKTNRK<br>VTVKQLKEDYFKKIECFDSVEISGVEDRFNASLGTYHDLLKIIKDKDFLDNEENEDILE<br>DIVLTLTLFEDREMIEERLKTYAHLFDDKVMKQLKRRRYTGWGRLSRKLINGIRDKQ<br>SGKTILDFLKSDGFANRNFMQLIHDDSLTFKEDIQKAQVSGQGDSLHEHIANLAGSPA<br>IKKGILQTVKVVDELVKVMGRHKPENIVIEMARENQTTQKGQKNSRERMKRIEEGIK<br>ELGSQILKEHPVENTQLQNEKLYLYYLQNGRDMYVDQELDINRLSDYDVDHIVPQSF<br>LKDDSIDNKVLTRSDKNRGKSDNVPSEEVVKKMKNYWRQLLNAKLITQRKFDNLTK<br>AERGGLSELDKAGFIKRQLVETRQITKHVAQILDSRMNTKYDENDKLIREVKVITLKS<br>KLVSDFRKDFQFYKVREINNYHHAHDAYLNAVVGTALIKKYPKLESEFVYGDYKVY<br>DVRKMIAKSEQEIGKATAKYFFYSNIMNFFKTEITLANGEIRKRPLIETNGETGEIVWD<br>KGRDFATVRKVLSMPQVNIVKKTEVQTGGFSKESILPKRNSDKLIARKKDWDPKKY<br>GGFDSPTVAYSVLVVAKVEKGKSKKLKSVKELLGITIMERSSFEKNPIDFLEAKGYKE<br>VKKDLIIKLPKYSLFELENGRKRMLASAGELQKGNELALPSKYVNFLYLASHYEKLK<br>GSPEDNEQKQLFVEQHKHYLDEIIEQISEFSKRVILADANLDKVLSAYNKHRDKPIRE<br>QAENIIHLFTLTNLGAPAAFKYFDTTIDRKRYTSTKEVLDATLIHQSITGLYETRIDLSQ<br>LGGDGSPKKKRKVSSDYKDHDGDYKDHDIDYKDDDDKAAG (SEQ ID NO: 155) |
| Intein-Cas9(T519)-NLS-3×FLAG:<br>MDKKYSIGLDIGTNSVGWAVITDEYKVPSKKFKVLGNTDRHSIKKNLIGALLFDSGE<br>TAEATRLKRTARRRYTRRKNRICYLQEIFSNEMAKVDDSFFHRLEESFLVEEDKKHE<br>RHPIFGNIVDEVAYHEKYPTIYHLRKKLVDSTDKADLRLIYLALAHMIKFRGHFLIEG<br>DLNPDNSDVDKLFIQLVQTYNQLFEENPINASGVDAKAILSARLSKSRRLENLIAQLP<br>GEKKNGLFGNLIALSLGLTPNFKSNFDLAEDAKLQLSKDTYDDDLDNLLAQIGDQYA<br>DLFLAAKNLSDAILLSDILRVNTEITKAPLSASMIKRYDEHHQDLTLLKALVRQQLPE<br>KYKEIFFDQSKNGYAGYIDGGASQEEFYKFIKPILEKMDGTEELLVKLNREDLLRKQR<br>TFDNGSIPHQIHLGELHAILRRQEDFYPFLKDNREKIEKILTFRIPYYVGPLARGNSRFA<br>WMTRKSEETITPWNFEEVVDKGASAQSFIERMTNFDKNLPNEKVLPKHSLLYEYFCL<br>AEGTRIFDPVTGTTHRIEDVVDGRKPIHVVAAAKDGTLLARPVVSWFDQGTRDVIGL<br>RIAGGAIVWATPDHKVLTEYGWRAAGELRKGDRVAGPGGSGNSLALSLTADQMVS<br>ALLDAEPPILYSEYDPTSPFSEASMMGLLTNLADRELVHMINWAKRVPGFVDLTLHD<br>QAHLLERAWLEILMIGLVWRSMEHPGKLLFAPNLLLDRNQGKCVEGMVEIFDMLLA<br>TSSRFRMMNLQGEEFVCLKSIILLNSGVYTFLSSTLKSLEEKDHIHRALDKITDTLIHL |

-continued

| Sequences |
| --- |
| MAKAGLTLQQQHQRLAQLLLILSHIRHMSNKGMEHLYSMKYKNVVPLYDLLLEML<br>DAHRLHAGGSGASRVQAFADALDDKFLHDMLAEGLRYSVIREVLPTRRARTFDLEV<br>EELHTLVAEGVVVHNCVYNELTKVKYVTEGMRKPAFLSGEQKKAIVDLLFKTNRKV<br>TVKQLKEDYFKKIECFDSVEISGVEDRFNASLGTYHDLLKIIKDKDFLDNEENEDILED<br>IVLTLTLFEDREMIEERLKTYAHLFDDKVMKQLKRRRYTGWGRLSRKLINGIRDKQS<br>GKTILDFLKSDGFANRNFMQLIHDDSLTFKEDIQKAQVSGQGDSLHEHIANLAGSPAI<br>KKGILQTVKVVDELVKVMGRHKPENIVIEMARENQTTQKGQKNSRERMKRIEEGIK<br>ELGSQILKEHPVENTQLQNEKLYLYYLQNGRDMYVDQELDINRLSDYDVDHIVPQSF<br>LKDDSIDNKVLTRSDKNRGKSDNVPSEEVVKKMKNYWRQLLNAKLITQRKFDNLTK<br>AERGGLSELDKAGFIKRQLVETRQITKHVAQILDSRMNTKYDENDKLIREVKVITLKS<br>KLVSDFRKDFQFYKVREINNYHHAHDAYLNAVVGTALIKKYPKLESEFVYGDYKVY<br>DVRKMIAKSEQEIGKATAKYFFYSNIMNFFKTEITLANGEIRKRPLIETNGETGEIVWD<br>KGRDFATVRKVLSMPQVNIVKKTEVQTGGFSKESILPKRNSDKLIARKKDWDPKKY<br>GGFDSPTVAYSVLVVAKVEKGKSKKLKSVKELLGITIMERSSFEKNPIDFLEAKGYKE<br>VKKDLIIKLPKYSLFELENGRKRMLASAGELQKGNELALPSKYVNFLYLASHYEKLK<br>QAENIIHLFTLTNLGAPAAFKYFDTTIDRKRYTSTKEVLDATLIHQSITGLYETRIDLSQ<br>LGGDGSPKKKRKVSSDYKDHDGDYKDHDIDYKDDDDKAAG (SEQ ID NO: 156) |
| Intein-Cas9(C574)-NLS-3×FLAG:<br>MDKKYSIGLDIGTNSVGWAVITDEYKVPSKKFKVLGNTDRHSIKKNLIGALLFDSGE<br>TAEATRLKRTARRRYTRRKNRICYLQEIFSNEMAKVDDSFFHRLEESFLVEEDKKHE<br>RHPIFGNIVDEVAYHEKYPTIYHLRKKLVDSTDKADLRLIYLALAHMIKFRGHFLIEG<br>DLNPDNSDVDKLFIQLVQTYNQLFEENPINASGVDAKAILSARLSKSRRLENLIAQLP<br>GEKKNGLFGNLIALSLGLTPNFKSNFDLAEDAKLQLSKDTYDDDLDNLLAQIGDQYA<br>DLFLAAKNLSDAILLSDILRVNTEITKAPLSASMIKRYDEHHQDLTLLKALVRQQLPE<br>KYKEIFFDQSKNGYAGYIDGGASQEEFYKFIKPILEKMDGTEELLVKLNREDLLRKQR<br>TFDNGSIPHQIHLGELHAILRRQEDFYPFLKDNREKIEKILTFRIPYYVGPLARGNSRFA<br>WMTRKSEETITPWNFEEVVDKGASAQSFIERMTNFDKNLPNEKVLPKHSLLYEYFTV<br>YNELTKVKYVTEGMRKPAFLSGEQKKAIVDLLFKTNRKVTVKQLKEDYFKKIECLA<br>EGTRIFDPVTGTTHRIEDVVDGRKPIHVVAAAKDGTLLARPVVSWFDQGTRDVIGLRI<br>AGGAIVWATPDHKVLTEYGWRAAGELRKGDRVAGPGGSGNSLALSLTADQMVSAL<br>LDAEPPILYSEYDPTSPFSEASMMGLLTNLADRELVHMINWAKRVPGFVDLTLHDQA<br>HLLERAWLEILMIGLVWRSMEHPGKLLFAPNLLLDRNQGKCVEGMVEIFDMLLATS<br>SRFRMMNLQGEEFVCLKSIILLNSGVYTFLSSTLKSLEEKDHIHRALDKITDTLIHLMA<br>KAGLTLQQQHQRLAQLLLILSHIRHMSNKGMEHLYSMKYKNVVPLYDLLLEMLDA<br>HRLHAGGSGASRVQAFADALDDKFLHDMLAEGLRYSVIREVLPTRRARTFDLEVEE<br>LHTLVAEGVVVHNCFDSVEISGVEDRFNASLGTYHDLLKIIKDKDFLDNEENEDILED<br>IVLTLTLFEDREMIEERLKTYAHLFDDKVMKQLKRRRYTGWGRLSRKLINGIRDKQS<br>GKTILDFLKSDGFANRNFMQLIHDDSLTFKEDIQKAQVSGQGDSLHEHIANLAGSPAI<br>KKGILQTVKVVDELVKVMGRHKPENIVIEMARENQTTQKGQKNSRERMKRIEEGIK<br>ELGSQILKEHPVENTQLQNEKLYLYYLQNGRDMYVDQELDINRLSDYDVDHIVPQSF<br>LKDDSIDNKVLTRSDKNRGKSDNVPSEEVVKKMKNYWRQLLNAKLITQRKFDNLTK<br>AERGGLSELDKAGFIKRQLVETRQITKHVAQILDSRMNTKYDENDKLIREVKVITLKS<br>KLVSDFRKDFQFYKVREINNYHHAHDAYLNAVVGTALIKKYPKLESEFVYGDYKVY<br>DVRKMIAKSEQEIGKATAKYFFYSNIMNFFKTEITLANGEIRKRPLIETNGETGEIVWD<br>KGRDFATVRKVLSMPQVNIVKKTEVQTGGFSKESILPKRNSDKLIARKKDWDPKKY<br>GGFDSPTVAYSVLVVAKVEKGKSKKLKSVKELLGITIMERSSFEKNPIDFLEAKGYKE<br>VKKDLIIKLPKYSLFELENGRKRMLASAGELQKGNELALPSKYVNFLYLASHYEKLK<br>GSPEDNEQKQLFVEQHKHYLDEIIEQISEFSKRVILADANLDKVLSAYNKHRDKPIRE<br>QAENIIHLFTLTNLGAPAAFKYFDTTIDRKRYTSTKEVLDATLIHQSITGLYETRIDLSQ<br>LGGDGSPKKKRKVSSDYKDHDGDYKDHDIDYKDDDDKAAG (SEQ ID NO: 157) |
| Intein-Cas9(T622)-NLS-3×FLAG:<br>MDKKYSIGLDIGTNSVGWAVITDEYKVPSKKFKVLGNTDRHSIKKNLIGALLFDSGE<br>TAEATRLKRTARRRYTRRKNRICYLQEIFSNEMAKVDDSFFHRLEESFLVEEDKKHE<br>RHPIFGNIVDEVAYHEKYPTIYHLRKKLVDSTDKADLRLIYLALAHMIKFRGHFLIEG<br>DLNPDNSDVDKLFIQLVQTYNQLFEENPINASGVDAKAILSARLSKSRRLENLIAQLP<br>GEKKNGLFGNLIALSLGLTPNFKSNFDLAEDAKLQLSKDTYDDDLDNLLAQIGDQYA<br>DLFLAAKNLSDAILLSDILRVNTEITKAPLSASMIKRYDEHHQDLTLLKALVRQQLPE<br>KYKEIFFDQSKNGYAGYIDGGASQEEFYKFIKPILEKMDGTEELLVKLNREDLLRKQR<br>TFDNGSIPHQIHLGELHAILRRQEDFYPFLKDNREKIEKILTFRIPYYVGPLARGNSRFA<br>WMTRKSEETITPWNFEEVVDKGASAQSFIERMTNFDKNLPNEKVLPKHSLLYEYFTV<br>YNELTKVKYVTEGMRKPAFLSGEQKKAIVDLLFKTNRKVTVKQLKEDYFKKIECFD<br>SVEISGVEDRFNASLGTYHDLLKIIKDKDFLDNEENEDILEDIVLCLAEGTRIFDPVTG<br>TTHRIEDVVDGRKPIHVVAAAKDGTLLARPVVSWFDQGTRDVIGLRIAGGAIVWATP<br>DHKVLTEYGWRAAGELRKGDRVAGPGGSGNSLALSLTADQMVSALLDAEPPILYSE<br>YDPTSPFSEASMMGLLTNLADRELVHMINWAKRVPGFVDLTLHDQAHLLERAWLEI<br>LMIGLVWRSMEHPGKLLFAPNLLLDRNQGKCVEGMVEIFDMLLATSSRFRMMNLQ<br>GEEFVCLKSIILLNSGVYTFLSSTLKSLEEKDHIHRALDKITDTLIHLMAKAGLTLQQQ<br>HQRLAQLLLILSHIRHMSNKGMEHLYSMKYKNVVPLYDLLLEMLDAHRLHAGGSG<br>ASRVQAFADALDDKFLHDMLAEGLRYSVIREVLPTRRARTFDLEVEELHTLVAEGV<br>VVHNCLTLFEDREMIEERLKTYAHLFDDKVMKQLKRRRYTGWGRLSRKLINGIRDK<br>QSGKTILDFLKSDGFANRNFMQLIHDDSLTFKEDIQKAQVSGQGDSLHEHIANLAGSP<br>AIKKGILQTVKVVDELVKVMGRHKPENIVIEMARENQTTQKGQKNSRERMKRIEEGI<br>KELGSQILKEHPVENTQLQNEKLYLYYLQNGRDMYVDQELDINRLSDYDVDHIVPQ<br>SFLKDDSIDNKVLTRSDKNRGKSDNVPSEEVVKKMKNYWRQLLNAKLITQRKFDNL<br>TKAERGGLSELDKAGFIKRQLVETRQITKHVAQILDSRMNTKYDENDKLIREVKVITL |

-continued

| Sequences |
|---|

KSKLVSDFRKDFQFYKVREINNYHHAHDAYLNAVVGTALIKKYPKLESEFVYGDYK
VYDVRKMIAKSEQEIGKATAKYFFYSNIMNFFKTEITLANGEIRKRPLIETNGETGEIV
WDKGRDFATVRKVLSMPQVNIVKKTEVQTGGFSKESILPKRNSDKLIARKKDWDPK
KYGGFDSPTVAYSVLVVAKVEKGKSKKLKSVKELLGITIMERSSFEKNPIDFLEAKG
YKEVKKDLIIKLPKYSLFELENGRKRMLASAGELQKGNELALPSKYVNFLYLASHYE
KLKGSPEDNEQKQLFVEQHKHYLDEIIEQISEFSKRVILADANLDKVLSAYNKHRDKP
IREQAENIIHLFTLTNLGAPAAFKYFDTTIDRKRYTSTKEVLDATLIHQSITGLYETRID
LSQLGGDGSPKKKRKVSSDYKDHDGDYKDHDIDYKDDDDKAAG (SEQ ID NO: 158)

Intein-Cas9(S701)-NLS-3×FLAG:
MDKKYSIGLDIGTNSVGWAVITDEYKVPSKKFKVLGNTDRHSIKKNLIGALLFDSGE
TAEATRLKRTARRRYTRRKNRICYLQEIFSNEMAKVDDSFFHRLEESFLVEEDKKHE
RHPIFGNIVDEVAYHEKYPTIYHLRKKLVDSTDKADLRLIYLALAHMIKFRGHFLIEG
DLNPDNSDVDKLFIQLVQTYNQLFEENPINASGVDAKAILSARLSKSRRLENLIAQLP
GEKKNGLFGNLIALSLGLTPNFKSNFDLAEDAKLQLSKDTYDDDLDNLLAQIGDQYA
DLFLAAKNLSDAILLSDILRVNTEITKAPLSASMIKRYDEHHQDLTLLKALVRQQLPE
KYKEIFFDQSKNGYAGYIDGGASQEEFYKFIKPILEKMDGTEELLVKLNREDLLRKQR
TFDNGSIPHQIHLGELHAILRRQEDFYPFLKDNREKIEKILTFRIPYYVGPLARGNSRFA
WMTRKSEETITPWNFEEVVDKGASAQSFIERMTNFDKNLPNEKVLPKHSLLYEYFTV
YNELTKVKYVTEGMRKPAFLSGEQKKAIVDLLFKTNRKVTVKQLKEDYFKKIECFD
SVEISGVEDRFNASLGTYHDLLKIIKDKDFLDNEENEDILEDIVLTLTLFEDREMIEERL
KTYAHLFDDKVMKQLKRRRYTGWGRLSRKLINGIRDKQSGKTILDFLKSDGFANRN
FMQLIHDDCLAEGTRIFDPVTGTTHRIEDVVDGRKPIHVVAAAKDGTLLARPVVSWF
DQGTRDVIGLRIAGGAIVWATPDHKVLTEYGWRAAGELRKGDRVAGPGGSGNSLA
LSLTADQMVSALLDAEPPILYSEYDPTSPFSEASMMGLLTNLADRELVHMINWAKRV
PGFVDLTLHDQAHLLERAWLEILMIGLVWRSMEHPGKLLFAPNLLLDRNQGKCVEG
MVEIFDMLLATSSRFRMMNLQGEEFVCLKSIILLNSGVYTFLSSTLKSLEEKDHIHRA
LDKITDTLIHLMAKAGLTLQQQHQRLAQLLLILSHIRHMSNKGMEHLYSMKYKNVV
PLYDLLLEMLDAHRLHAGGSGASRVQAFADALDDKFLHDMLAEGLRYSVIREVLPT
RRARTFDLEVEELHTLVAEGVVVHNCLTFKEDIQKAQVSGQGDSLHEHIANLAGSPA
IKKGILQTVKVVDELVKVMGRHKPENIVIEMARENQTTQKGQKNSRERMKRIEEGIK
ELGSQILKEHPVENTQLQNEKLYLYYLQNGRDMYVDQELDINRLSDYDVDHIVPQSF
LKDDSIDNKVLTRSDKNRGKSDNVPSEEVVKKMKNYWRQLLNAKLITQRKFDNLTK
AERGGLSELDKAGFIKRQLVETRQITKHVAQILDSRMNTKYDENDKLIREVKVITLKS
KLVSDFRKDFQFYKVREINNYHHAHDAYLNAVVGTALIKKYPKLESEFVYGDYKVY
DVRKMIAKSEQEIGKATAKYFFYSNIMNFFKTEITLANGEIRKRPLIETNGETGEIVWD
KGRDFATVRKVLSMPQVNIVKKTEVQTGGFSKESILPKRNSDKLIARKKDWDPKKY
GGFDSPTVAYSVLVVAKVEKGKSKKLKSVKELLGITIMERSSFEKNPIDFLEAKGYKE
VKKDLIIKLPKYSLFELENGRKRMLASAGELQKGNELALPSKYVNFLYLASHYEKLK
GSPEDNEQKQLFVEQHKHYLDEIIEQISEFSKRVILADANLDKVLSAYNKHRDKPIRE
QAENIIHLFTLTNLGAPAAFKYFDTTIDRKRYTSTKEVLDATLIHQSITGLYETRIDLSQ
LGGDGSPKKKRKVSSDYKDHDGDYKDHDIDYKDDDDKAAG (SEQ ID NO: 159)

Intein-Cas9(A728)-NLS-3×FLAG:
MDKKYSIGLDIGTNSVGWAVITDEYKVPSKKFKVLGNTDRHSIKKNLIGALLFDSGE
TAEATRLKRTARRRYTRRKNRICYLQEIFSNEMAKVDDSFFHRLEESFLVEEDKKHE
RHPIFGNIVDEVAYHEKYPTIYHLRKKLVDSTDKADLRLIYLALAHMIKFRGHFLIEG
DLNPDNSDVDKLFIQLVQTYNQLFEENPINASGVDAKAILSARLSKSRRLENLIAQLP
GEKKNGLFGNLIALSLGLTPNFKSNFDLAEDAKLQLSKDTYDDDLDNLLAQIGDQYA
DLFLAAKNLSDAILLSDILRVNTEITKAPLSASMIKRYDEHHQDLTLLKALVRQQLPE
KYKEIFFDQSKNGYAGYIDGGASQEEFYKFIKPILEKMDGTEELLVKLNREDLLRKQR
TFDNGSIPHQIHLGELHAILRRQEDFYPFLKDNREKIEKILTFRIPYYVGPLARGNSRFA
WMTRKSEETITPWNFEEVVDKGASAQSFIERMTNFDKNLPNEKVLPKHSLLYEYFTV
YNELTKVKYVTEGMRKPAFLSGEQKKAIVDLLFKTNRKVTVKQLKEDYFKKIECFD
SVEISGVEDRFNASLGTYHDLLKIIKDKDFLDNEENEDILEDIVLTLTLFEDREMIEERL
KTYAHLFDDKVMKQLKRRRYTGWGRLSRKLINGIRDKQSGKTILDFLKSDGFANRN
FMQLIHDDSLTFKEDIQKAQVSGQGDSLHEHIANLCLAEGTRIFDPVTGTTHRIEDVV
DGRKPIHVVAAAKDGTLLARPVVSWFDQGTRDVIGLRIAGGAIVWATPDHKVLTEY
GWRAAGELRKGDRVAGPGGSGNSLALSLTADQMVSALLDAEPPILYSEYDPTSPFSE
ASMMGLLTNLADRELVHMINWAKRVPGFVDLTLHDQAHLLERAWLEILMIGLVWR
SMEHPGKLLFAPNLLLDRNQGKCVEGMVEIFDMLLATSSRFRMMNLQGEEFVCLKS
IILLNSGVYTFLSSTLKSLEEKDHIHRALDKITDTLIHLMAKAGLTLQQQHQRLAQLLL
ILSHIRHMSNKGMEHLYSMKYKNVVPLYDLLLEMLDAHRLHAGGSGASRVQAFAD
ALDDKFLHDMLAEGLRYSVIREVLPTRRARTFDLEVEELHTLVAEGVVVHNCGSPAI
KKGILQTVKVVDELVKVMGRHKPENIVIEMARENQTTQKGQKNSRERMKRIEEGIK
ELGSQILKEHPVENTQLQNEKLYLYYLQNGRDMYVDQELDINRLSDYDVDHIVPQSF
LKDDSIDNKVLTRSDKNRGKSDNVPSEEVVKKMKNYWRQLLNAKLITQRKFDNLTK
AERGGLSELDKAGFIKRQLVETRQITKHVAQILDSRMNTKYDENDKLIREVKVITLKS
KLVSDFRKDFQFYKVREINNYHHAHDAYLNAVVGTALIKKYPKLESEFVYGDYKVY
DVRKMIAKSEQEIGKATAKYFFYSNIMNFFKTEITLANGEIRKRPLIETNGETGEIVWD
KGRDFATVRKVLSMPQVNIVKKTEVQTGGFSKESILPKRNSDKLIARKKDWDPKKY
GGFDSPTVAYSVLVVAKVEKGKSKKLKSVKELLGITIMERSSFEKNPIDFLEAKGYKE
VKKDLIIKLPKYSLFELENGRKRMLASAGELQKGNELALPSKYVNFLYLASHYEKLK
GSPEDNEQKQLFVEQHKHYLDEIIEQISEFSKRVILADANLDKVLSAYNKHRDKPIRE
QAENIIHLFTLTNLGAPAAFKYFDTTIDRKRYTSTKEVLDATLIHQSITGLYETRIDLSQ
LGGDGSPKKKRKVSSDYKDHDGDYKDHDIDYKDDDDKAAG (SEQ ID NO: 160)

-continued

Sequences

Intein-Cas9(T995)-NLS-3×FLAG:
MDKKYSIGLDIGTNSVGWAVITDEYKVPSKKFKVLGNTDRHSIKKNLIGALLFDSGE
TAEATRLKRTARRRYTRRKNRICYLQEIFSNEMAKVDDSFFHRLEESFLVEEDKKHE
RHPIFGNIVDEVAYHEKYPTIYHLRKKLVDSTDKADLRLIYLALAHMIKFRGHFLIEG
DLNPDNSDVDKLFIQLVQTYNQLFEENPINASGVDAKAILSARLSKSRRLENLIAQLP
GEKKNGLFGNLIALSLGLTPNFKSNFDLAEDAKLQLSKDTYDDDLDNLLAQIGDQYA
DLFLAAKNLSDAILLSDILRVNTEITKAPLSASMIKRYDEHHQDLTLLKALVRQQLPE
KYKEIFFDQSKNGYAGYIDGGASQEEFYKFIKPILEKMDGTEELLVKLNREDLLRKQR
TFDNGSIPHQIHLGELHAILRRQEDFYPFLKDNREKIEKILTFRIPYYVGPLARGNSRFA
WMTRKSEETITPWNFEEVVDKGASAQSFIERMTNFDKNLPNEKVLPKHSLLYEYFTV
YNELTKVKYVTEGMRKPAFLSGEQKKAIVDLLFKTNRKVTVKQLKEDYFKKIECFD
SVEISGVEDRFNASLGTYHDLLKIIKDKDFLDNEENEDILEDIVLTLTLFEDREMIEERL
KTYAHLFDDKVMKQLKRRRYTGWGRLSRKLINGIRDKQSGKTILDFLKSDGFANRN
FMQLIHDDSLTFKEDIQKAQVSGQGDSLHEHIANLAGSPAIKKGILQTVKVVDELVK
VMGRHKPENIVIEMARENQTTQKGQKNSRERMKRIEEGIKELGSQILKEHPVENTQL
QNEKLYLYYLQNGRDMYVDQELDINRLSDYDVDHIVPQSFLKDDSIDNKVLTRSDK
NRGKSDNVPSEEVVKKMKNYWRQLLNAKLITQRKFDNLTKAERGGLSELDKAGFIK
RQLVETRQITKHVAQILDSRMNTKYDENDKLIREVKVITLKSKLVSDFRKDFQFYKV
REINNYHHAHDAYLNAVVGCLAEGTRIFDPVTGTTHRIEDVVDGRKPIHVVAAAKD
GTLLARPVVSWFDQGTRDVIGLRIAGGAIVWATPDHKVLTEYGWRAAGELRKGDR
VAGPGGSGNSLALSLTADQMVSALLDAEPPILYSEYDPTSPFSEASMMGLLTNLADR
ELVHMINWAKRVPGFVDLTLHDQAHLLERAWLEILMIGLVWRSMEHPGKLLFAPNL
LLDRNQGKCVEGMVEIFDMLLATSSRFRMMNLQGEEFVCLKSIILLNSGVYTFLSSTL
KSLEEKDHIHRALDKITDTLIHLMAKAGLTLQQQHQRLAQLLLILSHIRHMSNKGME
HLYSMKYKNVVPLYDLLLEMLDAHRLHAGGSGASRVQAFADALDDKFLHDMLAE
GLRYSVIREVLPTRRARTFDLEVEELHTLVAEGVVVHNCALIKKYPKLESEFVYGDY
KVYDVRKMIAKSEQEIGKATAKYFFYSNIMNFFKTEITLANGEIRKRPLIETNGETGEI
VWDKGRDFATVRKVLSMPQVNIVKKTEVQTGGFSKESILPKRNSDKLIARKKDWDP
KKYGGFDSPTVAYSVLVVAKVEKGKSKKLKSVKELLGITIMERSSFEKNPIDFLEAK
GYKEVKKDLIIKLPKYSLFELENGRKRMLASAGELQKGNELALPSKYVNFLYLASHY
PIREQAENIIHLFTLTNLGAPAAFKYFDTTIDRKRYTSTKEVLDATLIHQSITGLYETRI
DLSQLGGDGSPKKKRKVSSDYKDHDGDYKDHDIDYKDDDDKAAG (SEQ ID NO: 161)

Intein-Cas9(S1006)-NLS-3×FLAG:
MDKKYSIGLDIGTNSVGWAVITDEYKVPSKKFKVLGNTDRHSIKKNLIGALLFDSGE
TAEATRLKRTARRRYTRRKNRICYLQEIFSNEMAKVDDSFFHRLEESFLVEEDKKHE
RHPIFGNIVDEVAYHEKYPTIYHLRKKLVDSTDKADLRLIYLALAHMIKFRGHFLIEG
DLNPDNSDVDKLFIQLVQTYNQLFEENPINASGVDAKAILSARLSKSRRLENLIAQLP
GEKKNGLFGNLIALSLGLTPNFKSNFDLAEDAKLQLSKDTYDDDLDNLLAQIGDQYA
DLFLAAKNLSDAILLSDILRVNTEITKAPLSASMIKRYDEHHQDLTLLKALVRQQLPE
KYKEIFFDQSKNGYAGYIDGGASQEEFYKFIKPILEKMDGTEELLVKLNREDLLRKQR
TFDNGSIPHQIHLGELHAILRRQEDFYPFLKDNREKIEKILTFRIPYYVGPLARGNSRFA
WMTRKSEETITPWNFEEVVDKGASAQSFIERMTNFDKNLPNEKVLPKHSLLYEYFTV
YNELTKVKYVTEGMRKPAFLSGEQKKAIVDLLFKTNRKVTVKQLKEDYFKKIECFD
SVEISGVEDRFNASLGTYHDLLKIIKDKDFLDNEENEDILEDIVLTLTLFEDREMIEERL
KTYAHLFDDKVMKQLKRRRYTGWGRLSRKLINGIRDKQSGKTILDFLKSDGFANRN
FMQLIHDDSLTFKEDIQKAQVSGQGDSLHEHIANLAGSPAIKKGILQTVKVVDELVK
VMGRHKPENIVIEMARENQTTQKGQKNSRERMKRIEEGIKELGSQILKEHPVENTQL
QNEKLYLYYLQNGRDMYVDQELDINRLSDYDVDHIVPQSFLKDDSIDNKVLTRSDK
NRGKSDNVPSEEVVKKMKNYWRQLLNAKLITQRKFDNLTKAERGGLSELDKAGFIK
RQLVETRQITKHVAQILDSRMNTKYDENDKLIREVKVITLKSKLVSDFRKDFQFYKV
REINNYHHAHDAYLNAVVGTALIKKYPKLECLAEGTRIFDPVTGTTHRIEDVVDGRK
PIHVVAAAKDGTLLARPVVSWFDQGTRDVIGLRIAGGAIVWATPDHKVLTEYGWRA
AGELRKGDRVAGPGGSGNSLALSLTADQMVSALLDAEPPILYSEYDPTSPFSEASMM
GLLTNLADRELVHMINWAKRVPGFVDLTLHDQAHLLERAWLEILMIGLVWRSMEH
PGKLLFAPNLLLDRNQGKCVEGMVEIFDMLLATSSRFRMMNLQGEEFVCLKSIILLN
SGVYTFLSSTLKSLEEKDHIHRALDKITDTLIHLMAKAGLTLQQQHQRLAQLLLILSHI
RHMSNKGMEHLYSMKYKNVVPLYDLLLEMLDAHRLHAGGSGASRVQAFADALDD
KFLHDMLAEGLRYSVIREVLPTRRARTFDLEVEELHTLVAEGVVVHNCEFVYGDYK
VYDVRKMIAKSEQEIGKATAKYFFYSNIMNFFKTEITLANGEIRKRPLIETNGETGEIV
WDKGRDFATVRKVLSMPQVNIVKKTEVQTGGFSKESILPKRNSDKLIARKKDWDPK
KYGGFDSPTVAYSVLVVAKVEKGKSKKLKSVKELLGITIMERSSFEKNPIDFLEAKG
YKEVKKDLIIKLPKYSLFELENGRKRMLASAGELQKGNELALPSKYVNFLYLASHYE
KLKGSPEDNEQKQLFVEQHKHYLDEIIEQISEFSKRVILADANLDKVLSAYNKHRDKP
IREQAENIIHLFTLTNLGAPAAFKYFDTTIDRKRYTSTKEVLDATLIHQSITGLYETRID
LSQLGGDGSPKKKRKVSSDYKDHDGDYKDHDIDYKDDDDKAAG (SEQ ID NO: 162)

Intein-Cas9(S1154)-NLS-3×FLAG:
MDKKYSIGLDIGTNSVGWAVITDEYKVPSKKFKVLGNTDRHSIKKNLIGALLFDSGE
TAEATRLKRTARRRYTRRKNRICYLQEIFSNEMAKVDDSFFHRLEESFLVEEDKKHE
RHPIFGNIVDEVAYHEKYPTIYHLRKKLVDSTDKADLRLIYLALAHMIKFRGHFLIEG
DLNPDNSDVDKLFIQLVQTYNQLFEENPINASGVDAKAILSARLSKSRRLENLIAQLP
GEKKNGLFGNLIALSLGLTPNFKSNFDLAEDAKLQLSKDTYDDDLDNLLAQIGDQYA
DLFLAAKNLSDAILLSDILRVNTEITKAPLSASMIKRYDEHHQDLTLLKALVRQQLPE
KYKEIFFDQSKNGYAGYIDGGASQEEFYKFIKPILEKMDGTEELLVKLNREDLLRKQR
TFDNGSIPHQIHLGELHAILRRQEDFYPFLKDNREKIEKILTFRIPYYVGPLARGNSRFA
WMTRKSEETITPWNFEEVVDKGASAQSFIERMTNFDKNLPNEKVLPKHSLLYEYFTV -continued

| Sequences |
|---|
| YNELTKVKYVTEGMRKPAFLSGEQKKAIVDLLFKTNRKVTVKQLKEDYFKKIECFD<br>SVEISGVEDRFNASLGTYHDLLKIIKDKDFLDNEENEDILEDIVLTLTLFEDREMIEERL<br>KTYAHLFDDKVMKQLKRRRYTGWGRLSRKLINGIRDKQSGKTILDFLKSDGFANRN<br>FMQLIHDDSLTFKEDIQKAQVSGQGDSLHEHIANLAGSPAIKKGILQTVKVVDELVK<br>VMGRHKPENIVIEMARENQTTQKGQKNSRERMKRIEEGIKELGSQILKEHPVENTQL<br>QNEKLYLYYLQNGRDMYVDQELDINRLSDYDVDHIVPQSFLKDDSIDNKVLTRSDK<br>NRGKSDNVPSEEVVKKMKNYWRQLLNAKLITQRKFDNLTKAERGGLSELDKAGFIK<br>RQLVETRQITKHVAQILDSRMNTKYDENDKLIREVKVITLKSKLVSDFRKDFQFYKV<br>REINNYHHAHDAYLNAVVGTALIKKYPKLESEFVYGDYKVYDVRKMIAKSEQEIGK<br>ATAKYFFYSNIMNFFKTEITLANGEIRKRPLIETNGETGEIVWDKGRDFATVRKVLSM<br>PQVNIVKKTEVQTGGFSKESILPKRNSDKLIARKKDWDPKKYGGFDSPTVAYSVLVV<br>AKVEKGKCLAEGTRIFDPVTGTTHRIEDVVDGRKPIHVVAAAKDGTLLARPVVSWF<br>DQGTRDVIGLRIAGGAIVWATPDHKVLTEYGWRAAGELRKGDRVAGPGGSGNSLA<br>LSLTADQMVSALLDAEPPILYSEYDPTSPFSEASMMGLLTNLADRELVHMINWAKRV<br>PGFVDLTLHDQAHLLERAWLEILMIGLVWRSMEHPGKLLFAPNLLLDRNQGKCVEG<br>MVEIFDMLLATSSRFRMMNLQGEEFVCLKSIILLNSGVYTFLSSTLKSLEEKDHIHRA<br>LDKITDTLIHLMAKAGLTLQQQHQRLAQLLLILSHIRHMSNKGMEHLYSMKYKNVV<br>PLYDLLLEMLDAHRLHAGGSGASRVQAFADALDDKFLHDMLAEGLRYSVIREVLPT<br>RRARTFDLEVEELHTLVAEGVVVHNCKKLKSVKELLGITIMERSSFEKNPIDFLEAKG<br>YKEVKKDLIIKLPKYSLFELENGRKRMLASAGELQKGNELALPSKYVNFLYLASHYE<br>IREQAENIIHLFTLTNLGAPAAFKYFDTTIDRKRYTSTKEVLDATLIHQSITGLYETRID<br>LSQLGGDGSPKKKRKVSSDYKDHDGDYKDHDIDYKDDDDKAAG (SEQ ID NO: 163)<br><br>Intein-Cas9(S1159)-NLS-3xFLAG:<br>MDKKYSIGLDIGTNSVGWAVITDEYKVPSKKFKVLGNTDRHSIKKNLIGALLFDSGE<br>TAEATRLKRTARRRYTRRKNRICYLQEIFSNEMAKVDDSFFHRLEESFLVEEDKKHE<br>RHPIFGNIVDEVAYHEKYPTIYHLRKKLVDSTDKADLRLIYLALAHMIKFRGHFLIEG<br>DLNPDNSDVDKLFIQLVQTYNQLFEENPINASGVDAKAILSARLSKSRRLENLIAQLP<br>GEKKNGLFGNLIALSLGLTPNFKSNFDLAEDAKLQLSKDTYDDDLDNLLAQIGDQYA<br>DLFLAAKNLSDAILLSDILRVNTEITKAPLSASMIKRYDEHHQDLTLLKALVRQQLPE<br>KYKEIFFDQSKNGYAGYIDGGASQEEFYKFIKPILEKMDGTEELLVKLNREDLLRKQR<br>TFDNGSIPHQIHLGELHAILRRQEDFYPFLKDNREKIEKILTFRIPYYVGPLARGNSRFA<br>WMTRKSEETITPWNFEEVVDKGASAQSFIERMTNFDKNLPNEKVLPKHSLLYEYFTV<br>YNELTKVKYVTEGMRKPAFLSGEQKKAIVDLLFKTNRKVTVKQLKEDYFKKIECFD<br>SVEISGVEDRFNASLGTYHDLLKIIKDKDFLDNEENEDILEDIVLTLTLFEDREMIEERL<br>KTYAHLFDDKVMKQLKRRRYTGWGRLSRKLINGIRDKQSGKTILDFLKSDGFANRN<br>FMQLIHDDSLTFKEDIQKAQVSGQGDSLHEHIANLAGSPAIKKGILQTVKVVDELVK<br>VMGRHKPENIVIEMARENQTTQKGQKNSRERMKRIEEGIKELGSQILKEHPVENTQL<br>QNEKLYLYYLQNGRDMYVDQELDINRLSDYDVDHIVPQSFLKDDSIDNKVLTRSDK<br>NRGKSDNVPSEEVVKKMKNYWRQLLNAKLITQRKFDNLTKAERGGLSELDKAGFIK<br>RQLVETRQITKHVAQILDSRMNTKYDENDKLIREVKVITLKSKLVSDFRKDFQFYKV<br>REINNYHHAHDAYLNAVVGTALIKKYPKLESEFVYGDYKVYDVRKMIAKSEQEIGK<br>ATAKYFFYSNIMNFFKTEITLANGEIRKRPLIETNGETGEIVWDKGRDFATVRKVLSM<br>PQVNIVKKTEVQTGGFSKESILPKRNSDKLIARKKDWDPKKYGGFDSPTVAYSVLVV<br>AKVEKGKSKKLKCLAEGTRIFDPVTGTTHRIEDVVDGRKPIHVVAAAKDGTLLARPV<br>VSWFDQGTRDVIGLRIAGGAIVWATPDHKVLTEYGWRAAGELRKGDRVAGPGGSG<br>NSLALSLTADQMVSALLDAEPPILYSEYDPTSPFSEASMMGLLTNLADRELVHMINW<br>AKRVPGFVDLTLHDQAHLLERAWLEILMIGLVWRSMEHPGKLLFAPNLLLDRNQGK<br>CVEGMVEIFDMLLATSSRFRMMNLQGEEFVCLKSIILLNSGVYTFLSSTLKSLEEKDH<br>IHRALDKITDTLIHLMAKAGLTLQQQHQRLAQLLLILSHIRHMSNKGMEHLYSMKYK<br>NVVPLYDLLLEMLDAHRLHAGGSGASRVQAFADALDDKFLHDMLAEGLRYSVIRE<br>VLPTRRARTFDLEVEELHTLVAEGVVVHNCVKELLGITIMERSSFEKNPIDFLEAKGY<br>KEVKKDLIIKLPKYSLFELENGRKRMLASAGELQKGNELALPSKYVNFLYLASHYEK<br>LKGSPEDNEQKQLFVEQHKHYLDEIIEQISEFSKRVILADANLDKVLSAYNKHRDKPI<br>REQAENIIHLFTLTNLGAPAAFKYFDTTIDRKRYTSTKEVLDATLIHQSITGLYETRIDL<br>SQLGGDGSPKKKRKVSSDYKDHDGDYKDHDIDYKDDDDKAAG (SEQ ID NO: 164)<br><br>Intein-Cas9(S1274)-NLS-3xFLAG:<br>MDKKYSIGLDIGTNSVGWAVITDEYKVPSKKFKVLGNTDRHSIKKNLIGALLFDSGE<br>TAEATRLKRTARRRYTRRKNRICYLQEIFSNEMAKVDDSFFHRLEESFLVEEDKKHE<br>RHPIFGNIVDEVAYHEKYPTIYHLRKKLVDSTDKADLRLIYLALAHMIKFRGHFLIEG<br>DLNPDNSDVDKLFIQLVQTYNQLFEENPINASGVDAKAILSARLSKSRRLENLIAQLP<br>GEKKNGLFGNLIALSLGLTPNFKSNFDLAEDAKLQLSKDTYDDDLDNLLAQIGDQYA<br>DLFLAAKNLSDAILLSDILRVNTEITKAPLSASMIKRYDEHHQDLTLLKALVRQQLPE<br>KYKEIFFDQSKNGYAGYIDGGASQEEFYKFIKPILEKMDGTEELLVKLNREDLLRKQR<br>TFDNGSIPHQIHLGELHAILRRQEDFYPFLKDNREKIEKILTFRIPYYVGPLARGNSRFA<br>WMTRKSEETITPWNFEEVVDKGASAQSFIERMTNFDKNLPNEKVLPKHSLLYEYFTV<br>YNELTKVKYVTEGMRKPAFLSGEQKKAIVDLLFKTNRKVTVKQLKEDYFKKIECFD<br>SVEISGVEDRFNASLGTYHDLLKIIKDKDFLDNEENEDILEDIVLTLTLFEDREMIEERL<br>KTYAHLFDDKVMKQLKRRRYTGWGRLSRKLINGIRDKQSGKTILDFLKSDGFANRN<br>FMQLIHDDSLTFKEDIQKAQVSGQGDSLHEHIANLAGSPAIKKGILQTVKVVDELVK<br>VMGRHKPENIVIEMARENQTTQKGQKNSRERMKRIEEGIKELGSQILKEHPVENTQL<br>QNEKLYLYYLQNGRDMYVDQELDINRLSDYDVDHIVPQSFLKDDSIDNKVLTRSDK<br>NRGKSDNVPSEEVVKKMKNYWRQLLNAKLITQRKFDNLTKAERGGLSELDKAGFIK<br>RQLVETRQITKHVAQILDSRMNTKYDENDKLIREVKVITLKSKLVSDFRKDFQFYKV<br>REINNYHHAHDAYLNAVVGTALIKKYPKLESEFVYGDYKVYDVRKMIAKSEQEIGK<br>ATAKYFFYSNIMNFFKTEITLANGEIRKRPLIETNGETGEIVWDKGRDFATVRKVLSM |

-continued

| Sequences |
|---|
| PQVNIVKKTEVQTGGFSKESILPKRNSDKLIARKKDWDPKKYGGFDSPTVAYSVLVV AKVEKGKSKKLKSVKELLGITIMERSSFEKNPIDFLEAKGYKEVKKDLIIKLPKYSLFE LENGRKRMLASAGELQKGNELALPSKYVNFLYLASHYEKLKGSPEDNEQKQLFVEQ HKHYLDEIIEQICLAEGTRIFDPVTGTTHRIEDVVDGRKPIHVVAAAKDGTLLARPVV SWFDQGTRDVIGLRIAGGAIVWATPDHKVLTEYGWRAAGELRKGDRVAGPGGSGN SLALSLTADQMVSALLDAEPPILYSEYDPTSPFSEASMMGLLTNLADRELVHMINWA KRVPGFVDLTLHDQAHLLERAWLEILMIGLVWRSMEHPGKLLFAPNLLLDRNQGKC VEGMVEIFDMLLATSSRFRMMNLQGEEFVCLKSIILLNSGVYTFLSSTLKSLEEKDHI HRALDKITDTLIHLMAKAGLTLQQQHQRLAQLLLILSHIRHMSNKGMEHLYSMKYK NVVPLYDLLLEMLDAHRLHAGGSGASRVQAFADALDDKFLHDMLAEGLRYSVIRE VLPTRRARTFDLEVEELHTLVAEGVVVHNCEFSKRVILADANLDKVLSAYNKHRDK PIREQAENIIHLFTLTNLGAPAAFKYFDTTIDRKRYTSTKEVLDATLIHQSITGLYETRI DLSQLGGDGSPKKKRKVSSDYKDHDGDYKDHDIDYKDDDDKAAG (SEQ ID NO: 165) |
| Intein-Cas9(S219-G521R))-NLS-3×FLAG: MDKKYSIGLDIGTNSVGWAVITDEYKVPSKKFKVLGNTDRHSIKKNLIGALLFDSGE TAEATRLKRTARRRYTRRKNRICYLQEIFSNEMAKVDDSFFHRLEESFLVEEDKKHE RHPIFGNIVDEVAYHEKYPTIYHLRKKLVDSTDKADLRLIYLALAHMIKFRGHFLIEG DLNPDNSDVDKLFIQLVQTYNQLFEENPINASGVDAKAILSARLSKCLAEGTRIFDPV TGTTHRIEDVVDGRKPIHVVAAAKDGTLLARPVVSWFDQGTRDVIGLRIAGGAIVW ATPDHKVLTEYGWRAAGELRKGDRVAGPGGSGNSLALSLTADQMVSALLDAEPPIL YSEYDPTSPFSEASMMGLLTNLADRELVHMINWAKRVPGFVDLTLHDQAHLLERA WLEILMIGLVWRSMEHPGKLLFAPNLLLDRNQGKCVEGMVEIFDMLLATSSRFRMM NLQGEEFVCLKSIILLNSGVYTFLSSTLKSLEEKDHIHRALDKITDTLIHLMAKAGLTL QQQHQRLAQLLLILSHIRHMSNKRMEHLYSMKYKNVVPLYDLLLEMLDAHRLHAG GSGASRVQAFADALDDKFLHDMLAEGLRYSVIREVLPTRRARTFDLEVEELHTLVAE GVVVHNCRRLENLIAQLPGEKKNGLFGNLIALSLGLTPNFKSNFDLAEDAKLQLSKD TYDDDLDNLLAQIGDQYADLFLAAKNLSDAILLSDILRVNTEITKAPLSASMIKRYDE HHQDLTLLKALVRQQLPEKYKEIFFDQSKNGYAGYIDGGASQEEFYKFIKPILEKMD GTEELLVKLNREDLLRKQRTFDNGSIPHQIHLGELHAILRRQEDFYPFLKDNREKIEKI LTFRIPYYVGPLARGNSRFAWMTRKSEETITPWNFEEVVDKGASAQSFIERMTNFDK NLPNEKVLPKHSLLYEYFTVYNELTKVKYVTEGMRKPAFLSGEQKKAIVDLLFKTNR KVTVKQLKEDYFKKIECFDSVEISGVEDRFNASLGTYHDLLKIIKDKDFLDNEENEDI LEDIVLTLTLFEDREMIEERLKTYAHLFDDKVMKQLKRRRYTGWGRLSRKLINGIRD KQSGKTILDFLKSDGFANRNFMQLIHDDSLTFKEDIQKAQVSGQGDSLHEHIANLAG SPAIKKGILQTVKVVDELVKVMGRHKPENIVIEMARENQTTQKGQKNSRERMKRIEE GIKELGSQILKEHPVENTQLQNEKLYLYYLQNGRDMYVDQELDINRLSDYDVDHIVP QSFLKDDSIDNKVLTRSDKNRGKSDNVPSEEVVKKMKNYWRQLLNAKLITQRKFDN LTKAERGGLSELDKAGFIKRQLVETRQITKHVAQILDSRMNTKYDENDKLIREVKVIT LKSKLVSDFRKDFQFYKVREINNYHHAHDAYLNAVVGTALIKKYPKLESEFVYGDY KVYDVRKMIAKSEQEIGKATAKYFFYSNIMNFFKTEITLANGEIRKRPLIETNGETGEI VWDKGRDFATVRKVLSMPQVNIVKKTEVQTGGFSKESILPKRNSDKLIARKKDWDP KKYGGFDSPTVAYSVLVVAKVEKGKSKKLKSVKELLGITIMERSSFEKNPIDFLEAK GYKEVKKDLIIKLPKYSLFELENGRKRMLASAGELQKGNELALPSKYVNFLYLASHY PIREQAENIIHLFTLTNLGAPAAFKYFDTTIDRKRYTSTKEVLDATLIHQSITGLYETRI DLSQLGGDGSPKKKRKVSSDYKDHDGDYKDHDIDYKDDDDKAAG (SEQ ID NO: 166) |
| Indel Calling Algorithm<br>Read 1:<br>@M00265:68:000000000-AA85W:1:1101:14923:1642 1:N:0:1<br>TGCAGTCTCATGACTTGGCCTTTGTAGGAAAACACCATTAGAAGAGTAGATGGTT GGGTAGTGGCT**CTCTTCTGCTTAGACTC**TTGTCTACTATGAATAAAGGGCTCTA TTTGCAAAGGCCGTGATGGGTTGAAGCACATTGAGAAAGAGGCT (SEQ ID NO: 167)<br>+<br>3>>A?FFFFFFFFGGGGBGGGGHHGHHHGHHGHHHGHHHHHGHHHGHHHHHHHHH GGGGHGHFHGGHHHHHHGHHHHHHHHHHHHHGHFHHGHHHHHHHHHHFGGHH HHHHHHHHHGHHHHG@EEHHHHHGGHHHHHHHHHHHHHHHHHHHGG |
| Read 2:<br>@M00265:68:000000000-AA85W:1:1101:14923:1642 2:N:0:1<br>CTCACCTGGGCGAGAAAGGTAACTTATGTTTCAGTAGCCTCTTTCTCAATGTGCTT CAACCCATCACGGCCTTTGCAAATAGAGCCCTTTATTCATAGTAGACAA**GAGTCT AAGCAGAAGAG**AGCCACTACCCAACCATCTACTCTTCTAATGGT (SEQ ID NO: 168)<br>**+**<br>3>>AAFCFFBBBGGGGGGGGGGHGHHHHHHHHHHHHHHHHHHHHHHHHHHHHHGH HHHHHHHHGGHHFHDFGGGHHHHHHHHHGHFHHHGGGHHHHHHHHHHFHHHHHH HHHHHGHHHHHGHHHGHGHHHHHHHHHHHGGGHHHGHHGHHHHHHHHH@ |

Step 1: Search for sequences (or reverse complements) flanking the on/off target sites in both Illumina reads from the following set:

| | target site | 5' flanking sequence | 3' flanking sequence |
|---|---|---|---|
| EMX_On | GAGTCCGAGCAGAAGAAGAAGGG (SEQ ID NO: 107) | AGCTGGAGGAGGAAGGGCCT (SEQ ID NO: 174) | CTCCCATCACATCAACCGGT (SEQ ID NO: 188) |
| EMX_Off1 | GAGGCCGAGCAGAAGAAAGACGG (SEQ ID NO: 108) | CCCCTTCTTCTGCAAATGAG (SEQ ID NO: 175) | CGACAGATGTTGGGGGGAGG (SEQ ID NO: 189) |
| EMX_Off2 | GAGTCCTAGCAGGAGAAGAAGAG (SEQ ID NO: 109) | GGCTGGGGCCAGCATGACCT (SEQ ID NO: 176) | GCAGCCTAGAGTCTTCTGTG (SEQ ID NO: 190) |
| EMX_Off3 | GAGTCTAAGCAGAAGAAGAAGAG (SEQ ID NO: 110) | CCTTTATTCATAGTAGACAA (SEQ ID NO: 177) | AGCCACTACCCAACCATCTA (SEQ ID NO: 191) |
| EMX_Off4 | GAGTTAGAGCAGAAGAAGAAAGG (SEQ ID NO: 111) | CATGGCAAGACAGATTGTCA (SEQ ID NO: 178) | CATGGAGTAAAGGCAATCTT (SEQ ID NO: 192) |
| VEGF_On | GGGTGGGGGGAGTTTGCTCCTGG (SEQ ID NO: 112) | GGGAATGGGCTTTGGAAAGG (SEQ ID NO: 179) | ACCCCCTATTTCTGACCTCC (SEQ ID NO: 193) |
| VEGF_Off1 | GGATGGAGGGAGTTTGCTCCTGG (SEQ ID NO: 113) | CATCTAAGGACGGATTTGTG (SEQ ID NO: 180) | GGTGTCAGAATGTCCTGTCT (SEQ ID NO: 194) |
| VEGF_Off2 | GGGAGGGTGGAGTTTGCTCCTGG (SEQ ID NO: 114) | CTGGTCAGCCCATTATGATA (SEQ ID NO: 181) | GGATGGAAGGGCCGGCTCCG (SEQ ID NO: 195) |
| VEGF_Off3 | CGGGGGAGGGAGTTTGCTCCTGG (SEQ ID NO: 115) | CTGGAGAGAGGCTCCCATCA (SEQ ID NO: 182) | GGAACCTGTGATCCCCACAG (SEQ ID NO: 196) |
| VEGF_Off4 | GGGGAGGGGAAGTTTGCTCCTGG (SEQ ID NO: 116) | CATTTTTGCTGTCACAACTC (SEQ ID NO: 183) | CATTCAGTGGGTAGAGTCCA (SEQ ID NO: 197) |
| CLTA On | GCAGATGTAGTGTTTCCACAGGG (SEQ ID NO: 117) | CTGAGTAGGATTAAGATATT (SEQ ID NO: 184) | TGGCTCTTCAGTGCACCAGC (SEQ ID NO: 198) |
| CLTA_Off1 | ACATATGTAGTATTTCCACAGGG (SEQ ID NO: 118) | GTTGGGAAGAGATGCATACA (SEQ ID NO: 185) | AATACAATGGACAAATAACC (SEQ ID NO: 199) |
| CLTA Off2 | CCAGATGTAGTATTCCCACAGGG (SEQ ID NO: 119) | GCCTCCTTGATTGAGGTGTC (SEQ ID NO: 186) | GTCTGGCAGGCCCCTCCTGT (SEQ ID NO: 200) |
| CLTA_Off3 | CTAGATGAAGTGCTTCCACATGG (SEQ ID NO: 120) | CTCATCTAGAGTTCTTTCCA (SEQ ID NO: 187) | CTTTCATTAGAGTTTAGTCC (SEQ ID NO: 201) |

Step 2: Extract the sequence between the target sites in both reads and ensure that it is identical (reverse complementary) in read 1 and read 2 and all positions within read 1 and read 2 have a quality score >='?' (Phred score >=30)

In above reads, CTCTTCTGCTTAGACTC (SEQ ID NO: 169) is reverse complement of GAGTCTAAGCAGAAGAG (SEQ ID NO: 170)

Step 3: Align extracted sequence to the reference sequence for the relevant on/off target sequence

```
reference sequence
                              (SEQ ID NO: 110)
GAGTCTAAGCAGAAGAAGAAGAG

sequence read
                              (SEQ ID NO: 202)
GAGTCTAAGC------AGAAGAG
```

Step 4: For deletions, count only if deletion occurred in close proximity to expected cleavage site (within 8 bp of 3' end of reference sequence)

Methods and Materials

Cas9, intein-Cas9, and sgRNA expression plasmids. A plasmid encoding the human codon-optimized *Streptococcus pyogenes* Cas9 nuclease with an NLS and 3×FLAG tag (Addgene plasmid 43861)[5] was used as the wild-type Cas9 expression plasmid. Intein 37R3-2 was subcloned at the described positions into the wild-type Cas9 expression plasmid using USER (NEB M5505) cloning. sgRNA expression plasmids used in this study have been described previously[11]. Plasmid constructs generated in this work will be deposited with Addgene.

Modification of genomic GFP. HEK293-GFP stable cells (GenTarget), which constitutively express Emerald GFP, served as the reporter cell line. Cells were maintained in "full serum media": Dulbecco's Modified Eagle's Media plus GlutaMax (Life Technologies) with 10% (vol/vol) FBS and penicillin/streptomycin (lx, Amresco). $5\times10^4$ cells were plated on 48-well collagen-coated Biocoat plates (Becton Dickinson). 16-18 h after plating, cells were transfected with Lipofectamine 2000 (Life Technologies) according to the manufacturer's protocol. Briefly, 1.5 μL of Lipofectamine 2000 was used to transfect 650 ng of total plasmid: 500 ng Cas9 expression plasmid, 125 ng sgRNA expression plasmid, and 25 ng near-infrared iRFP670 expressing plasmid (Addgene plasmid 45457)[26]. 12 h after transfection, the media was replaced with full serum media, with or without 4-HT (1 μM, Sigma-Aldrich T176). The media was replaced again 3-4 days after transfection. Five days after transfection, cells were trypsinized and resuspended in full serum media and analyzed on a C6 flow cytometer (Accuri) with a 488-nm laser excitation and 520-nm filter with a 20-nm band pass. Transfections and flow cytometry measurements were performed in triplicate.

High-throughput DNA sequencing of genome modifications. HEK293-GFP stable cells were transfected with plasmids expressing Cas9 (500 ng) and sgRNA (125 ng) as described above. For treatments in which a reduced amount of wild-type Cas9 expression plasmid was transfected, pUC19 plasmid was used to bring the total amount of plasmid to 500 ng. 4-HT (1 μM final), where appropriate, was added during transfection. 12 h after transfection, the media was replaced with full serum media without 4-HT. Genomic DNA was isolated and pooled from three biological replicates 60 h after transfection using a previously reported[11] protocol with a DNAdvance Kit (Agencourt). 150 ng or 200 ng of genomic DNA was used as a template to amplify by PCR the on-target and off-target genomic sites with flanking HTS primer pairs described previously[11]. PCR products were purified using RapidTips (Diffinity Genomics) and quantified using the PicoGreen dsDNA Assay Kit (Invitrogen). Purified DNA was PCR amplified with primers containing sequencing adaptors, purified with the MinElute PCR Purification Kit (Qiagen) and AMPure XP PCR Purification (Agencourt). Samples were sequenced on a MiSeq high-throughput DNA sequencer (Illumina), and sequencing data was analyzed as described previously[4].

Western blot analysis of intein splicing. HEK293-GFP stable cells were transfected with 500 ng Cas9 expression plasmid and 125 ng sgRNA expression plasmid. 12 h after transfection, the media was replaced with full serum media, with or without 4-HT (1 μM). Cells were lysed and pooled from three technical replicates 4, 8, 12, or 24 h after 4-HT treatment. Samples were run on a Bolt 4-12% Bis-Tris gel (Life Technologies). An anti-FLAG antibody (Sigma-Aldrich F1804) and an anti-mouse 800CW IRDye (LI-COR) were used to visualize the gel on an Odyssey IR imager.

Statistical analysis. Statistical tests were performed as described in the figure captions. All p-values were calculated with the R software package. p-values for the Fisher exact test were calculated using the fisher.test function, with a one-sided alternative hypothesis (alternative="greater" or alternative="less", as appropriate). Upper bounds on p-values that are close to zero were determined manually. The Benjamini-Hochberg adjustment was performed using the R function p.adjust (method="fdr").

Sensitivity limit of off-target cleavage assays. We used paired end sequencing to identify indels caused by genomic on- and off-target cleavage. Given that published studies (see the reference below) have shown that the Illumina platform has an indel rate that is several orders of magnitude lower than the ~0.1% substitution error rate, and our requirement that all called indels occur in both paired reads, the sensitivity of the high-throughput sequencing method for detecting genomic off-target cleavage in our study is limited by the amount genomic DNA (gDNA) input into the PCR amplification of each genomic target site. A 1 ng sample of human gDNA represents only ~330 unique genomes, and thus only ~330 unique copies of each genomic site are present. PCR amplification for each genomic target was performed on a total of 150 ng or 200 ng of input gDNA, which provides amplicons derived from at most 50,000 or 65,000 unique gDNA copies, respectively. Therefore, the high-throughput sequencing assay cannot detect rare genome modification events that occur at a frequency of less than approximately 1 in 50,000 (0.002%). When comparing between two conditions, such as wt Cas9 vs. intein-Cas9, this threshold becomes approximately 10 in 50,000 (0.02%) when using the Fisher exact test and a conservative multiple comparison correction (Bonferroni with 14 samples). See also Minoche, A. E., Dohm, J. C., & Himmelbauer, H. Evaluation of genomic high-throughput sequencing data generated on Illumina HiSeq and Genome Analyzer systems. *Genome Biology* 12, R112 (2011).

REFERENCES

1 Jinek, M. et al. A programmable dual-RNA-guided DNA endonuclease in adaptive bacterial immunity. *Science* 337, 816-821 (2012).

2 *Mali*, P. et al. RNA-guided human genome engineering via Cas9. *Science* 339, 823-826 (2013).

3 Hwang, W. Y. et al. Efficient genome editing in zebrafish using a CRISPR-Cas system. *Nature biotechnology* 31, 227-229 (2013).

4 Pattanayak, V. et al. High-throughput profiling of off-target DNA cleavage reveals RNA-programmed Cas9 nuclease specificity. *Nature biotechnology* 31, 839-843 (2013).

5 Fu, Y. et al. High-frequency off-target mutagenesis induced by CRISPR-Cas nucleases in human cells. *Nature biotechnology* 31, 822-826 (2013).

6 Hsu, P. D. et al. DNA targeting specificity of RNA-guided Cas9 nucleases. *Nature biotechnology* 31, 827-832 (2013).

7 Cho, S. W. et al. Analysis of off-target effects of CRISPR/Cas-derived RNA-guided endonucleases and nickases. *Genome research* 24, 132-141 (2014).

8 Tsai, S. Q. et al. GUIDE-seq enables genome-wide profiling of off-target cleavage by CRISPR-Cas nucleases. *Nature biotechnology* 33, 187-197 (2015).

9 Mali, P. et al. CAS9 transcriptional activators for target specificity screening and paired nickases for cooperative genome engineering. *Nature biotechnology* 31, 833-838 (2013).

10 Ran, F. A. et al. Double nicking by RNA-guided CRISPR Cas9 for enhanced genome editing specificity. *Cell* 154, 1380-1389 (2013).

11 Guilinger, J. P., Thompson, D. B. & Liu, D. R. Fusion of catalytically inactive Cas9 to FokI nuclease improves the specificity of genome modification. *Nature biotechnology* 32, 577-582 (2014).

12 Tsai, S. Q. et al. Dimeric CRISPR RNA-guided FokI nucleases for highly specific genome editing. *Nature biotechnology* 32 (2014).

13 Fu, Y., Sander, J. D., Reyon, D., Cascio, V. M. & Joung, J. K. Improving CRISPR-Cas nuclease specificity using truncated guide RNAs. *Nature biotechnology* 32 (2014).

14 Kim, S., Kim, D., Cho, S. W., Kim, J. & Kim, J. S. Highly efficient RNA-guided genome editing in human cells via delivery of purified Cas9 ribonucleoproteins. *Genome research* 24, 1012-1019 (2014).

15 Ramakrishna, S. et al. Gene disruption by cell-penetrating peptide-mediated delivery of Cas9 protein and guide RNA. *Genome research* 24, 1020-1027 (2014).

16 Zuris, J. A. et al. Cationic lipid-mediated delivery of proteins enables efficient protein-based genome editing in vitro and in vivo. *Nature biotechnology* 33, 73-80 (2015).

17 Wang, T., Wei, J. J., Sabatini, D. M. & Lander, E. S. Genetic screens in human cells using the CRISPR-Cas9 system. *Science* 343, 80-84 (2014).

18 Gonzalez, F. et al. An iCRISPR platform for rapid, multiplexable, and inducible genome editing in human pluripotent stem cells. *Cell stem cell* 15, 215-226 (2014).

19 Pruett-Miller, S. M., Reading, D. W., Porter, S. N. & Porteus, M. H. Attenuation of zinc finger nuclease toxicity by small-molecule regulation of protein levels. *PLoS genetics* 5, e1000376 (2009).

20 Buskirk, A. R., Ong, Y. C., Gartner, Z. J. & Liu, D. R. Directed evolution of ligand dependence: small-molecule-activated protein splicing. *Proceedings of the National Academy of Sciences of the United States of America* 101, 10505-10510 (2004).

21 Yuen, C. M., Rodda, S. J., Vokes, S. A., McMahon, A. P. & Liu, D. R. Control of transcription factor activity and osteoblast differentiation in mammalian cells using an evolved small-molecule-dependent intein. *Journal of the American Chemical Society* 128, 8939-8946 (2006).

22 Peck, S. H., Chen, I. & Liu, D. R. Directed evolution of a small-molecule-triggered intein with improved splicing properties in mammalian cells. *Chemistry & biology* 18, 619-630 (2011).

23 Jinek, M. et al. Structures of Cas9 endonucleases reveal RNA-mediated conformational activation. *Science* 343, 1247997 (2014).

24 Danielian, P. S., White, R., Hoare, S. A., Fawell, S. E. & Parker, M. G. Identification of residues in the estrogen receptor that confer differential sensitivity to estrogen and hydroxytamoxifen. *Molecular endocrinology* 7, 232-240 (1993).

25 Zetsche, B., Volz, S. E. & Zhang, F. A split-Cas9 architecture for inducible genome editing and transcription modulation. *Nature biotechnology* 33, 139-142 (2015).

26 Shcherbakova, D. M. & Verkhusha, V. V. Near-infrared fluorescent proteins for multicolor in vivo imaging. *Nature methods* 10, 751-754 (2013).

All publications, patents, patent applications, publication, and database entries (e.g., sequence database entries) mentioned herein, e.g., in the Background, Summary, Detailed Description, Examples, and References sections, are incorporated by reference in their entirety as if each individual publication, patent, patent application, publication, and database entry was specifically and individually incorporated herein by reference. In case of conflict, the present application, including any definitions herein, will control.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

All publications, patents and sequence database entries mentioned herein, including those items listed above, are hereby incorporated by reference in their entirety as if each individual publication or patent was specifically and individually indicated to be incorporated by reference. In case of conflict, the present application, including any definitions herein, will control.

What is claimed is:

1. A polynucleotide encoding a hybrid protein comprising an intein flanked by two extein sequences of a Cas9 protein, wherein the two extein sequences ligate to form the Cas9 protein upon excision of the intein.

2. The polynucleotide of claim 1, wherein an activity of the Cas9 protein is disrupted by the intein, and wherein the disrupted activity is restored upon excision of the intein from the Cas9 protein.

3. The polynucleotide of claim 1, wherein the Cas9 protein is capable of binding a guide RNA (gRNA) prior to excision of the intein.

4. The polynucleotide of claim 1, wherein the Cas9 protein has no or minimal gRNA binding activity prior to excision of the intein.

5. The polynucleotide of claim 1, wherein the intein is a ligand-dependent intein.

6. The polynucleotide of claim 1, wherein the intein comprises a ligand-binding domain.

7. The polynucleotide of claim 6, wherein the ligand-binding domain comprises an amino acid sequence having at least 90% identity to an amino acid sequence selected from the group consisting of SEQ ID NOs: 7-14.

8. The polynucleotide of claim 1, wherein the Cas9 protein comprises a nuclease-inactivated Cas9 (dCas9) domain.

9. The polynucleotide of claim 1, wherein the Cas9 protein comprises a Cas9 nickase.

10. The polynucleotide of claim 1, wherein the hybrid protein further comprises a nucleic acid-editing domain.

11. The polynucleotide of claim 10, wherein the nucleic acid-editing domain comprises a heterologous nuclease domain, a recombinase domain, or a deaminase domain.

12. The polynucleotide of claim 11, wherein the deaminase domain comprises a cytidine deaminase domain.

13. The polynucleotide of claim 11, wherein the deaminase domain comprises an adenosine deaminase domain.

14. The polynucleotide of claim 11, wherein the intein is a ligand-dependent intein.

15. The polynucleotide of claim 11, wherein the Cas9 protein comprises a nuclease-inactivated Cas9 (dCas9) domain.

16. The polynucleotide of claim 11, wherein the Cas9 protein comprises a Cas9 nickase.

17. The polynucleotide of claim 11, wherein the Cas9 protein and the deaminase domain are separated by a linker.

18. The polynucleotide of claim 17, wherein the linker comprises a peptide linker.

19. The polynucleotide of claim 17, wherein the linker comprises a non-peptide linker.

20. The polynucleotide of claim 1, wherein (a) the intein is a ligand-dependent intein, (b) the Cas9 protein comprises a dCas9 domain or is a Cas9 nickase, and (c) the Cas9 protein further comprises a deaminase domain.

21. The polynucleotide of claim 20, wherein the deaminase domain comprises a cytidine deaminase domain.

22. The polynucleotide of claim 20, wherein the deaminase domain comprises an adenosine deaminase domain.

23. The polynucleotide of claim 1, wherein the Cas9 protein comprises a Cas9 domain having the amino acid sequence selected from the group consisting of SEQ ID NO: 2 (Cas9), SEQ ID NO: 4 (Cas9 nickase) and SEQ ID NO: 5 (dCas9).

24. The polynucleotide of claim 1, wherein the intein is inserted at or replaces residue Cys80, Ala127, Thr146, Ser219, Thr333, Thr519, Cys574, Thr622, Ser701, Ala728, Thr995, Ser1006, Ser1154, Ser1159, or Ser1274 of a Cas9 protein having the amino acid sequence set forth as SEQ ID NO: 2, SEQ ID NO: 4, or SEQ ID NO: 5.

25. The polynucleotide of claim 1, wherein the hybrid protein comprises an amino acid sequence having at least 90% identity to any one of SEQ ID NOs: 27-41.

26. The polynucleotide of claim 17, wherein linker is a peptide linker.

27. The polynucleotide of claim 17, wherein linker is a non-peptide linker.

28. A method for site-specific DNA cleavage, comprising:

a) introducing the polynucleotide of claim 1 into a cell under conditions where the hybrid protein is expressed;

b) contacting the hybrid protein with a ligand, wherein binding of the ligand to the intein induces self-excision of the intein; and c) contacting a DNA with the Cas9 protein, wherein the Cas9 protein is associated with a gRNA, wherein self-excision of the intein from the hybrid protein in step (b) allows the Cas9 protein to cleave the DNA, thereby producing cleaved DNA.

29. A method of DNA editing, the method comprising:

a) introducing the polynucleotide of claim 10 into a cell under conditions where the hybrid protein is expressed, wherein the intein is a ligand-dependent intein, and wherein an activity of the Cas9 protein selected from the group consisting of nuclease activity, target nucleic acid binding activity, and gRNA binding activity is disrupted by the intein;

b) contacting the hybrid protein with a gRNA capable of targeting the Cas9 protein to a target nucleotide sequence in a DNA molecule;

c) contacting the hybrid protein with a ligand that binds to the ligand-dependent intein and induces self-excision of the ligand-dependent intein, thereby restoring the activity of the Cas9 protein; and d) contacting the target nucleotide sequence with the restored Cas9 protein, thereby editing the DNA molecule.

30. The method of DNA editing of claim 29, wherein the nucleic acid-editing domain comprises a cytidine deaminase domain.

31. The method of DNA editing of claim 29, wherein the nucleic acid-editing domain comprises an adenosine deaminase domain.

32. The polynucleotide of claim 6, wherein the ligand-binding domain comprises an amino acid sequence selected from the group consisting of SEQ ID NOs: 7-14.

33. The polynucleotide of claim 1, wherein the Cas9 protein comprises an amino acid sequence having at least about 90% identical to a sequence selected form the group consisting of SEQ ID NO: 2, SEQ ID NO: 4 and SEQ ID NO: 5.

* * * * *